US010208045B2

(12) United States Patent
Hendricks et al.

(10) Patent No.: US 10,208,045 B2

(45) **Date of Patent: *Feb. 19, 2019**

(54) AZA-PYRIDONE COMPOUNDS AND USES THEREOF

(71) Applicant: Alios BioPharma, Inc., South San Francisco, CA (US)

(72) Inventors: Robert Than Hendricks, San Carlos, CA (US); Leonid Beigelman, San Mateo, CA (US); David Bernard Smith, San Mateo, CA (US); Antitsa Dimitrova Stoycheva, Half Moon Bay, CA (US)

(73) Assignee: Alios BioPharma, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/065,627

(22) Filed: Mar. 9, 2016

(65) Prior Publication Data

US 2016/0264581 A1 Sep. 15, 2016

Related U.S. Application Data

(60) Provisional application No. 62/131,708, filed on Mar. 11, 2015.

(51) Int. Cl.

| | |
|---|---|
| *C07D 487/04* | (2006.01) |
| *C07H 17/02* | (2006.01) |
| *C07D 519/00* | (2006.01) |
| *A61K 45/06* | (2006.01) |
| *A61K 31/215* | (2006.01) |

(52) U.S. Cl.

CPC .......... *C07D 487/04* (2013.01); *A61K 31/215* (2013.01); *A61K 45/06* (2013.01); *C07D 519/00* (2013.01); *C07H 17/02* (2013.01)

(58) Field of Classification Search

CPC .................................................. C07D 487/04

See application file for complete search history.

(56) References Cited

U.S. PATENT DOCUMENTS

| | | | |
|---|---|---|---|
| 7,211,572 | B2 | 5/2007 | Susumu Miyazaki et al. |
| 8,383,638 | B2 | 2/2013 | Kuduk et al. |
| 8,455,475 | B2 | 6/2013 | Schunk et al. |
| 9,328,119 | B2 | 5/2016 | Hendricks et al. |
| 2005/0054645 | A1 | 3/2005 | Miyazaki et al. |
| 2006/0052596 | A1 | 3/2006 | Muller et al. |
| 2007/0135525 | A1 | 6/2007 | Liang et al. |
| 2009/0281107 | A1 | 11/2009 | Congy et al. |
| 2010/0143301 | A1 | 6/2010 | Desai et al. |
| 2010/0197651 | A1 | 8/2010 | Taniguchi et al. |
| 2011/0275608 | A1 | 11/2011 | Rodriguez et al. |
| 2012/0022251 | A1 | 1/2012 | Sumino et al. |
| 2012/0022255 | A1 | 1/2012 | Fujishita et al. |
| 2012/0070411 | A1 | 3/2012 | Beigelman et al. |
| 2012/0070415 | A1 | 3/2012 | Beigelman et al. |
| 2012/0071434 | A1 | 3/2012 | Smith et al. |
| 2012/0165286 | A1 | 6/2012 | Beigelman et al. |
| 2012/0184734 | A1 | 7/2012 | Akiyama et al. |
| 2013/0164261 | A1 | 6/2013 | Wang et al. |
| 2013/0165400 | A1 | 6/2013 | Beigelman et al. |
| 2013/0197219 | A1 | 8/2013 | Takahashi et al. |
| 2013/0231327 | A1 | 9/2013 | Schunk et al. |
| 2013/0252920 | A1 | 9/2013 | Blatt et al. |
| 2013/0253181 | A1 | 9/2013 | Serebryany et al. |
| 2013/0281687 | A1 | 10/2013 | Serebryany et al. |
| 2014/0179627 | A1 | 6/2014 | Beigelman et al. |
| 2014/0179910 | A1 | 6/2014 | Beigelman et al. |
| 2014/0303108 | A1 | 10/2014 | Beigelman et al. |
| 2014/0303113 | A1 | 10/2014 | Krop et al. |
| 2015/0011497 | A1 | 1/2015 | Beigelman et al. |
| 2015/0038451 | A1 | 2/2015 | Smith et al. |
| 2015/0051167 | A1 | 2/2015 | Wang et al. |
| 2015/0072982 | A1 | 3/2015 | Hendricks et al. |
| 2015/0105341 | A1 | 4/2015 | Beigelman et al. |
| 2015/0141363 | A1 | 5/2015 | Wang et al. |
| 2015/0175647 | A1 | 6/2015 | Kuldipkumar et al. |
| 2015/0183819 | A1 | 7/2015 | Beigelman et al. |
| 2015/0315228 | A1 | 11/2015 | Beigelman et al. |
| 2015/0366887 | A1 | 12/2015 | Blatt et al. |
| 2015/0366888 | A1 | 12/2015 | Blatt et al. |
| 2015/0368286 | A1 | 12/2015 | Serebryany et al. |

(Continued)

FOREIGN PATENT DOCUMENTS

| | | |
|---|---|---|
| AU | 2007330652 | 7/2009 |
| CN | 1594300 A | 3/2005 |

(Continued)

OTHER PUBLICATIONS

Henry R. Henze and Charles M. Blair "The Number of Structurally Isomeric Alcohols of the Methanol Series" Journal of the American Chemical Society 1931, 3042.*

Kräusslich in "Antiviral Strategies" Handbook of Experimental Pharmacology vol. 189 Chapter 1, pp. 1-24.*

Bunce, R.A. et al., "A Synthesis of Diphenyl Methyl Ketones" Synthetic Communications (1990) 20(19), 3007-3014.

Carey, Francis, Organic Chemistry, 2nd ed., McGraw Hill, Inc., New York (1992), pp. 328-331.

CAS Reg. No. 1259366-34-1, Entry Date Jan. 14, 2011, Retrieved on Dec. 2, 2014.

CAS Reg. No. 1422050-75-6, Entry Date Feb. 28, 2013, Retrieved on Dec. 2, 2014.

(Continued)

*Primary Examiner* — David K O'Dell

(74) *Attorney, Agent, or Firm* — Morrison & Foerster LLP

(57) ABSTRACT

Disclosed herein are aza-pyridone compounds, pharmaceutical compositions that include one or more aza-pyridone compounds, and methods of synthesizing the same. Also disclosed herein are methods of ameliorating and/or treating a disease and/or a condition, including an orthomyxovirus infection, with an aza-pyridone compound. Examples of an orthomyxovirus viral infection include an influenza infection.

39 Claims, 5 Drawing Sheets

Specification includes a Sequence Listing.

(56) References Cited

U.S. PATENT DOCUMENTS

| | | | |
|---|---|---|---|
| 2016/0016987 | A1 | 1/2016 | Beigelman et al. |
| 2016/0022724 | A1 | 1/2016 | Chanda et al. |
| 2016/0024136 | A1 | 1/2016 | Beigelman et al. |
| 2016/0039858 | A1 | 2/2016 | Beigelman et al. |
| 2016/0039861 | A1 | 2/2016 | Smith et al. |
| 2016/0115190 | A1 | 4/2016 | Serebryany et al. |
| 2016/0176910 | A1 | 6/2016 | Wang et al. |
| 2016/0176911 | A1 | 6/2016 | Beigelman et al. |
| 2016/0221963 | A1 | 8/2016 | Beigelman et al. |
| 2016/0228438 | A1 | 8/2016 | Hendricks et al. |
| 2016/0264581 | A1 | 9/2016 | Hendricks et al. |
| 2016/0264610 | A1 | 9/2016 | Beigelman et al. |
| 2016/0318967 | A1 | 11/2016 | Dyatkina et al. |
| 2016/0318969 | A1 | 11/2016 | Kuldipkumar et al. |
| 2016/0331770 | A1 | 11/2016 | Beigelman et al. |
| 2017/0002037 | A1 | 1/2017 | Beigelman et al. |
| 2017/0260189 | A1 | 9/2017 | Welch et al. |

FOREIGN PATENT DOCUMENTS

| | | |
|---|---|---|
| CN | 101340902 A | 1/2006 |
| EP | 2042502 | 4/2009 |
| EP | 2444400 | 4/2012 |
| WO | WO 1995/020583 | 8/1995 |
| WO | WO 2005/016927 | 2/2005 |
| WO | WO 2005/099688 | 10/2005 |
| WO | WO 2008/068424 | 6/2008 |
| WO | WO 2008/077188 | 7/2008 |
| WO | WO 2009/053799 | 4/2009 |
| WO | WO 2010/080864 | 7/2010 |
| WO | WO 2010/090737 | 8/2010 |
| WO | WO 2010/096338 | 8/2010 |
| WO | WO 2010/108140 | 9/2010 |
| WO | WO 2010/108651 | 9/2010 |
| WO | WO 2010/110231 | 9/2010 |
| WO | WO 2010/138419 | 12/2010 |
| WO | WO 2011/084371 | 7/2011 |
| WO | WO 2011/120153 | 10/2011 |
| WO | WO 2012/009194 | 1/2012 |
| WO | WO 2012/039414 | 3/2012 |
| WO | WO 2013/049352 | 4/2013 |
| WO | WO 2013/142124 | 9/2013 |
| WO | WO 2013/142159 | 9/2013 |
| WO | WO 2013/142525 | 9/2013 |
| WO | WO 2014/100498 | 6/2014 |
| WO | WO 2014/108406 | 7/2014 |
| WO | WO 2014/134251 | 9/2014 |
| WO | WO 2014/164533 | 10/2014 |
| WO | WO 2014/209983 | 12/2014 |
| WO | WO 2015/038655 | 3/2015 |
| WO | WO 2015/038660 | 3/2015 |
| WO | WO 2016/022464 | 2/2016 |
| WO | WO 2017/223231 | 12/2017 |

OTHER PUBLICATIONS

Clark, J.A., et al., “Substituted 3-amino-1,1-diaryl-2-propanols as potential antidepressant agents” J. Med. Chem. (1979) 22(11), 1373-1379.

Gilchrist, T.L., et al., “Formation of Pyridazino[6,1-c][1,4]oxazin-8(7H)-ones by Intramolecular Cycloaddition of Azoalkenes” Journal of the Chemical Society, Perkin Transactions I (1987) 11:2517-2522.

Greene, et al., Protective Groups in Organic Synthesis, 3. Ed., John Wiley & Sons, (1999) Cover & Contents pages.

Hassall, C.H., et al, “Amino-acids and Peptides. Part XII. The Molecular Structures of the Monamycins, Cyclodepsipeptide Antibiotics” Journal of the Chemical Society C: Organic (1971) 3:526-532.

“IUPAC-IUB Commission on Biochemical Nomenclature Abbreviated Nomenclature of Synthetic Polypeptides (Polymerized Amino Acids)* Revised Recommendations (1971)” *Biochemistry*. (1972) 11(5) :942-944.

Kumazawa, T. et al., “Inhibitors of Acyl-CoA:Cholesterol Acyltransferase. 1. Synthesis and Hypocholesterolemic Activity of Dibenz[b,e]oxepin-11-carboxanilides” J. Med. Chem. (1994) 37(6), 804-810.

McMurry, Organic Chemistry, 5th ed., Brooks/Cole, Pacific Grove, CA (2000), Chapter 11.5, pp. 398 and 408.

McOmie, J. F. W., Protective Groups in Organic Chemistry, Plenum Press, 1973. Cover & Contents pages only.

Prichard, M. N. et al., “A three-dimensional model to analyze drug-drug interactions” Antiviral Res. (1990) 14(4-5):181-205.

Snieckus et. al., “Regioselective N-methyl carbon lithiation of N-boc-methylalkylamines. Expedient synthesis of unsymmetrical amines” Tet. Lett. (1994) 35(24):4067-4070.

Streitwieser et al., Introduction to Organic Chemistry, 2nd ed., Macmillan Publishing Co. Inc., New York, NY, 1981, pp. 169-171.

International Search Report and Written Opinion dated May 17, 2016 for PCT Application No. PCT/US2016/021598, filed Mar. 9, 2016.

Zou et al., Chemical Journal of Chinese Universities (2002) 23(3):403-406.

International Preliminary Report on Patentability dated Sep. 12, 2017 for PCT Application No. PCT/US2016/021598, filed Mar. 9, 2016.

Eurasian Office Action dated Sep. 10, 2018 for Eurasian Patent Application 201792008 filed Oct. 10, 2017.

European Extended Search Report dated Oct. 12, 2018 for EP Application No. 16762448.5 filed Apr. 10, 2017.

* cited by examiner

| Name or CAS No. | IUPAC Name | Structure |
|---|---|---|
| amantadine | adamantan-1-amine |  |
| rimantadine | (RS)-1-(1-adamantyl)ethanamine |  |
| zanamivir | (2R,3R,4S)-4-guanidino-3-(prop-1-en-2-ylamino)-2-((1R,2R)-1,2,3-trihydroxypropyl)-3,4-dihydro-2H-pyran-6-carboxylic acid |  |
| oseltamivir | ethyl (3R,4R,5S)-5-amino-4-acetamido-3-(pentan-3-yloxy)-cyclohex-1-ene-1-carboxylate |  |

Figure 1 (cont.)

| Name or CAS No. | IUPAC Name | Structure |
|---|---|---|
| peramivir | (1S,2S,3S,4R)-3-[(1S)-1-acetamido-2-ethylbutyl]-4-(diaminomethylideneamino)-2-hydroxycyclopentane-1-carboxylic acid | 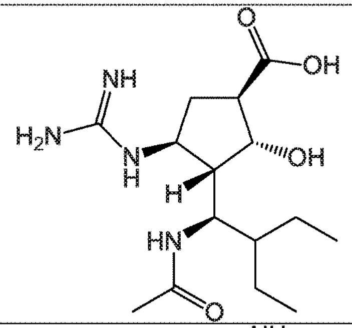 |
| laninamivir | (4S,5R,6R)-5-acetamido-4-carbamimidamido-6-[(1R,2R)-3-hydroxy-2-methoxypropyl]-5,6-dihydro-4H-pyran-2-carboxylic acid | 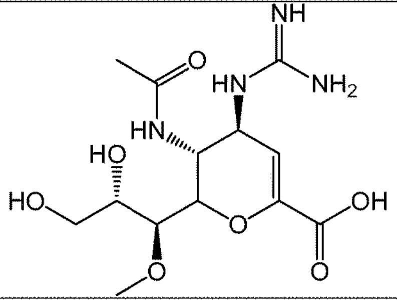 |
| laninamivir octanoate | (3R,4S)-3-acetamido-4-guanidino-2-((1S,2S)-2-hydroxy-1-methoxy-3-(octanoyloxy)propyl)-3,4-dihydro-2H-pyran-6-carboxylic acid | 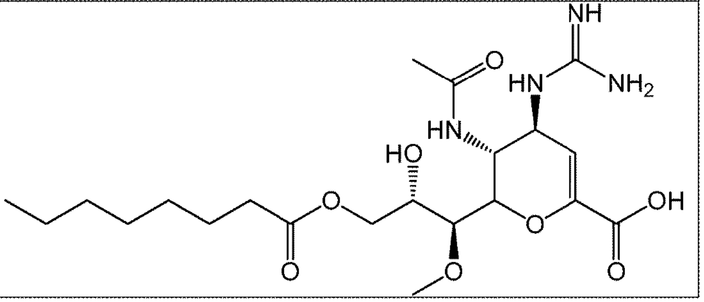 |

| Name or CAS No. | IUPAC Name | Structure |
|---|---|---|
| favipiravir | 6-fluoro-3-hydroxy-2-pyrazinecarboxamide |  |
| beraprost | 4-[2-hydroxy-1-[(E)-3-hydroxy-4-methyloct-1-en-6-ynyl]-2,3,3a,8b-tetrahydro-1H-cyclopenta[b][1]benzofuran-5-yl]butanoic acid |  |
| ribavirin | 1-[(2R,3R,4S,5R)-3,4-dihydroxy-5-(hydroxymethyl)oxolan-2-yl]-1H-1,2,4-triazole-3-carboxamide |  |

| Name or CAS No. | IUPAC Name | Structure |
|---|---|---|
| 1422050-75-6 | (R)-3-((5-fluoro-2-(5-fluoro-1H-pyrrolo[2,3-b]pyridin-3-yl)pyrimidin-4-yl)amino)-4,4-dimethylpentanoic acid |  |
| VX-787 | (2S,3S)-3-((5-fluoro-2-(5-fluoro-1H-pyrrolo[2,3-b]pyridin-3-yl)pyrimidin-4-yl)amino)bicyclo[2.2.2]octane-2-carboxylic acid |  |
| | (S)-8-benzhydryl-4-hydroxy-6-isopropyl-7,8-dihydro-3H-pyrazino[1,2-b]pyridazine-3,5(6H)-dione |  |

| Name or CAS No. | IUPAC Name | Structure |
| --- | --- | --- |
| | (S)-8-benzhydryl-6-isopropyl-3,5-dioxo-5,6,7,8-tetrahydro-3H-pyrazino[1,2-b]pyridazin-4-yl isobutyrate |  |

AZA-PYRIDONE COMPOUNDS AND USES THEREOF

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

SEQUENCE LISTING

The present application is being filed along with a Sequence Listing in electronic format. The Sequence Listing is provided as a file entitled ALIOS095.txt, created Mar. 8, 2016, which is 4 kb bytes in size. The information in the electronic format of the Sequence Listing is incorporated herein by reference in its entirety.

BACKGROUND

Field

The present application relates to the fields of chemistry, biochemistry and medicine. More particularly, disclosed herein are aza-pyridone compounds, pharmaceutical compositions that include one or more aza-pyridone compounds, and methods of synthesizing the same. Also disclosed herein are methods of ameliorating and/or treating an orthomyxovirus viral infection with one or more aza-pyridone compounds.

Description

The viruses of the Orthomyxoviridae family are negative-sense, single-stranded RNA viruses. The Orthomyxoviridae family contains several genera including Influenzavirus A, Influenzavirus B, Influenzavirus C, Isavirus and Thogotovirus. Influenzaviruses can cause respiratory viral infections, including upper and lower respiratory tract viral infections. Respiratory viral infections are a leading cause of death of millions of people each year. Upper respiratory tract viral infections involve the nose, sinuses, pharynx and/or larynx. Lower respiratory tract viral infections involve the respiratory system below the vocal cords, including the trachea, primary bronchi and lungs.

SUMMARY

Some embodiments disclosed herein relate to a compound of Formula (I), or a pharmaceutically acceptable salt thereof.

Some embodiments disclosed herein relate to methods of ameliorating and/or treating an orthomyxovirus viral infection that can include administering to a subject suffering from the orthomyxovirus viral infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating an orthomyxovirus viral infection. Still other embodiments described herein relate to a compound of Formula (I), or a pharmaceutically acceptable salt thereof, that can be used for ameliorating and/or treating an orthomyxovirus viral infection. Yet still other embodiments disclosed herein relate to methods of ameliorating and/or treating an orthomyxovirus viral infection that can include contacting a cell infected with the orthomyxovirus with an effective amount of one or more compounds of Formula (I), or a pharmaceutically acceptable salt thereof, or a pharmaceutical composition that includes one or more compounds of Formula (I), or a pharmaceutically acceptable salt thereof. Some embodiments disclosed herein relate to methods of preventing an orthomyxovirus infection that can include administering to a subject an effective amount of one or more compounds of Formula (I), or a pharmaceutically acceptable salt thereof, or a pharmaceutical composition that includes one or more compounds of Formula (I), or a pharmaceutically acceptable salt thereof. For example, the orthomyxovirus viral infection can be an influenza viral infection (such as influenza A, B and/or C).

Some embodiments disclosed herein relate to methods of inhibiting the replication of an orthomyxovirus that can include contacting a cell infected with the orthomyxovirus with an effective amount of one or more compounds of Formula (I), or a pharmaceutically acceptable salt thereof, or a pharmaceutical composition that includes one or more compounds of Formula (I), or a pharmaceutically acceptable salt thereof. For example, the orthomyxovirus viral infection can be an influenza viral infection (such as influenza A, B and/or C). Other embodiments disclosed herein relate to a method for inhibiting endonuclease activity of an influenza endonuclease that can include contacting the active site of the endonuclease with an effective amount of one or more compounds of Formula (I), or a pharmaceutically acceptable salt thereof, or a pharmaceutical composition that includes one or more compounds of Formula (I), or a pharmaceutically acceptable salt thereof. These and other embodiments are described in greater detail below.

DETAILED DESCRIPTION

Figure 1:
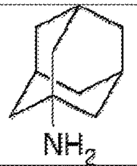
FIG. 1 shows example anti-influenza agents.
Figure 1:
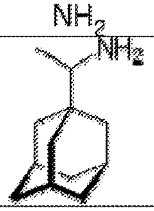
Figure 1:
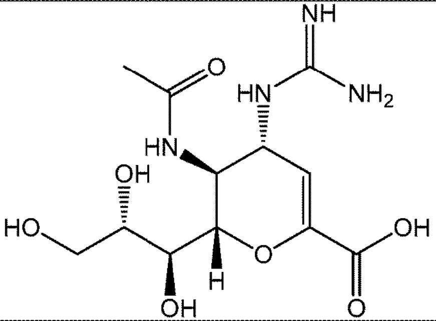
Figure 1:
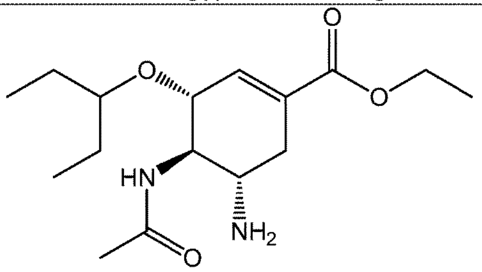
Figure 1:
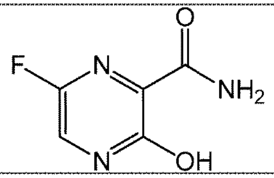
Figure 1:
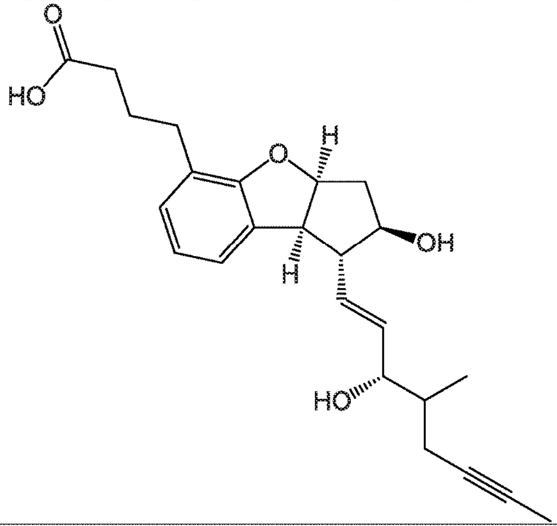
Figure 1:
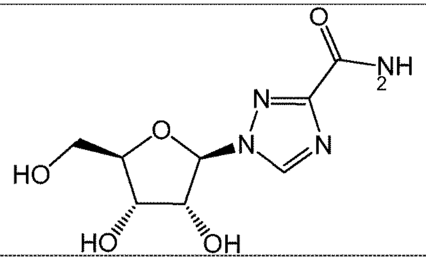
Figure 1:
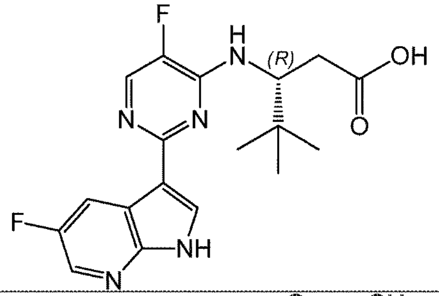
Figure 1:
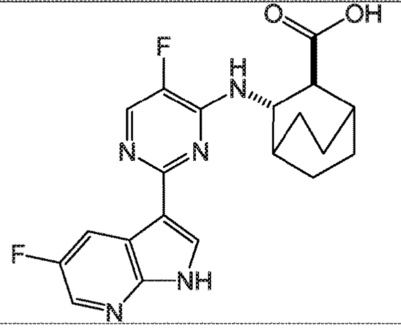
Figure 1:
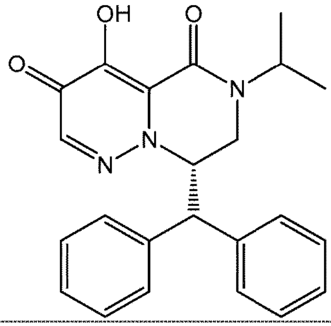
Figure 1:
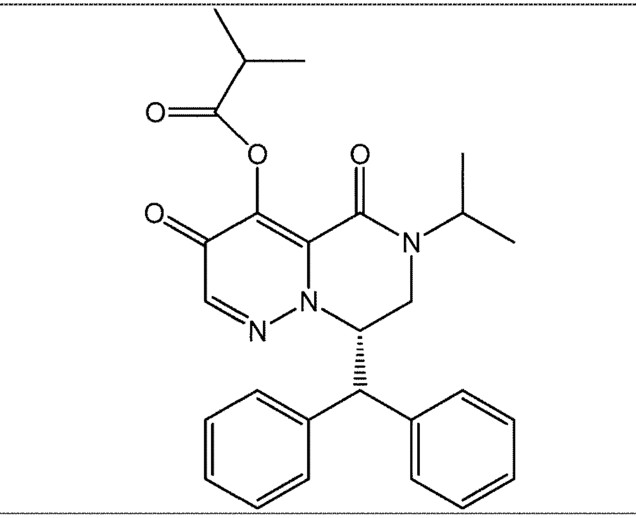

Influenza is a negative sense, single stranded RNA virus and a member of the Orthomyxoviridae family. There are currently three species of influenza; influenza A, influenza B and influenza C. Influenza A has a lipid membrane derived from the host cell, which contains the hemagglutinin, neuramididase and M2 proteins that project from the surface of the virus. Influenza A has been further classified based the hemagglutinin (H or HA) and the neuramididase (N). There are approximately 16H antigens (H1 to H16) and 9N antigens (N1 to N9). Influenza A includes several subtypes, including H1N1, H1N2, H2N2, H3N1, H3N2, H3N8, H5N1, H5N2, H5N3, H5N8, H5N9, H7N1, H7N2, H7N3, H7N4, H7N7, H7N9, H9N2 and H10N7. The influenza virus polymerase is a heterotrimer composed of three subunits, polymerase acid (PA), polymerase basic 1 (PB1) and polymerase basic 2 (PB2). This polymerase is responsible for replication and transcription of the viral RNA in the nuclei of infected cells. The PA subunit contains the endonuclease active site. The endonuclease activity of the PA cleaves the cellular mRNA, which is then used by the PB1 subunit as a primer for the viral mRNA synthesis.

Influenza viruses can be transmitted from person to person via direct contact with infected secretions and/or contaminated surfaces or objections. Complications from an influenza viral infection include pneumonia, bronchitis, dehydration, and sinus and ear infections. Medications currently approved by the FDA against an influenza infection include a limited number of neuraminidase inhibitors and M2 protein inhibitors. Examples of approved neuraminidase inhibitors and M2 protein inhibitors include amantadine, rimantadine, Relenza® (zanamivir, GlaxoSmithKline) and Tamiflu® (oseltamivir, Genentech).

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^{3a}$, $R^{3b}$, $R^4$ and $R^5$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

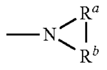

In addition, if two "R" groups are described as being "taken together" with the atom(s) to which they are attached to form a ring as an alternative, the R groups may not be limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), heterocyclyl(alkyl), deuterium, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, hydroxyalkyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl (straight and branched) and hexyl (straight and branched). The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) mono-cyclic or multi-cyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a mono-cyclic or multi-cyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered mono-cyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl or a heteroalicyclyl may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and/or aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaralkyl" and "heteroaryl(alkyl)" refer to a heteroaryl group connected, as a substituent, via a lower alkylene group. The lower alkylene and/or heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and/or heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl), and 1,3-thiazinan-4-yl(methyl).

"Lower alkylene groups" are straight-chained $—CH_2—$ tethering groups, forming bonds to connect molecular fragments via their terminal carbon atoms. Examples include but are not limited to methylene ($—CH_2—$), ethylene ($—CH_2CH_2—$), propylene ($—CH_2CH_2CH_2—$), and butylene ($—CH_2CH_2CH_2CH_2—$). A lower alkylene group can be substituted by replacing one or more hydrogen of the lower alkylene group with a substituent(s) listed under the definition of "substituted."

As used herein, "alkoxy" refers to the formula —OR wherein R is alkyl, alkenyl, alkynyl, cycloalkyl, cycloalkenyl, aryl, heteroaryl, heterocyclyl, cycloalkyl(alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl and acryl. An acyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group of the formula —O— alkyl in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(═O)OR" group in which R can be the same as defined with respect to O-carboxy. An ester and C-carboxy may be substituted or unsubstituted.

A "thiocarbonyl" group refers to a "—C(═S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "carbonyl" group refers to a C═O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(═O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(═O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(═S)—N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(═S)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(═O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(═O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl and isobutyryl); arylalkylcarbonyls and arylalkoxycarbonyls (e.g., benzyloxycarbonyl); substituted methyl ether (e.g. methoxymethyl ether and tetrahydropyranyl ether); substituted ethyl ether; a substituted benzyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl and t-butyldiphenylsilyl); esters (e.g. benzoate ester); carbonates (e.g. methoxymethylcarbonate); sulfonates (e.g. tosylate and mesylate); acyclic ketal (e.g. dimethyl acetal and diisopropyl acetal); cyclic ketals (e.g., 1,3-dioxane and 1,3-dioxolane); acyclic acetal; cyclic acetal; acyclic hemiacetal; cyclic hemiacetal; dithioacetals (both cyclic and acyclic); dithioketals (both cyclic and acyclic) (e.g., S,S'-dimethyl, S,S'-diethyl, S,S'-diispropyl, 1,3-dithiane and 1,3-dithiolane); orthoesters (including cyclic orthoesters, such as cyclic orthoformates); carbamates (e.g., N-phenylcarbamate) and triarylmethyl groups (e.g., trityl, monomethoxytrityl (MMTr), 4,4'-dimethoxytrityl (DMTr), and 4,4',4''-trimethoxytrityl (TMTr); and those described herein).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates, mesylates, trifluoroacetates and halogens (e.g., I, Br, and Cl). Non-limiting characteristics and examples of leaving groups can be found, for example in *Organic Chem-*

*istry,* 2d ed., Francis Carey (1992), pages 328-331*; Introduction to Organic Chemistry,* 2d ed., Andrew Streitwieser and Clayton Heathcock (1981), pages 169-171; and *Organic Chemistry,* $5^{th}$ ed., John McMurry (2000), pages 398 and 408; all of which are incorporated herein by reference for the limited purpose of disclosing characteristics and examples of leaving groups.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof,

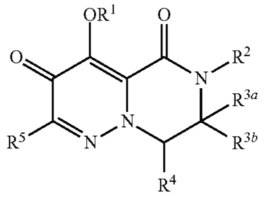

(I)

$R^1$ can be selected from hydrogen, an unsubstituted $C_{1-4}$ alkyl, an optionally substituted heterocyclyl, —C(═O)$Y^1$, —C(═O)—O—$Y^1$, —($CH_2$)—O—(C═O)—$Y^1$, —($CH_2$)—O—(C═O)—O—$Y^1$, —($CHCH_3$)—O—(C═O)—$Y^1$ and —($CHCH_3$)—O—(C═O)—O—$Y^1$; $R^2$ can be selected from hydrogen, an optionally substituted $C_{1-6}$ alkyl, an optionally substituted $C_{2-6}$ alkenyl, an optionally substituted heterocyclyl, an optionally substituted cycloalkyl($C_{1-6}$ alkyl), an optionally substituted aryl($C_{1-6}$ alkyl), an optionally substituted heteroaryl($C_{1-6}$ alkyl) and an optionally substituted heterocyclyl($C_{1-6}$ alkyl); $R^{3a}$ and $R^{3b}$ can be independently hydrogen or an optionally substituted $C_{1-4}$ alkyl; $R^4$ can be selected from:

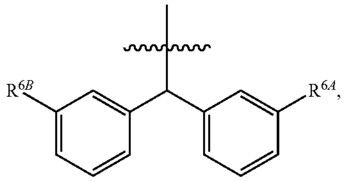

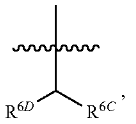

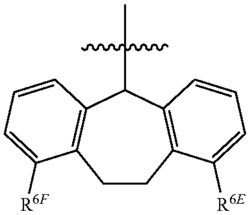

and

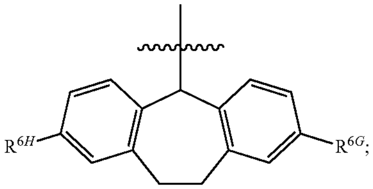

$R^{6A}$ and $R^{6B}$ can be each hydrogen, or each fluoro or each chloro; or $R^{6A}$ and $R^{6B}$ can be hydrogen, an unsubstituted $C_{1-4}$ alkyl or an unsubstituted $C_{2-4}$ alkynyl, provided that at least one of $R^{6A}$ and $R^{6B}$ is an unsubstituted $C_{1-4}$ alkyl or an unsubstituted $C_{2-4}$ alkynyl; $R^6$ can be an optionally substituted aryl or an optionally substituted heteroaryl; $R^{6D}$ can be an optionally substituted heteroaryl; $R^{6E}$ and $R^{6F}$ can be each hydrogen or each fluoro; $R^{6G}$ and $R^{6H}$ can be each fluoro or each chloro; $R^5$ can be selected from hydrogen, halogen, —CN, an optionally substituted $C_{1-6}$ alkyl, an optionally substituted aryl, an optionally substituted heteroaryl, —$CH_2$OH, —CH($Y^2$)(OH) and —C(O)$Y^2$; $Y^1$ and $Y^2$ can be independently selected from an optionally substituted $C_{1-6}$ alkyl, an optionally substituted $C_{3-6}$ cycloalkyl, an optionally substituted aryl, an optionally substituted heteroaryl, an optionally substituted heterocyclyl, a mono-substituted amino group, a di-substituted amino and —C($R^7$)$_2$NH$R^8$; and each $R^7$ and $R^8$ can be independently hydrogen or an optionally substituted $C_{1-4}$ alkyl;

Some embodiments disclosed herein relate to a compound of Formula (I), or a pharmaceutically acceptable salt thereof, wherein: $R^1$ can be selected from hydrogen, an unsubstituted $C_{1-4}$ alkyl, an optionally substituted heterocyclyl, —C(═O)$Y^1$, —C(═O)—O—$Y^1$, —($CH_2$)—O—(C═O)—$Y^1$, —($CH_2$)—O—(C═O)—O—$Y^1$, —($CHCH_3$)—O—(C═O)—$Y^1$ and —($CHCH_3$)—O—(C═O)—O—$Y^1$; $R^2$ can be selected from hydrogen, an optionally substituted $C_{1-6}$ alkyl, an optionally substituted heterocyclyl, an optionally substituted cycloalkyl($C_{1-6}$ alkyl), an optionally substituted aryl($C_{1-6}$ alkyl), an optionally substituted heteroaryl ($C_{1-6}$ alkyl) and an optionally substituted heterocyclyl($C_{1-6}$ alkyl); $R^{3a}$ and $R^{3b}$ can be independently hydrogen or an optionally substituted $C_{1-4}$ alkyl; $R^4$ can be selected from:

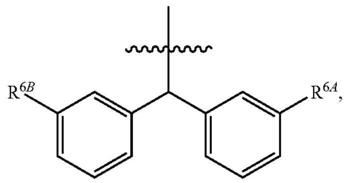

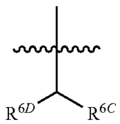

and

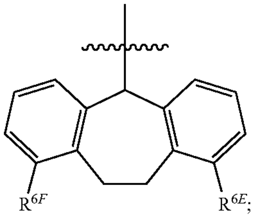

$R^{6A}$ and $R^{6B}$ are each hydrogen, or each fluoro or each chloro; or $R^{6A}$ and $R^{6B}$ can be hydrogen, an unsubstituted $C_{1-4}$ alkyl or an unsubstituted $C_{2-4}$ alkynyl, provided that at least one of $R^{6A}$ and $R^{6B}$ is an unsubstituted $C_{1-4}$ alkyl or an unsubstituted $C_{2-4}$ alkynyl; $R^6$ can be an optionally substituted aryl or an optionally substituted heteroaryl; $R^{6D}$ can be an optionally substituted heteroaryl; $R^{6E}$ and $R^{6F}$ can be each hydrogen or each fluoro; $R^5$ can be selected from hydrogen, halogen, —CN, an optionally substituted $C_{1-6}$ alkyl, an optionally substituted aryl, an optionally substituted heteroaryl, —$CH_2$OH, —CH($Y^2$)(OH) and —C(O)$Y^2$; $Y^1$ and $Y^2$ can be independently selected from an optionally substituted $C_{1-6}$ alkyl, an optionally substituted $C_{3-6}$ cycloalkyl, an optionally substituted aryl, an optionally substituted heteroaryl, an optionally substituted heterocyclyl, a mono-substituted amino group, a di-substituted amino and —C($R^7$)$_2$NH$R^8$; and each $R^7$ and $R^8$ can be independently hydrogen or an optionally substituted $C_{1-4}$ alkyl.

In some embodiments, $R^2$ can be hydrogen. In other embodiments, $R^2$ can be an optionally substituted $C_{1-6}$ alkyl. In some embodiments, $R^2$ can be an unsubstituted $C_{1-6}$ alkyl. The $C_{1-6}$ alkyl can be methyl, ethyl, n-propyl, isopropyl, n-butyl, iso-butyl, tert-butyl, pentyl (straight or branched) or hexyl (straight or branched). In some embodiments, $R^2$ can be an unsubstituted $C_{2-4}$ alkyl. In some embodiments, $R^2$ can be a substituted $C_{1-6}$ alkyl. Various substituents can substitute the $C_{1-6}$ alkyl of $R^2$. In some embodiments, the substituted $C_{1-6}$ alkyl of $R^2$ can be substituted one or more times with a substituents selected from halogen, deuterium, haloalkyl (such as $CF_3$), hydroxy and alkoxy. In some embodiments, $R^2$ can be substituted one or more times with fluoro. When substituted, in some embodiments, the one or more substituents on $R^2$ may not be present on the carbon closest to the nitrogen of the fused ring system. When $R_2$ is substituted at the carbon attached to the carbon closest to the nitrogen of the fused ring system of Formula (I), the carbon may be a chiral center. In some embodiments, the chiral center can be a (S)-chiral center. In other embodiments, the chiral center can be a (R)-chiral center.

In some embodiments, $R^2$ can be an optionally substituted $C_{2-6}$ alkenyl. In some embodiment, $R^2$ can be an unsubstituted $C_{2-6}$ alkenyl. In other embodiments, $R^2$ can be a substituted $C_{2-6}$ alkenyl. For example, $R^2$ can be substituted one or more times with halogen, such as fluoro.

In some embodiments, $R^2$ can be an optionally substituted cycloalkyl($C_{1-6}$ alkyl). In other embodiments, $R^2$ can be an optionally substituted heterocyclyl. In other embodiments, $R^2$ can be an optionally substituted aryl($C_{1-6}$ alkyl), such as an optionally substituted benzyl. The phenyl ring of the benzyl ring can be substituted 1, 2 or 3 or more times. When the phenyl ring of the benzyl group is mono-substituted, the phenyl ring can be substituted at the ortho-, meta- or para-position. In still other embodiments, $R^2$ can be an optionally substituted heteroaryl($C_{1-6}$ alkyl). In yet still other embodiments, $R^2$ can be an optionally substituted heterocyclyl($C_{1-6}$ alkyl). Examples of $R^2$ groups include, but are not limited to, hydrogen, methyl, ethyl, n-propyl, iso-propyl, n-butyl, isobutyl,

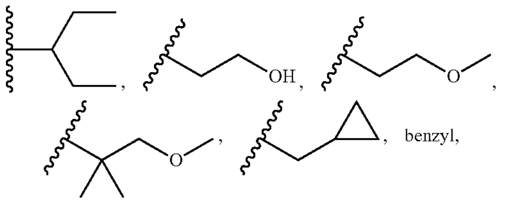

benzyl,

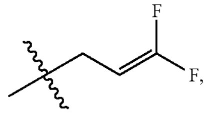

$-CH_2CF_3$, $-CH_2CH_2CF_3$, $-CH_2CHF_2$, $-CH_2CH_2CHF_2$, $-CH_2C(CH_3)F_2$ and $-CH_2CH_2C(CH_3)F_2$.

Various groups can be present at the $R^1$ position. In some embodiments, $R^1$ can be hydrogen. In other embodiments, $R^1$ can be an unsubstituted $C_{1-4}$ alkyl. For example, $R^1$ can be methyl, ethyl, n-propyl, iso-propyl, n-butyl, iso-butyl and t-butyl. In still other embodiments, $R^1$ can be an optionally substituted heterocyclyl. In some embodiments, $R^1$ can be an optionally substituted mono-cyclic heterocyclyl. For example, $R^1$ can be carbohydrate derivative such as an optionally substituted pyranose. In some embodiments, $R^1$ can be glucuronic acid. In yet still other embodiments, $R^1$ can be a group that in vivo is capable of providing a compound of Formula (I), wherein $R^1$ is hydrogen or absent. Those skilled in the art understand that when $R^1$ is absent, the oxygen adjacent to $R^1$ can possess an associated negative charge. Examples of $R^1$ moieties that are capable of providing a compound of Formula (I), wherein $R^1$ is hydrogen or absent, include $-C(=O)Y^1$, $-(CH_2)-O-(C=O)-Y^1$ and $-(CHCH_3)-O-(C=O)-Y^1$. Additional examples of $R^1$ moieties that are capable of providing a compound of Formula (I), wherein $R^1$ is hydrogen or absent, include $-C(=O)-O-Y^1$, $-(CH_2)-O-(C=O)-O-Y^1$ and $-(CHCH_3)-O-(C=O)-O-Y^1$. In some embodiments, $R^1$ can be a group that is enzymatically cleaved to provide a compound of Formula (I), wherein $R^1$ is hydrogen or absent.

As described herein, $Y^1$ can be a variety of substituents. In some embodiments, $Y^1$ can be a substituted $C_{1-6}$ alkyl. In other embodiments, $Y^1$ can be an unsubstituted $C_{1-6}$ alkyl. In still other embodiments, $Y^1$ can be a substituted $C_{3-6}$ cycloalkyl. In yet still other embodiments, $Y^1$ can be an unsubstituted $C_{3-6}$ cycloalkyl. In some embodiments, $Y^1$ can be a substituted aryl (for example, a substituted phenyl). In other embodiments, $Y^1$ can be an unsubstituted aryl (for example, an unsubstituted phenyl). In still other embodiments, $Y^1$ can be a substituted heteroaryl (such as a substituted mono-cyclic heteroaryl). In yet still other embodiments, $Y^1$ can be an unsubstituted heteroaryl (such as an unsubstituted heteroaryl). In some embodiments, $Y^1$ can be a substituted heterocyclyl (such as a substituted mono-cyclic heterocyclyl). In other embodiments, $Y^1$ can be an unsubstituted heterocyclyl (such as an unsubstituted mono-cyclic heterocyclyl). In still other embodiments, $Y^1$ can be a mono-substituted amino group. For example, the mono-substituted amino group can be

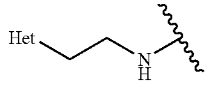

or

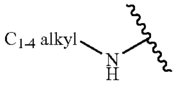

wherein Het can be an optionally substituted heteroaryl or an optionally substituted heterocyclyl. In yet still other embodiments, $Y^1$ can be a di-substituted amino group. In some embodiments, $Y^1$ can be $-C(R^7)_2NHR^8$, wherein each $R^7$ and $R^8$ can be independently hydrogen or an optionally substituted $C_{1-4}$ alkyl. In some embodiments, each $R^7$ can be hydrogen. In other embodiments, one $R^7$ can be hydrogen and the other $R^7$ can be an unsubstituted $C_{1-4}$ alkyl or a substituted $C_{1-4}$ alkyl. In some embodiments, each $R^7$ can be independently an unsubstituted $C_{1-4}$ alkyl or a substituted $C_{1-4}$ alkyl. In some embodiments, $R^8$ can be hydrogen. In other embodiments, $R^8$ can be an unsubstituted $C_{1-4}$ alkyl or a substituted $C_{1-4}$ alkyl. For example, $Y^1$ can be:

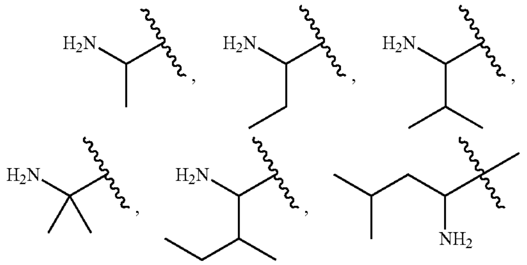

and

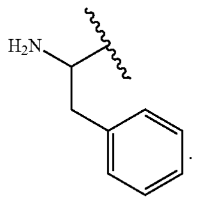

In some embodiments, $R^4$ can be

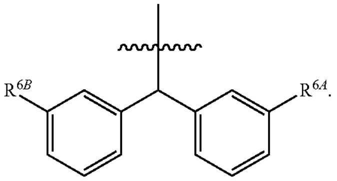

In some embodiments, when $R^4$ is

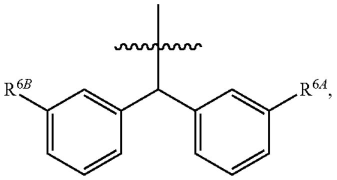

$R^{6A}$ and $R^{6B}$ can be each hydrogen such that $R^4$ can have the structure

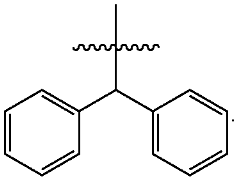 [SMILES: *C(c1ccccc1)c1ccccc1]

In other embodiments, when $R^4$ is

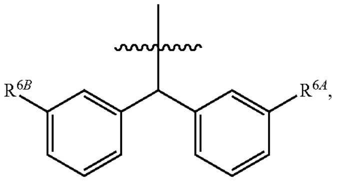

$R^{6A}$ and $R^{6B}$ can be each fluoro such that $R^4$ can be

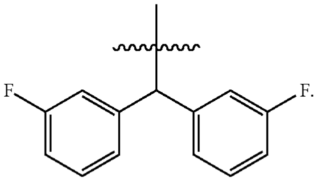 [SMILES: *C(c1cccc(F)c1)c1cccc(F)c1]

In still other embodiments, when $R^4$ is

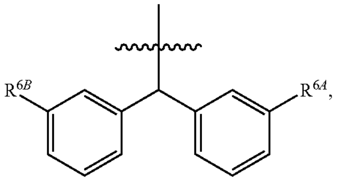

$R^{6A}$ and $R^{6B}$ can be each chloro such that $R^4$ can have the structure

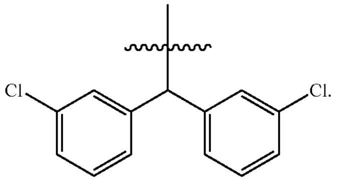 [SMILES: *C(c1cccc(Cl)c1)c1cccc(Cl)c1]

In yet still other embodiments, when $R^4$ is

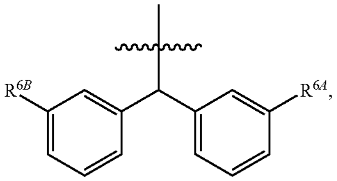

$R^{6A}$ and $R^{6B}$ can be hydrogen or an unsubstituted $C_{1-4}$ alkyl, provided that at least one of $R^{6A}$ and $R^{6B}$ is an unsubstituted $C_{1-4}$ alkyl. When at least one of $R^{6A}$ and $R^{6B}$ is an unsubstituted $C_{1-4}$ alkyl,

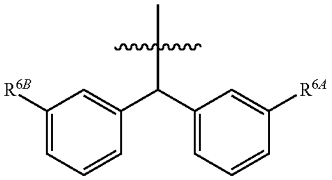

can be selected from

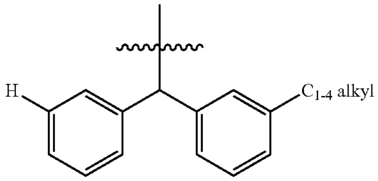

and

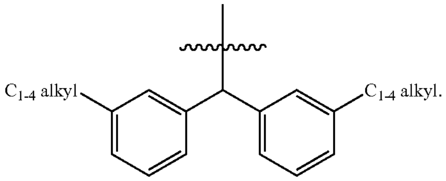

In some embodiments, at least one of $R^{6A}$ and $R^{6B}$ can be methyl. In some embodiments, $R^{6A}$ and $R^{6B}$ can be each methyl. In some embodiments, when $R^4$ is

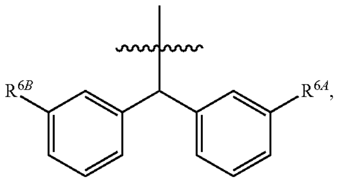

$R^{6A}$ and $R^{6B}$ can be hydrogen or an unsubstituted $C_{2-4}$ alkynyl, provided that at least one of $R^{6A}$ and $R^{6B}$ is an unsubstituted $C_{2-4}$ alkynyl. For example, $R^4$ can be

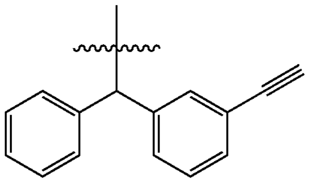

or

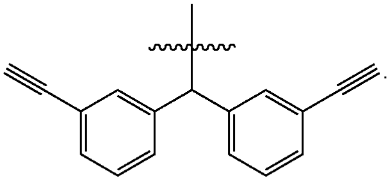

The substituents for $Y^2$ can also vary. In some embodiments, $Y^2$ can be an unsubstituted $C_{1-4}$ alkyl or a substituted $C_{1-4}$ alkyl. In other embodiments, $Y^2$ can be an optionally substituted $C_{3-6}$ cycloalkyl. In still other embodiments, $Y^2$ can be an optionally substituted aryl. In yet still other embodiments, $Y^2$ can be an optionally substituted heteroaryl. In some embodiments, $Y^2$ can be an optionally substituted heterocyclyl. In other embodiments, $Y^2$ can be a mono-substituted amino group. In still other embodiments, $Y^2$ can be a di-substituted amino. In yet still other embodiments, $Y^2$ can be $—C(R^7)_2NHR^8$; and each $R^7$ and $R^8$ can be independently hydrogen or an optionally substituted $C_{1-4}$ alkyl. A non-limiting list of examples of $Y^2$, such as $—C(R^7)_2$ $NHR^8$, are described herein with respect to $Y^1$. In some embodiments, $Y^2$ can be independently an optionally substituted $C_{1-6}$ alkyl or an optionally substituted aryl (such as an optionally substituted phenyl).

In some embodiments, $R^4$ can be

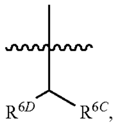

wherein one of $R^{6C}$ and $R^{6D}$ can be an optionally substituted aryl or an optionally substituted heteroaryl, and the other of $R^{6C}$ and $R^{6D}$ can be an optionally substituted heteroaryl. In some embodiments, the optionally substituted heteroaryl can be an optionally substituted mono-cyclic heteroaryl. In other embodiments, the optionally substituted heteroaryl can be an optionally substituted bicyclic heteroaryl. Examples of suitable optionally substituted heteroaryls include, but are not limited to, an optionally substituted pyrazole, an optionally substituted indole, an optionally substituted indazole, an optionally substituted pyrrolo[2,3-c]pyridine and an optionally substituted thiophene. In some embodiments, when $R^{6C}$ and/or $R^{6D}$ is an optionally substituted heteroaryl, the heteroaryl can be substituted with 1 substituent. In some embodiments, when $R^{6C}$ and/or $R^{6D}$ is an optionally substituted heteroaryl, the heteroaryl can be substituted with 2 substituents. In some embodiments, $R^{6C}$ and/or $R^{6D}$ can be an unsubstituted heteroaryl.

In some embodiments, $R^4$ can be

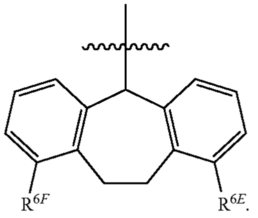

In some embodiments, when $R^4$ is

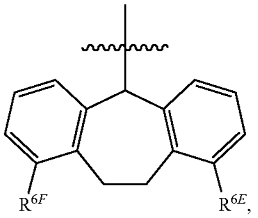

$R^{6E}$ and $R^{6F}$ can be each hydrogen such that $R^4$ can have the structure

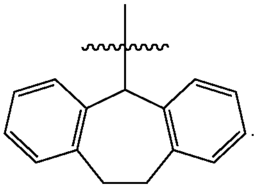 [SMILES: *C1c2ccccc2CCc2ccccc21]

In other embodiments, when $R^4$ is

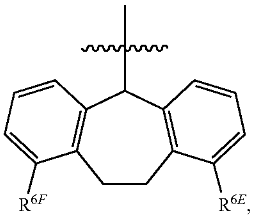

$R^{6E}$ and $R^{6F}$ can be each fluoro such that $R^4$ can be

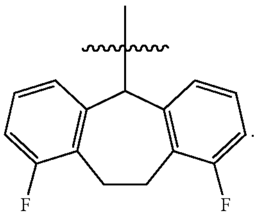 [SMILES: *C1c2cccc(F)c2CCc2c(F)cccc21]

In some embodiments, $R^4$ can be

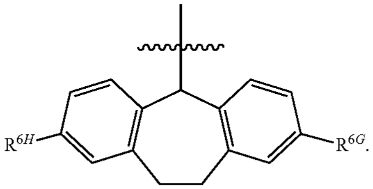

In some embodiments, when $R^4$ is

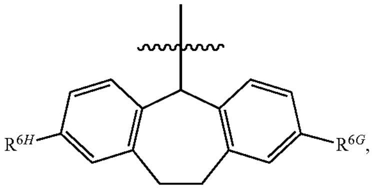

$R^{6G}$ and $R^{6H}$ can be each fluoro such that $R^4$ can have the structure

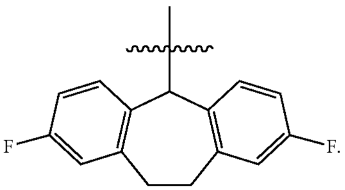

In other embodiments, when $R^4$ is

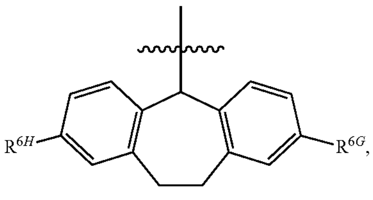

$R^{6G}$ and $R^{6H}$ can be each chloro such that $R^4$ can be

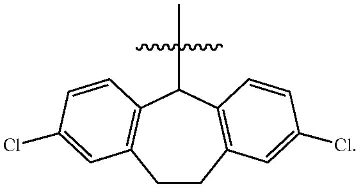 [SMILES: *C1c2ccc(Cl)cc2CCc2cc(Cl)ccc21]

Various substituents can be present on the fused rings of Formula (I). For example, in some embodiments, $R^5$ can be hydrogen. In other embodiments, $R^5$ can be halogen. In still other embodiments, $R^5$ can be —CN. In yet still other embodiments, $R^5$ can be an optionally substituted $C_{1-6}$ alkyl. For example, $R^5$ can be methyl, ethyl, propyl (straight or branched), butyl (straight or branched), pentyl (straight or branched) or hexyl (straight or branched). In some embodiments, $R^5$ can be an optionally substituted aryl (such as a mono-, di- or 3 or more substituted phenyl). In other embodiments, $R^5$ can be an optionally substituted heteroaryl. In still other embodiments, $R^5$ can be —$CH_2OH$, —$CH(Y^2)(OH)$ or —$C(O)Y^2$. In some embodiments, a portion of $R^5$ can be enzymatically cleaved to provide a compound of Formula (I), wherein OH or $O^-$ is present at $R^5$.

In some embodiments, $R^{3a}$ and $R^{3b}$ can be independently hydrogen or an optionally substituted $C_{1-4}$ alkyl. In some embodiments, $R^{3a}$ and $R^{3b}$ can be both hydrogen. In other embodiments, at least one of $R^{3a}$ and $R^{3b}$ can be an optionally substituted $C_{1-4}$ alkyl. For example, one or both of $R^{3a}$ and $R^{3b}$ can be an unsubstituted or substituted $C_{1-4}$ alkyl. In some embodiments, $R^{3a}$ and $R^{3b}$ can be both an unsubstituted $C_{1-4}$ alkyl, for example, both $R^{3a}$ and $R^{3b}$ can be methyl. In some embodiments, $R^{3a}$ and $R^{3b}$ can be the same. In other embodiments, $R^{3a}$ and $R^{3b}$ can be different.

In some embodiments, $R^2$ can be an unsubstituted $C_{2-4}$ alkyl, and $R^4$ can be

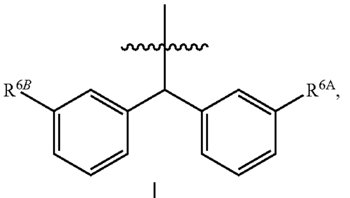

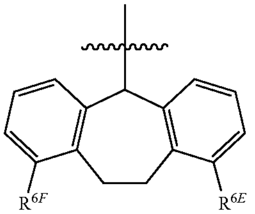

or

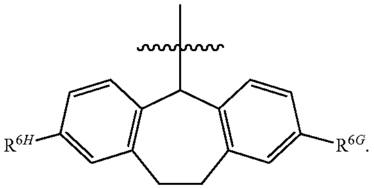

In some embodiments, $R^1$ can be hydrogen, $R^2$ can be an unsubstituted $C_{1-6}$ alkyl, and $R^4$ can be

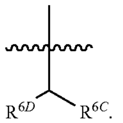

As described herein, one of $R^{6C}$ and $R^{6D}$ can be an optionally substituted aryl (such as an optionally substituted phenyl), and the other of $R^6$ and $R^{6D}$ can be an optionally substituted heteroaryl (for example, an optionally substituted pyrazole, an optionally substituted indole and an optionally substituted thiophene). In some embodiments, $R^1$ can be —C(═O)$Y^1$, wherein $Y^1$ can be an unsubstituted $C_{1-4}$ alkyl. In other embodiments, $R^1$ can be —($CH_2$)—O—(C═O)—O—$Y^1$, wherein $Y^1$ can be —$C(R^7)_2NHR^8$, such as those described herein. In still other embodiments, $R^1$ can be —($CHCH_3$)—O—(C═O)—O—$Y^1$, wherein $Y^1$ can be —$C(R^7)_2NHR^8$, including those described herein.

As described herein, at any position of a compound of Formula (I) that has a hydrogen, the hydrogen can be an isotope of hydrogen, such as hydrogen-2 (deuterium). In some embodiments, $R^1$ and/or $R^2$ can include one or more deuterium atoms. For example, $R^1$ can be deuterium or $R^1$ can be

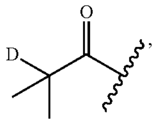 [SMILES: *C(=O)C([2H])(C)C]

and/or $R^2$ can be —$CH(CH_3)(CD_3)$ or $R^2$ can be —$CH(CH_3)(CD_3)$. In some embodiments, $R^4$ can include one or more deuteriums.

In some embodiments, a compound of Formula (I) has the structure

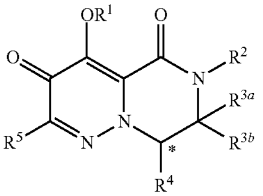

wherein the bond indicated with an * can be a (S)-chiral center or a (R)-chiral center as shown herein:

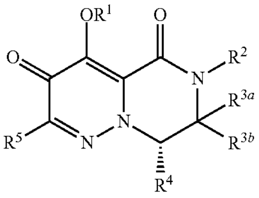

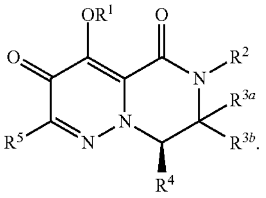

Examples of compounds of Formula (I) include the following:

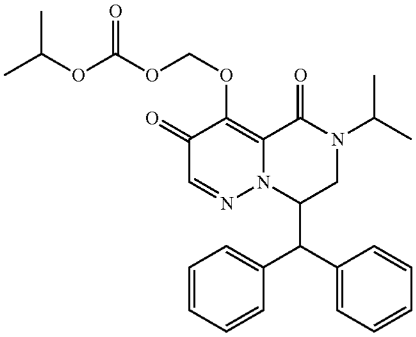
,

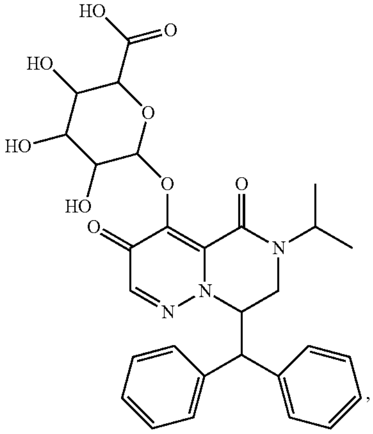
,

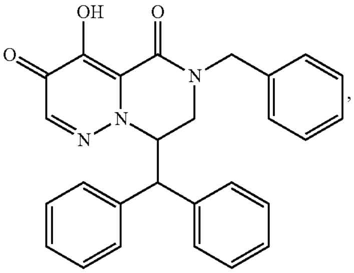
,

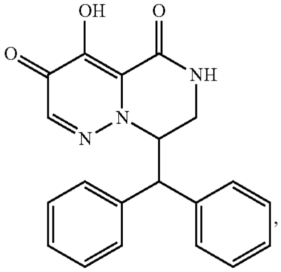
,

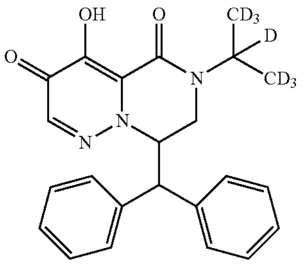
and

-continued
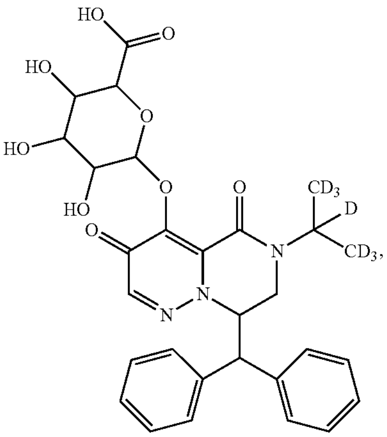 [SMILES: [2H]C([2H])([2H])C([2H])(N1CC(C(c2ccccc2)c2ccccc2)n2ncc(=O)c(OC3OC(C(=O)O)C(O)C(O)C3O)c2C1=O)C([2H])([2H])[2H]]
or a pharmaceutically acceptable salt of the foregoing.
Further examples of compounds of Formula (I) include the following:
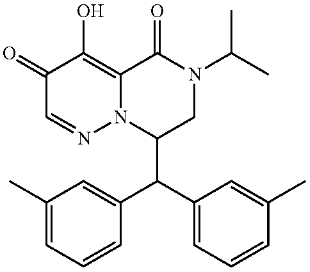
,
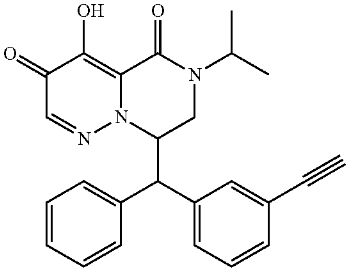
,
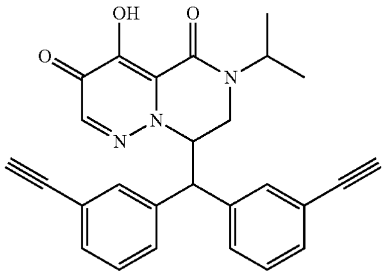
,
-continued
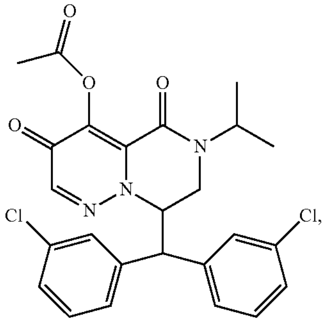
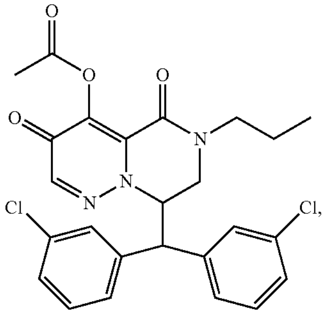
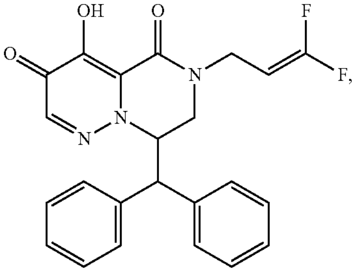
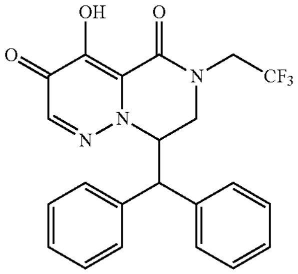
and
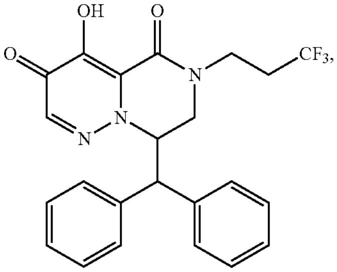
or a pharmaceutically acceptable salt of the foregoing.
Additional examples of compounds of Formula (I) include the following:

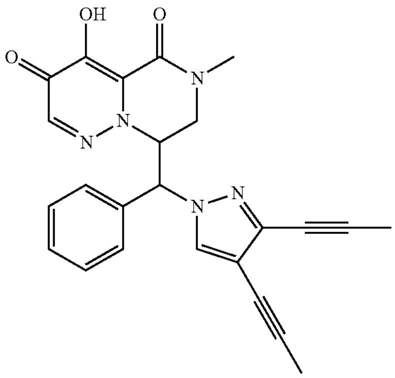
,
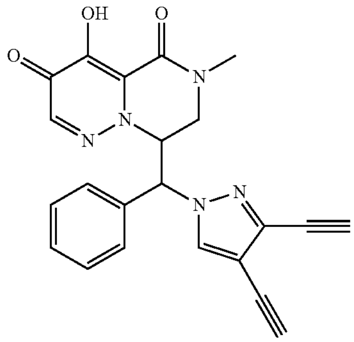
,
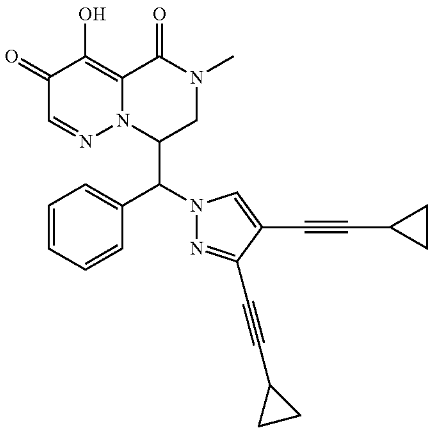
,
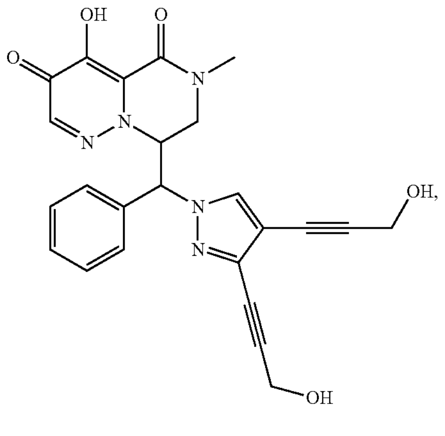
-continued
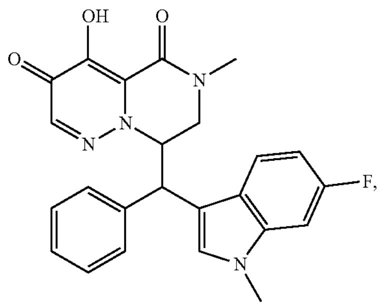
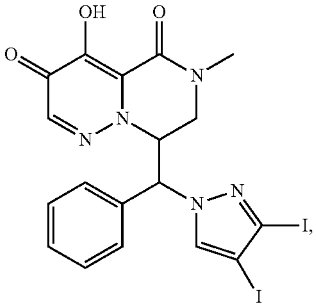
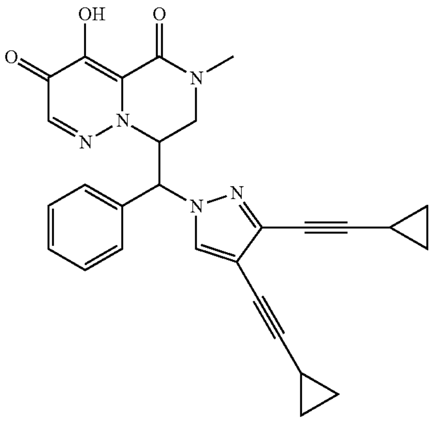
,
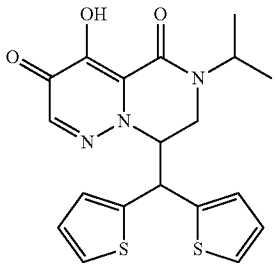
,
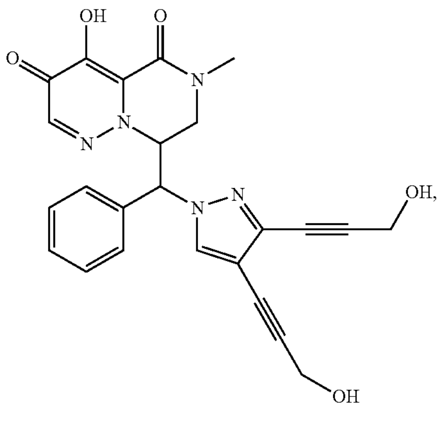

-continued
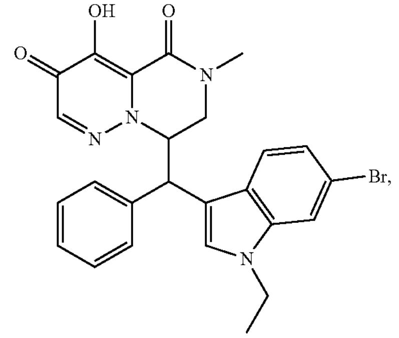
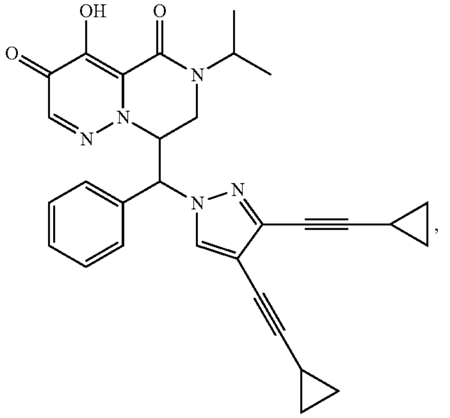
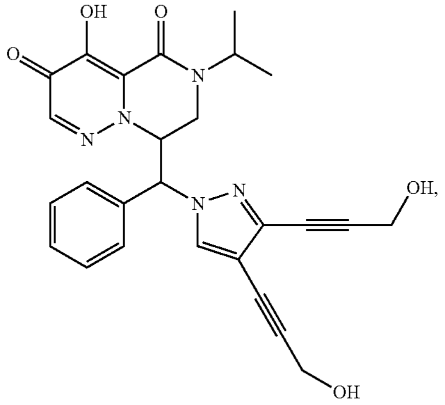
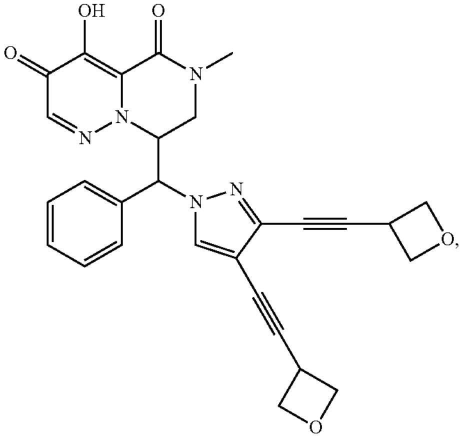
-continued
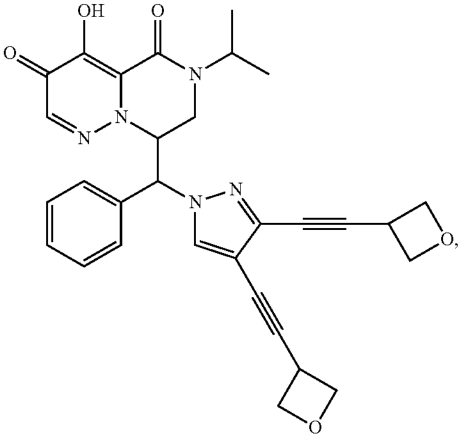
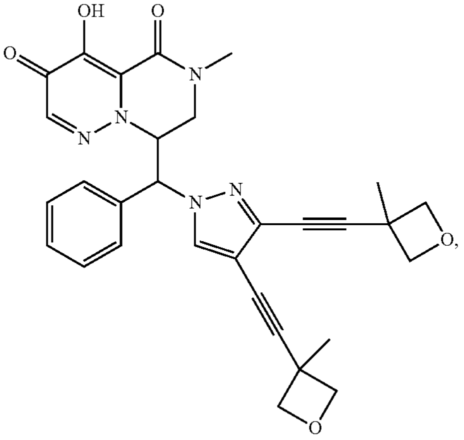
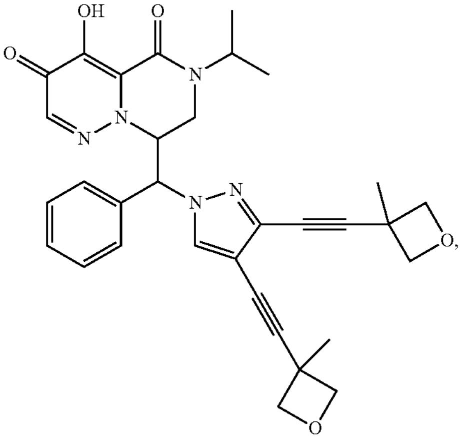

-continued
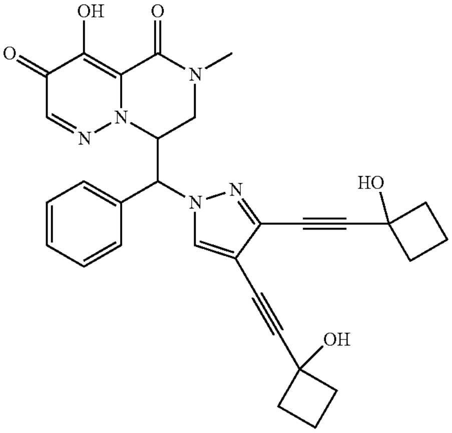
,
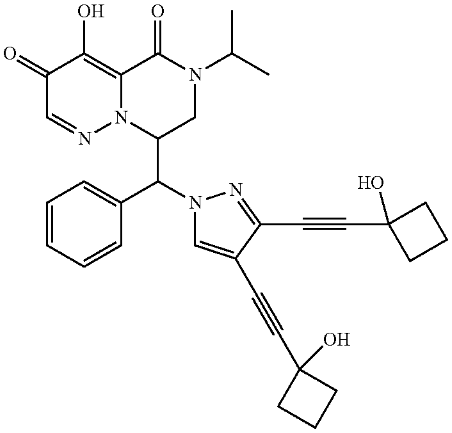
,
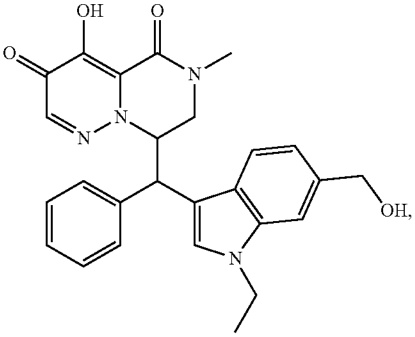
,
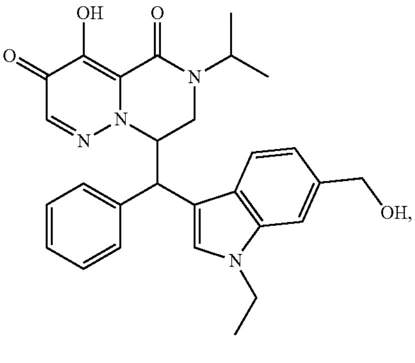
,
-continued
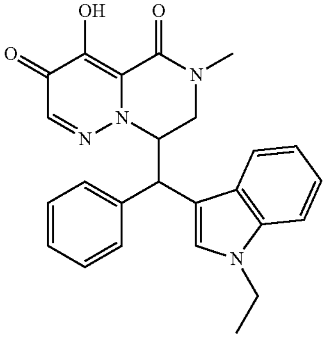
,
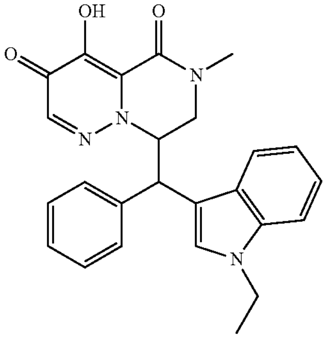
,
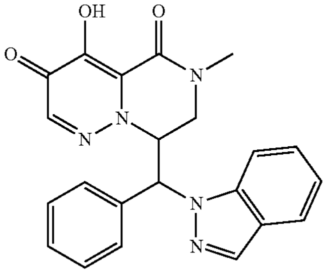
,
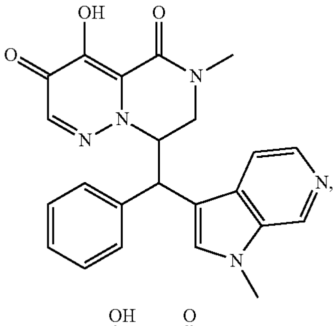
,
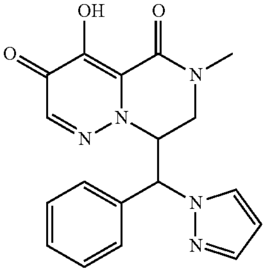
, -continued
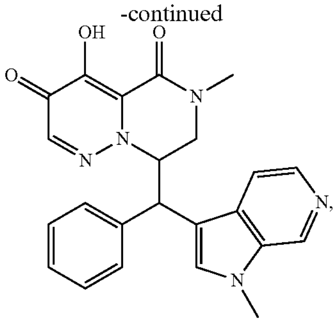
,
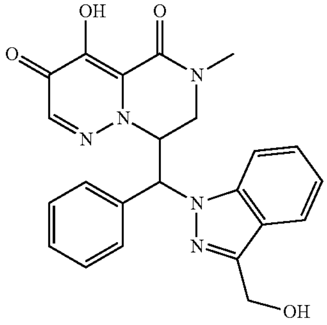
,
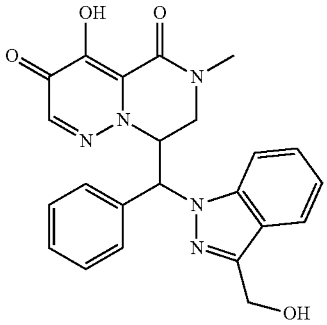
,
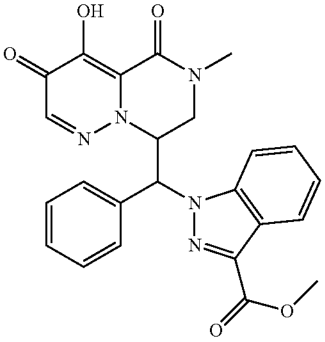
and
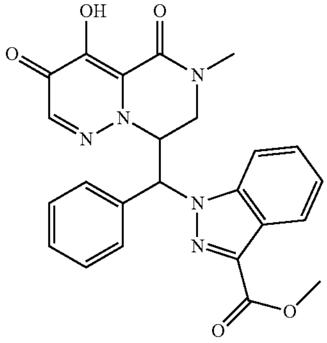
,
or a pharmaceutically acceptable salt of the foregoing.
Examples of compounds of Formula (I) include the following:
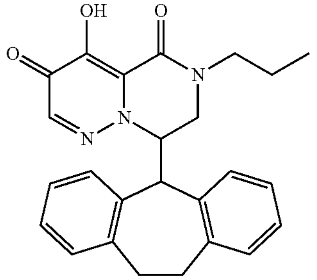
,
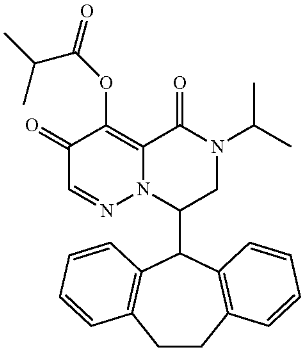
,
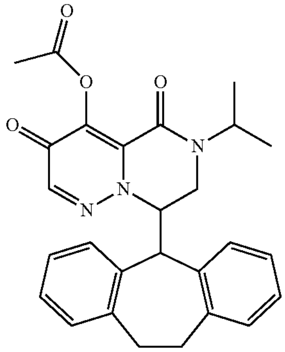
,
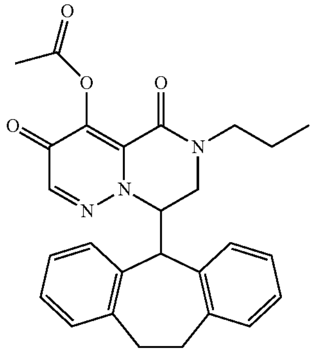
,
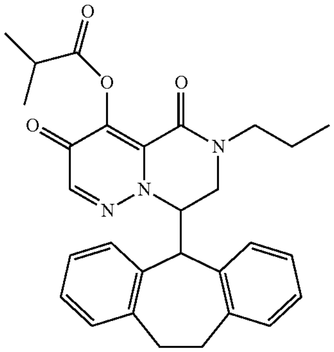
, -continued
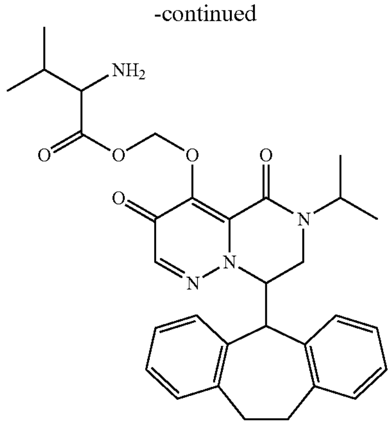,
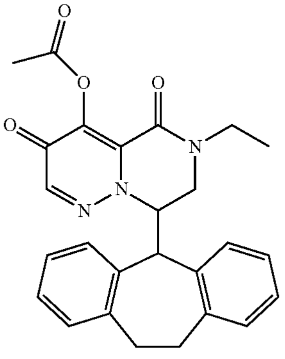,
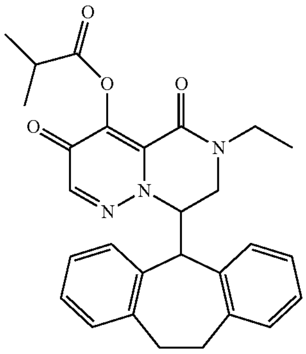,
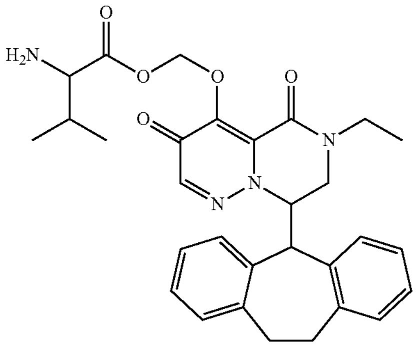,
-continued
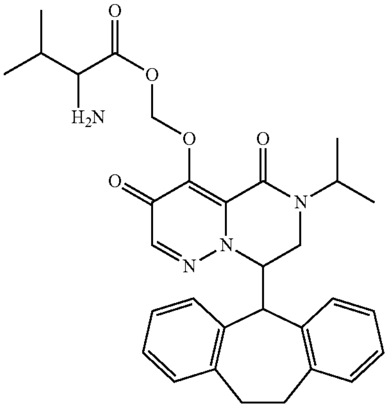,
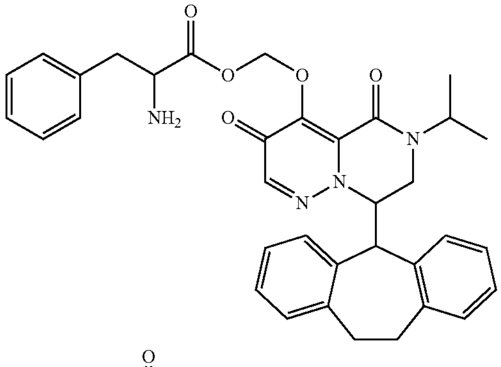,
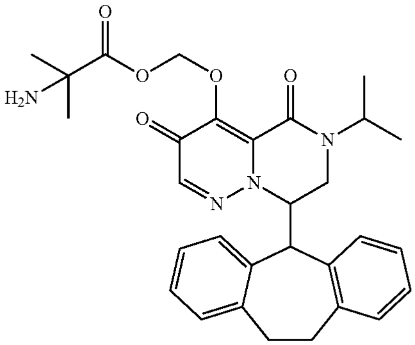,
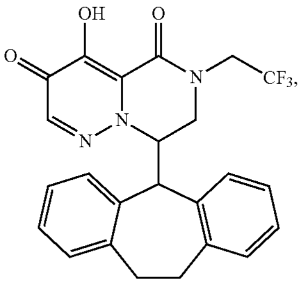
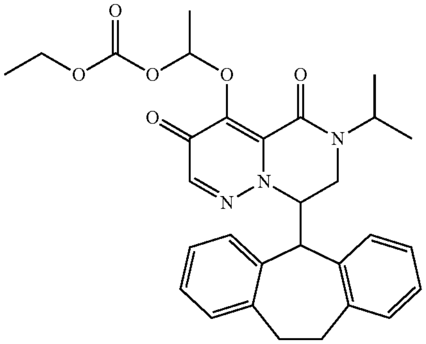, -continued
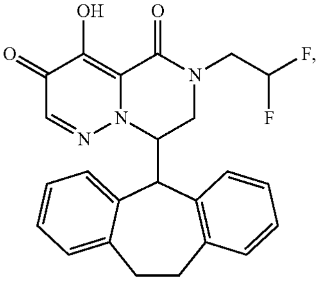
,
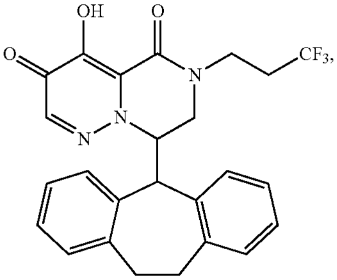
,
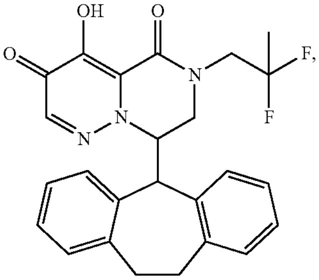
,
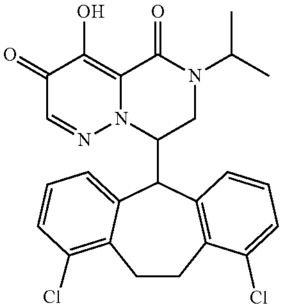
,
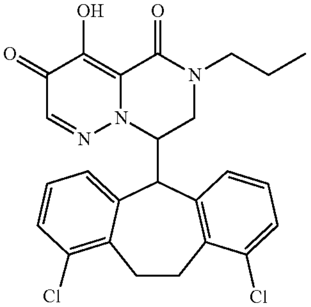
,
-continued
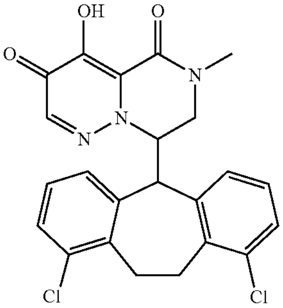
and
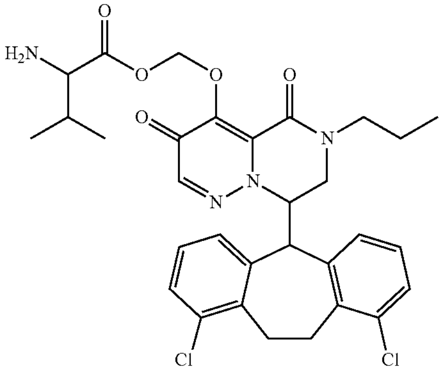
,
or a pharmaceutically acceptable salt of the foregoing.
Further examples of compounds of Formula (I) include the following:
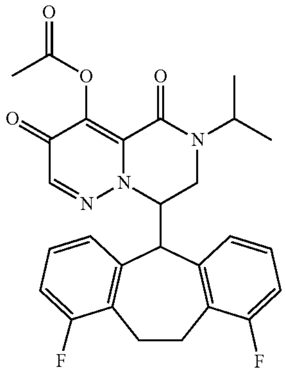
,
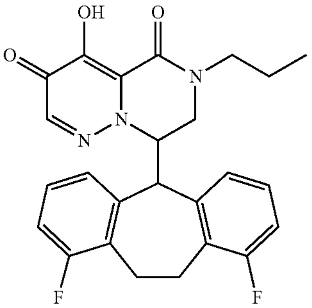
, -continued
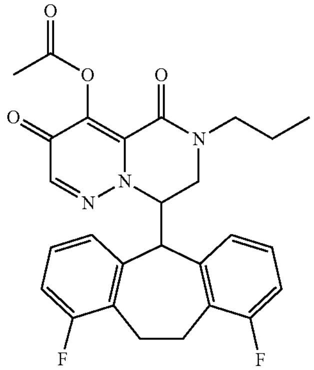
,
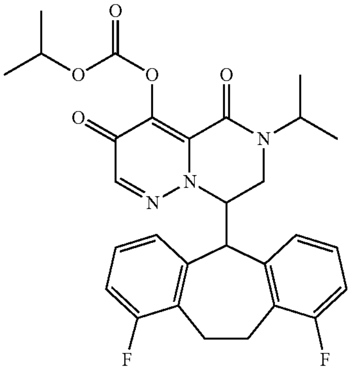
,
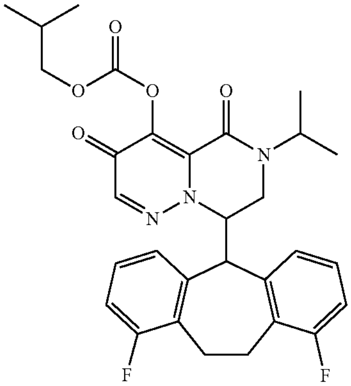
,
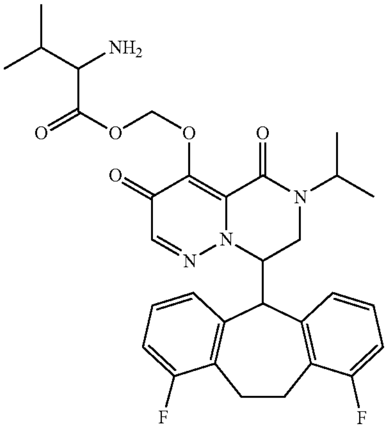
,
-continued
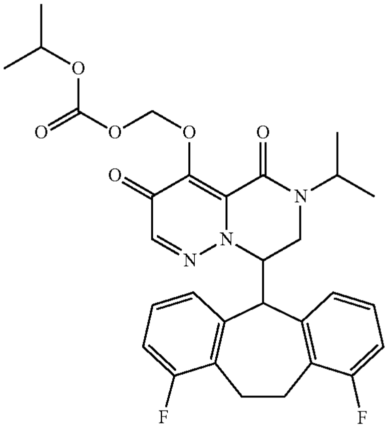
,
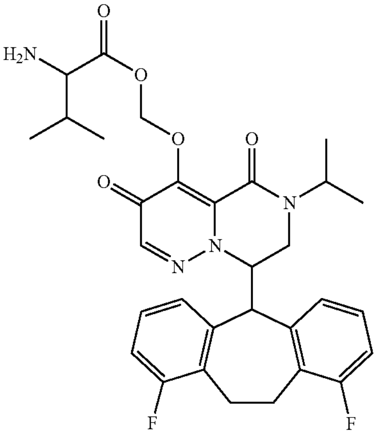
,
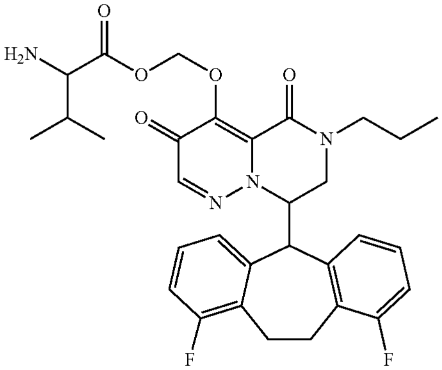
,
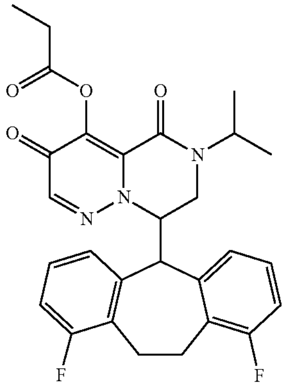
, -continued
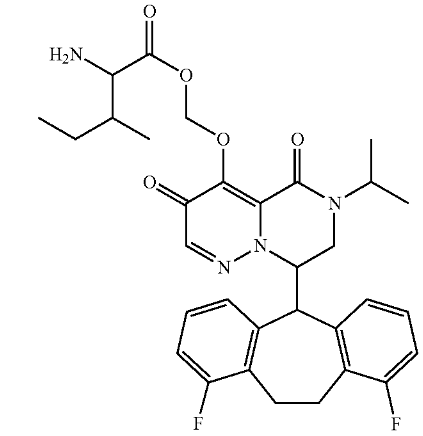
,
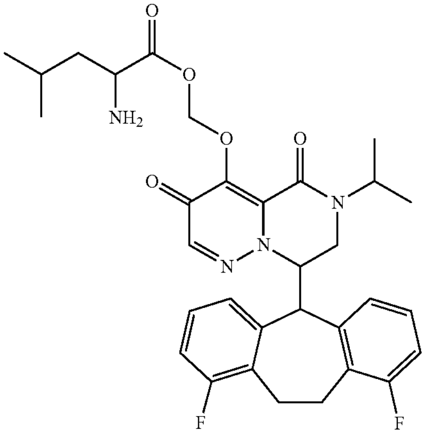
,
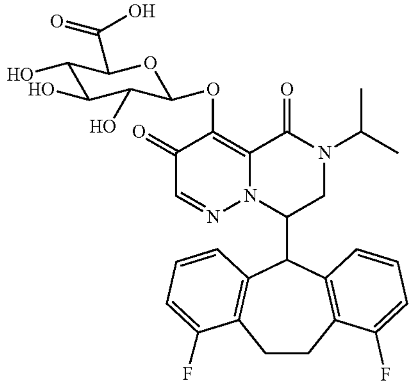
,
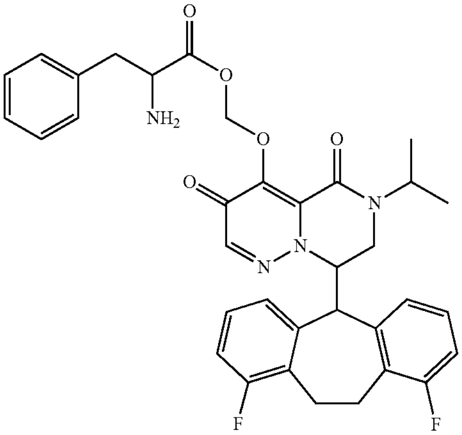
,
-continued
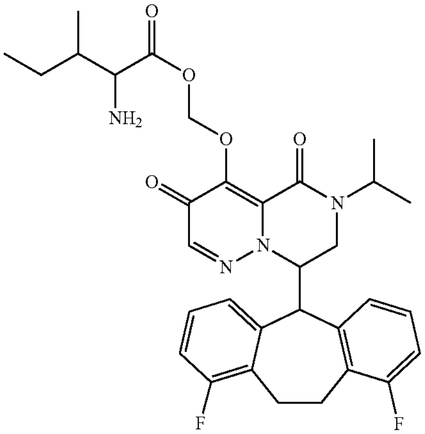
,
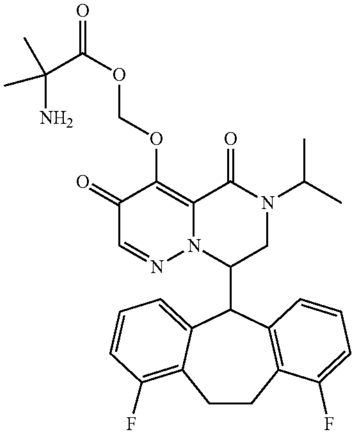
,
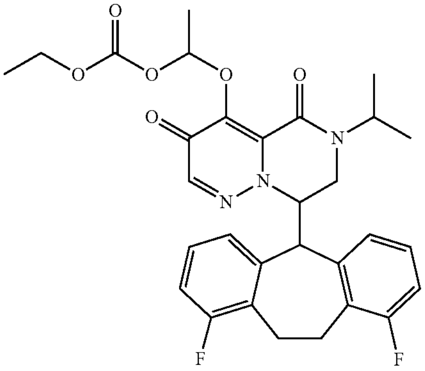
,
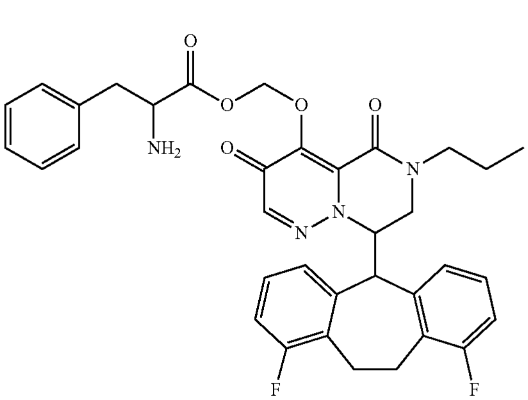
, -continued
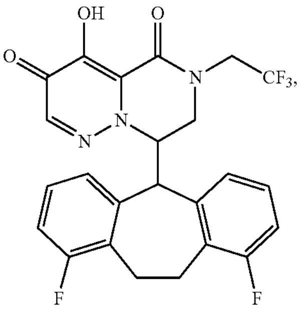
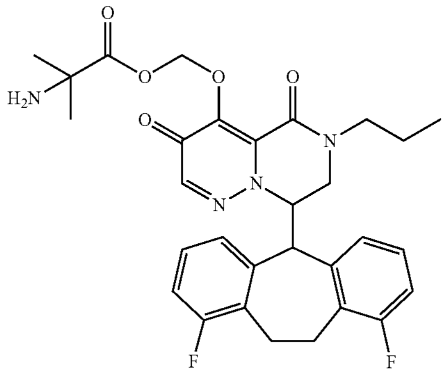
,
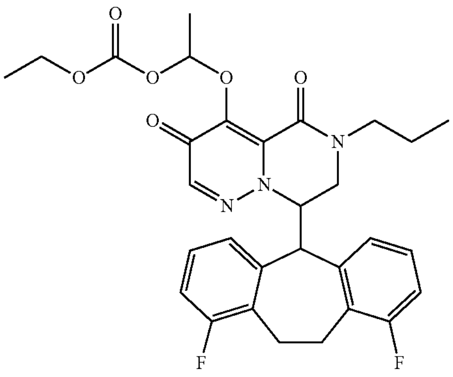
and
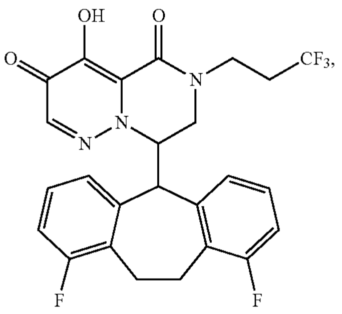
or a pharmaceutically acceptable salt of the foregoing.
Additional examples of compounds of Formula (I) include the following:
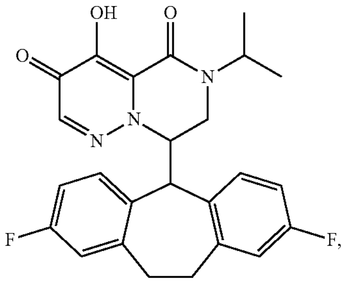
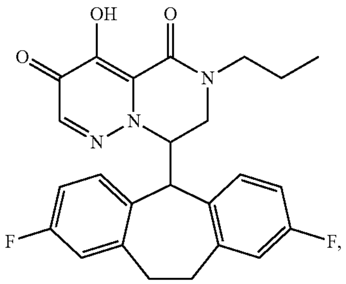
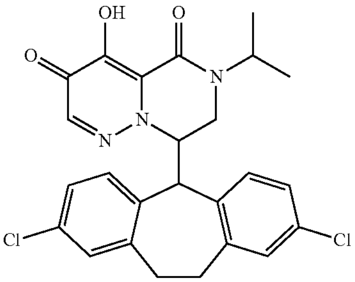
and
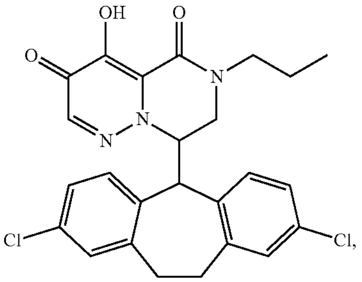
or a pharmaceutically acceptable salt of the foregoing.
Further examples of compounds of Formula (I) include the following:
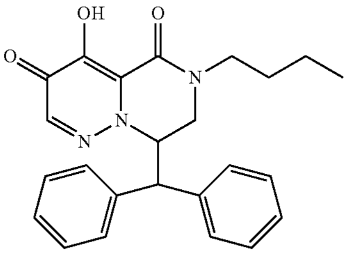
, -continued
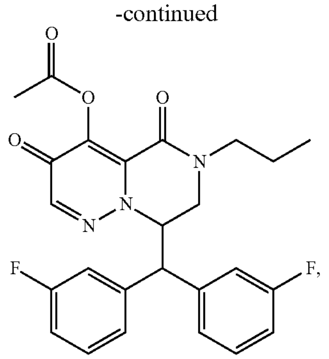
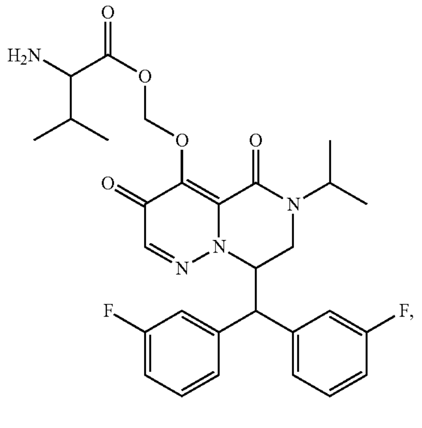
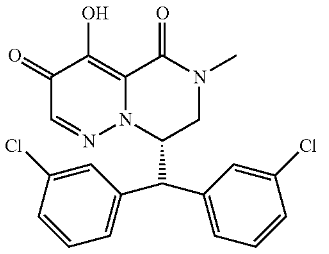
and
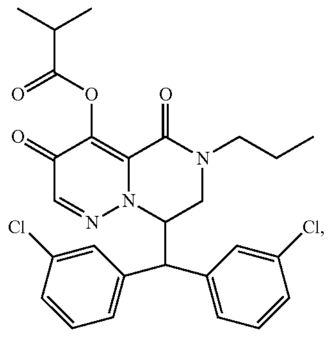
or a pharmaceutically acceptable salt of the foregoing.
Additional examples of compounds of Formula (I), or a pharmaceutically acceptable salt thereof, as provided below in Tables A and B.
TABLE A
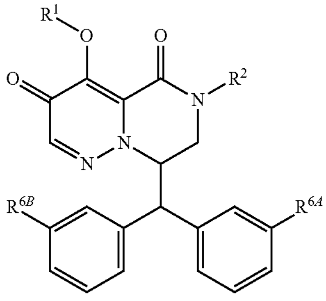
| $R^2$ | $R^1$ | $R^{6A}$ | $R^{6B}$ |
|---|---|---|---|
| 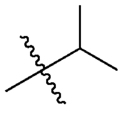 [SMILES: *C(C)C] | 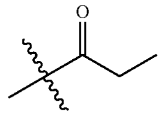 [SMILES: *C(=O)CC] | H | H |
| 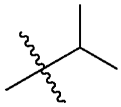 [SMILES: *C(C)C] | 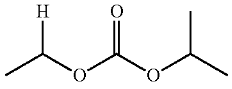 | H | H |
| 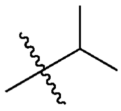 [SMILES: *C(C)C] | 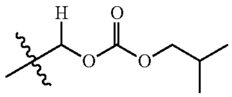 [SMILES: *COC(=O)OCC(C)C] | H | H |
| 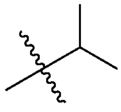 [SMILES: *C(C)C] | 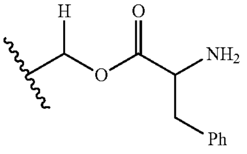 [SMILES: *COC(=O)C(N)Cc1ccccc1] | H | H |
| 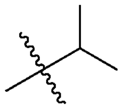 [SMILES: *C(C)C] | 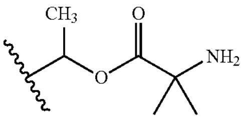 [SMILES: *C(C)OC(=O)C(C)(C)N] | H | H |
| 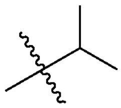 [SMILES: *C(C)C] | 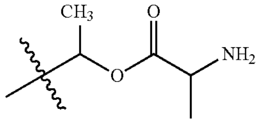 | H | H |
| 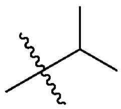 [SMILES: *C(C)C] | 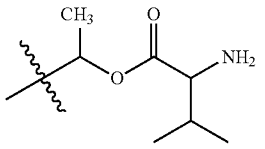 | H | H |
| 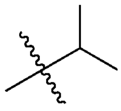 [SMILES: *C(C)C] | 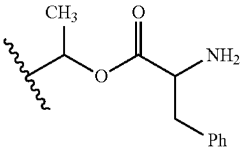 [SMILES: *C(C)OC(=O)C(N)Cc1ccccc1] | H | H |
| 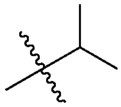 [SMILES: *C(C)C] | 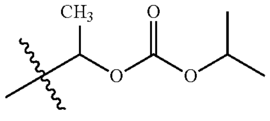 [SMILES: *C(C)OC(=O)OC(C)C] | H | H |

TABLE A-continued
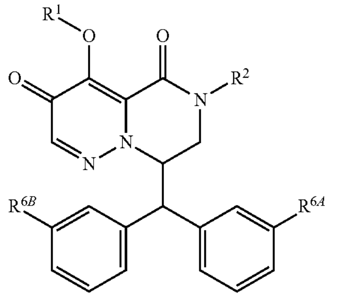
| $R^2$ | $R^1$ | $R^{6A}$ | $R^{6B}$ |
|---|---|---|---|
| 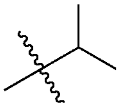 [SMILES: *C(C)C] | 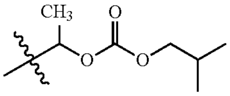 | H | H |
| —$CH_3$ | 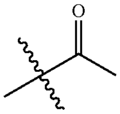 [SMILES: *C(C)=O] | H | H |
| —$CH_3$ | 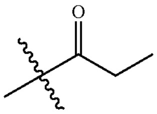 [SMILES: *C(=O)CC] | H | H |
| —$CH_3$ | 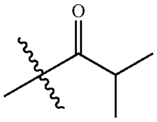 [SMILES: *C(=O)C(C)C] | H | H |
| —$CH_3$ | 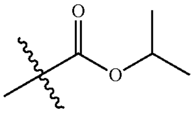 [SMILES: *C(=O)OC(C)C] | H | H |
| —$CH_3$ | 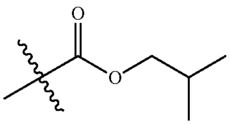 [SMILES: *C(=O)OCC(C)C] | H | H |
| —$CH_3$ | 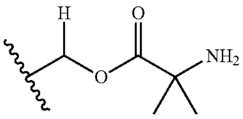 [SMILES: *COC(=O)C(C)(C)N] | H | H |
| —$CH_3$ | 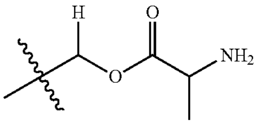 [SMILES: *COC(=O)C(C)N] | H | H |
| —$CH_3$ | 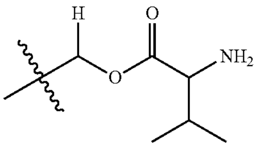 [SMILES: *COC(=O)C(N)C(C)C] | H | H |
TABLE A-continued
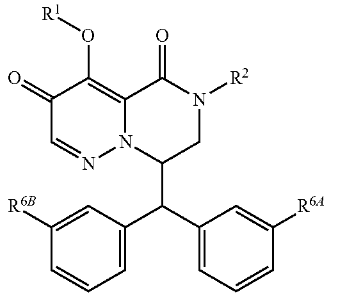
| $R^2$ | $R^1$ | $R^{6A}$ | $R^{6B}$ |
|---|---|---|---|
| —$CH_3$ | 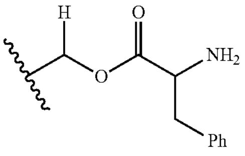 [SMILES: *COC(=O)C(N)Cc1ccccc1] | H | H |
| —$CH_3$ | 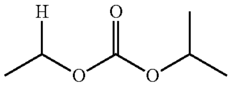 | H | H |
| —$CH_3$ | 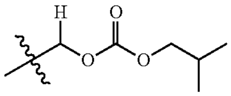 [SMILES: *COC(=O)OCC(C)C] | H | H |
| —$CH_3$ | 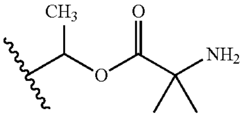 [SMILES: *C(C)OC(=O)C(C)(C)N] | H | H |
| —$CH_3$ | 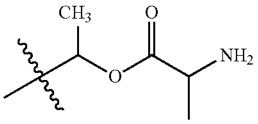 | H | H |
| —$CH_3$ | 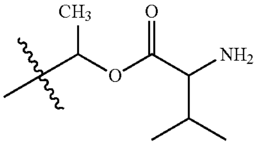 [SMILES: *C(C)OC(=O)C(N)C(C)C] | H | H |
| —$CH_3$ | 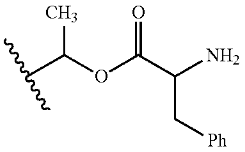 [SMILES: *C(C)OC(=O)C(N)Cc1ccccc1] | H | H |
| —$CH_3$ | 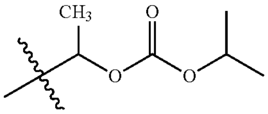 | H | H |
| —$CH_3$ | 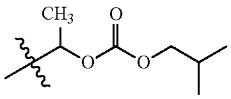 [SMILES: *C(C)OC(=O)OCC(C)C] | H | H |

TABLE A-continued
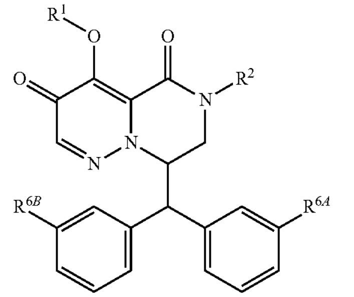
| $R^2$ | $R^1$ | $R^{6A}$ | $R^{6B}$ |
|---|---|---|---|
| $—CH_2CH_3$ | 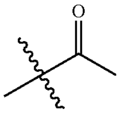 [SMILES: *C(C)=O] | H | H |
| $—CH_2CH_3$ | 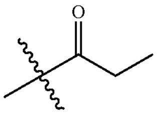 [SMILES: *C(=O)CC] | H | H |
| $—CH_2CH_3$ | 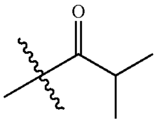 [SMILES: *C(=O)C(C)C] | H | H |
| $—CH_2CH_3$ | 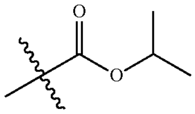 [SMILES: *C(=O)OC(C)C] | H | H |
| $—CH_2CH_3$ | 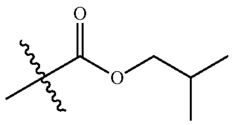 [SMILES: *C(=O)OCC(C)C] | H | H |
| $—CH_2CH_3$ | 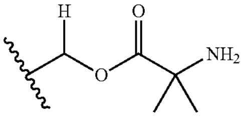 [SMILES: *COC(=O)C(C)(C)N] | H | H |
| $—CH_2CH_3$ | 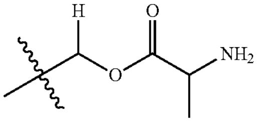 [SMILES: *COC(=O)C(C)N] | H | H |
| $—CH_2CH_3$ | 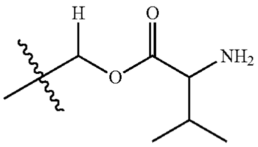 [SMILES: *COC(=O)C(N)C(C)C] | H | H |
| $—CH_2CH_3$ | 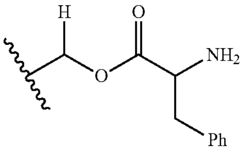 [SMILES: *COC(=O)C(N)Cc1ccccc1] | H | H |
TABLE A-continued
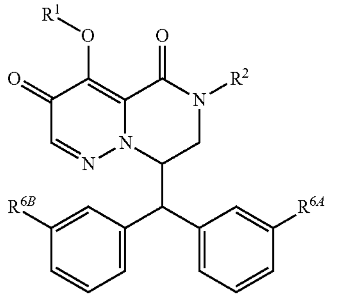
| $R^2$ | $R^1$ | $R^{6A}$ | $R^{6B}$ |
|---|---|---|---|
| $—CH_2CH_3$ | 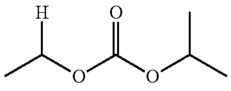 | H | H |
| $—CH_2CH_3$ | 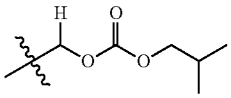 [SMILES: *COC(=O)OCC(C)C] | H | H |
| $—CH_2CH_3$ | 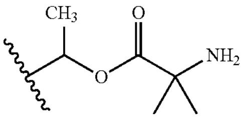 [SMILES: *C(C)OC(=O)C(C)(C)N] | H | H |
| $—CH_2CH_3$ | 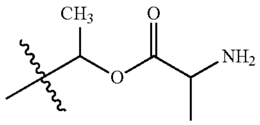 | H | H |
| $—CH_2CH_3$ | 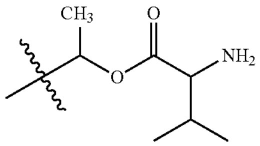 [SMILES: *C(C)OC(=O)C(N)C(C)C] | H | H |
| $—CH_2CH_3$ | 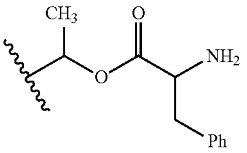 [SMILES: *C(C)OC(=O)C(N)Cc1ccccc1] | H | H |
| $—CH_2CH_3$ | 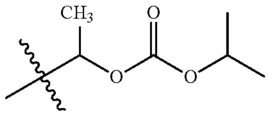 [SMILES: *C(C)OC(=O)OC(C)C] | H | H |
| $—CH_2CH_3$ | 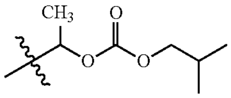 [SMILES: *C(C)OC(=O)OCC(C)C] | H | H |
| $—CH_2CH(CH_3)_2$ | 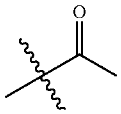 [SMILES: *C(C)=O] | H | H |
| $—CH_2CH(CH_3)_2$ | 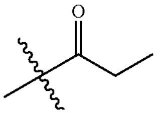 [SMILES: *C(=O)CC] | H | H |

TABLE A-continued
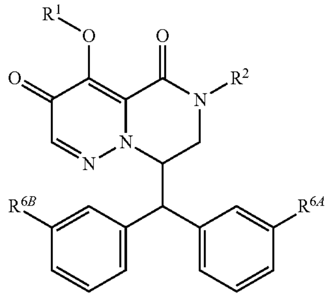
| $R^2$ | $R^1$ | $R^{6A}$ | $R^{6B}$ |
|---|---|---|---|
| $—CH_2CH(CH_3)_2$ | 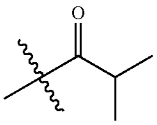 [SMILES: *C(=O)C(C)C] | H | H |
| $—CH_2CH(CH_3)_2$ | 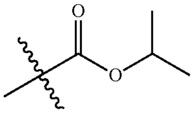 [SMILES: *C(=O)OC(C)C] | H | H |
| $—CH_2CH(CH_3)_2$ | 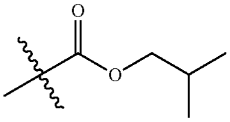 [SMILES: *C(=O)OCC(C)C] | H | H |
| $—CH_2CH(CH_3)_2$ | 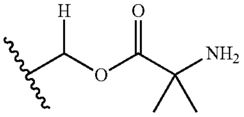 | H | H |
| $—CH_2CH(CH_3)_2$ | 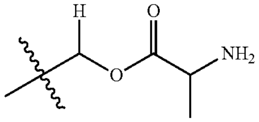 [SMILES: *COC(=O)C(C)N] | H | H |
| $—CH_2CH(CH_3)_2$ | 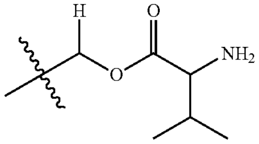 [SMILES: *COC(=O)C(N)C(C)C] | H | H |
| $—CH_2CH(CH_3)_2$ | 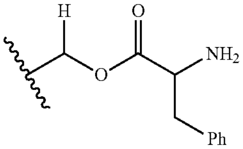 [SMILES: *COC(=O)C(N)Cc1ccccc1] | H | H |
| $—CH_2CH(CH_3)_2$ | 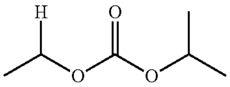 | H | H |
| $—CH_2CH(CH_3)_2$ | 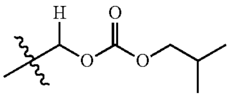 [SMILES: *COC(=O)OCC(C)C] | H | H |
TABLE A-continued
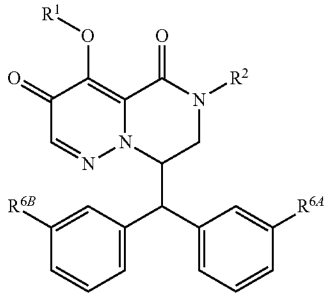
| $R^2$ | $R^1$ | $R^{6A}$ | $R^{6B}$ |
|---|---|---|---|
| $—CH_2CH(CH_3)_2$ | 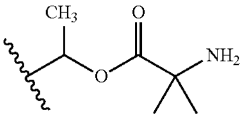 [SMILES: *C(C)OC(=O)C(C)(C)N] | H | H |
| $—CH_2CH(CH_3)_2$ | 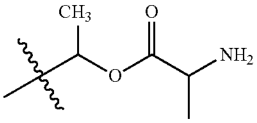 | H | H |
| $—CH_2CH(CH_3)_2$ | 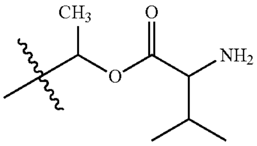 | H | H |
| $—CH_2CH(CH_3)_2$ | 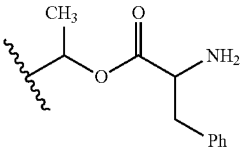 [SMILES: *C(C)OC(=O)C(N)Cc1ccccc1] | H | H |
| $—CH_2CH(CH_3)_2$ | 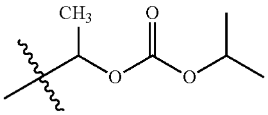 [SMILES: *C(C)OC(=O)OC(C)C] | H | H |
| $—CH_2CH(CH_3)_2$ | 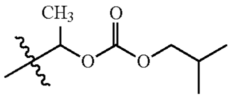 [SMILES: *C(C)OC(=O)OCC(C)C] | H | H |
| $—CH_2CH_2CH_3$ | 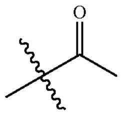 [SMILES: *C(C)=O] | H | H |
| $—CH_2CH_2CH_3$ | 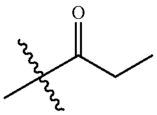 [SMILES: *C(=O)CC] | H | H |
| $—CH_2CH_2CH_3$ | 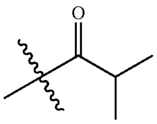 [SMILES: *C(=O)C(C)C] | H | H |

TABLE A-continued
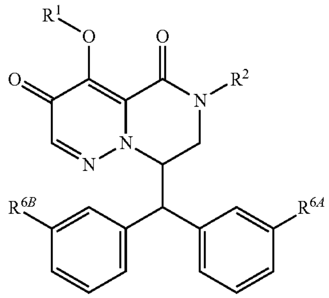
| $R^2$ | $R^1$ | $R^{6A}$ | $R^{6B}$ |
|---|---|---|---|
| $—CH_2CH_2CH_3$ | 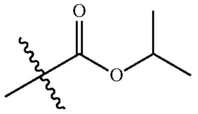 [SMILES: *C(=O)OC(C)C] | H | H |
| $—CH_2CH_2CH_3$ | 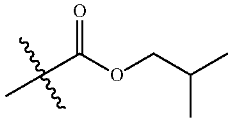 [SMILES: *C(=O)OCC(C)C] | H | H |
| $—CH_2CH_2CH_3$ | 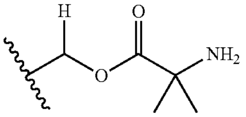 [SMILES: *COC(=O)C(C)(C)N] | H | H |
| $—CH_2CH_2CH_3$ | 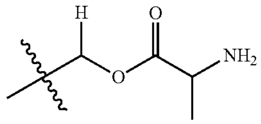 [SMILES: *COC(=O)C(C)N] | H | H |
| $—CH_2CH_2CH_3$ | 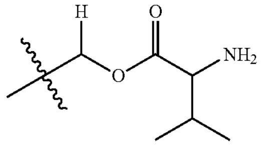 [SMILES: *COC(=O)C(N)C(C)C] | H | H |
| $—CH_2CH_2CH_3$ | 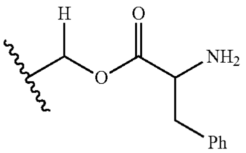 [SMILES: *COC(=O)C(N)Cc1ccccc1] | H | H |
| $—CH_2CH_2CH_3$ | 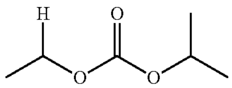 | H | H |
| $—CH_2CH_2CH_3$ | 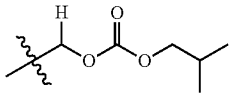 | H | H |
| $—CH_2CH_2CH_3$ | 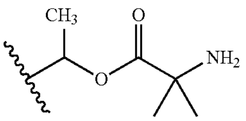 | H | H |
TABLE A-continued
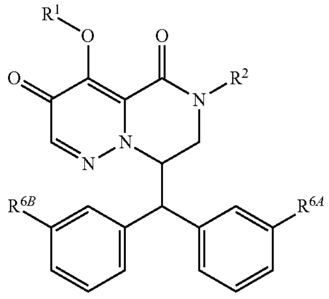
| $R^2$ | $R^1$ | $R^{6A}$ | $R^{6B}$ |
|---|---|---|---|
| $—CH_2CH_2CH_3$ | 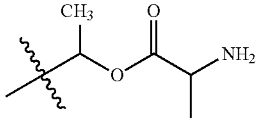 | H | H |
| $—CH_2CH_2CH_3$ | 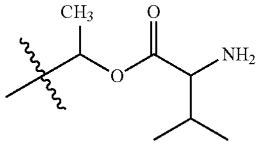 | H | H |
| $—CH_2CH_2CH_3$ | 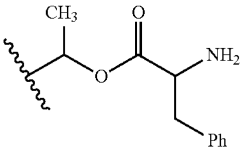 [SMILES: *C(C)OC(=O)C(N)Cc1ccccc1] | H | H |
| $—CH_2CH_2CH_3$ | 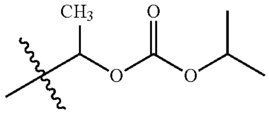 [SMILES: *C(C)OC(=O)OC(C)C] | H | H |
| $—CH_2CH_2CH_3$ | 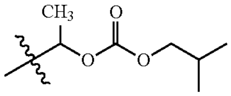 | H | H |
| $—CH_2CH_2CH_2CH_3$ | 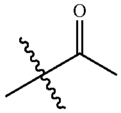 [SMILES: *C(C)=O] | H | H |
| $—CH_2CH_2CH_2CH_3$ | 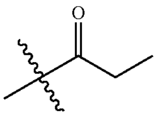 [SMILES: *C(=O)CC] | H | H |
| $—CH_2CH_2CH_2CH_3$ | 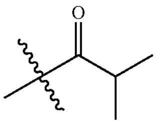 [SMILES: *C(=O)C(C)C] | H | H |
| $—CH_2CH_2CH_2CH_3$ | 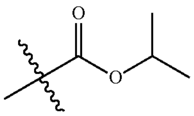 | H | H |

TABLE A-continued
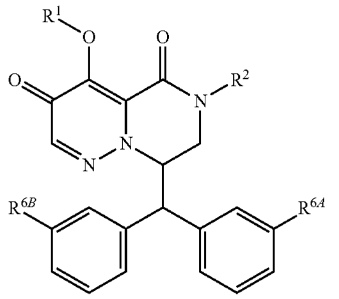
| $R^2$ | $R^1$ | $R^{6A}$ | $R^{6B}$ |
|---|---|---|---|
| $—CH_2CH_2CH_2CH_3$ | 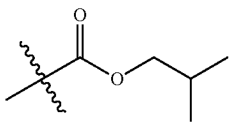 [SMILES: *C(=O)OCC(C)C] | H | H |
| $—CH_2CH_2CH_2CH_3$ | 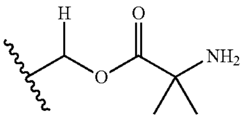 [SMILES: *COC(=O)C(C)(C)N] | H | H |
| $—CH_2CH_2CH_2CH_3$ | 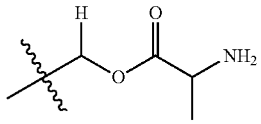 [SMILES: *COC(=O)C(C)N] | H | H |
| $—CH_2CH_2CH_2CH_3$ | 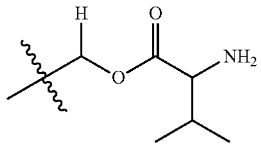 | H | H |
| $—CH_2CH_2CH_2CH_3$ | 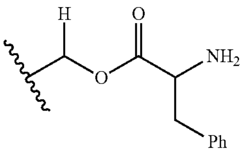 [SMILES: *COC(=O)C(N)Cc1ccccc1] | H | H |
| $—CH_2CH_2CH_2CH_3$ | 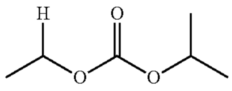 | H | H |
| $—CH_2CH_2CH_2CH_3$ | 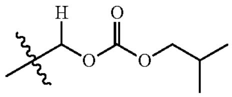 [SMILES: *COC(=O)OCC(C)C] | H | H |
| $—CH_2CH_2CH_2CH_3$ | 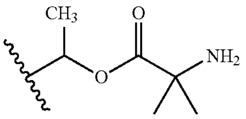 | H | H |
| $—CH_2CH_2CH_2CH_3$ | 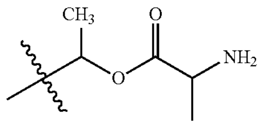 | H | H |
TABLE A-continued
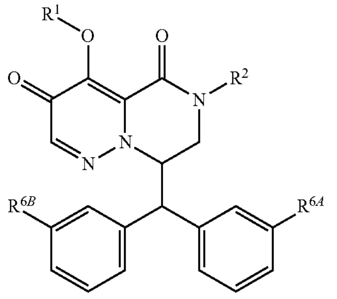
| $R^2$ | $R^1$ | $R^{6A}$ | $R^{6B}$ |
|---|---|---|---|
| $—CH_2CH_2CH_2CH_3$ | 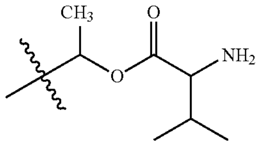 | H | H |
| $—CH_2CH_2CH_2CH_3$ | 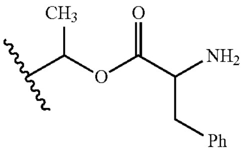 [SMILES: *C(C)OC(=O)C(N)Cc1ccccc1] | H | H |
| $—CH_2CH_2CH_2CH_3$ | 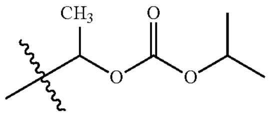 [SMILES: *C(C)OC(=O)OC(C)C] | H | H |
| $—CH_2CH_2CH_2CH_3$ | 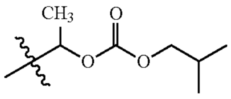 [SMILES: *C(C)OC(=O)OCC(C)C] | H | H |
| 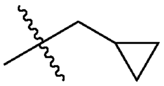 [SMILES: *CC1CC1] | 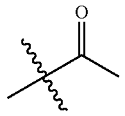 [SMILES: *C(C)=O] | H | H |
| 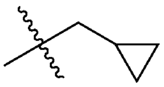 [SMILES: *CC1CC1] | 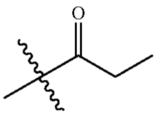 [SMILES: *C(=O)CC] | H | H |
| 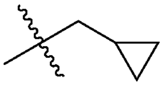 [SMILES: *CC1CC1] | 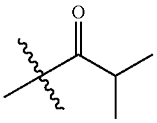 [SMILES: *C(=O)C(C)C] | H | H |
| 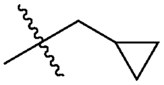 [SMILES: *CC1CC1] | 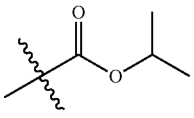 | H | H |
| 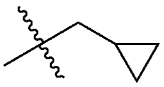 | 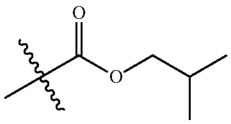 [SMILES: *C(=O)OCC(C)C] | H | H |

TABLE A-continued
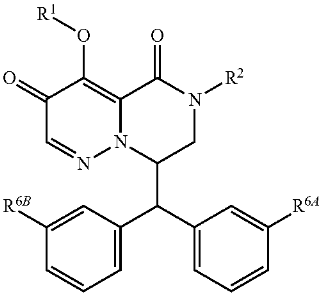
| $R^2$ | $R^1$ | $R^{6A}$ | $R^{6B}$ |
|---|---|---|---|
| 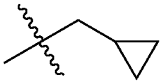 [SMILES: *CC1CC1] | 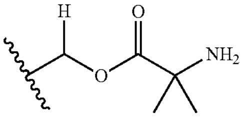 [SMILES: *COC(=O)C(C)(C)N] | H | H |
| 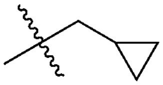 | 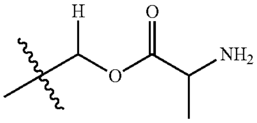 [SMILES: *COC(=O)C(C)N] | H | H |
| 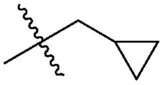 [SMILES: *CC1CC1] | 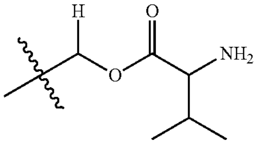 [SMILES: *COC(=O)C(N)C(C)C] | H | H |
| 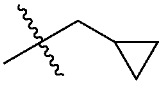 [SMILES: *CC1CC1] | 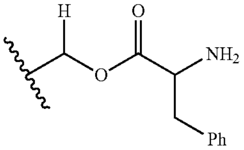 [SMILES: *COC(=O)C(N)Cc1ccccc1] | H | H |
| 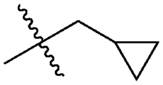 | 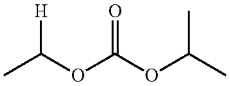 | H | H |
| 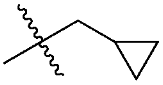 [SMILES: *CC1CC1] | 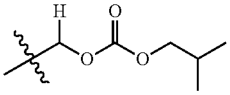 [SMILES: *COC(=O)OCC(C)C] | H | H |
| 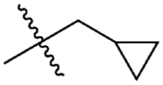 | 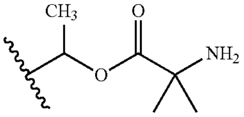 | H | H |
| 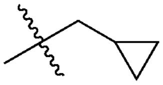 | 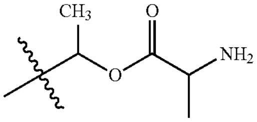 | H | H |
| 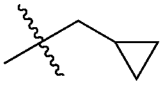 [SMILES: *CC1CC1] | 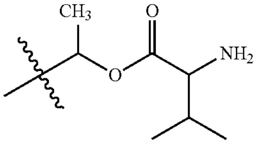 | H | H |
TABLE A-continued
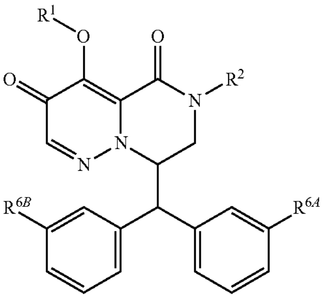
| $R^2$ | $R^1$ | $R^{6A}$ | $R^{6B}$ |
|---|---|---|---|
| 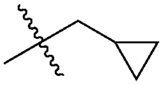 | 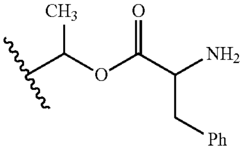 [SMILES: *C(C)OC(=O)C(N)Cc1ccccc1] | H | H |
| 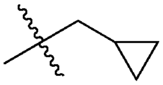 [SMILES: *CC1CC1] | 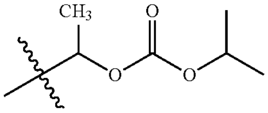 | H | H |
| 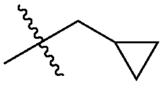 | 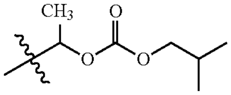 [SMILES: *C(C)OC(=O)OCC(C)C] | H | H |
| 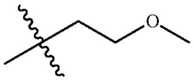 [SMILES: *CCOC] | 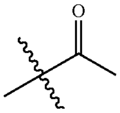 [SMILES: *C(C)=O] | H | H |
| 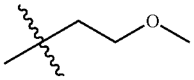 [SMILES: *CCOC] | 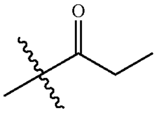 [SMILES: *C(=O)CC] | H | H |
| 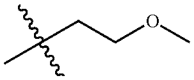 [SMILES: *CCOC] | 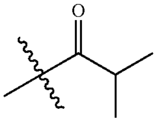 [SMILES: *C(=O)C(C)C] | H | H |
| 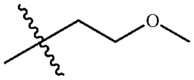 [SMILES: *CCOC] | 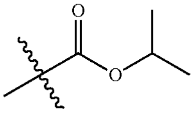 | H | H |
| 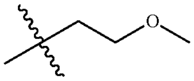 [SMILES: *CCOC] | 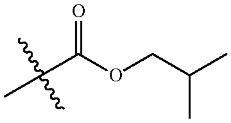 [SMILES: *C(=O)OCC(C)C] | H | H |
| 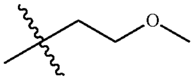 [SMILES: *CCOC] | 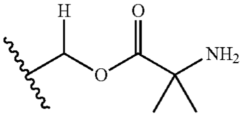 [SMILES: *COC(=O)C(C)(C)N] | H | H |

TABLE A-continued
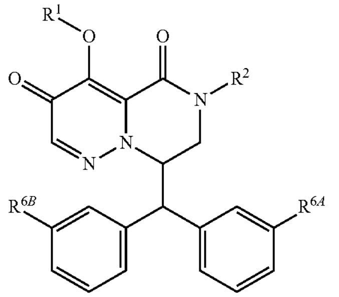
| $R^2$ | $R^1$ | $R^{6A}$ | $R^{6B}$ |
|---|---|---|---|
| 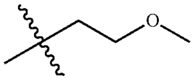 [SMILES: *CCOC] | 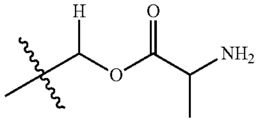 | H | H |
| 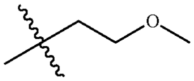 [SMILES: *CCOC] | 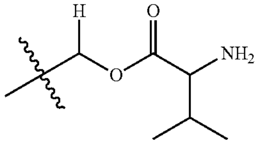 [SMILES: *COC(=O)C(N)C(C)C] | H | H |
| 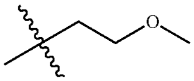 [SMILES: *CCOC] | 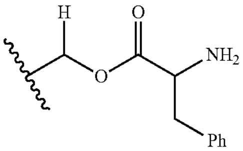 | H | H |
| 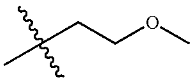 [SMILES: *CCOC] | 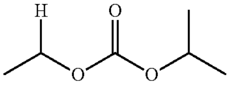 | H | H |
| 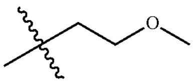 [SMILES: *CCOC] | 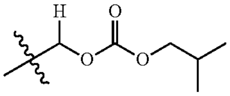 [SMILES: *COC(=O)OCC(C)C] | H | H |
| 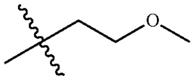 [SMILES: *CCOC] | 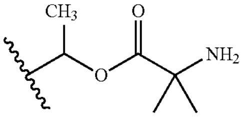 | H | H |
| 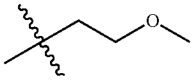 [SMILES: *CCOC] | 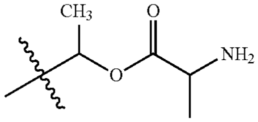 | H | H |
| 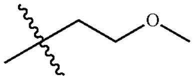 [SMILES: *CCOC] | 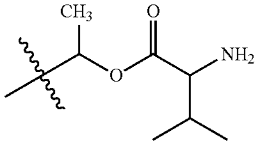 | H | H |
| 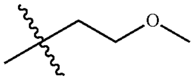 [SMILES: *CCOC] | 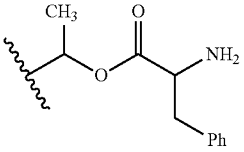 | H | H |
TABLE A-continued
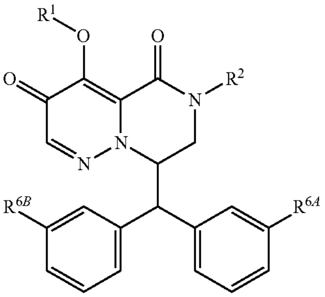
| $R^2$ | $R^1$ | $R^{6A}$ | $R^{6B}$ |
|---|---|---|---|
| 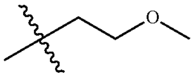 [SMILES: *CCOC] | 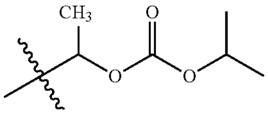 | H | H |
| 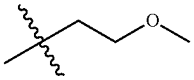 [SMILES: *CCOC] | 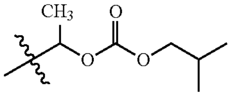 [SMILES: *C(C)OC(=O)OCC(C)C] | H | H |
| 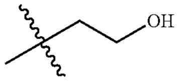 [SMILES: *CCO] | 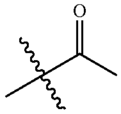 [SMILES: *C(C)=O] | H | H |
| 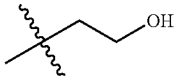 [SMILES: *CCO] | 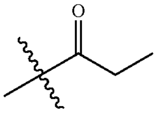 [SMILES: *C(=O)CC] | H | H |
| 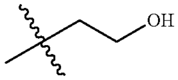 [SMILES: *CCO] | 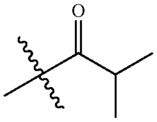 [SMILES: *C(=O)C(C)C] | H | H |
| 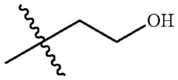 [SMILES: *CCO] | 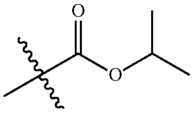 [SMILES: *C(=O)OC(C)C] | H | H |
| 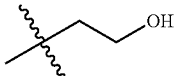 [SMILES: *CCO] | 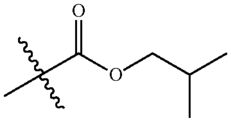 [SMILES: *C(=O)OCC(C)C] | H | H |
| 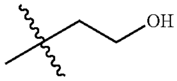 [SMILES: *CCO] | 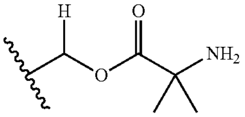 [SMILES: *COC(=O)C(C)(C)N] | H | H |
| 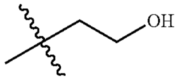 [SMILES: *CCO] | 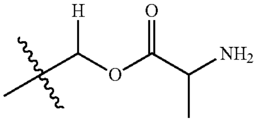 [SMILES: *COC(=O)C(C)N] | H | H |

TABLE A-continued
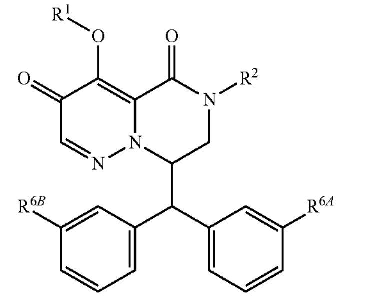
| $R^2$ | $R^1$ | $R^{6A}$ | $R^{6B}$ |
|---|---|---|---|
| 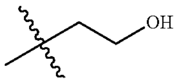 [SMILES: *CCO] | 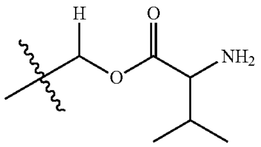 | H | H |
| 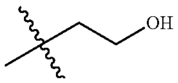 [SMILES: *CCO] | 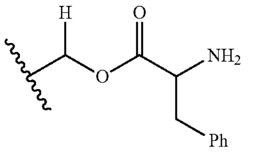 [SMILES: *COC(=O)C(N)Cc1ccccc1] | H | H |
| 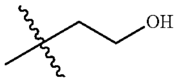 [SMILES: *CCO] | 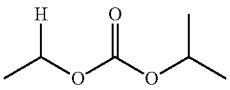 | H | H |
| 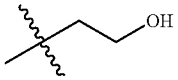 [SMILES: *CCO] | 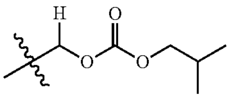 [SMILES: *COC(=O)OCC(C)C] | H | H |
| 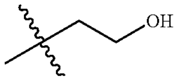 [SMILES: *CCO] | 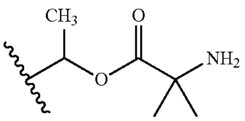 | H | H |
| 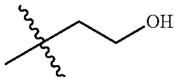 [SMILES: *CCO] | 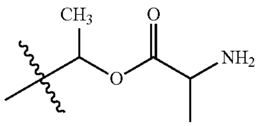 | H | H |
| 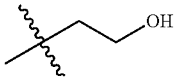 [SMILES: *CCO] | 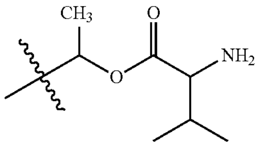 | H | H |
| 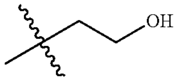 [SMILES: *CCO] | 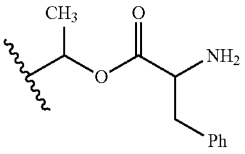 | H | H |
| 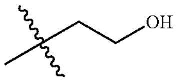 [SMILES: *CCO] | 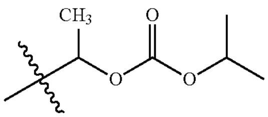 [SMILES: *C(C)OC(=O)OC(C)C] | H | H |
TABLE A-continued
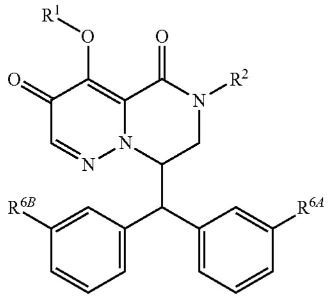
| $R^2$ | $R^1$ | $R^{6A}$ | $R^{6B}$ |
|---|---|---|---|
| 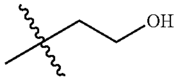 [SMILES: *CCO] | 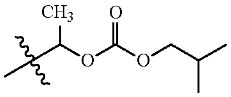 [SMILES: *C(C)OC(=O)OCC(C)C] | H | H |
| $—CH_2CH{=}CF_2$ | 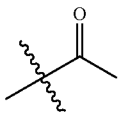 [SMILES: *C(C)=O] | H | H |
| $—CH_2CH{=}CF_2$ | 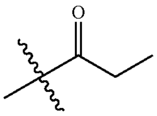 [SMILES: *C(=O)CC] | H | H |
| $—CH_2CH{=}CF_2$ | 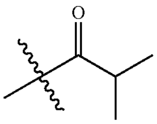 [SMILES: *C(=O)C(C)C] | H | H |
| $—CH_2CH{=}CF_2$ | 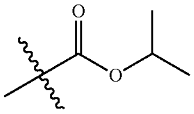 | H | H |
| $—CH_2CH{=}CF_2$ | 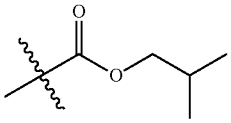 [SMILES: *C(=O)OCC(C)C] | H | H |
| $—CH_2CH{=}CF_2$ | 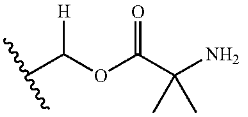 [SMILES: *COC(=O)C(C)(C)N] | H | H |
| $—CH_2CH{=}CF_2$ | 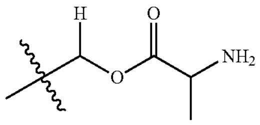 [SMILES: *COC(=O)C(C)N] | H | H |
| $—CH_2CH{=}CF_2$ | 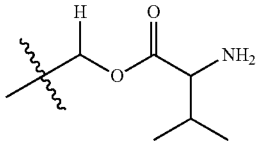 [SMILES: *COC(=O)C(N)C(C)C] | H | H |

TABLE A-continued
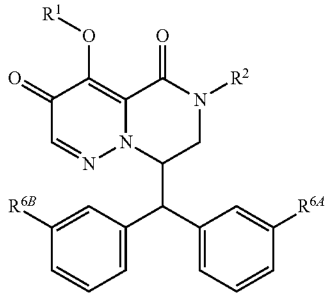
| $R^2$ | $R^1$ | $R^{6A}$ | $R^{6B}$ |
|---|---|---|---|
| $—CH_2CH═CF_2$ | 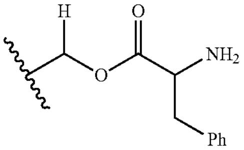 [SMILES: *COC(=O)C(N)Cc1ccccc1] | H | H |
| $—CH_2CH═CF_2$ | 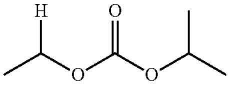 | H | H |
| $—CH_2CH═CF_2$ | 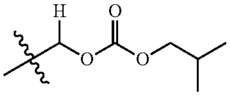 [SMILES: *COC(=O)OCC(C)C] | H | H |
| $—CH_2CH═CF_2$ | 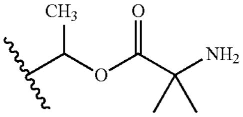 | H | H |
| $—CH_2CH═CF_2$ | 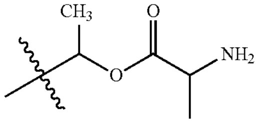 | H | H |
| $—CH_2CH═CF_2$ | 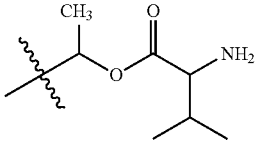 | H | H |
| $—CH_2CH═CF_2$ | 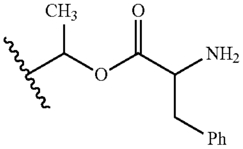 | H | H |
| $—CH_2CH═CF_2$ | 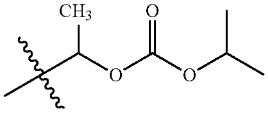 [SMILES: *C(C)OC(=O)OC(C)C] | H | H |
| $—CH_2CH═CF_2$ | 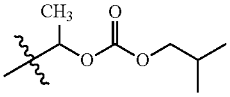 | H | H |
TABLE A-continued
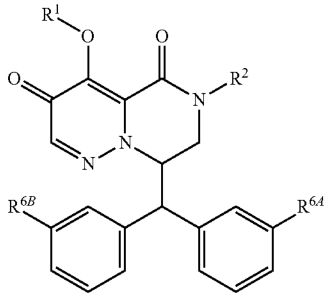
| $R^2$ | $R^1$ | $R^{6A}$ | $R^{6B}$ |
|---|---|---|---|
| $—CH_2CF_3$ | 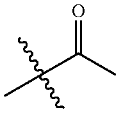 [SMILES: *C(C)=O] | H | H |
| $—CH_2CF_3$ | 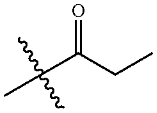 [SMILES: *C(=O)CC] | H | H |
| $—CH_2CF_3$ | 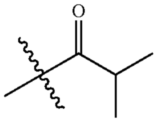 [SMILES: *C(=O)C(C)C] | H | H |
| $—CH_2CF_3$ | 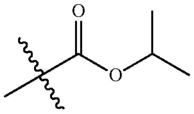 [SMILES: *C(=O)OC(C)C] | H | H |
| $—CH_2CF_3$ | 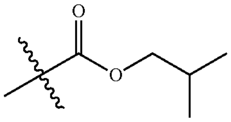 [SMILES: *C(=O)OCC(C)C] | H | H |
| $—CH_2CF_3$ | 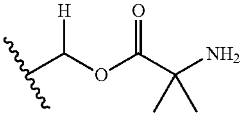 [SMILES: *COC(=O)C(C)(C)N] | H | H |
| $—CH_2CF_3$ | 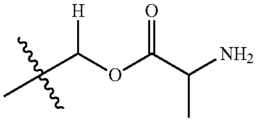 [SMILES: *COC(=O)C(C)N] | H | H |
| $—CH_2CF_3$ | 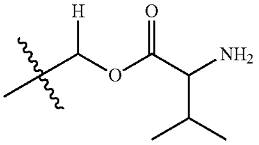 [SMILES: *COC(=O)C(N)C(C)C] | H | H |
| $—CH_2CF_3$ | 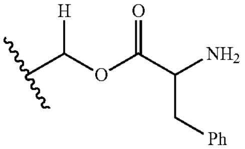 [SMILES: *COC(=O)C(N)Cc1ccccc1] | H | H |

TABLE A-continued
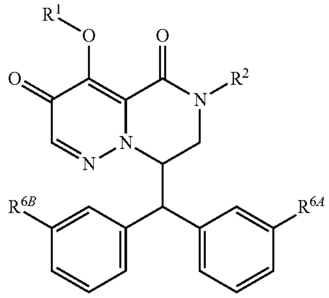
| $R^2$ | $R^1$ | $R^{6A}$ | $R^{6B}$ |
|---|---|---|---|
| $—CH_2CF_3$ | 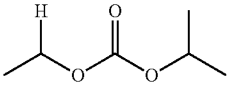 | H | H |
| $—CH_2CF_3$ | 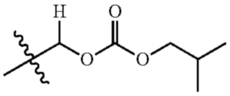 [SMILES: *COC(=O)OCC(C)C] | H | H |
| $—CH_2CF_3$ | 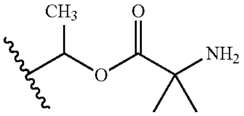 | H | H |
| $—CH_2CF_3$ | 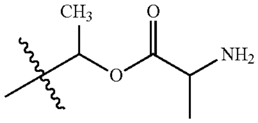 | H | H |
| $—CH_2CF_3$ | 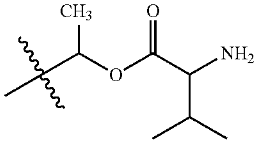 [SMILES: *C(C)OC(=O)C(N)C(C)C] | H | H |
| $—CH_2CF_3$ | 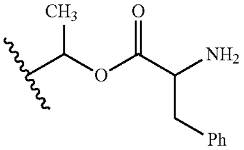 | H | H |
| $—CH_2CF_3$ | 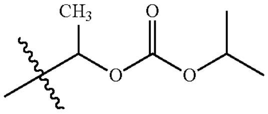 [SMILES: *C(C)OC(=O)OC(C)C] | H | H |
| $—CH_2CF_3$ | 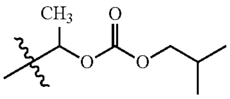 [SMILES: *C(C)OC(=O)OCC(C)C] | H | H |
| $—CH_2CH_2CF_3$ | 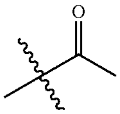 [SMILES: *C(C)=O] | H | H |
| $—CH_2CH_2CF_3$ | 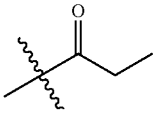 [SMILES: *C(=O)CC] | H | H |
TABLE A-continued
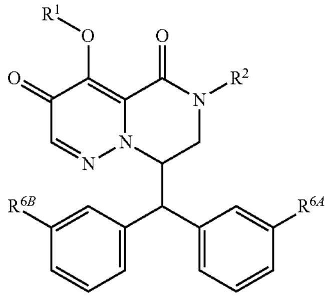
| $R^2$ | $R^1$ | $R^{6A}$ | $R^{6B}$ |
|---|---|---|---|
| $—CH_2CH_2CF_3$ | 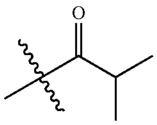 [SMILES: *C(=O)C(C)C] | H | H |
| $—CH_2CH_2CF_3$ | 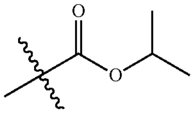 [SMILES: *C(=O)OC(C)C] | H | H |
| $—CH_2CH_2CF_3$ | 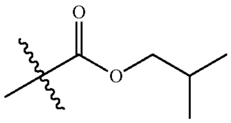 [SMILES: *C(=O)OCC(C)C] | H | H |
| $—CH_2CH_2CF_3$ | 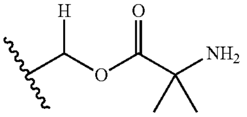 [SMILES: *COC(=O)C(C)(C)N] | H | H |
| $—CH_2CH_2CF_3$ | 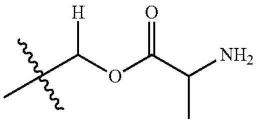 [SMILES: *COC(=O)C(C)N] | H | H |
| $—CH_2CH_2CF_3$ | 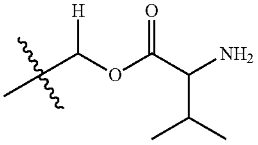 [SMILES: *COC(=O)C(N)C(C)C] | H | H |
| $—CH_2CH_2CF_3$ | 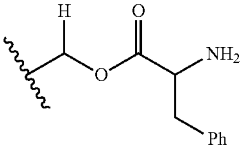 [SMILES: *COC(=O)C(N)Cc1ccccc1] | H | H |
| $—CH_2CH_2CF_3$ | 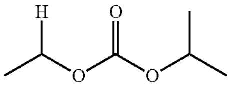 | H | H |
| $—CH_2CH_2CF_3$ | 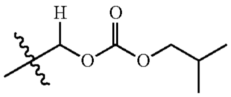 [SMILES: *COC(=O)OCC(C)C] | H | H |

TABLE A-continued
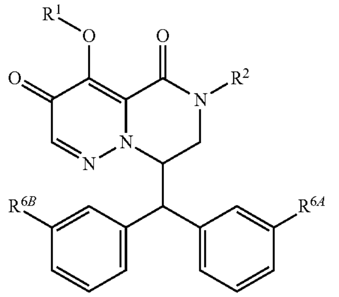
| $R^2$ | $R^1$ | $R^{6A}$ | $R^{6B}$ |
|---|---|---|---|
| $-CH_2CH_2CF_3$ | 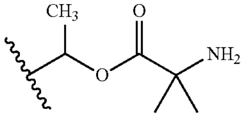 | H | H |
| $-CH_2CH_2CF_3$ | 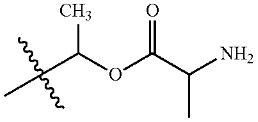 | H | H |
| $-CH_2CH_2CF_3$ | 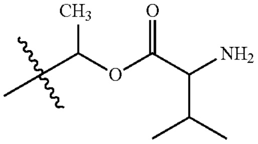 | H | H |
| $-CH_2CH_2CF_3$ | 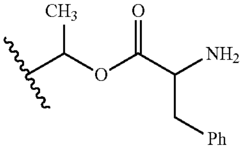 [SMILES: *C(C)OC(=O)C(N)Cc1ccccc1] | H | H |
| $-CH_2CH_2CF_3$ | 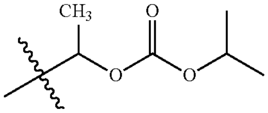 [SMILES: *C(C)OC(=O)OC(C)C] | H | H |
| $-CH_2CH_2CF_3$ | 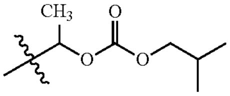 [SMILES: *C(C)OC(=O)OCC(C)C] | H | H |
| $-CH_2CHF_2$ | 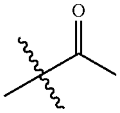 [SMILES: *C(C)=O] | H | H |
| $-CH_2CHF_2$ | 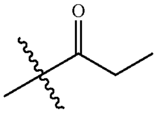 [SMILES: *C(=O)CC] | H | H |
| $-CH_2CHF_2$ | 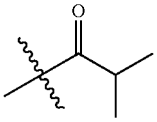 [SMILES: *C(=O)C(C)C] | H | H |
TABLE A-continued
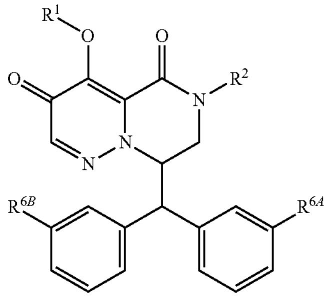
| $R^2$ | $R^1$ | $R^{6A}$ | $R^{6B}$ |
|---|---|---|---|
| $-CH_2CHF_2$ | 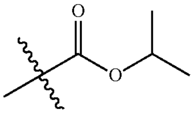 [SMILES: *C(=O)OC(C)C] | H | H |
| $-CH_2CHF_2$ | 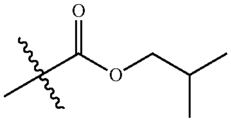 [SMILES: *C(=O)OCC(C)C] | H | H |
| $-CH_2CHF_2$ | 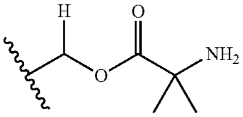 [SMILES: *COC(=O)C(C)(C)N] | H | H |
| $-CH_2CHF_2$ | 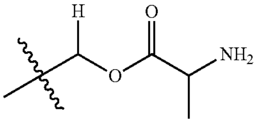 [SMILES: *COC(=O)C(C)N] | H | H |
| $-CH_2CHF_2$ | 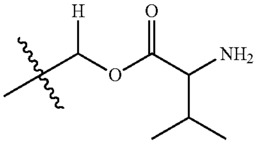 [SMILES: *COC(=O)C(N)C(C)C] | H | H |
| $-CH_2CHF_2$ | 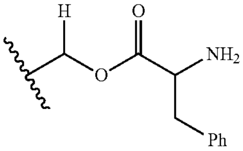 [SMILES: *COC(=O)C(N)Cc1ccccc1] | H | H |
| $-CH_2CHF_2$ | 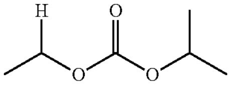 | H | H |
| $-CH_2CHF_2$ | 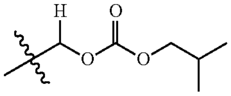 [SMILES: *COC(=O)OCC(C)C] | H | H |
| $-CH_2CHF_2$ | 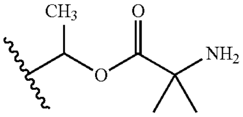 [SMILES: *C(C)OC(=O)C(C)(C)N] | H | H |

TABLE A-continued
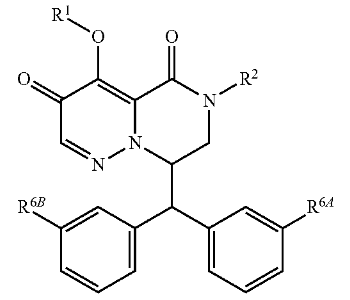
| $R^2$ | $R^1$ | $R^{6A}$ | $R^{6B}$ |
|---|---|---|---|
| $—CH_2CHF_2$ | 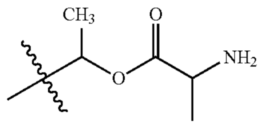 | H | H |
| $—CH_2CHF_2$ | 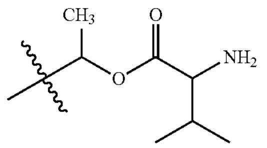 | H | H |
| $—CH_2CHF_2$ | 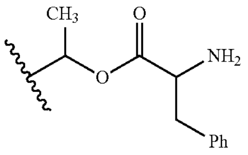 | H | H |
| $—CH_2CHF_2$ | 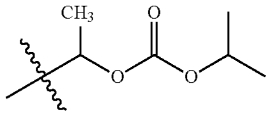 [SMILES: *C(C)OC(=O)OC(C)C] | H | H |
| $—CH_2CHF_2$ | 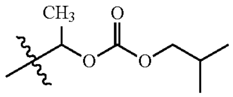 [SMILES: *C(C)OC(=O)OCC(C)C] | H | H |
| $—CH_2C(CH_3)F_2$ | 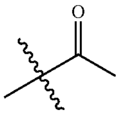 [SMILES: *C(C)=O] | H | H |
| $—CH_2C(CH_3)F_2$ | 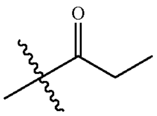 [SMILES: *C(=O)CC] | H | H |
| $—CH_2C(CH_3)F_2$ | 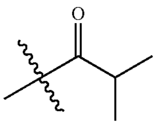 [SMILES: *C(=O)C(C)C] | H | H |
| $—CH_2C(CH_3)F_2$ | 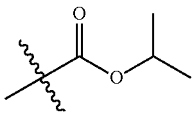 | H | H |
TABLE A-continued
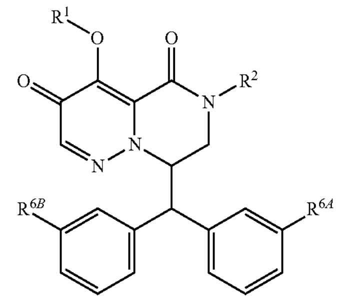
| $R^2$ | $R^1$ | $R^{6A}$ | $R^{6B}$ |
|---|---|---|---|
| $—CH_2C(CH_3)F_2$ | 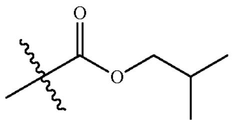 [SMILES: *C(=O)OCC(C)C] | H | H |
| $—CH_2C(CH_3)F_2$ | 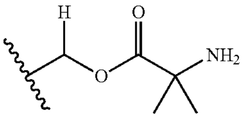 [SMILES: *COC(=O)C(C)(C)N] | H | H |
| $—CH_2C(CH_3)F_2$ | 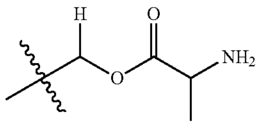 [SMILES: *COC(=O)C(C)N] | H | H |
| $—CH_2C(CH_3)F_2$ | 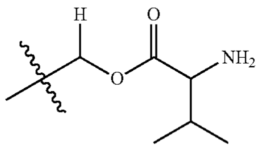 [SMILES: *COC(=O)C(N)C(C)C] | H | H |
| $—CH_2C(CH_3)F_2$ | 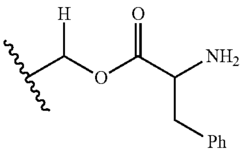 [SMILES: *COC(=O)C(N)Cc1ccccc1] | H | H |
| $—CH_2C(CH_3)F_2$ | 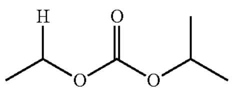 | H | H |
| $—CH_2C(CH_3)F_2$ | 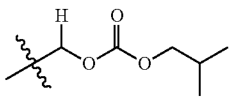 [SMILES: *COC(=O)OCC(C)C] | H | H |
| $—CH_2C(CH_3)F_2$ | 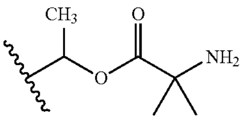 [SMILES: *C(C)OC(=O)C(C)(C)N] | H | H |
| $—CH_2C(CH_3)F_2$ | 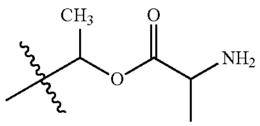 | H | H |

TABLE A-continued
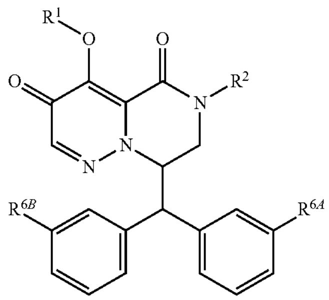
| $R^2$ | $R^1$ | $R^{6A}$ | $R^{6B}$ |
|---|---|---|---|
| $—CH_2C(CH_3)F_2$ | 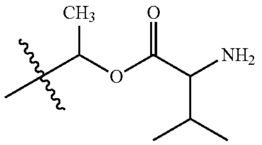 | H | H |
| $—CH_2C(CH_3)F_2$ | 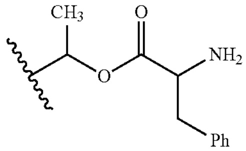 | H | H |
| $—CH_2C(CH_3)F_2$ | 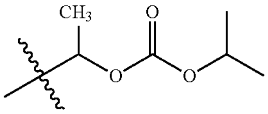 | H | H |
| $—CH_2C(CH_3)F_2$ | 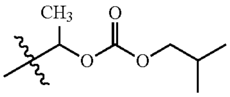 [SMILES: *C(C)OC(=O)OCC(C)C] | H | H |
| 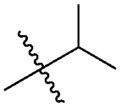 [SMILES: *C(C)C] | 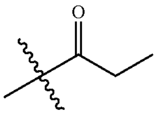 [SMILES: *C(=O)CC] | F | F |
| 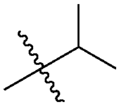 [SMILES: *C(C)C] | 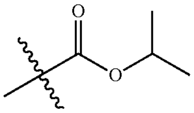 [SMILES: *C(=O)OC(C)C] | F | F |
| 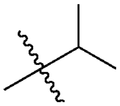 [SMILES: *C(C)C] | 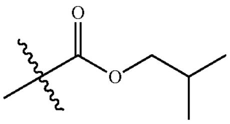 [SMILES: *C(=O)OCC(C)C] | F | F |
| 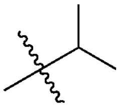 [SMILES: *C(C)C] | 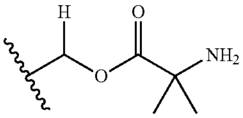 [SMILES: *COC(=O)C(C)(C)N] | F | F |
| 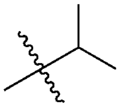 [SMILES: *C(C)C] | 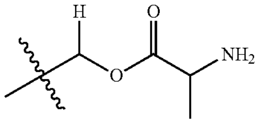 | F | F |
TABLE A-continued
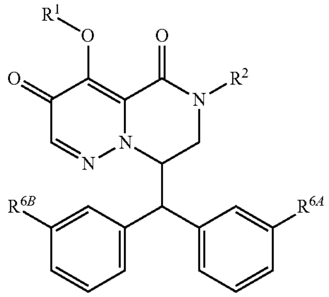
| $R^2$ | $R^1$ | $R^{6A}$ | $R^{6B}$ |
|---|---|---|---|
| 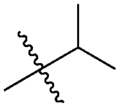 [SMILES: *C(C)C] | 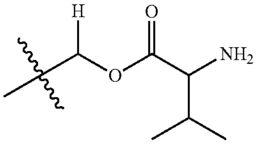 [SMILES: *COC(=O)C(N)C(C)C] | F | F |
| 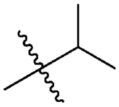 [SMILES: *C(C)C] | 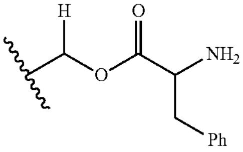 [SMILES: *COC(=O)C(N)Cc1ccccc1] | F | F |
| 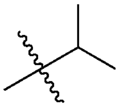 [SMILES: *C(C)C] | 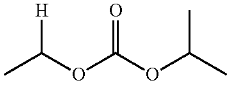 | F | F |
| 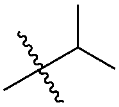 [SMILES: *C(C)C] | 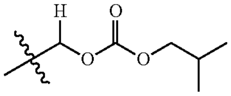 [SMILES: *COC(=O)OCC(C)C] | F | F |
| 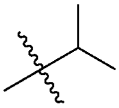 [SMILES: *C(C)C] | 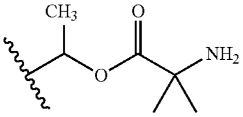 [SMILES: *C(C)OC(=O)C(C)(C)N] | F | F |
| 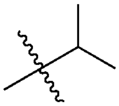 [SMILES: *C(C)C] | 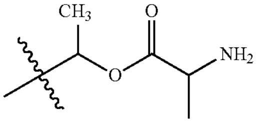 | F | F |
| 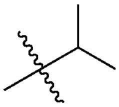 [SMILES: *C(C)C] | 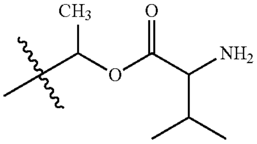 [SMILES: *C(C)OC(=O)C(N)C(C)C] | F | F |
| 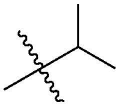 [SMILES: *C(C)C] | 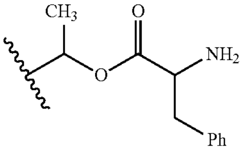 [SMILES: *C(C)OC(=O)C(N)Cc1ccccc1] | F | F |
| 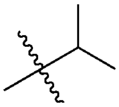 [SMILES: *C(C)C] | 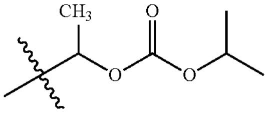 [SMILES: *C(C)OC(=O)OC(C)C] | F | F |

TABLE A-continued
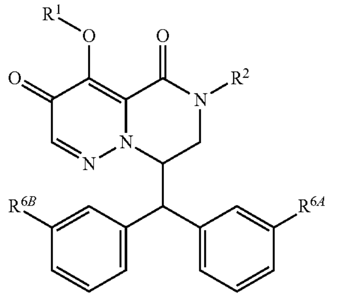
| $R^2$ | $R^1$ | $R^{6A}$ | $R^{6B}$ |
|---|---|---|---|
| 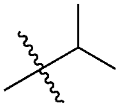 [SMILES: *C(C)C] | 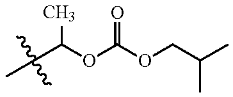 [SMILES: *C(C)OC(=O)OCC(C)C] | F | F |
| —$CH_3$ | 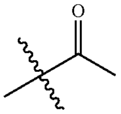 [SMILES: *C(C)=O] | F | F |
| —$CH_3$ | 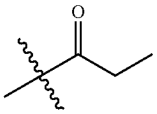 [SMILES: *C(=O)CC] | F | F |
| —$CH_3$ | 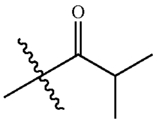 [SMILES: *C(=O)C(C)C] | F | F |
| —$CH_3$ | 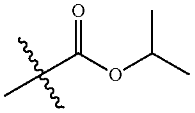 [SMILES: *C(=O)OC(C)C] | F | F |
| —$CH_3$ | 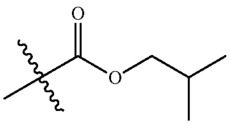 [SMILES: *C(=O)OCC(C)C] | F | F |
| —$CH_3$ | 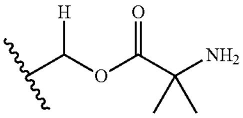 [SMILES: *COC(=O)C(C)(C)N] | F | F |
| —$CH_3$ | 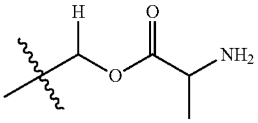 [SMILES: *COC(=O)C(C)N] | F | F |
| —$CH_3$ | 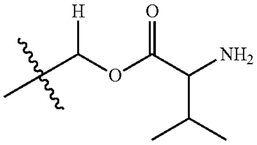 [SMILES: *COC(=O)C(N)C(C)C] | F | F |
TABLE A-continued
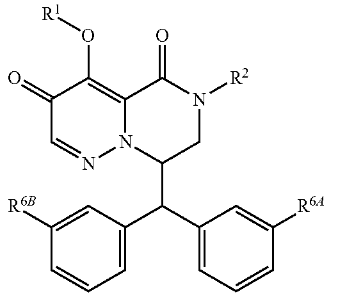
| $R^2$ | $R^1$ | $R^{6A}$ | $R^{6B}$ |
|---|---|---|---|
| —$CH_3$ | 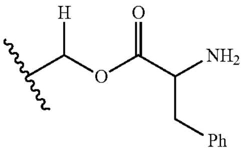 [SMILES: *COC(=O)C(N)Cc1ccccc1] | F | F |
| —$CH_3$ | 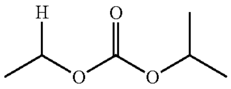 | F | F |
| —$CH_3$ | 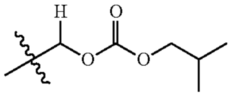 [SMILES: *COC(=O)OCC(C)C] | F | F |
| —$CH_3$ | 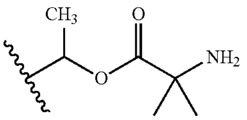 [SMILES: *C(C)OC(=O)C(C)(C)N] | F | F |
| —$CH_3$ | 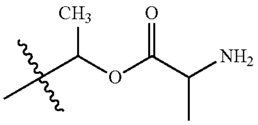 | F | F |
| —$CH_3$ | 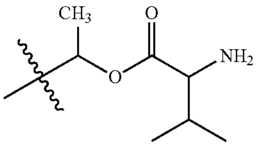 [SMILES: *C(C)OC(=O)C(N)C(C)C] | F | F |
| —$CH_3$ | 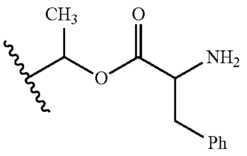 [SMILES: *C(C)OC(=O)C(N)Cc1ccccc1] | F | F |
| —$CH_3$ | 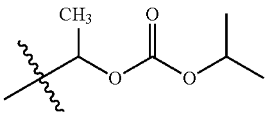 [SMILES: *C(C)OC(=O)OC(C)C] | F | F |
| —$CH_3$ | 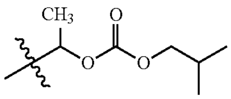 [SMILES: *C(C)OC(=O)OCC(C)C] | F | F |

TABLE A-continued
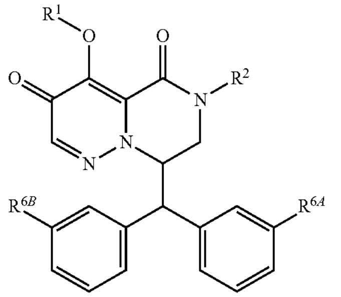
| $R^2$ | $R^1$ | $R^{6A}$ | $R^{6B}$ |
|---|---|---|---|
| —$CH_2CH_3$ | 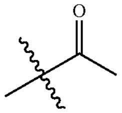 [SMILES: *C(C)=O] | F | F |
| —$CH_2CH_3$ | 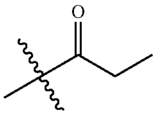 [SMILES: *C(=O)CC] | F | F |
| —$CH_2CH_3$ | 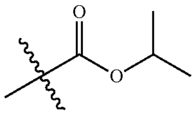 [SMILES: *C(=O)OC(C)C] | F | F |
| —$CH_2CH_3$ | 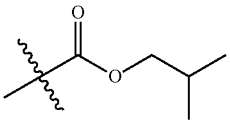 [SMILES: *C(=O)OCC(C)C] | F | F |
| —$CH_2CH_3$ | 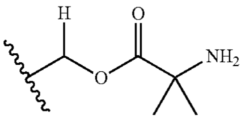 [SMILES: *COC(=O)C(C)(C)N] | F | F |
| —$CH_2CH_3$ | 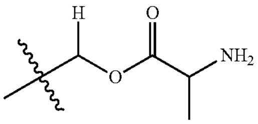 | F | F |
| —$CH_2CH_3$ | 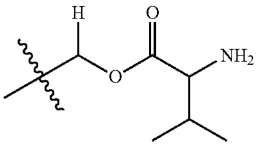 [SMILES: *COC(=O)C(N)C(C)C] | F | F |
| —$CH_2CH_3$ | 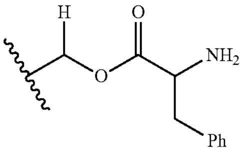 [SMILES: *COC(=O)C(N)Cc1ccccc1] | F | F |
| —$CH_2CH_3$ | 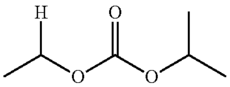 | F | F |
TABLE A-continued
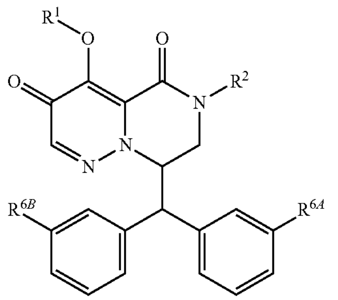
| $R^2$ | $R^1$ | $R^{6A}$ | $R^{6B}$ |
|---|---|---|---|
| —$CH_2CH_3$ | 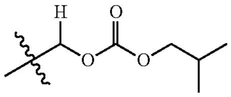 [SMILES: *COC(=O)OCC(C)C] | F | F |
| —$CH_2CH_3$ | 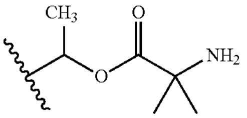 [SMILES: *C(C)OC(=O)C(C)(C)N] | F | F |
| —$CH_2CH_3$ | 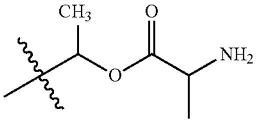 | F | F |
| —$CH_2CH_3$ | 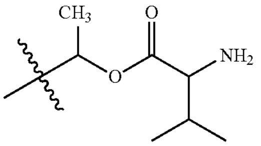 | F | F |
| —$CH_2CH_3$ | 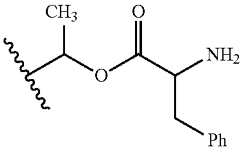 [SMILES: *C(C)OC(=O)C(N)Cc1ccccc1] | F | F |
| —$CH_2CH_3$ | 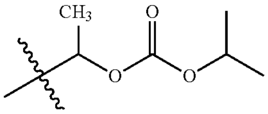 | F | F |
| —$CH_2CH_3$ | 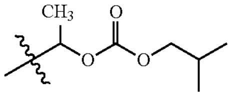 | F | F |
| —$CH_2CH(CH_3)_2$ | 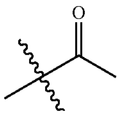 [SMILES: *C(C)=O] | F | F |
| —$CH_2CH(CH_3)_2$ | 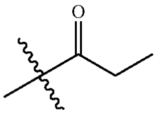 [SMILES: *C(=O)CC] | F | F |

TABLE A-continued
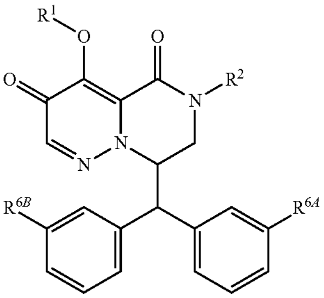
| $R^2$ | $R^1$ | $R^{6A}$ | $R^{6B}$ |
|---|---|---|---|
| $—CH_2CH(CH_3)_2$ | 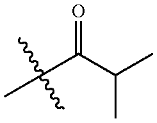 [SMILES: *C(=O)C(C)C] | F | F |
| $—CH_2CH(CH_3)_2$ | 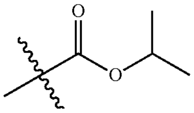 [SMILES: *C(=O)OC(C)C] | F | F |
| $—CH_2CH(CH_3)_2$ | 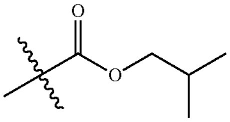 [SMILES: *C(=O)OCC(C)C] | F | F |
| $—CH_2CH(CH_3)_2$ | 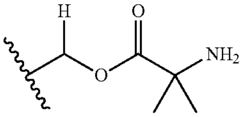 [SMILES: *COC(=O)C(C)(C)N] | F | F |
| $—CH_2CH(CH_3)_2$ | 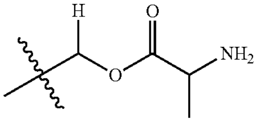 [SMILES: *COC(=O)C(C)N] | F | F |
| $—CH_2CH(CH_3)_2$ | 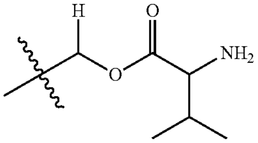 [SMILES: *COC(=O)C(N)C(C)C] | F | F |
| $—CH_2CH(CH_3)_2$ | 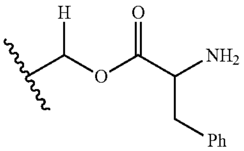 [SMILES: *COC(=O)C(N)Cc1ccccc1] | F | F |
| $—CH_2CH(CH_3)_2$ | 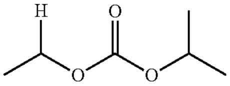 | F | F |
| $—CH_2CH(CH_3)_2$ | 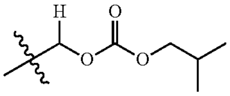 [SMILES: *COC(=O)OCC(C)C] | F | F |
TABLE A-continued
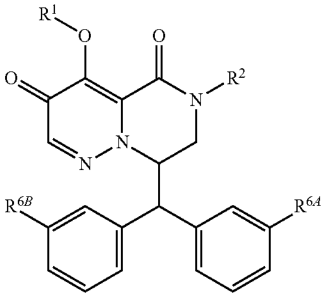
| $R^2$ | $R^1$ | $R^{6A}$ | $R^{6B}$ |
|---|---|---|---|
| $—CH_2CH(CH_3)_2$ | 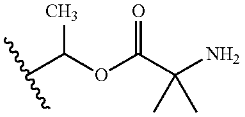 [SMILES: *C(C)OC(=O)C(C)(C)N] | F | F |
| $—CH_2CH(CH_3)_2$ | 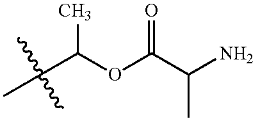 | F | F |
| $—CH_2CH(CH_3)_2$ | 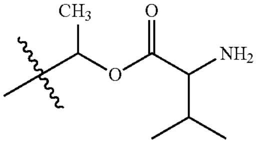 | F | F |
| $—CH_2CH(CH_3)_2$ | 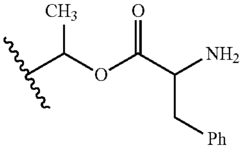 [SMILES: *C(C)OC(=O)C(N)Cc1ccccc1] | F | F |
| $—CH_2CH(CH_3)_2$ | 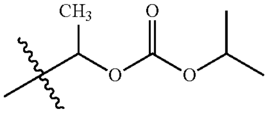 [SMILES: *C(C)OC(=O)OC(C)C] | F | F |
| $—CH_2CH(CH_3)_2$ | 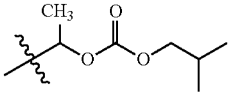 [SMILES: *C(C)OC(=O)OCC(C)C] | F | F |
| $—CH_2CH_2CH_3$ | 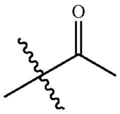 [SMILES: *C(C)=O] | F | F |
| $—CH_2CH_2CH_3$ | 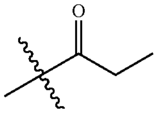 [SMILES: *C(=O)CC] | F | F |
| $—CH_2CH_2CH_3$ | 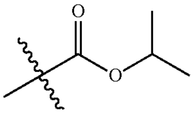 | F | F |

TABLE A-continued
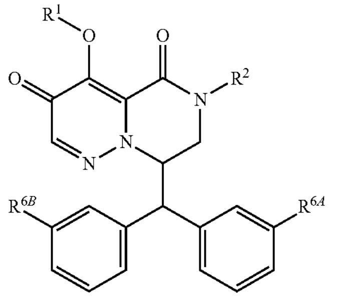
| $R^2$ | $R^1$ | $R^{6A}$ | $R^{6B}$ |
|---|---|---|---|
| $—CH_2CH_2CH_3$ | 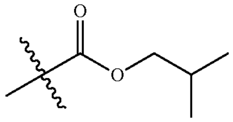 [SMILES: *C(=O)OCC(C)C] | F | F |
| $—CH_2CH_2CH_3$ | 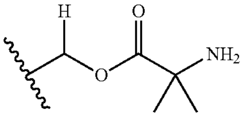 [SMILES: *COC(=O)C(C)(C)N] | F | F |
| $—CH_2CH_2CH_3$ | 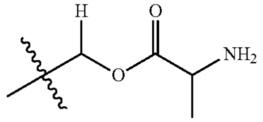 [SMILES: *COC(=O)C(C)N] | F | F |
| $—CH_2CH_2CH_3$ | 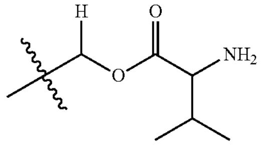 [SMILES: *COC(=O)C(N)C(C)C] | F | F |
| $—CH_2CH_2CH_3$ | 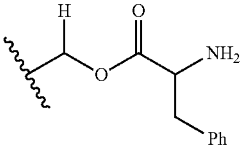 [SMILES: *COC(=O)C(N)Cc1ccccc1] | F | F |
| $—CH_2CH_2CH_3$ | 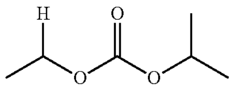 | F | F |
| $—CH_2CH_2CH_3$ | 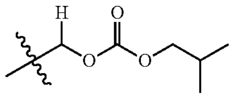 [SMILES: *COC(=O)OCC(C)C] | F | F |
| $—CH_2CH_2CH_3$ | 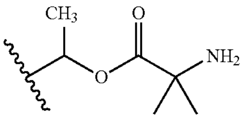 | F | F |
| $—CH_2CH_2CH_3$ | 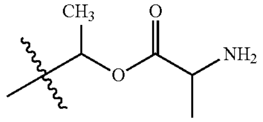 | F | F |
TABLE A-continued
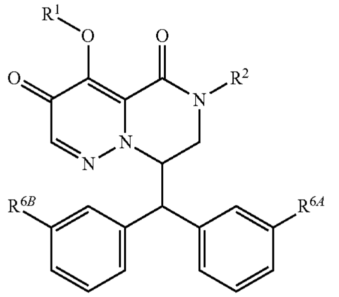
| $R^2$ | $R^1$ | $R^{6A}$ | $R^{6B}$ |
|---|---|---|---|
| $—CH_2CH_2CH_3$ | 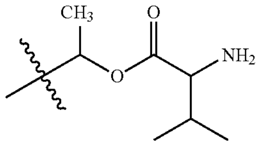 | F | F |
| $—CH_2CH_2CH_3$ | 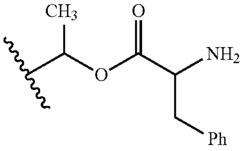 [SMILES: *C(C)OC(=O)C(N)Cc1ccccc1] | F | F |
| $—CH_2CH_2CH_3$ | 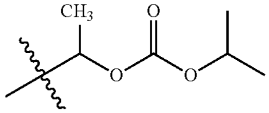 [SMILES: *C(C)OC(=O)OC(C)C] | F | F |
| $—CH_2CH_2CH_3$ | 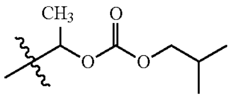 [SMILES: *C(C)OC(=O)OCC(C)C] | F | F |
| $—CH_2CH_2CH_2CH_3$ | 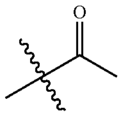 [SMILES: *C(C)=O] | F | F |
| $—CH_2CH_2CH_2CH_3$ | 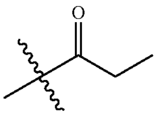 [SMILES: *C(=O)CC] | F | F |
| $—CH_2CH_2CH_2CH_3$ | 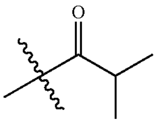 [SMILES: *C(=O)C(C)C] | F | F |
| $—CH_2CH_2CH_2CH_3$ | 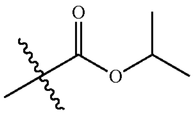 | F | F |
| $—CH_2CH_2CH_2CH_3$ | 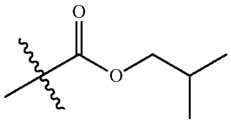 [SMILES: *C(=O)OCC(C)C] | F | F |

TABLE A-continued
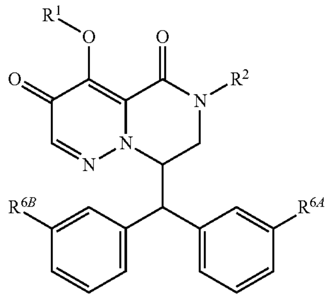
| $R^2$ | $R^1$ | $R^{6A}$ | $R^{6B}$ |
|---|---|---|---|
| $—CH_2CH_2CH_2CH_3$ | 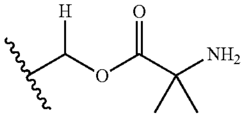 [SMILES: *COC(=O)C(C)(C)N] | F | F |
| $—CH_2CH_2CH_2CH_3$ | 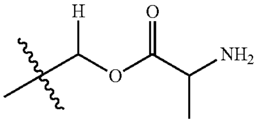 [SMILES: *COC(=O)C(C)N] | F | F |
| $—CH_2CH_2CH_2CH_3$ | 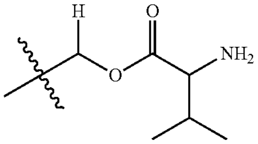 [SMILES: *COC(=O)C(N)C(C)C] | F | F |
| $—CH_2CH_2CH_2CH_3$ | 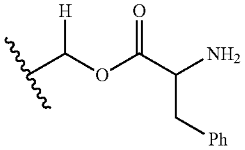 [SMILES: *COC(=O)C(N)Cc1ccccc1] | F | F |
| $—CH_2CH_2CH_2CH_3$ | 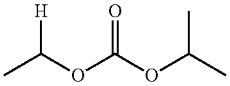 | F | F |
| $—CH_2CH_2CH_2CH_3$ | 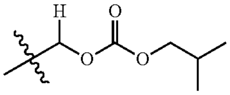 [SMILES: *COC(=O)OCC(C)C] | F | F |
| $—CH_2CH_2CH_2CH_3$ | 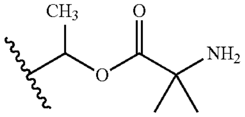 | F | F |
| $—CH_2CH_2CH_2CH_3$ | 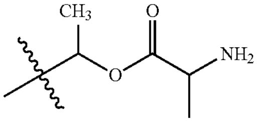 | F | F |
| $—CH_2CH_2CH_2CH_3$ | 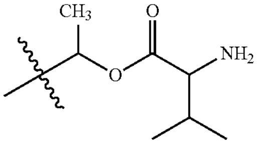 | F | F |
TABLE A-continued
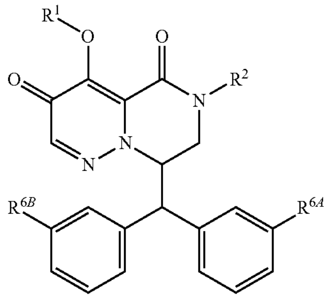
| $R^2$ | $R^1$ | $R^{6A}$ | $R^{6B}$ |
|---|---|---|---|
| $—CH_2CH_2CH_2CH_3$ | 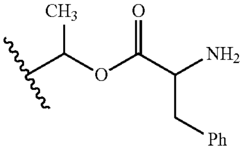 [SMILES: *C(C)OC(=O)C(N)Cc1ccccc1] | F | F |
| $—CH_2CH_2CH_2CH_3$ | 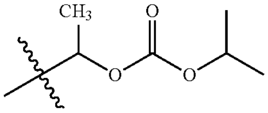 | F | F |
| $—CH_2CH_2CH_2CH_3$ | 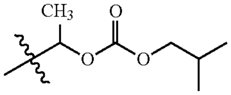 [SMILES: *C(C)OC(=O)OCC(C)C] | F | F |
| 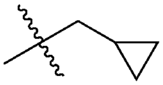 [SMILES: *CC1CC1] | 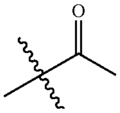 [SMILES: *C(C)=O] | F | F |
| 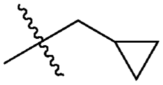 [SMILES: *CC1CC1] | 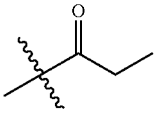 [SMILES: *C(=O)CC] | F | F |
| 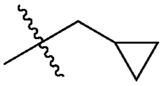 [SMILES: *CC1CC1] | 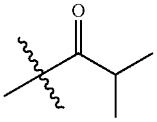 [SMILES: *C(=O)C(C)C] | F | F |
| 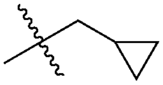 [SMILES: *CC1CC1] | 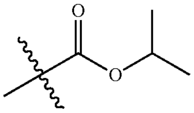 | F | F |
| 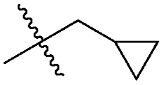 [SMILES: *CC1CC1] | 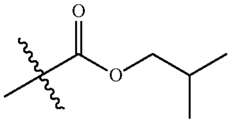 [SMILES: *C(=O)OCC(C)C] | F | F |
| 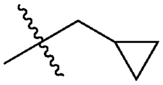 [SMILES: *CC1CC1] | 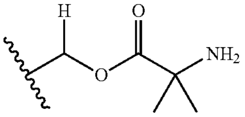 [SMILES: *COC(=O)C(C)(C)N] | F | F |

TABLE A-continued
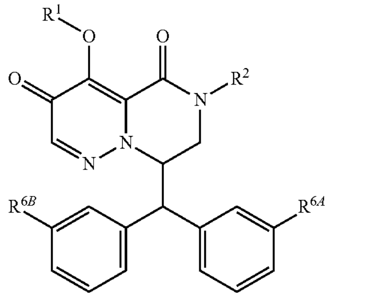
| $R^2$ | $R^1$ | $R^{6A}$ | $R^{6B}$ |
|---|---|---|---|
| 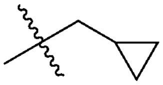 | 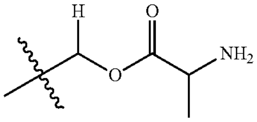 | F | F |
| 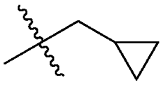 [SMILES: *CC1CC1] | 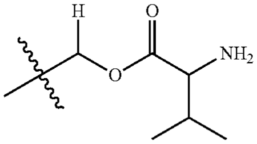 [SMILES: *COC(=O)C(N)C(C)C] | F | F |
| 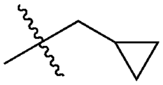 [SMILES: *CC1CC1] | 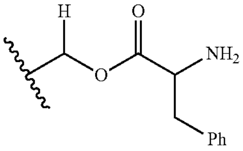 | F | F |
| 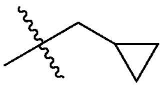 [SMILES: *CC1CC1] | 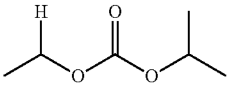 | F | F |
| 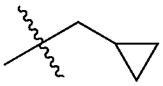 [SMILES: *CC1CC1] | 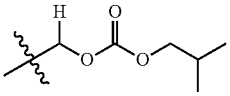 [SMILES: *COC(=O)OCC(C)C] | F | F |
| 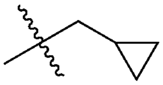 | 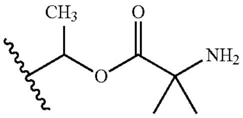 | F | F |
| 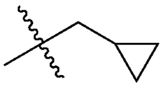 [SMILES: *CC1CC1] | 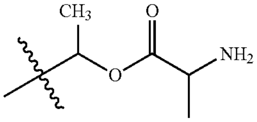 | F | F |
| 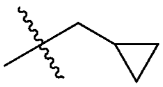 [SMILES: *CC1CC1] | 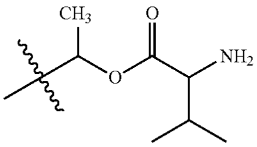 | F | F |
| 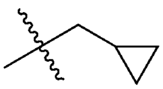 | 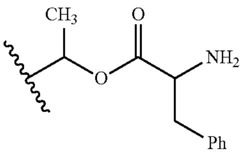 | F | F |
TABLE A-continued
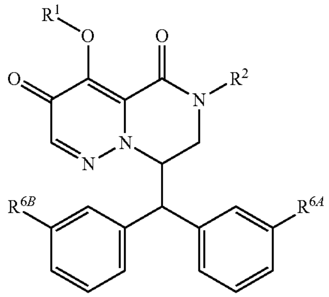
| $R^2$ | $R^1$ | $R^{6A}$ | $R^{6B}$ |
|---|---|---|---|
| 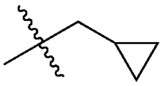 [SMILES: *CC1CC1] | 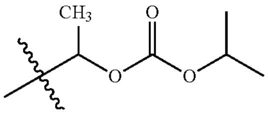 | F | F |
| 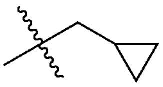 [SMILES: *CC1CC1] | 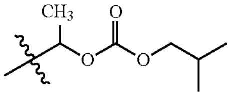 [SMILES: *C(C)OC(=O)OCC(C)C] | F | F |
| 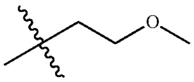 [SMILES: *CCOC] | 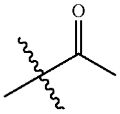 [SMILES: *C(C)=O] | F | F |
| 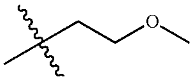 [SMILES: *CCOC] | 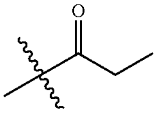 [SMILES: *C(=O)CC] | F | F |
| 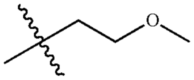 [SMILES: *CCOC] | 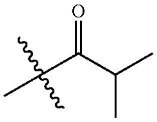 [SMILES: *C(=O)C(C)C] | F | F |
| 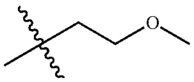 [SMILES: *CCOC] | 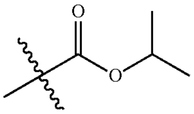 [SMILES: *C(=O)OC(C)C] | F | F |
| 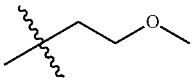 [SMILES: *CCOC] | 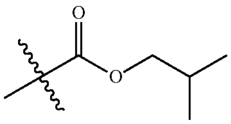 [SMILES: *C(=O)OCC(C)C] | F | F |
| 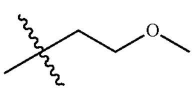 [SMILES: *CCOC] | 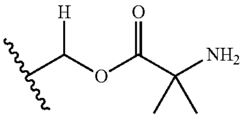 [SMILES: *COC(=O)C(C)(C)N] | F | F |
| 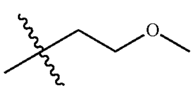 [SMILES: *CCOC] | 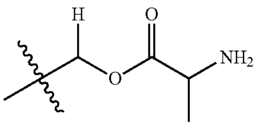 [SMILES: *COC(=O)C(C)N] | F | F |

TABLE A-continued
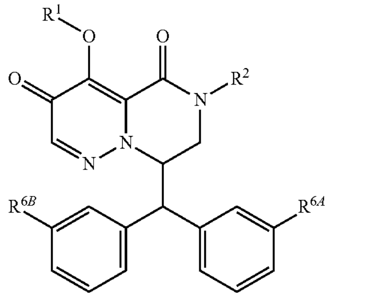
| $R^2$ | $R^1$ | $R^{6A}$ | $R^{6B}$ |
|---|---|---|---|
| 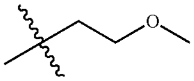 [SMILES: *CCOC] | 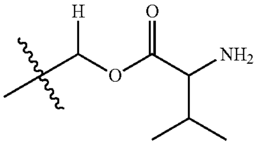 | F | F |
| 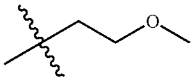 [SMILES: *CCOC] | 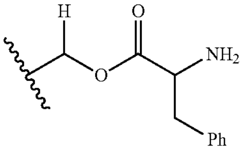 [SMILES: *COC(=O)C(N)Cc1ccccc1] | F | F |
| 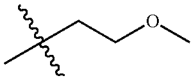 [SMILES: *CCOC] | 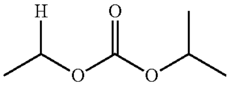 | F | F |
| 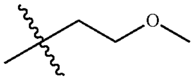 [SMILES: *CCOC] | 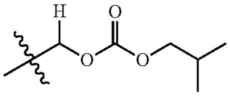 [SMILES: *COC(=O)OCC(C)C] | F | F |
| 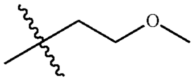 [SMILES: *CCOC] | 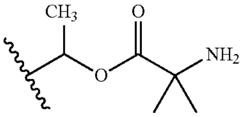 | F | F |
| 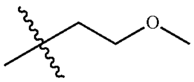 [SMILES: *CCOC] | 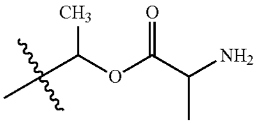 | F | F |
| 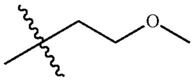 [SMILES: *CCOC] | 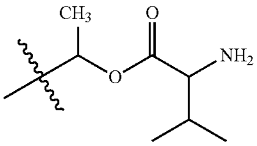 | F | F |
| 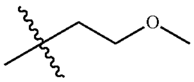 [SMILES: *CCOC] | 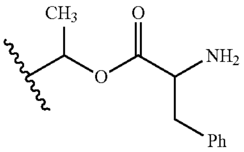 | F | F |
| 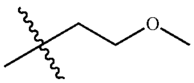 [SMILES: *CCOC] | 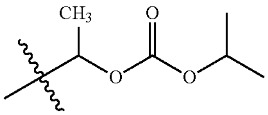 [SMILES: *C(C)OC(=O)OC(C)C] | F | F |
TABLE A-continued
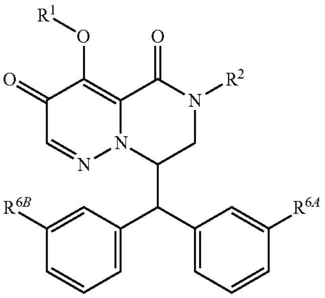
| $R^2$ | $R^1$ | $R^{6A}$ | $R^{6B}$ |
|---|---|---|---|
| 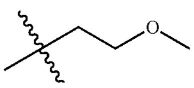 [SMILES: *CCOC] | 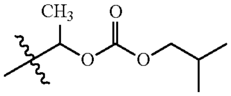 [SMILES: *C(C)OC(=O)OCC(C)C] | F | F |
| 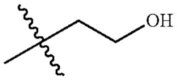 [SMILES: *CCO] | 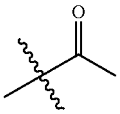 [SMILES: *C(C)=O] | F | F |
| 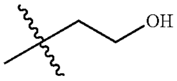 [SMILES: *CCO] | 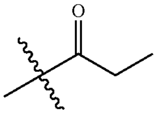 [SMILES: *C(=O)CC] | F | F |
| 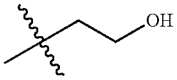 [SMILES: *CCO] | 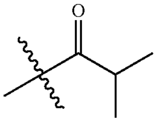 [SMILES: *C(=O)C(C)C] | F | F |
| 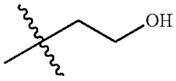 [SMILES: *CCO] | 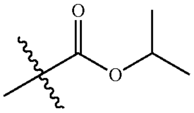 | F | F |
| 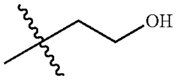 [SMILES: *CCO] | 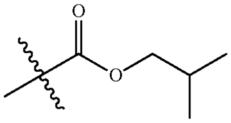 [SMILES: *C(=O)OCC(C)C] | F | F |
| 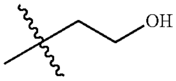 [SMILES: *CCO] | 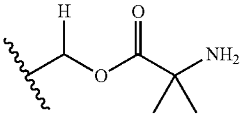 [SMILES: *COC(=O)C(C)(C)N] | F | F |
| 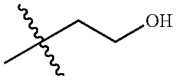 [SMILES: *CCO] | 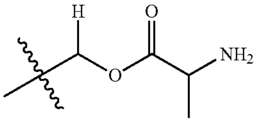 [SMILES: *COC(=O)C(C)N] | F | F |
| 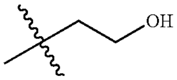 [SMILES: *CCO] | 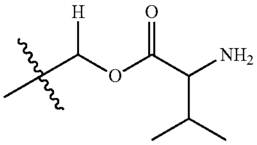 [SMILES: *COC(=O)C(N)C(C)C] | F | F |

TABLE A-continued
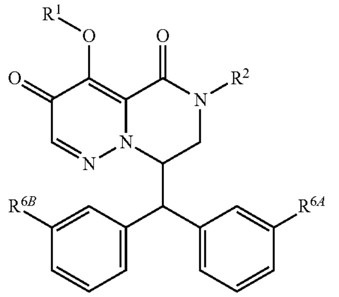
| $R^2$ | $R^1$ | $R^{6A}$ | $R^{6B}$ |
|---|---|---|---|
| 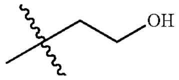 [SMILES: *CCO] | 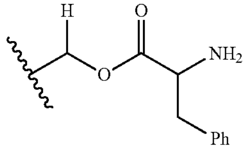 [SMILES: *COC(=O)C(N)Cc1ccccc1] | F | F |
| 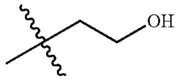 [SMILES: *CCO] | 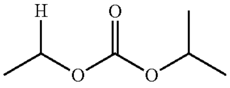 | F | F |
| 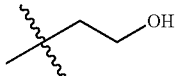 [SMILES: *CCO] | 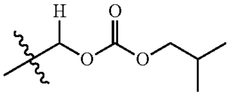 [SMILES: *COC(=O)OCC(C)C] | F | F |
| 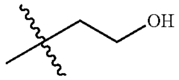 [SMILES: *CCO] | 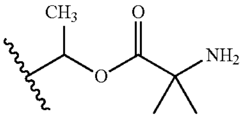 | F | F |
| 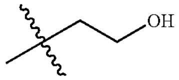 [SMILES: *CCO] | 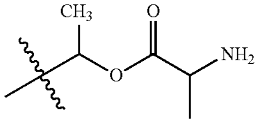 | F | F |
| 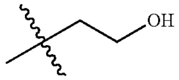 [SMILES: *CCO] | 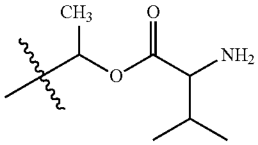 | F | F |
| 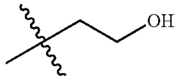 [SMILES: *CCO] | 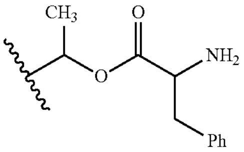 | F | F |
| 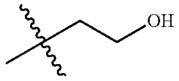 [SMILES: *CCO] | 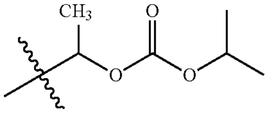 [SMILES: *C(C)OC(=O)OC(C)C] | F | F |
| 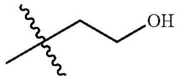 [SMILES: *CCO] | 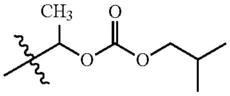 [SMILES: *C(C)OC(=O)OCC(C)C] | F | F |
TABLE A-continued
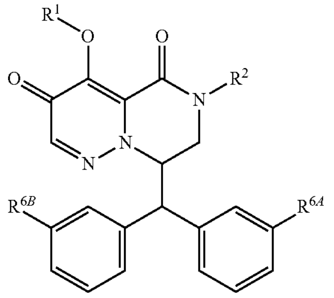
| $R^2$ | $R^1$ | $R^{6A}$ | $R^{6B}$ |
|---|---|---|---|
| $—CH_2CH{=}CF_2$ | 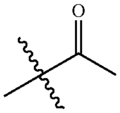 [SMILES: *C(C)=O] | F | F |
| $—CH_2CH{=}CF_2$ | 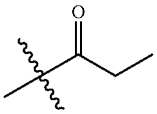 [SMILES: *C(=O)CC] | F | F |
| $—CH_2CH{=}CF_2$ | 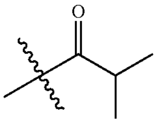 [SMILES: *C(=O)C(C)C] | F | F |
| $—CH_2CH{=}CF_2$ | 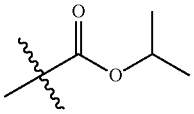 [SMILES: *C(=O)OC(C)C] | F | F |
| $—CH_2CH{=}CF_2$ | 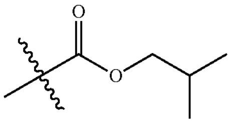 [SMILES: *C(=O)OCC(C)C] | F | F |
| $—CH_2CH{=}CF_2$ | 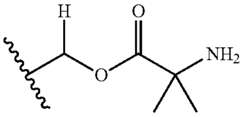 [SMILES: *COC(=O)C(C)(C)N] | F | F |
| $—CH_2CH{=}CF_2$ | 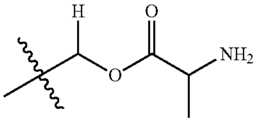 [SMILES: *COC(=O)C(C)N] | F | F |
| $—CH_2CH{=}CF_2$ | 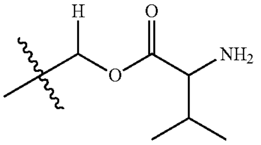 [SMILES: *COC(=O)C(N)C(C)C] | F | F |
| $—CH_2CH{=}CF_2$ | 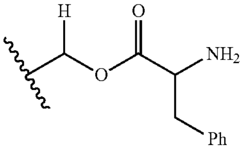 [SMILES: *COC(=O)C(N)Cc1ccccc1] | F | F |

TABLE A-continued
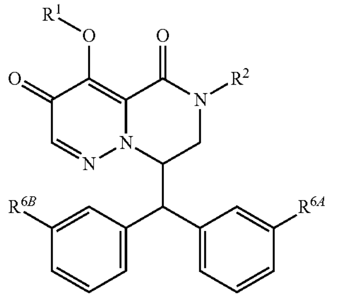
| $R^2$ | $R^1$ | $R^{6A}$ | $R^{6B}$ |
|---|---|---|---|
| $—CH_2CH{=}CF_2$ | 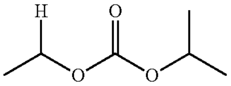 | F | F |
| $—CH_2CH{=}CF_2$ | 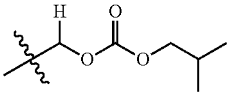 [SMILES: *COC(=O)OCC(C)C] | F | F |
| $—CH_2CH{=}CF_2$ | 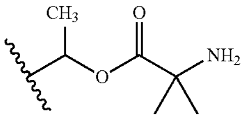 | F | F |
| $—CH_2CH{=}CF_2$ | 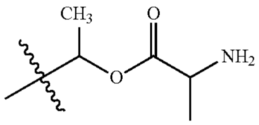 | F | F |
| $—CH_2CH{=}CF_2$ | 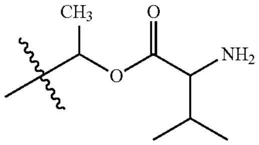 [SMILES: *C(C)OC(=O)C(N)C(C)C] | F | F |
| $—CH_2CH{=}CF_2$ | 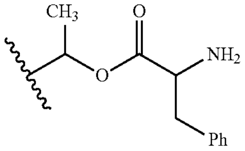 | F | F |
| $—CH_2CH{=}CF_2$ | 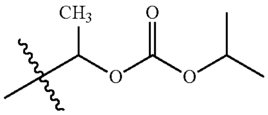 [SMILES: *C(C)OC(=O)OC(C)C] | F | F |
| $—CH_2CH{=}CF_2$ | 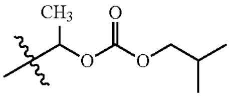 [SMILES: *C(C)OC(=O)OCC(C)C] | F | F |
| $—CH_2CF_3$ | 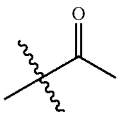 [SMILES: *C(C)=O] | F | F |
| $—CH_2CF_3$ | 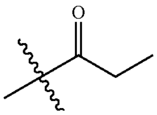 [SMILES: *C(=O)CC] | F | F |
TABLE A-continued
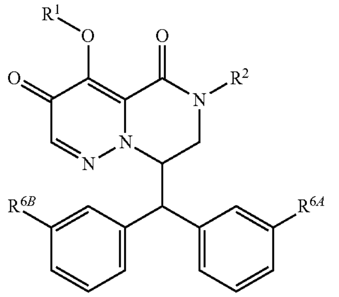
| $R^2$ | $R^1$ | $R^{6A}$ | $R^{6B}$ |
|---|---|---|---|
| $—CH_2CF_3$ | 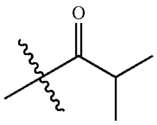 [SMILES: *C(=O)C(C)C] | F | F |
| $—CH_2CF_3$ | 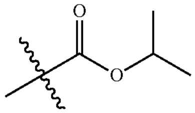 [SMILES: *C(=O)OC(C)C] | F | F |
| $—CH_2CF_3$ | 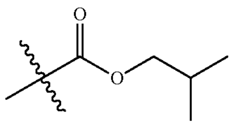 [SMILES: *C(=O)OCC(C)C] | F | F |
| $—CH_2CF_3$ | 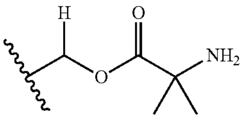 [SMILES: *COC(=O)C(C)(C)N] | F | F |
| $—CH_2CF_3$ | 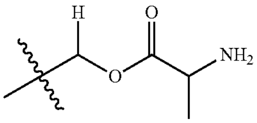 [SMILES: *COC(=O)C(C)N] | F | F |
| $—CH_2CF_3$ | 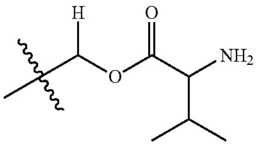 [SMILES: *COC(=O)C(N)C(C)C] | F | F |
| $—CH_2CF_3$ | 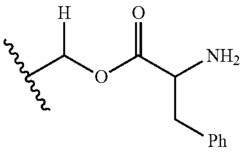 [SMILES: *COC(=O)C(N)Cc1ccccc1] | F | F |
| $—CH_2CF_3$ | 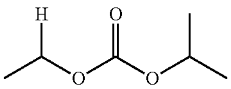 | F | F |
| $—CH_2CF_3$ | 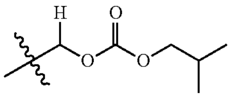 [SMILES: *COC(=O)OCC(C)C] | F | F |

TABLE A-continued
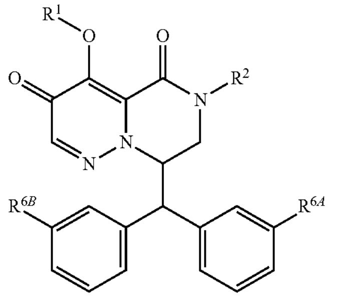
| $R^2$ | $R^1$ | $R^{6A}$ | $R^{6B}$ |
|---|---|---|---|
| $—CH_2CF_3$ | 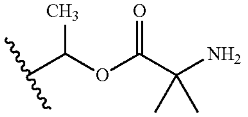 | F | F |
| $—CH_2CF_3$ | 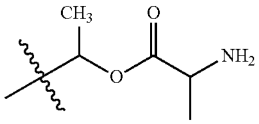 | F | F |
| $—CH_2CF_3$ | 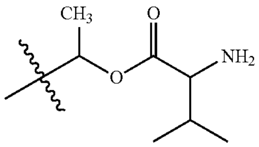 | F | F |
| $—CH_2CF_3$ | 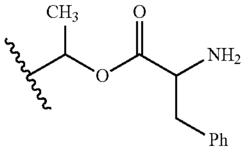 [SMILES: *C(C)OC(=O)C(N)Cc1ccccc1] | F | F |
| $—CH_2CF_3$ | 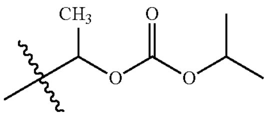 [SMILES: *C(C)OC(=O)OC(C)C] | F | F |
| $—CH_2CF_3$ | 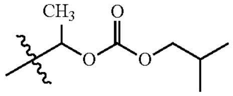 [SMILES: *C(C)OC(=O)OCC(C)C] | F | F |
| $—CH_2CH_2CF_3$ | 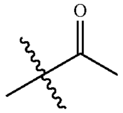 [SMILES: *C(C)=O] | F | F |
| $—CH_2CH_2CF_3$ | 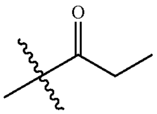 [SMILES: *C(=O)CC] | F | F |
| $—CH_2CH_2CF_3$ | 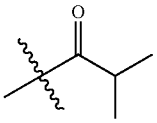 [SMILES: *C(=O)C(C)C] | F | F |
TABLE A-continued
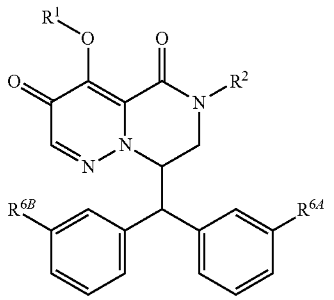
| $R^2$ | $R^1$ | $R^{6A}$ | $R^{6B}$ |
|---|---|---|---|
| $—CH_2CH_2CF_3$ | 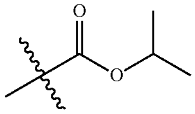 [SMILES: *C(=O)OC(C)C] | F | F |
| $—CH_2CH_2CF_3$ | 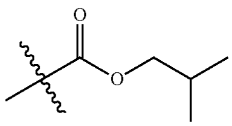 [SMILES: *C(=O)OCC(C)C] | F | F |
| $—CH_2CH_2CF_3$ | 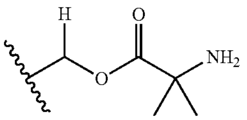 [SMILES: *COC(=O)C(C)(C)N] | F | F |
| $—CH_2CH_2CF_3$ | 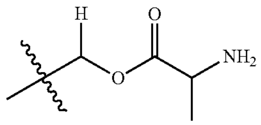 [SMILES: *COC(=O)C(C)N] | F | F |
| $—CH_2CH_2CF_3$ | 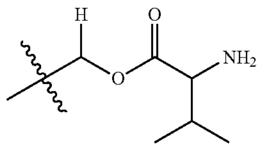 [SMILES: *COC(=O)C(N)C(C)C] | F | F |
| $—CH_2CH_2CF_3$ | 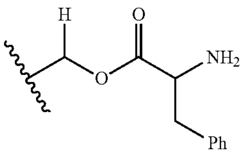 [SMILES: *COC(=O)C(N)Cc1ccccc1] | F | F |
| $—CH_2CH_2CF_3$ | 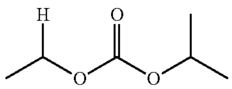 | F | F |
| $—CH_2CH_2CF_3$ | 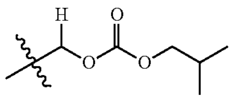 [SMILES: *COC(=O)OCC(C)C] | F | F |
| $—CH_2CH_2CF_3$ | 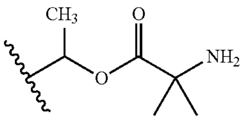 [SMILES: *C(C)OC(=O)C(C)(C)N] | F | F |

TABLE A-continued
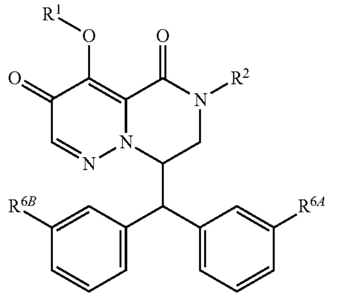
| $R^2$ | $R^1$ | $R^{6A}$ | $R^{6B}$ |
|---|---|---|---|
| $—CH_2CH_2CF_3$ | 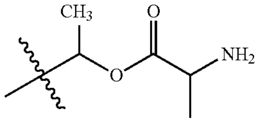 | F | F |
| $—CH_2CH_2CF_3$ | 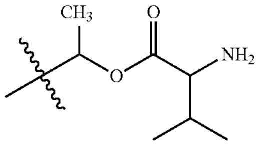 | F | F |
| $—CH_2CH_2CF_3$ | 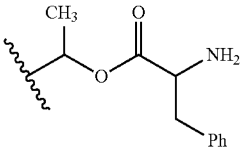 [SMILES: *C(C)OC(=O)C(N)Cc1ccccc1] | F | F |
| $—CH_2CH_2CF_3$ | 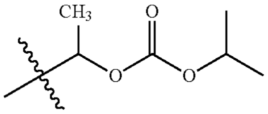 [SMILES: *C(C)OC(=O)OC(C)C] | F | F |
| $—CH_2CH_2CF_3$ | 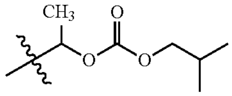 [SMILES: *C(C)OC(=O)OCC(C)C] | F | F |
| $—CH_2CHF_2$ | 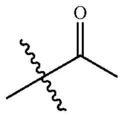 [SMILES: *C(C)=O] | F | F |
| $—CH_2CHF_2$ | 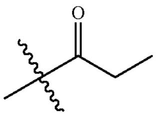 [SMILES: *C(=O)CC] | F | F |
| $—CH_2CHF_2$ | 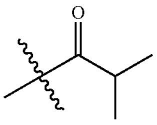 [SMILES: *C(=O)C(C)C] | F | F |
| $—CH_2CHF_2$ | 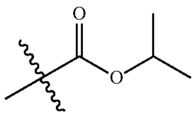 | F | F |
TABLE A-continued
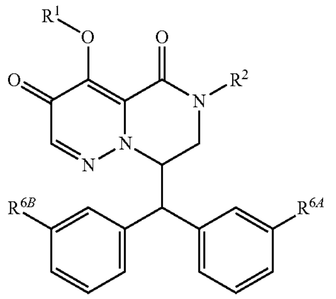
| $R^2$ | $R^1$ | $R^{6A}$ | $R^{6B}$ |
|---|---|---|---|
| $—CH_2CHF_2$ | 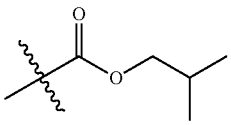 [SMILES: *C(=O)OCC(C)C] | F | F |
| $—CH_2CHF_2$ | 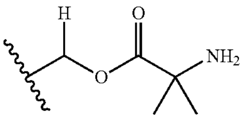 [SMILES: *COC(=O)C(C)(C)N] | F | F |
| $—CH_2CHF_2$ | 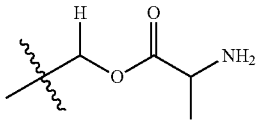 [SMILES: *COC(=O)C(C)N] | F | F |
| $—CH_2CHF_2$ | 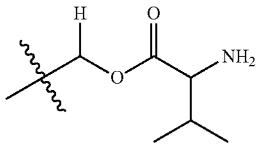 [SMILES: *COC(=O)C(N)C(C)C] | F | F |
| $—CH_2CHF_2$ | 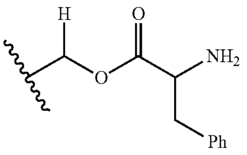 [SMILES: *COC(=O)C(N)Cc1ccccc1] | F | F |
| $—CH_2CHF_2$ | 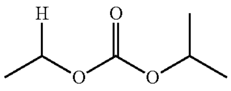 | F | F |
| $—CH_2CHF_2$ | 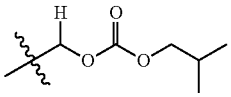 [SMILES: *COC(=O)OCC(C)C] | F | F |
| $—CH_2CHF_2$ | 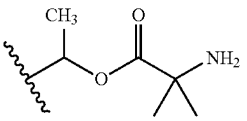 [SMILES: *C(C)OC(=O)C(C)(C)N] | F | F |
| $—CH_2CHF_2$ | 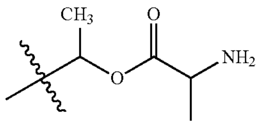 | F | F |

TABLE A-continued
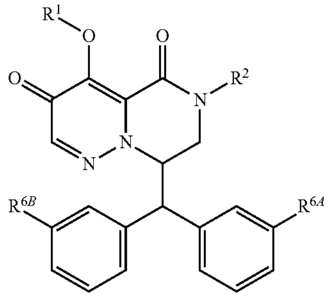
| $R^2$ | $R^1$ | $R^{6A}$ | $R^{6B}$ |
|---|---|---|---|
| $—CH_2CHF_2$ | 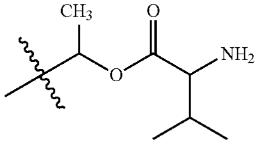 | F | F |
| $—CH_2CHF_2$ | 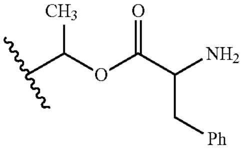 | F | F |
| $—CH_2CHF_2$ | 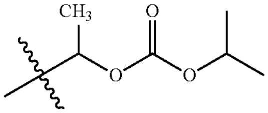 [SMILES: *C(C)OC(=O)OC(C)C] | F | F |
| $—CH_2CHF_2$ | 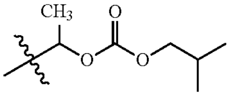 [SMILES: *C(C)OC(=O)OCC(C)C] | F | F |
| $—CH_2C(CH_3)F_2$ | 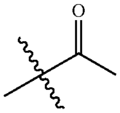 [SMILES: *C(C)=O] | F | F |
| $—CH_2C(CH_3)F_2$ | 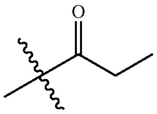 [SMILES: *C(=O)CC] | F | F |
| $—CH_2C(CH_3)F_2$ | 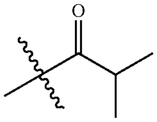 [SMILES: *C(=O)C(C)C] | F | F |
| $—CH_2C(CH_3)F_2$ | 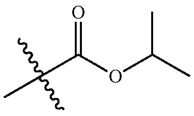 [SMILES: *C(=O)OC(C)C] | F | F |
| $—CH_2C(CH_3)F_2$ | 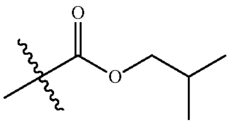 [SMILES: *C(=O)OCC(C)C] | F | F |
TABLE A-continued
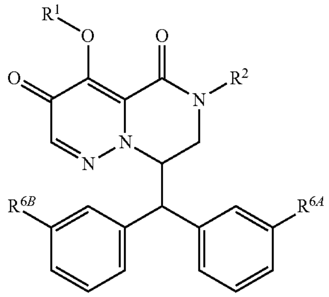
| $R^2$ | $R^1$ | $R^{6A}$ | $R^{6B}$ |
|---|---|---|---|
| $—CH_2C(CH_3)F_2$ | 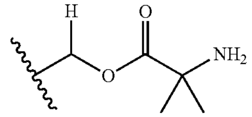 [SMILES: *COC(=O)C(C)(C)N] | F | F |
| $—CH_2C(CH_3)F_2$ | 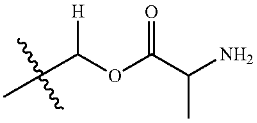 [SMILES: *COC(=O)C(C)N] | F | F |
| $—CH_2C(CH_3)F_2$ | 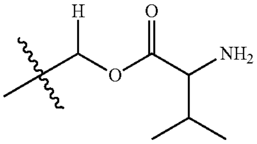 [SMILES: *COC(=O)C(N)C(C)C] | F | F |
| $—CH_2C(CH_3)F_2$ | 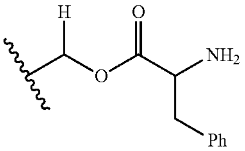 [SMILES: *COC(=O)C(N)Cc1ccccc1] | F | F |
| $—CH_2C(CH_3)F_2$ | 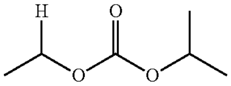 | F | F |
| $—CH_2C(CH_3)F_2$ | 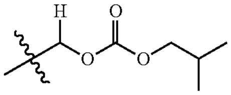 [SMILES: *COC(=O)OCC(C)C] | F | F |
| $—CH_2C(CH_3)F_2$ | 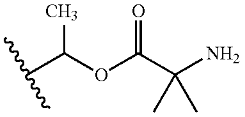 [SMILES: *C(C)OC(=O)C(C)(C)N] | F | F |
| $—CH_2C(CH_3)F_2$ | 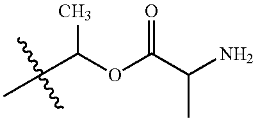 | F | F |
| $—CH_2C(CH_3)F_2$ | 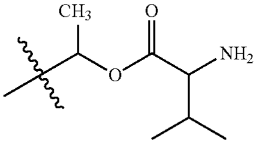 | F | F |

TABLE A-continued
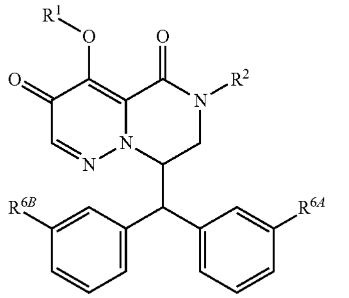
| $R^2$ | $R^1$ | $R^{6A}$ | $R^{6B}$ |
|---|---|---|---|
| $—CH_2C(CH_3)F_2$ | 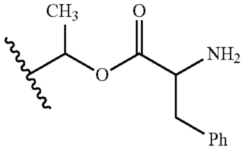 | F | F |
| $—CH_2C(CH_3)F_2$ | 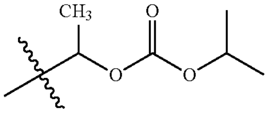 | F | F |
| $—CH_2C(CH_3)F_2$ | 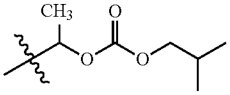 [SMILES: *C(C)OC(=O)OCC(C)C] | F | F |
| 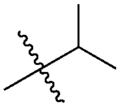 | 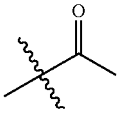 [SMILES: *C(C)=O] | Cl | Cl |
| 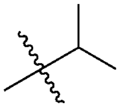 [SMILES: *C(C)C] | 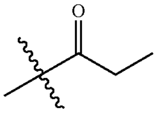 [SMILES: *C(=O)CC] | Cl | Cl |
| 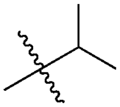 [SMILES: *C(C)C] | 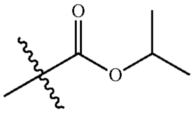 [SMILES: *C(=O)OC(C)C] | Cl | Cl |
| 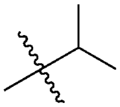 [SMILES: *C(C)C] | 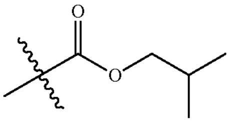 [SMILES: *C(=O)OCC(C)C] | Cl | Cl |
| 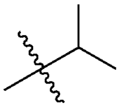 [SMILES: *C(C)C] | 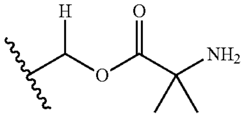 | Cl | Cl |
| 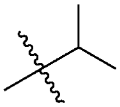 | 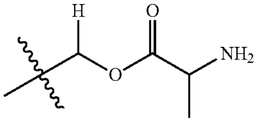 [SMILES: *COC(=O)C(C)N] | Cl | Cl |
TABLE A-continued
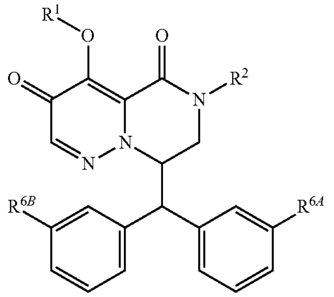
| $R^2$ | $R^1$ | $R^{6A}$ | $R^{6B}$ |
|---|---|---|---|
| 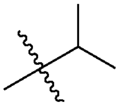 [SMILES: *C(C)C] | 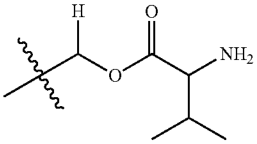 [SMILES: *COC(=O)C(N)C(C)C] | Cl | Cl |
| 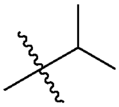 [SMILES: *C(C)C] | 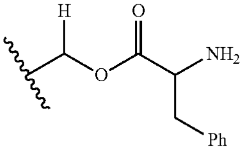 [SMILES: *COC(=O)C(N)Cc1ccccc1] | Cl | Cl |
| 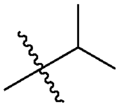 [SMILES: *C(C)C] | 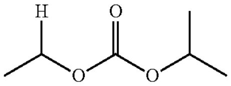 | Cl | Cl |
| 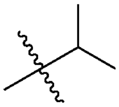 [SMILES: *C(C)C] | 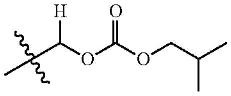 [SMILES: *COC(=O)OCC(C)C] | Cl | Cl |
| 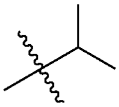 [SMILES: *C(C)C] | 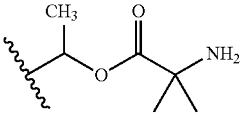 [SMILES: *C(C)OC(=O)C(C)(C)N] | Cl | Cl |
| 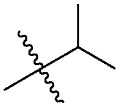 [SMILES: *C(C)C] | 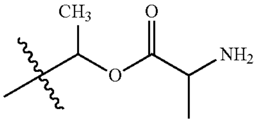 | Cl | Cl |
| 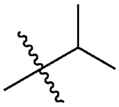 [SMILES: *C(C)C] | 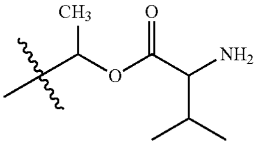 [SMILES: *C(C)OC(=O)C(N)C(C)C] | Cl | Cl |
| 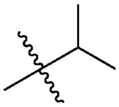 [SMILES: *C(C)C] | 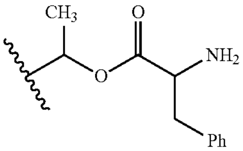 [SMILES: *C(C)OC(=O)C(N)Cc1ccccc1] | Cl | Cl |
| 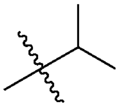 [SMILES: *C(C)C] | 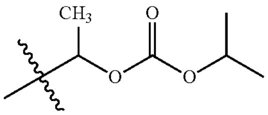 [SMILES: *C(C)OC(=O)OC(C)C] | Cl | Cl |

TABLE A-continued
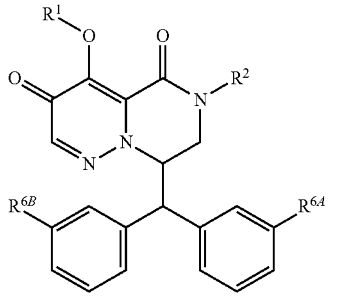
| $R^2$ | $R^1$ | $R^{6A}$ | $R^{6B}$ |
|---|---|---|---|
| 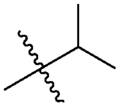 [SMILES: *C(C)C] | 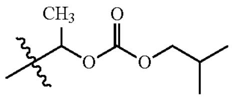 [SMILES: *C(C)OC(=O)OCC(C)C] | Cl | Cl |
| —$CH_3$ | 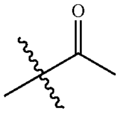 [SMILES: *C(C)=O] | Cl | Cl |
| —$CH_3$ | 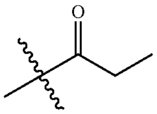 [SMILES: *C(=O)CC] | Cl | Cl |
| —$CH_3$ | 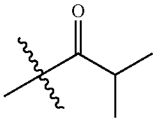 [SMILES: *C(=O)C(C)C] | Cl | Cl |
| —$CH_3$ | 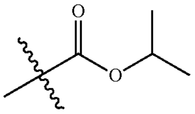 [SMILES: *C(=O)OC(C)C] | Cl | Cl |
| —$CH_3$ | 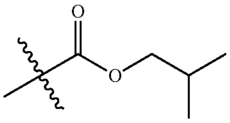 [SMILES: *C(=O)OCC(C)C] | Cl | Cl |
| —$CH_3$ | 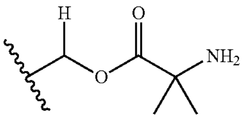 [SMILES: *COC(=O)C(C)(C)N] | Cl | Cl |
| —$CH_3$ | 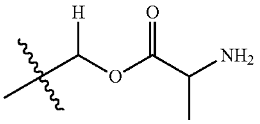 [SMILES: *COC(=O)C(C)N] | Cl | Cl |
| —$CH_3$ | 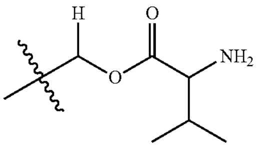 [SMILES: *COC(=O)C(N)C(C)C] | Cl | Cl |
TABLE A-continued
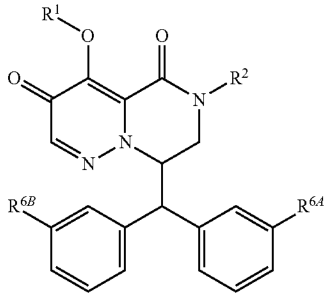
| $R^2$ | $R^1$ | $R^{6A}$ | $R^{6B}$ |
|---|---|---|---|
| —$CH_3$ | 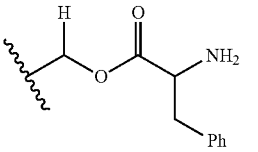 [SMILES: *COC(=O)C(N)Cc1ccccc1] | Cl | Cl |
| —$CH_3$ | 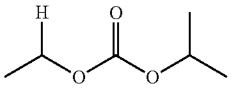 | Cl | Cl |
| —$CH_3$ | 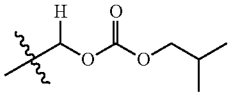 [SMILES: *COC(=O)OCC(C)C] | Cl | Cl |
| —$CH_3$ | 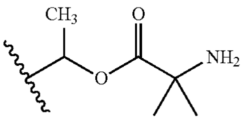 [SMILES: *C(C)OC(=O)C(C)(C)N] | Cl | Cl |
| —$CH_3$ | 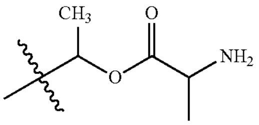 | Cl | Cl |
| —$CH_3$ | 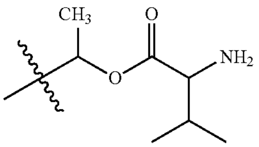 [SMILES: *C(C)OC(=O)C(N)C(C)C] | Cl | Cl |
| —$CH_3$ | 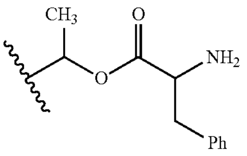 [SMILES: *C(C)OC(=O)C(N)Cc1ccccc1] | Cl | Cl |
| —$CH_3$ | 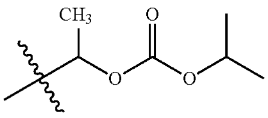 [SMILES: *C(C)OC(=O)OC(C)C] | Cl | Cl |
| —$CH_3$ | 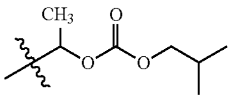 [SMILES: *C(C)OC(=O)OCC(C)C] | Cl | Cl |

TABLE A-continued
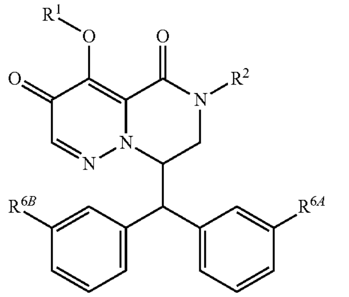
| $R^2$ | $R^1$ | $R^{6A}$ | $R^{6B}$ |
|---|---|---|---|
| $—CH_2CH_3$ | 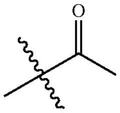 [SMILES: *C(C)=O] | Cl | Cl |
| $—CH_2CH_3$ | 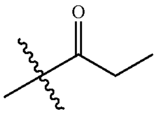 [SMILES: *C(=O)CC] | Cl | Cl |
| $—CH_2CH_3$ | 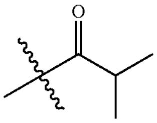 [SMILES: *C(=O)C(C)C] | Cl | Cl |
| $—CH_2CH_3$ | 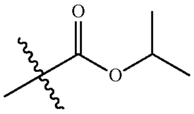 [SMILES: *C(=O)OC(C)C] | Cl | Cl |
| $—CH_2CH_3$ | 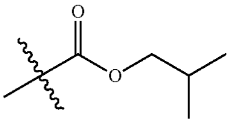 [SMILES: *C(=O)OCC(C)C] | Cl | Cl |
| $—CH_2CH_3$ | 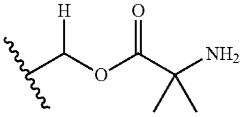 [SMILES: *COC(=O)C(C)(C)N] | Cl | Cl |
| $—CH_2CH_3$ | 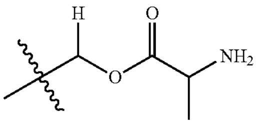 [SMILES: *COC(=O)C(C)N] | Cl | Cl |
| $—CH_2CH_3$ | 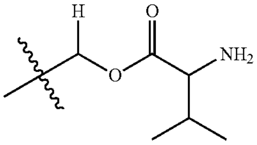 [SMILES: *COC(=O)C(N)C(C)C] | Cl | Cl |
| $—CH_2CH_3$ | 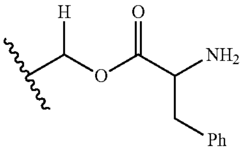 [SMILES: *COC(=O)C(N)Cc1ccccc1] | Cl | Cl |
TABLE A-continued
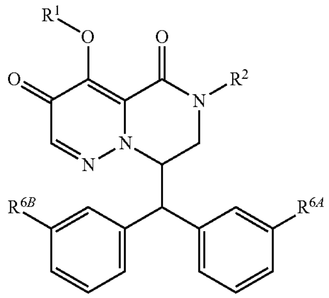
| $R^2$ | $R^1$ | $R^{6A}$ | $R^{6B}$ |
|---|---|---|---|
| $—CH_2CH_3$ | 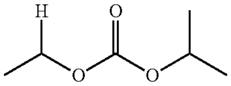 | Cl | Cl |
| $—CH_2CH_3$ | 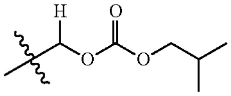 [SMILES: *COC(=O)OCC(C)C] | Cl | Cl |
| $—CH_2CH_3$ | 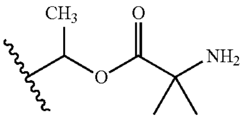 [SMILES: *C(C)OC(=O)C(C)(C)N] | Cl | Cl |
| $—CH_2CH_3$ | 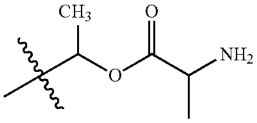 | Cl | Cl |
| $—CH_2CH_3$ | 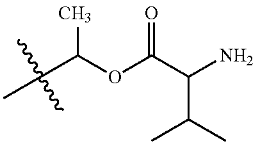 | Cl | Cl |
| $—CH_2CH_3$ | 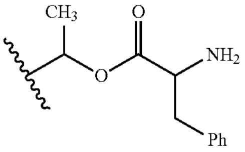 [SMILES: *C(C)OC(=O)C(N)Cc1ccccc1] | Cl | Cl |
| $—CH_2CH_3$ | 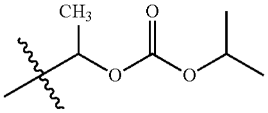 [SMILES: *C(C)OC(=O)OC(C)C] | Cl | Cl |
| $—CH_2CH_3$ | 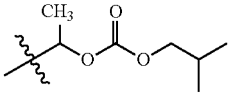 [SMILES: *C(C)OC(=O)OCC(C)C] | Cl | Cl |
| $—CH_2CH(CH_3)_2$ | H | Cl | Cl |
| $—CH_2CH(CH_3)_2$ | 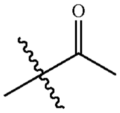 [SMILES: *C(C)=O] | Cl | Cl |

TABLE A-continued
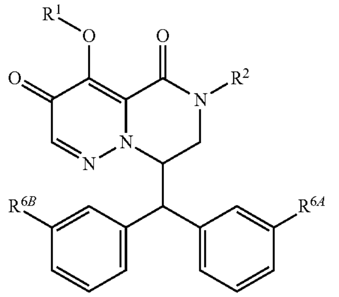
| $R^2$ | $R^1$ | $R^{6A}$ | $R^{6B}$ |
|---|---|---|---|
| $—CH_2CH(CH_3)_2$ | 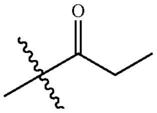 [SMILES: *C(=O)CC] | Cl | Cl |
| $—CH_2CH(CH_3)_2$ | 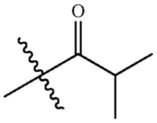 [SMILES: *C(=O)C(C)C] | Cl | Cl |
| $—CH_2CH(CH_3)_2$ | 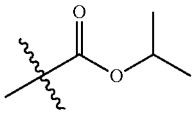 [SMILES: *C(=O)OC(C)C] | Cl | Cl |
| $—CH_2CH(CH_3)_2$ | 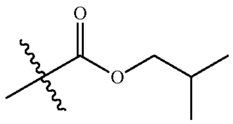 [SMILES: *C(=O)OCC(C)C] | Cl | Cl |
| $—CH_2CH(CH_3)_2$ | 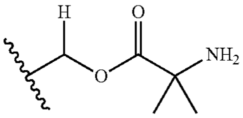 [SMILES: *COC(=O)C(C)(C)N] | Cl | Cl |
| $—CH_2CH(CH_3)_2$ | 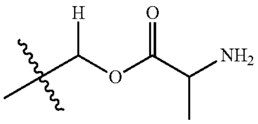 | Cl | Cl |
| $—CH_2CH(CH_3)_2$ | 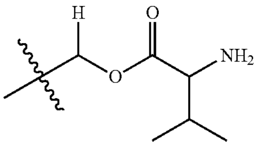 [SMILES: *COC(=O)C(N)C(C)C] | Cl | Cl |
| $—CH_2CH(CH_3)_2$ | 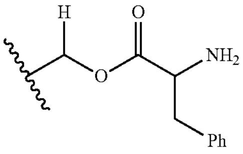 [SMILES: *COC(=O)C(N)Cc1ccccc1] | Cl | Cl |
| $—CH_2CH(CH_3)_2$ | 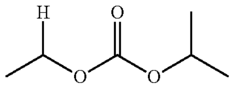 | Cl | Cl |
TABLE A-continued
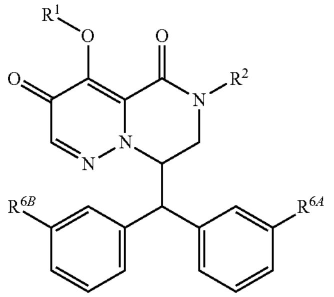
| $R^2$ | $R^1$ | $R^{6A}$ | $R^{6B}$ |
|---|---|---|---|
| $—CH_2CH(CH_3)_2$ | 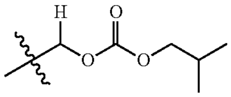 [SMILES: *COC(=O)OCC(C)C] | Cl | Cl |
| $—CH_2CH(CH_3)_2$ | 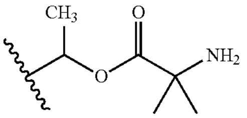 [SMILES: *C(C)OC(=O)C(C)(C)N] | Cl | Cl |
| $—CH_2CH(CH_3)_2$ | 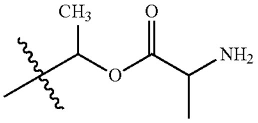 | Cl | Cl |
| $—CH_2CH(CH_3)_2$ | 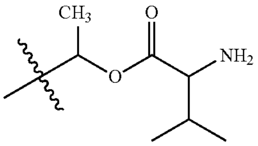 | Cl | Cl |
| $—CH_2CH(CH_3)_2$ | 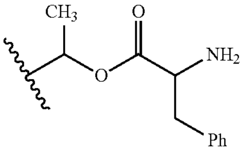 [SMILES: *C(C)OC(=O)C(N)Cc1ccccc1] | Cl | Cl |
| $—CH_2CH(CH_3)_2$ | 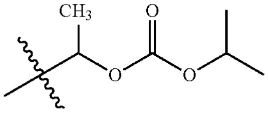 | Cl | Cl |
| $—CH_2CH(CH_3)_2$ | 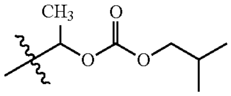 | Cl | Cl |
| $—CH_2CH_2CH_3$ | 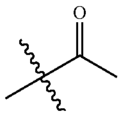 [SMILES: *C(C)=O] | Cl | Cl |
| $—CH_2CH_2CH_3$ | 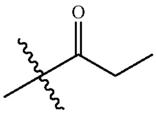 [SMILES: *C(=O)CC] | Cl | Cl |

TABLE A-continued

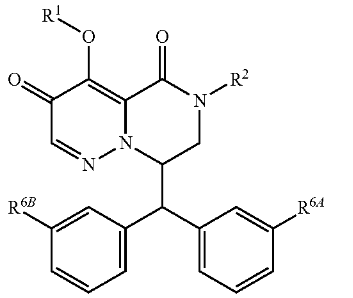

| $R^2$ | $R^1$ | $R^{6A}$ | $R^{6B}$ |
|---|---|---|---|
| $—CH_2CH_2CH_3$ | 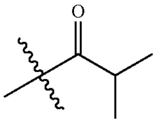 [SMILES: *C(=O)C(C)C] | Cl | Cl |
| $—CH_2CH_2CH_3$ | 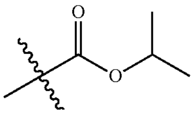 [SMILES: *C(=O)OC(C)C] | Cl | Cl |
| $—CH_2CH_2CH_3$ | 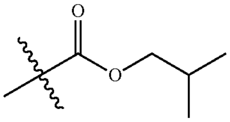 [SMILES: *C(=O)OCC(C)C] | Cl | Cl |
| $—CH_2CH_2CH_3$ | 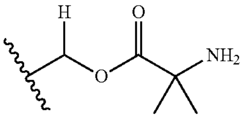 [SMILES: *COC(=O)C(C)(C)N] | Cl | Cl |
| $—CH_2CH_2CH_3$ | 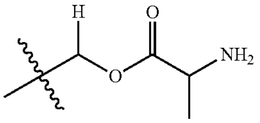 [SMILES: *COC(=O)C(C)N] | Cl | Cl |
| $—CH_2CH_2CH_3$ | 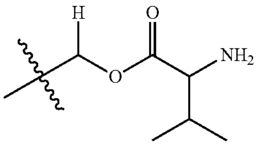 [SMILES: *COC(=O)C(N)C(C)C] | Cl | Cl |
| $—CH_2CH_2CH_3$ | 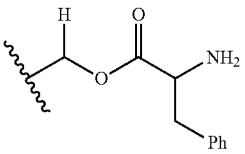 [SMILES: *COC(=O)C(N)Cc1ccccc1] | Cl | Cl |
| $—CH_2CH_2CH_3$ | 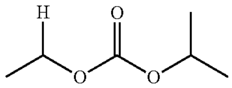 | Cl | Cl |
| $—CH_2CH_2CH_3$ | 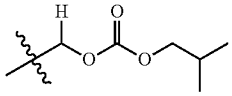 [SMILES: *COC(=O)OCC(C)C] | Cl | Cl |

TABLE A-continued

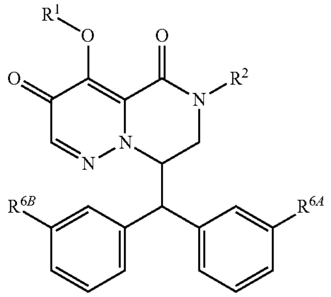

| $R^2$ | $R^1$ | $R^{6A}$ | $R^{6B}$ |
|---|---|---|---|
| $—CH_2CH_2CH_3$ | 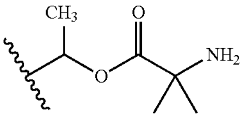 [SMILES: *C(C)OC(=O)C(C)(C)N] | Cl | Cl |
| $—CH_2CH_2CH_3$ | 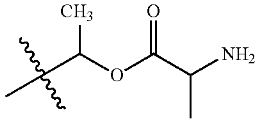 | Cl | Cl |
| $—CH_2CH_2CH_3$ | 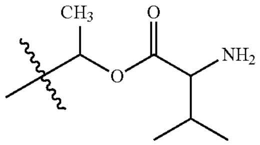 [SMILES: *C(C)OC(=O)C(N)C(C)C] | Cl | Cl |
| $—CH_2CH_2CH_3$ | 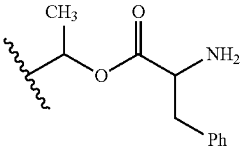 [SMILES: *C(C)OC(=O)C(N)Cc1ccccc1] | Cl | Cl |
| $—CH_2CH_2CH_3$ | 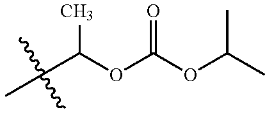 | Cl | Cl |
| $—CH_2CH_2CH_3$ | 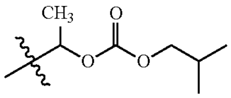 [SMILES: *C(C)OC(=O)OCC(C)C] | Cl | Cl |
| $—CH_2CH_2CH_2CH_3$ | H | Cl | Cl |
| $—CH_2CH_2CH_2CH_3$ | 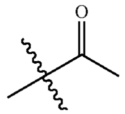 [SMILES: *C(C)=O] | Cl | Cl |
| $—CH_2CH_2CH_2CH_3$ | 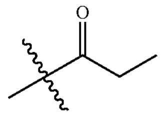 [SMILES: *C(=O)CC] | Cl | Cl |
| $—CH_2CH_2CH_2CH_3$ | 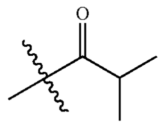 [SMILES: *C(=O)C(C)C] | Cl | Cl |

TABLE A-continued
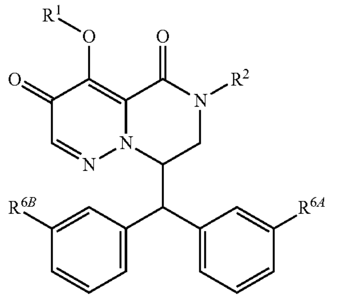
| $R^2$ | $R^1$ | $R^{6A}$ | $R^{6B}$ |
|---|---|---|---|
| $—CH_2CH_2CH_2CH_3$ | 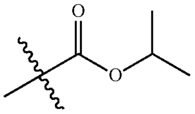 [SMILES: *C(=O)OC(C)C] | Cl | Cl |
| $—CH_2CH_2CH_2CH_3$ | 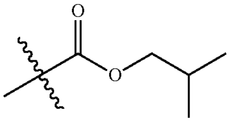 [SMILES: *C(=O)OCC(C)C] | Cl | Cl |
| $—CH_2CH_2CH_2CH_3$ | 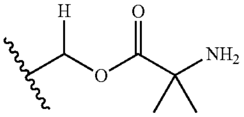 [SMILES: *COC(=O)C(C)(C)N] | Cl | Cl |
| $—CH_2CH_2CH_2CH_3$ | 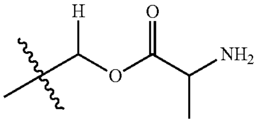 [SMILES: *COC(=O)C(C)N] | Cl | Cl |
| $—CH_2CH_2CH_2CH_3$ | 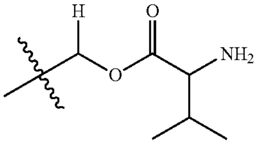 [SMILES: *COC(=O)C(N)C(C)C] | Cl | Cl |
| $—CH_2CH_2CH_2CH_3$ | 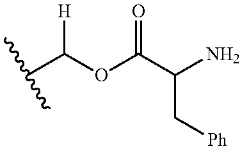 [SMILES: *COC(=O)C(N)Cc1ccccc1] | Cl | Cl |
| $—CH_2CH_2CH_2CH_3$ | 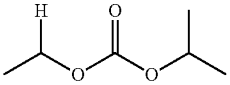 | Cl | Cl |
| $—CH_2CH_2CH_2CH_3$ | 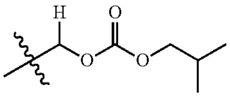 [SMILES: *COC(=O)OCC(C)C] | Cl | Cl |
| $—CH_2CH_2CH_2CH_3$ | 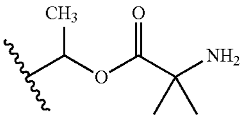 | Cl | Cl |
TABLE A-continued
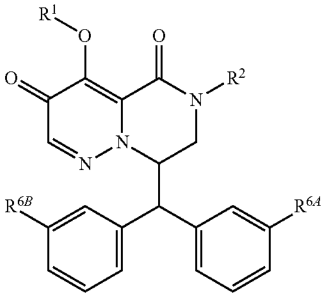
| $R^2$ | $R^1$ | $R^{6A}$ | $R^{6B}$ |
|---|---|---|---|
| $—CH_2CH_2CH_2CH_3$ | 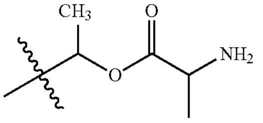 | Cl | Cl |
| $—CH_2CH_2CH_2CH_3$ | 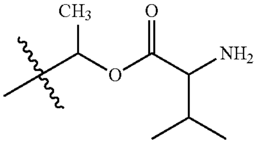 | Cl | Cl |
| $—CH_2CH_2CH_2CH_3$ | 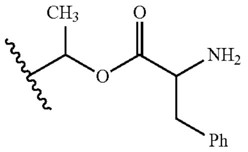 [SMILES: *C(C)OC(=O)C(N)Cc1ccccc1] | Cl | Cl |
| $—CH_2CH_2CH_2CH_3$ | 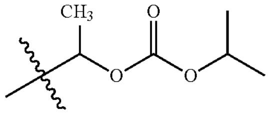 [SMILES: *C(C)OC(=O)OC(C)C] | Cl | Cl |
| $—CH_2CH_2CH_2CH_3$ | 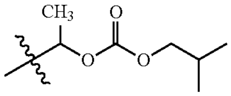 | Cl | Cl |
| 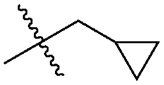 [SMILES: *CC1CC1] | 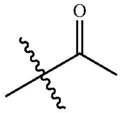 [SMILES: *C(C)=O] | Cl | Cl |
| 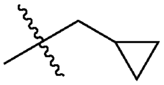 [SMILES: *CC1CC1] | 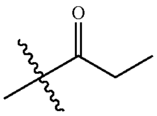 [SMILES: *C(=O)CC] | Cl | Cl |
| 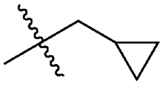 | 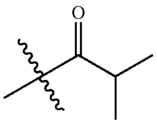 [SMILES: *C(=O)C(C)C] | Cl | Cl |
| 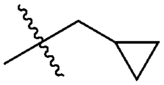 [SMILES: *CC1CC1] | 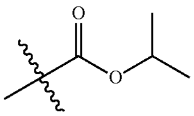 | Cl | Cl |

TABLE A-continued
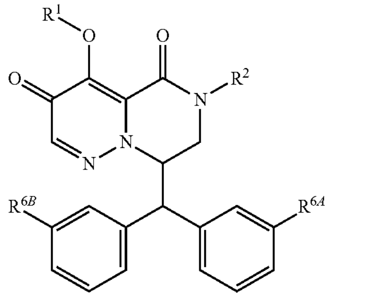
| $R^2$ | $R^1$ | $R^{6A}$ | $R^{6B}$ |
|---|---|---|---|
| 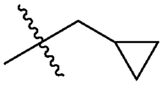 [SMILES: *CC1CC1] | 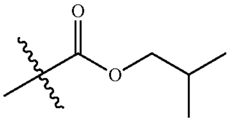 [SMILES: *C(=O)OCC(C)C] | Cl | Cl |
| 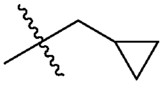 [SMILES: *CC1CC1] | 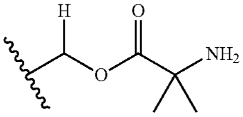 [SMILES: *COC(=O)C(C)(C)N] | Cl | Cl |
| 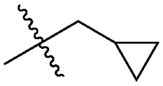 | 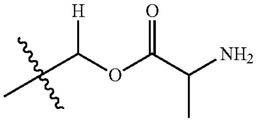 [SMILES: *COC(=O)C(C)N] | Cl | Cl |
| 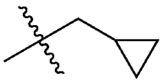 [SMILES: *CC1CC1] | 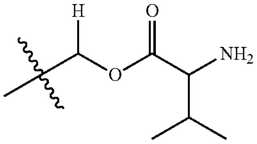 | Cl | Cl |
| 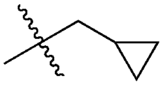 [SMILES: *CC1CC1] | 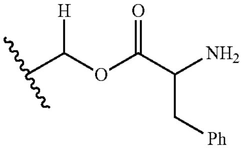 [SMILES: *COC(=O)C(N)Cc1ccccc1] | Cl | Cl |
| 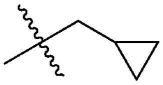 [SMILES: *CC1CC1] | 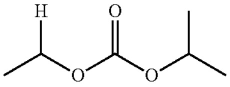 | Cl | Cl |
| 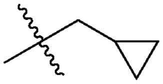 [SMILES: *CC1CC1] | 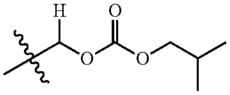 [SMILES: *COC(=O)OCC(C)C] | Cl | Cl |
| 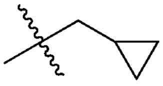 | 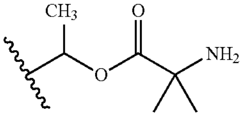 | Cl | Cl |
| 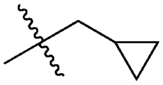 | 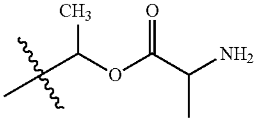 | Cl | Cl |
TABLE A-continued
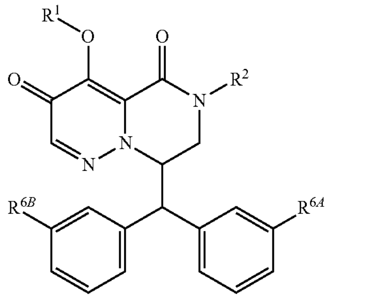
| $R^2$ | $R^1$ | $R^{6A}$ | $R^{6B}$ |
|---|---|---|---|
| 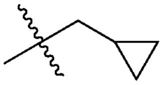 [SMILES: *CC1CC1] | 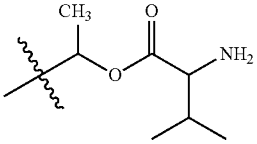 | Cl | Cl |
| 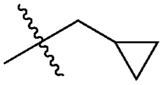 | 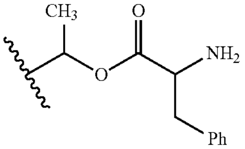 [SMILES: *C(C)OC(=O)C(N)Cc1ccccc1] | Cl | Cl |
| 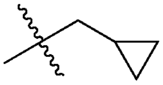 [SMILES: *CC1CC1] | 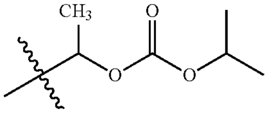 [SMILES: *C(C)OC(=O)OC(C)C] | Cl | Cl |
| 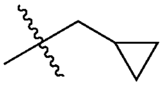 [SMILES: *CC1CC1] | 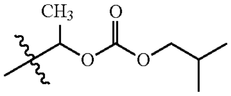 [SMILES: *C(C)OC(=O)OCC(C)C] | Cl | Cl |
| 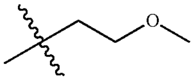 [SMILES: *CCOC] | H | Cl | Cl |
| 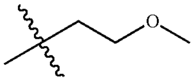 [SMILES: *CCOC] | 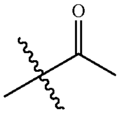 [SMILES: *C(C)=O] | Cl | Cl |
| 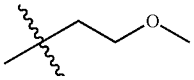 [SMILES: *CCOC] | 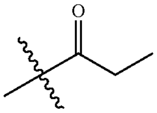 [SMILES: *C(=O)CC] | Cl | Cl |
| 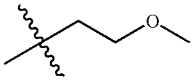 [SMILES: *CCOC] | 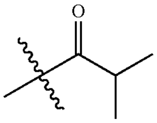 [SMILES: *C(=O)C(C)C] | Cl | Cl |
| 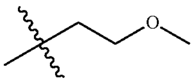 [SMILES: *CCOC] | 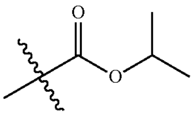 [SMILES: *C(=O)OC(C)C] | Cl | Cl |

TABLE A-continued
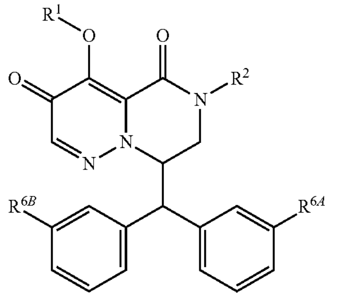
| $R^2$ | $R^1$ | $R^{6A}$ | $R^{6B}$ |
|---|---|---|---|
| 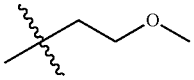 [SMILES: *CCOC] | 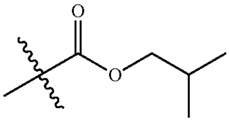 [SMILES: *C(=O)OCC(C)C] | Cl | Cl |
| 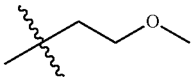 [SMILES: *CCOC] | 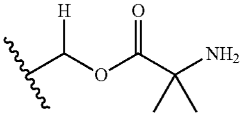 [SMILES: *COC(=O)C(C)(C)N] | Cl | Cl |
| 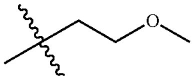 [SMILES: *CCOC] | 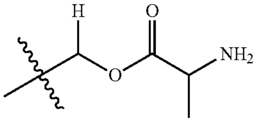 [SMILES: *COC(=O)C(C)N] | Cl | Cl |
| 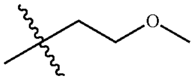 [SMILES: *CCOC] | 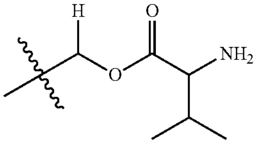 [SMILES: *COC(=O)C(N)C(C)C] | Cl | Cl |
| 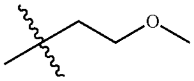 [SMILES: *CCOC] | 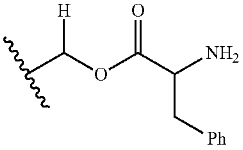 [SMILES: *COC(=O)C(N)Cc1ccccc1] | Cl | Cl |
| 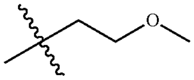 [SMILES: *CCOC] | 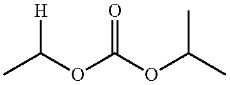 | Cl | Cl |
| 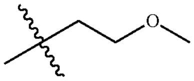 [SMILES: *CCOC] | 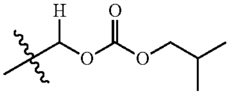 [SMILES: *COC(=O)OCC(C)C] | Cl | Cl |
| 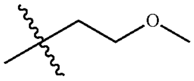 [SMILES: *CCOC] | 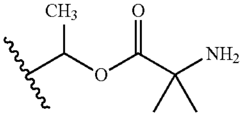 | Cl | Cl |
| 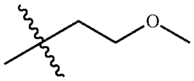 [SMILES: *CCOC] | 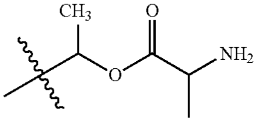 | Cl | Cl |
TABLE A-continued
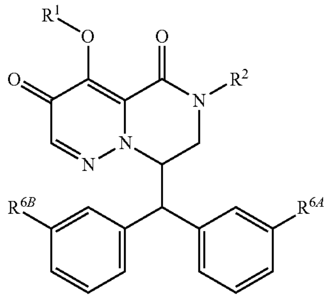
| $R^2$ | $R^1$ | $R^{6A}$ | $R^{6B}$ |
|---|---|---|---|
| 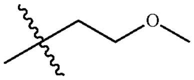 [SMILES: *CCOC] | 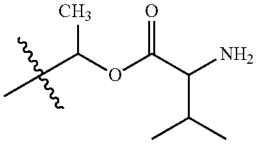 | Cl | Cl |
| 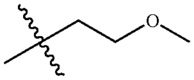 [SMILES: *CCOC] | 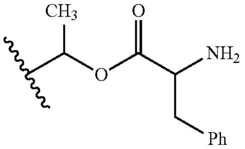 [SMILES: *C(C)OC(=O)C(N)Cc1ccccc1] | Cl | Cl |
| 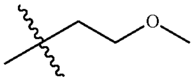 [SMILES: *CCOC] | 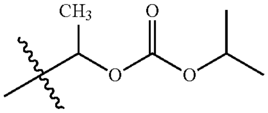 [SMILES: *C(C)OC(=O)OC(C)C] | Cl | Cl |
| 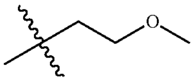 [SMILES: *CCOC] | 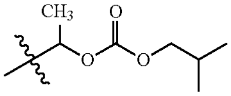 [SMILES: *C(C)OC(=O)OCC(C)C] | Cl | Cl |
| 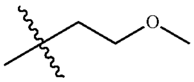 [SMILES: *CCOC] | H | Cl | Cl |
| 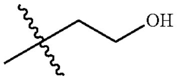 [SMILES: *CCO] | 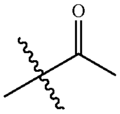 [SMILES: *C(C)=O] | Cl | Cl |
| 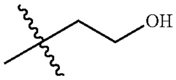 [SMILES: *CCO] | 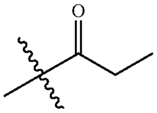 [SMILES: *C(=O)CC] | Cl | Cl |
| 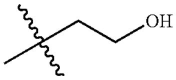 [SMILES: *CCO] | 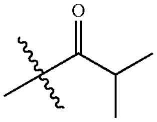 [SMILES: *C(=O)C(C)C] | Cl | Cl |
| 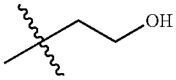 [SMILES: *CCO] | 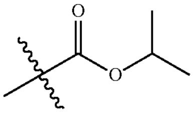 [SMILES: *C(=O)OC(C)C] | Cl | Cl |

TABLE A-continued
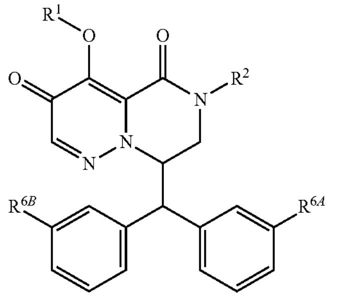
| $R^2$ | $R^1$ | $R^{6A}$ | $R^{6B}$ |
|---|---|---|---|
| 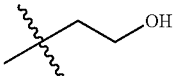 [SMILES: *CCO] | 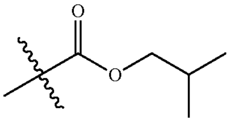 [SMILES: *C(=O)OCC(C)C] | Cl | Cl |
| 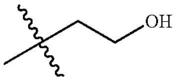 [SMILES: *CCO] | 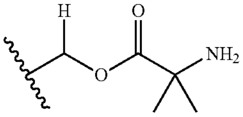 [SMILES: *COC(=O)C(C)(C)N] | Cl | Cl |
| 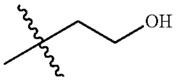 [SMILES: *CCO] | 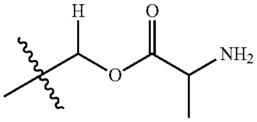 [SMILES: *COC(=O)C(C)N] | Cl | Cl |
| 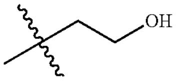 [SMILES: *CCO] | 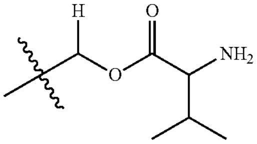 [SMILES: *COC(=O)C(N)C(C)C] | Cl | Cl |
| 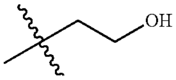 [SMILES: *CCO] | 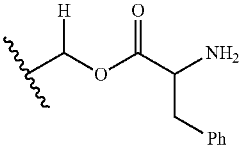 [SMILES: *COC(=O)C(N)Cc1ccccc1] | Cl | Cl |
| 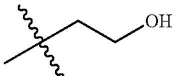 [SMILES: *CCO] | 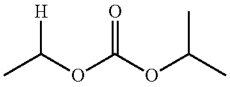 | Cl | Cl |
| 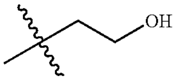 [SMILES: *CCO] | 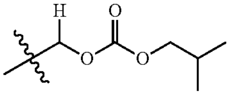 [SMILES: *COC(=O)OCC(C)C] | Cl | Cl |
| 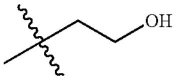 [SMILES: *CCO] | 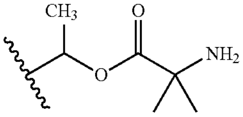 | Cl | Cl |
| 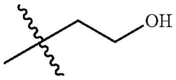 [SMILES: *CCO] | 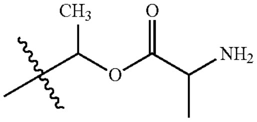 | Cl | Cl |
TABLE A-continued
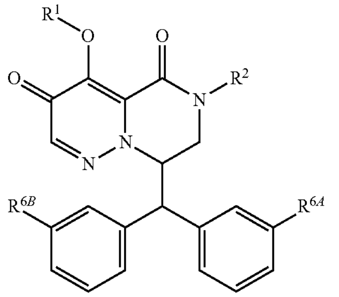
| $R^2$ | $R^1$ | $R^{6A}$ | $R^{6B}$ |
|---|---|---|---|
| 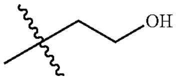 [SMILES: *CCO] | 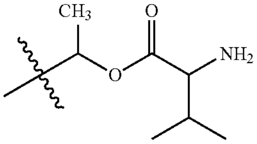 | Cl | Cl |
| 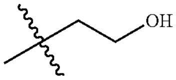 [SMILES: *CCO] | 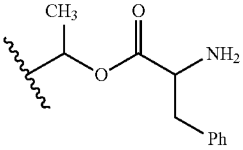 [SMILES: *C(C)OC(=O)C(N)Cc1ccccc1] | Cl | Cl |
| 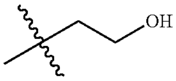 [SMILES: *CCO] | 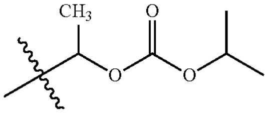 [SMILES: *C(C)OC(=O)OC(C)C] | Cl | Cl |
| 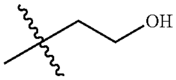 [SMILES: *CCO] | 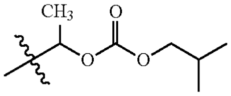 [SMILES: *C(C)OC(=O)OCC(C)C] | Cl | Cl |
| $—CH_2CH{=}CF_2$ | 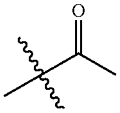 [SMILES: *C(C)=O] | Cl | Cl |
| $—CH_2CH{=}CF_2$ | 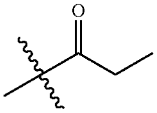 [SMILES: *C(=O)CC] | Cl | Cl |
| $—CH_2CH{=}CF_2$ | 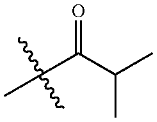 [SMILES: *C(=O)C(C)C] | Cl | Cl |
| $—CH_2CH{=}CF_2$ | 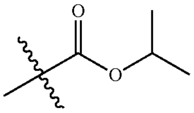 | Cl | Cl |
| $—CH_2CH{=}CF_2$ | 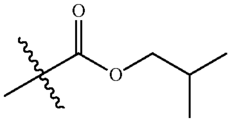 [SMILES: *C(=O)OCC(C)C] | Cl | Cl |

TABLE A-continued
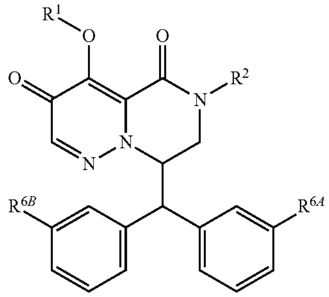
| $R^2$ | $R^1$ | $R^{6A}$ | $R^{6B}$ |
|---|---|---|---|
| —$CH_2CH{=}CF_2$ | 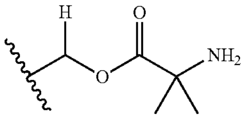 [SMILES: *COC(=O)C(C)(C)N] | Cl | Cl |
| —$CH_2CH{=}CF_2$ | 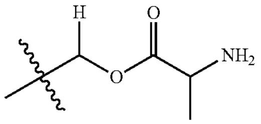 [SMILES: *COC(=O)C(C)N] | Cl | Cl |
| —$CH_2CH{=}CF_2$ | 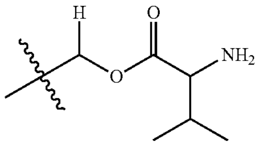 [SMILES: *COC(=O)C(N)C(C)C] | Cl | Cl |
| —$CH_2CH{=}CF_2$ | 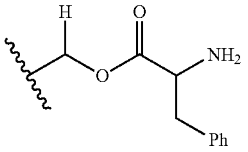 [SMILES: *COC(=O)C(N)Cc1ccccc1] | Cl | Cl |
| —$CH_2CH{=}CF_2$ | 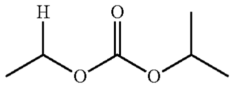 | Cl | Cl |
| —$CH_2CH{=}CF_2$ | 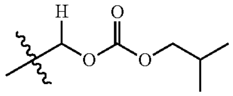 [SMILES: *COC(=O)OCC(C)C] | Cl | Cl |
| —$CH_2CH{=}CF_2$ | 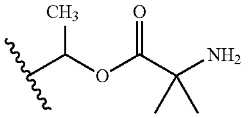 [SMILES: *C(C)OC(=O)C(C)(C)N] | Cl | Cl |
| —$CH_2CH{=}CF_2$ | 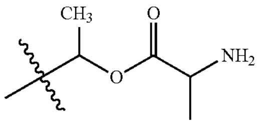 | Cl | Cl |
| —$CH_2CH{=}CF_2$ | 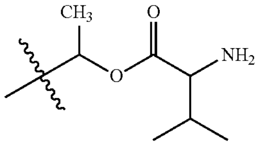 | Cl | Cl |
TABLE A-continued
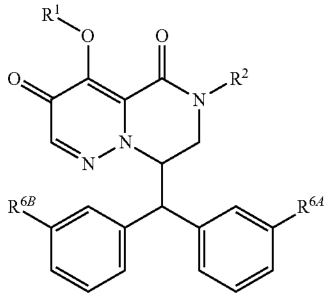
| $R^2$ | $R^1$ | $R^{6A}$ | $R^{6B}$ |
|---|---|---|---|
| —$CH_2CH{=}CF_2$ | 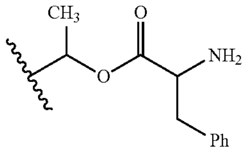 [SMILES: *C(C)OC(=O)C(N)Cc1ccccc1] | Cl | Cl |
| —$CH_2CH{=}CF_2$ | 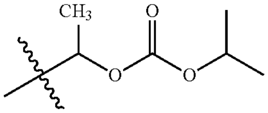 [SMILES: *C(C)OC(=O)OC(C)C] | Cl | Cl |
| —$CH_2CH{=}CF_2$ | 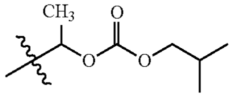 [SMILES: *C(C)OC(=O)OCC(C)C] | Cl | Cl |
| —$CH_2CF_3$ | 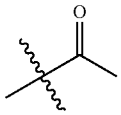 [SMILES: *C(C)=O] | Cl | Cl |
| —$CH_2CF_3$ | 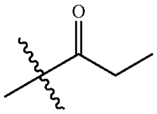 [SMILES: *C(=O)CC] | Cl | Cl |
| —$CH_2CF_3$ | 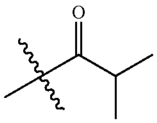 [SMILES: *C(=O)C(C)C] | Cl | Cl |
| —$CH_2CF_3$ | 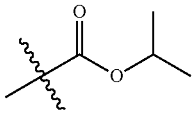 [SMILES: *C(=O)OC(C)C] | Cl | Cl |
| —$CH_2CF_3$ | 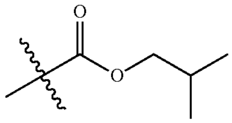 [SMILES: *C(=O)OCC(C)C] | Cl | Cl |
| —$CH_2CF_3$ | 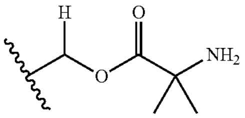 [SMILES: *COC(=O)C(C)(C)N] | Cl | Cl |

TABLE A-continued
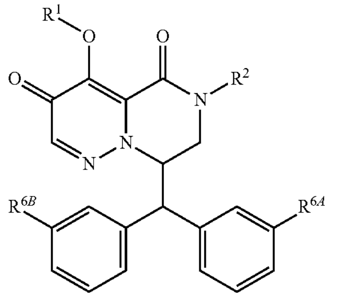
| $R^2$ | $R^1$ | $R^{6A}$ | $R^{6B}$ |
|---|---|---|---|
| $—CH_2CF_3$ | 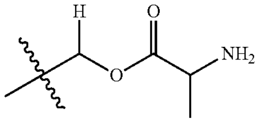 [SMILES: *COC(=O)C(C)N] | Cl | Cl |
| $—CH_2CF_3$ | 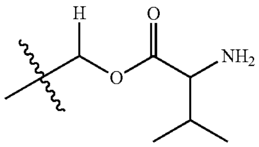 [SMILES: *COC(=O)C(N)C(C)C] | Cl | Cl |
| $—CH_2CF_3$ | 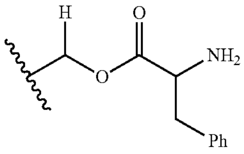 [SMILES: *COC(=O)C(N)Cc1ccccc1] | Cl | Cl |
| $—CH_2CF_3$ | 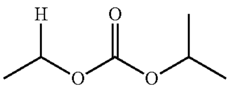 | Cl | Cl |
| $—CH_2CF_3$ | 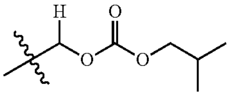 [SMILES: *COC(=O)OCC(C)C] | Cl | Cl |
| $—CH_2CF_3$ | 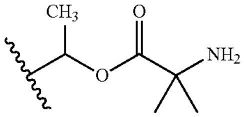 | Cl | Cl |
| $—CH_2CF_3$ | 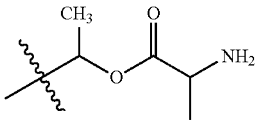 | Cl | Cl |
| $—CH_2CF_3$ | 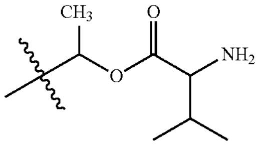 | Cl | Cl |
| $—CH_2CF_3$ | 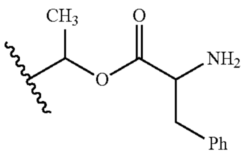 | Cl | Cl |
TABLE A-continued
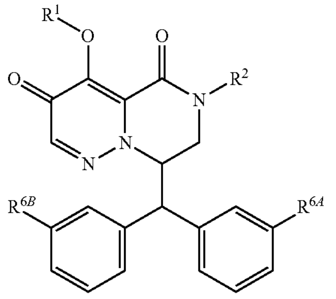
| $R^2$ | $R^1$ | $R^{6A}$ | $R^{6B}$ |
|---|---|---|---|
| $—CH_2CF_3$ | 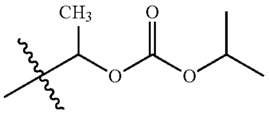 | Cl | Cl |
| $—CH_2CF_3$ | 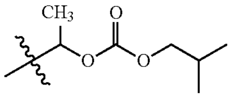 | Cl | Cl |
| $—CH_2CH_2CF_3$ | 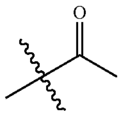 [SMILES: *C(C)=O] | Cl | Cl |
| $—CH_2CH_2CF_3$ | 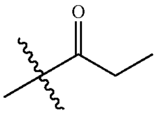 [SMILES: *C(=O)CC] | Cl | Cl |
| $—CH_2CH_2CF_3$ | 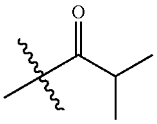 [SMILES: *C(=O)C(C)C] | Cl | Cl |
| $—CH_2CH_2CF_3$ | 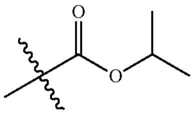 [SMILES: *C(=O)OC(C)C] | Cl | Cl |
| $—CH_2CH_2CF_3$ | 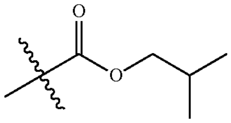 [SMILES: *C(=O)OCC(C)C] | Cl | Cl |
| $—CH_2CH_2CF_3$ | 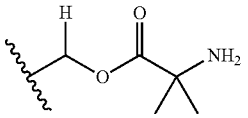 | Cl | Cl |
| $—CH_2CH_2CF_3$ | 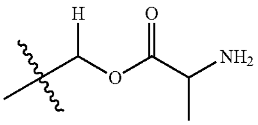 [SMILES: *COC(=O)C(C)N] | Cl | Cl |

TABLE A-continued
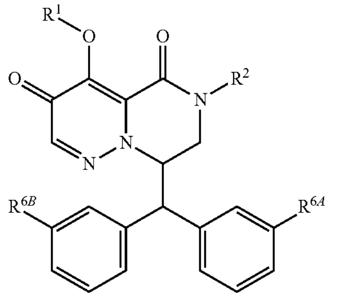
| $R^2$ | $R^1$ | $R^{6A}$ | $R^{6B}$ |
|---|---|---|---|
| $-CH_2CH_2CF_3$ | 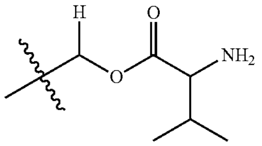 [SMILES: *COC(=O)C(N)C(C)C] | Cl | Cl |
| $-CH_2CH_2CF_3$ | 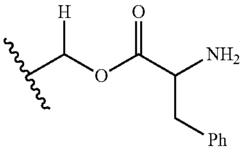 [SMILES: *COC(=O)C(N)Cc1ccccc1] | Cl | Cl |
| $-CH_2CH_2CF_3$ | 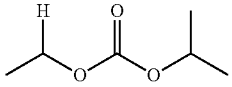 | Cl | Cl |
| $-CH_2CH_2CF_3$ | 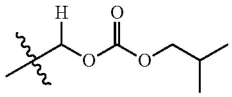 [SMILES: *COC(=O)OCC(C)C] | Cl | Cl |
| $-CH_2CH_2CF_3$ | 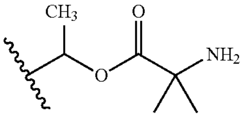 | Cl | Cl |
| $-CH_2CH_2CF_3$ | 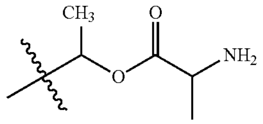 | Cl | Cl |
| $-CH_2CH_2CF_3$ | 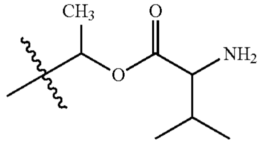 | Cl | Cl |
| $-CH_2CH_2CF_3$ | 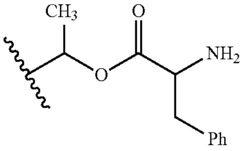 [SMILES: *C(C)OC(=O)C(N)Cc1ccccc1] | Cl | Cl |
| $-CH_2CH_2CF_3$ | 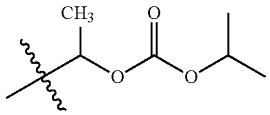 [SMILES: *C(C)OC(=O)OC(C)C] | Cl | Cl |
TABLE A-continued
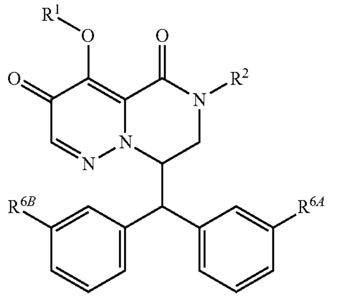
| $R^2$ | $R^1$ | $R^{6A}$ | $R^{6B}$ |
|---|---|---|---|
| $-CH_2CH_2CF_3$ | 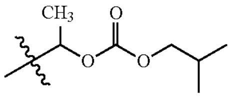 [SMILES: *C(C)OC(=O)OCC(C)C] | Cl | Cl |
| $-CH_2CHF_2$ | 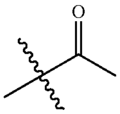 [SMILES: *C(C)=O] | Cl | Cl |
| $-CH_2CHF_2$ | 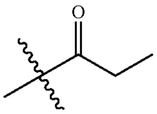 [SMILES: *C(=O)CC] | Cl | Cl |
| $-CH_2CHF_2$ | 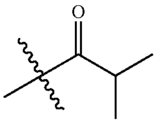 [SMILES: *C(=O)C(C)C] | Cl | Cl |
| $-CH_2CHF_2$ | 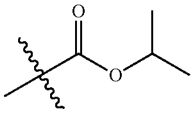 [SMILES: *C(=O)OC(C)C] | Cl | Cl |
| $-CH_2CHF_2$ | 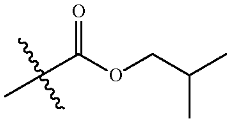 [SMILES: *C(=O)OCC(C)C] | Cl | Cl |
| $-CH_2CHF_2$ | 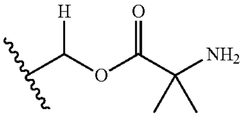 [SMILES: *COC(=O)C(C)(C)N] | Cl | Cl |
| $-CH_2CHF_2$ | 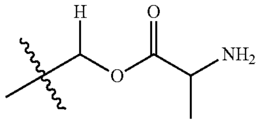 [SMILES: *COC(=O)C(C)N] | Cl | Cl |
| $-CH_2CHF_2$ | 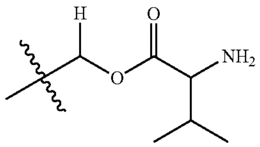 [SMILES: *COC(=O)C(N)C(C)C] | Cl | Cl |

TABLE A-continued
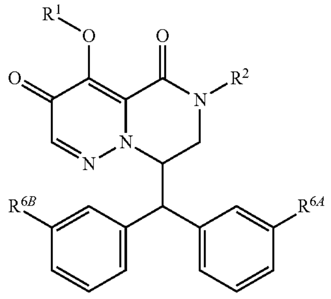
| $R^2$ | $R^1$ | $R^{6A}$ | $R^{6B}$ |
|---|---|---|---|
| $—CH_2CHF_2$ | 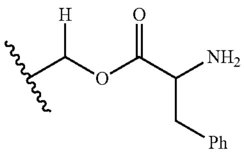 | Cl | Cl |
| $—CH_2CHF_2$ | 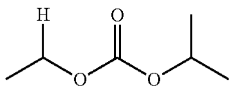 | Cl | Cl |
| $—CH_2CHF_2$ | 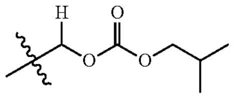 [SMILES: *COC(=O)OCC(C)C] | Cl | Cl |
| $—CH_2CHF_2$ | 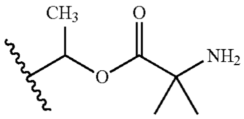 | Cl | Cl |
| $—CH_2CHF_2$ | 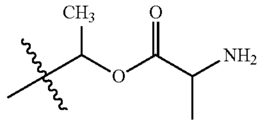 | Cl | Cl |
| $—CH_2CHF_2$ | 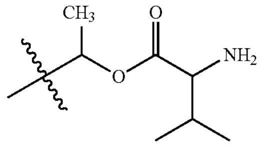 | Cl | Cl |
| $—CH_2CHF_2$ | 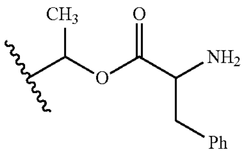 [SMILES: *C(C)OC(=O)C(N)Cc1ccccc1] | Cl | Cl |
| $—CH_2CHF_2$ | 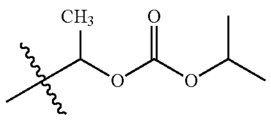 [SMILES: *C(C)OC(=O)OC(C)C] | Cl | Cl |
| $—CH_2CHF_2$ | 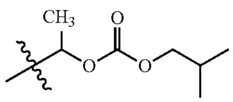 [SMILES: *C(C)OC(=O)OCC(C)C] | Cl | Cl |
TABLE A-continued
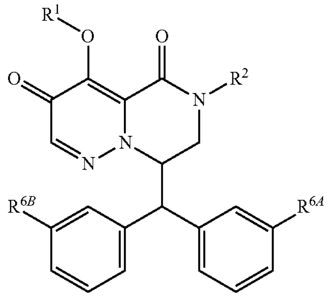
| $R^2$ | $R^1$ | $R^{6A}$ | $R^{6B}$ |
|---|---|---|---|
| $—CH_2C(CH_3)F_2$ | 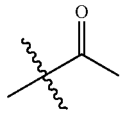 [SMILES: *C(C)=O] | Cl | Cl |
| $—CH_2C(CH_3)F_2$ | 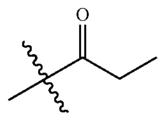 [SMILES: *C(=O)CC] | Cl | Cl |
| $—CH_2C(CH_3)F_2$ | 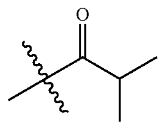 [SMILES: *C(=O)C(C)C] | Cl | Cl |
| $—CH_2C(CH_3)F_2$ | 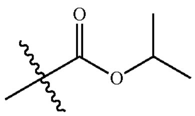 [SMILES: *C(=O)OC(C)C] | Cl | Cl |
| $—CH_2C(CH_3)F_2$ | 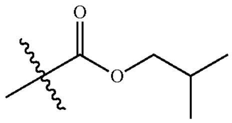 [SMILES: *C(=O)OCC(C)C] | Cl | Cl |
| $—CH_2C(CH_3)F_2$ | 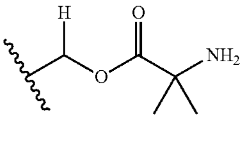 [SMILES: *COC(=O)C(C)(C)N] | Cl | Cl |
| $—CH_2C(CH_3)F_2$ | 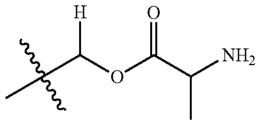 [SMILES: *COC(=O)C(C)N] | Cl | Cl |
| $—CH_2C(CH_3)F_2$ | 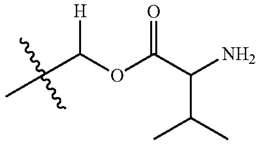 [SMILES: *COC(=O)C(N)C(C)C] | Cl | Cl |
| $—CH_2C(CH_3)F_2$ | 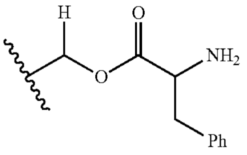 [SMILES: *COC(=O)C(N)Cc1ccccc1] | Cl | Cl |

TABLE A-continued
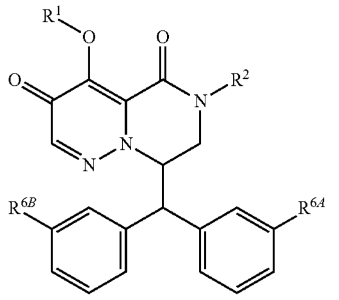
| $R^2$ | $R^1$ | $R^{6A}$ | $R^{6B}$ |
|---|---|---|---|
| $-CH_2C(CH_3)F_2$ | 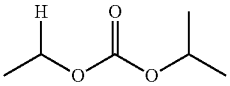 | Cl | Cl |
| $-CH_2C(CH_3)F_2$ | 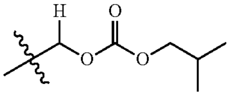 [SMILES: *COC(=O)OCC(C)C] | Cl | Cl |
| $-CH_2C(CH_3)F_2$ | 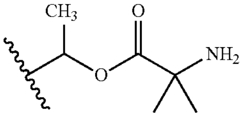 [SMILES: *C(C)OC(=O)C(C)(C)N] | Cl | Cl |
| $-CH_2C(CH_3)F_2$ | 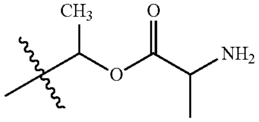 | Cl | Cl |
| $-CH_2C(CH_3)F_2$ | 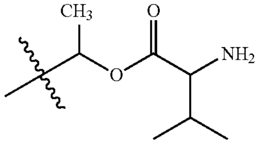 | Cl | Cl |
| $-CH_2C(CH_3)F_2$ | 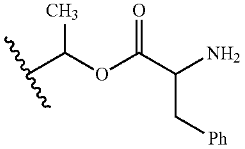 [SMILES: *C(C)OC(=O)C(N)Cc1ccccc1] | Cl | Cl |
| $-CH_2C(CH_3)F_2$ | 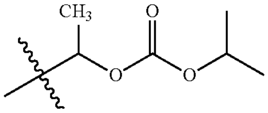 | Cl | Cl |
| $-CH_2C(CH_3)F_2$ | 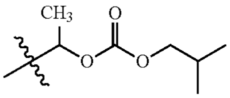 [SMILES: *C(C)OC(=O)OCC(C)C] | Cl | Cl |
TABLE B
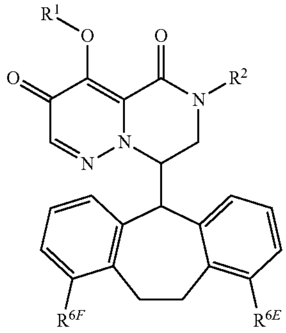
| $R^2$ | $R^1$ | $R^{6E}$ | $R^{6F}$ |
|---|---|---|---|
| 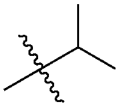 [SMILES: *C(C)C] | 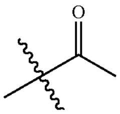 [SMILES: *C(C)=O] | H | H |
| 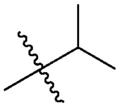 [SMILES: *C(C)C] | 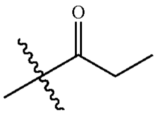 [SMILES: *C(=O)CC] | H | H |
| 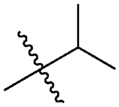 [SMILES: *C(C)C] | 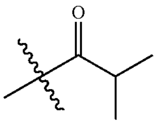 [SMILES: *C(=O)C(C)C] | H | H |
| 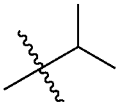 [SMILES: *C(C)C] | 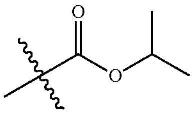 | H | H |
| 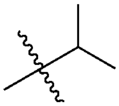 [SMILES: *C(C)C] | 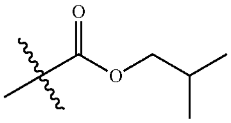 [SMILES: *C(=O)OCC(C)C] | H | H |
| 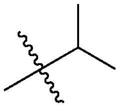 [SMILES: *C(C)C] | 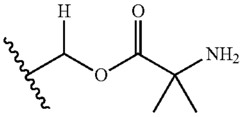 [SMILES: *COC(=O)C(C)(C)N] | H | H |
| 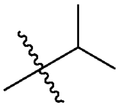 [SMILES: *C(C)C] | 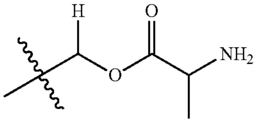 [SMILES: *COC(=O)C(C)N] | H | H |
| 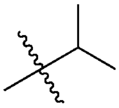 [SMILES: *C(C)C] | 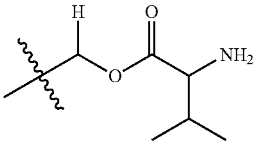 [SMILES: *COC(=O)C(N)C(C)C] | H | H |
| 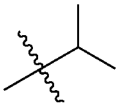 [SMILES: *C(C)C] | 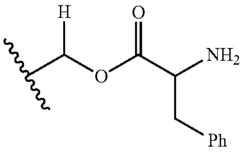 [SMILES: *COC(=O)C(N)Cc1ccccc1] | H | H |

TABLE B-continued
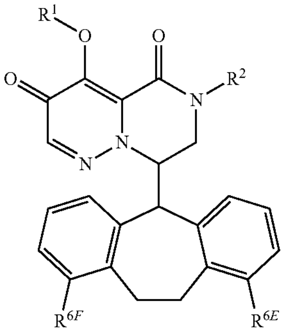
| $R^2$ | $R^1$ | $R^{6E}$ | $R^{6F}$ |
|---|---|---|---|
| 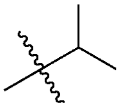 [SMILES: *C(C)C] | 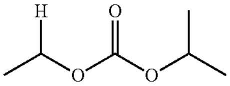 | H | H |
| 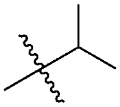 [SMILES: *C(C)C] | 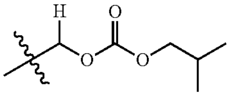 [SMILES: *COC(=O)OCC(C)C] | H | H |
| 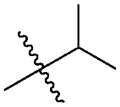 [SMILES: *C(C)C] | 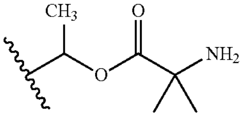 | H | H |
| 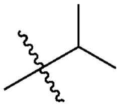 [SMILES: *C(C)C] | 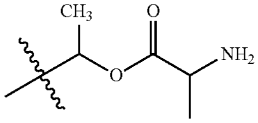 | H | H |
| 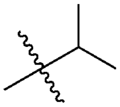 [SMILES: *C(C)C] | 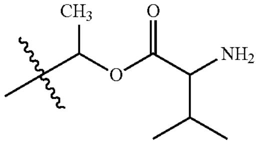 | H | H |
| 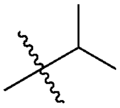 [SMILES: *C(C)C] | 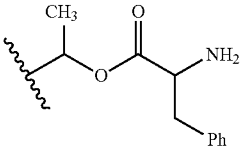 [SMILES: *C(C)OC(=O)C(N)Cc1ccccc1] | H | H |
| 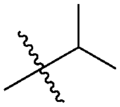 [SMILES: *C(C)C] | 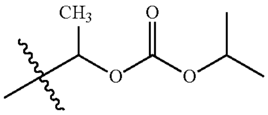 [SMILES: *C(C)OC(=O)OC(C)C] | H | H |
| 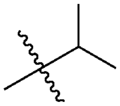 [SMILES: *C(C)C] | 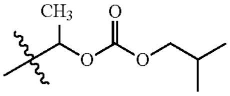 | H | H |
| $—CH_3$ | 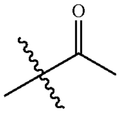 [SMILES: *C(C)=O] | H | H |
TABLE B-continued
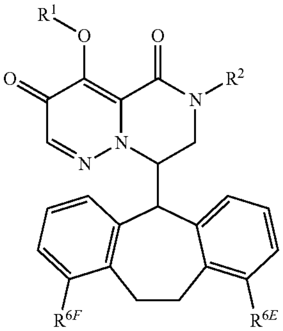
| $R^2$ | $R^1$ | $R^{6E}$ | $R^{6F}$ |
|---|---|---|---|
| $—CH_3$ | 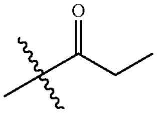 [SMILES: *C(=O)CC] | H | H |
| $—CH_3$ | 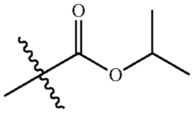 [SMILES: *C(=O)OC(C)C] | H | H |
| $—CH_3$ | 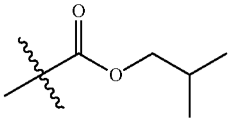 [SMILES: *C(=O)OCC(C)C] | H | H |
| $—CH_3$ | 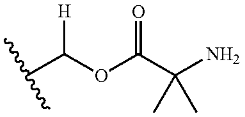 [SMILES: *COC(=O)C(C)(C)N] | H | H |
| $—CH_3$ | 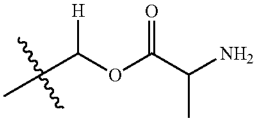 [SMILES: *COC(=O)C(C)N] | H | H |
| $—CH_3$ | 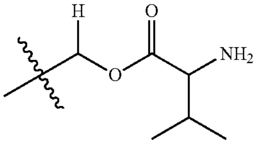 [SMILES: *COC(=O)C(N)C(C)C] | H | H |
| $—CH_3$ | 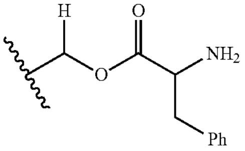 [SMILES: *COC(=O)C(N)Cc1ccccc1] | H | H |
| $—CH_3$ | 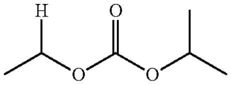 | H | H |
| $—CH_3$ | 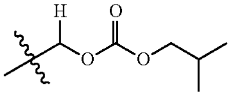 [SMILES: *COC(=O)OCC(C)C] | H | H |

TABLE B-continued
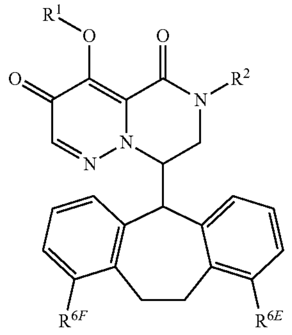
| $R^2$ | $R^1$ | $R^{6E}$ | $R^{6F}$ |
|---|---|---|---|
| —$CH_3$ | 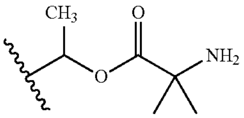 | H | H |
| —$CH_3$ | 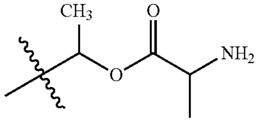 | H | H |
| —$CH_3$ | 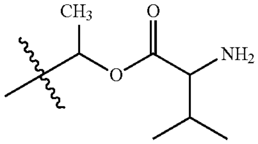 | H | H |
| —$CH_3$ | 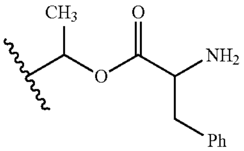 | H | H |
| —$CH_3$ | 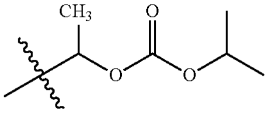 [SMILES: *C(C)OC(=O)OC(C)C] | H | H |
| —$CH_3$ | 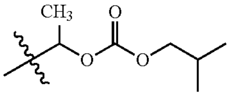 | H | H |
| —$CH_2CH_3$ | 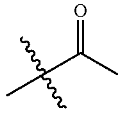 [SMILES: *C(C)=O] | H | H |
| —$CH_2CH_3$ | 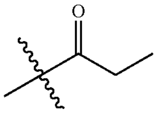 [SMILES: *C(=O)CC] | H | H |
| —$CH_2CH_3$ | 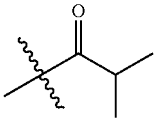 [SMILES: *C(=O)C(C)C] | H | H |
TABLE B-continued
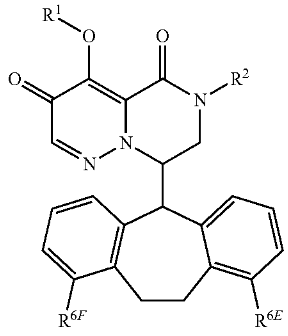
| $R^2$ | $R^1$ | $R^{6E}$ | $R^{6F}$ |
|---|---|---|---|
| —$CH_2CH_3$ | 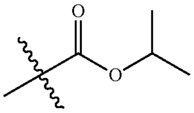 | H | H |
| —$CH_2CH_3$ | 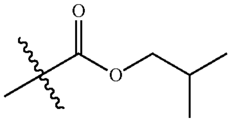 [SMILES: *C(=O)OCC(C)C] | H | H |
| —$CH_2CH_3$ | 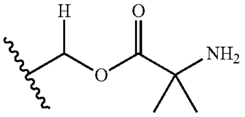 [SMILES: *COC(=O)C(C)(C)N] | H | H |
| —$CH_2CH_3$ | 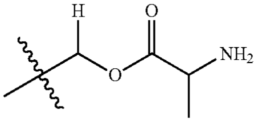 [SMILES: *COC(=O)C(C)N] | H | H |
| —$CH_2CH_3$ | 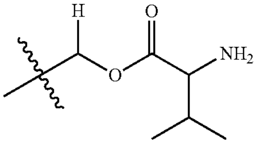 [SMILES: *COC(=O)C(N)C(C)C] | H | H |
| —$CH_2CH_3$ | 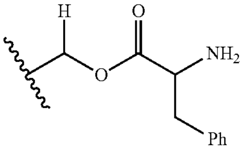 [SMILES: *COC(=O)C(N)Cc1ccccc1] | H | H |
| —$CH_2CH_3$ | 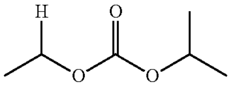 | H | H |
| —$CH_2CH_3$ | 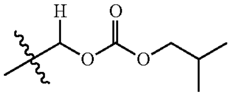 [SMILES: *COC(=O)OCC(C)C] | H | H |
| —$CH_2CH_3$ | 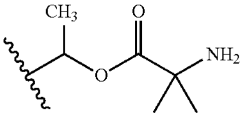 [SMILES: *C(C)OC(=O)C(C)(C)N] | H | H |

TABLE B-continued
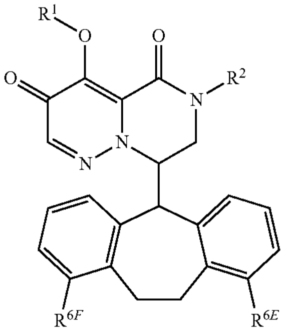
| $R^2$ | $R^1$ | $R^{6E}$ | $R^{6F}$ |
|---|---|---|---|
| $—CH_2CH_3$ | 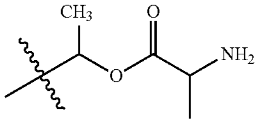 | H | H |
| $—CH_2CH_3$ | 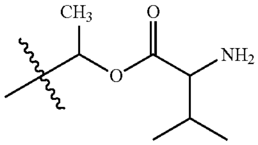 | H | H |
| $—CH_2CH_3$ | 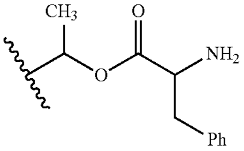 | H | H |
| $—CH_2CH_3$ | 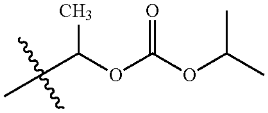 | H | H |
| $—CH_2CH_3$ | 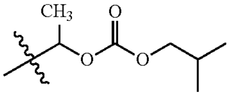 | H | H |
| $—CH_2CH(CH_3)_2$ | H | H | H |
| $—CH_2CH(CH_3)_2$ | 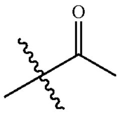 [SMILES: *C(C)=O] | H | H |
| $—CH_2CH(CH_3)_2$ | 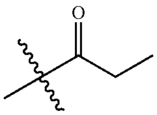 [SMILES: *C(=O)CC] | H | H |
| $—CH_2CH(CH_3)_2$ | 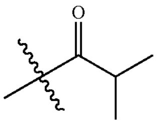 [SMILES: *C(=O)C(C)C] | H | H |
| $—CH_2CH(CH_3)_2$ | 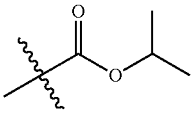 [SMILES: *C(=O)OC(C)C] | H | H |
TABLE B-continued
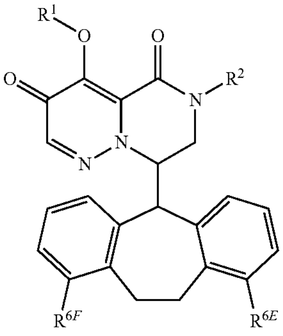
| $R^2$ | $R^1$ | $R^{6E}$ | $R^{6F}$ |
|---|---|---|---|
| $—CH_2CH(CH_3)_2$ | 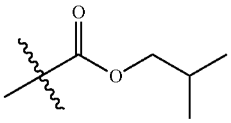 [SMILES: *C(=O)OCC(C)C] | H | H |
| $—CH_2CH(CH_3)_2$ | 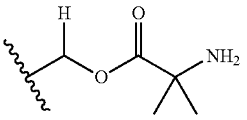 [SMILES: *COC(=O)C(C)(C)N] | H | H |
| $—CH_2CH(CH_3)_2$ | 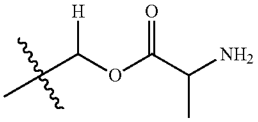 [SMILES: *COC(=O)C(C)N] | H | H |
| $—CH_2CH(CH_3)_2$ | 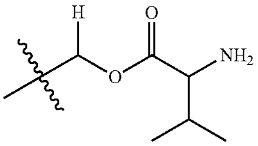 [SMILES: *COC(=O)C(N)C(C)C] | H | H |
| $—CH_2CH(CH_3)_2$ | 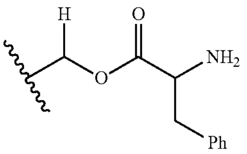 [SMILES: *COC(=O)C(N)Cc1ccccc1] | H | H |
| $—CH_2CH(CH_3)_2$ | 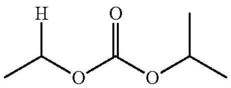 | H | H |
| $—CH_2CH(CH_3)_2$ | 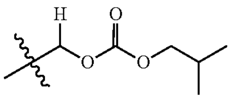 [SMILES: *COC(=O)OCC(C)C] | H | H |
| $—CH_2CH(CH_3)_2$ | 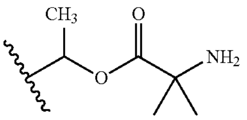 [SMILES: *C(C)OC(=O)C(C)(C)N] | H | H |
| $—CH_2CH(CH_3)_2$ | 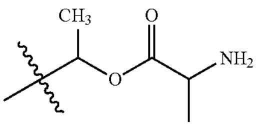 | H | H |

TABLE B-continued
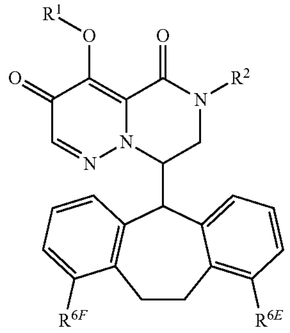
| $R^2$ | $R^1$ | $R^{6E}$ | $R^{6F}$ |
|---|---|---|---|
| —$CH_2CH(CH_3)_2$ | 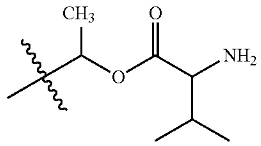 | H | H |
| —$CH_2CH(CH_3)_2$ | 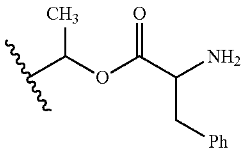 [SMILES: *C(C)OC(=O)C(N)Cc1ccccc1] | H | H |
| —$CH_2CH(CH_3)_2$ | 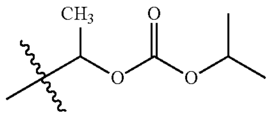 [SMILES: *C(C)OC(=O)OC(C)C] | H | H |
| —$CH_2CH(CH_3)_2$ | 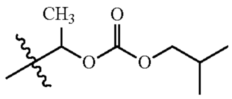 | H | H |
| —$CH_2CH_2CH_3$ | H | H | H |
| —$CH_2CH_2CH_3$ | 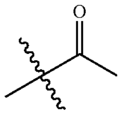 [SMILES: *C(C)=O] | H | H |
| —$CH_2CH_2CH_3$ | 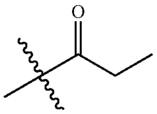 [SMILES: *C(=O)CC] | H | H |
| —$CH_2CH_2CH_3$ | 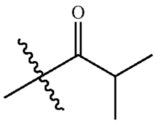 [SMILES: *C(=O)C(C)C] | H | H |
| —$CH_2CH_2CH_3$ | 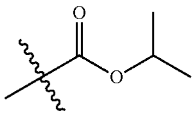 [SMILES: *C(=O)OC(C)C] | H | H |
| —$CH_2CH_2CH_3$ | 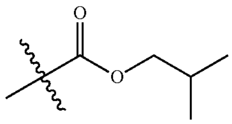 [SMILES: *C(=O)OCC(C)C] | H | H |
TABLE B-continued
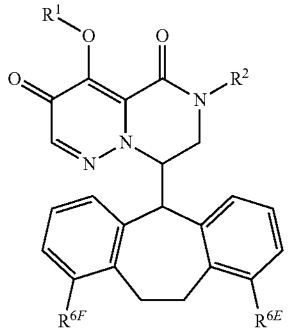
| $R^2$ | $R^1$ | $R^{6E}$ | $R^{6F}$ |
|---|---|---|---|
| —$CH_2CH_2CH_3$ | 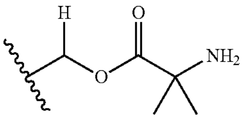 [SMILES: *COC(=O)C(C)(C)N] | H | H |
| —$CH_2CH_2CH_3$ | 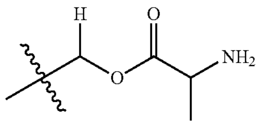 [SMILES: *COC(=O)C(C)N] | H | H |
| —$CH_2CH_2CH_3$ | 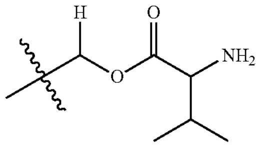 [SMILES: *COC(=O)C(N)C(C)C] | H | H |
| —$CH_2CH_2CH_3$ | 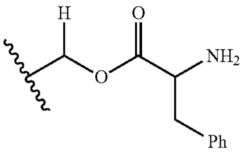 [SMILES: *COC(=O)C(N)Cc1ccccc1] | H | H |
| —$CH_2CH_2CH_3$ | 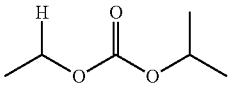 | H | H |
| —$CH_2CH_2CH_3$ | 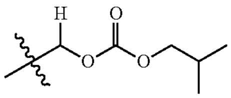 [SMILES: *COC(=O)OCC(C)C] | H | H |
| —$CH_2CH_2CH_3$ | 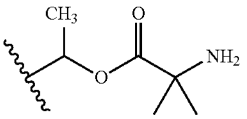 [SMILES: *C(C)OC(=O)C(C)(C)N] | H | H |
| —$CH_2CH_2CH_3$ | 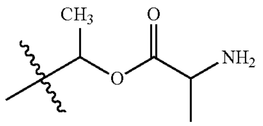 [SMILES: *C(C)OC(=O)C(C)N] | H | H |
| —$CH_2CH_2CH_3$ | 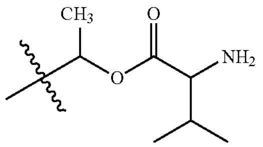 [SMILES: *C(C)OC(=O)C(N)C(C)C] | H | H |

TABLE B-continued
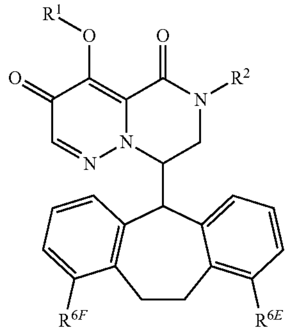
| $R^2$ | $R^1$ | $R^{6E}$ | $R^{6F}$ |
|---|---|---|---|
| $—CH_2CH_2CH_3$ | 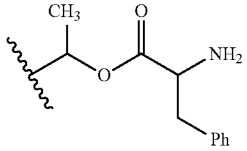 | H | H |
| $—CH_2CH_2CH_3$ | 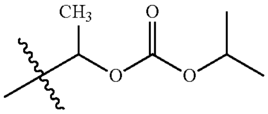 | H | H |
| $—CH_2CH_2CH_3$ | 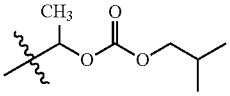 | H | H |
| $—CH_2CH_2CH_2CH_3$ | H | H | H |
| $—CH_2CH_2CH_2CH_3$ | 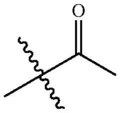 [SMILES: *C(C)=O] | H | H |
| $—CH_2CH_2CH_2CH_3$ | 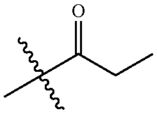 [SMILES: *C(=O)CC] | H | H |
| $—CH_2CH_2CH_2CH_3$ | 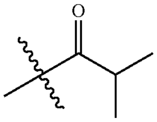 [SMILES: *C(=O)C(C)C] | H | H |
| $—CH_2CH_2CH_2CH_3$ | 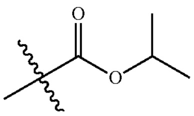 [SMILES: *C(=O)OC(C)C] | H | H |
| $—CH_2CH_2CH_2CH_3$ | 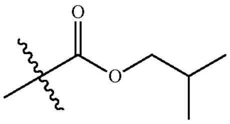 [SMILES: *C(=O)OCC(C)C] | H | H |
| $—CH_2CH_2CH_2CH_3$ | 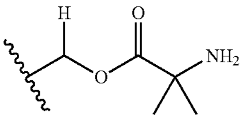 [SMILES: *COC(=O)C(C)(C)N] | H | H |
TABLE B-continued
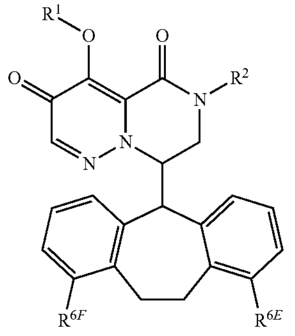
| $R^2$ | $R^1$ | $R^{6E}$ | $R^{6F}$ |
|---|---|---|---|
| $—CH_2CH_2CH_2CH_3$ | 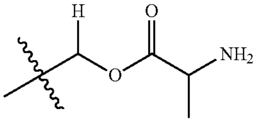 [SMILES: *COC(=O)C(C)N] | H | H |
| $—CH_2CH_2CH_2CH_3$ | 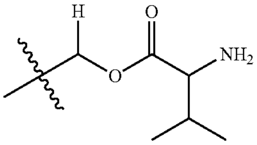 [SMILES: *COC(=O)C(N)C(C)C] | H | H |
| $—CH_2CH_2CH_2CH_3$ | 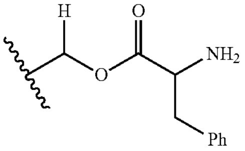 [SMILES: *COC(=O)C(N)Cc1ccccc1] | H | H |
| $—CH_2CH_2CH_2CH_3$ | 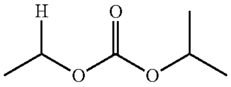 | H | H |
| $—CH_2CH_2CH_2CH_3$ | 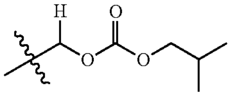 [SMILES: *COC(=O)OCC(C)C] | H | H |
| $—CH_2CH_2CH_2CH_3$ | 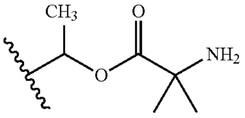 [SMILES: *C(C)OC(=O)C(C)(C)N] | H | H |
| $—CH_2CH_2CH_2CH_3$ | 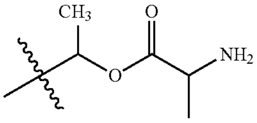 | H | H |
| $—CH_2CH_2CH_2CH_3$ | 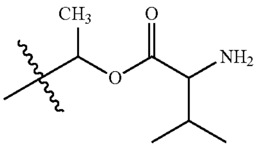 | H | H |
| $—CH_2CH_2CH_2CH_3$ | 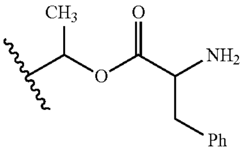 [SMILES: *C(C)OC(=O)C(N)Cc1ccccc1] | H | H |

TABLE B-continued
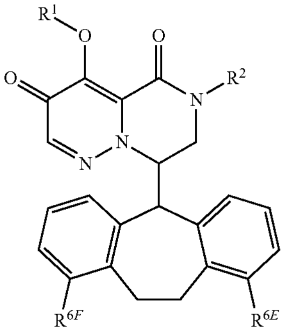
| $R^2$ | $R^1$ | $R^{6E}$ | $R^{6F}$ |
|---|---|---|---|
| $—CH_2CH_2CH_2CH_3$ | 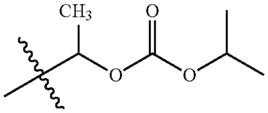 | H | H |
| $—CH_2CH_2CH_2CH_3$ | 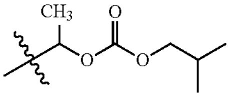 | H | H |
| 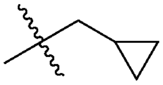 [SMILES: *CC1CC1] | H | H | H |
| 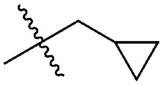 [SMILES: *CC1CC1] | 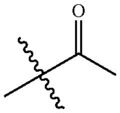 [SMILES: *C(C)=O] | H | H |
| 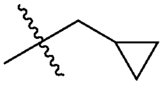 [SMILES: *CC1CC1] | 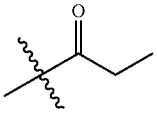 [SMILES: *C(=O)CC] | H | H |
| 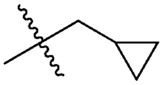 | 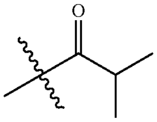 [SMILES: *C(=O)C(C)C] | H | H |
| 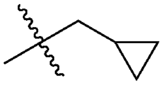 | 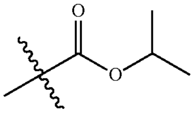 | H | H |
| 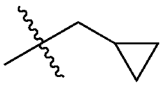 [SMILES: *CC1CC1] | 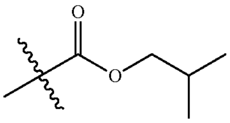 [SMILES: *C(=O)OCC(C)C] | H | H |
| 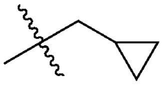 [SMILES: *CC1CC1] | 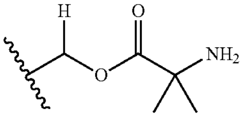 [SMILES: *COC(=O)C(C)(C)N] | H | H |
| 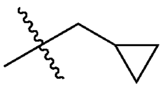 [SMILES: *CC1CC1] | 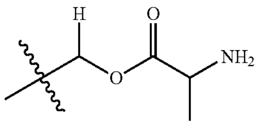 [SMILES: *COC(=O)C(C)N] | H | H |
TABLE B-continued
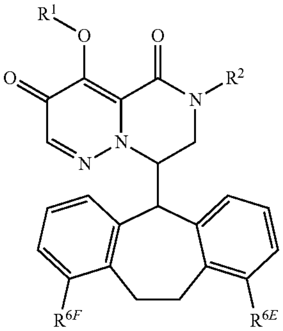
| $R^2$ | $R^1$ | $R^{6E}$ | $R^{6F}$ |
|---|---|---|---|
| 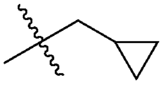 | 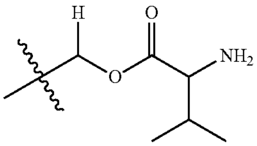 [SMILES: *COC(=O)C(N)C(C)C] | H | H |
| 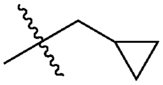 [SMILES: *CC1CC1] | 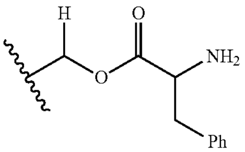 [SMILES: *COC(=O)C(N)Cc1ccccc1] | H | H |
| 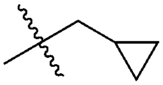 [SMILES: *CC1CC1] | 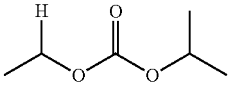 | H | H |
| 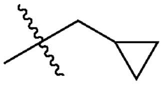 [SMILES: *CC1CC1] | 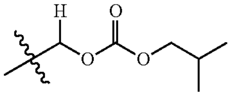 [SMILES: *COC(=O)OCC(C)C] | H | H |
| 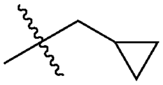 | 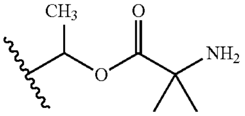 [SMILES: *C(C)OC(=O)C(C)(C)N] | H | H |
| 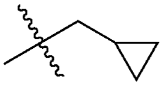 [SMILES: *CC1CC1] | 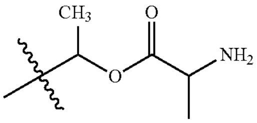 | H | H |
| 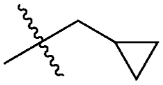 [SMILES: *CC1CC1] | 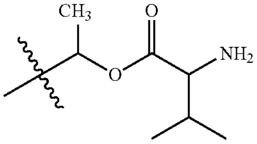 [SMILES: *C(C)OC(=O)C(N)C(C)C] | H | H |
| 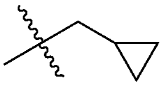 [SMILES: *CC1CC1] | 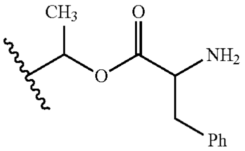 [SMILES: *C(C)OC(=O)C(N)Cc1ccccc1] | H | H |
| 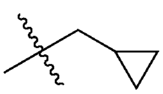 | 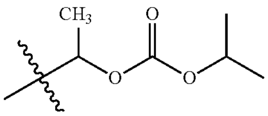 [SMILES: *C(C)OC(=O)OC(C)C] | H | H |

TABLE B-continued
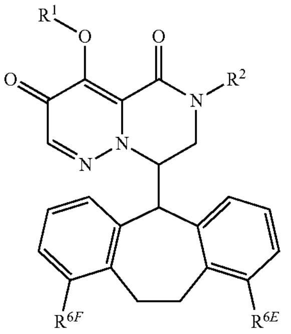
| R2 | R1 | R6E | R6F |
| --- | --- | --- | --- |
| 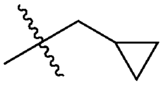 | 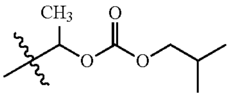 | H | H |
| 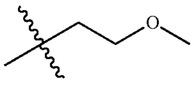 [SMILES: *CCOC] | H | H | H |
| 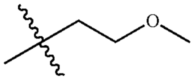 [SMILES: *CCOC] | 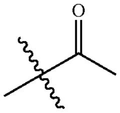 [SMILES: *C(C)=O] | H | H |
| 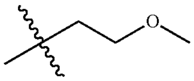 [SMILES: *CCOC] | 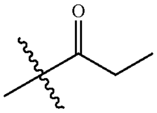 [SMILES: *C(=O)CC] | H | H |
| 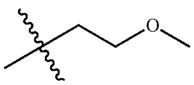 [SMILES: *CCOC] | 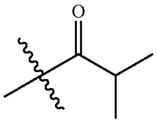 [SMILES: *C(=O)C(C)C] | H | H |
| 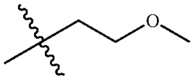 [SMILES: *CCOC] | 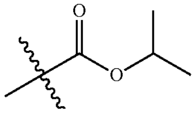 [SMILES: *C(=O)OC(C)C] | H | H |
| 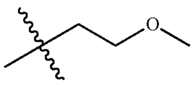 [SMILES: *CCOC] | 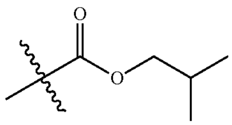 [SMILES: *C(=O)OCC(C)C] | H | H |
| 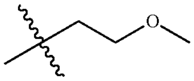 [SMILES: *CCOC] | 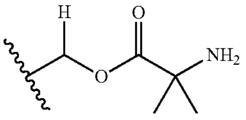 [SMILES: *COC(=O)C(C)(C)N] | H | H |
| 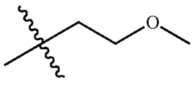 [SMILES: *CCOC] | 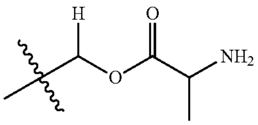 [SMILES: *COC(=O)C(C)N] | H | H |
TABLE B-continued
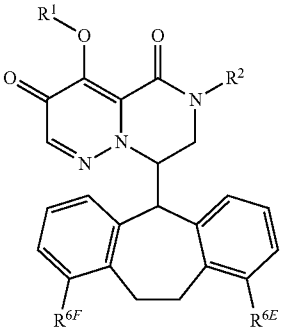
| R2 | R1 | R6E | R6F |
| --- | --- | --- | --- |
| 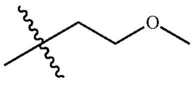 [SMILES: *CCOC] | 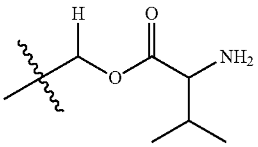 [SMILES: *COC(=O)C(N)C(C)C] | H | H |
| 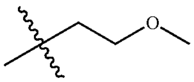 [SMILES: *CCOC] | 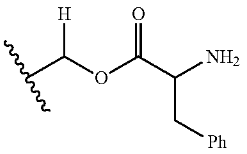 [SMILES: *COC(=O)C(N)Cc1ccccc1] | H | H |
| 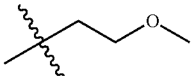 [SMILES: *CCOC] | 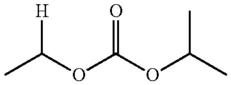 | H | H |
| 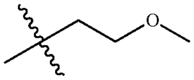 [SMILES: *CCOC] | 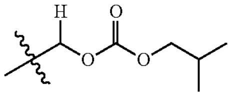 [SMILES: *COC(=O)OCC(C)C] | H | H |
| 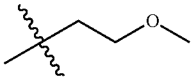 [SMILES: *CCOC] | 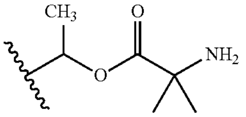 [SMILES: *C(C)OC(=O)C(C)(C)N] | H | H |
| 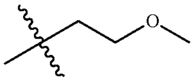 [SMILES: *CCOC] | 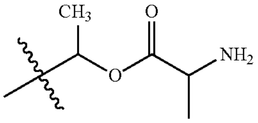 [SMILES: *C(C)OC(=O)C(C)N] | H | H |
| 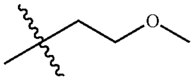 [SMILES: *CCOC] | 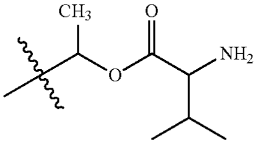 | H | H |
| 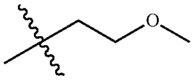 [SMILES: *CCOC] | 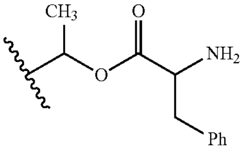 [SMILES: *C(C)OC(=O)C(N)Cc1ccccc1] | H | H |
| 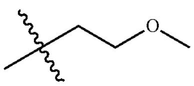 [SMILES: *CCOC] | 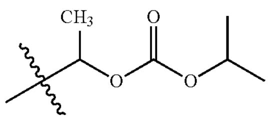 | H | H |

TABLE B-continued
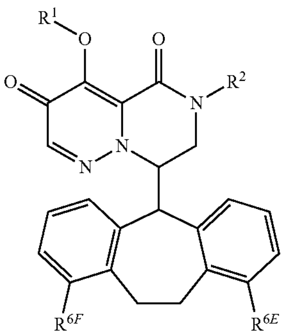
| $R^2$ | $R^1$ | $R^{6E}$ | $R^{6F}$ |
|---|---|---|---|
| 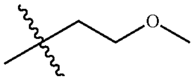 [SMILES: *CCOC] | 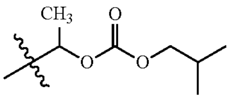 [SMILES: *C(C)OC(=O)OCC(C)C] | H | H |
| 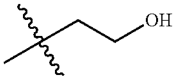 [SMILES: *CCO] | H | H | H |
| 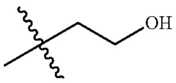 [SMILES: *CCO] | 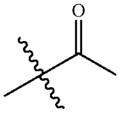 [SMILES: *C(C)=O] | H | H |
| 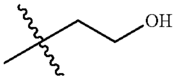 [SMILES: *CCO] | 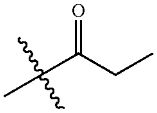 [SMILES: *C(=O)CC] | H | H |
| 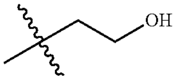 [SMILES: *CCO] | 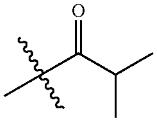 [SMILES: *C(=O)C(C)C] | H | H |
| 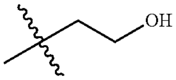 [SMILES: *CCO] | 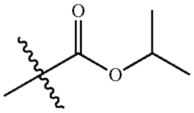 [SMILES: *C(=O)OC(C)C] | H | H |
| 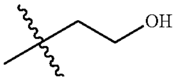 [SMILES: *CCO] | 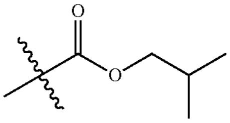 [SMILES: *C(=O)OCC(C)C] | H | H |
| 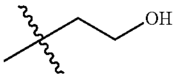 [SMILES: *CCO] | 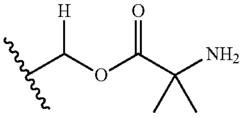 [SMILES: *COC(=O)C(C)(C)N] | H | H |
| 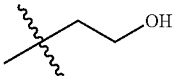 [SMILES: *CCO] | 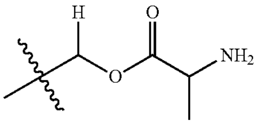 [SMILES: *COC(=O)C(C)N] | H | H |
TABLE B-continued
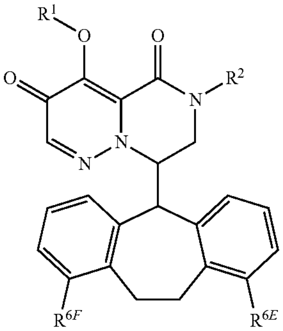
| $R^2$ | $R^1$ | $R^{6E}$ | $R^{6F}$ |
|---|---|---|---|
| 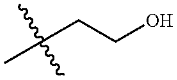 [SMILES: *CCO] | 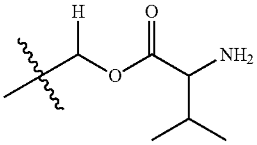 [SMILES: *COC(=O)C(N)C(C)C] | H | H |
| 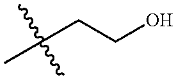 [SMILES: *CCO] | 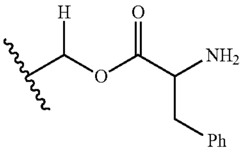 [SMILES: *COC(=O)C(N)Cc1ccccc1] | H | H |
| 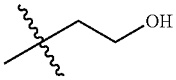 [SMILES: *CCO] | 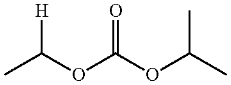 | H | H |
| 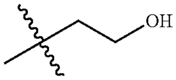 [SMILES: *CCO] | 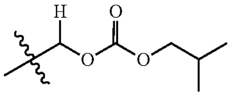 [SMILES: *COC(=O)OCC(C)C] | H | H |
| 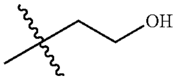 [SMILES: *CCO] | 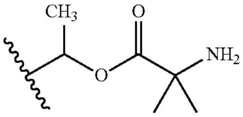 [SMILES: *C(C)OC(=O)C(C)(C)N] | H | H |
| 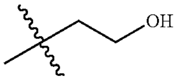 [SMILES: *CCO] | 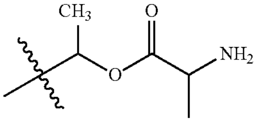 | H | H |
| 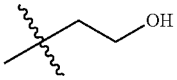 [SMILES: *CCO] | 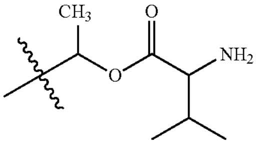 | H | H |
| 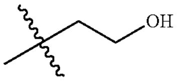 [SMILES: *CCO] | 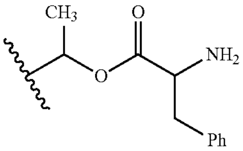 [SMILES: *C(C)OC(=O)C(N)Cc1ccccc1] | H | H |
| 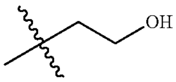 [SMILES: *CCO] | 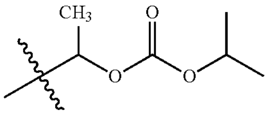 | H | H |

TABLE B-continued
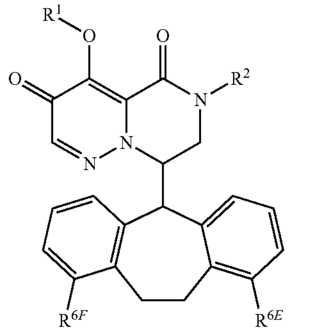
| $R^2$ | $R^1$ | $R^{6E}$ | $R^{6F}$ |
|---|---|---|---|
| 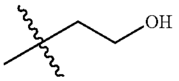 [SMILES: *CCO] | 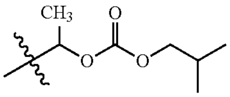 | H | H |
| $—CH_2CH{=}CF_2$ | 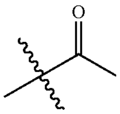 | H | H |
| $—CH_2CH{=}CF_2$ | 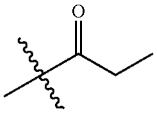 [SMILES: *C(=O)CC] | H | H |
| $—CH_2CH{=}CF_2$ | 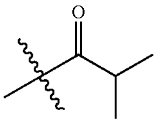 [SMILES: *C(=O)C(C)C] | H | H |
| $—CH_2CH{=}CF_2$ | 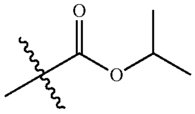 [SMILES: *C(=O)OC(C)C] | H | H |
| $—CH_2CH{=}CF_2$ | 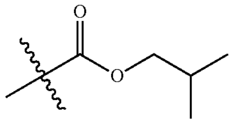 [SMILES: *C(=O)OCC(C)C] | H | H |
| $—CH_2CH{=}CF_2$ | 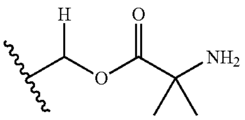 [SMILES: *COC(=O)C(C)(C)N] | H | H |
| $—CH_2CH{=}CF_2$ | 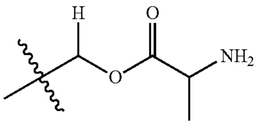 [SMILES: *COC(=O)C(C)N] | H | H |
| $—CH_2CH{=}CF_2$ | 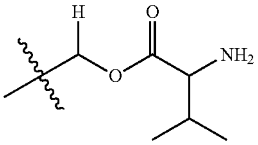 [SMILES: *COC(=O)C(N)C(C)C] | H | H |
TABLE B-continued
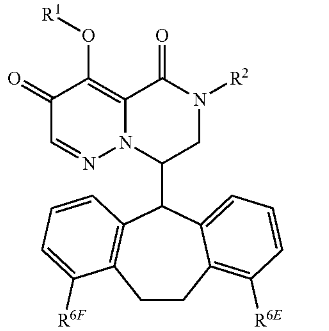
| $R^2$ | $R^1$ | $R^{6E}$ | $R^{6F}$ |
|---|---|---|---|
| $—CH_2CH{=}CF_2$ | 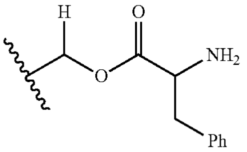 [SMILES: *COC(=O)C(N)Cc1ccccc1] | H | H |
| $—CH_2CH{=}CF_2$ | 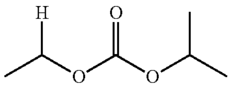 | H | H |
| $—CH_2CH{=}CF_2$ | 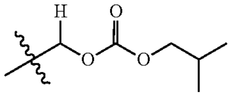 [SMILES: *COC(=O)OCC(C)C] | H | H |
| $—CH_2CH{=}CF_2$ | 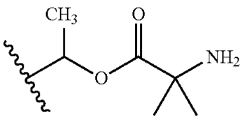 [SMILES: *C(C)OC(=O)C(C)(C)N] | H | H |
| $—CH_2CH{=}CF_2$ | 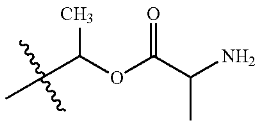 | H | H |
| $—CH_2CH{=}CF_2$ | 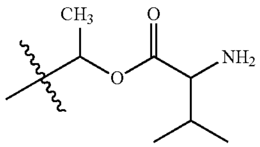 | H | H |
| $—CH_2CH{=}CF_2$ | 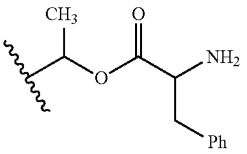 [SMILES: *C(C)OC(=O)C(N)Cc1ccccc1] | H | H |
| $—CH_2CH{=}CF_2$ | 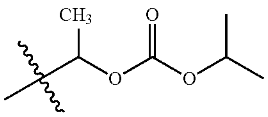 | H | H |
| $—CH_2CH{=}CF_2$ | 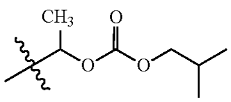 | H | H |

TABLE B-continued
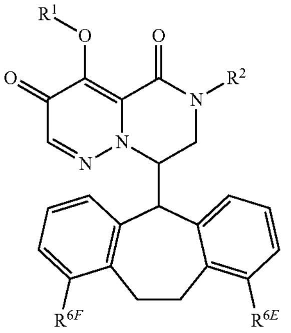
| $R^2$ | $R^1$ | $R^{6E}$ | $R^{6F}$ |
|---|---|---|---|
| $-CH_2CF_3$ | 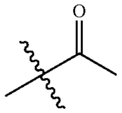 [SMILES: *C(C)=O] | H | H |
| $-CH_2CF_3$ | 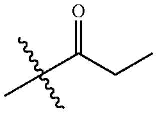 [SMILES: *C(=O)CC] | H | H |
| $-CH_2CF_3$ | 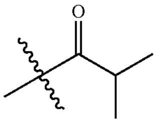 [SMILES: *C(=O)C(C)C] | H | H |
| $-CH_2CF_3$ | 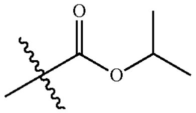 [SMILES: *C(=O)OC(C)C] | H | H |
| $-CH_2CF_3$ | 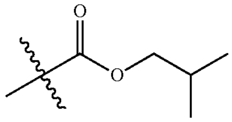 [SMILES: *C(=O)OCC(C)C] | H | H |
| $-CH_2CF_3$ | 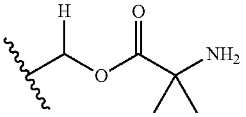 [SMILES: *COC(=O)C(C)(C)N] | H | H |
| $-CH_2CF_3$ | 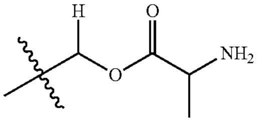 [SMILES: *COC(=O)C(C)N] | H | H |
| $-CH_2CF_3$ | 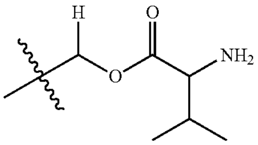 [SMILES: *COC(=O)C(N)C(C)C] | H | H |
| $-CH_2CF_3$ | 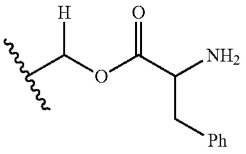 [SMILES: *COC(=O)C(N)Cc1ccccc1] | H | H |
TABLE B-continued
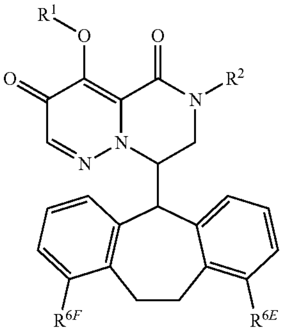
| $R^2$ | $R^1$ | $R^{6E}$ | $R^{6F}$ |
|---|---|---|---|
| $-CH_2CF_3$ | 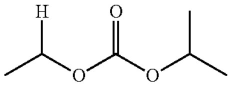 | H | H |
| $-CH_2CF_3$ | 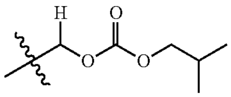 [SMILES: *COC(=O)OCC(C)C] | H | H |
| $-CH_2CF_3$ | 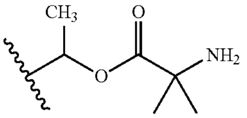 [SMILES: *C(C)OC(=O)C(C)(C)N] | H | H |
| $-CH_2CF_3$ | 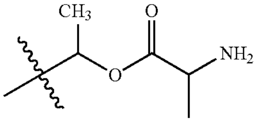 | H | H |
| $-CH_2CF_3$ | 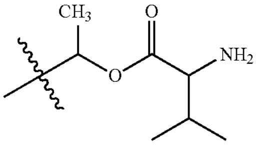 [SMILES: *C(C)OC(=O)C(N)C(C)C] | H | H |
| $-CH_2CF_3$ | 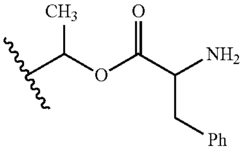 [SMILES: *C(C)OC(=O)C(N)Cc1ccccc1] | H | H |
| $-CH_2CF_3$ | 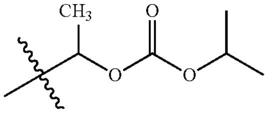 | H | H |
| $-CH_2CF_3$ | 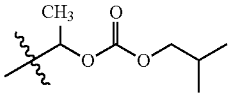 | H | H |
| $-CH_2CH_2CF_3$ | 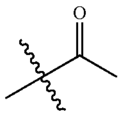 [SMILES: *C(C)=O] | H | H |

TABLE B-continued
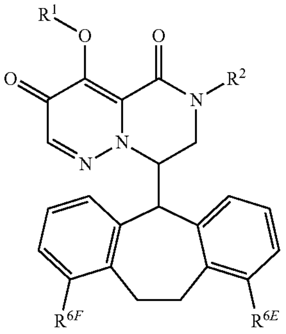
| $R^2$ | $R^1$ | $R^{6E}$ | $R^{6F}$ |
|---|---|---|---|
| $—CH_2CH_2CF_3$ | 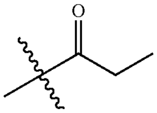 [SMILES: *C(=O)CC] | H | H |
| $—CH_2CH_2CF_3$ | 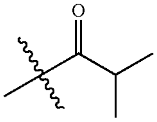 [SMILES: *C(=O)C(C)C] | H | H |
| $—CH_2CH_2CF_3$ | 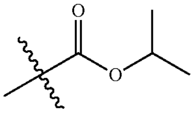 [SMILES: *C(=O)OC(C)C] | H | H |
| $—CH_2CH_2CF_3$ | 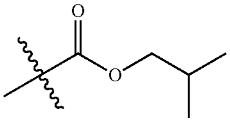 [SMILES: *C(=O)OCC(C)C] | H | H |
| $—CH_2CH_2CF_3$ | 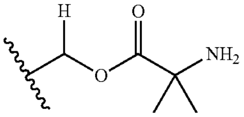 [SMILES: *COC(=O)C(C)(C)N] | H | H |
| $—CH_2CH_2CF_3$ | 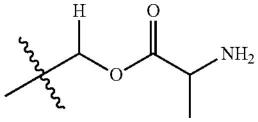 [SMILES: *COC(=O)C(C)N] | H | H |
| $—CH_2CH_2CF_3$ | 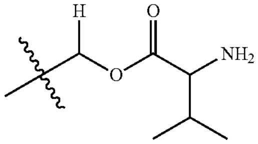 [SMILES: *COC(=O)C(N)C(C)C] | H | H |
| $—CH_2CH_2CF_3$ | 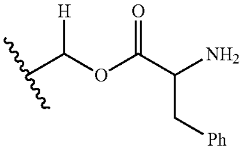 [SMILES: *COC(=O)C(N)Cc1ccccc1] | H | H |
| $—CH_2CH_2CF_3$ | 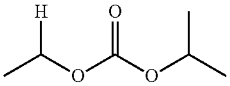 | H | H |
TABLE B-continued
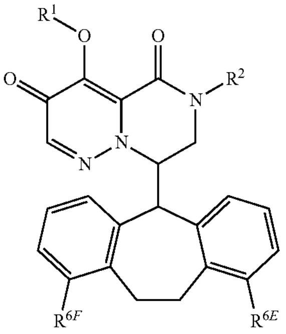
| $R^2$ | $R^1$ | $R^{6E}$ | $R^{6F}$ |
|---|---|---|---|
| $—CH_2CH_2CF_3$ | 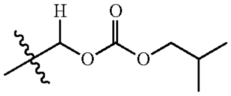 [SMILES: *COC(=O)OCC(C)C] | H | H |
| $—CH_2CH_2CF_3$ | 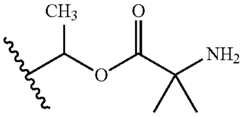 [SMILES: *C(C)OC(=O)C(C)(C)N] | H | H |
| $—CH_2CH_2CF_3$ | 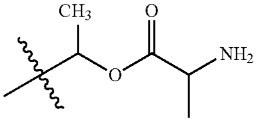 | H | H |
| $—CH_2CH_2CF_3$ | 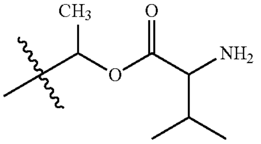 [SMILES: *C(C)OC(=O)C(N)C(C)C] | H | H |
| $—CH_2CH_2CF_3$ | 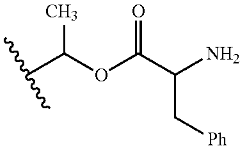 [SMILES: *C(C)OC(=O)C(N)Cc1ccccc1] | H | H |
| $—CH_2CH_2CF_3$ | 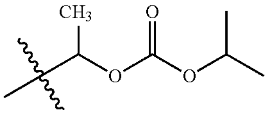 [SMILES: *C(C)OC(=O)OC(C)C] | H | H |
| $—CH_2CH_2CF_3$ | 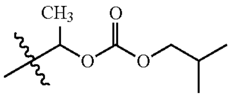 | H | H |
| $—CH_2CHF_2$ | 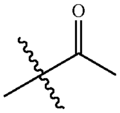 [SMILES: *C(C)=O] | H | H |
| $—CH_2CHF_2$ | 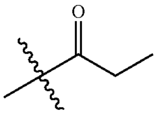 [SMILES: *C(=O)CC] | H | H |

TABLE B-continued
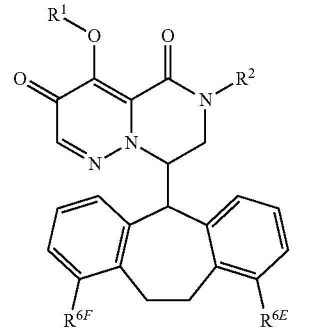
| $R^2$ | $R^1$ | $R^{6E}$ | $R^{6F}$ |
|---|---|---|---|
| $—CH_2CHF_2$ | 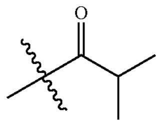 [SMILES: *C(=O)C(C)C] | H | H |
| $—CH_2CHF_2$ | 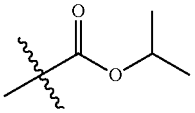 [SMILES: *C(=O)OC(C)C] | H | H |
| $—CH_2CHF_2$ | 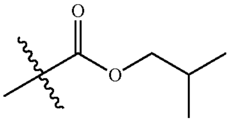 [SMILES: *C(=O)OCC(C)C] | H | H |
| $—CH_2CHF_2$ | 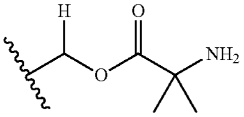 [SMILES: *COC(=O)C(C)(C)N] | H | H |
| $—CH_2CHF_2$ | 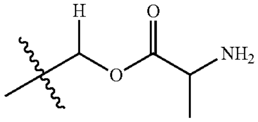 [SMILES: *COC(=O)C(C)N] | H | H |
| $—CH_2CHF_2$ | 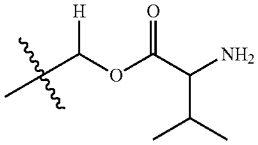 [SMILES: *COC(=O)C(N)C(C)C] | H | H |
| $—CH_2CHF_2$ | 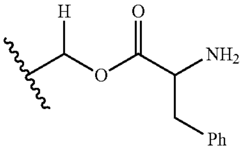 [SMILES: *COC(=O)C(N)Cc1ccccc1] | H | H |
| $—CH_2CHF_2$ | 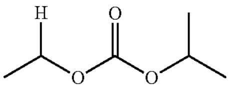 | H | H |
| $—CH_2CHF_2$ | 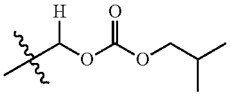 [SMILES: *COC(=O)OCC(C)C] | H | H |
TABLE B-continued
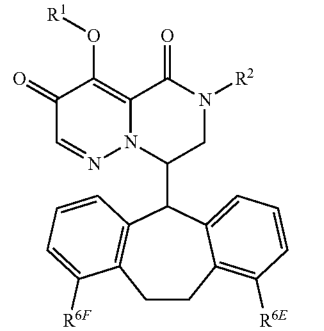
| $R^2$ | $R^1$ | $R^{6E}$ | $R^{6F}$ |
|---|---|---|---|
| $—CH_2CHF_2$ | 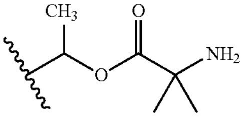 | H | H |
| $—CH_2CHF_2$ | 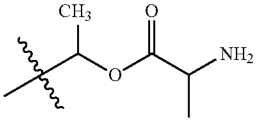 | H | H |
| $—CH_2CHF_2$ | 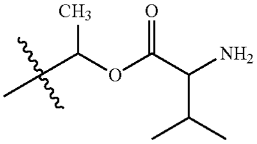 | H | H |
| $—CH_2CHF_2$ | 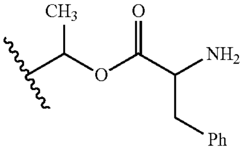 [SMILES: *C(C)OC(=O)C(N)Cc1ccccc1] | H | H |
| $—CH_2CHF_2$ | 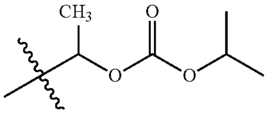 | H | H |
| $—CH_2CHF_2$ | 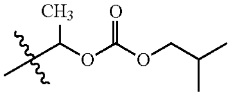 | H | H |
| $—CH_2C(CH_3)F_2$ | 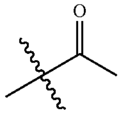 [SMILES: *C(C)=O] | H | H |
| $—CH_2C(CH_3)F_2$ | 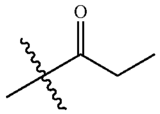 [SMILES: *C(=O)CC] | H | H |
| $—CH_2C(CH_3)F_2$ | 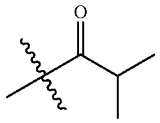 [SMILES: *C(=O)C(C)C] | H | H |

TABLE B-continued
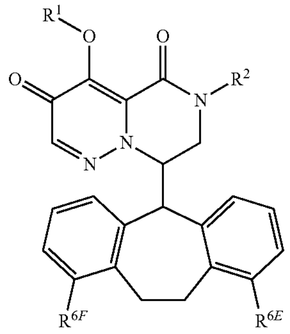
| $R^2$ | $R^1$ | $R^{6E}$ | $R^{6F}$ |
|---|---|---|---|
| $—CH_2C(CH_3)F_2$ | 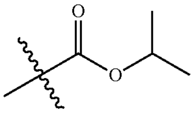 [SMILES: *C(=O)OC(C)C] | H | H |
| $—CH_2C(CH_3)F_2$ | 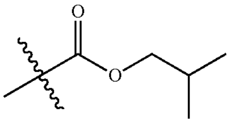 [SMILES: *C(=O)OCC(C)C] | H | H |
| $—CH_2C(CH_3)F_2$ | 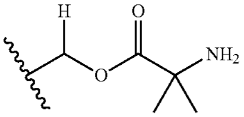 [SMILES: *COC(=O)C(C)(C)N] | H | H |
| $—CH_2C(CH_3)F_2$ | 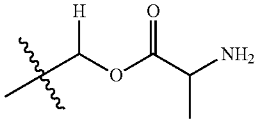 [SMILES: *COC(=O)C(C)N] | H | H |
| $—CH_2C(CH_3)F_2$ | 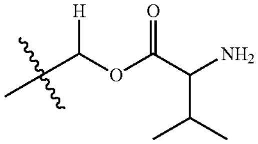 [SMILES: *COC(=O)C(N)C(C)C] | H | H |
| $—CH_2C(CH_3)F_2$ | 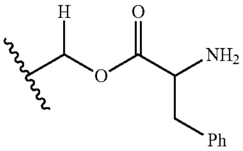 [SMILES: *COC(=O)C(N)Cc1ccccc1] | H | H |
| $—CH_2C(CH_3)F_2$ | 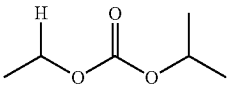 | H | H |
| $—CH_2C(CH_3)F_2$ | 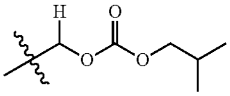 [SMILES: *COC(=O)OCC(C)C] | H | H |
| $—CH_2C(CH_3)F_2$ | 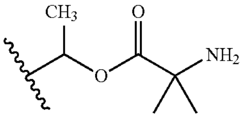 | H | H |
TABLE B-continued
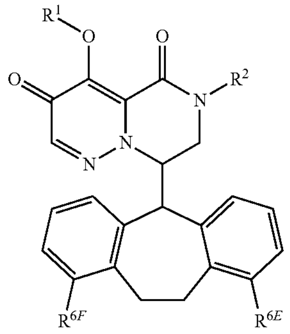
| $R^2$ | $R^1$ | $R^{6E}$ | $R^{6F}$ |
|---|---|---|---|
| $—CH_2C(CH_3)F_2$ | 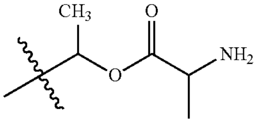 [SMILES: *C(C)OC(=O)C(C)N] | H | H |
| $—CH_2C(CH_3)F_2$ | 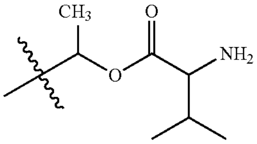 | H | H |
| $—CH_2C(CH_3)F_2$ | 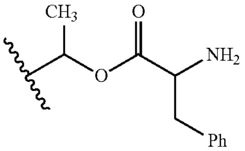 [SMILES: *C(C)OC(=O)C(N)Cc1ccccc1] | H | H |
| $—CH_2C(CH_3)F_2$ | 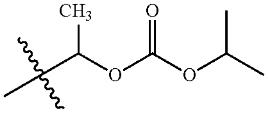 | H | H |
| $—CH_2C(CH_3)F_2$ | 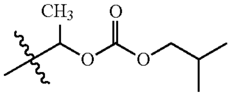 [SMILES: *C(C)OC(=O)OCC(C)C] | H | H |
| 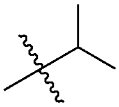 [SMILES: *C(C)C] | 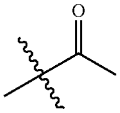 [SMILES: *C(C)=O] | F | F |
| 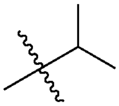 [SMILES: *C(C)C] | 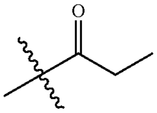 [SMILES: *C(=O)CC] | F | F |
| 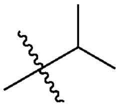 [SMILES: *C(C)C] | 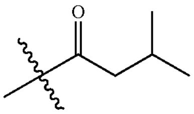 [SMILES: *C(=O)CC(C)C] | F | F |
| 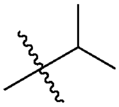 [SMILES: *C(C)C] | 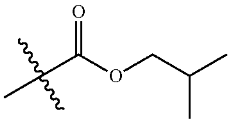 [SMILES: *C(=O)OCC(C)C] | F | F |

TABLE B-continued
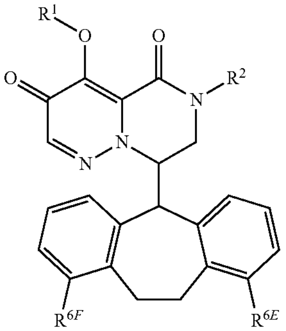
| $R^2$ | $R^1$ | $R^{6E}$ | $R^{6F}$ |
|---|---|---|---|
| 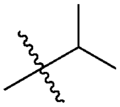 [SMILES: *C(C)C] | 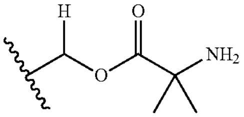 [SMILES: *COC(=O)C(C)(C)N] | F | F |
| 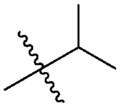 [SMILES: *C(C)C] | 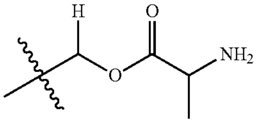 | F | F |
| 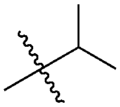 [SMILES: *C(C)C] | 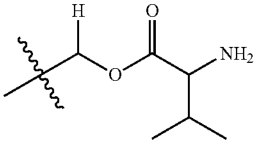 | F | F |
| 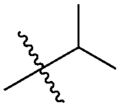 [SMILES: *C(C)C] | 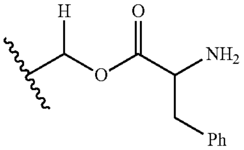 [SMILES: *COC(=O)C(N)Cc1ccccc1] | F | F |
| 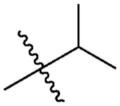 [SMILES: *C(C)C] | 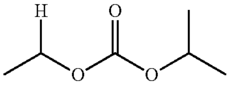 | F | F |
| 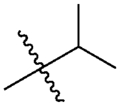 [SMILES: *C(C)C] | 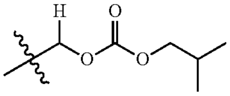 [SMILES: *COC(=O)OCC(C)C] | F | F |
| 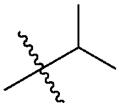 [SMILES: *C(C)C] | 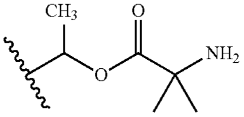 | F | F |
| 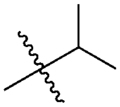 [SMILES: *C(C)C] | 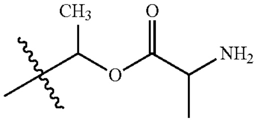 [SMILES: *C(C)OC(=O)C(C)N] | F | F |
| 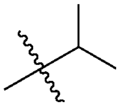 [SMILES: *C(C)C] | 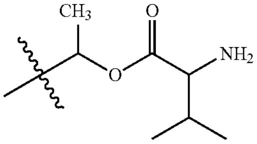 | F | F |
TABLE B-continued
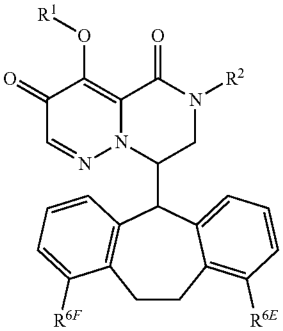
| $R^2$ | $R^1$ | $R^{6E}$ | $R^{6F}$ |
|---|---|---|---|
| 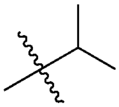 [SMILES: *C(C)C] | 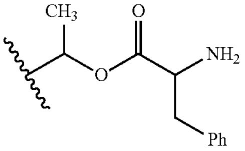 [SMILES: *C(C)OC(=O)C(N)Cc1ccccc1] | F | F |
| 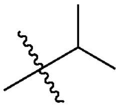 [SMILES: *C(C)C] | 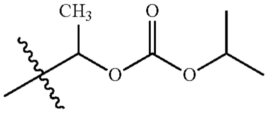 [SMILES: *C(C)OC(=O)OC(C)C] | F | F |
| 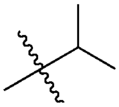 [SMILES: *C(C)C] | 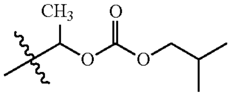 [SMILES: *C(C)OC(=O)OCC(C)C] | F | F |
| $—CH_3$ | 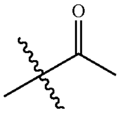 [SMILES: *C(C)=O] | F | F |
| $—CH_3$ | 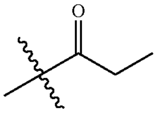 [SMILES: *C(=O)CC] | F | F |
| $—CH_3$ | 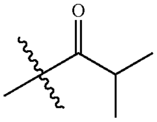 [SMILES: *C(=O)C(C)C] | F | F |
| $—CH_3$ | 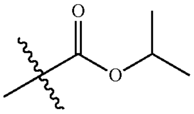 [SMILES: *C(=O)OC(C)C] | F | F |
| $—CH_3$ | 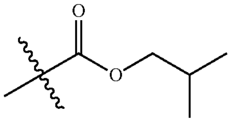 [SMILES: *C(=O)OCC(C)C] | F | F |
| $—CH_3$ | 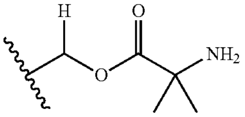 [SMILES: *COC(=O)C(C)(C)N] | F | F |

TABLE B-continued
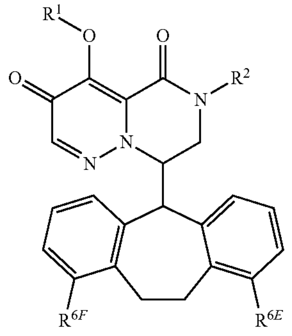
| $R^2$ | $R^1$ | $R^{6E}$ | $R^{6F}$ |
|---|---|---|---|
| —$CH_3$ | 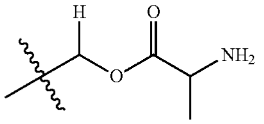 [SMILES: *COC(=O)C(C)N] | F | F |
| —$CH_3$ | 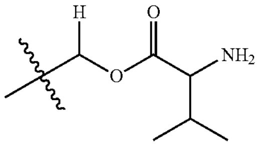 [SMILES: *COC(=O)C(N)C(C)C] | F | F |
| —$CH_3$ | 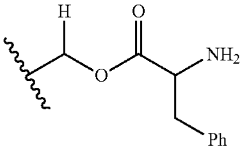 [SMILES: *COC(=O)C(N)Cc1ccccc1] | F | F |
| —$CH_3$ | 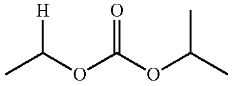 | F | F |
| —$CH_3$ | 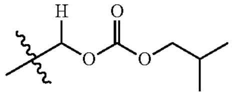 [SMILES: *COC(=O)OCC(C)C] | F | F |
| —$CH_3$ | 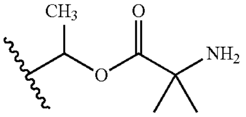 | F | F |
| —$CH_3$ | 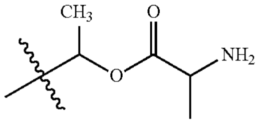 | F | F |
| —$CH_3$ | 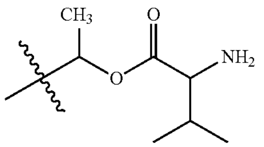 [SMILES: *C(C)OC(=O)C(N)C(C)C] | F | F |
| —$CH_3$ | 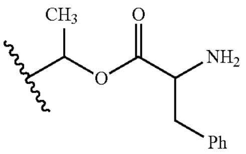 | F | F |
TABLE B-continued
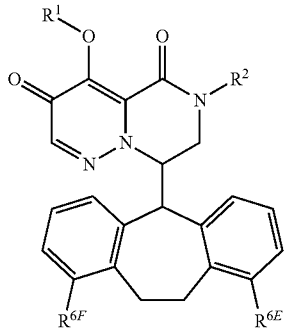
| $R^2$ | $R^1$ | $R^{6E}$ | $R^{6F}$ |
|---|---|---|---|
| —$CH_3$ | 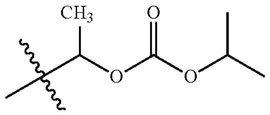 [SMILES: *C(C)OC(=O)OC(C)C] | F | F |
| —$CH_3$ | 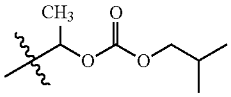 [SMILES: *C(C)OC(=O)OCC(C)C] | F | F |
| —$CH_2CH_3$ | H | F | F |
| —$CH_2CH_3$ | 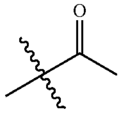 [SMILES: *C(C)=O] | F | F |
| —$CH_2CH_3$ | 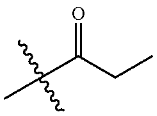 [SMILES: *C(=O)CC] | F | F |
| —$CH_2CH_3$ | 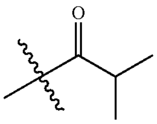 [SMILES: *C(=O)C(C)C] | F | F |
| —$CH_2CH_3$ | 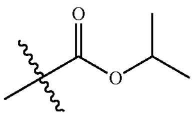 [SMILES: *C(=O)OC(C)C] | F | F |
| —$CH_2CH_3$ | 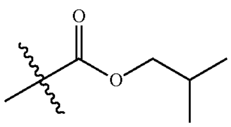 [SMILES: *C(=O)OCC(C)C] | F | F |
| —$CH_2CH_3$ | 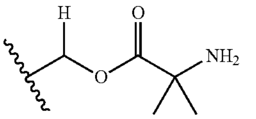 [SMILES: *COC(=O)C(C)(C)N] | F | F |
| —$CH_2CH_3$ | 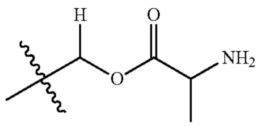 [SMILES: *COC(=O)C(C)N] | F | F |

TABLE B-continued
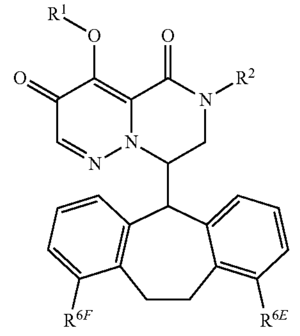
| $R^2$ | $R^1$ | $R^{6E}$ | $R^{6F}$ |
|---|---|---|---|
| $-CH_2CH_3$ | 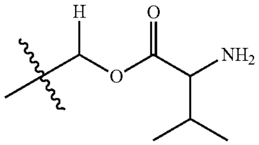 [SMILES: *COC(=O)C(N)C(C)C] | F | F |
| $-CH_2CH_3$ | 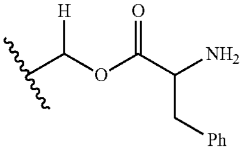 [SMILES: *COC(=O)C(N)Cc1ccccc1] | F | F |
| $-CH_2CH_3$ | 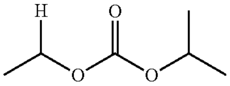 | F | F |
| $-CH_2CH_3$ | 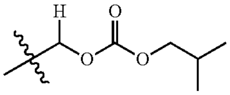 [SMILES: *COC(=O)OCC(C)C] | F | F |
| $-CH_2CH_3$ | 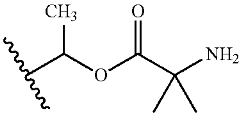 | F | F |
| $-CH_2CH_3$ | 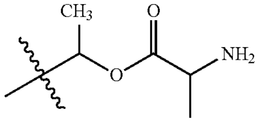 | F | F |
| $-CH_2CH_3$ | 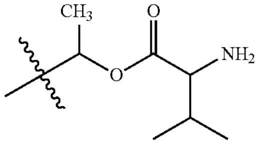 [SMILES: *C(C)OC(=O)C(N)C(C)C] | F | F |
| $-CH_2CH_3$ | 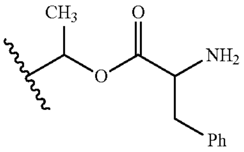 | F | F |
| $-CH_2CH_3$ | 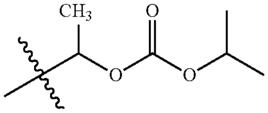 [SMILES: *C(C)OC(=O)OC(C)C] | F | F |
TABLE B-continued
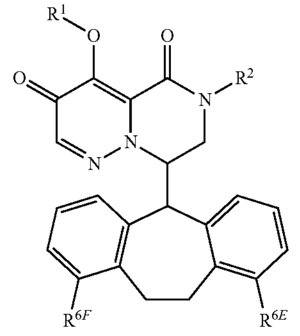
| $R^2$ | $R^1$ | $R^{6E}$ | $R^{6F}$ |
|---|---|---|---|
| $-CH_2CH_3$ | 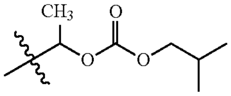 | F | F |
| $-CH_2CH(CH_3)_2$ | H | F | F |
| $-CH_2CH(CH_3)_2$ | 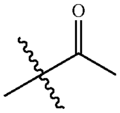 [SMILES: *C(C)=O] | F | F |
| $-CH_2CH(CH_3)_2$ | 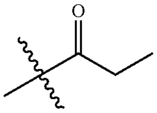 [SMILES: *C(=O)CC] | F | F |
| $-CH_2CH(CH_3)_2$ | 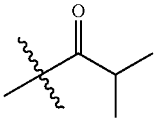 [SMILES: *C(=O)C(C)C] | F | F |
| $-CH_2CH(CH_3)_2$ | 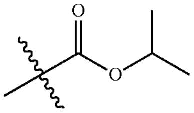 [SMILES: *C(=O)OC(C)C] | F | F |
| $-CH_2CH(CH_3)_2$ | 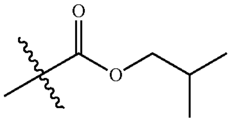 [SMILES: *C(=O)OCC(C)C] | F | F |
| $-CH_2CH(CH_3)_2$ | 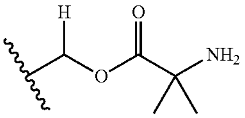 [SMILES: *COC(=O)C(C)(C)N] | F | F |
| $-CH_2CH(CH_3)_2$ | 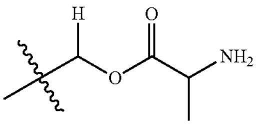 [SMILES: *COC(=O)C(C)N] | F | F |
| $-CH_2CH(CH_3)_2$ | 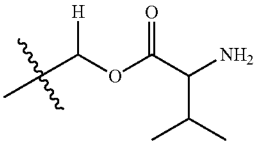 [SMILES: *COC(=O)C(N)C(C)C] | F | F |

TABLE B-continued
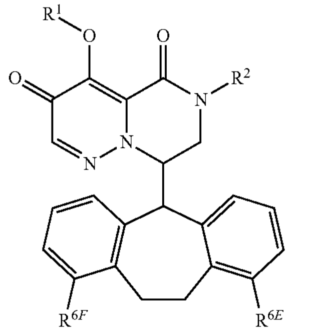
| $R^2$ | $R^1$ | $R^{6E}$ | $R^{6F}$ |
|---|---|---|---|
| $—CH_2CH(CH_3)_2$ | 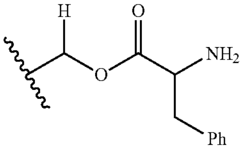 [SMILES: *COC(=O)C(N)Cc1ccccc1] | F | F |
| $—CH_2CH(CH_3)_2$ | 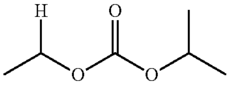 | F | F |
| $—CH_2CH(CH_3)_2$ | 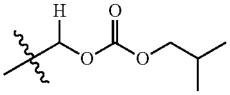 [SMILES: *COC(=O)OCC(C)C] | F | F |
| $—CH_2CH(CH_3)_2$ | 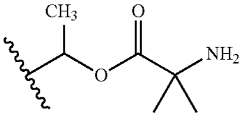 | F | F |
| $—CH_2CH(CH_3)_2$ | 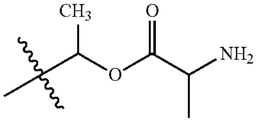 | F | F |
| $—CH_2CH(CH_3)_2$ | 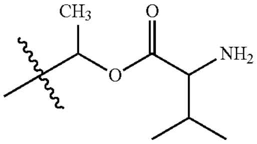 | F | F |
| $—CH_2CH(CH_3)_2$ | 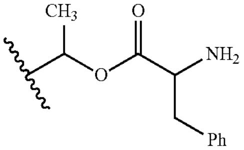 | F | F |
| $—CH_2CH(CH_3)_2$ | 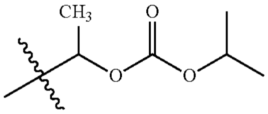 | F | F |
| $—CH_2CH(CH_3)_2$ | 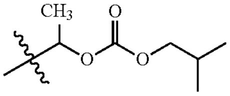 | F | F |
| $—CH_2CH_2CH_3$ | H | F | F |
TABLE B-continued
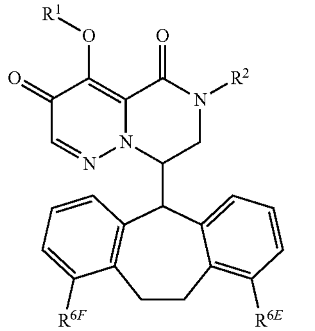
| $R^2$ | $R^1$ | $R^{6E}$ | $R^{6F}$ |
|---|---|---|---|
| $—CH_2CH_2CH_3$ | 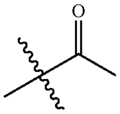 [SMILES: *C(C)=O] | F | F |
| $—CH_2CH_2CH_3$ | 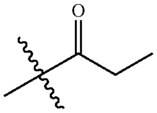 [SMILES: *C(=O)CC] | F | F |
| $—CH_2CH_2CH_3$ | 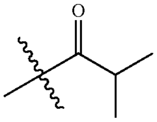 [SMILES: *C(=O)C(C)C] | F | F |
| $—CH_2CH_2CH_3$ | 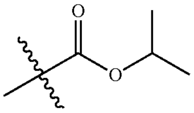 | F | F |
| $—CH_2CH_2CH_3$ | 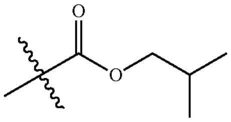 [SMILES: *C(=O)OCC(C)C] | F | F |
| $—CH_2CH_2CH_3$ | 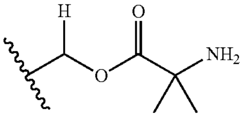 [SMILES: *COC(=O)C(C)(C)N] | F | F |
| $—CH_2CH_2CH_3$ | 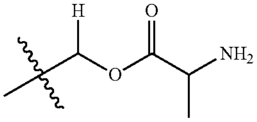 [SMILES: *COC(=O)C(C)N] | F | F |
| $—CH_2CH_2CH_3$ | 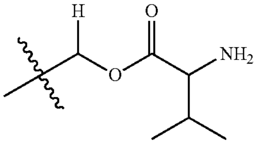 [SMILES: *COC(=O)C(N)C(C)C] | F | F |
| $—CH_2CH_2CH_3$ | 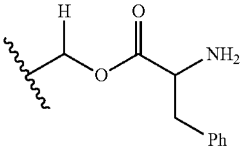 [SMILES: *COC(=O)C(N)Cc1ccccc1] | F | F |

TABLE B-continued
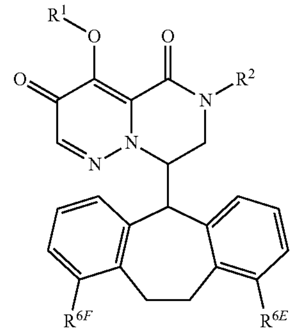
| $R^2$ | $R^1$ | $R^{6E}$ | $R^{6F}$ |
|---|---|---|---|
| $—CH_2CH_2CH_3$ | 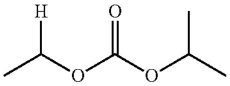 | F | F |
| $—CH_2CH_2CH_3$ | 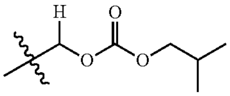 [SMILES: *COC(=O)OCC(C)C] | F | F |
| $—CH_2CH_2CH_3$ | 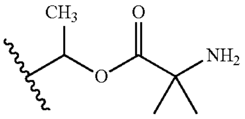 | F | F |
| $—CH_2CH_2CH_3$ | 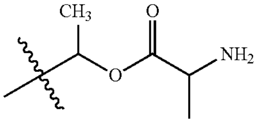 | F | F |
| $—CH_2CH_2CH_3$ | 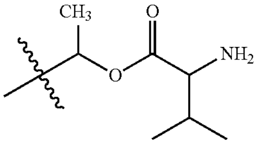 [SMILES: *C(C)OC(=O)C(N)C(C)C] | F | F |
| $—CH_2CH_2CH_3$ | 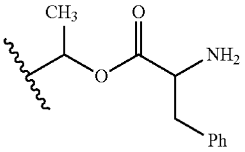 | F | F |
| $—CH_2CH_2CH_3$ | 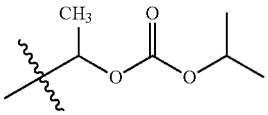 [SMILES: *C(C)OC(=O)OC(C)C] | F | F |
| $—CH_2CH_2CH_3$ | 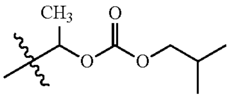 | F | F |
| $—CH_2CH_2CH_2CH_3$ | H | F | F |
| $—CH_2CH_2CH_2CH_3$ | 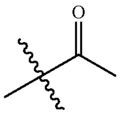 [SMILES: *C(C)=O] | F | F |
TABLE B-continued
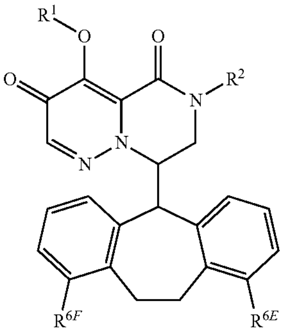
| $R^2$ | $R^1$ | $R^{6E}$ | $R^{6F}$ |
|---|---|---|---|
| $—CH_2CH_2CH_2CH_3$ | 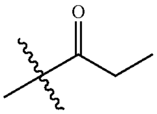 [SMILES: *C(=O)CC] | F | F |
| $—CH_2CH_2CH_2CH_3$ | 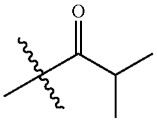 [SMILES: *C(=O)C(C)C] | F | F |
| $—CH_2CH_2CH_2CH_3$ | 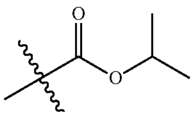 [SMILES: *C(=O)OC(C)C] | F | F |
| $—CH_2CH_2CH_2CH_3$ | 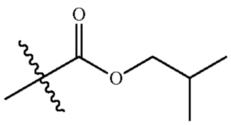 [SMILES: *C(=O)OCC(C)C] | F | F |
| $—CH_2CH_2CH_2CH_3$ | 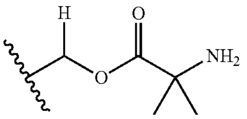 [SMILES: *COC(=O)C(C)(C)N] | F | F |
| $—CH_2CH_2CH_2CH_3$ | 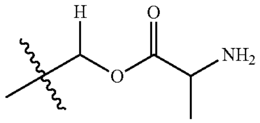 [SMILES: *COC(=O)C(C)N] | F | F |
| $—CH_2CH_2CH_2CH_3$ | 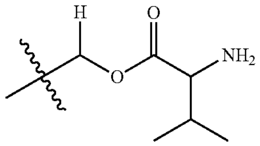 [SMILES: *COC(=O)C(N)C(C)C] | F | F |
| $—CH_2CH_2CH_2CH_3$ | 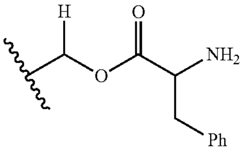 [SMILES: *COC(=O)C(N)Cc1ccccc1] | F | F |
| $—CH_2CH_2CH_2CH_3$ | 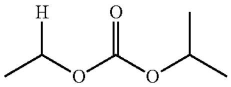 | F | F |

TABLE B-continued
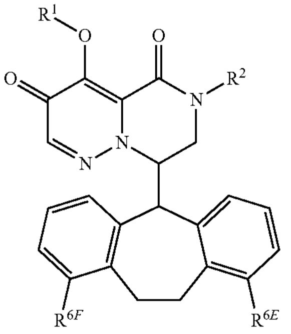
| $R^2$ | $R^1$ | $R^{6E}$ | $R^{6F}$ |
|---|---|---|---|
| $—CH_2CH_2CH_2CH_3$ | 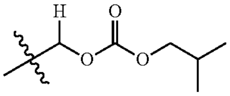 [SMILES: *COC(=O)OCC(C)C] | F | F |
| $—CH_2CH_2CH_2CH_3$ | 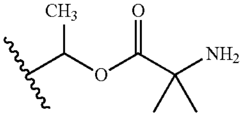 | F | F |
| $—CH_2CH_2CH_2CH_3$ | 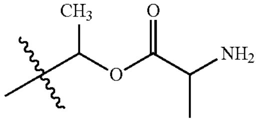 | F | F |
| $—CH_2CH_2CH_2CH_3$ | 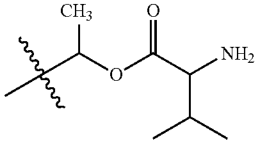 | F | F |
| $—CH_2CH_2CH_2CH_3$ | 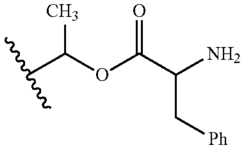 | F | F |
| $—CH_2CH_2CH_2CH_3$ | 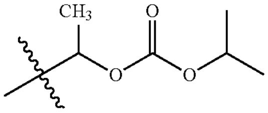 | F | F |
| $—CH_2CH_2CH_2CH_3$ | 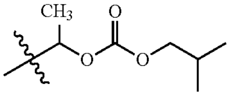 | F | F |
| 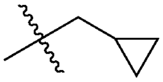 [SMILES: *CC1CC1] | H | F | F |
| 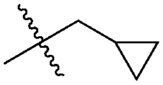 | 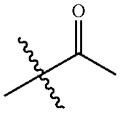 [SMILES: *C(C)=O] | F | F |
TABLE B-continued
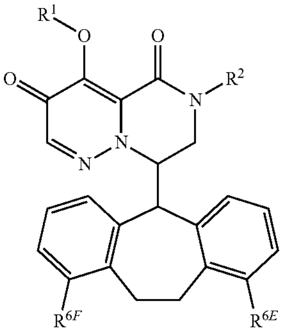
| $R^2$ | $R^1$ | $R^{6E}$ | $R^{6F}$ |
|---|---|---|---|
| 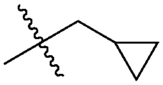 | 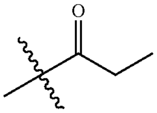 [SMILES: *C(=O)CC] | F | F |
| 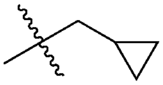 [SMILES: *CC1CC1] | 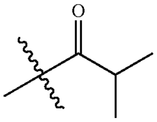 [SMILES: *C(=O)C(C)C] | F | F |
| 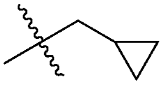 [SMILES: *CC1CC1] | 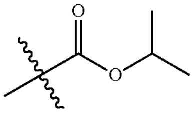 [SMILES: *C(=O)OC(C)C] | F | F |
| 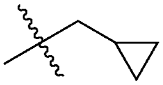 | 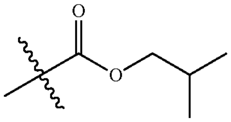 [SMILES: *C(=O)OCC(C)C] | F | F |
| 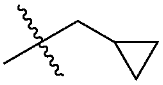 [SMILES: *CC1CC1] | 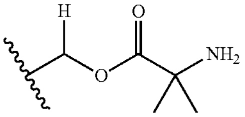 [SMILES: *COC(=O)C(C)(C)N] | F | F |
| 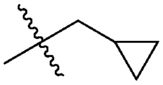 [SMILES: *CC1CC1] | 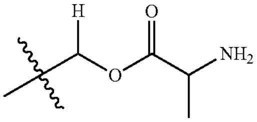 [SMILES: *COC(=O)C(C)N] | F | F |
| 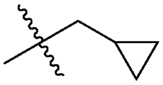 [SMILES: *CC1CC1] | 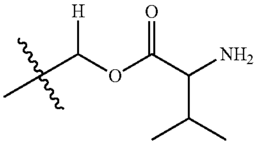 [SMILES: *COC(=O)C(N)C(C)C] | F | F |
| 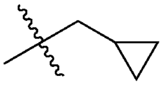 | 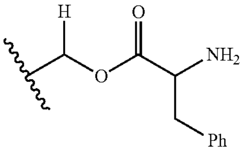 [SMILES: *COC(=O)C(N)Cc1ccccc1] | F | F |
| 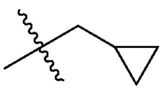 [SMILES: *CC1CC1] | 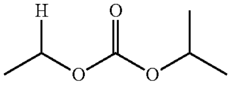 | F | F |

TABLE B-continued
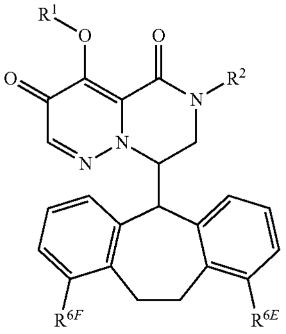
| $R^2$ | $R^1$ | $R^{6E}$ | $R^{6F}$ |
|---|---|---|---|
| 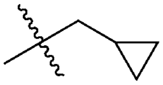 [SMILES: *CC1CC1] | 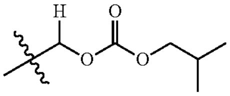 [SMILES: *COC(=O)OCC(C)C] | F | F |
| 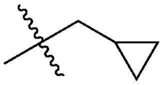 | 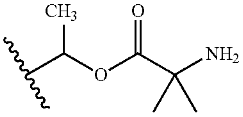 | F | F |
| 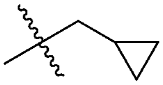 [SMILES: *CC1CC1] | 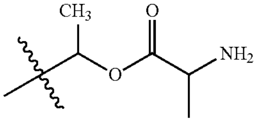 | F | F |
| 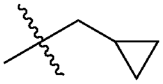 [SMILES: *CC1CC1] | 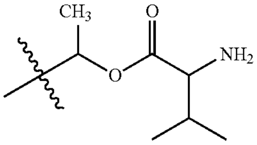 | F | F |
| 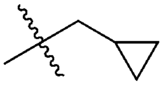 | 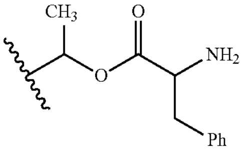 | F | F |
| 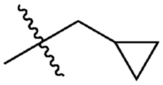 | 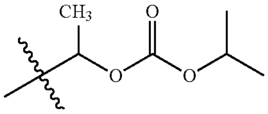 [SMILES: *C(C)OC(=O)OC(C)C] | F | F |
| 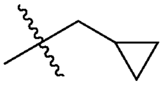 | 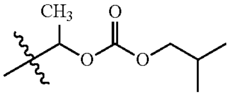 | F | F |
| 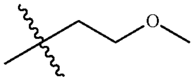 [SMILES: *CCOC] | H | F | F |
| 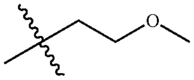 [SMILES: *CCOC] | 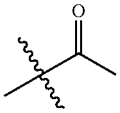 [SMILES: *C(C)=O] | F | F |
TABLE B-continued
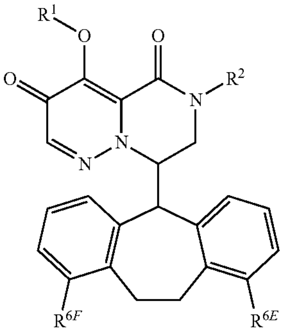
| $R^2$ | $R^1$ | $R^{6E}$ | $R^{6F}$ |
|---|---|---|---|
| 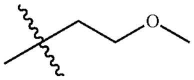 [SMILES: *CCOC] | 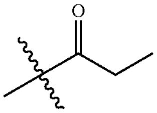 [SMILES: *C(=O)CC] | F | F |
| 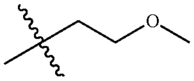 [SMILES: *CCOC] | 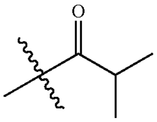 [SMILES: *C(=O)C(C)C] | F | F |
| 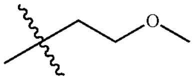 [SMILES: *CCOC] | 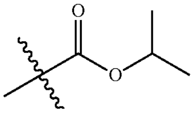 [SMILES: *C(=O)OC(C)C] | F | F |
| 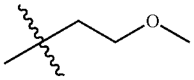 [SMILES: *CCOC] | 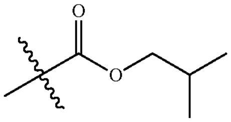 [SMILES: *C(=O)OCC(C)C] | F | F |
| 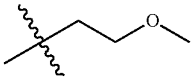 [SMILES: *CCOC] | 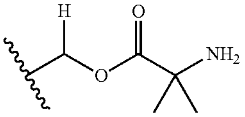 [SMILES: *COC(=O)C(C)(C)N] | F | F |
| 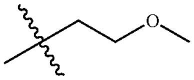 [SMILES: *CCOC] | 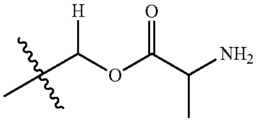 [SMILES: *COC(=O)C(C)N] | F | F |
| 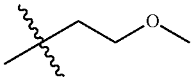 [SMILES: *CCOC] | 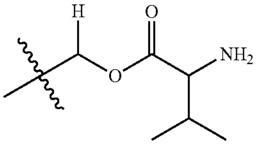 [SMILES: *COC(=O)C(N)C(C)C] | F | F |
| 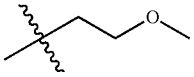 [SMILES: *CCOC] | 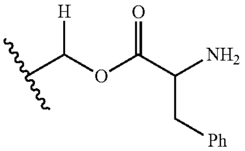 [SMILES: *COC(=O)C(N)Cc1ccccc1] | F | F |
| 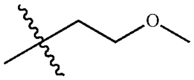 [SMILES: *CCOC] | 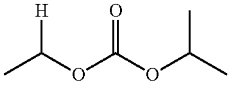 | F | F |

TABLE B-continued
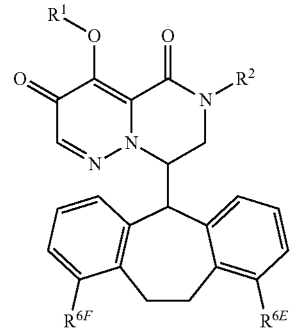
| $R^2$ | $R^1$ | $R^{6E}$ | $R^{6F}$ |
|---|---|---|---|
| 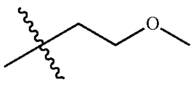 [SMILES: *CCOC] | 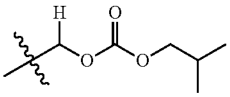 [SMILES: *COC(=O)OCC(C)C] | F | F |
| 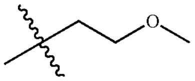 [SMILES: *CCOC] | 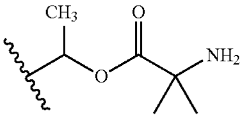 | F | F |
| 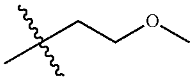 [SMILES: *CCOC] | 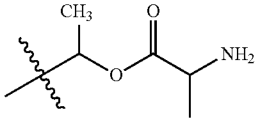 | F | F |
| 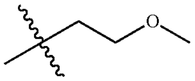 [SMILES: *CCOC] | 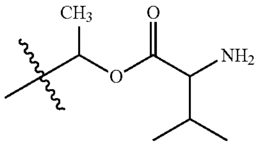 | F | F |
| 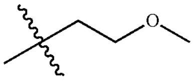 [SMILES: *CCOC] | 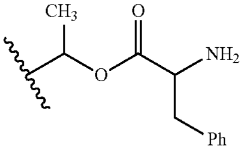 [SMILES: *C(C)OC(=O)C(N)Cc1ccccc1] | F | F |
| 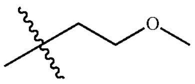 [SMILES: *CCOC] | 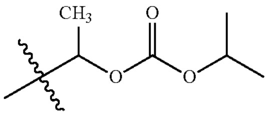 [SMILES: *C(C)OC(=O)OC(C)C] | F | F |
| 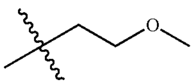 [SMILES: *CCOC] | 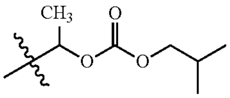 | F | F |
| 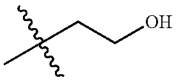 [SMILES: *CCO] | H | F | F |
| 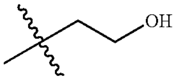 [SMILES: *CCO] | 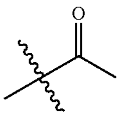 [SMILES: *C(C)=O] | F | F |
TABLE B-continued
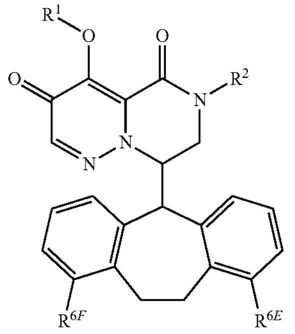
| $R^2$ | $R^1$ | $R^{6E}$ | $R^{6F}$ |
|---|---|---|---|
| 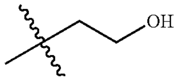 [SMILES: *CCO] | 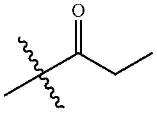 [SMILES: *C(=O)CC] | F | F |
| 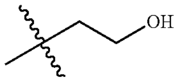 [SMILES: *CCO] | 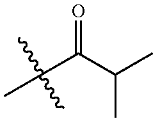 [SMILES: *C(=O)C(C)C] | F | F |
| 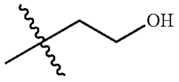 [SMILES: *CCO] | 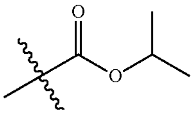 [SMILES: *C(=O)OC(C)C] | F | F |
| 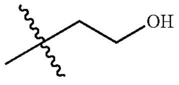 [SMILES: *CCO] | 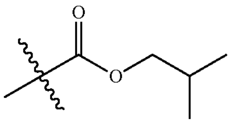 [SMILES: *C(=O)OCC(C)C] | F | F |
| 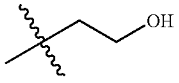 [SMILES: *CCO] | 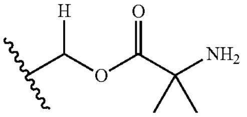 [SMILES: *COC(=O)C(C)(C)N] | F | F |
| 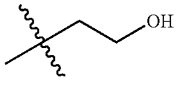 [SMILES: *CCO] | 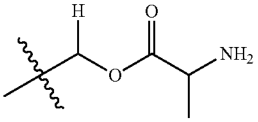 [SMILES: *COC(=O)C(C)N] | F | F |
| 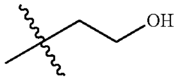 [SMILES: *CCO] | 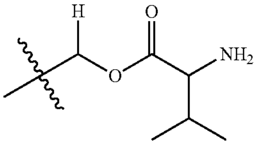 [SMILES: *COC(=O)C(N)C(C)C] | F | F |
| 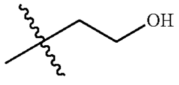 [SMILES: *CCO] | 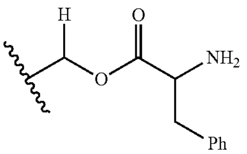 [SMILES: *COC(=O)C(N)Cc1ccccc1] | F | F |
| 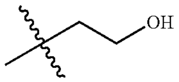 [SMILES: *CCO] | 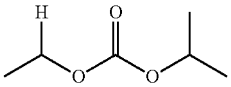 | F | F |

TABLE B-continued
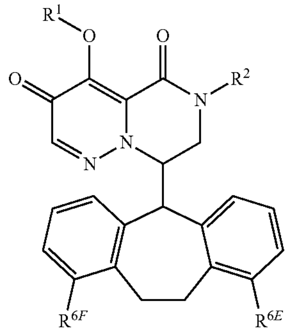
| $R^2$ | $R^1$ | $R^{6E}$ | $R^{6F}$ |
|---|---|---|---|
| 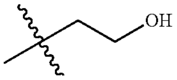 [SMILES: *CCO] | 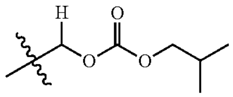 [SMILES: *COC(=O)OCC(C)C] | F | F |
| 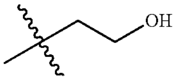 [SMILES: *CCO] | 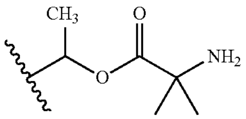 | F | F |
| 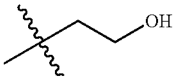 [SMILES: *CCO] | 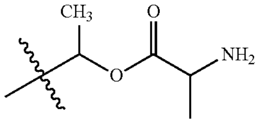 | F | F |
| 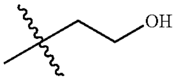 [SMILES: *CCO] | 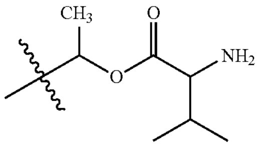 | F | F |
| 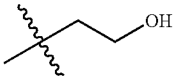 [SMILES: *CCO] | 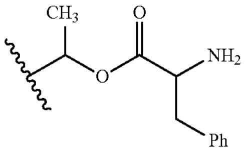 | F | F |
| 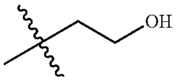 [SMILES: *CCO] | 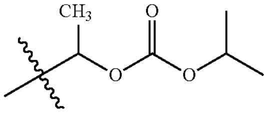 [SMILES: *C(C)OC(=O)OC(C)C] | F | F |
| 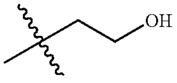 [SMILES: *CCO] | 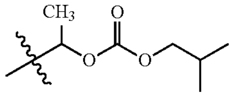 | F | F |
| $—CH_2CH{=}CF_2$ | 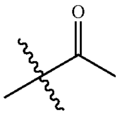 [SMILES: *C(C)=O] | F | F |
| $—CH_2CH{=}CF_2$ | 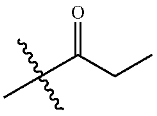 [SMILES: *C(=O)CC] | F | F |
TABLE B-continued
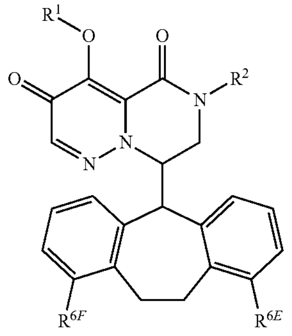
| $R^2$ | $R^1$ | $R^{6E}$ | $R^{6F}$ |
|---|---|---|---|
| $—CH_2CH{=}CF_2$ | 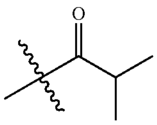 [SMILES: *C(=O)C(C)C] | F | F |
| $—CH_2CH{=}CF_2$ | 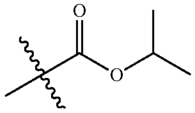 | F | F |
| $—CH_2CH{=}CF_2$ | 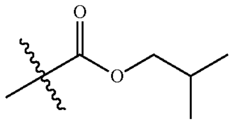 [SMILES: *C(=O)OCC(C)C] | F | F |
| $—CH_2CH{=}CF_2$ | 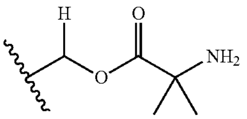 [SMILES: *COC(=O)C(C)(C)N] | F | F |
| $—CH_2CH{=}CF_2$ | 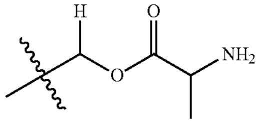 [SMILES: *COC(=O)C(C)N] | F | F |
| $—CH_2CH{=}CF_2$ | 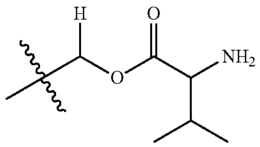 [SMILES: *COC(=O)C(N)C(C)C] | F | F |
| $—CH_2CH{=}CF_2$ | 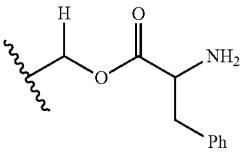 [SMILES: *COC(=O)C(N)Cc1ccccc1] | F | F |
| $—CH_2CH{=}CF_2$ | 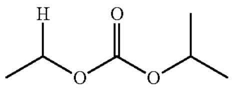 | F | F |
| $—CH_2CH{=}CF_2$ | 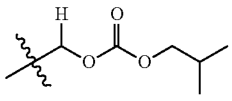 [SMILES: *COC(=O)OCC(C)C] | F | F |

TABLE B-continued
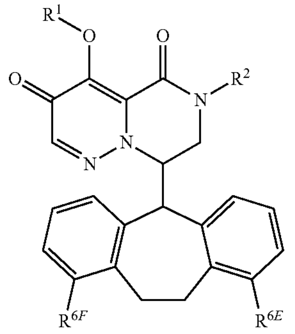
| $R^2$ | $R^1$ | $R^{6E}$ | $R^{6F}$ |
|---|---|---|---|
| $—CH_2CH{=}CF_2$ | 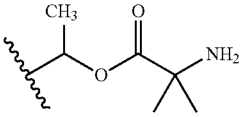 | F | F |
| $—CH_2CH{=}CF_2$ | 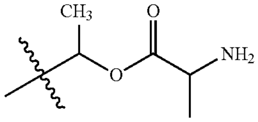 | F | F |
| $—CH_2CH{=}CF_2$ | 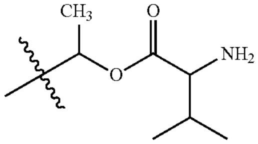 [SMILES: *C(C)OC(=O)C(N)C(C)C] | F | F |
| $—CH_2CH{=}CF_2$ | 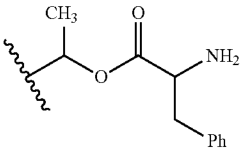 | F | F |
| $—CH_2CH{=}CF_2$ | 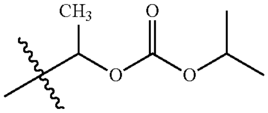 [SMILES: *C(C)OC(=O)OC(C)C] | F | F |
| $—CH_2CH{=}CF_2$ | 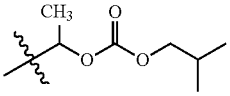 | F | F |
| $—CH_2CF_3$ | 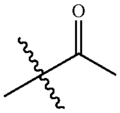 [SMILES: *C(C)=O] | F | F |
| $—CH_2CF_3$ | 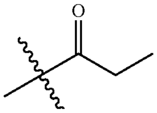 [SMILES: *C(=O)CC] | F | F |
| $—CH_2CF_3$ | 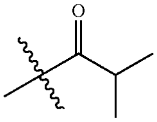 [SMILES: *C(=O)C(C)C] | F | F |
TABLE B-continued
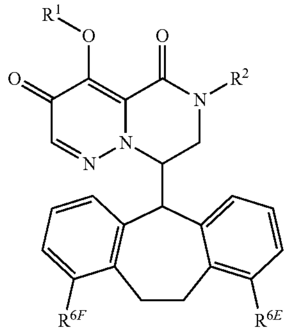
| $R^2$ | $R^1$ | $R^{6E}$ | $R^{6F}$ |
|---|---|---|---|
| $—CH_2CF_3$ | 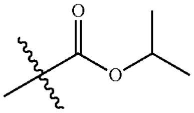 [SMILES: *C(=O)OC(C)C] | F | F |
| $—CH_2CF_3$ | 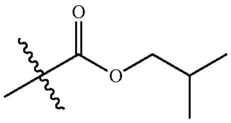 [SMILES: *C(=O)OCC(C)C] | F | F |
| $—CH_2CF_3$ | 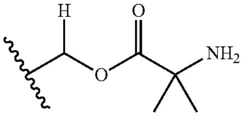 [SMILES: *COC(=O)C(C)(C)N] | F | F |
| $—CH_2CF_3$ | 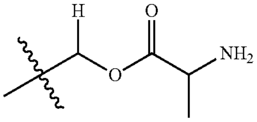 [SMILES: *COC(=O)C(C)N] | F | F |
| $—CH_2CF_3$ | 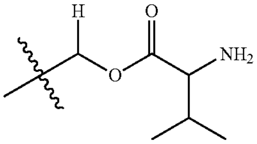 [SMILES: *COC(=O)C(N)C(C)C] | F | F |
| $—CH_2CF_3$ | 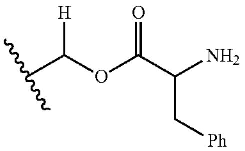 [SMILES: *COC(=O)C(N)Cc1ccccc1] | F | F |
| $—CH_2CF_3$ | 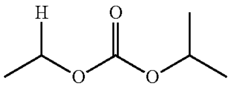 | F | F |
| $—CH_2CF_3$ | 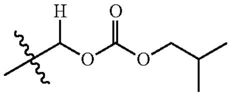 [SMILES: *COC(=O)OCC(C)C] | F | F |
| $—CH_2CF_3$ | 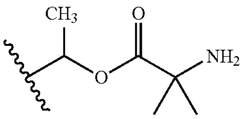 [SMILES: *C(C)OC(=O)C(C)(C)N] | F | F |

TABLE B-continued
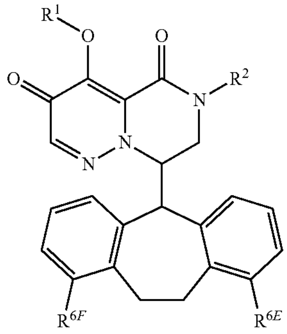
| $R^2$ | $R^1$ | $R^{6E}$ | $R^{6F}$ |
|---|---|---|---|
| $—CH_2CF_3$ | 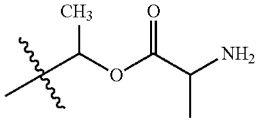 | F | F |
| $—CH_2CF_3$ | 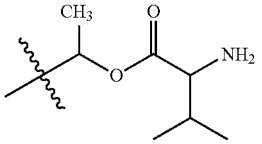 | F | F |
| $—CH_2CF_3$ | 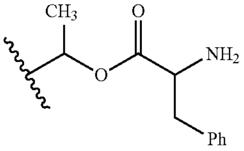 | F | F |
| $—CH_2CF_3$ | 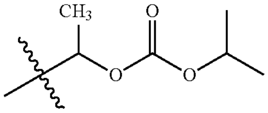 [SMILES: *C(C)OC(=O)OC(C)C] | F | F |
| $—CH_2CF_3$ | 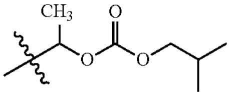 | F | F |
| $—CH_2CH_2CF_3$ | 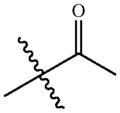 [SMILES: *C(C)=O] | F | F |
| $—CH_2CH_2CF_3$ | 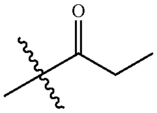 [SMILES: *C(=O)CC] | F | F |
| $—CH_2CH_2CF_3$ | 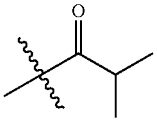 [SMILES: *C(=O)C(C)C] | F | F |
| $—CH_2CH_2CF_3$ | 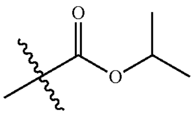 [SMILES: *C(=O)OC(C)C] | F | F |
TABLE B-continued
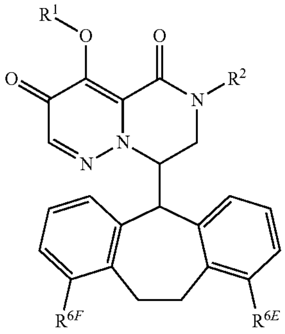
| $R^2$ | $R^1$ | $R^{6E}$ | $R^{6F}$ |
|---|---|---|---|
| $—CH_2CH_2CF_3$ | 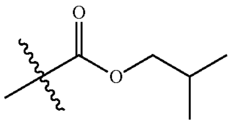 [SMILES: *C(=O)OCC(C)C] | F | F |
| $—CH_2CH_2CF_3$ | 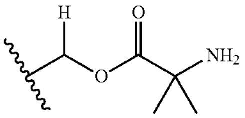 [SMILES: *COC(=O)C(C)(C)N] | F | F |
| $—CH_2CH_2CF_3$ | 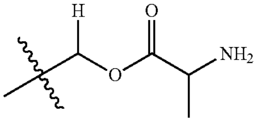 [SMILES: *COC(=O)C(C)N] | F | F |
| $—CH_2CH_2CF_3$ | 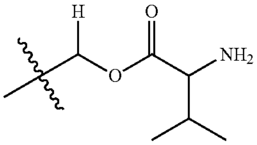 [SMILES: *COC(=O)C(N)C(C)C] | F | F |
| $—CH_2CH_2CF_3$ | 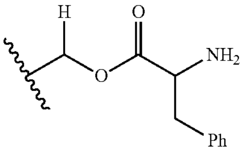 [SMILES: *COC(=O)C(N)Cc1ccccc1] | F | F |
| $—CH_2CH_2CF_3$ | 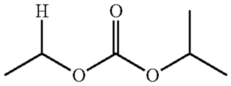 | F | F |
| $—CH_2CH_2CF_3$ | 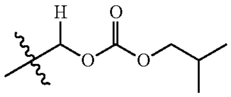 [SMILES: *COC(=O)OCC(C)C] | F | F |
| $—CH_2CH_2CF_3$ | 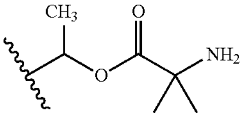 [SMILES: *C(C)OC(=O)C(C)(C)N] | F | F |
| $—CH_2CH_2CF_3$ | 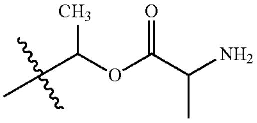 | F | F |

TABLE B-continued
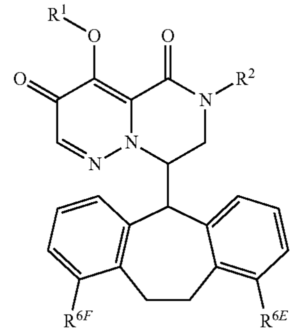
| $R^2$ | $R^1$ | $R^{6E}$ | $R^{6F}$ |
|---|---|---|---|
| $—CH_2CH_2CF_3$ | 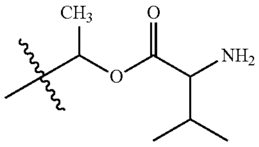 | F | F |
| $—CH_2CH_2CF_3$ | 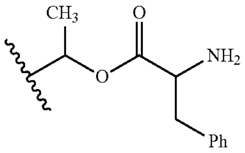 | F | F |
| $—CH_2CH_2CF_3$ | 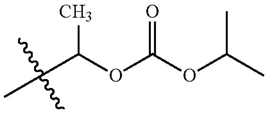 [SMILES: *C(C)OC(=O)OC(C)C] | F | F |
| $—CH_2CH_2CF_3$ | 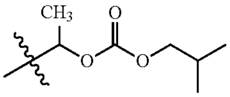 | F | F |
| $—CH_2CHF_2$ | 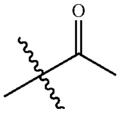 [SMILES: *C(C)=O] | F | F |
| $—CH_2CHF_2$ | 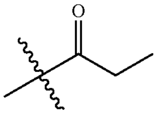 [SMILES: *C(=O)CC] | F | F |
| $—CH_2CHF_2$ | 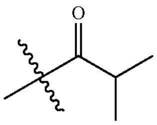 [SMILES: *C(=O)C(C)C] | F | F |
| $—CH_2CHF_2$ | 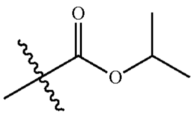 [SMILES: *C(=O)OC(C)C] | F | F |
| $—CH_2CHF_2$ | 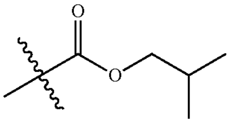 [SMILES: *C(=O)OCC(C)C] | F | F |
TABLE B-continued
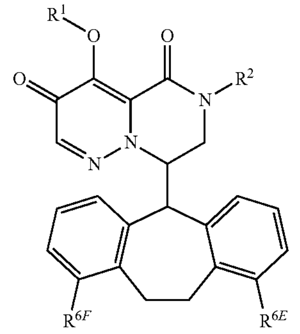
| $R^2$ | $R^1$ | $R^{6E}$ | $R^{6F}$ |
|---|---|---|---|
| $—CH_2CHF_2$ | 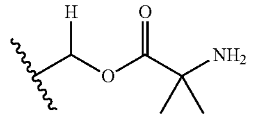 [SMILES: *COC(=O)C(C)(C)N] | F | F |
| $—CH_2CHF_2$ | 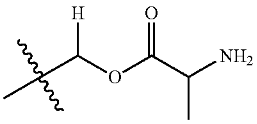 [SMILES: *COC(=O)C(C)N] | F | F |
| $—CH_2CHF_2$ | 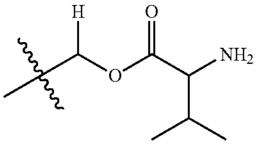 [SMILES: *COC(=O)C(N)C(C)C] | F | F |
| $—CH_2CHF_2$ | 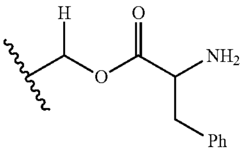 [SMILES: *COC(=O)C(N)Cc1ccccc1] | F | F |
| $—CH_2CHF_2$ | 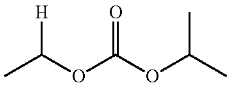 | F | F |
| $—CH_2CHF_2$ | 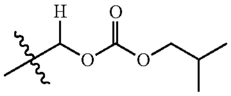 [SMILES: *COC(=O)OCC(C)C] | F | F |
| $—CH_2CHF_2$ | 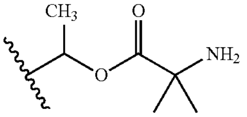 [SMILES: *C(C)OC(=O)C(C)(C)N] | F | F |
| $—CH_2CHF_2$ | 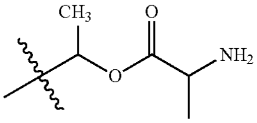 | F | F |
| $—CH_2CHF_2$ | 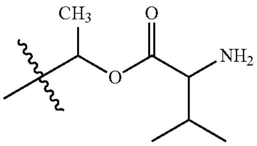 | F | F |

TABLE B-continued
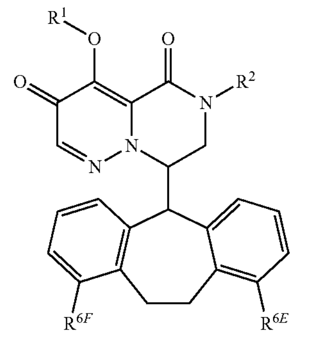
| $R^2$ | $R^1$ | $R^{6E}$ | $R^{6F}$ |
|---|---|---|---|
| $—CH_2CHF_2$ | 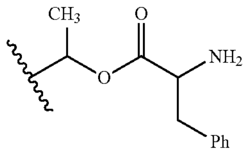 | F | F |
| $—CH_2CHF_2$ | 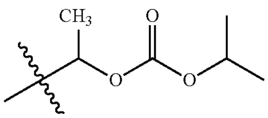 [SMILES: *C(C)OC(=O)OC(C)C] | F | F |
| $—CH_2CHF_2$ | 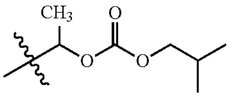 | F | F |
| $—CH_2C(CH_3)F_2$ | 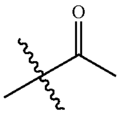 [SMILES: *C(C)=O] | F | F |
| $—CH_2C(CH_3)F_2$ | 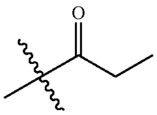 [SMILES: *C(=O)CC] | F | F |
| $—CH_2C(CH_3)F_2$ | 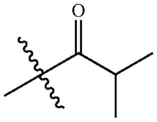 [SMILES: *C(=O)C(C)C] | F | F |
| $—CH_2C(CH_3)F_2$ | 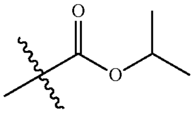 [SMILES: *C(=O)OC(C)C] | F | F |
| $—CH_2C(CH_3)F_2$ | 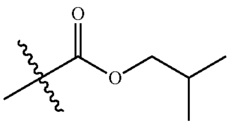 [SMILES: *C(=O)OCC(C)C] | F | F |
| $—CH_2C(CH_3)F_2$ | 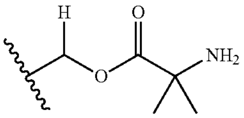 [SMILES: *COC(=O)C(C)(C)N] | F | F |
TABLE B-continued
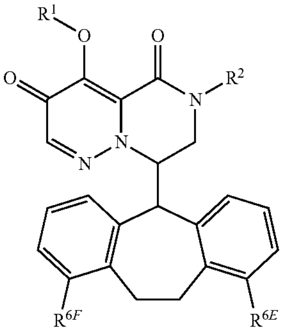
| $R^2$ | $R^1$ | $R^{6E}$ | $R^{6F}$ |
|---|---|---|---|
| $—CH_2C(CH_3)F_2$ | 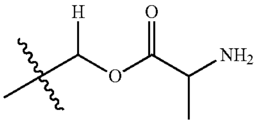 [SMILES: *COC(=O)C(C)N] | F | F |
| $—CH_2C(CH_3)F_2$ | 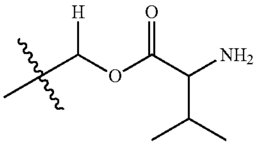 [SMILES: *COC(=O)C(N)C(C)C] | F | F |
| $—CH_2C(CH_3)F_2$ | 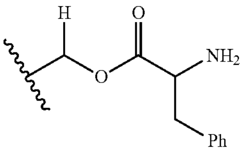 [SMILES: *COC(=O)C(N)Cc1ccccc1] | F | F |
| $—CH_2C(CH_3)F_2$ | 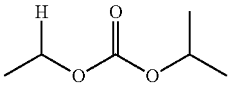 | F | F |
| $—CH_2C(CH_3)F_2$ | 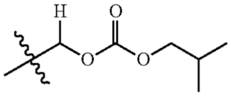 [SMILES: *COC(=O)OCC(C)C] | F | F |
| $—CH_2C(CH_3)F_2$ | 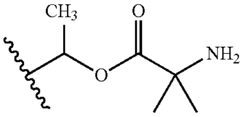 [SMILES: *C(C)OC(=O)C(C)(C)N] | F | F |
| $—CH_2C(CH_3)F_2$ | 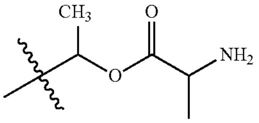 | F | F |
| $—CH_2C(CH_3)F_2$ | 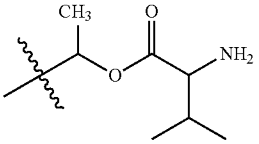 | F | F |
| $—CH_2C(CH_3)F_2$ | 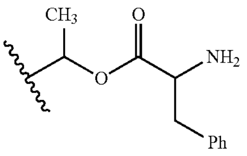 [SMILES: *C(C)OC(=O)C(N)Cc1ccccc1] | F | F |

TABLE B-continued
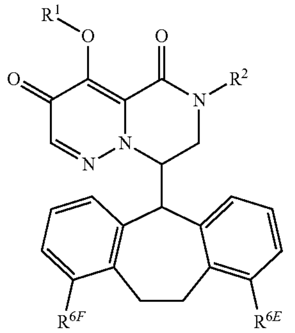
| $R^2$ | $R^1$ | $R^{6E}$ | $R^{6F}$ |
|---|---|---|---|
| $—CH_2C(CH_3)F_2$ | 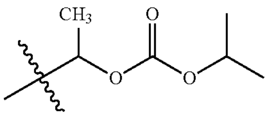 | F | F |
| $—CH_2C(CH_3)F_2$ | 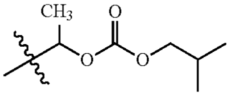 | F | F |
TABLE C
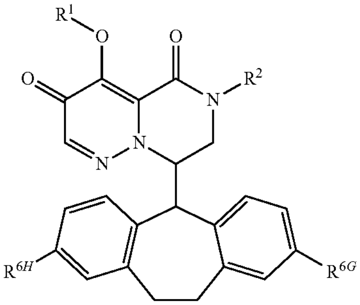
| $R^2$ | $R^1$ | $R^{6G}$ | $R^{6H}$ |
|---|---|---|---|
| 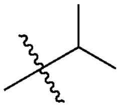 [SMILES: *C(C)C] | 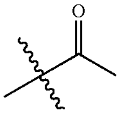 [SMILES: *C(C)=O] | Cl | Cl |
| 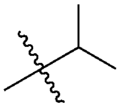 [SMILES: *C(C)C] | 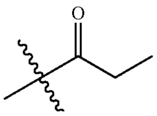 [SMILES: *C(=O)CC] | Cl | Cl |
| 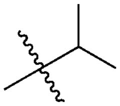 [SMILES: *C(C)C] | 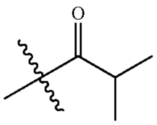 [SMILES: *C(=O)C(C)C] | Cl | Cl |
| 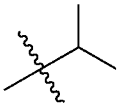 [SMILES: *C(C)C] | 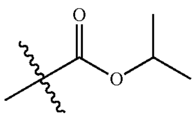 [SMILES: *C(=O)OC(C)C] | Cl | Cl |
TABLE C-continued
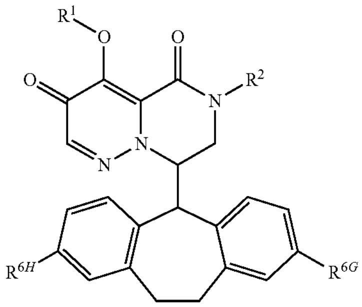
| $R^2$ | $R^1$ | $R^{6G}$ | $R^{6H}$ |
|---|---|---|---|
| 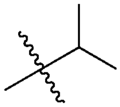 [SMILES: *C(C)C] | 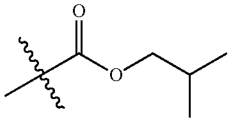 [SMILES: *C(=O)OCC(C)C] | Cl | Cl |
| 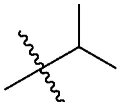 [SMILES: *C(C)C] | 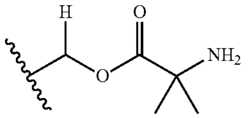 [SMILES: *COC(=O)C(C)(C)N] | Cl | Cl |
| 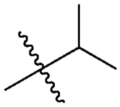 [SMILES: *C(C)C] | 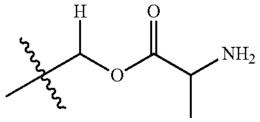 [SMILES: *COC(=O)C(C)N] | Cl | Cl |
| 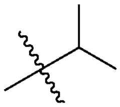 [SMILES: *C(C)C] | 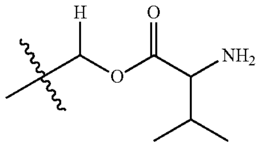 [SMILES: *COC(=O)C(N)C(C)C] | Cl | Cl |
| 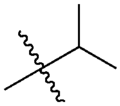 [SMILES: *C(C)C] | 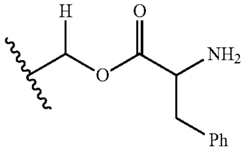 [SMILES: *COC(=O)C(N)Cc1ccccc1] | Cl | Cl |
| 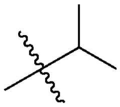 [SMILES: *C(C)C] | 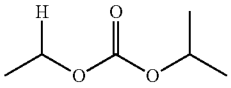 | Cl | Cl |
| 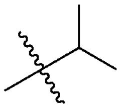 [SMILES: *C(C)C] | 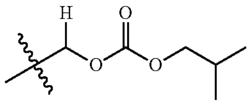 [SMILES: *COC(=O)OCC(C)C] | Cl | Cl |
| 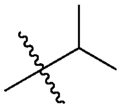 [SMILES: *C(C)C] | 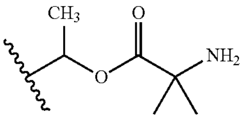 [SMILES: *C(C)OC(=O)C(C)(C)N] | Cl | Cl |
| 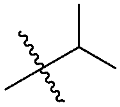 [SMILES: *C(C)C] | 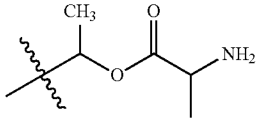 | Cl | Cl |

TABLE C-continued
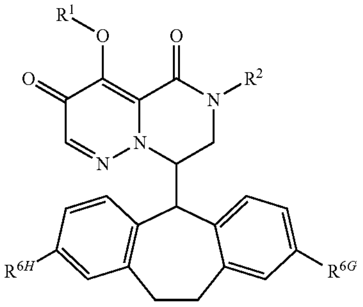
| $R^2$ | $R^1$ | $R^{6G}$ | $R^{6H}$ |
|---|---|---|---|
| 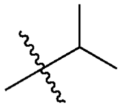 [SMILES: *C(C)C] | 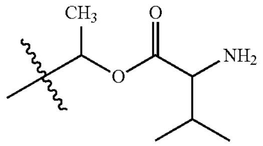 [SMILES: *C(C)OC(=O)C(N)C(C)C] | Cl | Cl |
| 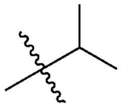 [SMILES: *C(C)C] | 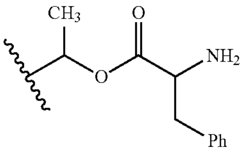 | Cl | Cl |
| 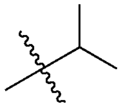 [SMILES: *C(C)C] | 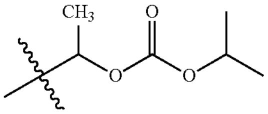 [SMILES: *C(C)OC(=O)OC(C)C] | Cl | Cl |
| 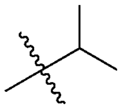 [SMILES: *C(C)C] | 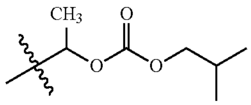 [SMILES: *C(C)OC(=O)OCC(C)C] | Cl | Cl |
| —$CH_3$ | 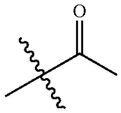 [SMILES: *C(C)=O] | Cl | Cl |
| —$CH_3$ | 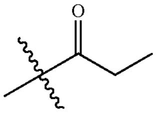 [SMILES: *C(=O)CC] | Cl | Cl |
| —$CH_3$ | 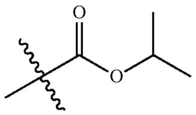 [SMILES: *C(=O)OC(C)C] | Cl | Cl |
| —$CH_3$ | 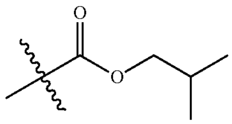 [SMILES: *C(=O)OCC(C)C] | Cl | Cl |
| —$CH_3$ | 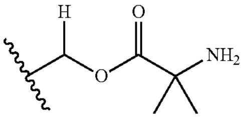 [SMILES: *COC(=O)C(C)(C)N] | Cl | Cl |
TABLE C-continued
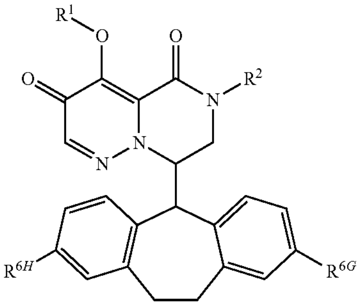
| $R^2$ | $R^1$ | $R^{6G}$ | $R^{6H}$ |
|---|---|---|---|
| —$CH_3$ | 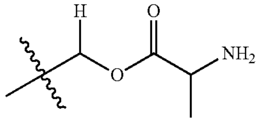 [SMILES: *COC(=O)C(C)N] | Cl | Cl |
| —$CH_3$ | 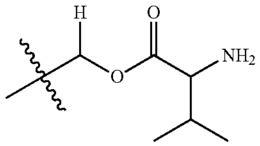 [SMILES: *COC(=O)C(N)C(C)C] | Cl | Cl |
| —$CH_3$ | 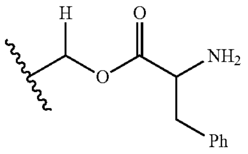 [SMILES: *COC(=O)C(N)Cc1ccccc1] | Cl | Cl |
| —$CH_3$ | 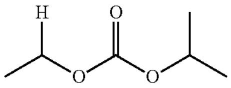 | Cl | Cl |
| —$CH_3$ | 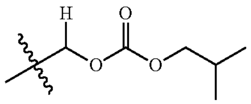 [SMILES: *COC(=O)OCC(C)C] | Cl | Cl |
| —$CH_3$ | 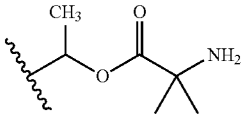 [SMILES: *C(C)OC(=O)C(C)(C)N] | Cl | Cl |
| —$CH_3$ | 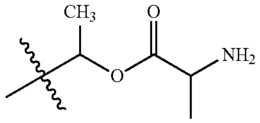 | Cl | Cl |
| —$CH_3$ | 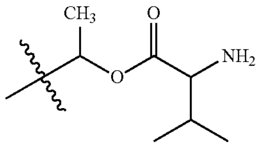 [SMILES: *C(C)OC(=O)C(N)C(C)C] | Cl | Cl |
| —$CH_3$ | 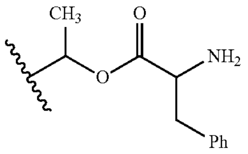 [SMILES: *C(C)OC(=O)C(N)Cc1ccccc1] | Cl | Cl |

TABLE C-continued
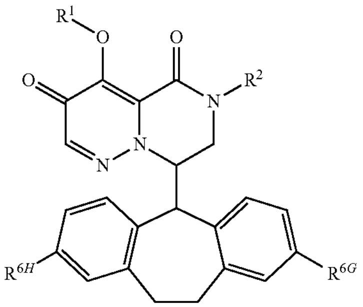
| $R^2$ | $R^1$ | $R^{6G}$ | $R^{6H}$ |
|---|---|---|---|
| —$CH_3$ | 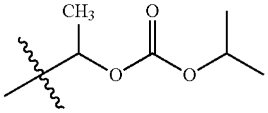 [SMILES: *C(C)OC(=O)OC(C)C] | Cl | Cl |
| —$CH_3$ | 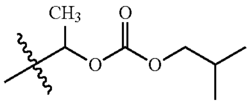 [SMILES: *C(C)OC(=O)OCC(C)C] | Cl | Cl |
| —$CH_2CH_3$ | 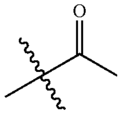 [SMILES: *C(C)=O] | Cl | Cl |
| —$CH_2CH_3$ | 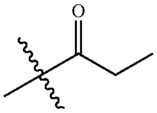 [SMILES: *C(=O)CC] | Cl | Cl |
| —$CH_2CH_3$ | 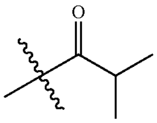 [SMILES: *C(=O)C(C)C] | Cl | Cl |
| —$CH_2CH_3$ | 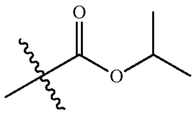 [SMILES: *C(=O)OC(C)C] | Cl | Cl |
| —$CH_2CH_3$ | 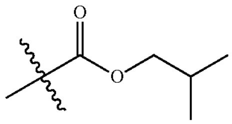 [SMILES: *C(=O)OCC(C)C] | Cl | Cl |
| —$CH_2CH_3$ | 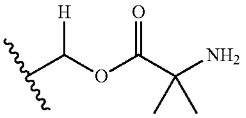 [SMILES: *COC(=O)C(C)(C)N] | Cl | Cl |
| —$CH_2CH_3$ | 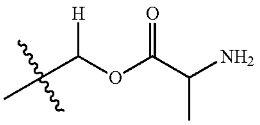 [SMILES: *COC(=O)C(C)N] | Cl | Cl |
TABLE C-continued
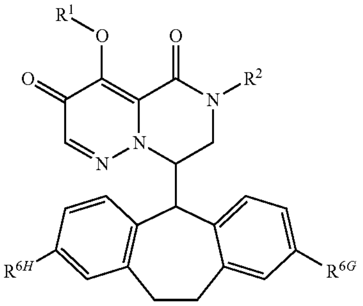
| $R^2$ | $R^1$ | $R^{6G}$ | $R^{6H}$ |
|---|---|---|---|
| —$CH_2CH_3$ | 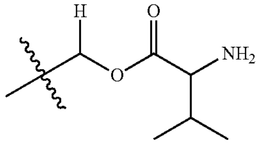 [SMILES: *COC(=O)C(N)C(C)C] | Cl | Cl |
| —$CH_2CH_3$ | 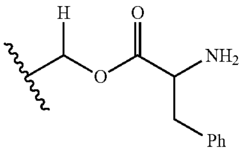 [SMILES: *COC(=O)C(N)Cc1ccccc1] | Cl | Cl |
| —$CH_2CH_3$ | 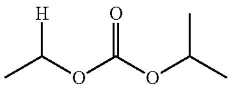 | Cl | Cl |
| —$CH_2CH_3$ | 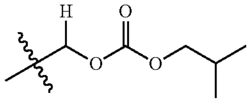 | Cl | Cl |
| —$CH_2CH_3$ | 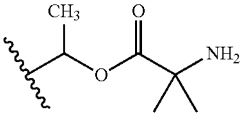 [SMILES: *C(C)OC(=O)C(C)(C)N] | Cl | Cl |
| —$CH_2CH_3$ | 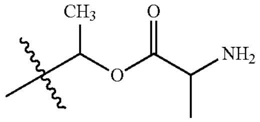 | Cl | Cl |
| —$CH_2CH_3$ | 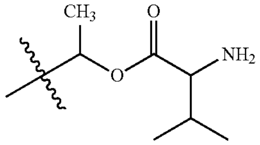 | Cl | Cl |
| —$CH_2CH_3$ | 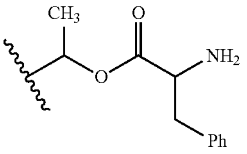 [SMILES: *C(C)OC(=O)C(N)Cc1ccccc1] | Cl | Cl |
| —$CH_2CH_3$ | 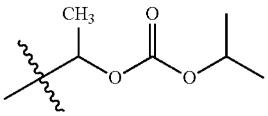 [SMILES: *C(C)OC(=O)OC(C)C] | Cl | Cl |

TABLE C-continued

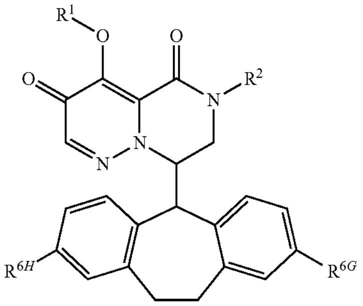

| $R^2$ | $R^1$ | $R^{6G}$ | $R^{6H}$ |
|---|---|---|---|
| $—CH_2CH_3$ | 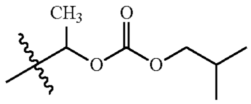 [SMILES: *C(C)OC(=O)OCC(C)C] | Cl | Cl |
| $—CH_2CH(CH_3)_2$ | H | Cl | Cl |
| $—CH_2CH(CH_3)_2$ | 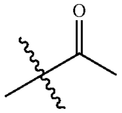 [SMILES: *C(C)=O] | Cl | Cl |
| $—CH_2CH(CH_3)_2$ | 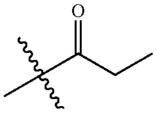 [SMILES: *C(=O)CC] | Cl | Cl |
| $—CH_2CH(CH_3)_2$ | 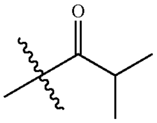 [SMILES: *C(=O)C(C)C] | Cl | Cl |
| $—CH_2CH(CH_3)_2$ | 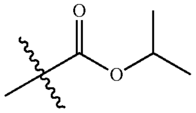 [SMILES: *C(=O)OC(C)C] | Cl | Cl |
| $—CH_2CH(CH_3)_2$ | 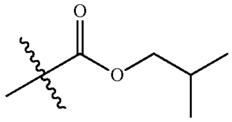 [SMILES: *C(=O)OCC(C)C] | Cl | Cl |
| $—CH_2CH(CH_3)_2$ | 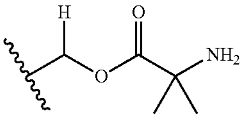 [SMILES: *COC(=O)C(C)(C)N] | Cl | Cl |
| $—CH_2CH(CH_3)_2$ | 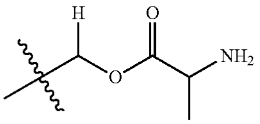 [SMILES: *COC(=O)C(C)N] | Cl | Cl |
| $—CH_2CH(CH_3)_2$ | 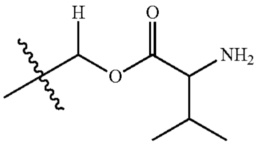 [SMILES: *COC(=O)C(N)C(C)C] | Cl | Cl |

TABLE C-continued

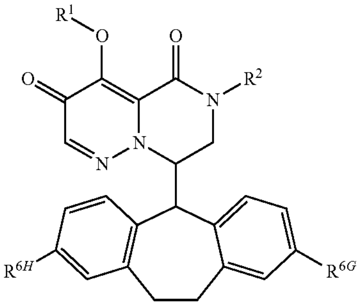

| $R^2$ | $R^1$ | $R^{6G}$ | $R^{6H}$ |
|---|---|---|---|
| $—CH_2CH(CH_3)_2$ | 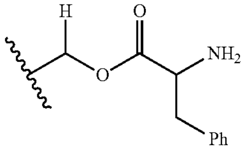 [SMILES: *COC(=O)C(N)Cc1ccccc1] | Cl | Cl |
| $—CH_2CH(CH_3)_2$ | 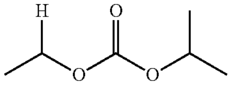 | Cl | Cl |
| $—CH_2CH(CH_3)_2$ | 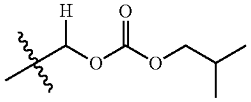 | Cl | Cl |
| $—CH_2CH(CH_3)_2$ | 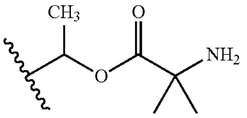 [SMILES: *C(C)OC(=O)C(C)(C)N] | Cl | Cl |
| $—CH_2CH(CH_3)_2$ | 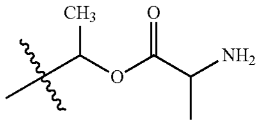 | Cl | Cl |
| $—CH_2CH(CH_3)_2$ | 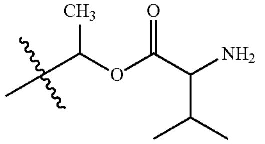 [SMILES: *C(C)OC(=O)C(N)C(C)C] | Cl | Cl |
| $—CH_2CH(CH_3)_2$ | 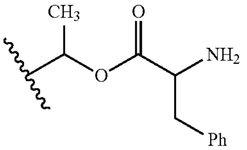 [SMILES: *C(C)OC(=O)C(N)Cc1ccccc1] | Cl | Cl |
| $—CH_2CH(CH_3)_2$ | 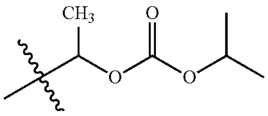 [SMILES: *C(C)OC(=O)OC(C)C] | Cl | Cl |
| $—CH_2CH(CH_3)_2$ | 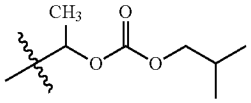 | Cl | Cl |
| $—CH_2CH_2CH_3$ | H | Cl | Cl |

TABLE C-continued
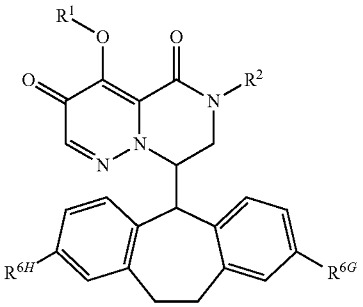
| $R^2$ | $R^1$ | $R^{6G}$ | $R^{6H}$ |
|---|---|---|---|
| $—CH_2CH_2CH_3$ | 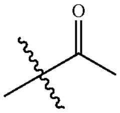 [SMILES: *C(C)=O] | Cl | Cl |
| $—CH_2CH_2CH_3$ | 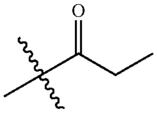 [SMILES: *C(=O)CC] | Cl | Cl |
| $—CH_2CH_2CH_3$ | 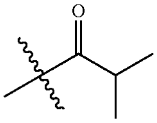 [SMILES: *C(=O)C(C)C] | Cl | Cl |
| $—CH_2CH_2CH_3$ | 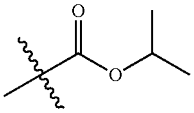 [SMILES: *C(=O)OC(C)C] | Cl | Cl |
| $—CH_2CH_2CH_3$ | 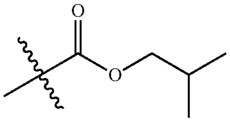 [SMILES: *C(=O)OCC(C)C] | Cl | Cl |
| $—CH_2CH_2CH_3$ | 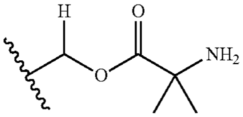 [SMILES: *COC(=O)C(C)(C)N] | Cl | Cl |
| $—CH_2CH_2CH_3$ | 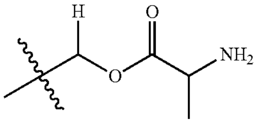 [SMILES: *COC(=O)C(C)N] | Cl | Cl |
| $—CH_2CH_2CH_3$ | 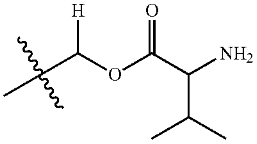 [SMILES: *COC(=O)C(N)C(C)C] | Cl | Cl |
| $—CH_2CH_2CH_3$ | 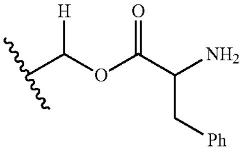 [SMILES: *COC(=O)C(N)Cc1ccccc1] | Cl | Cl |
TABLE C-continued
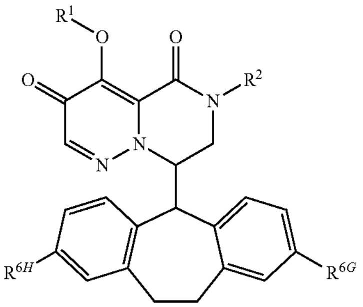
| $R^2$ | $R^1$ | $R^{6G}$ | $R^{6H}$ |
|---|---|---|---|
| $—CH_2CH_2CH_3$ | 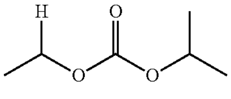 | Cl | Cl |
| $—CH_2CH_2CH_3$ | 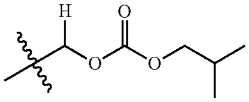 | Cl | Cl |
| $—CH_2CH_2CH_3$ | 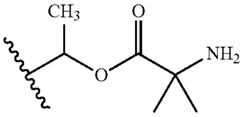 | Cl | Cl |
| $—CH_2CH_2CH_3$ | 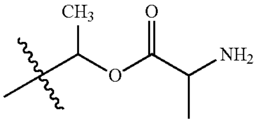 | Cl | Cl |
| $—CH_2CH_2CH_3$ | 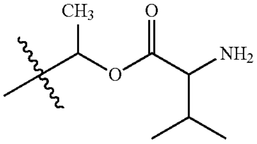 [SMILES: *C(C)OC(=O)C(N)C(C)C] | Cl | Cl |
| $—CH_2CH_2CH_3$ | 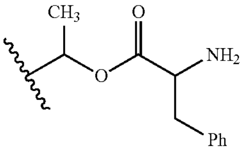 [SMILES: *C(C)OC(=O)C(N)Cc1ccccc1] | Cl | Cl |
| $—CH_2CH_2CH_3$ | 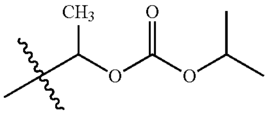 [SMILES: *C(C)OC(=O)OC(C)C] | Cl | Cl |
| $—CH_2CH_2CH_3$ | 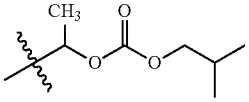 | Cl | Cl |
| $—CH_2CH_2CH_2CH_3$ | H | Cl | Cl |
| $—CH_2CH_2CH_2CH_3$ | 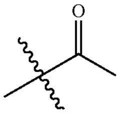 [SMILES: *C(C)=O] | Cl | Cl |

TABLE C-continued
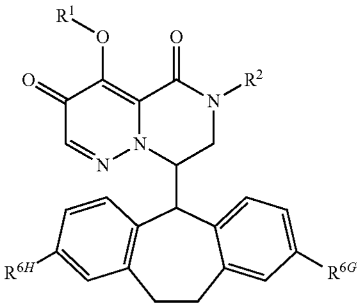
| $R^2$ | $R^1$ | $R^{6G}$ | $R^{6H}$ |
|---|---|---|---|
| $—CH_2CH_2CH_2CH_3$ | 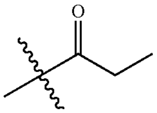 [SMILES: *C(=O)CC] | Cl | Cl |
| $—CH_2CH_2CH_2CH_3$ | 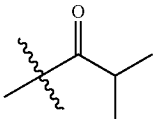 [SMILES: *C(=O)C(C)C] | Cl | Cl |
| $—CH_2CH_2CH_2CH_3$ | 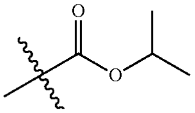 [SMILES: *C(=O)OC(C)C] | Cl | Cl |
| $—CH_2CH_2CH_2CH_3$ | 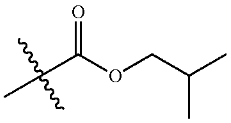 [SMILES: *C(=O)OCC(C)C] | Cl | Cl |
| $—CH_2CH_2CH_2CH_3$ | 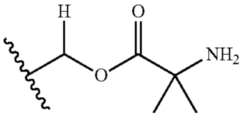 [SMILES: *COC(=O)C(C)(C)N] | Cl | Cl |
| $—CH_2CH_2CH_2CH_3$ | 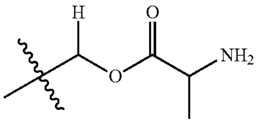 [SMILES: *COC(=O)C(C)N] | Cl | Cl |
| $—CH_2CH_2CH_2CH_3$ | 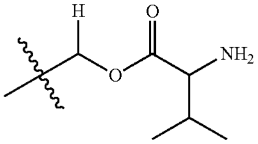 [SMILES: *COC(=O)C(N)C(C)C] | Cl | Cl |
| $—CH_2CH_2CH_2CH_3$ | 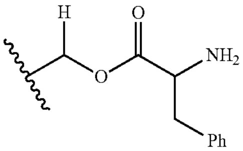 [SMILES: *COC(=O)C(N)Cc1ccccc1] | Cl | Cl |
| $—CH_2CH_2CH_2CH_3$ | 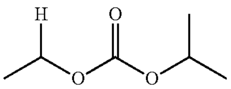 | Cl | Cl |
TABLE C-continued
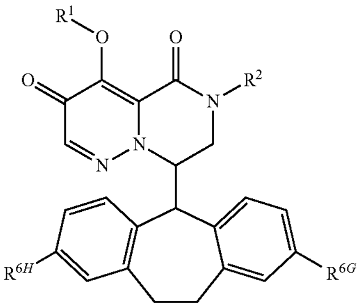
| $R^2$ | $R^1$ | $R^{6G}$ | $R^{6H}$ |
|---|---|---|---|
| $—CH_2CH_2CH_2CH_3$ | 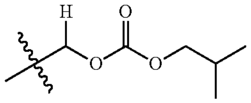 [SMILES: *COC(=O)OCC(C)C] | Cl | Cl |
| $—CH_2CH_2CH_2CH_3$ | 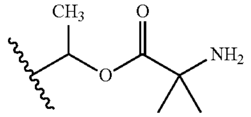 [SMILES: *C(C)OC(=O)C(C)(C)N] | Cl | Cl |
| $—CH_2CH_2CH_2CH_3$ | 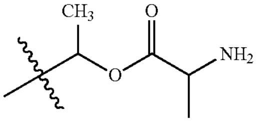 [SMILES: *C(C)OC(=O)C(C)N] | Cl | Cl |
| $—CH_2CH_2CH_2CH_3$ | 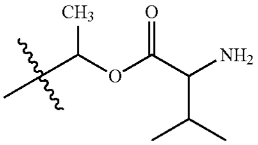 | Cl | Cl |
| $—CH_2CH_2CH_2CH_3$ | 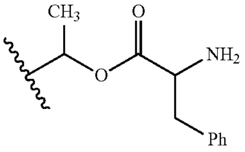 [SMILES: *C(C)OC(=O)C(N)Cc1ccccc1] | Cl | Cl |
| $—CH_2CH_2CH_2CH_3$ | 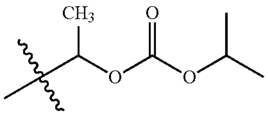 [SMILES: *C(C)OC(=O)OC(C)C] | Cl | Cl |
| $—CH_2CH_2CH_2CH_3$ | 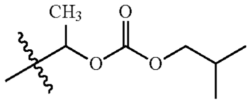 [SMILES: *C(C)OC(=O)OCC(C)C] | Cl | Cl |
| 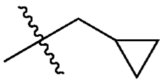 [SMILES: *CC1CC1] | H | Cl | Cl |
| 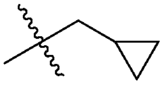 [SMILES: *CC1CC1] | 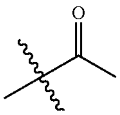 [SMILES: *C(C)=O] | Cl | Cl |

TABLE C-continued
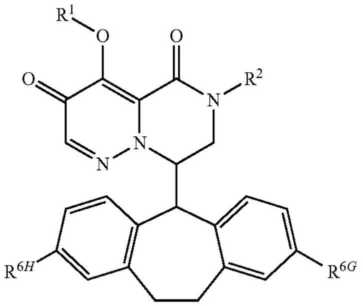
| $R^2$ | $R^1$ | $R^{6G}$ | $R^{6H}$ |
|---|---|---|---|
| 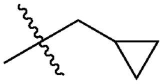 [SMILES: *CC1CC1] | 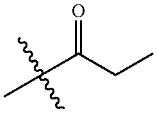 [SMILES: *C(=O)CC] | Cl | Cl |
| 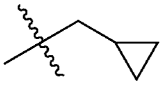 | 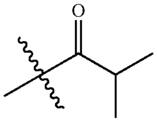 [SMILES: *C(=O)C(C)C] | Cl | Cl |
| 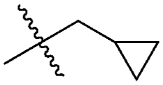 [SMILES: *CC1CC1] | 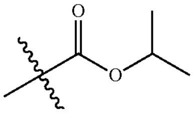 [SMILES: *C(=O)OC(C)C] | Cl | Cl |
| 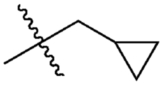 | 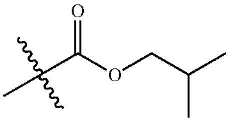 [SMILES: *C(=O)OCC(C)C] | Cl | Cl |
| 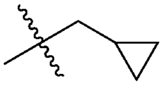 | 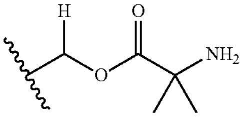 [SMILES: *COC(=O)C(C)(C)N] | Cl | Cl |
| 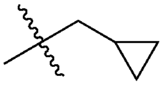 [SMILES: *CC1CC1] | 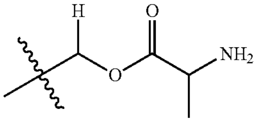 [SMILES: *COC(=O)C(C)N] | Cl | Cl |
| 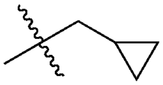 [SMILES: *CC1CC1] | 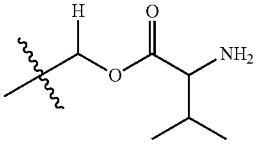 [SMILES: *COC(=O)C(N)C(C)C] | Cl | Cl |
| 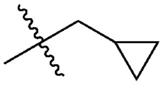 | 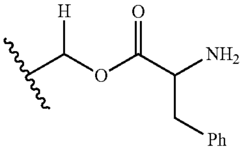 [SMILES: *COC(=O)C(N)Cc1ccccc1] | Cl | Cl |
| 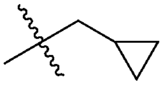 [SMILES: *CC1CC1] | 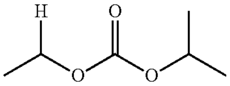 | Cl | Cl |
TABLE C-continued
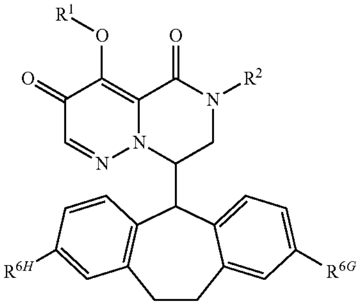
| $R^2$ | $R^1$ | $R^{6G}$ | $R^{6H}$ |
|---|---|---|---|
| 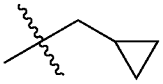 [SMILES: *CC1CC1] | 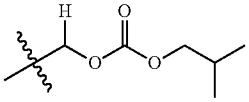 [SMILES: *COC(=O)OCC(C)C] | Cl | Cl |
| 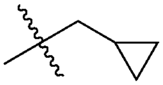 | 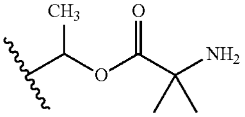 [SMILES: *C(C)OC(=O)C(C)(C)N] | Cl | Cl |
| 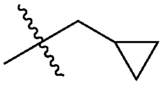 [SMILES: *CC1CC1] | 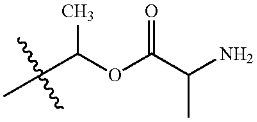 [SMILES: *C(C)OC(=O)C(C)N] | Cl | Cl |
| 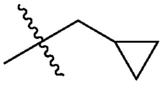 [SMILES: *CC1CC1] | 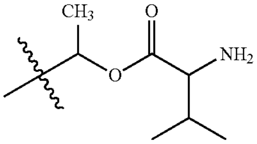 | Cl | Cl |
| 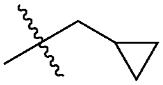 | 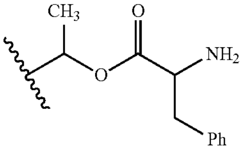 [SMILES: *C(C)OC(=O)C(N)Cc1ccccc1] | Cl | Cl |
| 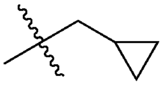 [SMILES: *CC1CC1] | 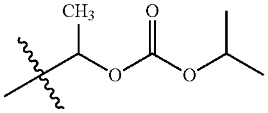 [SMILES: *C(C)OC(=O)OC(C)C] | Cl | Cl |
| 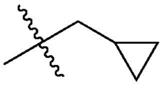 [SMILES: *CC1CC1] | 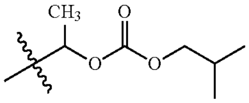 [SMILES: *C(C)OC(=O)OCC(C)C] | Cl | Cl |
| 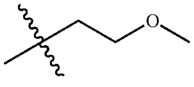 [SMILES: *CCOC] | H | Cl | Cl |
| 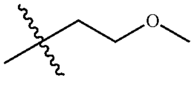 [SMILES: *CCOC] | 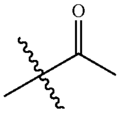 [SMILES: *C(C)=O] | Cl | Cl |

TABLE C-continued
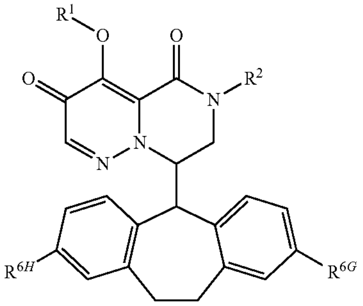
| $R^2$ | $R^1$ | $R^{6G}$ | $R^{6H}$ |
|---|---|---|---|
| 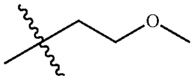 [SMILES: *CCOC] | 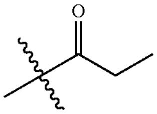 [SMILES: *C(=O)CC] | Cl | Cl |
| 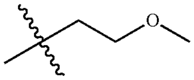 [SMILES: *CCOC] | 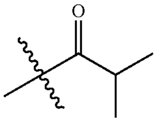 [SMILES: *C(=O)C(C)C] | Cl | Cl |
| 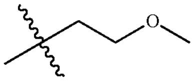 [SMILES: *CCOC] | 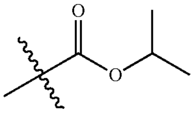 [SMILES: *C(=O)OC(C)C] | Cl | Cl |
| 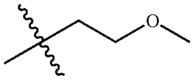 [SMILES: *CCOC] | 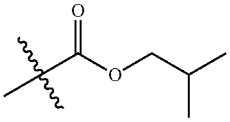 [SMILES: *C(=O)OCC(C)C] | Cl | Cl |
| 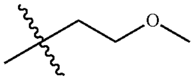 [SMILES: *CCOC] | 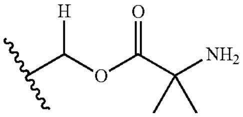 [SMILES: *COC(=O)C(C)(C)N] | Cl | Cl |
| 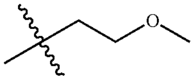 [SMILES: *CCOC] | 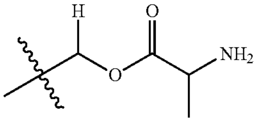 [SMILES: *COC(=O)C(C)N] | Cl | Cl |
| 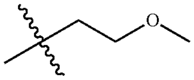 [SMILES: *CCOC] | 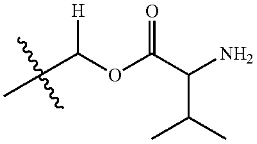 [SMILES: *COC(=O)C(N)C(C)C] | Cl | Cl |
| 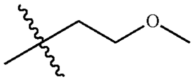 [SMILES: *CCOC] | 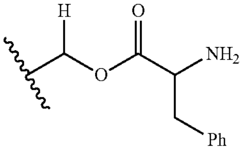 [SMILES: *COC(=O)C(N)Cc1ccccc1] | Cl | Cl |
| 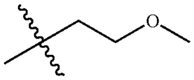 [SMILES: *CCOC] | 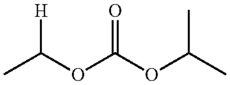 | Cl | Cl |
TABLE C-continued
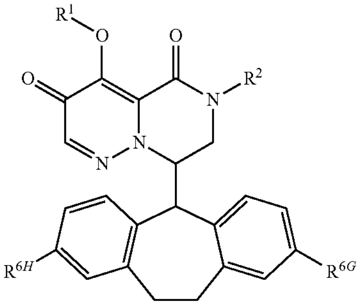
| $R^2$ | $R^1$ | $R^{6G}$ | $R^{6H}$ |
|---|---|---|---|
| 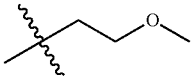 [SMILES: *CCOC] | 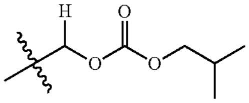 [SMILES: *COC(=O)OCC(C)C] | Cl | Cl |
| 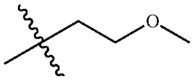 [SMILES: *CCOC] | 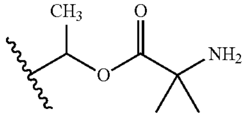 [SMILES: *C(C)OC(=O)C(C)(C)N] | Cl | Cl |
| 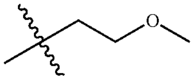 [SMILES: *CCOC] | 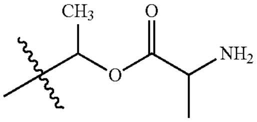 [SMILES: *C(C)OC(=O)C(C)N] | Cl | Cl |
| 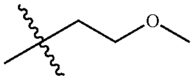 [SMILES: *CCOC] | 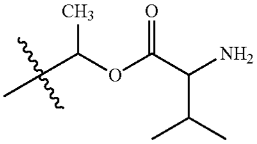 [SMILES: *C(C)OC(=O)C(N)C(C)C] | Cl | Cl |
| 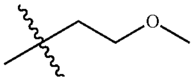 [SMILES: *CCOC] | 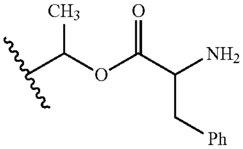 [SMILES: *C(C)OC(=O)C(N)Cc1ccccc1] | Cl | Cl |
| 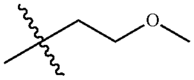 [SMILES: *CCOC] | 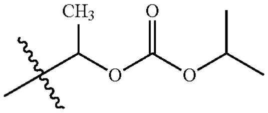 [SMILES: *C(C)OC(=O)OC(C)C] | Cl | Cl |
| 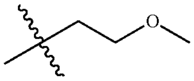 [SMILES: *CCOC] | 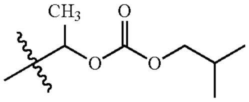 [SMILES: *C(C)OC(=O)OCC(C)C] | Cl | Cl |
| 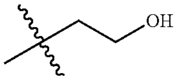 [SMILES: *CCO] | H | Cl | Cl |
| 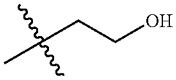 [SMILES: *CCO] | 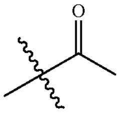 [SMILES: *C(C)=O] | Cl | Cl |

TABLE C-continued
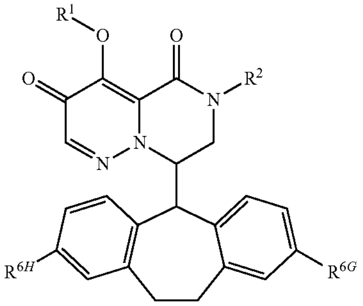
| $R^2$ | $R^1$ | $R^{6G}$ | $R^{6H}$ |
|---|---|---|---|
| 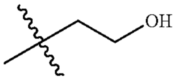 [SMILES: *CCO] | 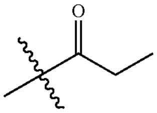 [SMILES: *C(=O)CC] | Cl | Cl |
| 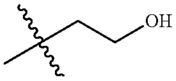 [SMILES: *CCO] | 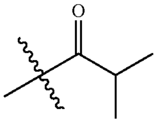 [SMILES: *C(=O)C(C)C] | Cl | Cl |
| 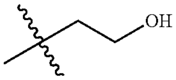 [SMILES: *CCO] | 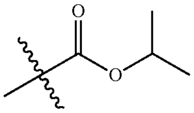 [SMILES: *C(=O)OC(C)C] | Cl | Cl |
| 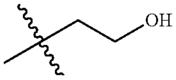 [SMILES: *CCO] | 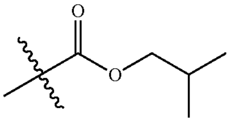 [SMILES: *C(=O)OCC(C)C] | Cl | Cl |
| 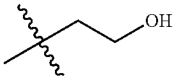 [SMILES: *CCO] | 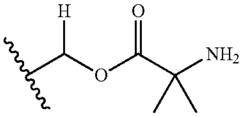 [SMILES: *COC(=O)C(C)(C)N] | Cl | Cl |
| 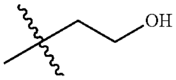 [SMILES: *CCO] | 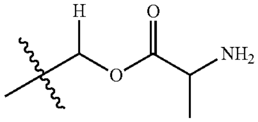 [SMILES: *COC(=O)C(C)N] | Cl | Cl |
| 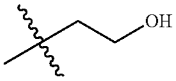 [SMILES: *CCO] | 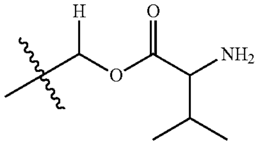 [SMILES: *COC(=O)C(N)C(C)C] | Cl | Cl |
| 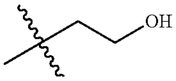 [SMILES: *CCO] | 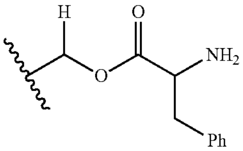 [SMILES: *COC(=O)C(N)Cc1ccccc1] | Cl | Cl |
| 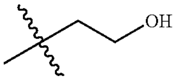 [SMILES: *CCO] | 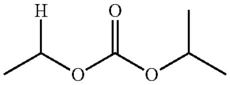 | Cl | Cl |
TABLE C-continued
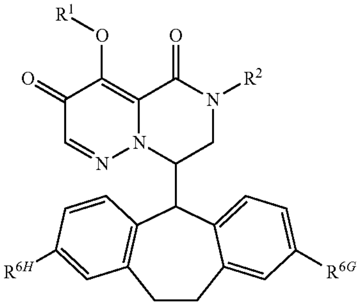
| $R^2$ | $R^1$ | $R^{6G}$ | $R^{6H}$ |
|---|---|---|---|
| 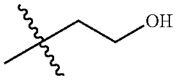 [SMILES: *CCO] | 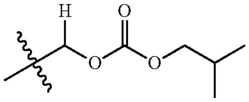 [SMILES: *COC(=O)OCC(C)C] | Cl | Cl |
| 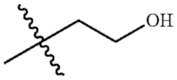 [SMILES: *CCO] | 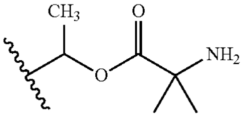 [SMILES: *C(C)OC(=O)C(C)(C)N] | Cl | Cl |
| 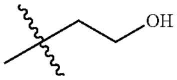 | 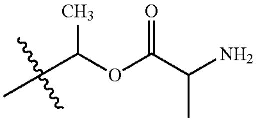 [SMILES: *C(C)OC(=O)C(C)N] | Cl | Cl |
| 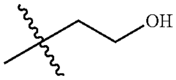 [SMILES: *CCO] | 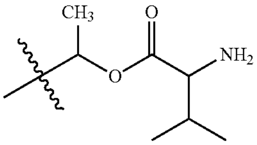 [SMILES: *C(C)OC(=O)C(N)C(C)C] | Cl | Cl |
| 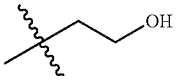 [SMILES: *CCO] | 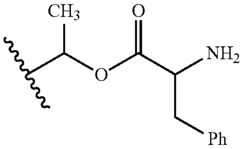 [SMILES: *C(C)OC(=O)C(N)Cc1ccccc1] | Cl | Cl |
| 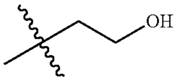 | 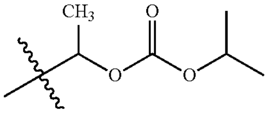 [SMILES: *C(C)OC(=O)OC(C)C] | Cl | Cl |
| 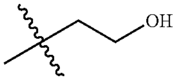 [SMILES: *CCO] | 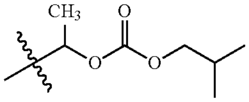 [SMILES: *C(C)OC(=O)OCC(C)C] | Cl | Cl |
| $—CH_2CH{=}CF_2$ | 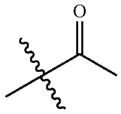 [SMILES: *C(C)=O] | Cl | Cl |
| $—CH_2CH{=}CF_2$ | 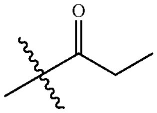 [SMILES: *C(=O)CC] | Cl | Cl |

TABLE C-continued
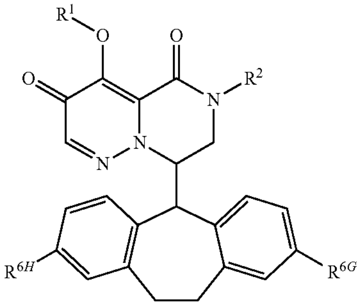
| $R^2$ | $R^1$ | $R^{6G}$ | $R^{6H}$ |
|---|---|---|---|
| $—CH_2CH═CF_2$ | 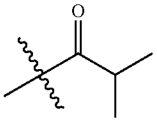 [SMILES: *C(=O)C(C)C] | Cl | Cl |
| $—CH_2CH═CF_2$ | 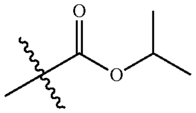 [SMILES: *C(=O)OC(C)C] | Cl | Cl |
| $—CH_2CH═CF_2$ | 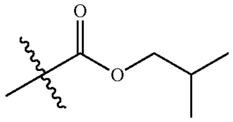 [SMILES: *C(=O)OCC(C)C] | Cl | Cl |
| $—CH_2CH═CF_2$ | 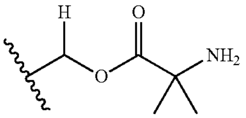 [SMILES: *COC(=O)C(C)(C)N] | Cl | Cl |
| $—CH_2CH═CF_2$ | 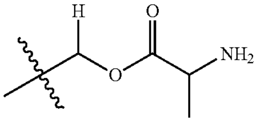 [SMILES: *COC(=O)C(C)N] | Cl | Cl |
| $—CH_2CH═CF_2$ | 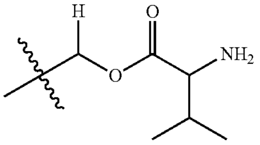 [SMILES: *COC(=O)C(N)C(C)C] | Cl | Cl |
| $—CH_2CH═CF_2$ | 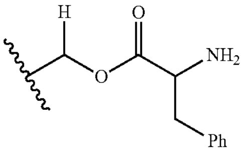 [SMILES: *COC(=O)C(N)Cc1ccccc1] | Cl | Cl |
| $—CH_2CH═CF_2$ | 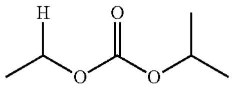 | Cl | Cl |
| $—CH_2CH═CF_2$ | 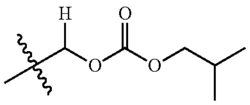 [SMILES: *COC(=O)OCC(C)C] | Cl | Cl |
TABLE C-continued
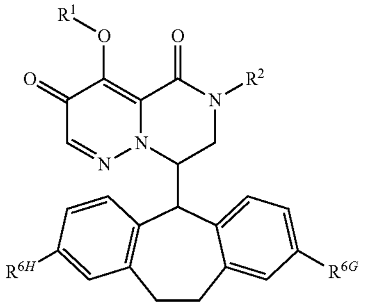
| $R^2$ | $R^1$ | $R^{6G}$ | $R^{6H}$ |
|---|---|---|---|
| $—CH_2CH═CF_2$ | 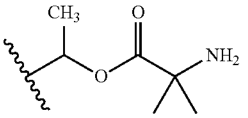 [SMILES: *C(C)OC(=O)C(C)(C)N] | Cl | Cl |
| $—CH_2CH═CF_2$ | 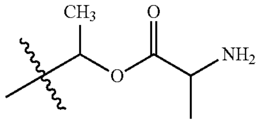 [SMILES: *C(C)OC(=O)C(C)N] | Cl | Cl |
| $—CH_2CH═CF_2$ | 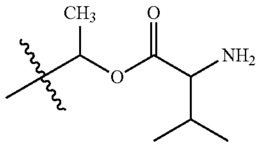 [SMILES: *C(C)OC(=O)C(N)C(C)C] | Cl | Cl |
| $—CH_2CH═CF_2$ | 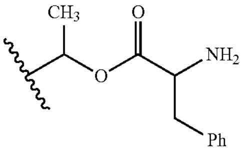 [SMILES: *C(C)OC(=O)C(N)Cc1ccccc1] | Cl | Cl |
| $—CH_2CH═CF_2$ | 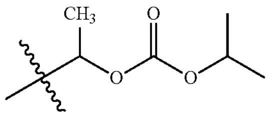 [SMILES: *C(C)OC(=O)OC(C)C] | Cl | Cl |
| $—CH_2CH═CF_2$ | 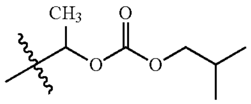 | Cl | Cl |
| $—CH_2CF_3$ | 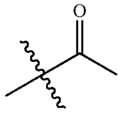 [SMILES: *C(C)=O] | Cl | Cl |
| $—CH_2CF_3$ | 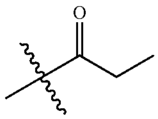 [SMILES: *C(=O)CC] | Cl | Cl |
| $—CH_2CF_3$ | 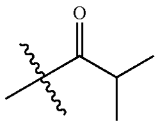 [SMILES: *C(=O)C(C)C] | Cl | Cl |

TABLE C-continued
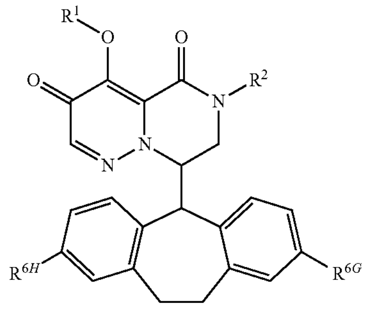
| $R^2$ | $R^1$ | $R^{6G}$ | $R^{6H}$ |
|---|---|---|---|
| $—CH_2CF_3$ | 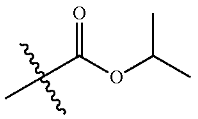 [SMILES: *C(=O)OC(C)C] | Cl | Cl |
| $—CH_2CF_3$ | 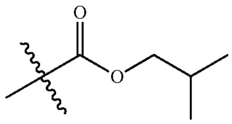 [SMILES: *C(=O)OCC(C)C] | Cl | Cl |
| $—CH_2CF_3$ | 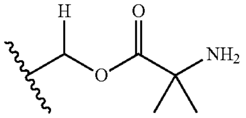 [SMILES: *COC(=O)C(C)(C)N] | Cl | Cl |
| $—CH_2CF_3$ | 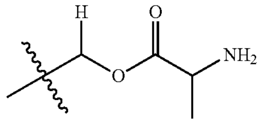 [SMILES: *COC(=O)C(C)N] | Cl | Cl |
| $—CH_2CF_3$ | 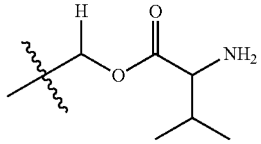 [SMILES: *COC(=O)C(N)C(C)C] | Cl | Cl |
| $—CH_2CF_3$ | 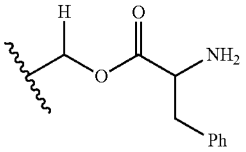 [SMILES: *COC(=O)C(N)Cc1ccccc1] | Cl | Cl |
| $—CH_2CF_3$ | 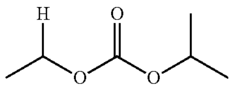 | Cl | Cl |
| $—CH_2CF_3$ | 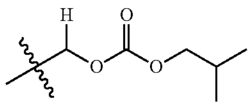 [SMILES: *COC(=O)OCC(C)C] | Cl | Cl |
| $—CH_2CF_3$ | 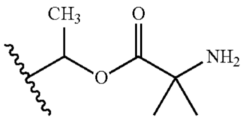 | Cl | Cl |
TABLE C-continued
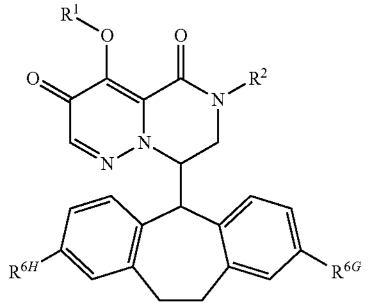
| $R^2$ | $R^1$ | $R^{6G}$ | $R^{6H}$ |
|---|---|---|---|
| $—CH_2CF_3$ | 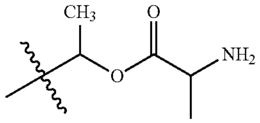 [SMILES: *C(C)OC(=O)C(C)N] | Cl | Cl |
| $—CH_2CF_3$ | 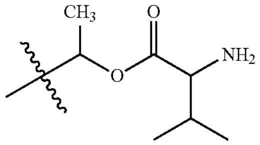 [SMILES: *C(C)OC(=O)C(N)C(C)C] | Cl | Cl |
| $—CH_2CF_3$ | 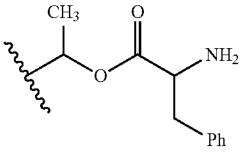 [SMILES: *C(C)OC(=O)C(N)Cc1ccccc1] | Cl | Cl |
| $—CH_2CF_3$ | 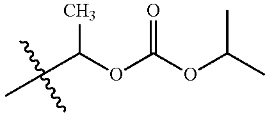 [SMILES: *C(C)OC(=O)OC(C)C] | Cl | Cl |
| $—CH_2CF_3$ | 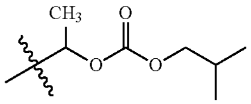 [SMILES: *C(C)OC(=O)OCC(C)C] | Cl | Cl |
| $—CH_2CH_2CF_3$ | 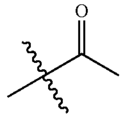 [SMILES: *C(C)=O] | Cl | Cl |
| $—CH_2CH_2CF_3$ | 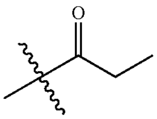 [SMILES: *C(=O)CC] | Cl | Cl |
| $—CH_2CH_2CF_3$ | 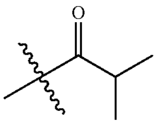 [SMILES: *C(=O)C(C)C] | Cl | Cl |
| $—CH_2CH_2CF_3$ | 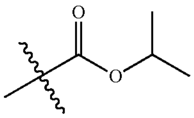 [SMILES: *C(=O)OC(C)C] | Cl | Cl |

TABLE C-continued
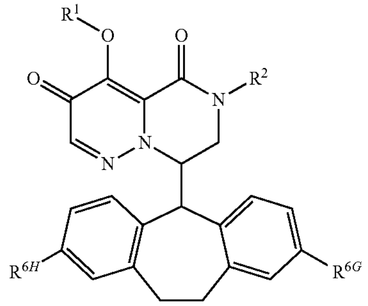
| $R^2$ | $R^1$ | $R^{6G}$ | $R^{6H}$ |
| --- | --- | --- | --- |
| $—CH_2CH_2CF_3$ | 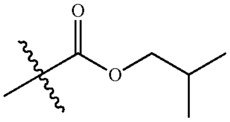 [SMILES: *C(=O)OCC(C)C] | Cl | Cl |
| $—CH_2CH_2CF_3$ | 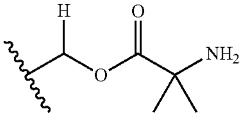 [SMILES: *COC(=O)C(C)(C)N] | Cl | Cl |
| $—CH_2CH_2CF_3$ | 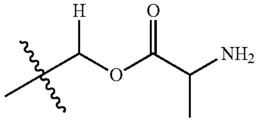 [SMILES: *COC(=O)C(C)N] | Cl | Cl |
| $—CH_2CH_2CF_3$ | 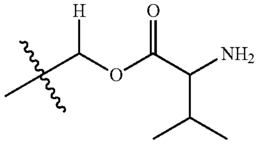 [SMILES: *COC(=O)C(N)C(C)C] | Cl | Cl |
| $—CH_2CH_2CF_3$ | 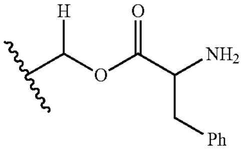 [SMILES: *COC(=O)C(N)Cc1ccccc1] | Cl | Cl |
| $—CH_2CH_2CF_3$ | 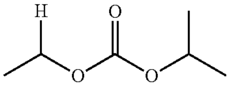 | Cl | Cl |
| $—CH_2CH_2CF_3$ | 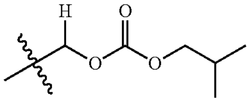 [SMILES: *COC(=O)OCC(C)C] | Cl | Cl |
| $—CH_2CH_2CF_3$ | 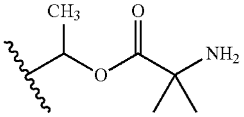 [SMILES: *C(C)OC(=O)C(C)(C)N] | Cl | Cl |
| $—CH_2CH_2CF_3$ | 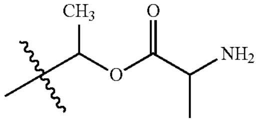 [SMILES: *C(C)OC(=O)C(C)N] | Cl | Cl |
TABLE C-continued
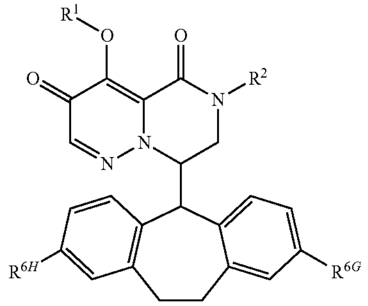
| $R^2$ | $R^1$ | $R^{6G}$ | $R^{6H}$ |
| --- | --- | --- | --- |
| $—CH_2CH_2CF_3$ | 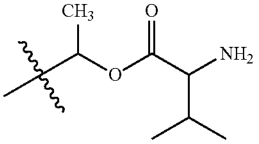 [SMILES: *C(C)OC(=O)C(N)C(C)C] | Cl | Cl |
| $—CH_2CH_2CF_3$ | 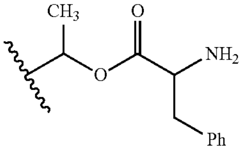 [SMILES: *C(C)OC(=O)C(N)Cc1ccccc1] | Cl | Cl |
| $—CH_2CH_2CF_3$ | 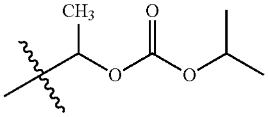 [SMILES: *C(C)OC(=O)OC(C)C] | Cl | Cl |
| $—CH_2CH_2CF_3$ | 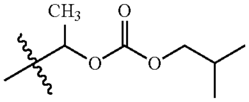 [SMILES: *C(C)OC(=O)OCC(C)C] | Cl | Cl |
| $—CH_2CHF_2$ | 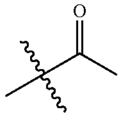 [SMILES: *C(C)=O] | Cl | Cl |
| $—CH_2CHF_2$ | 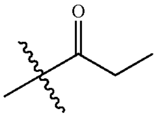 [SMILES: *C(=O)CC] | Cl | Cl |
| $—CH_2CHF_2$ | 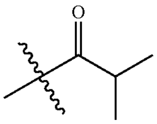 [SMILES: *C(=O)C(C)C] | Cl | Cl |
| $—CH_2CHF_2$ | 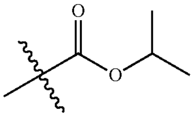 [SMILES: *C(=O)OC(C)C] | Cl | Cl |
| $—CH_2CHF_2$ | 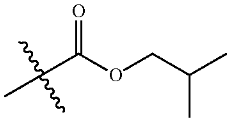 [SMILES: *C(=O)OCC(C)C] | Cl | Cl |

TABLE C-continued
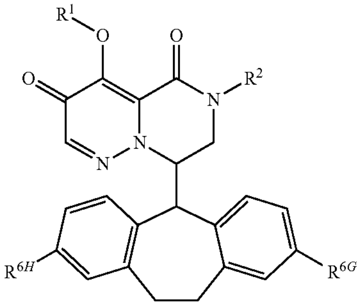
| $R^2$ | $R^1$ | $R^{6G}$ | $R^{6H}$ |
|---|---|---|---|
| $—CH_2CHF_2$ | 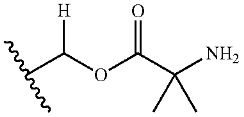 [SMILES: *COC(=O)C(C)(C)N] | Cl | Cl |
| $—CH_2CHF_2$ | 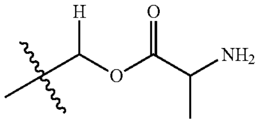 [SMILES: *COC(=O)C(C)N] | Cl | Cl |
| $—CH_2CHF_2$ | 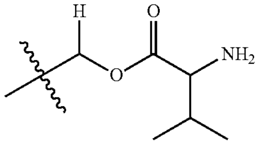 [SMILES: *COC(=O)C(N)C(C)C] | Cl | Cl |
| $—CH_2CHF_2$ | 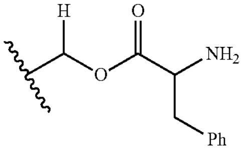 [SMILES: *COC(=O)C(N)Cc1ccccc1] | Cl | Cl |
| $—CH_2CHF_2$ | 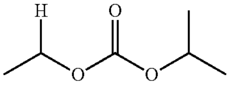 | Cl | Cl |
| $—CH_2CHF_2$ | 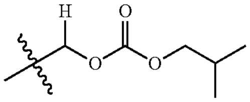 [SMILES: *COC(=O)OCC(C)C] | Cl | Cl |
| $—CH_2CHF_2$ | 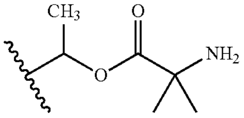 [SMILES: *C(C)OC(=O)C(C)(C)N] | Cl | Cl |
| $—CH_2CHF_2$ | 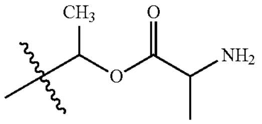 [SMILES: *C(C)OC(=O)C(C)N] | Cl | Cl |
| $—CH_2CHF_2$ | 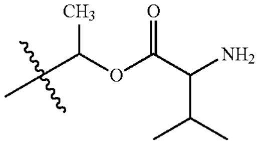 [SMILES: *C(C)OC(=O)C(N)C(C)C] | Cl | Cl |
TABLE C-continued
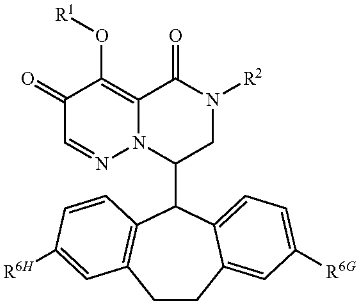
| $R^2$ | $R^1$ | $R^{6G}$ | $R^{6H}$ |
|---|---|---|---|
| $—CH_2CHF_2$ | 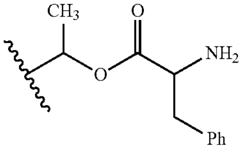 [SMILES: *C(C)OC(=O)C(N)Cc1ccccc1] | Cl | Cl |
| $—CH_2CHF_2$ | 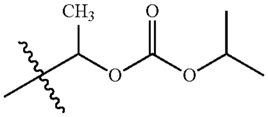 [SMILES: *C(C)OC(=O)OC(C)C] | Cl | Cl |
| $—CH_2CHF_2$ | 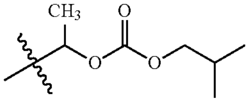 [SMILES: *C(C)OC(=O)OCC(C)C] | Cl | Cl |
| $—CH_2C(CH_3)F_2$ | 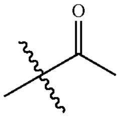 [SMILES: *C(C)=O] | Cl | Cl |
| $—CH_2C(CH_3)F_2$ | 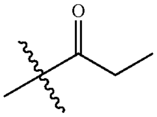 [SMILES: *C(=O)CC] | Cl | Cl |
| $—CH_2C(CH_3)F_2$ | 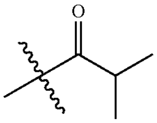 [SMILES: *C(=O)C(C)C] | Cl | Cl |
| $—CH_2C(CH_3)F_2$ | 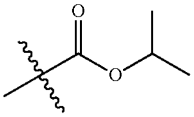 [SMILES: *C(=O)OC(C)C] | Cl | Cl |
| $—CH_2C(CH_3)F_2$ | 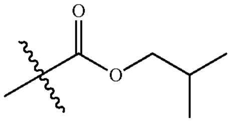 [SMILES: *C(=O)OCC(C)C] | Cl | Cl |
| $—CH_2C(CH_3)F_2$ | 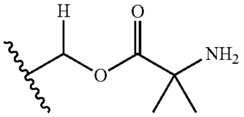 [SMILES: *COC(=O)C(C)(C)N] | Cl | Cl |

TABLE C-continued
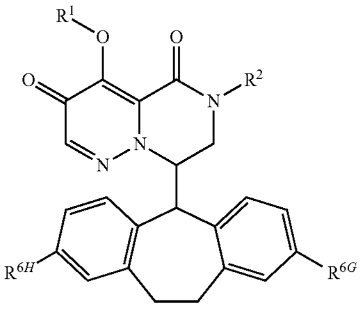
| $R^2$ | $R^1$ | $R^{6G}$ | $R^{6H}$ |
|---|---|---|---|
| $-CH_2C(CH_3)F_2$ | 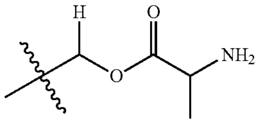 [SMILES: *COC(=O)C(C)N] | Cl | Cl |
| $-CH_2C(CH_3)F_2$ | 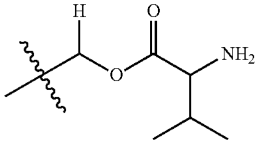 [SMILES: *COC(=O)C(N)C(C)C] | Cl | Cl |
| $-CH_2C(CH_3)F_2$ | 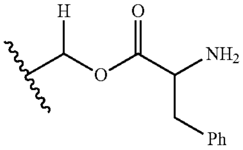 | Cl | Cl |
| $-CH_2C(CH_3)F_2$ | 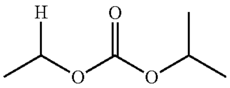 | Cl | Cl |
| $-CH_2C(CH_3)F_2$ | 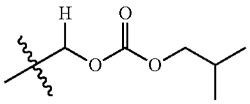 [SMILES: *COC(=O)OCC(C)C] | Cl | Cl |
| $-CH_2C(CH_3)F_2$ | 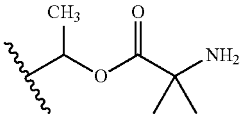 [SMILES: *C(C)OC(=O)C(C)(C)N] | Cl | Cl |
| $-CH_2C(CH_3)F_2$ | 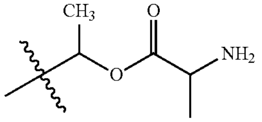 [SMILES: *C(C)OC(=O)C(C)N] | Cl | Cl |
| $-CH_2C(CH_3)F_2$ | 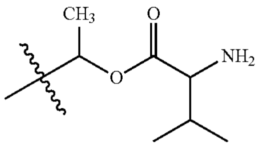 [SMILES: *C(C)OC(=O)C(N)C(C)C] | Cl | Cl |
| $-CH_2C(CH_3)F_2$ | 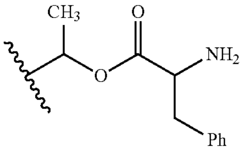 | Cl | Cl |
TABLE C-continued
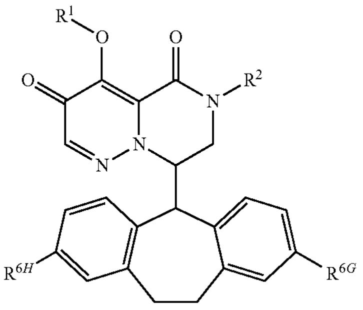
| $R^2$ | $R^1$ | $R^{6G}$ | $R^{6H}$ |
|---|---|---|---|
| $-CH_2C(CH_3)F_2$ | 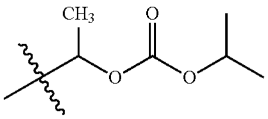 [SMILES: *C(C)OC(=O)OC(C)C] | Cl | Cl |
| $-CH_2C(CH_3)F_2$ | 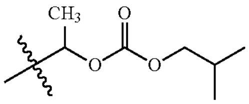 [SMILES: *C(C)OC(=O)OCC(C)C] | Cl | Cl |
| 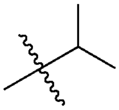 [SMILES: *C(C)C] | 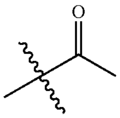 [SMILES: *C(C)=O] | F | F |
| 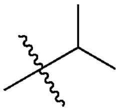 [SMILES: *C(C)C] | 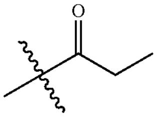 [SMILES: *C(=O)CC] | F | F |
| 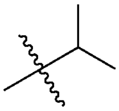 [SMILES: *C(C)C] | 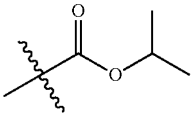 [SMILES: *C(=O)OC(C)C] | F | F |
| 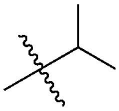 [SMILES: *C(C)C] | 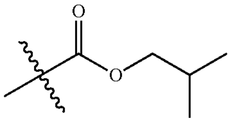 [SMILES: *C(=O)OCC(C)C] | F | F |
| 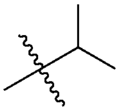 [SMILES: *C(C)C] | 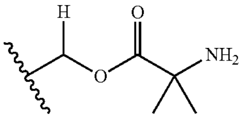 [SMILES: *COC(=O)C(C)(C)N] | F | F |
| 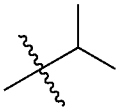 [SMILES: *C(C)C] | 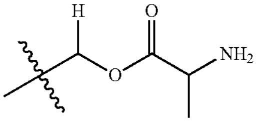 [SMILES: *COC(=O)C(C)N] | F | F |
| 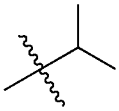 [SMILES: *C(C)C] | 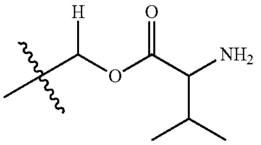 [SMILES: *COC(=O)C(N)C(C)C] | F | F |

TABLE C-continued
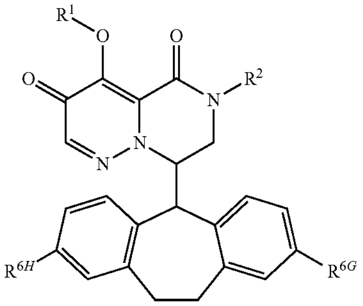
| $R^2$ | $R^1$ | $R^{6G}$ | $R^{6H}$ |
|---|---|---|---|
| 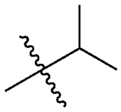 [SMILES: *C(C)C] | 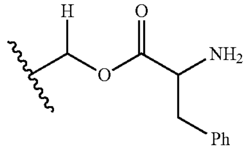 [SMILES: *COC(=O)C(N)Cc1ccccc1] | F | F |
| 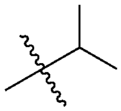 [SMILES: *C(C)C] | 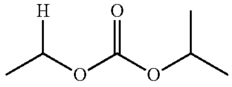 | F | F |
| 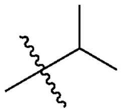 [SMILES: *C(C)C] | 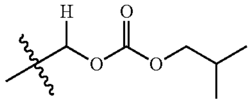 [SMILES: *COC(=O)OCC(C)C] | F | F |
| 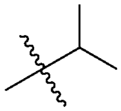 [SMILES: *C(C)C] | 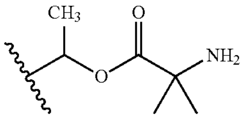 [SMILES: *C(C)OC(=O)C(C)(C)N] | F | F |
| 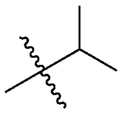 [SMILES: *C(C)C] | 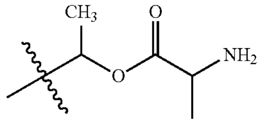 [SMILES: *C(C)OC(=O)C(C)N] | F | F |
| 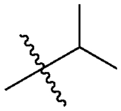 [SMILES: *C(C)C] | 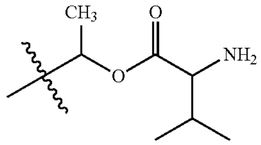 [SMILES: *C(C)OC(=O)C(N)C(C)C] | F | F |
| 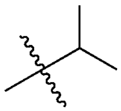 [SMILES: *C(C)C] | 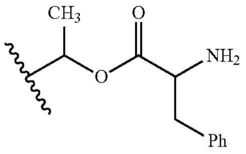 | F | F |
| 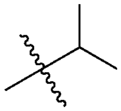 [SMILES: *C(C)C] | 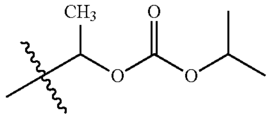 [SMILES: *C(C)OC(=O)OC(C)C] | F | F |
| 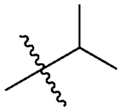 [SMILES: *C(C)C] | 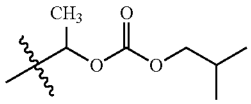 [SMILES: *C(C)OC(=O)OCC(C)C] | F | F |
TABLE C-continued
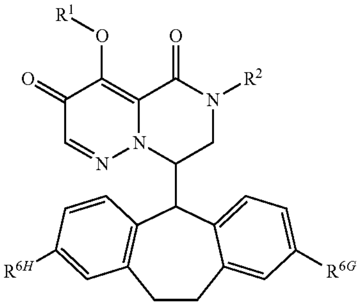
| $R^2$ | $R^1$ | $R^{6G}$ | $R^{6H}$ |
|---|---|---|---|
| $—CH_3$ | 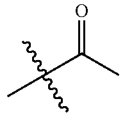 [SMILES: *C(C)=O] | F | F |
| $—CH_3$ | 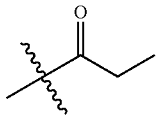 [SMILES: *C(=O)CC] | F | F |
| $—CH_3$ | 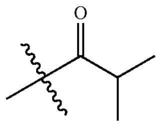 [SMILES: *C(=O)C(C)C] | F | F |
| $—CH_3$ | 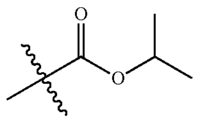 [SMILES: *C(=O)OC(C)C] | F | F |
| $—CH_3$ | 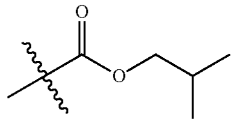 [SMILES: *C(=O)OCC(C)C] | F | F |
| $—CH_3$ | 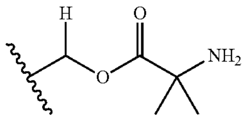 [SMILES: *COC(=O)C(C)(C)N] | F | F |
| $—CH_3$ | 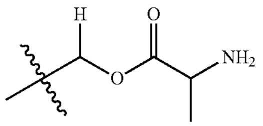 [SMILES: *COC(=O)C(C)N] | F | F |
| $—CH_3$ | 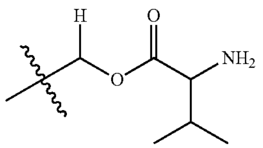 [SMILES: *COC(=O)C(N)C(C)C] | F | F |
| $—CH_3$ | 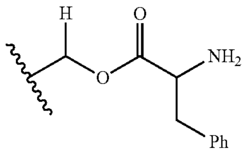 [SMILES: *COC(=O)C(N)Cc1ccccc1] | F | F |

TABLE C-continued
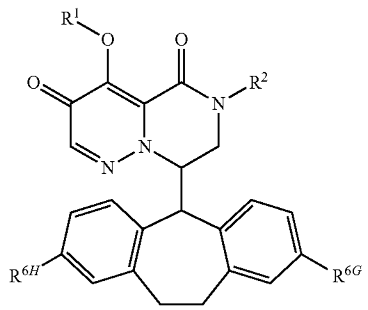
| $R^2$ | $R^1$ | $R^{6G}$ | $R^{6H}$ |
|---|---|---|---|
| —$CH_3$ | 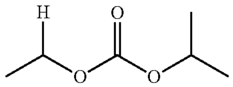 | F | F |
| —$CH_3$ | 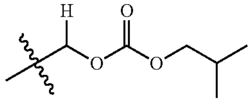 [SMILES: *COC(=O)OCC(C)C] | F | F |
| —$CH_3$ | 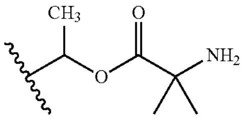 | F | F |
| —$CH_3$ | 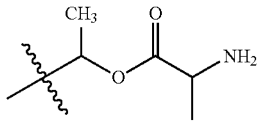 [SMILES: *C(C)OC(=O)C(C)N] | F | F |
| —$CH_3$ | 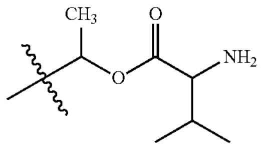 [SMILES: *C(C)OC(=O)C(N)C(C)C] | F | F |
| —$CH_3$ | 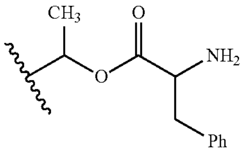 [SMILES: *C(C)OC(=O)C(N)Cc1ccccc1] | F | F |
| —$CH_3$ | 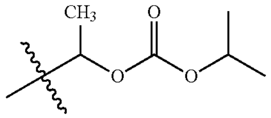 [SMILES: *C(C)OC(=O)OC(C)C] | F | F |
| —$CH_3$ | 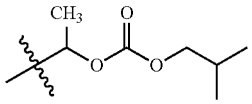 [SMILES: *C(C)OC(=O)OCC(C)C] | F | F |
| —$CH_2CH_3$ | H | F | F |
| —$CH_2CH_3$ | 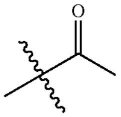 [SMILES: *C(C)=O] | F | F |
TABLE C-continued
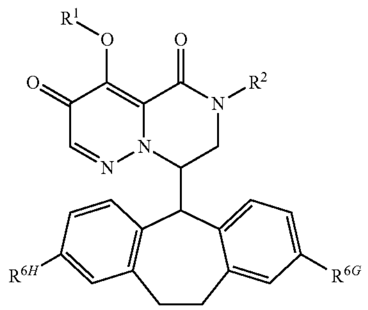
| $R^2$ | $R^1$ | $R^{6G}$ | $R^{6H}$ |
|---|---|---|---|
| —$CH_2CH_3$ | 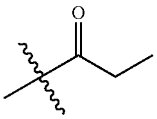 [SMILES: *C(=O)CC] | F | F |
| —$CH_2CH_3$ | 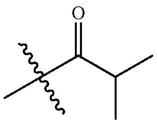 [SMILES: *C(=O)C(C)C] | F | F |
| —$CH_2CH_3$ | 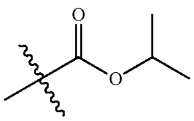 [SMILES: *C(=O)OC(C)C] | F | F |
| —$CH_2CH_3$ | 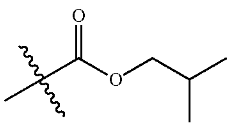 [SMILES: *C(=O)OCC(C)C] | F | F |
| —$CH_2CH_3$ | 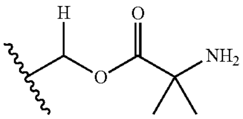 [SMILES: *COC(=O)C(C)(C)N] | F | F |
| —$CH_2CH_3$ | 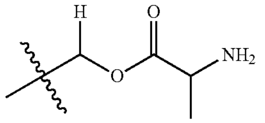 [SMILES: *COC(=O)C(C)N] | F | F |
| —$CH_2CH_3$ | 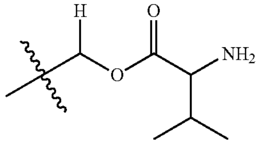 [SMILES: *COC(=O)C(N)C(C)C] | F | F |
| —$CH_2CH_3$ | 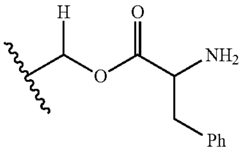 [SMILES: *COC(=O)C(N)Cc1ccccc1] | F | F |
| —$CH_2CH_3$ | 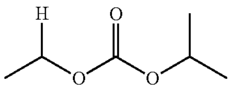 | F | F |

TABLE C-continued
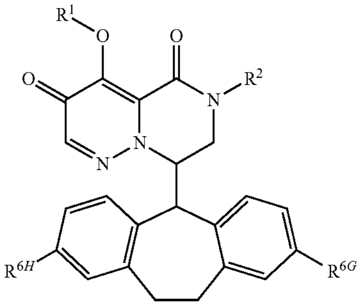
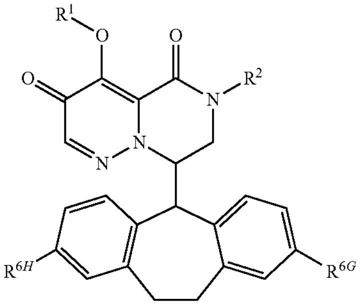
| $R^2$ | $R^1$ | $R^{6G}$ | $R^{6H}$ |
|---|---|---|---|
| $—CH_2CH_3$ | 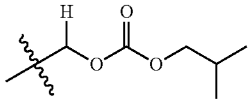 [SMILES: *COC(=O)OCC(C)C] | F | F |
| $—CH_2CH_3$ | 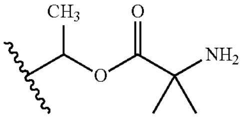 [SMILES: *C(C)OC(=O)C(C)(C)N] | F | F |
| $—CH_2CH_3$ | 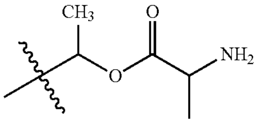 [SMILES: *C(C)OC(=O)C(C)N] | F | F |
| $—CH_2CH_3$ | 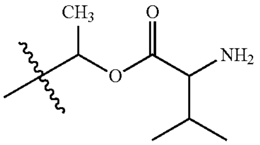 [SMILES: *C(C)OC(=O)C(N)C(C)C] | F | F |
| $—CH_2CH_3$ | 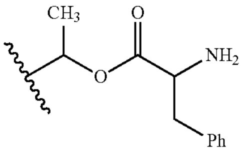 | F | F |
| $—CH_2CH_3$ | 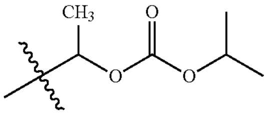 [SMILES: *C(C)OC(=O)OC(C)C] | F | F |
| $—CH_2CH_3$ | 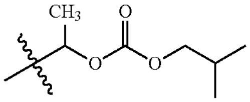 [SMILES: *C(C)OC(=O)OCC(C)C] | F | F |
| $—CH_2CH(CH_3)_2$ | H | F | F |
| $—CH_2CH(CH_3)_2$ | 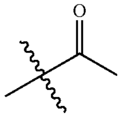 [SMILES: *C(C)=O] | F | F |
| $—CH_2CH(CH_3)_2$ | 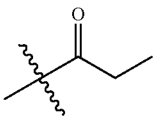 [SMILES: *C(=O)CC] | F | F |
| $—CH_2CH(CH_3)_2$ | 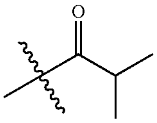 [SMILES: *C(=O)C(C)C] | F | F |
| $—CH_2CH(CH_3)_2$ | 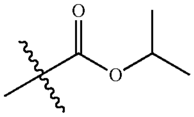 [SMILES: *C(=O)OC(C)C] | F | F |
| $—CH_2CH(CH_3)_2$ | 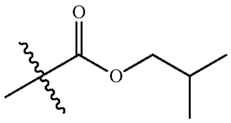 [SMILES: *C(=O)OCC(C)C] | F | F |
| $—CH_2CH(CH_3)_2$ | 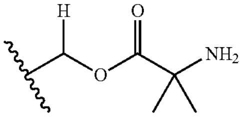 [SMILES: *COC(=O)C(C)(C)N] | F | F |
| $—CH_2CH(CH_3)_2$ | 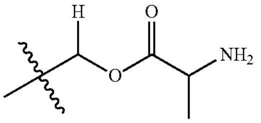 [SMILES: *COC(=O)C(C)N] | F | F |
| $—CH_2CH(CH_3)_2$ | 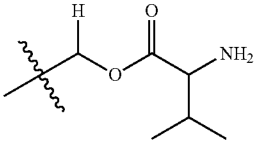 [SMILES: *COC(=O)C(N)C(C)C] | F | F |
| $—CH_2CH(CH_3)_2$ | 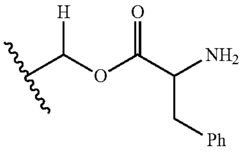 [SMILES: *COC(=O)C(N)Cc1ccccc1] | F | F |
| $—CH_2CH(CH_3)_2$ | 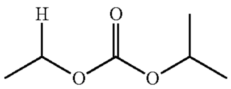 | F | F |
| $—CH_2CH(CH_3)_2$ | 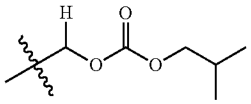 [SMILES: *COC(=O)OCC(C)C] | F | F |

TABLE C-continued
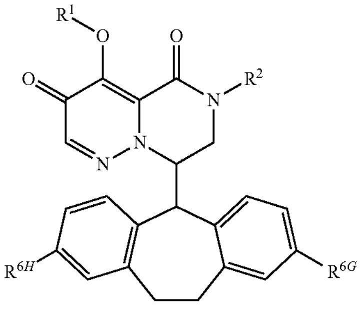
| $R^2$ | $R^1$ | $R^{6G}$ | $R^{6H}$ |
|---|---|---|---|
| $—CH_2CH(CH_3)_2$ | 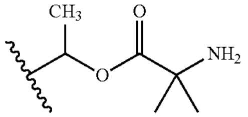 | F | F |
| $—CH_2CH(CH_3)_2$ | 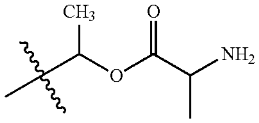 [SMILES: *C(C)OC(=O)C(C)N] | F | F |
| $—CH_2CH(CH_3)_2$ | 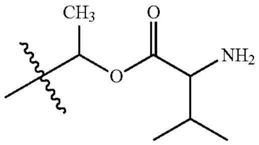 [SMILES: *C(C)OC(=O)C(N)C(C)C] | F | F |
| $—CH_2CH(CH_3)_2$ | 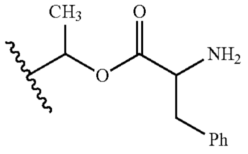 | F | F |
| $—CH_2CH(CH_3)_2$ | 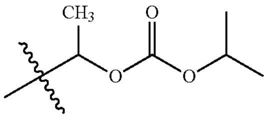 [SMILES: *C(C)OC(=O)OC(C)C] | F | F |
| $—CH_2CH(CH_3)_2$ | 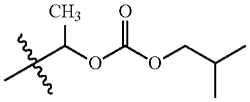 [SMILES: *C(C)OC(=O)OCC(C)C] | F | F |
| $—CH_2CH_2CH_3$ | H | F | F |
| $—CH_2CH_2CH_3$ | 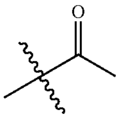 [SMILES: *C(C)=O] | F | F |
| $—CH_2CH_2CH_3$ | 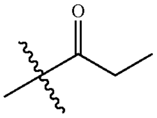 [SMILES: *C(=O)CC] | F | F |
| $—CH_2CH_2CH_3$ | 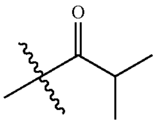 [SMILES: *C(=O)C(C)C] | F | F |
TABLE C-continued
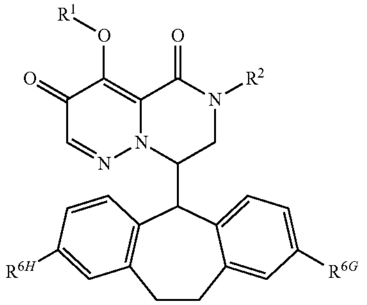
| $R^2$ | $R^1$ | $R^{6G}$ | $R^{6H}$ |
|---|---|---|---|
| $—CH_2CH_2CH_3$ | 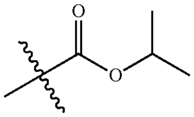 [SMILES: *C(=O)OC(C)C] | F | F |
| $—CH_2CH_2CH_3$ | 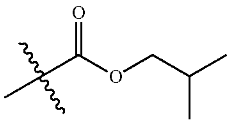 [SMILES: *C(=O)OCC(C)C] | F | F |
| $—CH_2CH_2CH_3$ | 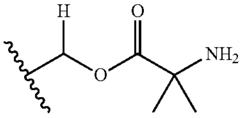 [SMILES: *COC(=O)C(C)(C)N] | F | F |
| $—CH_2CH_2CH_3$ | 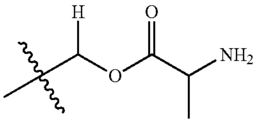 [SMILES: *COC(=O)C(C)N] | F | F |
| $—CH_2CH_2CH_3$ | 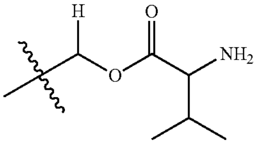 [SMILES: *COC(=O)C(N)C(C)C] | F | F |
| $—CH_2CH_2CH_3$ | 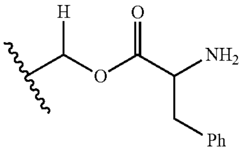 [SMILES: *COC(=O)C(N)Cc1ccccc1] | F | F |
| $—CH_2CH_2CH_3$ | 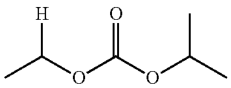 | F | F |
| $—CH_2CH_2CH_3$ | 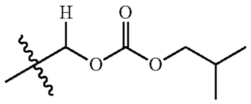 [SMILES: *COC(=O)OCC(C)C] | F | F |
| $—CH_2CH_2CH_3$ | 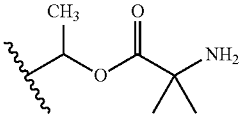 [SMILES: *C(C)OC(=O)C(C)(C)N] | F | F |

TABLE C-continued
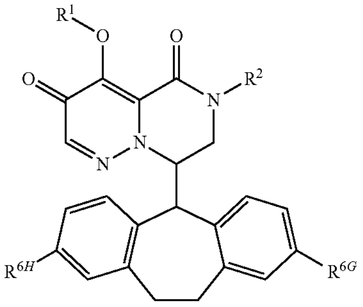
| $R^2$ | $R^1$ | $R^{6G}$ | $R^{6H}$ |
|---|---|---|---|
| $—CH_2CH_2CH_3$ | 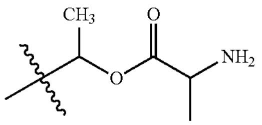 [SMILES: *C(C)OC(=O)C(C)N] | F | F |
| $—CH_2CH_2CH_3$ | 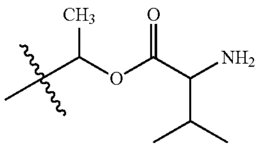 [SMILES: *C(C)OC(=O)C(N)C(C)C] | F | F |
| $—CH_2CH_2CH_3$ | 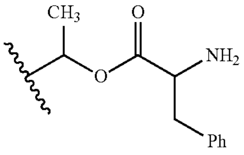 [SMILES: *C(C)OC(=O)C(N)Cc1ccccc1] | F | F |
| $—CH_2CH_2CH_3$ | 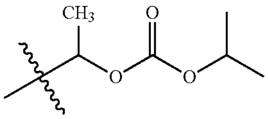 [SMILES: *C(C)OC(=O)OC(C)C] | F | F |
| $—CH_2CH_2CH_3$ | 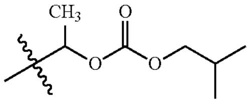 | F | F |
| $—CH_2CH_2CH_2CH_3$ | H | F | F |
| $—CH_2CH_2CH_2CH_3$ | 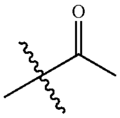 [SMILES: *C(C)=O] | F | F |
| $—CH_2CH_2CH_2CH_3$ | 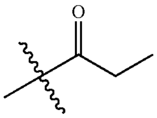 [SMILES: *C(=O)CC] | F | F |
| $—CH_2CH_2CH_2CH_3$ | 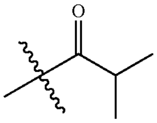 [SMILES: *C(=O)C(C)C] | F | F |
| $—CH_2CH_2CH_2CH_3$ | 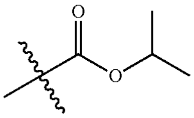 [SMILES: *C(=O)OC(C)C] | F | F |
TABLE C-continued
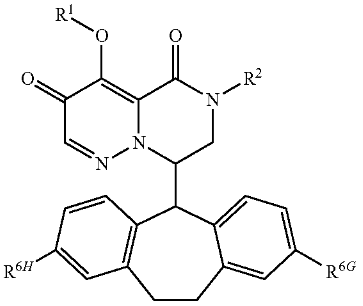
| $R^2$ | $R^1$ | $R^{6G}$ | $R^{6H}$ |
|---|---|---|---|
| $—CH_2CH_2CH_2CH_3$ | 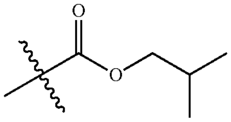 [SMILES: *C(=O)OCC(C)C] | F | F |
| $—CH_2CH_2CH_2CH_3$ | 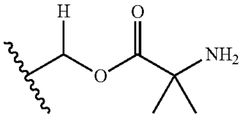 [SMILES: *COC(=O)C(C)(C)N] | F | F |
| $—CH_2CH_2CH_2CH_3$ | 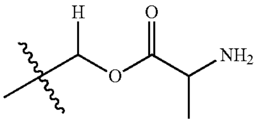 [SMILES: *COC(=O)C(C)N] | F | F |
| $—CH_2CH_2CH_2CH_3$ | 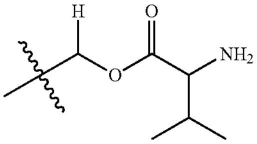 [SMILES: *COC(=O)C(N)C(C)C] | F | F |
| $—CH_2CH_2CH_2CH_3$ | 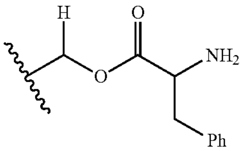 [SMILES: *COC(=O)C(N)Cc1ccccc1] | F | F |
| $—CH_2CH_2CH_2CH_3$ | 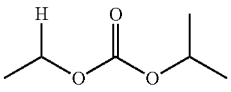 | F | F |
| $—CH_2CH_2CH_2CH_3$ | 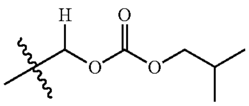 [SMILES: *COC(=O)OCC(C)C] | F | F |
| $—CH_2CH_2CH_2CH_3$ | 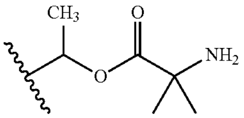 [SMILES: *C(C)OC(=O)C(C)(C)N] | F | F |
| $—CH_2CH_2CH_2CH_3$ | 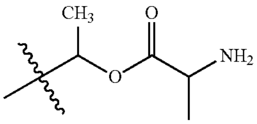 [SMILES: *C(C)OC(=O)C(C)N] | F | F |

TABLE C-continued
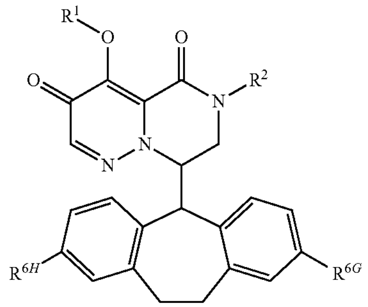
| $R^2$ | $R^1$ | $R^{6G}$ | $R^{6H}$ |
|---|---|---|---|
| $—CH_2CH_2CH_2CH_3$ | 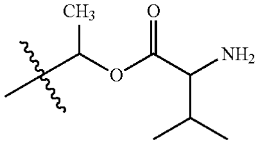 [SMILES: *C(C)OC(=O)C(N)C(C)C] | F | F |
| $—CH_2CH_2CH_2CH_3$ | 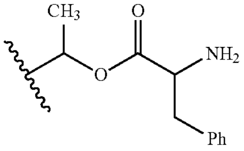 | F | F |
| $—CH_2CH_2CH_2CH_3$ | 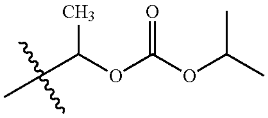 [SMILES: *C(C)OC(=O)OC(C)C] | F | F |
| $—CH_2CH_2CH_2CH_3$ | 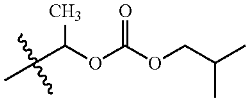 [SMILES: *C(C)OC(=O)OCC(C)C] | F | F |
| 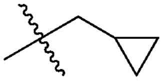 [SMILES: *CC1CC1] | H | F | F |
| 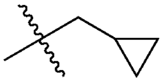 [SMILES: *CC1CC1] | 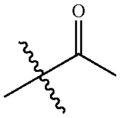 [SMILES: *C(C)=O] | F | F |
| 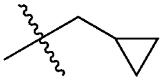 [SMILES: *CC1CC1] | 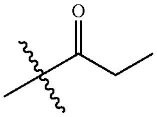 [SMILES: *C(=O)CC] | F | F |
| 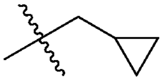 [SMILES: *CC1CC1] | 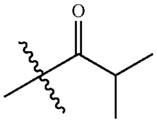 [SMILES: *C(=O)C(C)C] | F | F |
| 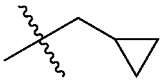 [SMILES: *CC1CC1] | 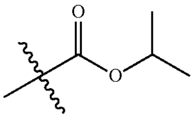 [SMILES: *C(=O)OC(C)C] | F | F |
TABLE C-continued
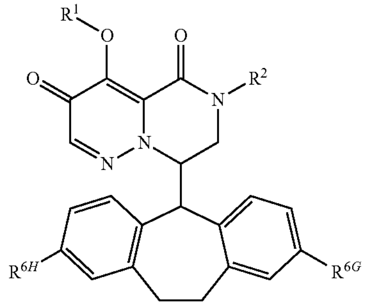
| $R^2$ | $R^1$ | $R^{6G}$ | $R^{6H}$ |
|---|---|---|---|
| 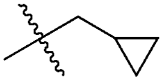 [SMILES: *CC1CC1] | 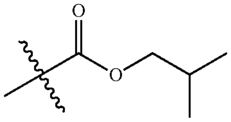 [SMILES: *C(=O)OCC(C)C] | F | F |
| 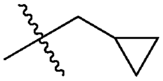 [SMILES: *CC1CC1] | 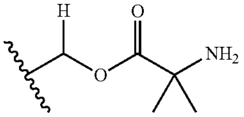 [SMILES: *COC(=O)C(C)(C)N] | F | F |
| 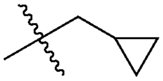 [SMILES: *CC1CC1] | 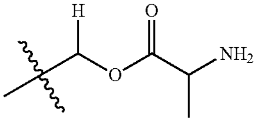 [SMILES: *COC(=O)C(C)N] | F | F |
| 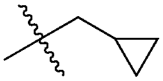 [SMILES: *CC1CC1] | 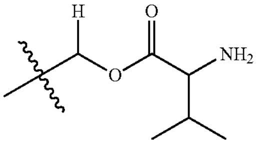 [SMILES: *COC(=O)C(N)C(C)C] | F | F |
| 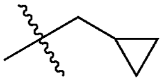 [SMILES: *CC1CC1] | 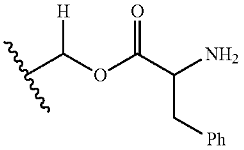 [SMILES: *COC(=O)C(N)Cc1ccccc1] | F | F |
| 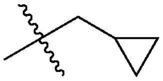 [SMILES: *CC1CC1] | 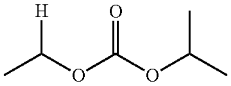 | F | F |
| 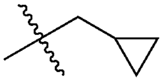 [SMILES: *CC1CC1] | 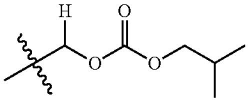 [SMILES: *COC(=O)OCC(C)C] | F | F |
| 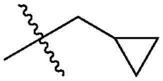 [SMILES: *CC1CC1] | 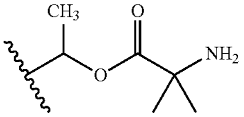 [SMILES: *C(C)OC(=O)C(C)(C)N] | F | F |
| 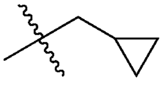 [SMILES: *CC1CC1] | 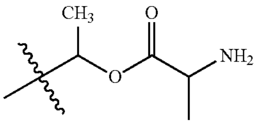 [SMILES: *C(C)OC(=O)C(C)N] | F | F |

TABLE C-continued
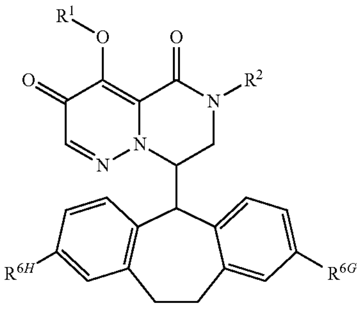
| $R^2$ | $R^1$ | $R^{6G}$ | $R^{6H}$ |
|---|---|---|---|
| 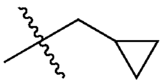 [SMILES: *CC1CC1] | 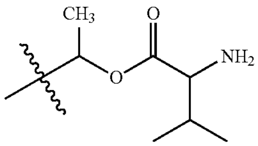 [SMILES: *C(C)OC(=O)C(N)C(C)C] | F | F |
| 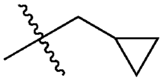 | 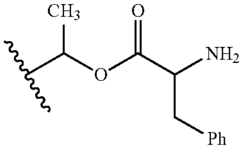 | F | F |
| 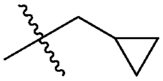 [SMILES: *CC1CC1] | 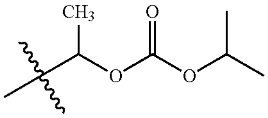 [SMILES: *C(C)OC(=O)OC(C)C] | F | F |
| 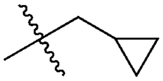 [SMILES: *CC1CC1] | 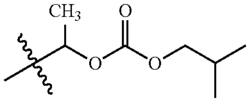 [SMILES: *C(C)OC(=O)OCC(C)C] | F | F |
| 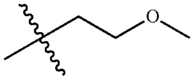 [SMILES: *CCOC] | H | F | F |
| 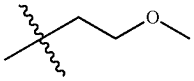 [SMILES: *CCOC] | 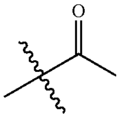 [SMILES: *C(C)=O] | F | F |
| 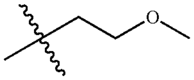 [SMILES: *CCOC] | 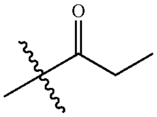 [SMILES: *C(=O)CC] | F | F |
| 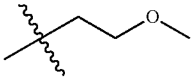 | 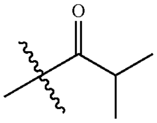 [SMILES: *C(=O)C(C)C] | F | F |
| 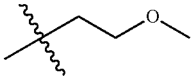 | 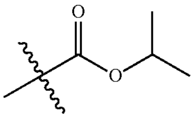 [SMILES: *C(=O)OC(C)C] | F | F |
TABLE C-continued
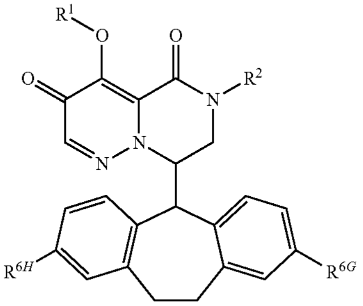
| $R^2$ | $R^1$ | $R^{6G}$ | $R^{6H}$ |
|---|---|---|---|
| 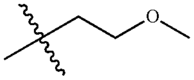 [SMILES: *CCOC] | 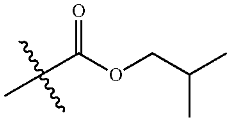 [SMILES: *C(=O)OCC(C)C] | F | F |
| 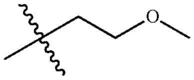 | 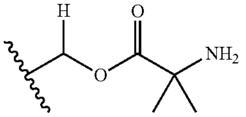 [SMILES: *COC(=O)C(C)(C)N] | F | F |
| 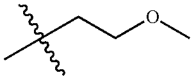 [SMILES: *CCOC] | 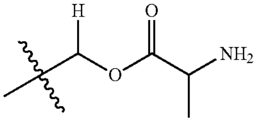 [SMILES: *COC(=O)C(C)N] | F | F |
| 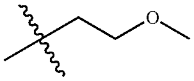 [SMILES: *CCOC] | 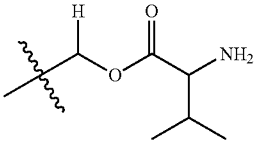 [SMILES: *COC(=O)C(N)C(C)C] | F | F |
| 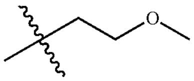 [SMILES: *CCOC] | 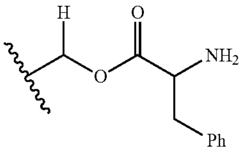 [SMILES: *COC(=O)C(N)Cc1ccccc1] | F | F |
| 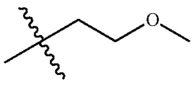 [SMILES: *CCOC] | 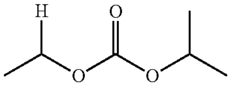 | F | F |
| 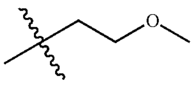 [SMILES: *CCOC] | 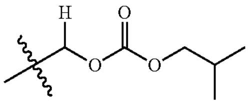 [SMILES: *COC(=O)OCC(C)C] | F | F |
| 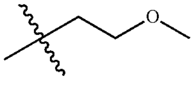 [SMILES: *CCOC] | 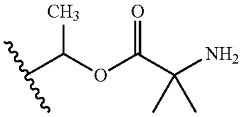 [SMILES: *C(C)OC(=O)C(C)(C)N] | F | F |
| 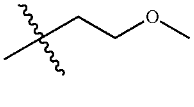 [SMILES: *CCOC] | 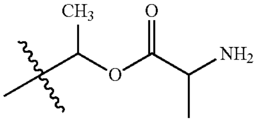 [SMILES: *C(C)OC(=O)C(C)N] | F | F |

TABLE C-continued
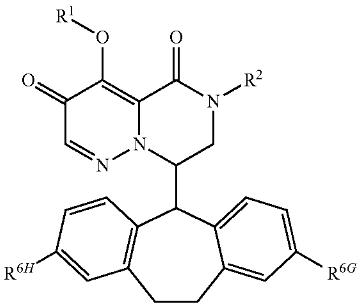
| $R^2$ | $R^1$ | $R^{6G}$ | $R^{6H}$ |
|---|---|---|---|
| 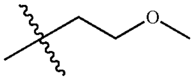 [SMILES: *CCOC] | 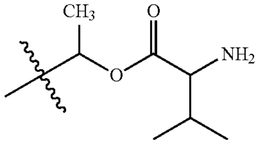 [SMILES: *C(C)OC(=O)C(N)C(C)C] | F | F |
| 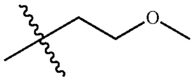 [SMILES: *CCOC] | 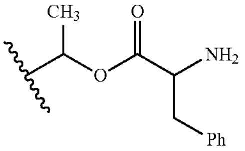 | F | F |
| 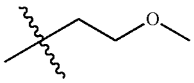 | 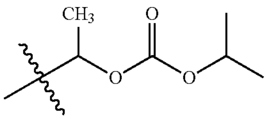 [SMILES: *C(C)OC(=O)OC(C)C] | F | F |
| 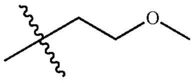 [SMILES: *CCOC] | 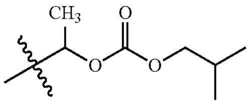 [SMILES: *C(C)OC(=O)OCC(C)C] | F | F |
| 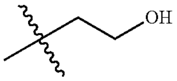 [SMILES: *CCO] | H | F | F |
| 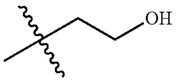 [SMILES: *CCO] | 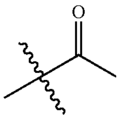 [SMILES: *C(C)=O] | F | F |
| 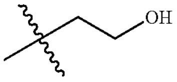 [SMILES: *CCO] | 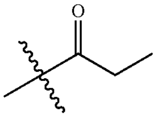 [SMILES: *C(=O)CC] | F | F |
| 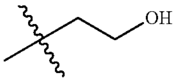 [SMILES: *CCO] | 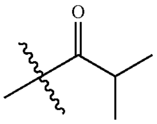 [SMILES: *C(=O)C(C)C] | F | F |
| 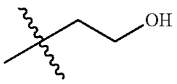 [SMILES: *CCO] | 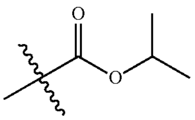 [SMILES: *C(=O)OC(C)C] | F | F |
TABLE C-continued
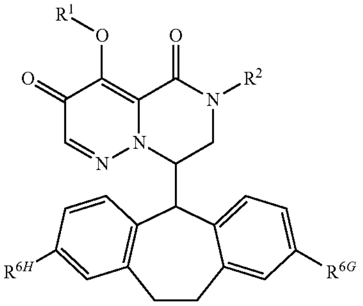
| $R^2$ | $R^1$ | $R^{6G}$ | $R^{6H}$ |
|---|---|---|---|
| 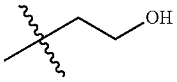 [SMILES: *CCO] | 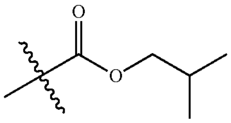 [SMILES: *C(=O)OCC(C)C] | F | F |
| 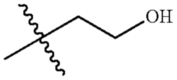 | 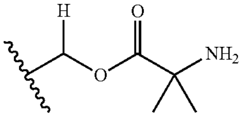 [SMILES: *COC(=O)C(C)(C)N] | F | F |
| 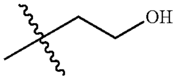 [SMILES: *CCO] | 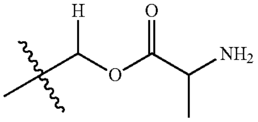 [SMILES: *COC(=O)C(C)N] | F | F |
| 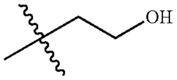 | 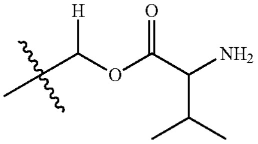 [SMILES: *COC(=O)C(N)C(C)C] | F | F |
| 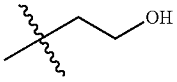 [SMILES: *CCO] | 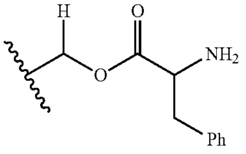 [SMILES: *COC(=O)C(N)Cc1ccccc1] | F | F |
| 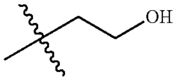 [SMILES: *CCO] | 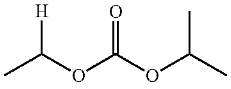 | F | F |
| 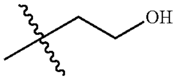 [SMILES: *CCO] | 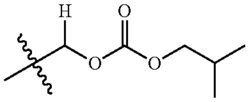 [SMILES: *COC(=O)OCC(C)C] | F | F |
| 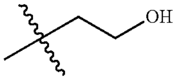 [SMILES: *CCO] | 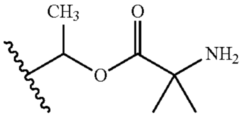 [SMILES: *C(C)OC(=O)C(C)(C)N] | F | F |
| 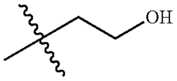 [SMILES: *CCO] | 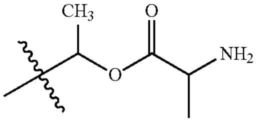 [SMILES: *C(C)OC(=O)C(C)N] | F | F |

TABLE C-continued
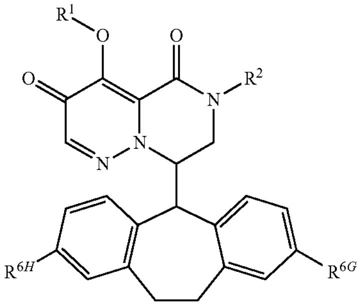
| R2 | R1 | R6G | R6H |
|---|---|---|---|
| 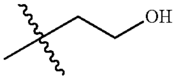 [SMILES: *CCO] | 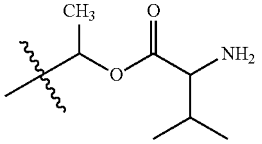 [SMILES: *C(C)OC(=O)C(N)C(C)C] | F | F |
| 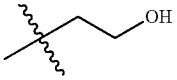 [SMILES: *CCO] | 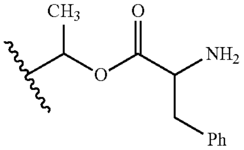 [SMILES: *C(C)OC(=O)C(N)Cc1ccccc1] | F | F |
| 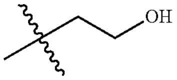 [SMILES: *CCO] | 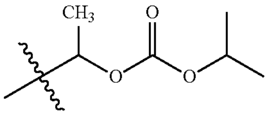 [SMILES: *C(C)OC(=O)OC(C)C] | F | F |
| 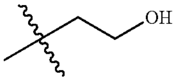 [SMILES: *CCO] | 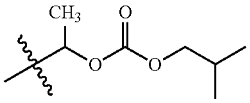 [SMILES: *C(C)OC(=O)OCC(C)C] | F | F |
| —$CH_2CH{=}CF_2$ | 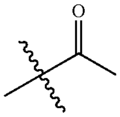 [SMILES: *C(C)=O] | F | F |
| —$CH_2CH{=}CF_2$ | 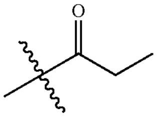 [SMILES: *C(=O)CC] | F | F |
| —$CH_2CH{=}CF_2$ | 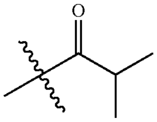 [SMILES: *C(=O)C(C)C] | F | F |
| —$CH_2CH{=}CF_2$ | 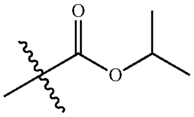 [SMILES: *C(=O)OC(C)C] | F | F |
| —$CH_2CH{=}CF_2$ | 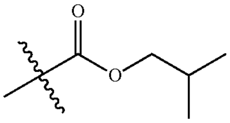 [SMILES: *C(=O)OCC(C)C] | F | F |
TABLE C-continued
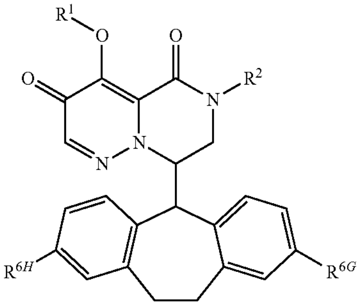
| R2 | R1 | R6G | R6H |
|---|---|---|---|
| —$CH_2CH{=}CF_2$ | 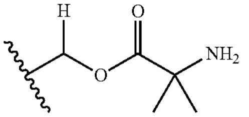 [SMILES: *COC(=O)C(C)(C)N] | F | F |
| —$CH_2CH{=}CF_2$ | 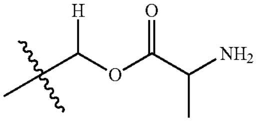 [SMILES: *COC(=O)C(C)N] | F | F |
| —$CH_2CH{=}CF_2$ | 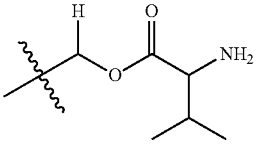 [SMILES: *COC(=O)C(N)C(C)C] | F | F |
| —$CH_2CH{=}CF_2$ | 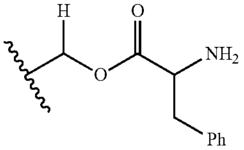 [SMILES: *COC(=O)C(N)Cc1ccccc1] | F | F |
| —$CH_2CH{=}CF_2$ | 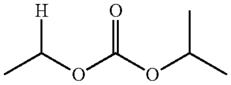 | F | F |
| —$CH_2CH{=}CF_2$ | 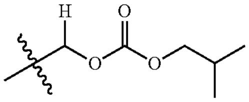 [SMILES: *COC(=O)OCC(C)C] | F | F |
| —$CH_2CH{=}CF_2$ | 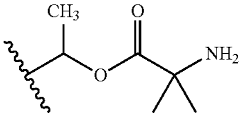 [SMILES: *C(C)OC(=O)C(C)(C)N] | F | F |
| —$CH_2CH{=}CF_2$ | 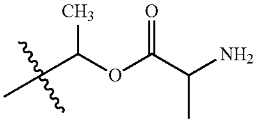 [SMILES: *C(C)OC(=O)C(C)N] | F | F |
| —$CH_2CH{=}CF_2$ | 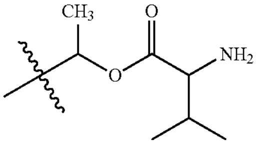 [SMILES: *C(C)OC(=O)C(N)C(C)C] | F | F |

TABLE C-continued
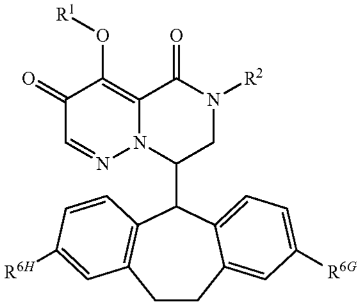
| $R^2$ | $R^1$ | $R^{6G}$ | $R^{6H}$ |
|---|---|---|---|
| $—CH_2CH{=}CF_2$ | 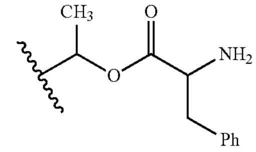 | F | F |
| $—CH_2CH{=}CF_2$ | 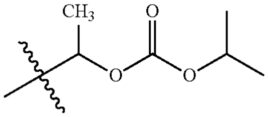 [SMILES: *C(C)OC(=O)OC(C)C] | F | F |
| $—CH_2CH{=}CF_2$ | 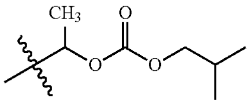 [SMILES: *C(C)OC(=O)OCC(C)C] | F | F |
| $—CH_2CF_3$ | 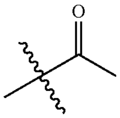 [SMILES: *C(C)=O] | F | F |
| $—CH_2CF_3$ | 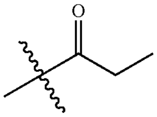 [SMILES: *C(=O)CC] | F | F |
| $—CH_2CF_3$ | 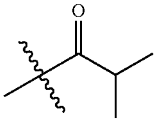 [SMILES: *C(=O)C(C)C] | F | F |
| $—CH_2CF_3$ | 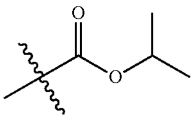 [SMILES: *C(=O)OC(C)C] | F | F |
| $—CH_2CF_3$ | 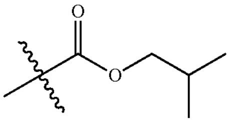 [SMILES: *C(=O)OCC(C)C] | F | F |
| $—CH_2CF_3$ | 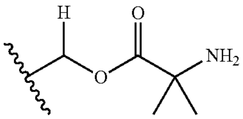 [SMILES: *COC(=O)C(C)(C)N] | F | F |
TABLE C-continued
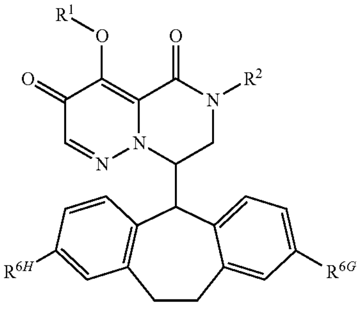
| $R^2$ | $R^1$ | $R^{6G}$ | $R^{6H}$ |
|---|---|---|---|
| $—CH_2CF_3$ | 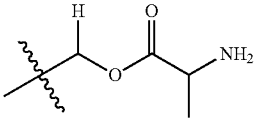 [SMILES: *COC(=O)C(C)N] | F | F |
| $—CH_2CF_3$ | 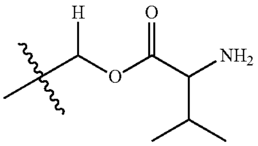 [SMILES: *COC(=O)C(N)C(C)C] | F | F |
| $—CH_2CF_3$ | 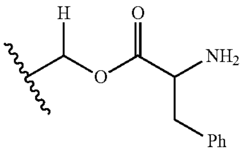 [SMILES: *COC(=O)C(N)Cc1ccccc1] | F | F |
| $—CH_2CF_3$ | 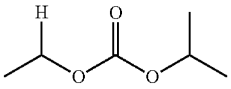 | F | F |
| $—CH_2CF_3$ | 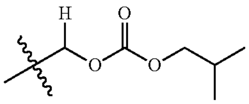 [SMILES: *COC(=O)OCC(C)C] | F | F |
| $—CH_2CF_3$ | 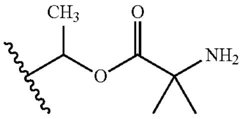 [SMILES: *C(C)OC(=O)C(C)(C)N] | F | F |
| $—CH_2CF_3$ | 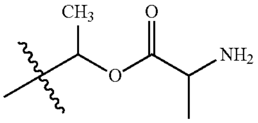 [SMILES: *C(C)OC(=O)C(C)N] | F | F |
| $—CH_2CF_3$ | 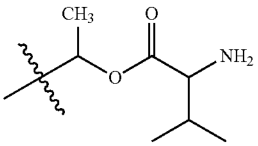 [SMILES: *C(C)OC(=O)C(N)C(C)C] | F | F |
| $—CH_2CF_3$ | 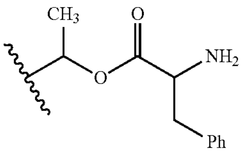 [SMILES: *C(C)OC(=O)C(N)Cc1ccccc1] | F | F |

TABLE C-continued
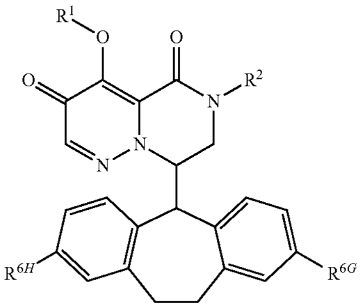
| $R^2$ | $R^1$ | $R^{6G}$ | $R^{6H}$ |
|---|---|---|---|
| $—CH_2CF_3$ | 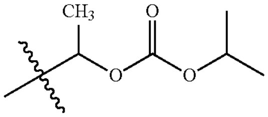 [SMILES: *C(C)OC(=O)OC(C)C] | F | F |
| $—CH_2CF_3$ | 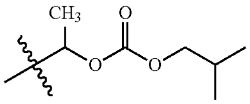 [SMILES: *C(C)OC(=O)OCC(C)C] | F | F |
| $—CH_2CH_2CF_3$ | 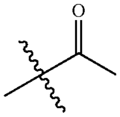 [SMILES: *C(C)=O] | F | F |
| $—CH_2CH_2CF_3$ | 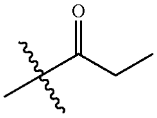 [SMILES: *C(=O)CC] | F | F |
| $—CH_2CH_2CF_3$ | 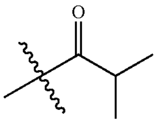 [SMILES: *C(=O)C(C)C] | F | F |
| $—CH_2CH_2CF_3$ | 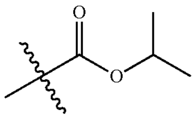 [SMILES: *C(=O)OC(C)C] | F | F |
| $—CH_2CH_2CF_3$ | 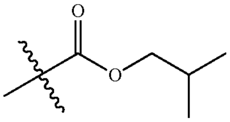 [SMILES: *C(=O)OCC(C)C] | F | F |
| $—CH_2CH_2CF_3$ | 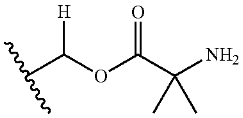 [SMILES: *COC(=O)C(C)(C)N] | F | F |
| $—CH_2CH_2CF_3$ | 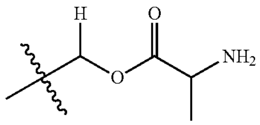 [SMILES: *COC(=O)C(C)N] | F | F |
TABLE C-continued
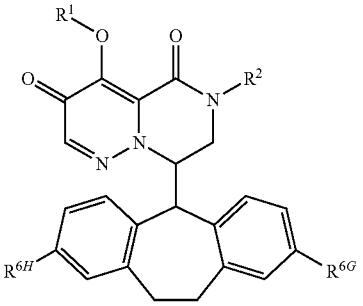
| $R^2$ | $R^1$ | $R^{6G}$ | $R^{6H}$ |
|---|---|---|---|
| $—CH_2CH_2CF_3$ | 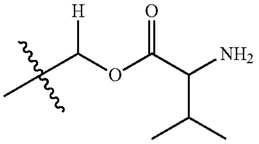 [SMILES: *COC(=O)C(N)C(C)C] | F | F |
| $—CH_2CH_2CF_3$ | 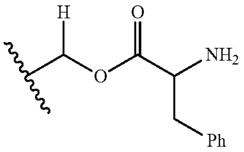 [SMILES: *COC(=O)C(N)Cc1ccccc1] | F | F |
| $—CH_2CH_2CF_3$ | 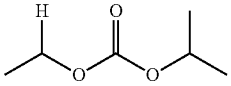 | F | F |
| $—CH_2CH_2CF_3$ | 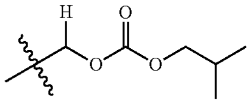 [SMILES: *COC(=O)OCC(C)C] | F | F |
| $—CH_2CH_2CF_3$ | 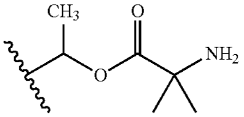 | F | F |
| $—CH_2CH_2CF_3$ | 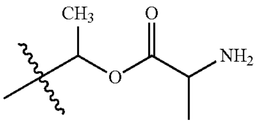 [SMILES: *C(C)OC(=O)C(C)N] | F | F |
| $—CH_2CH_2CF_3$ | 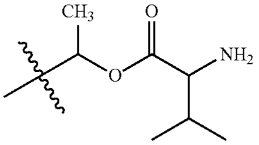 [SMILES: *C(C)OC(=O)C(N)C(C)C] | F | F |
| $—CH_2CH_2CF_3$ | 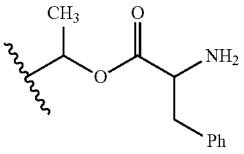 [SMILES: *C(C)OC(=O)C(N)Cc1ccccc1] | F | F |
| $—CH_2CH_2CF_3$ | 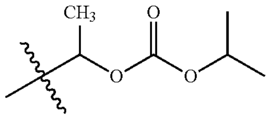 [SMILES: *C(C)OC(=O)OC(C)C] | F | F |

TABLE C-continued
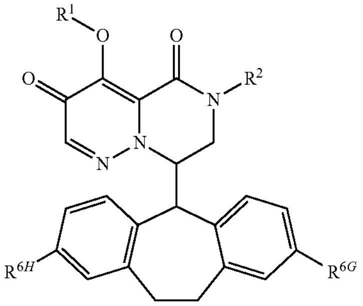
| $R^2$ | $R^1$ | $R^{6G}$ | $R^{6H}$ |
|---|---|---|---|
| $—CH_2CH_2CF_3$ | 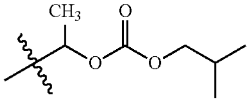 [SMILES: *C(C)OC(=O)OCC(C)C] | F | F |
| $—CH_2CHF_2$ | 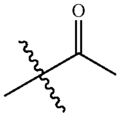 [SMILES: *C(C)=O] | F | F |
| $—CH_2CHF_2$ | 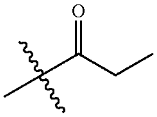 [SMILES: *C(=O)CC] | F | F |
| $—CH_2CHF_2$ | 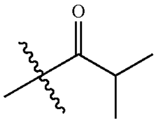 [SMILES: *C(=O)C(C)C] | F | F |
| $—CH_2CHF_2$ | 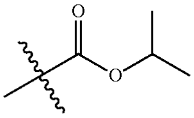 [SMILES: *C(=O)OC(C)C] | F | F |
| $—CH_2CHF_2$ | 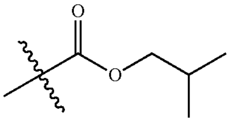 [SMILES: *C(=O)OCC(C)C] | F | F |
| $—CH_2CHF_2$ | 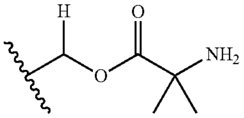 [SMILES: *COC(=O)C(C)(C)N] | F | F |
| $—CH_2CHF_2$ | 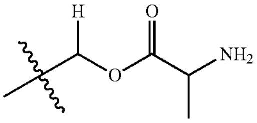 [SMILES: *COC(=O)C(C)N] | F | F |
| $—CH_2CHF_2$ | 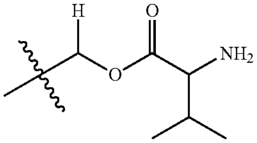 [SMILES: *COC(=O)C(N)C(C)C] | F | F |
TABLE C-continued
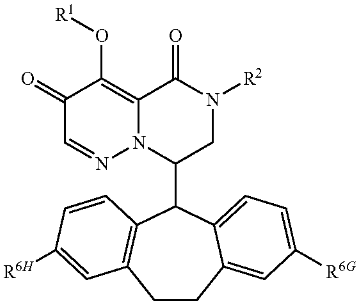
| $R^2$ | $R^1$ | $R^{6G}$ | $R^{6H}$ |
|---|---|---|---|
| $—CH_2CHF_2$ | 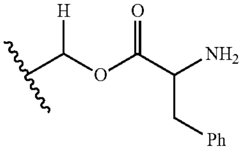 [SMILES: *COC(=O)C(N)Cc1ccccc1] | F | F |
| $—CH_2CHF_2$ | 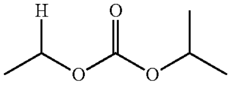 | F | F |
| $—CH_2CHF_2$ | 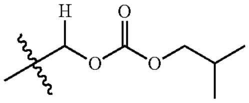 [SMILES: *COC(=O)OCC(C)C] | F | F |
| $—CH_2CHF_2$ | 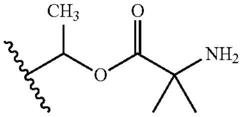 [SMILES: *C(C)OC(=O)C(C)(C)N] | F | F |
| $—CH_2CHF_2$ | 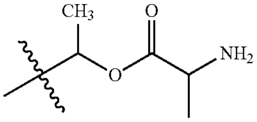 [SMILES: *C(C)OC(=O)C(C)N] | F | F |
| $—CH_2CHF_2$ | 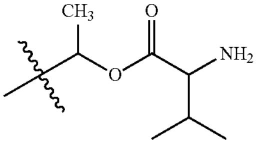 [SMILES: *C(C)OC(=O)C(N)C(C)C] | F | F |
| $—CH_2CHF_2$ | 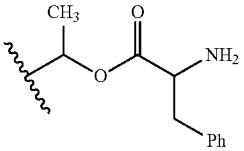 [SMILES: *C(C)OC(=O)C(N)Cc1ccccc1] | F | F |
| $—CH_2CHF_2$ | 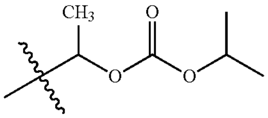 [SMILES: *C(C)OC(=O)OC(C)C] | F | F |
| $—CH_2CHF_2$ | 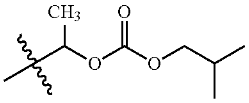 [SMILES: *C(C)OC(=O)OCC(C)C] | F | F |

TABLE C-continued
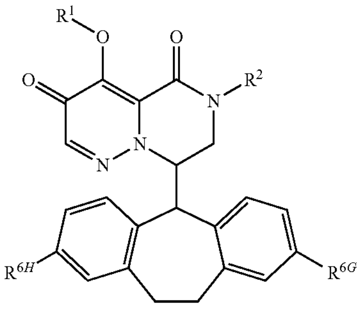
| $R^2$ | $R^1$ | $R^{6G}$ | $R^{6H}$ |
|---|---|---|---|
| $—CH_2C(CH_3)F_2$ | 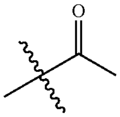 [SMILES: *C(C)=O] | F | F |
| $—CH_2C(CH_3)F_2$ | 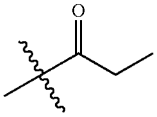 [SMILES: *C(=O)CC] | F | F |
| $—CH_2C(CH_3)F_2$ | 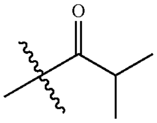 [SMILES: *C(=O)C(C)C] | F | F |
| $—CH_2C(CH_3)F_2$ | 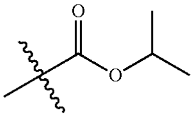 [SMILES: *C(=O)OC(C)C] | F | F |
| $—CH_2C(CH_3)F_2$ | 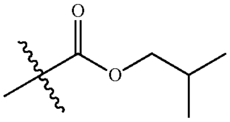 [SMILES: *C(=O)OCC(C)C] | F | F |
| $—CH_2C(CH_3)F_2$ | 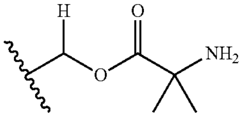 [SMILES: *COC(=O)C(C)(C)N] | F | F |
| $—CH_2C(CH_3)F_2$ | 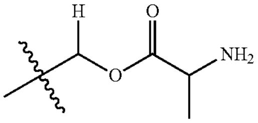 [SMILES: *COC(=O)C(C)N] | F | F |
| $—CH_2C(CH_3)F_2$ | 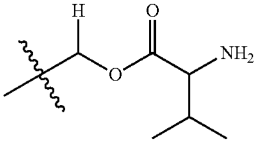 [SMILES: *COC(=O)C(N)C(C)C] | F | F |
| $—CH_2C(CH_3)F_2$ | 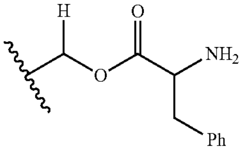 [SMILES: *COC(=O)C(N)Cc1ccccc1] | F | F |
TABLE C-continued
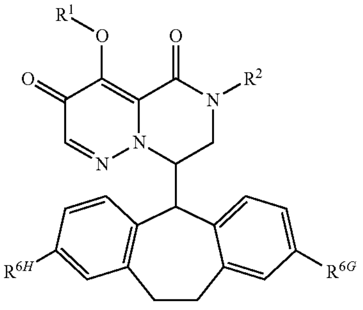
| $R^2$ | $R^1$ | $R^{6G}$ | $R^{6H}$ |
|---|---|---|---|
| $—CH_2C(CH_3)F_2$ | 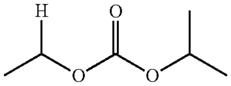 | F | F |
| $—CH_2C(CH_3)F_2$ | 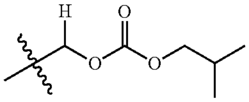 [SMILES: *COC(=O)OCC(C)C] | F | F |
| $—CH_2C(CH_3)F_2$ | 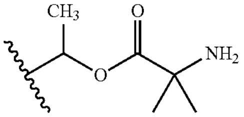 | F | F |
| $—CH_2C(CH_3)F_2$ | 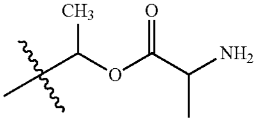 [SMILES: *C(C)OC(=O)C(C)N] | F | F |
| $—CH_2C(CH_3)F_2$ | 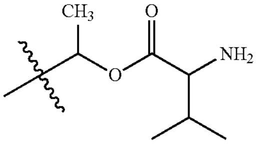 [SMILES: *C(C)OC(=O)C(N)C(C)C] | F | F |
| $—CH_2C(CH_3)F_2$ | 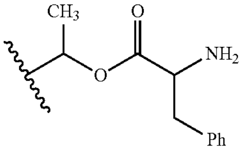 [SMILES: *C(C)OC(=O)C(N)Cc1ccccc1] | F | F |
| $—CH_2C(CH_3)F_2$ | 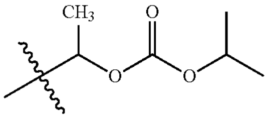 [SMILES: *C(C)OC(=O)OC(C)C] | F | F |
| $—CH_2C(CH_3)F_2$ | 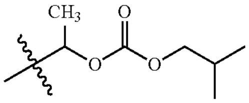 [SMILES: *C(C)OC(=O)OCC(C)C] | F | F |

In some embodiments, when $R^4$ is

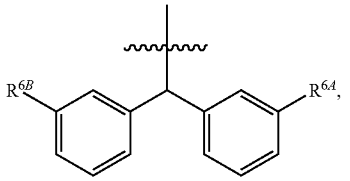

wherein $R^{6A}$ and $R^{6B}$ are each hydrogen, and $R^2$ is hydrogen, $-CH_3$, $-CH_2CH_3$, $-CH_2CH_2CH_3$, $-CH_2CH_2CH_2CH_3$, $-CH(CH_3)_2$, $-CH(CH_2CH_3)_2$, $-CH_2CH(CH_3)_2$, $-CH(CH_3)CF_3$, $-CH_2-(C_3\text{-cyclopropyl})$, tetrahydro-2H-pyran, $-CH_2CH_2OH$, $-CH_2CH_2OCH_3$ or $-C(CH_3)_2CH_2OCH_3$; then $R^1$ cannot be hydrogen, $-C(=O)CH_3$, $-C(=O)CH(CH_3)_2$, $-C(=O)CH_2CH(CH_3)_2$, $-C(=O)-(C_{5-6}\text{-cyclo alkyl})$, $-C(=O)$-(tetrahydro-2H-pyran), $-C(=O)-O-CH(CH_3)_2$, $-C(=O)-O-CH_2CH(CH_3)_2$, $-CH_2-O-C(=O)CH(CH_3)(NH_2)$, $-CH_2-O-C(=O)CH(CH(CH_3)_2)(NH_2)$ or $-CH_2-O-C(=O)C((CH_3)_2)(NH_2)$. In some embodiments, when $R^4$ is

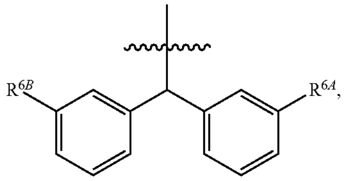

wherein $R^{6A}$ and $R^{6B}$ are each fluoro, and $R^2$ is $-CH_3$, $-CH_2CH_3$, $-CH_2CH_2CH_3$, $-CH_2CH_2CH_2CH_3$, $-CH(CH_3)_2$, $-CH_2CH(CH_3)_2$, $-CH_2-(C_3\text{-cyclopropyl})$, -unsubstituted benzyl, $-CH_2CH_2OH$, or $-CH_2CH_2OCH_3$; then $R^1$ cannot be hydrogen, $-CH_2CH_3$, $-C(=O)CH_3$, $-C(=O)CH(CH_3)_2$, $-CH_2-O-C(=O)-O$-(phenyl substituted with methyl and nitro), $-CH_2-O-C(=O)-NH-CH_2CH_2$-(morpholine), $-CH_2-O-C(=O)CH(CH(CH_3)_2)(NH_2)$ or $-CH_2-O-C(=O)NH(CH_3)$. In some embodiments, when $R^4$ is

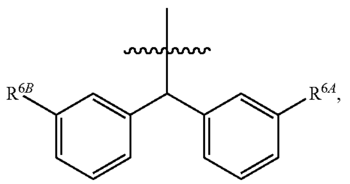

wherein $R^{6A}$ and $R^{6B}$ are each fluoro, and $R^2$ is $-CH_3$, $-CH_2CH_3$, $-CH_2CH_2CH_3$, $-CH_2CH_2CH_2CH_3$, $-CH(CH_3)_2$, $-CH_2CH(CH_3)_2$, $-CH_2-(C_3\text{-cyclopropyl})$, -unsubstituted benzyl, $-CH_2CH_2OH$, or $-CH_2CH_2OCH_3$; then $R^1$ cannot be $-CH_2-O-C(=O)-O$-(an optionally substituted phenyl) or $-CH_2-O-C(=O)-NH-CH_2CH_2$-(an optionally substituted heterocyclyl). In some embodiments, when $R^4$ is

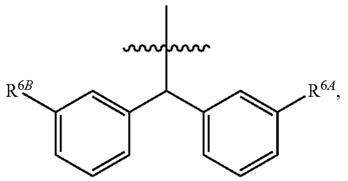

wherein $R^{6A}$ and $R^{6B}$ are each chloro, and $R^2$ is $-CH_3$, $-CH_2CH_3$, $-CH_2CH_2CH_3$, $-CH_2CH_2CH_2CH_3$, $-CH(CH_3)_2$, $-CH_2CH(CH_3)_2$, $-CH_2-(C_3\text{-cyclopropyl})$, $-CH_2CH_2OH$, or $-CH_2CH_2OCH_3$; then $R^1$ cannot be hydrogen or $-C(=O)CH(CH_3)_2$. In some embodiments, when $R^4$ is

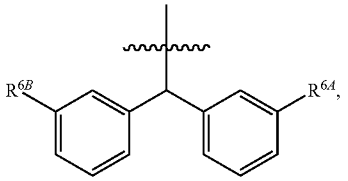

wherein one of $R^{6A}$ and $R^{6B}$ is an unsubstituted $C_{1-4}$ alkyl (for example, one of $R^{6A}$ and $R^{6B}$ is methyl); then $R^1$ cannot be hydrogen. In some embodiments, when $R^4$ is

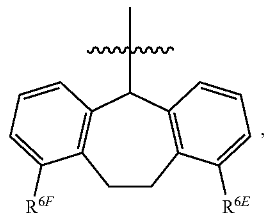

wherein $R^{6E}$ and $R^{6F}$ are each hydrogen, and $R^2$ is $-CH_3$, $-CH_2CH_3$, $-CH_2CH_2CH_3$, $-CH_2CH_2CH_2CH_3$, $-CH(CH_3)_2$, $-CH_2CH(CH_3)_2$, $-CH_2-(C_3\text{-cyclopropyl})$, an unsubstituted benzyl, $-CH(CH_3)CF_3$, $-CH_2CH_2OH$, or $-CH_2CH_2OCH_3$; then $R^1$ cannot be hydrogen or $-C(=O)CH(CH_3)_2$. In some embodiments, when $R^4$ is

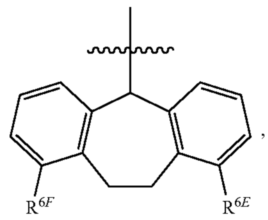

wherein $R^{6E}$ and $R^{6F}$ are each fluoro, and $R^2$ is $-CH_3$, $-CH_2CH_3$, $-CH_2CH_2CH_3$, $-CH_2CH_2CH_2CH_3$, $-CH(CH_3)_2$, $-CH_2CH(CH_3)_2$, $-CH_2-(C_3\text{-cyclopropyl})$, $-CH_2CH_2OH$, or $-CH_2CH_2OCH_3$; then $R^1$ cannot be hydrogen or $-C(=O)CH(CH_3)_2$. In some embodiments, when $R^4$ is

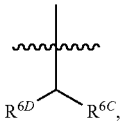

wherein $R^{6C}$ is pyrazolyl and $R^{6D}$ is unsubstituted phenyl, then $R^{6C}$ is a di-substituted pyrazolyl. In some embodiments, when $R^4$ is

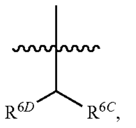

wherein $R^{6C}$ is an optionally substituted imidazolyl or an optionally substituted pyridinyl, then $R^{6D}$ is not an unsubstituted phenyl. In some embodiments, when $R^4$ is

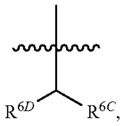

wherein $R^{6C}$ is an optionally substituted imidazolyl or an optionally substituted pyridinyl, then $R^{6D}$ is not an optionally substituted phenyl. In some embodiments, when $R^4$ is

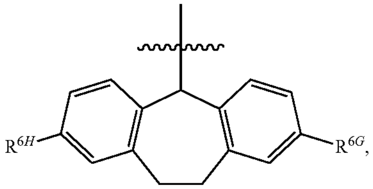

wherein $R^{6G}$ and $R^{6H}$ are each fluoro or each chloro, and $R^2$ is —$CH_3$, then $R^1$ is not hydrogen In some embodiments, $R^4$ cannot be

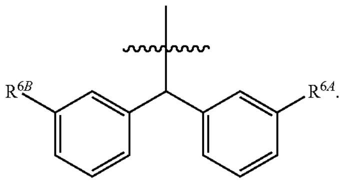

For example, $R^4$ cannot be one or more of the following:

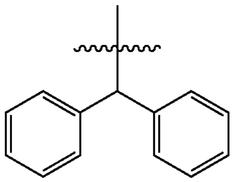

,

-continued

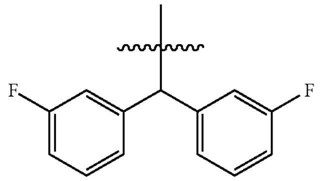

or

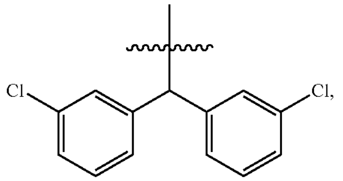

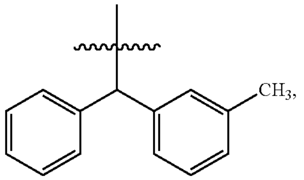

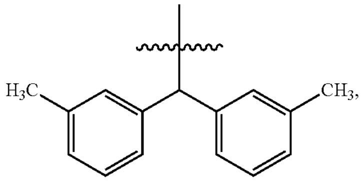

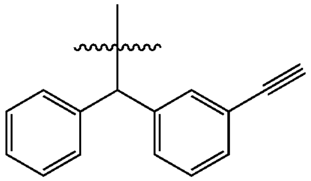

or

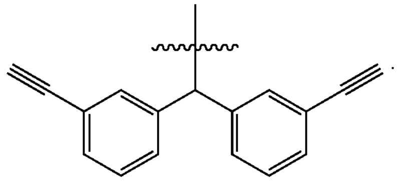

In some embodiments, $R^4$ cannot be

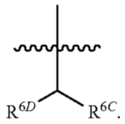

In some embodiments, $R^6$ and/or $R^{6D}$ cannot be an unsubstituted pyrazolyl or a mono-substituted pyrazolyl. In some embodiments, $R^4$ cannot be

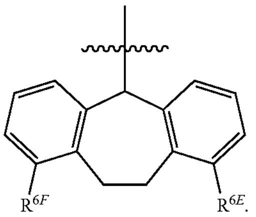

For example, $R^4$ cannot be one or more of the following:

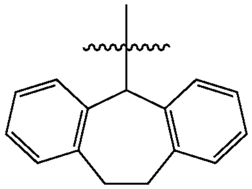

or

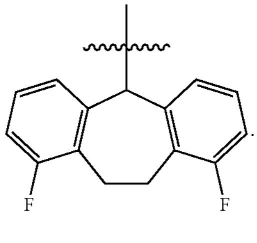

In some embodiments, $R^4$ cannot be

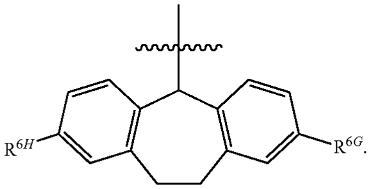

For example, $R^4$ cannot be one or more of the following:

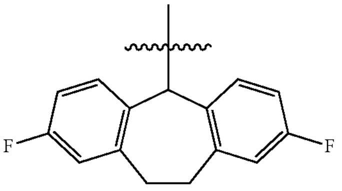

or

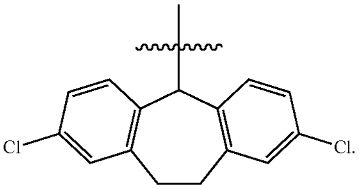

In some embodiments, $R^1$ cannot be hydrogen. In some embodiments, a compound of Formula (I), or a pharmaceutically acceptable salt, cannot be a compound in U.S. Publication No. 2015/0072982, filed Sep. 10, 2014 and/or a compound in PCT Application No. PCT/US2014/055012, filed Sep. 10, 2014.

Synthesis

Compounds of Formula (I), and those described herein may be prepared in various ways. General synthetic routes to compounds of Formula (I), and some examples of starting materials used to synthesize compounds of Formula (I) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formula (I) can be prepared starting from various protected intermediates, including the two shown below.

Intermediate A

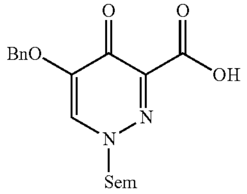

Intermediate B

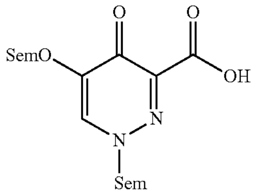

Bn=benzyl

SEM=[2-(Trimethylsilyl)ethoxy]methyl

Methods for forming a compound of Formula (I) starting from an intermediate and an amino alcohol shown herein, such as Intermediate A or Intermediate B, is shown in Schemes 1, 2, 3, 4, 5 and 6. In Schemes 1, 2 and 3, $R^{2a}$ and $R^{4a}$ can be the same as $R^2$ and $R^4$ as described herein for Formula (I), $PG^1$ can be a benzyl or SEM group and $LG^1$ can be a leaving group. In Schemes 1, 2, 3, 4, 5 and 6, $R^{3a}$, $R^{3b}$ and $R^5$ are not shown, but can be present.

Scheme 1

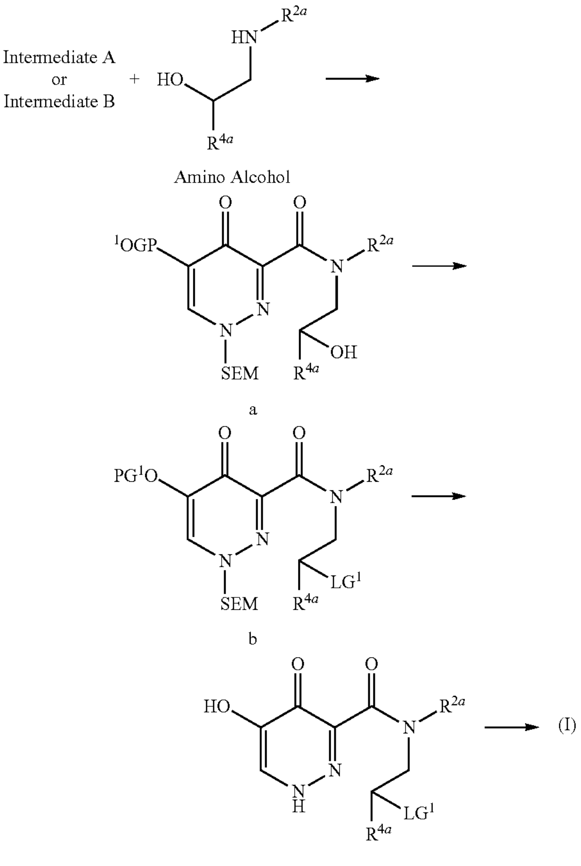

As shown in Scheme 1, Intermediate A or Intermediate B can be coupled with a 1,2-amino alcohol. Examples of suitable reaction conditions for coupling the aforementioned intermediate with a 1,2-amino alcohol include, but are not limited to, a carbodiimide (for example, N,N'-dicyclohexylcarbodiimide (DCC), N,N'-diisopropylcarbodiimide (DIC) or 1-ethyl-3-(3-dimethylaminopropyl)carbodiimide (EDCI)); O-(7-azabenzotriazol-1-yl)-N,N,N',N'-tetramethyluronium hexafluorophosphate (HATU), O-benzotriazole-N,N,N',N'-tetramethyl-uronium-hexafluoro-phosphate (HBTU) or O-(benzotriazol-1-yl)-N,N,N',N'-tetramethyluronium tetrafluoroborate (TBTU) in the presence of an amine base (such as N,N-diisopropylethylamine (DIPEA) or triethylamine (TEA)) in DMF; and propylphosphonic anhydride (T3P) in the presence of an amine base (such as those described herein).

The hydrogen of the unprotected secondary alcohol of compound a can be replaced to provide a suitable leaving group moiety, $LG^1$. Suitable leaving groups are known to those skilled in the art. In some embodiments, the leaving group can include I, Br, Cl, a mesyl moiety, a tosyl moiety and/or trifluoroacetyl moiety.

The $PG^1$ and the SEM group attached to the nitrogen of compound b can be removed using methods known to those skilled in the art. For example, the benzyl group can be removed via hydrogenolysis. Hydrogenolysis can be accomplished using various methods, such as a Pd or Pt catalyst (e.g., Pd/C or $PtO_2$) in combination with a hydrogen source (e.g., $H_2$ or formic acid), a strong acid, oxidation to the benzoate and subsequent hydrolysis under basic conditions and 2,3-dichloro-5,6-dicyano-p-benzoquinone (DDQ). The SEM group(s) can be removed using concentrated HF, tetra-n-butylammonium fluoride (TBAF), cesium fluoride, lithium tetrafluoroborate, trifluoroacetic acid (TFA) or pyridinium p-toluene sulfonate in ethanol at reflux temperature.

The leaving group moiety, $LG^1$, can be displaced and the compound can undergo cyclization using an acid or a base to form a compound of Formula (I). Suitable acids and bases are known to those skilled in the art. In some embodiments, the base can be potassium carbonate. Additional bases include sodium carbonate, calcium carbonate, cesium carbonate, sodium bicarbonate, potassium bicarbonate, calcium carbonate, cesium carbonate, triethylamine, diisopropyl ethyl amine, pyridine, KOH and NaOH. Suitable acids include sulfonic acids (e.g., methane sulfonic acid and p-toluenesulfonic acid), trifluoroacetic acid (TFA) and HCl. In some cases, the reagent(s) used to remove the $PG^1$ and SEM groups, for example, cesium fluoride or tetra-n-butylammonium fluoride (TBAF), can then promote cyclization to a compound of Formula (I).

Scheme 2

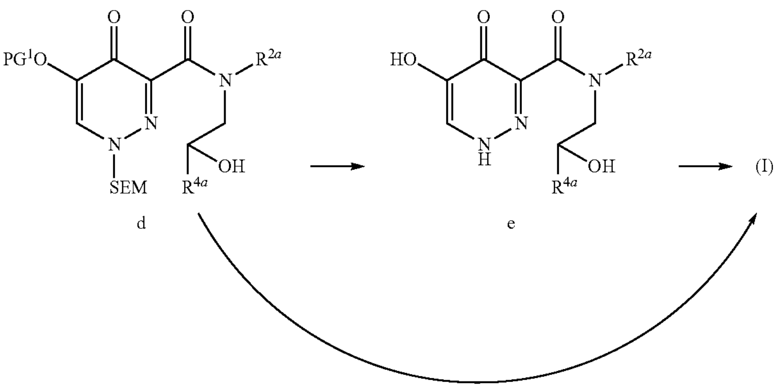

d e (I)

As shown in Scheme 2, the $PG^1$ and the SEM groups attached to the nitrogen can be removed from compound d using one or more methods described herein. A compound of Formula (I) can be then formed via a Mitsunobu ring-closure cyclization. The Mitsunobu ring-closure cyclization can be accomplished using a phosphine reagent (for example, triphenylphosphine, a tri-alkyl phosphine, a tri-aryl phosphine or polymer-supported triphenylphosphine) in combination with an azodicarboxylate, such as diethyl azodicarboxylate (DEAD) or diisopropyl azodicarboxylate (DIAD). Alternatively, the $PG^1$ and the SEM groups can be removed and the ring closed to form a compound of Formula (I) in a single step using a suitable acid, for example, trifluoroacetic acid, at an elevated temperature.

Scheme 3

Intermediate A
or
Intermediate B
+

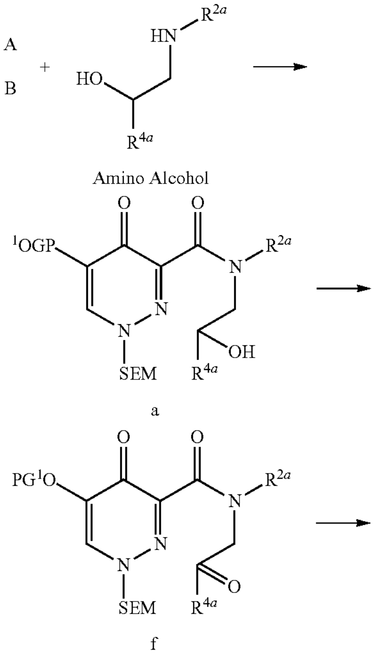

Amino Alcohol a f

-continued

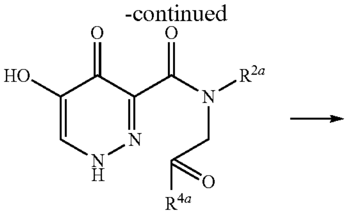

g

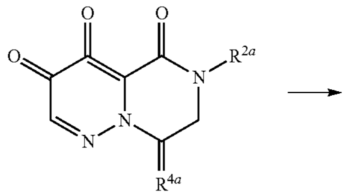

(I)

In Scheme 3, compound a can be formed as described herein. The secondary alcohol can be oxidized to a ketone using reagent(s) and conditions known to those skilled in the art. Examples of suitable oxidizing reagents and conditions include, but are not limited to, Dess-Martin periodinane, IBX (2-iodoxybenzoic acid), TPAP/NMO (tetrapropylammonium perruthenate/N-methylmorpholine N-oxide), Swern oxidation reagent, PCC (pyridinium chlorochromate), PDC (pyridinium dichromate), sodium periodate, Collin's reagent, Corey-Kim's reagent, Moffatt reagent, Jones' reagent, Oppenauer's reagent, ceric ammonium nitrate (CAN), $Na_2Cr_2O_7$ in water, $Ag_2CO_3$ on celite, hot $HNO_3$ in aqueous glyme, $O_2$-pyridine CuCl, $Pb(OAc)_4$-pyridine, potassium dichromate, and benzoyl peroxide-$NiBr_2$.

The $PG^1$ and the SEM group attached to the nitrogen can be removed using one or more methods described herein to provide compound g. The six-membered ring can be formed under acidic. Examples of suitable acids include, but are not limited to, sulfonic acids (e.g., methane sulfonic acid and p-toluenesulfonic acid), sulfuric acid, trifluoroacetic acid (TFA) and HCl. The double bond can be hydrogenated to a single bond using hydrogen gas in the presence of a palladium or platinum catalyst (such as Pd/C or $PtO_2$).

Amino alcohols that can be used in the preparation of a compound of Formula (I) can be commercially obtained or prepared according to a procedure provided herein, for example, a procedure shown in Schemes 4-6.

Scheme 4

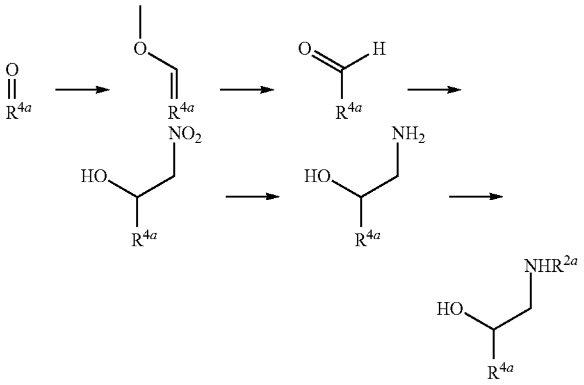

As shown in Scheme 4, the ketone undergoes olefination using an alkoxy-based phosphonium halide under Wittig-type reaction conditions to form a vinyl alkoxy intermediate. The vinyl alkoxy intermediate can be hydrolyzed to an aldehyde using methods known to those skilled in the art, such as perchloric acid. Nitromethane can be added to the aldehyde via a nitro-aldol reaction. Utilizing methods and conditions known to those skilled in the art, the nitro group can be reduced to a $NH_2$ group. The $NH_2$ group can undergo reductive alkylation to form the amino alcohol.

Scheme 5

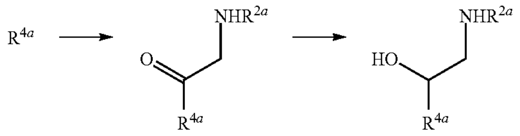

Another method for forming the amino alcohol is shown in Scheme 5. An amino acid ester can be added to the anion of the starting material, generated using a method known to those skilled in the art, for example, using n-BuLi. The ketone can be reduced to a hydroxy group using one or more suitable reagents and conditions, such as those described herein. To minimize side reactions and/or facilitate the reaction(s), the nitrogen of the amino acid ester can be protected with a suitable protecting group. The protecting group can be removed before or after reduction of the ketone using methods known to those skilled in the alt Scheme 6

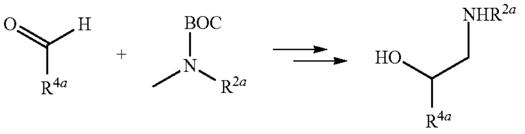

Scheme 6 shows a further method for forming the amino alcohol. The amino alcohol can be formed by a directed lithiation followed by a condensation-type reaction, using a method known to those skilled in the art, Snieckus et. al., *Tet. Lett.* (1994) 35(24):4067-4070. Additional details for preparing a compound described herein, including methods, materials and reagents, are provided in U.S. application Ser. No. 14/482,886, filed Sep. 10, 2014, and PCT Application No. PCT/US2014/055012, filed Sep. 10, 2014.

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering intramuscular. In other embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering intranasal. In still other embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering intradermal. In yet still other embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering orally.

When administered orally, one or more compounds described herein (e.g., a compound of Formula (I), or a pharmaceutically acceptable salt thereof) can be formulated as tablets, pills, dragees, capsules, liquids, gels, syrups, slurries, suspensions and the like, for oral ingestion by a subject to be treated. Injectables can be prepared in conventional forms, either as liquid solutions or suspensions, solid forms suitable for solution or suspension in liquid prior to injection, or as emulsions. Pharmaceutical compositions for intranasal delivery may also include drops and sprays often prepared to assist in simulating nasal secretions.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use:

Some embodiments described herein relate to a method of ameliorating, treating and/or preventing an orthomyxovirus infection, which can include administering an effective amount of one or more compounds described herein, or a pharmaceutical composition that includes one or more compounds described herein (e.g., a compound of Formula (I), or a pharmaceutically acceptable salt thereof).

Other embodiments described herein relate to a method of inhibiting an orthomyxovirus viral replication, which can include contacting a cell infected with the orthomyxovirus virus with an effective amount of a compound of Formula (I), or a pharmaceutically acceptable salt thereof and/or a pharmaceutical composition that includes one or more compounds described herein (e.g., a compound of Formula (I), or a pharmaceutically acceptable salt thereof).

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate an influenza viral infection. In other embodiments, an effective amount of one or more compounds of Formula (I), or a pharmaceutically acceptable salt thereof and/or a pharmaceutical composition that includes one or more compounds described herein (e.g., a compound of Formula (I), or a pharmaceutically acceptable salt thereof) can be used to prevent an influenza viral infection.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication an influenza virus. In some embodiments, an effective amount of one or more compounds of Formula (I), or a pharmaceutically acceptable salt thereof and/or a pharmaceutical composition that includes one or more compounds described herein (e.g., a compound of Formula (I), or a pharmaceutically acceptable salt thereof) can be used to inhibit the influenza polymerase complex. In some embodiments, an effective amount of one or more compounds of Formula (I), or a pharmaceutically acceptable salt thereof and/or a pharmaceutical composition that includes one or more compounds described herein (e.g., a compound of Formula (I), or a pharmaceutically acceptable salt thereof) can be used for inhibiting and/or reducing the endonuclease activity of an influenza endonuclease that can include contacting the active site of the endonuclease with a compound of Formula (I), or a pharmaceutically acceptable salt thereof. In some embodiments, one or more compounds described herein inhibits and/or reduces the ability of the endonuclease to cleave the mRNA.

In some embodiments, including those embodiments in the previous paragraphs, the influenza viral infection can be an influenza A viral infection. In other embodiments, including those embodiments in the previous paragraphs, the influenza viral infection can be an influenza B viral infection. In still other embodiments, including those embodiments in the previous paragraphs, the influenza viral infection can be an influenza C viral infection. In some embodiments, a compound of Formula (I), or a pharmaceutically acceptable salt thereof, can be used to treat and/or ameliorate one or more subtypes of influenza. For example, a compound of Formula (I), or a pharmaceutically acceptable salt thereof, can be used to treat H1N1 and/or H3N2. In addition or in the alternative, a compound of Formula (I), or a pharmaceutically acceptable salt thereof, can be used to treat H2N2, H5N1 and/or H7N9. In some embodiments, a compound described herein (a compound of Formula (I), or a pharmaceutically acceptable salt thereof) can be effective against more than 1 subtype of influenza. For example, a compound described herein (a compound of Formula (I), or a pharmaceutically acceptable salt thereof can be effective against 2, 3, 4, and/or 5 or more subtypes of influenza.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate an upper respiratory viral infection attributed to (directly and/or indirectly) an influenza virus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate a lower respiratory viral infection (directly and/or indirectly) an influenza virus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate one or more symptoms of an influenza virus infection (such as those described herein). In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate bronchiolitis and/or tracheobronchitis due to an influenza virus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate pneumonia due to an influenza virus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate coup due to an influenza virus infection.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used lessen the severity of one or more symptoms of an influenza infection. Examples of symptoms include, but are not limited to, the following: fever, chills, cough, sore throat, runny nose, stuffy nose, muscle aches, body aches, headache, fatigue, vomiting and/or diarrhea.

As used herein, the terms "prevent" and "preventing," mean a subject does not develop an infection because the subject has an immunity against the infection, or if a subject becomes infected, the severity of the disease is less compared to the severity of the disease if the subject has not been administered/received the compound. Examples of forms of prevention include prophylactic administration to a subject who has been or may be exposed to an infectious agent, such as an orthomyxovirus (e.g., an influenza virus).

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

Various indicators for determining the effectiveness of a method for treating an orthomyxovirus viral infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator of disease response.

In some embodiments, an effective amount of a compound of Formula (I), or a pharmaceutically acceptable salt thereof, is an amount that is effective to reduce viral titers to a lower level, for example, from about 10E4 TCID50/mL (TCID=tissue culture infectious dose) to about 10E3 TCID50/mL, or to about 100 TCID50/mL, or to about 10 TCID50/mL. In some embodiments, an effective amount of a compound of Formula (I), or a pharmaceutically acceptable salt thereof, is an amount that is effective to reduce viral load compared to the viral load before administration of the compound of Formula (I), or a pharmaceutically acceptable salt thereof. For example, wherein the viral load is measure before administration of the compound of Formula (I), or a pharmaceutically acceptable salt thereof, and again after initiation of the treatment regime with the compound of Formula (I), or a pharmaceutically acceptable salt thereof (for example, 10 days after initiation of treatment). In some embodiments, an effective amount of a compound of Formula (I), or a pharmaceutically acceptable salt thereof, can be an amount that is effective to reduce viral load to lower than about 10E4 TCID50/mL. In some embodiments, an effective amount of a compound of Formula (I), or a pharmaceutically acceptable salt thereof, is an amount that is effective to achieve a reduction in viral titer in a nasal/pharyngeal swab or nasal wash sample of the subject in the range of about 1.5-log to about a 2.5-log reduction or about a 3-log to about a 4-log reduction compared to the viral load before administration of the compound of Formula (I), or a pharmaceutically acceptable salt thereof. For example, wherein the viral load is measure before administration of the compound of Formula (I), or a pharmaceutically acceptable salt thereof, and again after initiation of the treatment regime with the compound of Formula (I), or a pharmaceutically acceptable salt thereof (for example, 10 days after initiation of treatment).

In some embodiments, a compound of Formula (I), or a pharmaceutically acceptable salt of the foregoing, can result in one or more overall quality of life health, such as reduced illness duration, reduced illness severity, reduced time to return to normal health and normal activity, and reduced time to alleviation of one or more symptoms of orthomyxovirus infection, compared to a subject who is untreated. In some embodiments, a compound of Formula (I), or a pharmaceutically acceptable salt of the foregoing, can result in a reduction in the length and/or severity of one or more symptoms associated with an orthomyxovirus infection compared to an untreated subject. Symptoms of an orthomyxovirus infection are described herein and include but not limited to cough, myalgia (muscle pain), nasal obstruction, sore throat, fatigue, headache and fever. In some embodiments, a compound of Formula (I), or a pharmaceutically acceptable salt of the thereof, can result in a reduction in one or more secondary complications associated with an orthomyxovirus infection, including but not limited to otitis media (ear inflammation), sinusitis, bronchitis and pneumonia compared to an untreated subject.

In some embodiments, a compound of Formula (I), or a pharmaceutically acceptable salt of the foregoing, can result in at least a 1, 2, 3, 4, 5, 10, 15, 20, 25, 50, 75, 100-fold or more reduction in the replication of an orthomyxovirus relative to pre-treatment levels in a subject, as determined after initiation of the treatment regime (for example, 10 days after initiation of treatment). In some embodiments, a compound of Formula (I), or a pharmaceutically acceptable salt of the foregoing, can result in a reduction of the replication of an orthomyxovirus relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of orthomyxovirus replication in the range of 1 to 1.5 log, 1.5 log to 2 log, 2 log to 2.5 log, 2.5 to 3 log, or 3 to 3.5 log reduction of orthomyxovirus replication compared to the reduction of orthomyxovirus reduction achieved by oseltamivir (Tamiflu®), or may achieve the same reduction as that of oseltamivir (Tamiflu®) therapy in a shorter period of time, for example, in one day, two days, three days, or four days as compared to the reduction achieved after 5 days of oseltamivir (Tamiflu®) therapy.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be administered to a subject infected with an influenza virus that is resistant to one or more different anti-influenza agents (for example, amantadine, rimantadine and/or oseltamivir). In some embodiments, a compound of Formula (I), or a pharmaceutically acceptable salt thereof, can be administered to a subject infected with an influenza virus that is resistant to a M2 protein inhibitor. In some embodiments, development of resistant influenza strains is delayed when subjects are treated with a compound of Formula (I), or a pharmaceutically acceptable salt thereof, compared to the development of influenza strains resistant to other influenza drugs.

In some embodiments, a compound of Formula (I), or a pharmaceutically acceptable salt thereof, can decrease the percentage of subjects that experience complications from an influenza viral infection compared to the percentage of subjects that experience complication being treated with oseltamivir. For example, the percentage of subjects being treated with a compound of Formula (I), or a pharmaceutically acceptable salt thereof, that experience complications can be 10%, 25%, 40%, 50%, 60%, 70%, 80% and 90% less compared to subjects being treated with oseltamivir.

In some embodiments, a compound of Formula (I), or a pharmaceutically acceptable salt thereof, or a pharmaceutical composition that includes a compound described herein, can be used in combination with one or more additional agent(s). In some embodiments, a compound of Formula (I), or a pharmaceutically acceptable salt thereof, can be used in combination with one or more agents currently used in a conventional standard of care for treating influenza. For example, the additional agent can be amantadine (adamantan-1-amine, Symmetrel), rimantadine (Flumadine), zanamivir (Relenza) and oseltamivir (Tamiflu). For the treatment of influenza, additional agents include but are not limited to a neuraminidase inhibitor, a M2 protein inhibitor, a polymerase inhibitor, a PB2 inhibitor, peramivir ((1S,2S,3S,4R)-3-[(1S)-1-acetamido-2-ethylbutyl]-4-(diaminomethylideneamino)-2-hydroxycyclopentane-1-carboxylic acid, BioCryst Pharmaceuticals), laninamivir ((4S,5R,6R)-5-acetamido-4-carbamimidamido-6-[(1R,2R)-3-hydroxy-2-methoxypropyl]-5,6-dihydro-4H-pyran-2-carboxylic acid), favipiravir (T-705, 6-fluoro-3-hydroxy-2-pyrazinecarboxamide), laninamivir octanoate ((3R,4S)-3-acetamido-4-guanidino-2-((1S,2S)-2-hydroxy-1-methoxy-3-(octanoyloxy)propyl)-3,4-dihydro-2H-pyran-6-carboxylic acid) fludase (DAS181, NexBio), ADS-8902 (amantadine HCl/oseltamivir/ribavirin, Adamas Pharmaceuticals), an immuno-modulator (for example, a Type 1 interferon), beraprost (4-[2-hydroxy-1-[(E)-3-hydroxy-4-methyloct-1-en-6-ynyl]-2,3,3a,8b-tetrahydro-1H-cyclopenta[b][1]benzofuran-5-yl]butanoic acid), Neugene®, ribavirin, (R)-3-((5-fluoro-2-(5-fluoro-1H-pyrrolo[2,3-b]pyridin-3-yl) pyrimidin-4-yl)amino)-4,4-dimethylpentanoic acid (CAS Reg. No. 1422050-75-6), (2S,3S)-3-((5-fluoro-2-(5-fluoro-1H-pyrrolo[2,3-b]pyridin-3-yl)pyrimidin-4-yl)amino)bicyclo[2.2.2]octane-2-carboxylic acid (CAS Reg. No. 1259366-34-1, VX-787), (S)-8-benzhydryl-4-hydroxy-6-isopropyl-7, 8-dihydro-3H-pyrazino[1,2-b]pyridazine-3,5(6H)-dione, (S)-8-benzhydryl-6-isopropyl-3,5-dioxo-5,6,7,8-tetrahydro-3H-pyrazino[1,2-b]pyridazin-4-yl isobutyrate FluMist Quadrivalent® (MedImmune), Fluarix® Quadrivalent (GlaxoSmithKline), Fluzone® Quadrivalent (Sanofi Pasteur), Flucelvax® (Novartis) and FluBlok® (Protein Sciences). In some embodiments, a compound of Formula (I), or a pharmaceutically acceptable salt thereof, or a pharmaceutical composition that includes a compound described herein, can be used in combination with oseltamivir.

Type 1 interferons are known to those skilled in the art. A non-limiting list of examples include: alpha-interferons, beta-interferons, delta-interferons, omega-interferons, tau-interferons, x-interferons, consensus interferons and asialo-interferons. Type 1 interferons can be pegylated. Examples of specific type 1 interferons include interferon alpha 1A, interferon alpha 1B, interferon alpha 2A, interferon alpha 2B, pegylated-interferon alpha 2a (PEGASYS, Roche), recombinant interferon alpha 2a (ROFERON, Roche), inhaled interferon alpha 2b (AERX, Aradigm), pegylated-interferon alpha 2b (ALBUFERON, Human Genome Sciences/Novartis, PEGINTRON, Schering), recombinant interferon alpha 2b (INTRON A, Schering), pegylated interferon alpha 2b (PEG-INTRON, Schering, VIRAFERON-PEG, Schering), interferon beta-1a (REBIF, Serono, Inc. and Pfizer), consensus interferon alpha (INFERGEN, Valeant Pharmaceutical).

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) can result in an additive effect. In some embodiments, the combination of a compound of Formula (I), or a pharmaceutically acceptable salt thereof, in combination with one or more additional agent(s) can result in a synergistic effect. In some embodiments, the combination of a compound of Formula (I), or a pharmaceutically acceptable salt thereof, in combination with one or more additional agent(s) can result in a strongly synergistic effect. In some embodiments, the combination of a compound of Formula (I), or a pharmaceutically acceptable salt thereof, in combination with one or more additional agent(s) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more of the additional agent(s) described above, including pharmaceutically acceptable salts and prodrugs thereof, may be a reduction in the required amount(s) of the one or more additional agents, including pharmaceutically acceptable salts and prodrugs thereof, that is effective in treating a disease condition disclosed herein (for example, influenza), as compared to the amount required to achieve the same therapeutic result when one or more of the additional agents, including pharmaceutically acceptable salts and prodrugs thereof, are administered without a compound of Formula (I), or a pharmaceutically acceptable salt thereof. For example, the amount of an additional agent described above, including a pharmaceutically acceptable salt and prodrug thereof, can be less when administered in combination with a compound of Formula (I), or a pharmaceutically acceptable salt thereof, compared to the amount of additional agent, including a pharmaceutically acceptable salt and prodrug thereof, needed to achieve the same viral load reduction when administered as a monotherapy. Another potential advantage of utilizing a compound of Formula (I), or a pharmaceutically acceptable salt thereof, in combination with one or more of the additional agent(s) described above, including pharmaceutically acceptable salts and prodrugs thereof, is that the use of two or more compounds having different mechanisms of action can create a higher barrier to the development of resistant viral strains compared to the barrier when a compound is administered as monotherapy.

Additional advantages of utilizing a compound of Formula (I), or a pharmaceutically acceptable salt thereof, in combination with one or more of the additional agent(s) described above, including pharmaceutically acceptable salts and prodrugs thereof, may include little to no cross resistance between a compound of Formula (I), or a pharmaceutically acceptable salt thereof, and the one or more additional agent(s) described above (including pharmaceutically acceptable salts and prodrugs thereof); different routes for elimination of a compound of Formula (I), or a pharmaceutically acceptable salt thereof, and the one or more additional agent(s) described above (including pharmaceutically acceptable salts and prodrugs thereof); little to no overlapping toxicities between a compound of Formula (I), or a pharmaceutically acceptable salt thereof, and the one or more additional agent(s) described above (including pharmaceutically acceptable salts and prodrugs thereof); little to no significant effects on cytochrome P450; and/or little to no pharmacokinetic interactions between a compound of Formula (I), or a pharmaceutically acceptable salt thereof, and the one or more additional agent(s) described above, including pharmaceutically acceptable salts and prodrugs thereof.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Example 1A

Synthesis of Intermediate A

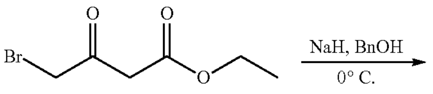

A

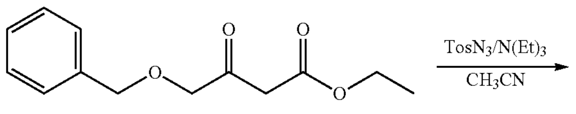

B

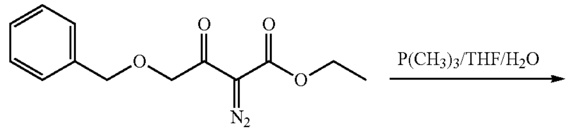

C

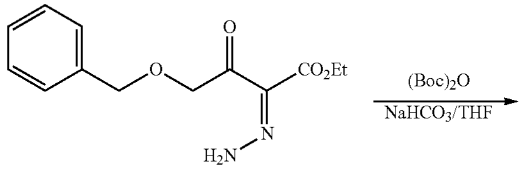

D

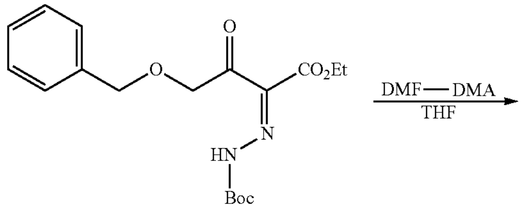

E

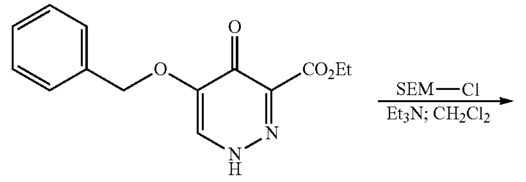

F

-continued

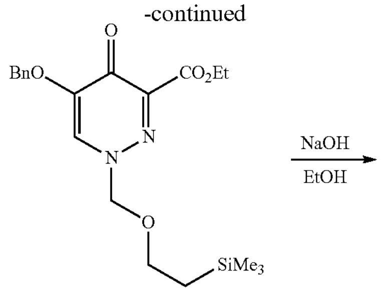

G

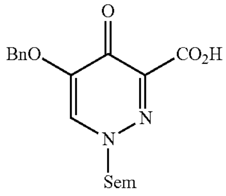
Intermediate A

To a stirred solution of NaH (21.8 g, 912 mmol 3.0 eq.) in THF (300 mL) was added BnOH (32.8 g, 304.0 mmol 1.0 eq.) under a $N_2$ atmosphere at 0° C. After addition, the mixture was stirred for 30 min. Compound A (63.5 g, 304.0 mmol 1.0 eq.) was added portionwise. The mixture was allowed to warm to ambient temperature and stirred for another 12 h. The reaction was monitored by TLC (petroleum ether(PE):EtOAc=5:1). The mixture was poured into 2M HCl solution to a ~pH 6. The solution was exacted with EtOAc (200 mL×3). The combined organic phases were dried over $Na_2SO_4$, filtered and concentrated. The residue was purified by column chromatography on silica gel (PE:EtOAc=30:1 to 5:1) to give compound B as a colorless oil (46 g, 88.5%). $^1H$ NMR ($CDCl_3$) δ 7.39-7.29 (m, 5H), 4.59 (s, 2H), 4.17-4.24 (q, 2H), 4.14 (s, 2H), 3.53 (s, 2H), 1.31-1.22 (t, 3H).

To a stirred solution of compound B (10.0 g, 42.3 mmol 1.0 eq.) in $CH_3CN$ (20 mL) under a $N_2$ atmosphere at 0° C., was added $TosN_3$ (8.35 g, 42.3 mmol 1.0 eq.) and TEA (12.84 g, 127.1 mmol 3.0 eq.). The mixture was stirred at 0° C. for 2 h. The mixture was warmed to room temperature (RT) and stirred for 6 h. The reaction was monitored by TLC (PE:EtOAc=5:1). After complete conversion was observed, the solvent was removed under reduced pressure, and the residue was purified by column chromatography on silica gel (PE:EtOAc=30:1 to 5:1) to give compound C as a colorless oil (4.5 g, 40.5%). $^1H$ NMR ($CDCl_3$) δ 7.39-7.26 (m, 5H), 4.64 (s, 2H), 4.60 (s, 2H), 4.29-4.24 (q, 2H), 1.32-1.28 (t, 3H).

To a solution of compound C (4.04 g, 15.4 mmol 1.0 eq.) in THF (5 mL) was added $P(CH_3)_3$/THF solution (16.9 mL, 16.9 mM, 1.1 eq.) at RT. The mixture was stirred for 15 min (indicated by TLC, PE:EtOAc=2:1) and then quenched with water (2.8 mL). The mixture was stirred for 15 min and concentrated under reduced pressure. The crude residue was purified by column chromatography on silica gel (PE:EtOAc=5:1 to 2:1) to give compound D as a yellow solid (4.0 g, 98.2%). $^1H$ NMR ($CDCl_3$) δ 7.39-7.24 (m, 5H), 4.66-4.66 (s, 1H), 4.66-4.61 (s, 2H), 4.53-4.53 (s, 1H), 4.31-4.24 (m, 2H), 1.35-1.29 (m, 3H).

To a stirred solution of compound D (20.0 g, 75.7 mmol, 1.0 eq.) in THF (100 mL) was added $NaHCO_3$ (19.1 g, 227.3 mmol 3.0 eq.) and $(Boc)_2O$ (22.84 g, 113.6 mmol 1.5 eq.). The mixture was heated to reflux for 6 h and monitored by TLC (PE:EtOAc=2:1). After complete conversion was observed, the solution was concentrated under reduced pressure. The residue was dissolved in EtOAc (200 mL) and washed with water (80 mL×2). The organic layer was separated, dried over $Na_2SO_4$ and filtered. The mixture was concentrated under reduced pressure, and the residue was purified by column chromatography on silica gel (PE:EtOAc=8:1) to give compound E as a white solid (15 g, 54.30%). $^1H$ NMR ($CDCl_3$) δ 11.59 (s, 1H), 7.40-7.26 (m, 5H), 4.71-4.61 (m, 2H), 4.39 (s, 2H), 4.71-4.27 (q, 2H), 1.70-1.48 (m, 9H), 1.38-1.24 (t, 3H).

To a solution of compound E (4.2 g, 11.5 mmol 1 eq.) in THF (100 mL) at RT, was added DMF-DMA (6.15 g, 51.7 mmol, 4.5 eq.). The mixture was stirred at RT for 16 h. After complete conversion was observed as indicated by TLC, the reaction was treated with water (5~6 mL) and stirred for 30 min. The solvent was evaporated under reduced pressure at 40-50° C. The residue was crystallized from EtOAc to give the pure product as a white solid, (0.5 g). The mother liquor was concentrated and purified by column chromatography on silica gel (DCM:MeOH=50:1 to 10:1) to give compound F as a solid (2.4 g, total 75.95%). LCMS (ESI) m/z=275.2 $[M+H]^+$ (calc.=274.1). Retention Time=1.097 min.

To a solution of compound F (2.74 g, 10 mmol) and TEA (3.03 g, 30 mmol) in DCM (40 mL) at 0° C., was added 2-trimethylsilylethyoxymethyl chloride (SEMCl, 2.86 g 0.20 mmol) dropwise. After addition, the mixture was stirred at 0° C. for 1 h. The solution was then slowly warmed to RT and stirred for 2 h. The mixture was quenched, washed with 1 M HCl aqueous solution (30 mL×3), saturated aq. $NaHCO_3$ (20 mL×2) and water. The organic layer was washed with brine, dried over $Na_2SO_4$, and concentrated to give a crude oil (3.8 g), which was then purified by column chromatography on silica gel to give compound G as a colorless oil (3.0 g, 74%).

To a stirred solution of compound G (2.02 g, 5.0 mmol) in MeOH (20 mL) at 0° C., was added aq. NaOH (1 M, 5 mL) dropwise. After addition, the mixture was stirred for 30 min. MeOH was removed under reduced pressure. The resulting aqueous solution was neutralized with 1 M HCl to pH~2.0. A white solid was precipitated, which was then filtered, washed with water and dried in vacuum to get Intermediate A (1.5 g, 83%) with a high purity. $^1H$ NMR (400 MHz, DMSO-d 6): δ 8.88 (s, 1H), 7.49-7.41 (m, 5H), 5.57 (s, 2H), 522 (s, 2H), 3.63 (t, J=8 Hz, 2H), 0.87 (t, J=8 Hz, 2H), 0.02 (S, 9H).

Example 1B

Synthesis of Intermediate B

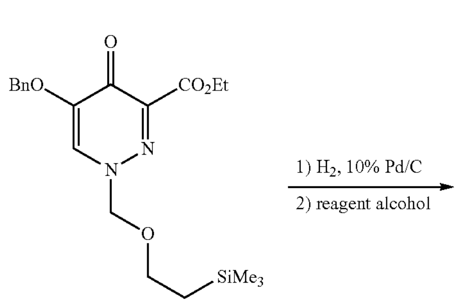

G

-continued

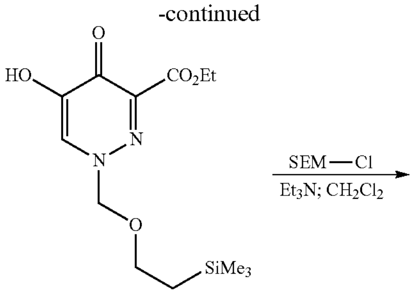

J

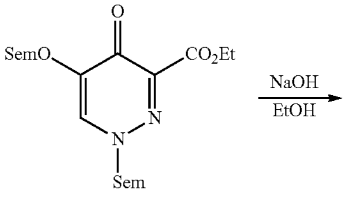

K

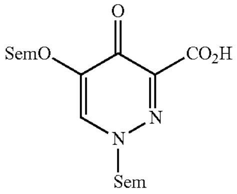
Intermediate B

To a solution of compound G (9.0 g, 22.2 mmol) in reagent alcohol (110 mL) was added 10% Pd on carbon (700 mg; 3 mol %). The reaction flask was vacuum purged with hydrogen, and the suspension was rapidly stirred at RT under a hydrogen atmosphere (balloon pressure) for 2 h (LCMS analysis indicated complete conversion). The mixture was filtered through celite, followed by a rinse using 10% MeOH/$CH_2Cl_2$ (50 mL). The filtrate was concentrated to give compound J as a tan crystalline solid (6.9 g) that was used without further purification.

To a solution of compound J (6.9 g, 22 mmol) and triethylamine (9.2 mL g, 22 mmol) in DCM (80 mL) at 0° C., was added 2-trimethylsilylethyoxymethyl chloride (SEMCl, 5.27 mL, 29.8 mmol), dropwise. After addition, the ice bath was removed and the mixture was stirred at RT overnight. TLC analysis indicated compound J was still present. Additional 2-trimethylsilylethyoxymethyl chloride (SEMCl, 2 mL, 11.2 mmol) was added. TLC analysis after 2 h indicated the reaction was complete. The mixture was quenched with sat. aqueous $NH_4Cl$ (100 mL) and 2 M HCl aqueous solution (20 mL, final pH~7), and the layers were separated. The aqueous layer was extracted with DCM (80 mL) and the combined organic layers were washed with water, followed by brine, and dried over $Na_2SO_4$. The solution was concentrated to give an orange oil that was purified by column chromatography (silica gel; 45-75% EtOAc/hexanes) to give compound K as a colorless oil (7.95 g, 81%) that solidified on standing.

To a stirred solution of compound K (7.95 g, 17.9 mmol) in reagent alcohol (120 mL) at RT was added aq. NaOH (2 M, 54 mL, 108 mmol). The mixture was stirred for 3 h (LCMS indicated complete conversion) and was then concentrated to approx. half volume under reduced pressure (45° C.). The mixture was cooled at 0° C. and acidified with 2 M HCl to pH-2-3 (pH paper). An oily white solid precipitated during the acidification, which was extracted with DCM (150 mL). The layers were separated, and the aqueous layer was extracted with DCM (2×50 mL). The combined organic layers were washed with brine, dried over $Na_2SO_4$, and concentrated to give Intermediate B (6.8 g) as an off-white solid. LCMS: m/z=415 $[M-H]^-$; $^1H$ NMR (400 MHzCDCl$_3$): δ 8.38 (s, 1H), 5.57 (s, 2H), 5.40 (s, 2H), 3.8 (dd, J=8.8, 8.8 Hz, 2H), 3.68 (dd, J=8.4, 8.4 Hz, 2H), 0.965 (dd, J=16.8, 6.8 Hz, 4H), 0.01 (s, 18H).

Example 1

Compound 1

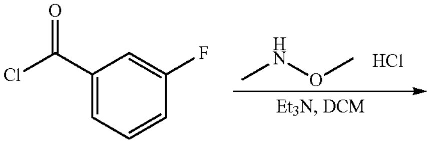

1-1

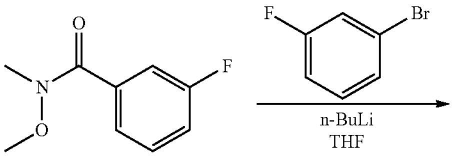

1-2

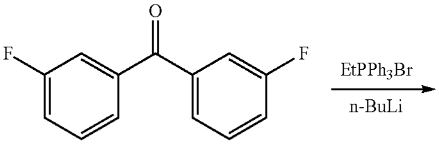

1-3

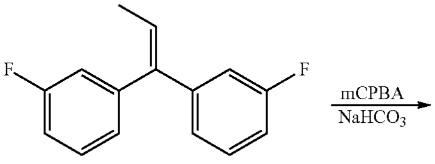

1-4

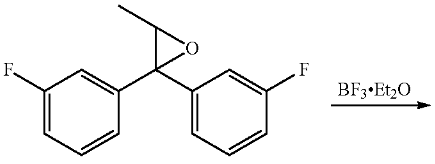

1-5

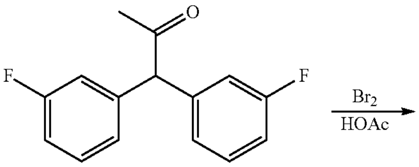

1-6

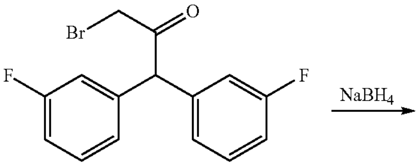

1-7

-continued

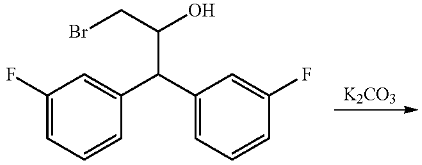

1-8

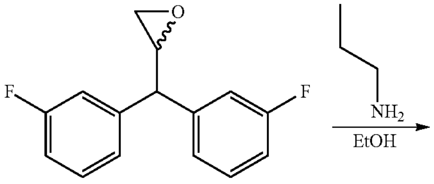

1-9

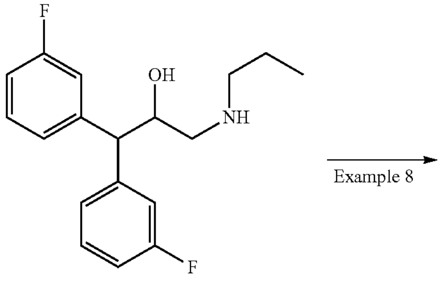

1-10

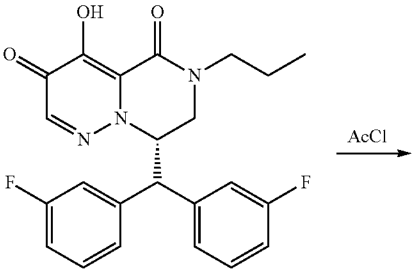

1-11

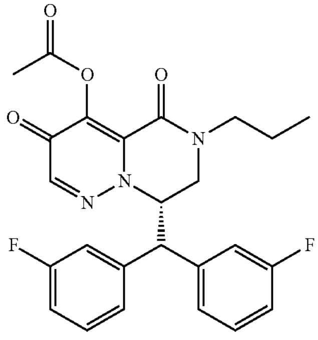

1

To a solution of N,O-dimethylhydroxylamine hydrochloride (138 g, 1.42 mol) in DCM (1.5 L) was added $Et_3N$ (383 g, 3.78 mol) at room temperature (RT). To the stirred mixture, 1-1 (150 g, 946 mmol) was added dropwise at 0° C. under $N_2$ atmosphere. The solution was stirred at the same temperature for 1 h, and then slowly warmed to RT for 10 h. The mixture was added to water (~1 L) and extracted with EtOAc (2×500 mL). The combined organic phases were dried with $Na_2SO_4$, filtered and concentrated. The residue was purified by flash column chromatography (eluent: PE) to give 1-2 as a white solid (150 g, yield: 86.5%). $^1H$ NMR (400 MHz, $CDCl_3$): δ 7.49-7.43 (1H, m), 7.41-7.32 (2H, m), 7.18-7.10 (1H, m), 3.54 (3H, s), 3.34 (3H, s).

To a solution of 1-bromo-3-fluorobenzene (133 g, 764 mmol) in THF (1 L) at −78° C. under $N_2$ atmosphere, was added n-BuLi (305 mL, 764 mmol) dropwise over 1 h. The solution was treated with a solution of 1-2 (100 g, 546 mmol) in THF. After addition, the mixture was slowly warmed to RT and stirred for 16 h. The solution was quenched with water (1 L) and extracted with EtOAc (3×400 mL). The combined organic layers were dried over with $Na_2SO_4$, filtered and concentrated. The residue was purified by silica gel column chromatography (PE:EtOAc=50:1) to provide 1-3 as a white solid (104 g, yield: 87.3%).

To a solution of $EtPPh_3Br$ (442 g, 1.19 mol) in THF (1.0 L) at 0° C. under $N_2$, was added n-BuLi (476 mL, 1.19 mol) dropwise over 1 h. The mixture was slowly warmed and a solution of 1-3 (104 g, 476 mmol) in THF was added dropwise over 1 h. The reaction was quenched with water (1.0 L) and extracted with EtOAc (3×400 mL). The combined organic layers were dried over with $Na_2SO_4$, filtered and concentrated. The residue was purified by silica gel column chromatography (PE:EtOAc=100:1) to afford 1-4 as a colorless oil (90 g, yield: 82%).

To a solution of 1-4 (30 g, 130 mmol) in DCM (2.0 L) was added $NaHCO_3$ (23 g, 273 mmol). The stirred mixture was cooled to 0° C. and treated with m-CPBA (56.2 g, 325 mmol) portionwise. After addition, the mixture was stirred at the same temperature for 3 h. The reaction was quenched with sat. aq. $Na_2S_2O_4$ and extracted with DCM (3×500 mL). The combined organic layers were dried over with $Na_2SO_4$, filtered and concentrated. The residue was purified by silica gel column chromatography (PE:EtOAc=100:1) to provide 1-5 as a yellow oil (13 g, 40.5%). $^1H$ NMR ($CDCl_3$): δ 7.26-7.24 (m, 1H), 7.17-7.15 (m, 1H), 7.08-6.99 (m, 6H), 3.48-3.43 (m, 1H), 1.25-1.17 (m, 3H).

To a solution of 1-5 (20 g, 81.2 mmol) in THF (300 mL) was added $BF_3/Et_2O$ (100 mL) at RT. The mixture was stirred at the same temperature for 2 h. After complete conversion, the reaction was quenched with sat. aq. $NaHCO_3$ and extracted with EtOAc (3×100 mL). The combined organic layers were dried over with $Na_2SO_4$, filtered and concentrated. The residue was purified by silica gel column chromatography (PE:EtOAc=10:1) to afford 1-6 as a yellow oil (15 g, yield: 75%). $^1H$ NMR (CDCl3): δ 7.35-7.29 (m, 2H), 7.02-7.96 (m, 6H), 5.10 (s, 1H), 2.27 (s, 3H).

To a solution of 1-6 (15 g, 60.9 mmol) in AcOH (120 mL) at 60° C., was added $Br_2$ (9.73 g, 60.9 mmol) dropwise under $N_2$ atmosphere. The mixture was stirred at 60° C. for 2 h (indicated by TLC, PE:EtOAc=20:1). The mixture was slowly poured into ice-water (200 mL). The mixture was extracted with EA (3×50 mL). The combined organic layers were washed with $NaHCO_3$, brine, dried over with $Na_2SO_4$ and filtered. The solvent was removed under reduced pressure to give crude 1-7 (25 g), which was used in the next step without further purification.

To a solution of crude 1-7 (50 g) in THF (300 mL) at 0° C. under $N_2$ atmosphere, was added $NaBH_4$ (20 g, 529 mmol) portionwise. The mixture was stirred at RT for 3 h. The reaction was quenched with $H_2O$ (500 mL). The solution was extracted with EtOAc (3×300 mL). The combined organic layers were washed with brine, dried with $NaSO_4$, filtered and concentrated. The residue was purified by flash column chromatography to give 1-8 as a colorless oil (36 g, yield: 71.6%). $^1H$ NMR (CDCl3): δ 7.36-7.29 (m, 2H), 7.19-7.11 (m, 3H), 7.07-6.95 (m, 3H), 4.53-4.48 (m, 1H), 4.19-4.17 (m, 1H), 3.57-3.54 (m, 1H), 3.37-3.33 (m, 1H).

To a solution of 1-8 (36 g, 110.72 mmol) in MeOH (200 mL) was added $K_2CO_3$ (39.54 g, 286.1 mmol) at RT. The mixture was stirred at the same temperature for 1 h (indicated by TLC, PE:EtOAc=10:1). The mixture was filtered, and the filtrate cake was washed with DCM. The combined filtrates were concentrated in vacuum. The residue was purified by flash column chromatography (PE:EtOAc=100:1) to give 1-9 as a colorless oil (19 g, yield: 70.1%). $^1H$ NMR ($CDCl_3$): δ 7.29-7.27 (m, 2H), 7.06-6.92 (m, 6H), 3.84-3.82 (d, J=6.8, 1H), 3.78-3.88 (m, 1H), 2.88-2.85 (t, J=4.4, 1H), 2.51-2.49 (m, 1H).

Compound 1-9 (8.3 g, 33.7 mmol) was added into a solution of n-propylamine in EtOH (100 mL, v/v, 9:1). The mixture was stirred at RT overnight (indicated by TLC, PE:EtOAc=10:1). The mixture was concentrated under reduced pressure to afford amino alcohol 1-10 as an oil (7.7 g, yield: 75%).

Following Example 8, replacing 10-2 with 1-10, and performing the final TFA deprotection step, gives 1-11.

To a solution of 1-11 (175 mg, 0.41 mmol) in EtOAc (2.5 mL) was added triethylamine (0.13 mL, 0.93 mmol) followed by acetyl chloride (0.04 mL, 051 mmol). The mixture was stirred at RT for 2.5 h, and then treated with 0.25 mL of MeOH. The mixture was diluted with 20 mL of EtOAC and washed sequentially with saturated ammonium chloride solution, saturated $NaHCO_3$ solution, and finally brine. The organic layer was dried over $Na_2SO_4$ and concentrated under reduced pressure to give an oil that was purified by $SiO_2$ chromatography (25%-75% EtOAc/hexane). Separation of single enantiomers was accomplished using SFC chromatography (Column: Chiralpak AS-H 150*4.6 mm I.D., Sum Mobile phase: ethanol (0.05% DEA) in $CO_2$ from 5% to 40%). The isolated product was dissolved in a small amount of iPrOAc and hexane was added until just cloudy and let stand at RT overnight. The precipitated solid was filtered and rinsed with hexane to give 1 as a white solid (65%). LSMC (ESI) m/z=468 $[M+H]^+$.

Example 2

Compound 2

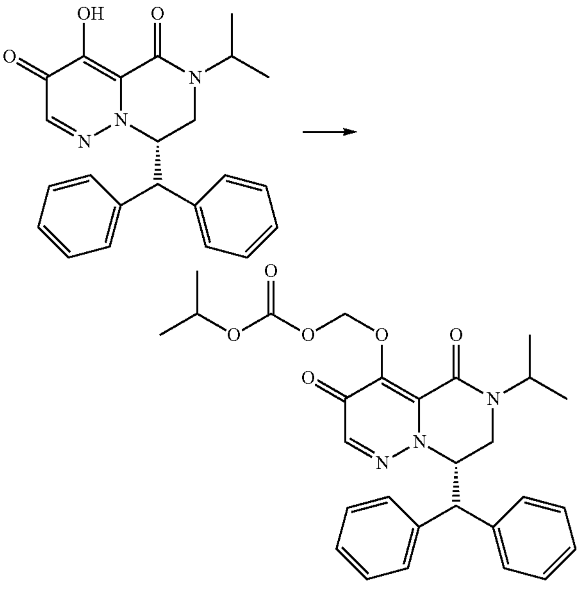

2

A solution of (S)-8-benzhydryl-4-hydroxy-6-isopropyl-7,8-dihydro-3H-pyrazino[1,2-b]pyridazine-3,5(6H)-dione (150 mg, 0.38 mmol) in DMF (1.5 mL) was treated with $K_2CO_3$ (133 mg, 0.96 mmol) and iodomethyl isopropyl carbonate (132 mg, 0.54 mmol). The mixture was stirred at room temperature (RT) overnight. The reaction was diluted with water, quenched with 1M HCl (0.6 mL) and extracted with EtOAc (2×20 mL). The organic layer was washed with sat. $NaHCO_3$ solution and brine, dried over $Na_2SO_4$, and concentrated under reduced pressure. The residue was taken up in EtOAc (2.5 mL) and treated with hexanes while stirring. The solid was filtered gave 2 (100 mg) as a white solid. LCMS (ESI) m/z=506 $[M+H]^+$.

39

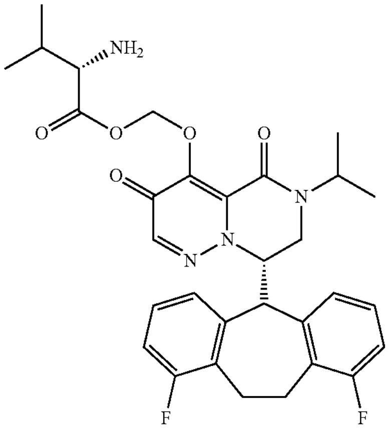

Compound 39 was prepared using methods similar to those described in Example 2, using (S)-iodomethyl 3-(((benzyloxy)carbonyl)amino)-4-methylpentanoate, followed by Pd/C hydrogenolysis in EtOAC/MeOH containing anhydrous HCl. HPLC purification ((0.1% formic acid/ACN) gives 39 as a partial formic acid salt as a white powder. LCMS (ESI) m/z=581 $[M+H]^+$.

40

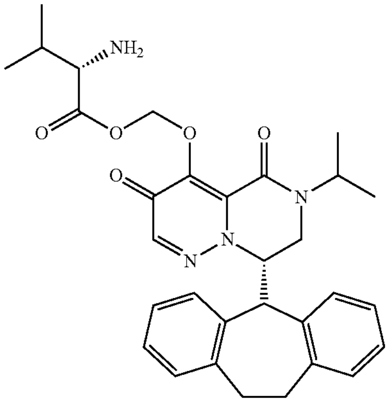

Compound 40 was prepared using methods similar to those described in Example 2, using (S)-iodomethyl 3-(((benzyloxy)carbonyl)amino)-4-methylpentanoate, followed by Pd/C hydrogenolysis in EtOAC/MeOH containing anhydrous HCl. HPLC purification ((0.1% formic acid/ACN) gives 40 as a partial formic acid salt as a white powder. LCMS (ESI) m/z=545 $[M+H]^+$.

41

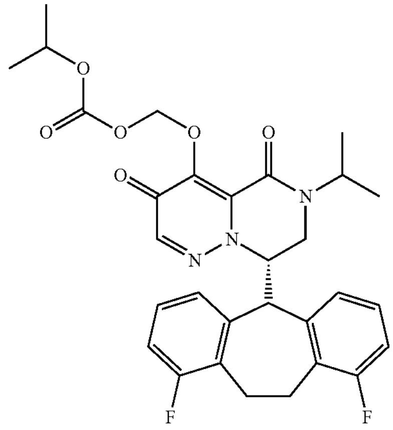

Compound 41 was prepared using methods similar to those described in Example 2. LCMS (ESI) m/z=568 $[M+H]^+$.

Example 3

Compound 3

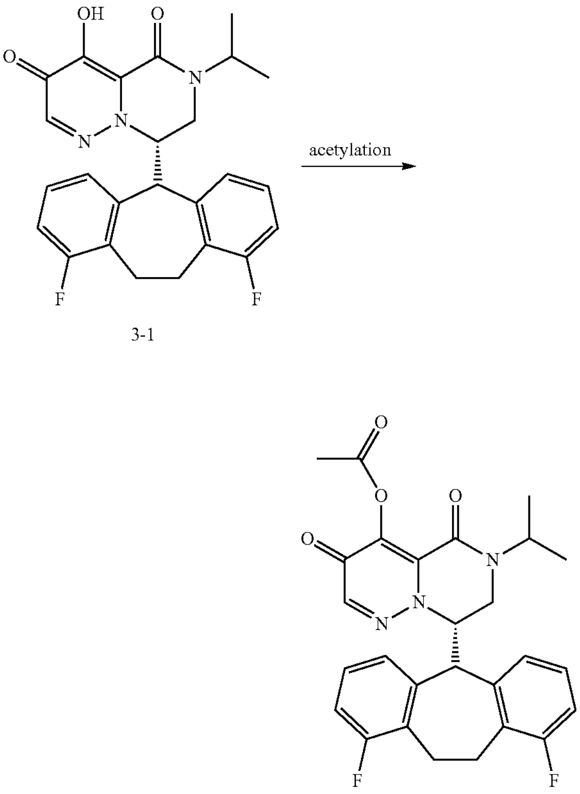

3-1

3

Compound 3 was prepared by acetylating 3-1 using methods similar to those described in Example 1. LCMS (ESI) m/z=494 [M+H]+.

Example 4

Compound 4

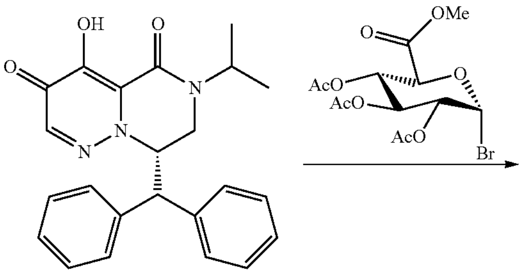

4-1

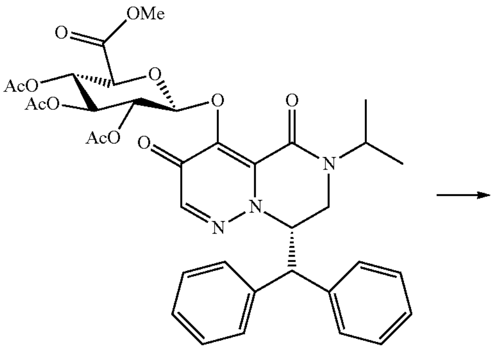

4-2

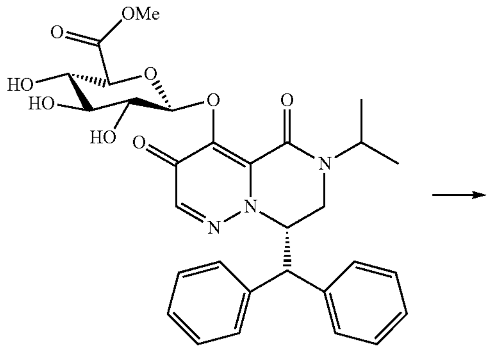

4-3

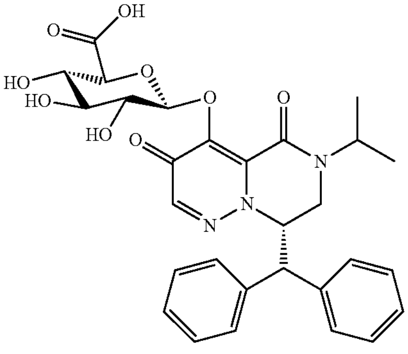

4

A mixture of 4-1 (601 mg, 1.54 mmol) and (2R,3R,4S,5S,6S)-2-bromo-6-(methoxycarbonyl)tetrahydro-2H-pyran-3,4,5-triyl triacetate (918 mg, 2.31 mmol) in toluene (10.3 mL) was treated with silver (II) oxide (AgO, 892 mg, 3.85 mmol) and heated at 110° C. for 3.5 h. The mixture was cooled to RT, diluted with EtOAc (25 mL) and filtered through celite. The filtrate was concentrated under reduced pressure, and the residue was purified using silica gel chromatography (Biotage 50 g HP-Sil; 70% EtOAc/hexanes-100% EtOAc gradient) gave 4-2 (965 mg) as a white solid.

To 4-2 was added MeOH (24 mL, partially soluble) and $K_2CO_3$ (0.48 mmol, 50 mmol in MeOH). The mixture was stirred at RT for 3 h. The reaction was quenched by adding $Et_3N$—HOAc buffer (4.62 mL, 1M in water), followed by water (10 mL). The mixture was filtered through a medium frit funnel gave 4-3 (338 mg) as a white solid. LCMS (ESI) m/z=580 $[M+1]^+$.

Compound 4-3 was combined with 1,4-dioxane (6.4 mL) and water (3.2 mL), and then treated with $K_2CO_3$ (89 mg, 0.64 mmol). The mixture was heated at 50° C. for 40 mins. The mixture was cooled to RT, treated with $Et_3N$—HOAc buffer (4.5 mL, 1M in water) and filtered. The filtrate was concentrated under reduced pressure and mixed with DMSO (4.5 mL). Purification by prep-HPLC (0.1% formic acid/ACN) gave 4 (55 mg; lyophilized powder) as a white solid. LCMS (ESI) m/z=566 $[M+1]^+$.

32

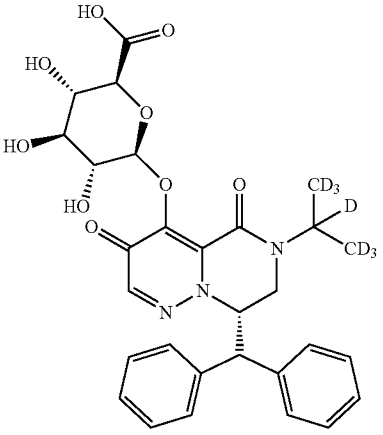

Compound 32 was prepared according to procedures similar to 4 using 17. LCMS (ESI) m/z=573 $[M+1]^+$.

Compound 72 was prepared according to procedures similar to 4 using (S)-8-(1,9-difluoro-10,11-dihydro-5H-dibenzo[a,d][7]annulen-5-yl)-4-hydroxy-6-isopropyl-7,8-dihydro-3H-pyrazino[1,2-b]pyridazine-3,5(6H)-dione. LCMS (ESI) m/z=623 $[M+1]^+$.

Example 5

Compound 5

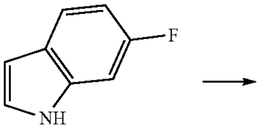

5-1

-continued
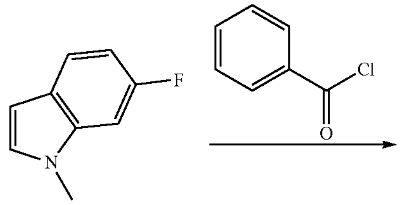
5-2
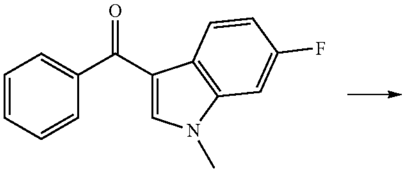
5-3
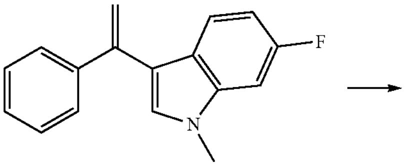
5-4
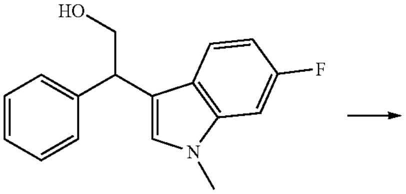
5-5
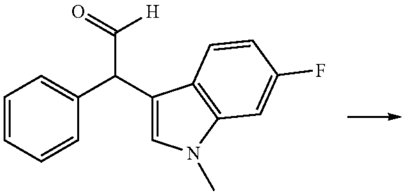
5-6
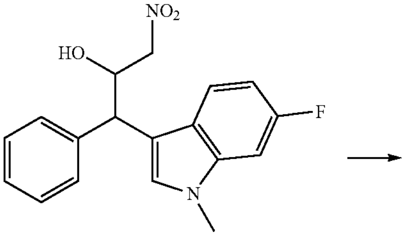
5-7
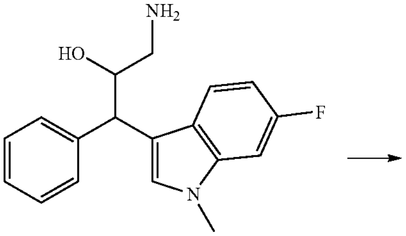
5-8
-continued
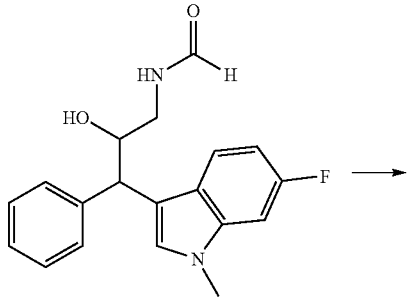
5-9
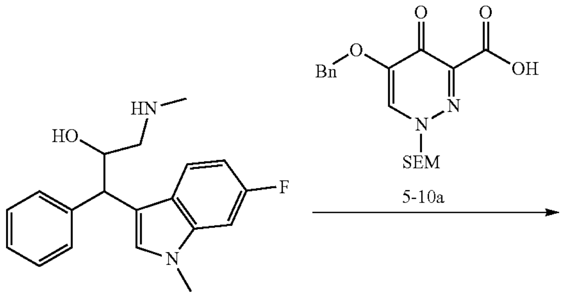
5-10a
5-10
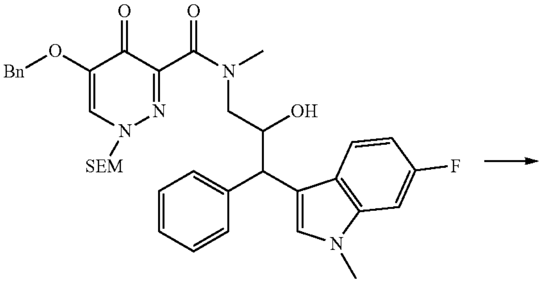
5-11
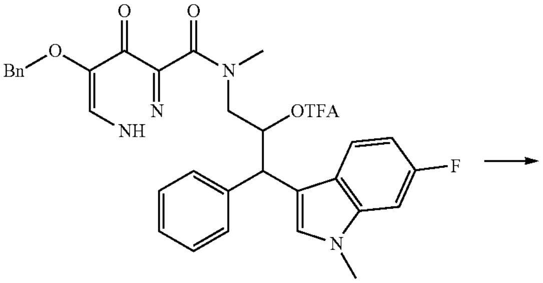
5-12
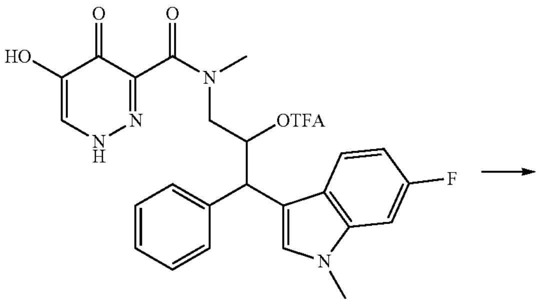
5-13

-continued

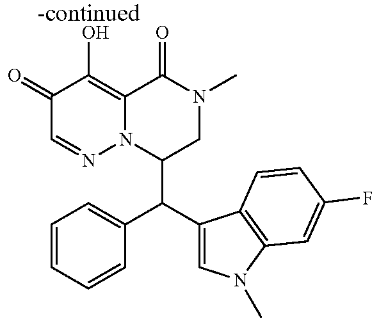

5

To a solution of 5-1 (16.00 g, 118.40 mmol) in THF (50.00 mL) was added NaH (9.47 g, 236.80 mmol) portion-wise at 0° C. The mixture was stirred at 0° C. for 30 mins and then MeI (59.50 g, 419.19 mmol) was added. The mixture was warmed to 25° C. and stirred at 25° C. for 1 hr. TLC (PE:EA=10:1) showed that the starting material was consumed. The reaction was quenched with water (70 mL) and concentrated under reduced pressure. The mixture was extracted with EtOAc (2×200 mL). The combined organic layers were washed with brine (100 mL), dried over anhydrous sodium sulfate and concentrated gave 5-2 (22 g,) as a yellow oil that was used directly in the next step.

To a solution of 5-2 (11.00 g, 73.7 mmol) in DCM (100.00 mL) at 0° C. was added anhydrous $ZnCl_2$ (20.10 g, 147 mmol). The suspension was warmed to 25° C. and stirred at 25° C. for 1 h. To the suspension was added, benzoyl chloride (15.55 g, 110.63 mmol) dropwise over 15 mins. The mixture was stirring for 1 h and then $AlCl_3$ (10.82 g, 81.12 mmol) was added. The mixture was vigorously stirred for 2 h with monitoring by TLC (EA:PE=10:1). The reaction was quenched with ice (50 mL). The aqueous phase was extracted with DCM (3×250 mL). The combined organic phase was washed with sat. brine (2×50 mL). The combined extracts were dried by $Na_2SO_4$, filtered and concentrated under reduced pressure. The residue was purified by silica gel chromatography (PE:EA=10:1, 5:1) gave 5-3 (18.00 g) as a light green solid.

To a solution of methyltriphenylphosphonium bromide (106.00 g, 297.00 mmol) in THF (100.00 mL) was added LiHMDS (1 M, 327.00 mL) dropwise at 0° C. The mixture was stirred at 0° C. for 1 h. Compound 5-3 (15.00 g, 19.74 mmol) in THF (20.00 mL) was added. The mixture was warmed to 25° C. and stirred at 25° C. for 2 h. TLC (PE:EA=10:1) showed that the starting material was consumed. The reaction was quenched with water (70 mL), concentrated under reduced pressure and extracted with EtOAc (3×150 mL). The combined organic layers were washed with brine (50 mL), dried over anhydrous sodium sulfate and concentrated. The crude product was purified by silica chromatography (PE:EtOAc=100-80:1) gave 5-4 (13.40 g) as a white solid.

To a solution of 5-4 (10.00 g, 39.79 mmol) in THF (40.00 mL) was added $BH_3$-$Me_2S$ (10 M, 20.00 mL), dropwise, at 0° C. The mixture was stirred at 0° C. for 2 h and then NaOH (1 M, 50.60 mL) and $H_2O_2$ (26.4 mL, 274.79 mmol) were each added dropwise. The mixture was warmed to 25° C. and stirred for 1 hr. EtOAc (150 mL) was added, and the layers were separated. The aqueous phase was extracted with EtOAc (3×200 mL). The combined organic layers were washed with brine (50 mL), dried over anhydrous sodium sulfate and concentrated gave 5-5 (6.00 g) as a green oil To a solution of 5-5 (1.50 g, 5.57 mmol) in DMSO (20.00 mL) was added IBX (2.34 g, 8.36 mmol). The mixture was stirred at 25° C. for 3 h. TLC (PE:EA=3:1) showed that the starting material was consumed. Water (40 mL) was added, and the aqueous phase was extracted with EtOAc (3×100 mL). The combined organic layer was washed with brine (40 mL), dried over anhydrous sodium sulfate and concentrated. The crude product was purified by silica chromatography (PE:EA=30:1-15:1) gave 5-6 (1.2 g) as a brown oil.

To a solution of 5-6 (1.20 g, 4.49 mmol) in $CH_3NO_2$ (20.00 mL) was added TEA (4.00 mL). The mixture was stirred at 25° C. for 2 h. LCMS showed that the starting material was consumed. The solvent was removed under reduced pressure gave 5-7 as a brown oil that was used directly in the next step.

To a solution of 5-7 (1.56 g, 4.75 mmol) in EtOH (25.00 mL) and $H_2O$ (5.00 mL) were added Fe (1.33 g, 23.75 mmol) and $NH_4Cl$ (1.27 g, 23.75 mmol). the mixture was heated to 80° C. and stirred for 12 h. LCMS showed that the starting material was consumed. The mixture was filtered, and the filtrate was concentrated. The crude product was purified by silica chromatography DCM:MeOH=30:1-5:1) gave 5-8 (620 mg) as a yellow solid.

A solution of 5-8 (620.00 mg, 2.08 mmol) in ethyl formate (30.00 mL) was heated to 80° C. and stirred for 4 h. LCMS showed that the starting material was consumed. The solvent was removed under reduced pressure and gave 5-9 (730 mg) as a brown oil that was used directly in the next step.

To a solution of 5-9 (730.00 mg) in THF (20.00 mL) was added BH3-$Me_2S$ (10 M, 1.20 mL), dropwise, at 0° C. The mixture was stirred at 0° C. for 30 mins and then warmed to 25° C. After stirring for 1 h, the mixture was heated to 80° C. and stirred for 3 h. TLC (DCM:MeOH=10:1) showed that the starting material was consumed. The mixture was cooled to 0° C., and the reaction was quenched with MeOH (5 mL). The solvent was removed under reduced pressure, and water (25 mL) was added. The mixture was extracted with EtOAc (3×100 mL), and the combined organic layer was washed with brine (40 mL), dried over anhydrous sodium sulfate, filtered and concentrated under reduced pressure. The crude product was purified by silica chromatography (DCM: MeOH=100:1-50:1) gave 5-10 (412.00 mg) as a light yellow solid.

To a solution of 5-10a (596.34 mg, 1.58 mmol) in DCM (25.00 mL) were added HATU (1.00 g, 2.64 mmol) and DIEA (682.39 mg, 5.28 mmol). The mixture was stirred at 25° C. for 30 mins. 5-10 (412.00 mg, 1.32 mmol) dissolved in DCM (3.00 mL) was added. The mixture was stirred at 25° C. for 3 h. and then sat. $NaHCO_3$ (30 mL) solution was added. The layers were separated, and the aqueous phase was extracted with DCM (3×150 mL). The combined organic layers were washed with sat. $Na_2CO_3$ solution (50 mL) and brine (30 mL), dried over anhydrous sodium sulfate and concentrated under reduced pressure. The crude product was purified by silica chromatography gave 5-11 (890.00 mg) as a yellow oil.

To a solution of 5-11 (890.00 mg, 298.13 μmol) in DCM (20.00 mL) was added TFAA (5.00 mL). The mixture was stirred at 25° C. for 5 h. The mixture was concentrated under reduced pressure at 30° C. and gave 5-12 (1.00 g) as a brown oil that was used directly in the next step.

To a solution of 5-12 (1.00 g, 1.57 mmol) in toluene (10.00 mL) were added BSA (638.77 mg, 3.14 mmol) and 10% Pd/C (500.00 mg). The mixture was stirred at 20° C. under the atmosphere of $H_2$ (15 Psi) for 2 h. The mixture was filtered, and the cake was washed with DCM (3×50 mL).

The combined organic phases were concentrated under reduced pressure and gave 5-13 (1.60 g) as a yellow oil.

To a solution of 5-13 (1.60 g, 1.26 mmol) in toluene (15.00 mL) was added DIEA (1.48 g, 11.45 mmol). The mixture was stirred at 110° C. for 1 h. The solvent was removed under reduced pressure, and the crude product was purified by prep-HPLC (0.1% formic acid buffer/ACN) and gave 5 (3.20 mg) as a white solid. LCMS (ESI) m/z=433 $[M+1]^+$.

6

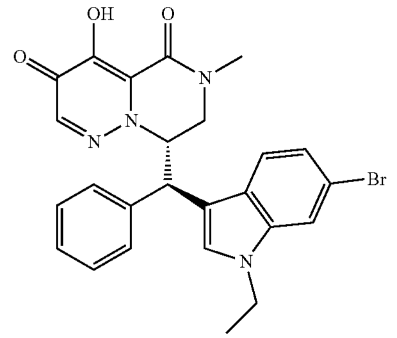

Compound 6 was prepared as a single diastereomer according to similar procedures described for 5 starting with Step 2, using 6-bromo-1-ethyl-1H-indole and isolating the earlier eluting peak following HPLC purification. LCMS (ESI) m/z=507 and 509 $[M+1]^+$. The stereochemistry is relatively assigned.

Example 6

Compounds 7 and 8

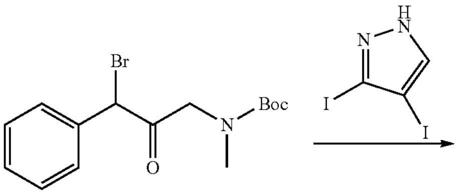

7-1

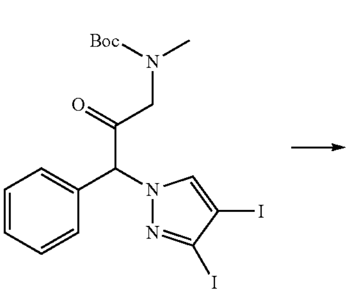

7-2

-continued

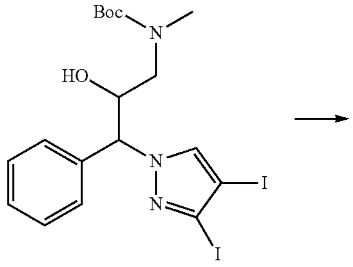

7-3

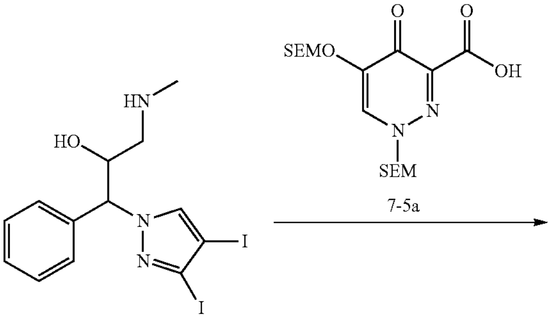

7-5a 7-4

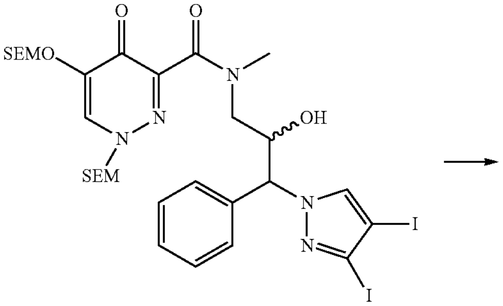

7-5

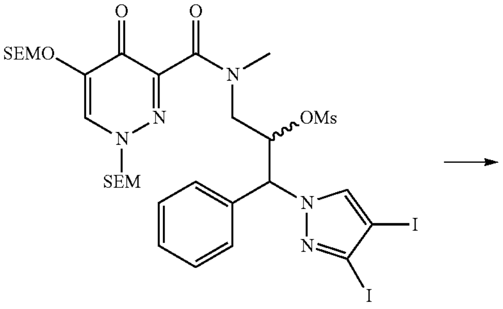

7-6

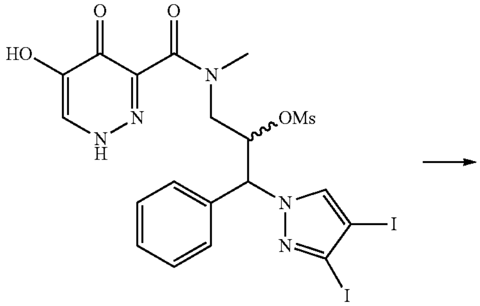

7-7

-continued

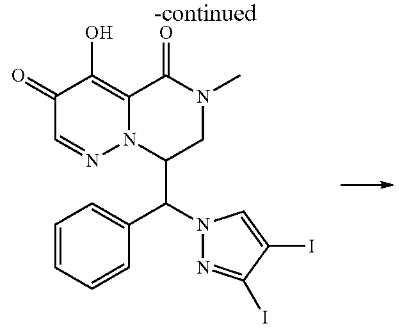

7-8a/7-8b

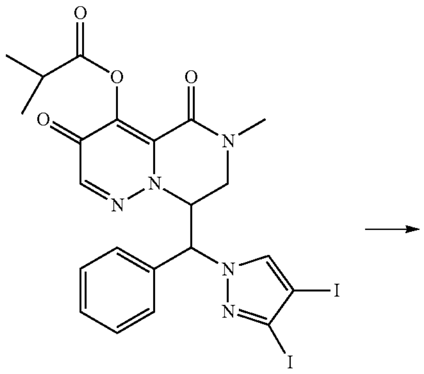

7-9a/7-9b

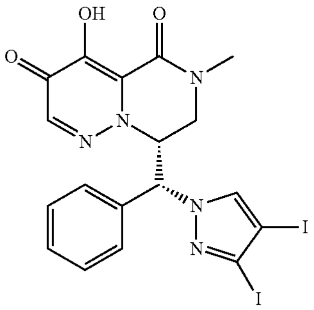

7

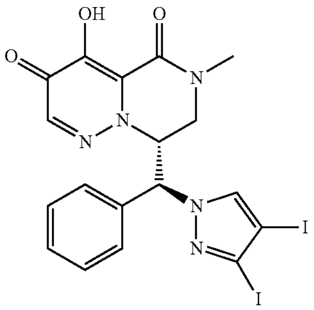

8

To a solution of 3,4-diiodo-1H-pyrazole (8.74 g, 27.32 mmol) in DMF (90 mL) was added $K_2CO_3$ (13.73 g, 99.36 mmol) at 0° C. The mixture was stirred at 0° C. for 0.5 h and then a solution of 7-1 (8.50 g, 24.84 mmol) in DMF (90 mL) was added. The mixture was stirred at 25° C. for 1.5 h. The mixture was filtered, and the solid was washed with EA (2×150 mL). The filtrate was washed with water (3×100 mL) and brine (200 mL), dried over anhydrous $Na_2SO_4$ and filtered. The filtrate was concentrated under reduced pressure to afford 7-2 (12.13 g) as a yellow oil that was used for next step without further purification To a solution of 7-2 (12.13 g, 20.87 mmol) in THF (60 mL) and MeOH (40 mL) was added $NaBH_4$ (3.16 g, 83.49 mmol) at 25° C. The mixture was stirred at 25° C. for 1 h under $N_2$. The reaction was quenched with water (120 mL), and extracted with EA (250 mL). The organic layer was washed with brine (200 mL), dried over anhydrous $Na_2SO_4$ and concentrated under reduced pressure. The residue was purified by column chromatography (PE:EA=30:1, 5:1) to give 7-3 (11.80 g) as a yellow oil.

Compound 7-3 (11.80 g, 20.23 mmol) in DCM:TFA=2:1 (30 mL) was stirred at 25° C. for 1 h. The mixture was concentrated under reduced pressure to afford 7-4 (14.35 g) as a brown oil that was used directly in the next step.

To a solution of 7-5a (7.04 g, 16.90 mmol) in DMF (80 mL) was added HATU (10.71 g, 28.16 mmol) and DIPEA (5.46 g, 42.24 mmol) at 25° C. under $N_2$. The mixture was stirred at 25° C. for 1 h. To the solution was added 7-4 (6.80 g, 14.08 mmol, 1.00 eq.) in DMF (40 mL). The mixture was stirred at 25° C. for 1 h. TLC (DCM:MeOH=20:1) showed the reaction was completed. The reaction was quenched with water (100 mL), extracted with EA (250 mL). The organic layer was washed with sat. brine (200 mL), critic acid (200 mL), sat. $NaHCO_3$ (200 mL) and sat. brine (200 mL), dried with anhydrous $Na_2SO_4$ and filtered. The filtrate was concentrated under reduced pressure. The residue was purified by silica gel chromatography (DCM:MeOH=200:1, 10:1) to afford 7-5 (10.10 g) as a brown oil.

To a solution of 7-5 (3.00 g, 3.40 mmol) and TEA (3.78 g, 37.40 mmol) in DCM (30 mL) was added MsCl (3.89 g, 34.00 mmol) at 0° C. under $N_2$. The mixture was stirred at 25° C. for 2 h. The reaction was quenched with water (25 mL). The aqueous phase was extracted with DCM (2×40 mL). The combined organic phase was washed with sat. brine (40 mL), dried with anhydrous $Na_2SO_4$, filtered and concentrated under reduced pressure. The residue was purified by silica gel chromatography (DCM:MeOH=200:1 to 20:1) to afford 7-6 (3.20 g) as a yellow oil.

A solution of 7-6 (3.20 g, 3.33 mmol) in TFA (30 mL) was stirred at 25° C. for 1 h. The mixture was concentrated under reduced pressure to afford 7-7 (2.98 g), which was used in the next step without further purification.

To a solution of 7-7 (6.05 g, 8.65 mmol) in toluene (60 mL) was added DIPEA (8 mL) under $N_2$ at 110° C. The mixture was stirred at 110° C. for 2 h, and the solvent was removed under reduced pressure. The crude product was purified by prep-HPLC (0.1% formic acid/ACN) and gave 7-8a and 7-8b as two separated diastereomers (805.0 mg, 695.0 mg) as pale brown solids.

To the earlier eluting diastereomer 7-8a (627 mg, 1.04 mmol) and TEA (631.43 mg, 6.24 mmol) in DCM (10.00 mL) was added 2-methylpropanoyl chloride (554.06 mg, 5.20 mmol) at 0° C. under $N_2$. The mixture was stirred at 25° C. for 2 h. TLC (PE:EtOAc=1:1) showed the starting material was consumed. The reaction was quenched with water (15 mL) at 0° C., and the aqueous phase was extracted with DCM (2×5 mL). The combined organic phases were washed with sat. brine (3×15 mL), dried with anhydrous $Na_2SO_4$, filtered and concentrated via vacuum. The isolated residue (7-9a) was purified by SFC (Column: Chiralpak AS-H 150*4.6 mm I.D., Sum Mobile phase: ethanol (0.05% DEA) in $CO_2$ from 5% to 40%) to give two fractions. A solution of the later eluting fraction in ethanol (~300 m L, 0.05% DEA) was warmed for 30 mins, and concentrated under reduced pressure in the a water bath at 50° C. and gave 7 as a single enantiomer (263 mg) as a light brown solid. LCMS (ESI)

m/z=604 [M+1]$^+$. Following a similar procedure using 7-8b, but isolating the earlier eluting enantiomer gave 8. LCMS (ESI) m/z=604 [M+1]$^+$.

Example 7

Compound 9

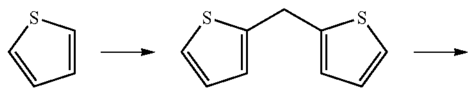

9-1 9-2

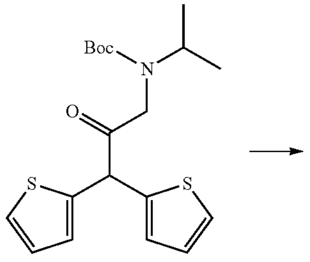

9-3

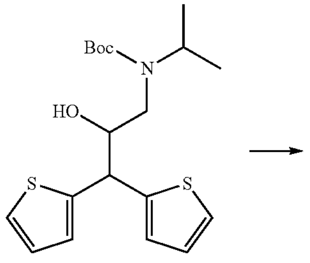

9-4

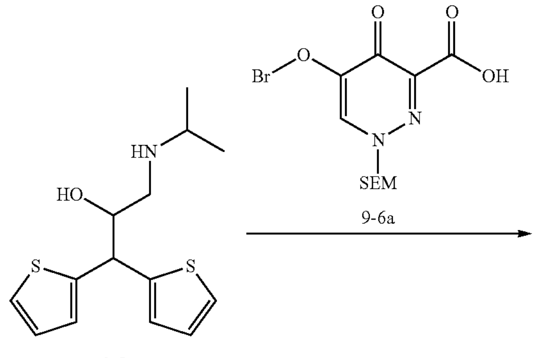

9-6a 9-5

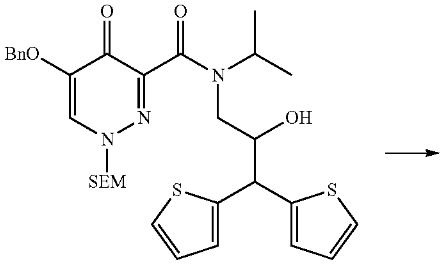

9-6

-continued

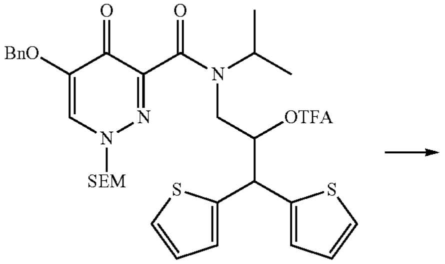

9-7

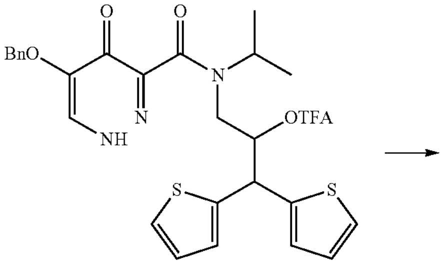

9-8

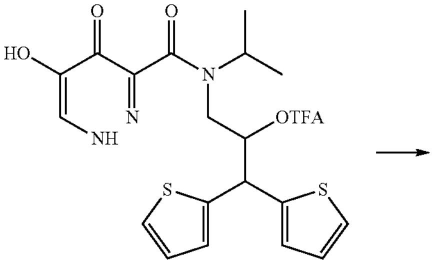

9-9

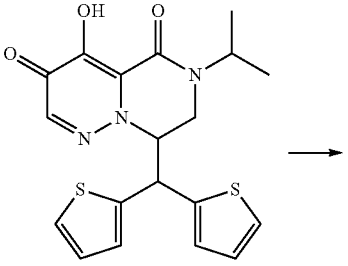

9-10

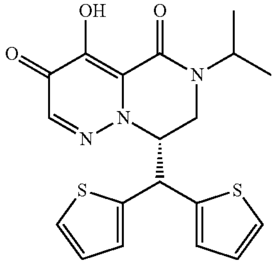

9

To a solution of $NaHSO_4.H_2O$ (4.14 g, 0.03 mol) in water (20 mL) in a 100-mL beaker containing a stir bar was added $SiO_2$ (10 g, 200-300 mesh). The mixture was stirred for 15 mins and then gently heated on a hot plate, with intermittent swirling, until a free-flowing white solid was obtained. The catalyst was further dried by placing the beaker in an oven maintained at 120° C. for at least 48 h prior to use.

A suspension solution of paraformaldehyde (4.82 g, 53.51 mmol), $NaHSO_4$ $SiO_2$ (2.00 g) and 9-1 (22.51 g, 267.55 mmol) was heated at 85° C. for 2 h under an $N_2$ atmosphere. TLC showed the desired product was obtained. The mixture was cooled to RT and evaporated to dryness in vacuo. The residue was purified by silica gel column chromatography (PE:EA=100:1) and afforded 9-2 (1.10 g) as a colorless oil.

A solution of LDA (2 M, 33.40 mL) was added dropwise into a solution of 9-2 (8.03 g, 44.54 mmol) in THF (80.00 mL) at 0° C. The mixture was stirred at 0° C. After 30 mins, methyl 2-((tert-butoxycarbonyl)(isopropyl)amino)acetate (5.15 g, 22.27 mmol) was added at 0° C. The mixture was warmed to RT and stirred for 1.5 h. The reaction was quenched with sat. $NH_4Cl$ solution (60 mL), and extracted with EA (150 mL). The organic layer was washed with brine (60 mL), dried with $Na_2SO_4$ and filtered. The filtrate was concentrated under reduced pressure. The residue was purified by column chromatography (PE:EA=120:1 to 30:1) gave 9-3 (5.19 g) as a yellow solid. +ESI-MS: m/z=404.0 $[M+Na]^+$.

To a solution of 9-3 (5.19 g, 13.67 mmol) in MeOH (25.00 mL) and THF (25.00 mL) was added $NaBH_4$ (2.59 g, 68.35 mmol) at RT. The mixture was stirred at RT for 1 h. LCMS showed the reaction was completed. The reaction was quenched with sat. $NH_4Cl$ solution (100 mL) and extracted with EA (500 mL). The organic layer was washed with brine (100 mL), dried with $Na_2SO_4$ and filtered. The filtrate was concentrated under reduced pressure. The residue was purified by silica gel column chromatography (PE:EA=100:1 to 30:1) gave 9-4 (4.52 g) as a yellow oil. +ESI-MS: m/z=404.0 $[M+Na]^+$.

A solution of 9-4 (4.52 g, 11.85 mmol, 1.00 eq.) in TFA (10.00 mL) and DCM (40.00 mL) was stirred at RT for 1 h. TLC showed the reaction was completed. The solvent was removed under reduced pressure. The residue was dissolved in EA (150 mL) and washed with sat. $NaHCO_3$ solution (50 mL). The organic layer was washed with brine (80 mL), dried with $Na_2SO_4$ and filtered. The filtrate was concentrated under reduced pressure and gave 9-5 (2.5 g) as a yellow solid that was used in the next step without further purification.

A mixture of 9-6a (3.71 g, 9.84 mmol), HATU (6.81 g, 17.90 mmol) and DIEA (4.63 g, 35.80 mmol) in DCM (20.00 mL) was stirred at RT for 30 mins. A solution of 9-5 (2.52 g, 8.95 mmol) in DCM (20.00 mL) was added. The mixture was stirred at RT for 12 h. LCMS showed the reaction was completed. The reaction was quenched with brine (200 mL) and extracted with DCM (400 mL). The organic layer was washed with citric acid (2×200 mL), sat. $NaHCO_3$ solution (2×200 mL) and brine (200 mL), and dried with $Na_2SO_4$. The mixture was filtered, and the filtrate was concentrated under reduced pressure. The residue was purified by column chromatography (DCM:MeOH=200:1 to 20:1) and gave 9-6 (4.65 g) as a yellow wax. +ESI-MS: m/z=640.0 $[M+H]^+$.

A solution of 9-6 (2.00 g, 3.13 mmol) in trifluoroacetic anhydride (20.00 mL) and DCM (20.00 mL) was stirred at RT for 2 h. The solvent was moved under reduced pressure at 30° C. and gave 9-7 (2.50 g) as yellow oil. The isolated product was used in the next step without further purification. +ESI-MS: m/z=736.1 $[M+H]^+$.

A solution of 9-7 (2.50 g, 3.40 mmol) in HCl/dioxane (4 M, 39.97 mL) was heated at 50° C. for 1 h. LCMS showed the reaction was completed. The solvent was moved under reduced pressure and gave 9-8 (2.24 g, crude) as a yellow oil that was used in the next step without further purification. +ESI-MS: m/z=606.0 $[M+H]^+$.

To a solution of 9-8 (825.00 mg, 1.36 mmol) in THF (10.00 mL) was added Pd/C (1.00 g) under $N_2$. The suspension was degassed under vacuum and purged with $H_2$ several times. The mixture was stirred at RT for 12 h. The mixture was filtered through a pad of celite, and the pad was washed with THF (3×20 mL). The filtrate was concentrated under reduced pressure and gave 9-9 as a yellow oil that was used directly in the next step. +ESI-MS: m/z=515.9 $[M+H]^+$.

To the crude 9-9 was added toluene (60.00 mL), followed by DIEA (7.40 g, 57.26 mmol). The mixture was heated at 110° C. for 2 h. The mixture was concentrated under reduced pressure, and the residue was purified by prep-HPLC (0.1% formic acid) and gave 9-10 (56 mg) as a yellow solid. +ESI-MS: m/z=402.0 $[M+H]^+$.

To a solution of 9-10 (56 mg, 0.14 mmol) and TEA (71 mg, 0.7 mmol, 5.00 eq.) in DCM (1.00 mL) was added isobutyryl chloride (74 mg, 0.71 mmol, 5.00 eq.) at 0° C. The mixture was warmed to RT and stirred for 2 h. The reaction was quenched with water (20 mL) and extracted with DCM (60 mL). The organic layer was washed brine (20 mL), dried with $Na_2SO_4$ and filtered. The filtrated was concentrated under reduced pressure. The residue was purified by silica gel chromatography (PE:EA=1:1) and gave a clear oil that was further purified by SFC (Column: Chiralpak IC-3M; 40% methanol (0.05% DEA) in $CO_2$), which gave 9-11 (32 mg, a white solid) as the (R)-enantiomer. To a solution of 9-11 in MeOH (1.00 mL) was added NaOH (2 M, 1.42 mL). The mixture was stirred for 2 h at RT. The solvent was concentrated under reduced pressure, acidified with 2M HCl (20 mL), and extracted with EA (60 mL). The organic layer was concentrated under reduced pressure to give 9 (27%) as a pale yellow solid. LCMS (ESI) m/z=402 $[M+1]^+$.

Example 8

Compound 10

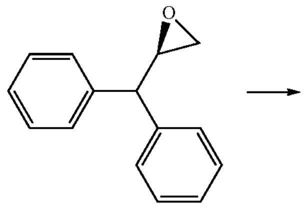

10-1

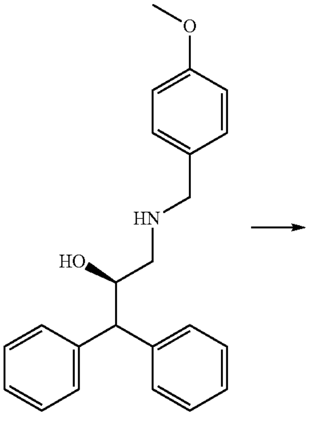

10-2

-continued

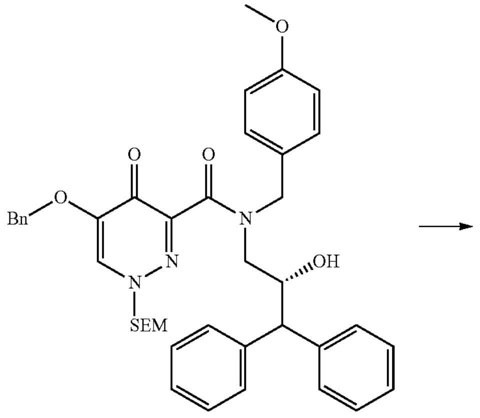

10-3

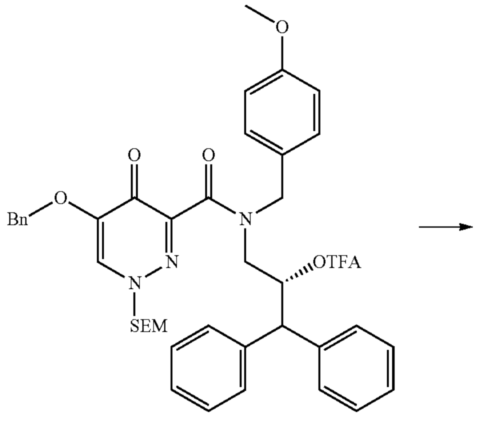

10-4

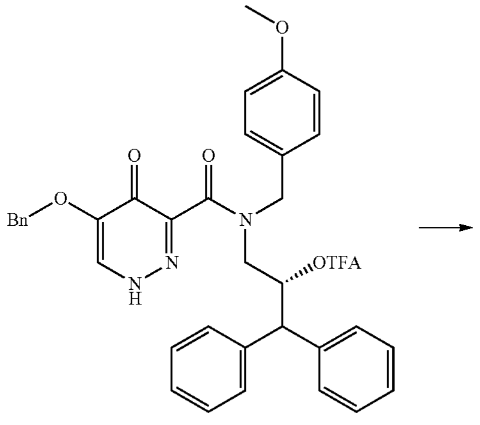

10-5

-continued

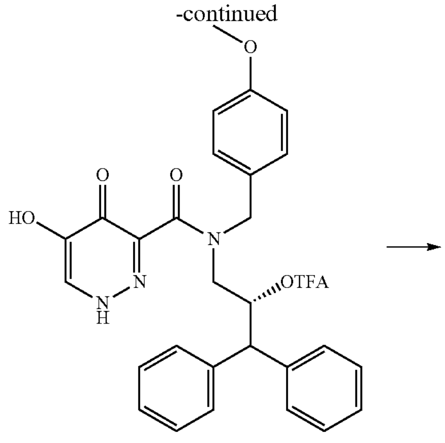

10-6

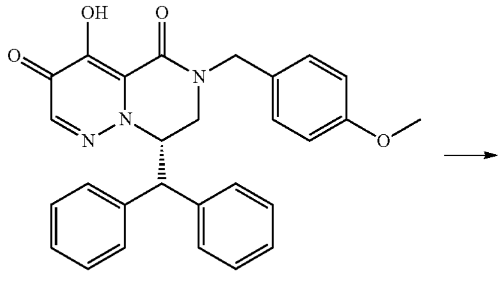

10-7

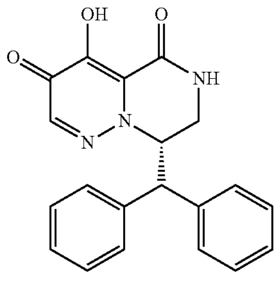

10

To a solution of 10-1 (7.70 g, 36.6 mmol) in EtOH (40.00 mL) was added (4-methoxyphenyl)methanamine (5.02 g, 36.6 mmol). The mixture was stirred at 50° C. for 12 h. TLC (DCM:MeOH=20:1) showed that the starting material was consumed. The solvent was removed under reduced pressure, and the crude material was purification by silica chromatography (DCM:MeOH=30:1-10:1) and gave 10-2 (6.00 g).

To a solution of 5-benzyloxy-4-oxo-1-(2-trimethylsilylethoxymethyl)pyridazine-3-carboxylic acid (9.96 g, 26.46 mmol) in DCM (50.00 mL) were added HATU (12.58 g, 33.08 mmol) and DIEA (11.40 g, 88.20 mmol). The mixture was stirred at 20° C. for 1 h. A solution of 10-2 (7.00 g, 22.05 mmol) in DCM (5.00 mL) was added. The mixture was stirred at 20° C. for 2 h. TLC (DCM:MeOH=10:1) indicated the starting material was consumed. Sat. $NaHCO_3$ solution (100 mL) was added, and the mixture was separated. The aqueous phase was extracted with DCM (3×200 mL). The combined organic layers were washed with 1M HCl solution (50 mL) and brine (50 mL), dried over anhydrous sodium sulfate and concentrated. The crude product was purification by silica chromatography (DCM:MeOH=100:1-50:1) and gave 10-3 (72%) as a brown solid.

To a solution of 10-3 (2.50 g, 3.54 mmol) in DCM (10.00 mL) was added trifluoroacetic anhydride (20.00 mL). The mixture was heated to 40° C. and stirred for 3 h. The solvent was removed under reduced pressure and gave 10-4 as brown oil that was used directly in the next step.

To a solution of 10-4 (3.10 g) in dioxane (10.00 mL) was added HCl/dioxane (4M, 20 mL). The mixture was heated to 40° C. and stirred for 3 h. The solvent was removed under reduced pressure and gave 10-5 as a yellow oil that was used directly in the next step.

To a solution of 10-5 (2.60 g) in toluene (25.00 mL) were added Pd/C (1.00 g) and BSA (1.57 g, 7.74 mmol). The suspension was degassed under vacuum, purged with $H_2$ and stirred under $H_2$ (~15 psi) at 40° C. for 3 h. The mixture was filtered, and the filtrate was concentrated and gave 10-6 as brown oil that was used directly in the next step.

A solution of 10-6 (1.70 g, 2.92 mmol) in toluene (5.00 mL) was added to hot toluene (105° C., 30 mL)). Diisopropylethyl amine (4 mL) was added. The mixture was stirred at 110° C. for 12 h. The solvent was removed under reduced pressure. The crude product was dissolved in EtOAc (20 mL), and then PE (80 mL) was added. The solid was filtered and dried to give 10-7 (76%) as a brown solid.

To a solution of 10-7 (950.00 mg, 1.77 mmol) in TFA (12.00 mL) was added $CF_3SO_3H$ (3.00 mL). The mixture was heated to 60° C. and stirred for 12 h. The solvent was removed under reduced pressure. Water (50 mL) was added, and the mixture was extracted with EtOAc (3×250 mL). The combined organic layers were washed with brine (50 mL) and sat. $Na_2CO_3$ solution (30 mL), dried over anhydrous sodium sulfate and concentrated. The crude material was purification by prep-HPLC (0.1% formic acid/ACN) and gave 10 (36%) as a pale yellow solid. ESI-MS: m/z=348 $[M+H]^+$.

37

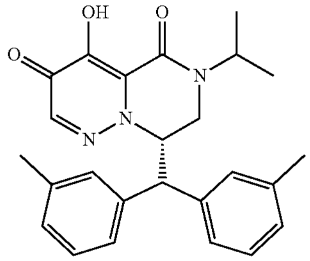

Compound 37 was prepared as generally described in Example 8, without the final TFA deprotection step. ESI-MS: m/z=418 $[M+H]^+$.

38

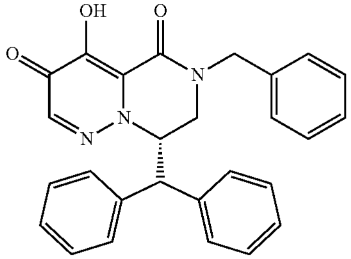

Compound 38 was prepared following Example 8, using benzyl amine, and without the final TFA deprotection step. ESI-MS: m/z=438 $[M+H]^+$.

Example 9

Compound 11

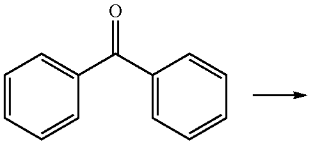

11-1

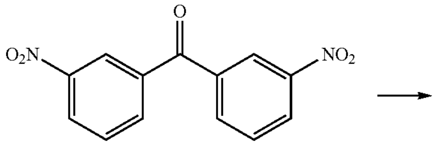

11-2

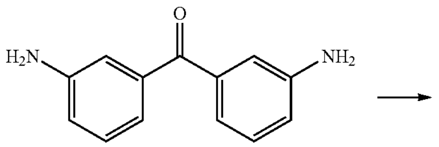

11-3

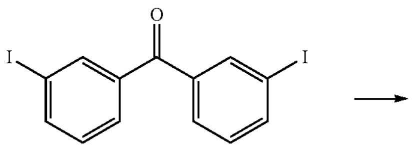

11-4

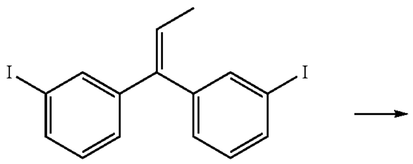

11-5

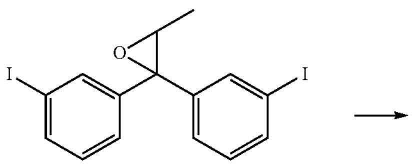

11-6

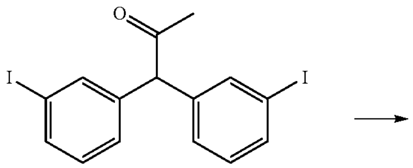

11-7

-continued

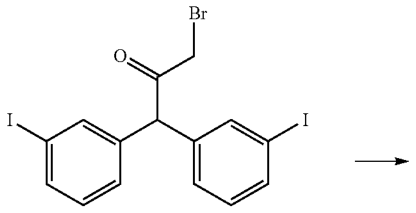

11-8

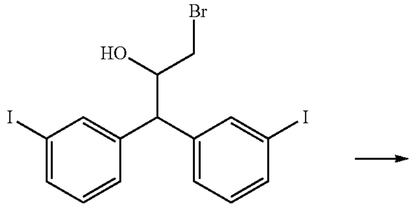

11-9

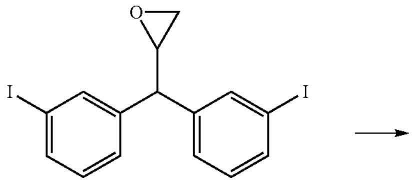

11-10

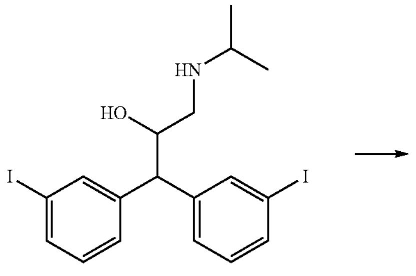

11-11

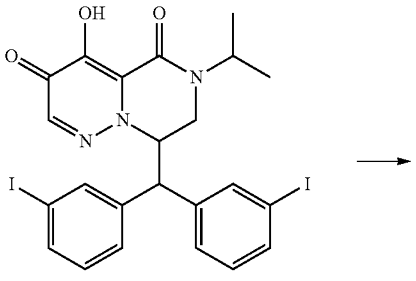

11-12

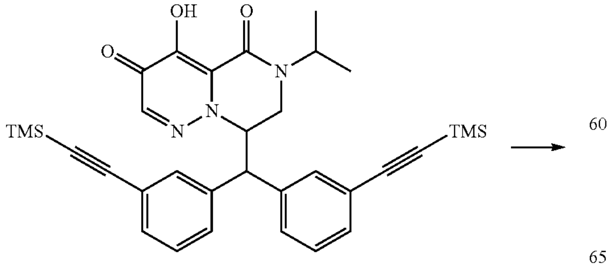

11-13

-continued

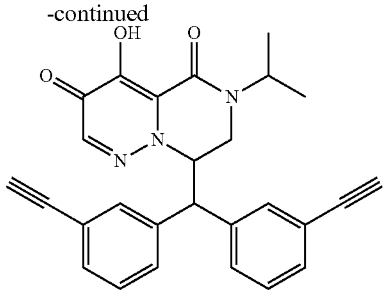

11

To a mixture of 11-1 (10.0 g, 54.9 mmol) in $H_2SO_4$ (50.0 mL) was added $HNO_3$ (5.0 mL) in one portion. The mixture heated to 75° C. and then maintained at 75° C. for 1 h. The mixture was cooled to RT and then poured onto crushed ice. The gummy mass that formed hardened was mechanically broken up and washed with water until the washings were neutral. The filtrate cake was air dried and recrystallized from butanone (73 mL). A solid slowly formed overnight, which was filtered and then washed cool with butanone followed by cold EtOH to give 11-2 (12.10 g, crude) as a yellow solid.

To a mixture of 11-2 (9.1 g, 33.4 mmol) in EtOH (30.0 mL) and $H_2O$ (30.0 mL) was added Fe (7.5 g, 133.7 mmol) and $NH_4Cl$ (8.9 g, 167.2 mmol) in one portion under $N_2$. The mixture was stirred at 80° C. for 4 h and filtered. The filtrate was poured into ice:water (w:w=1:1) (50 mL) and stirred for 2 mins. The aqueous phase was extracted with EA (3×100 mL). The combined organic phase was washed with brine (2×80 mL), dried with anhydrous $Na_2SO_4$, filtered and concentrated under reduced pressure. The residue was purified by silica gel chromatography (100-200 mesh silica gel, PE:EA=1:0-2:1) and gave 11-3 (5.80 g) as a yellow solid.

To a mixture of 11-3 (4.5 g, 21.0 mmol) in conc. HCl (100.0 mL) was added $NaNO_2$ (3.8 g, 54.5 mmol) in portions at 0-5° C. under $N_2$. The mixture was stirred at 0-5° C. for 2 h, and then NaI (18.9 g, 125.8 mmol) was added. The mixture was stirred for 4 h at 25° C. The mixture was diluted with water (75 mL) and extracted with EA (4×60 mL). The combined organic layer was washed with $Na_2SO_3$ solution (3×30 mL) and sat. brine, dried with anhydrous $Na_2SO_4$, filtered and concentrated under reduced pressure. The residue was purified by silica gel chromatography (100-200 mesh silica gel, PE:EA=1:0-5:1) and gave 11-4 (4.5 g) as an off-white solid.

To a mixture of ethyltriphenylphosphonium bromide (5.1 g, 13.8 mmol) in THF (10.0 mL) was added t-BuOK (1.6 g, 13.8 mmol) portionwise at 0° C. under $N_2$. The mixture was stirred at 0° C. for 30 mins, and then 11-4 (3.0 g, 6.9 mmol) was added. The mixture was stirred at 20° C. for 2.5 h. The reaction was quenched with ice:water (w:w=1:1, 20 mL) and stirred for 2 mins. The aqueous phase was extracted with EA (3×80 mL). The combined organic phase was washed with brine, dried with anhydrous $Na_2SO_4$, filtered and concentrated under reduced pressure. The residue was purified by silica gel chromatography (100-200 mesh silica gel, PE:EA=1:0-20:1) and gave 11-5 (2.5 g) as a colorless oil.

To a mixture of 11-5 (5.0 g, 11.2 mmol) in DCM (20.0 mL) was added m-CPBA (4.8 g, 28.0 mmol) and $NaHCO_3$ (1.9 g, 22.4 mmol) in one portion at 0° C. under $N_2$. The mixture was stirred at 0° C. for 30 mins, then heated to 80° C. and stirred for 4.5 h. The mixture was poured into water (30 mL) and stirred for 2 mins. The aqueous phase was extracted with EA (2×100 mL). The combined organic phase was washed with brine, dried over anhydrous $Na_2SO_4$, filtered and concentrated under reduced pressure. The residue was purified by silica gel chromatography (100-200 mesh silica gel, PE:EA=1:0-20:1) and gave 11-6 (1.7 g) as a colorless oil.

To a mixture of 11-6 (1.7 g, 3.7 mmol) in DCM (20.0 mL) was added $BF_3.Et_2O$ (5.2 g, 36.8 mmol) in one portion at 0° C. under $N_2$. The mixture was stirred at 0° C. for 30 mins, then heated to 20° C. and stirred for 0.5 h. The reaction was quenched with water (30 mL), and the aqueous phase was extracted with EA (3×60 mL). The combined organic phase was washed with brine, dried with anhydrous $Na_2SO_4$, filtered and concentrated under reduced pressure. The residue was purified by silica gel chromatography (100-200 mesh silica gel, PE:EA=1:0-8:1) and gave 11-7 (500 mg) as a colorless oil.

To a solution of 11-7 (0.5 g, 1.1 mmol) in DCM (10.0 mL) was added $Et_3N$ (0.55 g, 5.5 mmol) in one portion at 0° C. under $N_2$. The mixture was stirred at 0° C. for 30 mins, then TMSOTf (0.98 g, 4.4 mmol) was added dropwise at 0° C. The mixture was stirred at 0° C. for 30 mins, warmed to 20° C. and stirred for 1 h. The reaction was quenched with water (10 mL) and extracted with EA (3×20 mL). The combined organic phase was washed with brine, dried over anhydrous $Na_2SO_4$, filtered and concentrated in vacuum to give a residue. The residue was dissolved in $H_2O$ (10.0 mL) and THF (10.0 mL). NBS (0.19 g, 1.1 mmol) was added at 0° C. and stirred for 1 h. The mixture was washed with water (10 mL) and extracted with EA (3×20 mL). The combined organic phase was washed with sat. brine (2×20 mL), dried with anhydrous $Na_2SO_4$, filtered and concentrated under reduced pressure. The residue was purified by silica gel chromatography (PE:EtOAc=1:0-10:1) and gave 11-8 (0.31 g) as a yellow oil.

To a mixture of 11-8 (0.31 g, 0.57 mmol) in THF (10.0 mL) was added $NaBH_4$ (216.6 mg, 5.7 mmol) in one portion at 20° C. under $N_2$. The mixture was stirred at 20° C. for 0.5 h. $H_2O$ (2.0 mL) was added and stirred for 0.5 h. The reaction was quenched with water (10 mL), and the aqueous phase was extracted with EA (3×20 m). The combined organic phase was washed with brine, dried over anhydrous $Na_2SO_4$, filtered and concentrated under reduced pressure. The residue was purified by silica gel chromatography (100-200 mesh silica gel, PE:EA=1:0-5:1) and gave 11-9 (0.24 g) as a yellow oil.

To a mixture of 11-9 (0.46 g, 0.85 mmol) in MeOH (10.0 mL) was added $K_2CO_3$ (0.59 g, 4.25 mmol) in one portion at 20° C. under $N_2$. The mixture was stirred at 20° C. for 12 h, filtered and concentrated under reduced pressure. The residue was purified by silica gel chromatography (100-200 mesh silica gel, PE:EA=1:0-10:1) and gave 11-10 (0.38 g) as a yellow oil.

To a mixture of 11-10 (2.3 g, 5.0 mmol) in EtOH (20.0 mL) was added $i\text{-}Pr_2NH$ (5.0 g, 49.8 mmol) in one portion at under $N_2$. The mixture was stirred at 60° C. for 1 h and then concentrated under reduced pressure. The residue was purified by silica gel chromatography (100-200 mesh silica gel, PE:EA=10:1-1:1) and gave 11-11 (2.0 g) as a yellow oil.

Using a method similar for preparing 9, 11-11 was converted to 11-12. To a mixture of 11-12 (500 mg, 780 μmol) and ethynyl(trimethyl)silane (460 mg, 4.7 mmol) in THF (12.0 mL) was added $Pd(dppf)Cl_2$ (29 mg, 39 mol), $Et_3N$ (789 mg, 7.8 mmol) and CuI (8 mg, 39 μmol) in single portions under $N_2$. The mixture was stirred at 60° C. for 1 h and then concentrated under reduced pressure to give 11-13 (460 mg), which was used in the next step without further purification.

To a mixture of 11-13 (460 mg, 791 μmol) in MeOH (15.0 mL) was added $NH_4F$ (586 mg, 15.8 mmol) in one portion under $N_2$. The mixture was stirred at 60° C. for 1 h. The mixture was concentrated in vacuum to give a residue. The residue was purified by prep-HPLC (0.1% formic acid/ACN) followed by lyophilization give 11 (15 mg) as a beige solid. LCMS (ESI) m/z=438 $[M+1]^+$.

12

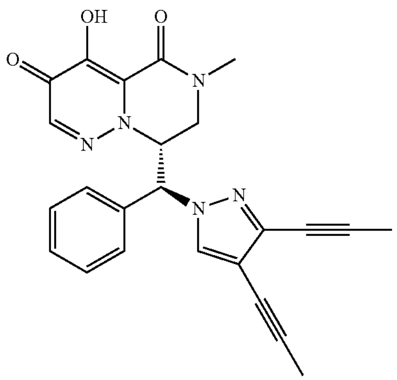

Compound 12 was prepared following a procedure similar to preparing 11-13 using 8-((3,4-diiodo-1H-pyrazol-1-yl)(phenyl)methyl)-4-hydroxy-6-methyl-7,8-dihydro-3H-pyrazino[1,2-b]pyridazine-3,5(6H)-dione, trimethyl(prop-1-yn-1-yl)silane, and $Pd(PPh_3)_2Cl_2$, and heating for 12 h. Compound 12 was obtained as single diastereomer after prep-HPLC purification (0.1% formic acid/ACN; first eluting peak isolated). LCMS (ESI) m/z=428 $[M+1]^+$. The stereochemistry is relatively assigned.

13

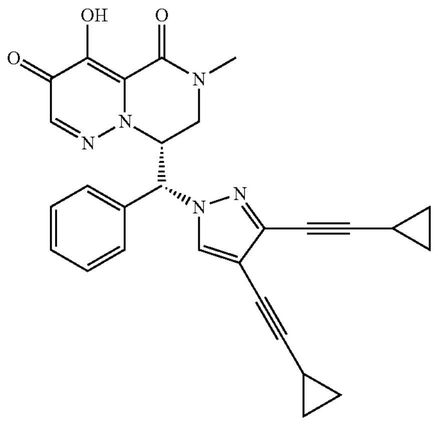

Compound 13 was prepared following a procedure similar to preparing 11-13 using a single stereoisomer of 8-((3,4-diiodo-1H-pyrazol-1-yl)(phenyl)methyl)-4-hydroxy-6-methyl-7,8-dihydro-3H-pyrazino[1,2-b]pyridazine-3,5(6H)-dione, (cyclopropylethynyl)trimethylsilane and $Pd(PPh_3)_2Cl_2$, and heating for 12 h. Compound 13 was obtained after prep-HPLC purification (0.1% formic acid/ACN). LCMS (ESI) m/z=480 $[M+1]^+$.

14

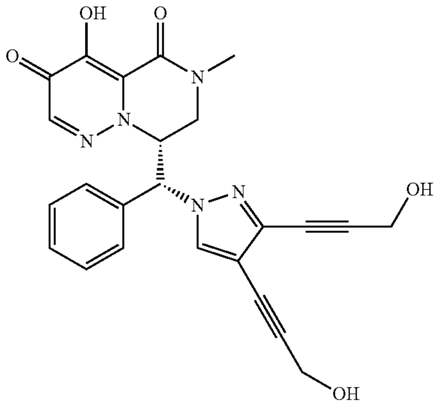

Compound 14 was prepared following a procedure similar to preparing 11-13 using a single stereoisomer of 8-((3,4-diiodo-1H-pyrazol-1-yl)(phenyl)methyl)-4-hydroxy-6-methyl-7,8-dihydro-3H-pyrazino[1,2-b]pyridazine-3,5(6H)-dione, prop-2-yn-1-ol and $Pd(PPh_3)_2Cl_2$, and heating for 12 h. Compound 14 was obtained after prep-HPLC purification (0.1% formic acid/ACN). LCMS (ESI) m/z=460 $[M+1]^+$.

15

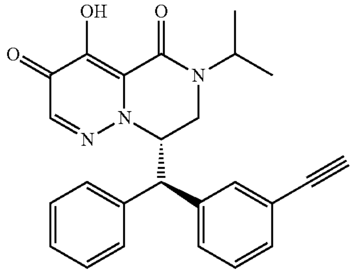

Compound 15 was prepared following a procedure similar to preparing 11-13 and 11 using 4-hydroxy-8-((3-iodophenyl)(phenyl)methyl)-6-isopropyl-7,8-dihydro-3H-pyrazino[1,2-b]pyridazine-3,5(6H)-dione, followed by SFC separation of enantiomers and isolating the last eluting peak LCMS (ESI) m/z=414 $[M+1]^+$.

16

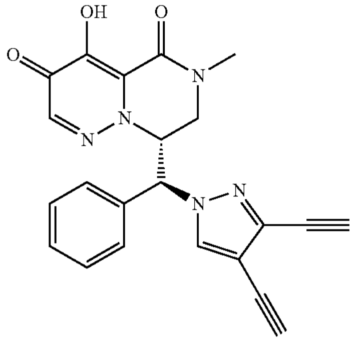

Compound 16 was prepared as a single diastereomer following a procedure similar to preparing 11-13 and 11 using 8-((3,4-diiodo-1H-pyrazol-1-yl)(phenyl)methyl)-4-hydroxy-6-methyl-7,8-dihydro-3H-pyrazino[1,2-b]pyridazine-3,5(6H)-dione, followed by HPLC purification and isolating the first eluting peak. LCMS (ESI) m/z=400 $[M+1]^+$. The stereochemistry is relatively assigned.

33

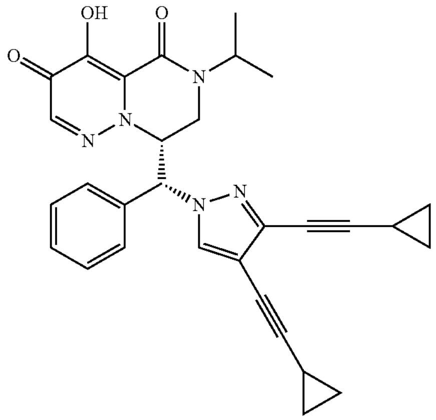

Compound 33 was prepared according procedures similar to preparing 13. LCMS (ESI) m/z=508 $[M+1]^+$.

34

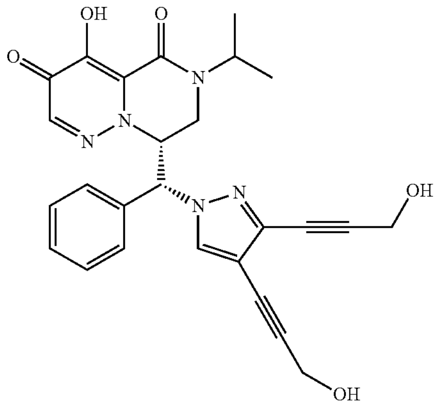

Compound 34 was prepared according procedures similar to preparing 14. LCMS (ESI) m/z=488 $[M+1]^+$.

35

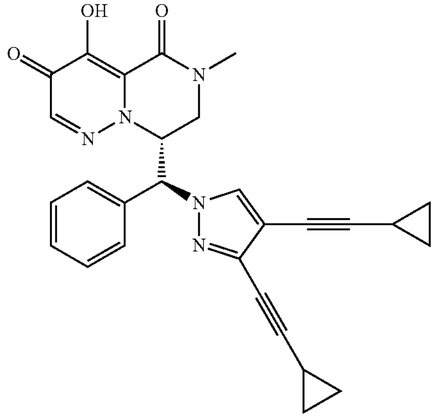

Compound 35 was prepared following a procedure similar to preparing 11-8-((3,4-diiodo-1H-pyrazol-1-yl)(phenyl) methyl)-4-hydroxy-6-methyl-7,8-dihydro-3H-pyrazino[1,2-b]pyridazine-3,5(6H)-dione, (cyclopropylethynyl)trimethylsilane and $Pd(PPh_3)_2Cl_2$, and heating for 12 h. Compound 35 was obtained as a single diastereomer after prep-HPLC purification (0.1% formic acid/ACN; first eluting peak). LCMS (ESI) m/z=480 $[M+1]^+$. The stereochemistry is relatively assigned.

36

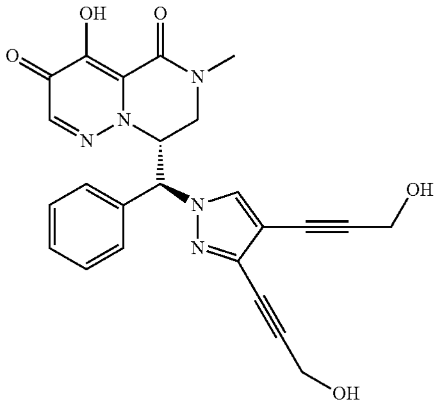

Compound 36 was prepared following a procedure similar to preparing 11-13 using 8-((3,4-diiodo-1H-pyrazol-1-yl)(phenyl)methyl)-4-hydroxy-6-methyl-7,8-dihydro-3H-pyrazino[1,2-b]pyridazine-3,5(6H)-dione, prop-2-yn-1-ol and $Pd(PPh_3)_2Cl_2$, and heating for 12 h. Compound 36 was obtained as a single diastereomer after prep-HPLC purification (0.1% formic acid/ACN; first eluting peak). LCMS (ESI) m/z=460 $[M+1]^+$. The stereochemistry is relatively assigned.

Example 10

Compound 17

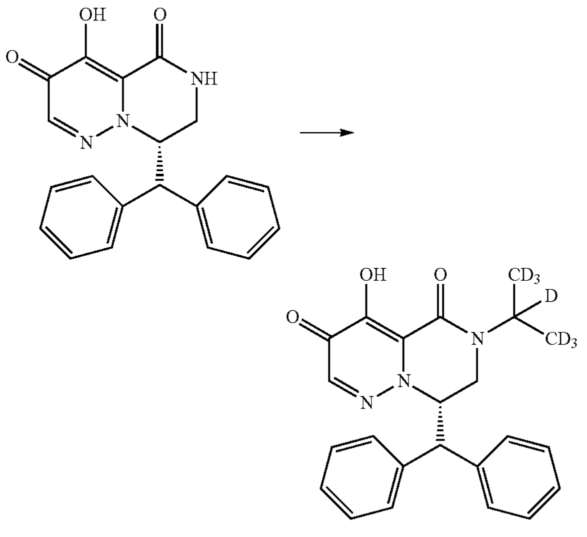

17

An ice cold solution of (S)-8-benzhydryl-4-hydroxy-7,8-dihydro-3H-pyrazino[1,2-b]pyridazine-3,5(6H)-dione (25 mg, 0.075 mmol) in DMF (1 mL) was treated with NaH (29 mg, 0.72 mmol, 60 wt % in mineral oil). The mixture was stirred at 0° C. for 1 h and then 2-iodopropane-($D_7$) (72 μL, 0.72 mmol) was added. The mixture was stirred and allowed to slowly warm to RT overnight. The resulting pale yellow mixture was cooled in ice water, quenched with 1M HCl (3 mL), diluted with water (25 mL) and extracted with EtOAc (2×15 mL). The organic layer was washed with brine, dried over $Na_2SO_4$, and concentrated under reduced pressure. The residue was taken up in toluene (10 mL) and concentrated to dryness (3×), and then isopropanol (0.75 mL) was added. The solution was stirred in ice water for 1 h. The solid precipitates were filtered and give 17 (20 mg) as a beige solid. LCMS (ESI) m/z=397 $[M+1]^+$.

18

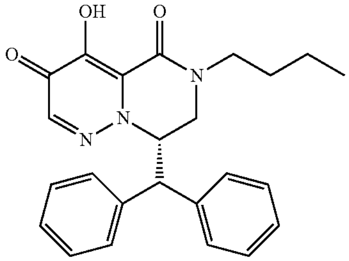

Compound 18 was prepared following a procedure similar to preparing 17 using 1-bromobutane and prep-HPLC (0.1% formic acid buffer). LCMS (ESI) m/z=404 $[M+1]^+$.

Example 11

Compounds 19 and 20

19

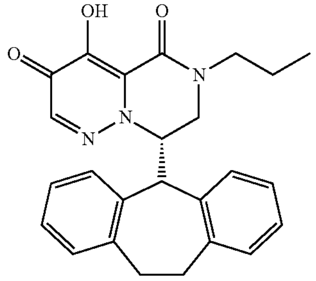

20

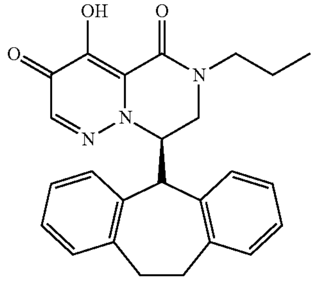

Compounds 19 and 20 were prepared according to similar procedure as described in Example 1, using (S—)- or (R—)-2-(10,11-dihydro-5H-dibenzo[a,d][7]annulen-5-yl) oxirane. 19: LCMS (ESI) m/z=416 $[M+1]^+$ and 20: LCMS (ESI) m/z=416 $[M+1]^+$.

Example 12

Compounds 21 and 22

21

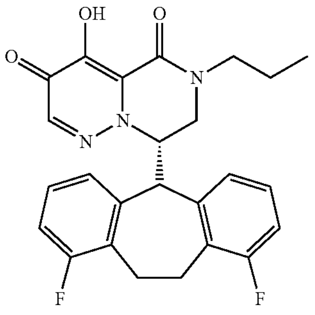

22

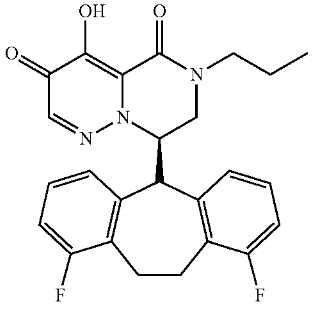

Compounds 21 and 22 were prepared according to similar procedure as in Example 1, using (S—)- or (R—)-(2-(1,9-difluoro-10,11-dihydro-5H-dibenzo[a,d][7]annulen-5-yl) oxirane. 21: LCMS (ESI) m/z=452 $[M+1]^+$ and 22: LCMS (ESI) m/z=452 $[M+1]^+$.

Example 13

Compound 23

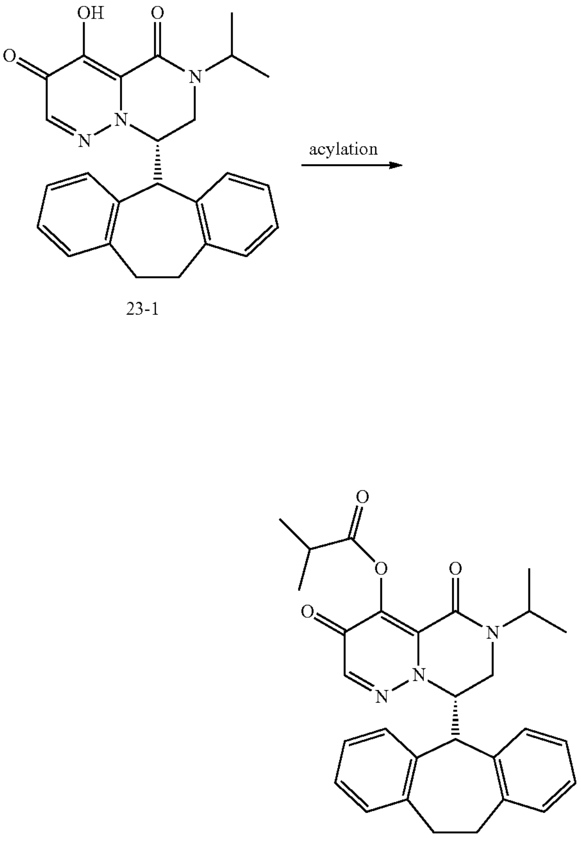

23-1

23

Compound 23 was prepared by acylating 23-1 using methods similar to those described in Example 1. LCMS (ESI) m/z=486 $[M+H]^+$.

The following compounds were also prepared using methods similar to those described in Example 1 via acylating.

| Starting Material | Compound | Mass Spec. |
|---|---|---|
| 23-1 | 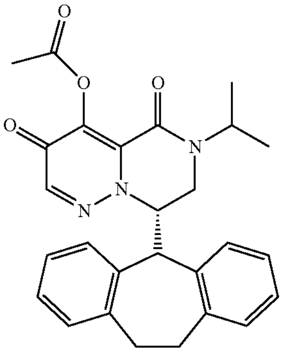 24 | M + H: 458 |

-continued
| Starting Material | Compound | Mass Spec. |
| --- | --- | --- |
| 19 | 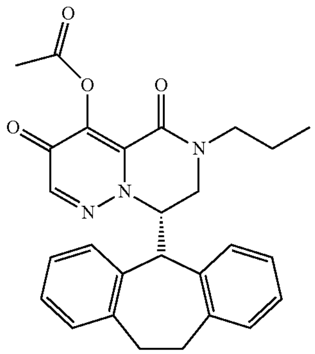 25 | M + H: 458 |
| 19 | 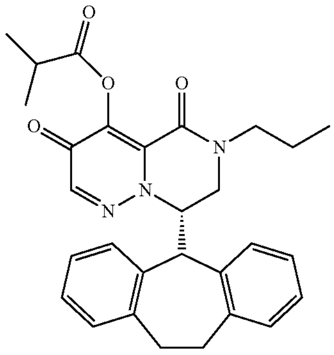 26 | M + H: 486 |
| 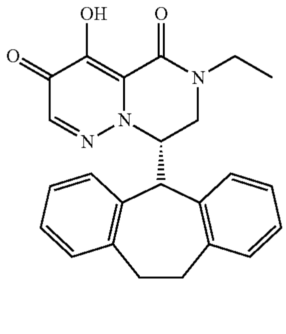 | 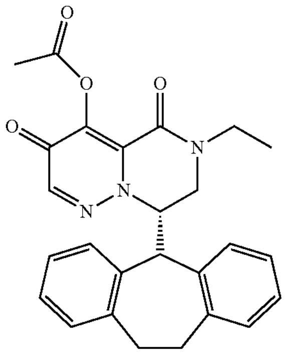 27 | M + H: 444 |
| 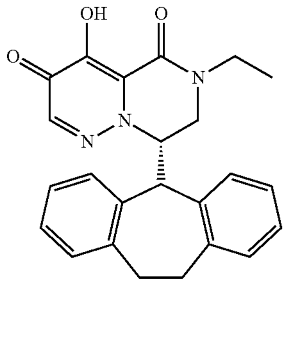 | 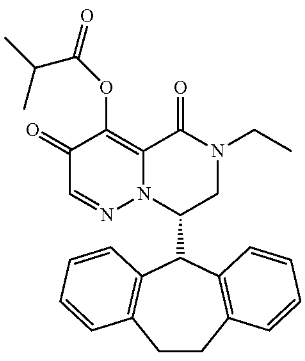 28 | M + H: 472 |

-continued
| Starting Material | Compound | Mass Spec. |
| --- | --- | --- |
| 21 | 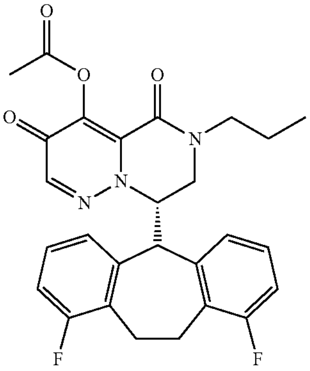 29 | M + H: 494 |
| 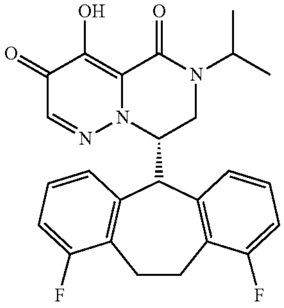 | 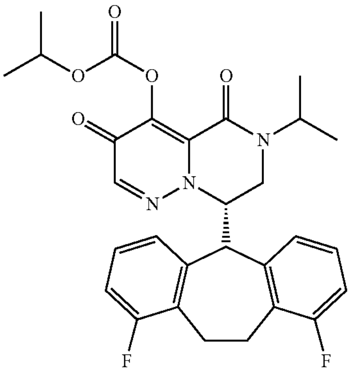 30 | M + H: 538 |
| 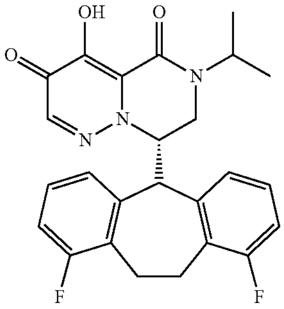 | 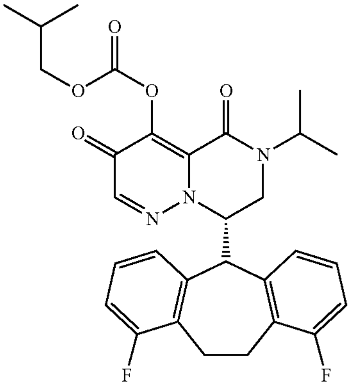 31 | M + H: 552 |

The following compounds were also prepared using methods similar to those described in noted example.
| Compound | Example No. | Mass Spec. |
|---|---|---|
| 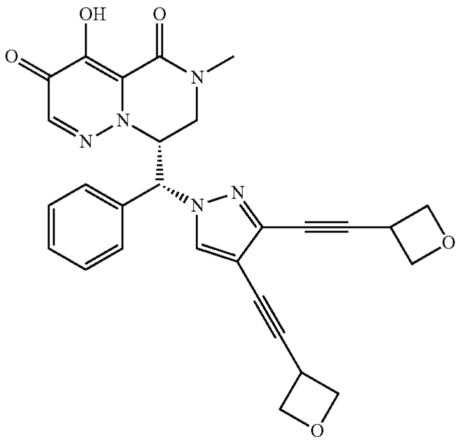 42 | 9 | M + H: 512 |
| 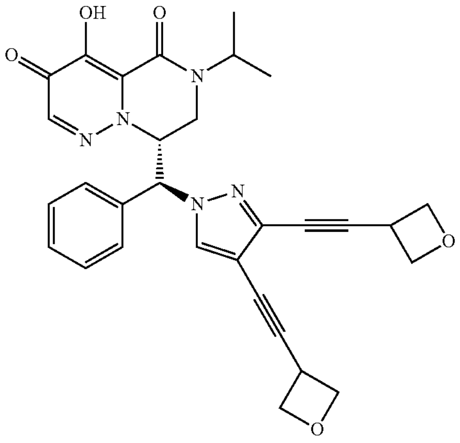 43 | 9 | M + H: 512 |
| 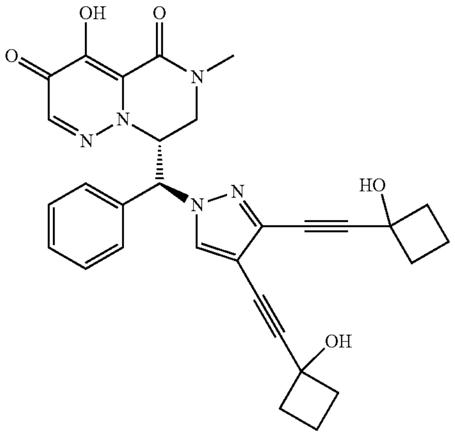 46 | 9 | M + H: 544 |

-continued
| Compound | Example No. | Mass Spec. |
|---|---|---|
| 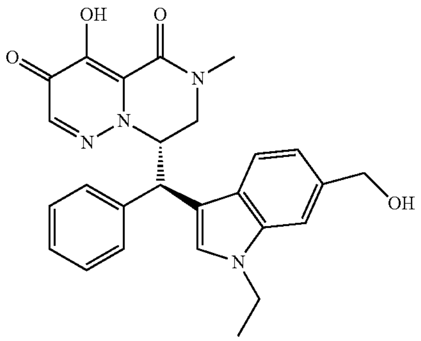 48 | 5 | M + H: 459 |
| 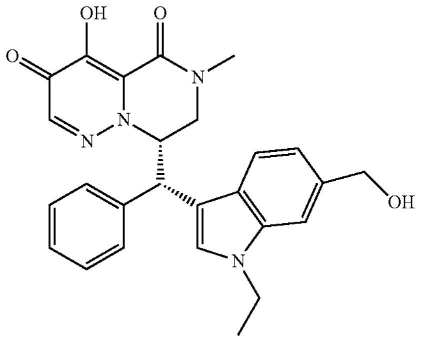 49 | 5 | M + H: 459 |
| 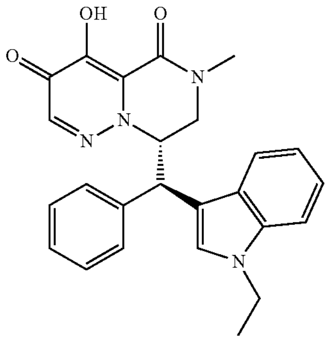 50 | 5 | M + H: 429 |
| 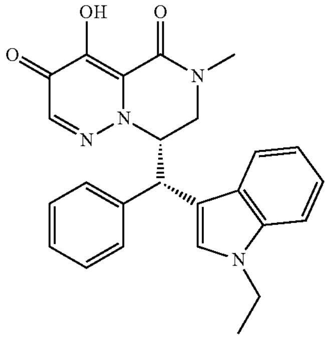 51 | 5 | M + H: 429 |

-continued
| Compound | Example No. | Mass Spec. |
|---|---|---|
| 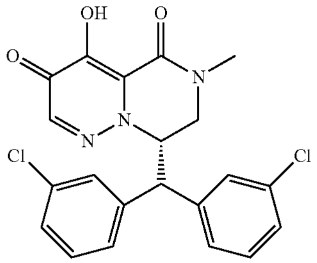 52 | 1 | M + H: 431 |
| 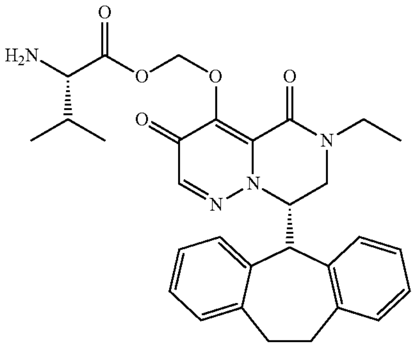 53 | 2 | M + H: 531 |
| 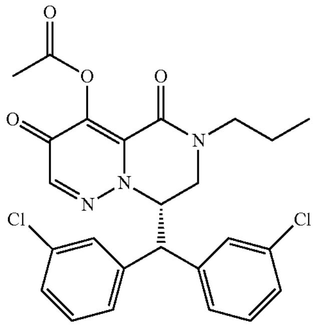 54 | 3 | M + H: 501 |
| 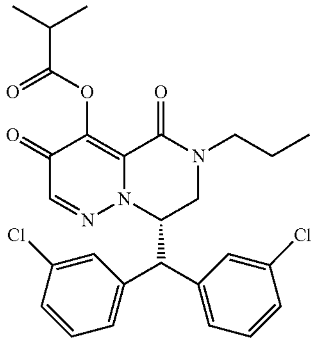 55 | 3 | M + H: 529 |

-continued
| Compound | Example No. | Mass Spec. |
|---|---|---|
| 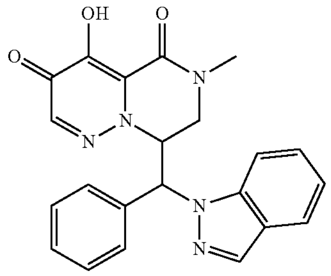 56 | 6 | M + H: 402 |
| 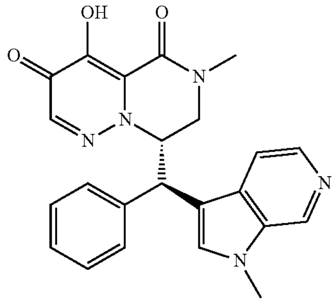 57 | 5 | M + H: 416 |
| 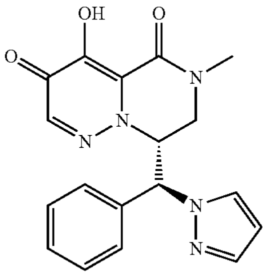 58 | 6 | M + H: 352 |
| 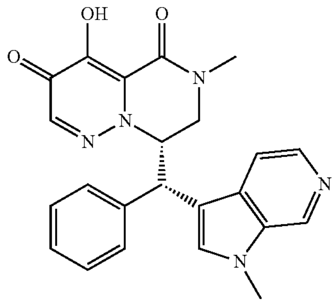 59 | 5 | M + H: 416 |

-continued
| Compound | Example No. | Mass Spec. |
|---|---|---|
| 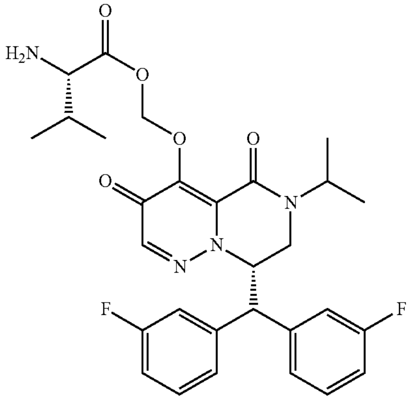 60 | 2 | M + H: 416 |
| 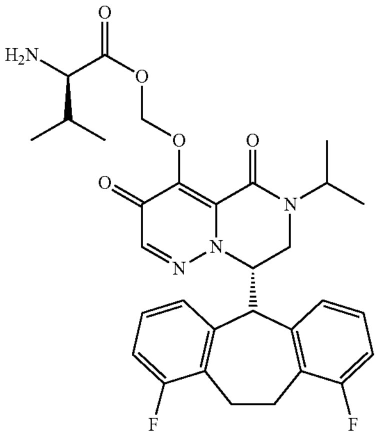 61 | 2 | M + H: 581 |
| 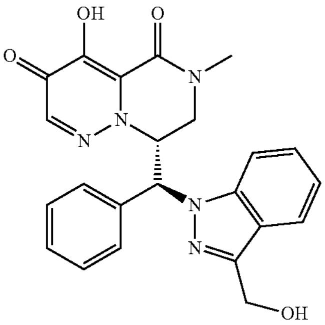 62 | 6 | M + H: 432 |

-continued
| Compound | Example No. | Mass Spec. |
|---|---|---|
| 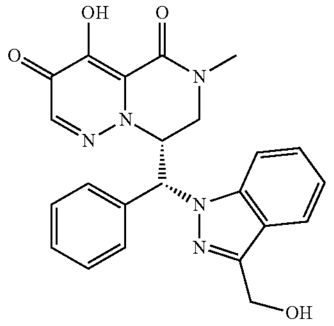 63 | 6 | M + H: 432 |
| 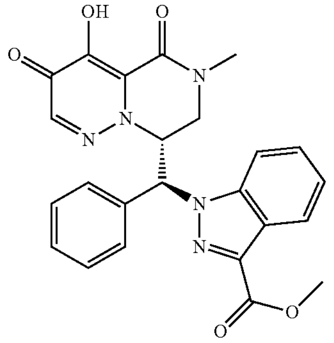 64 | 6 | M + H: 460 |
| 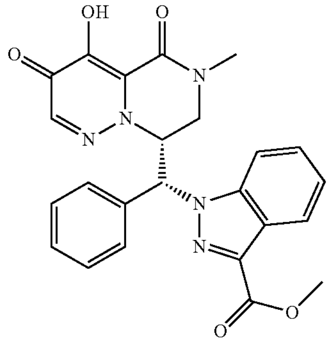 65 | 6 | M + H: 460 |
| 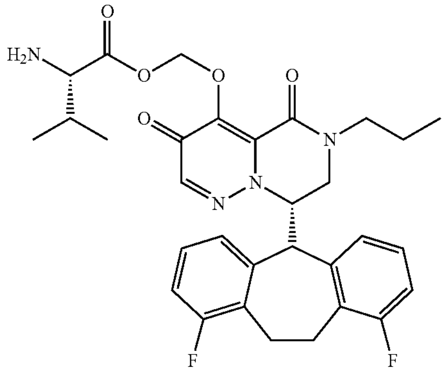 66 | 2 | M + H: 581 |

-continued
| Compound | Example No. | Mass Spec. |
|---|---|---|
| 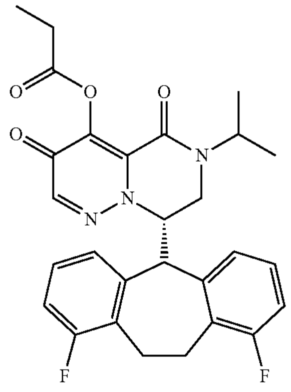 67 | 3 | M + H: 508 |
| 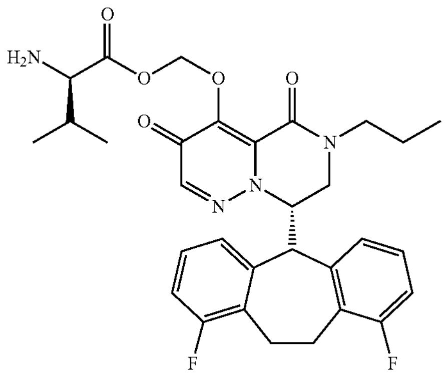 68 | 2 | M + H: 581 |
| 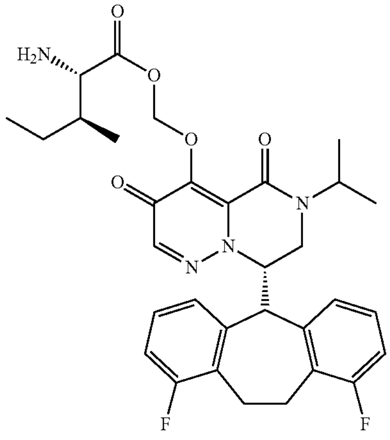 69 | 2 | M + H: 595 |

-continued
| Compound | Example No. | Mass Spec. |
|---|---|---|
| 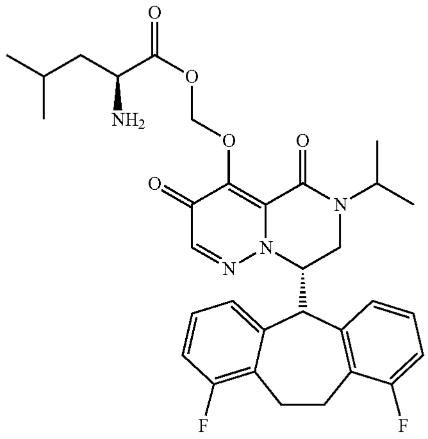 70 | 2 | M + H: 595 |
| 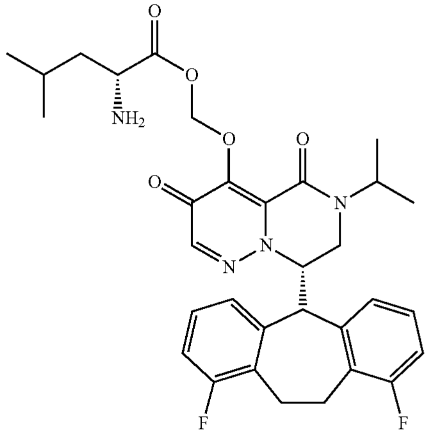 71 | 2 | M + H: 595 |
| 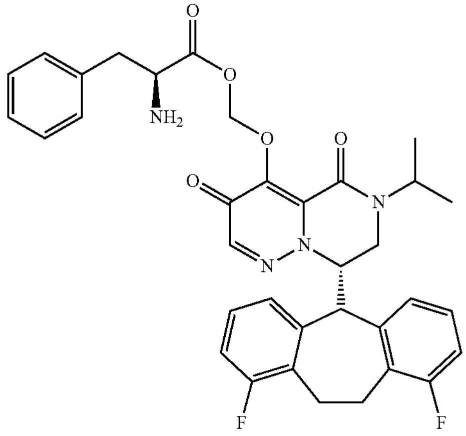 73 | 2 | M + H: 629 |

-continued
| Compound | Example No. | Mass Spec. |
|---|---|---|
| 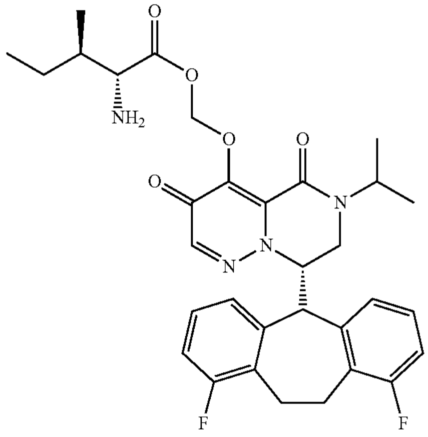 74 | 2 | M + H: 595 |
| 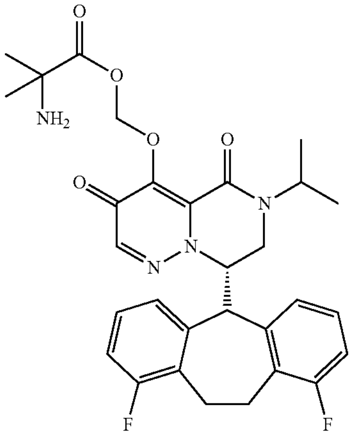 75 | 2 | M + H: 567 |
| 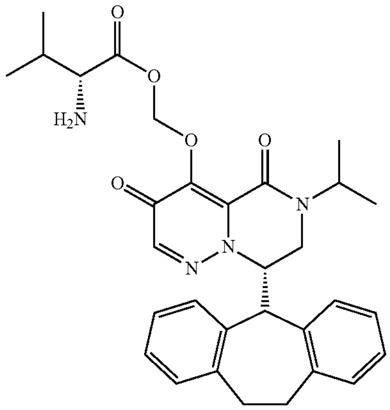 76 | 2 | M + H: 545 |

-continued
| Compound | Example No. | Mass Spec. |
|---|---|---|
| 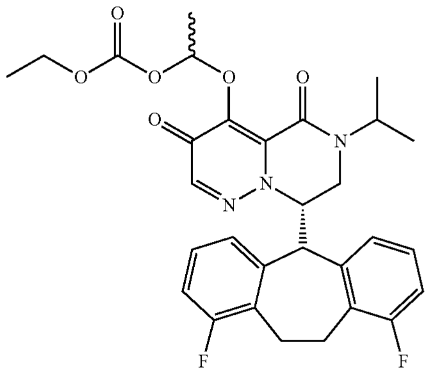 77 | 2 | M + H: 568 |
| 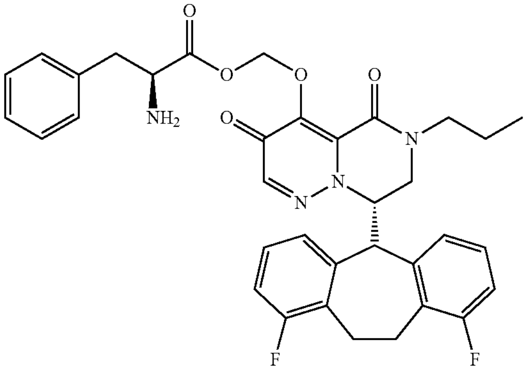 78 | 2 | M + H: 629 |
| 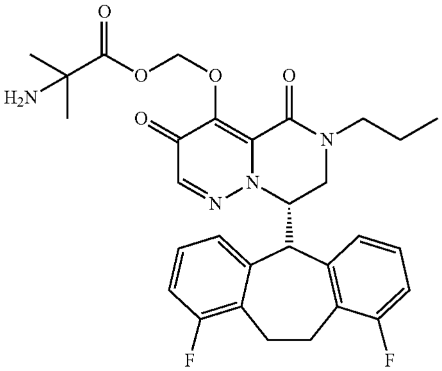 79 | 2 | M + H: 567 |

-continued
| Compound | Example No. | Mass Spec. |
|---|---|---|
| 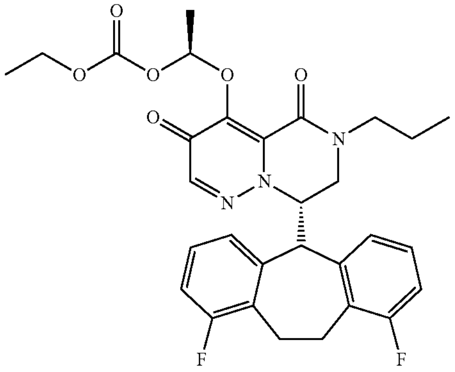 80 | 2 | M + H: 568 |
| 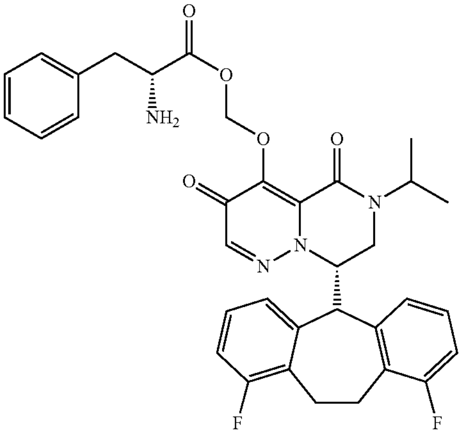 81 | 2 | M + H: 629 |
| 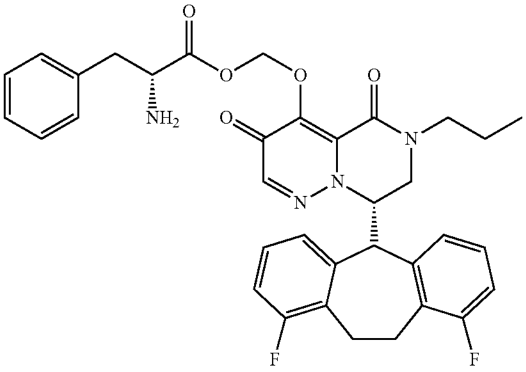 82 | 2 | M + H: 629 |

-continued
| Compound | Example No. | Mass Spec. |
|---|---|---|
| 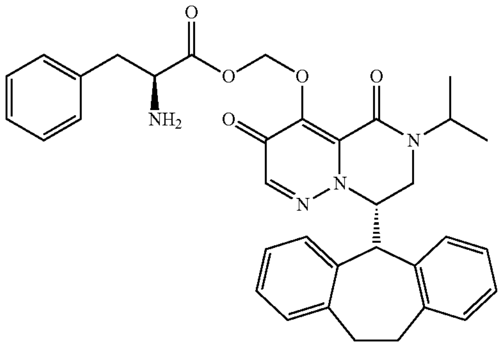 83 | 2 | M + H: 593 |
| 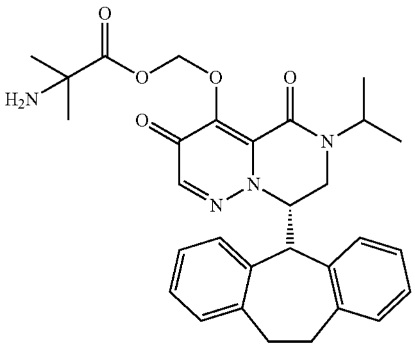 84 | 2 | M + H: 531 |
| 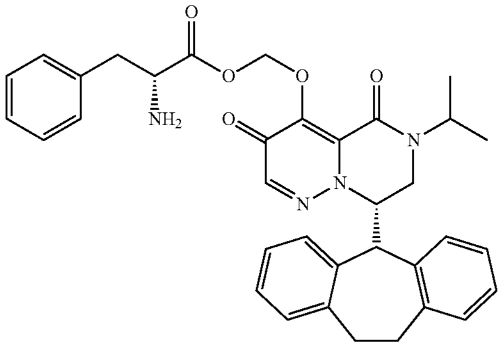 85 | 2 | M + H: 593 |
| 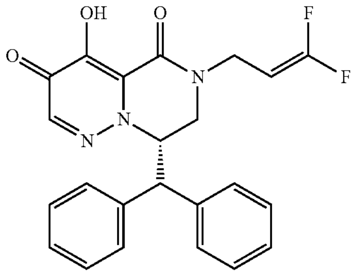 86 | 1 | M + H: 424 |

-continued
| Compound | Example No. | Mass Spec. |
|---|---|---|
| 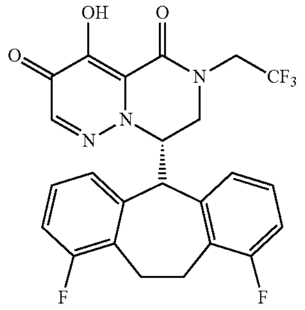 87 | 1 | M + H: 492 |
| 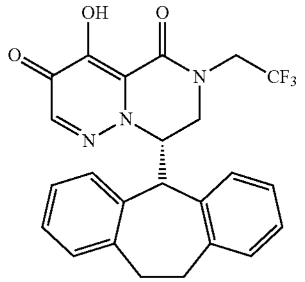 88 | 1 | M + H: 456 |
| 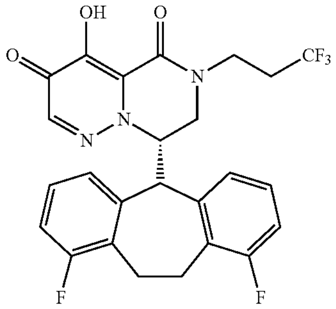 89 | 1 | M + H: 506 |
| 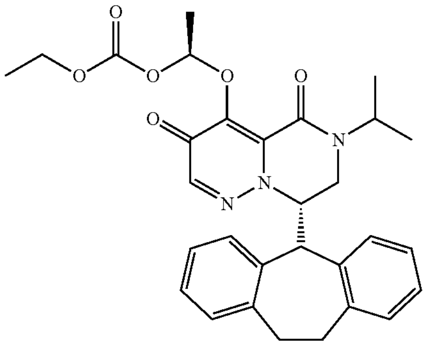 90 | 2 | M + H: 532 |

-continued
| Compound | Example No. | Mass Spec. |
|---|---|---|
| 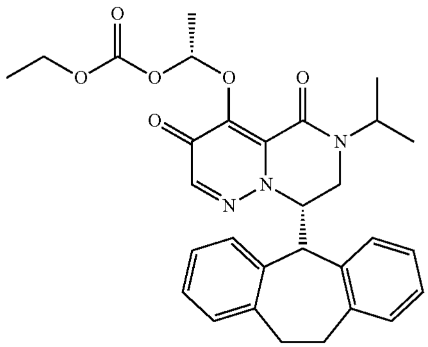 91 | 2 | M + H: 532 |
| 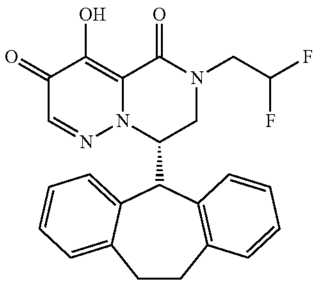 92 | 1 | M + H: 438 |
| 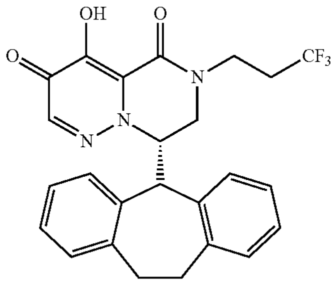 93 | 1 | M + H: 470 |
| 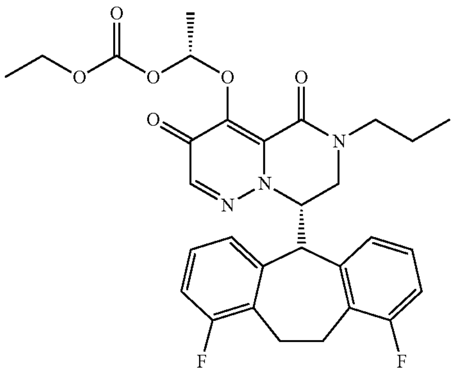 94 | 2 | M + H: 568 |

-continued
| Compound | Example No. | Mass Spec. |
|---|---|---|
| 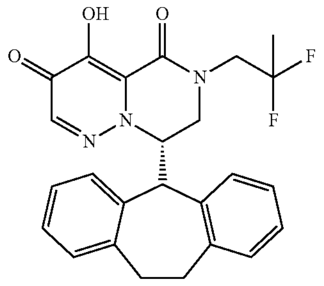 95 | 1 | M + H: 452 |
| 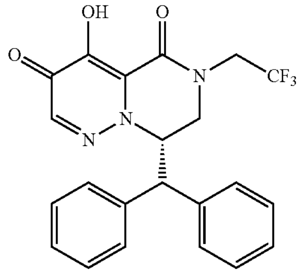 96 | 1 | M + H: 430 |
| 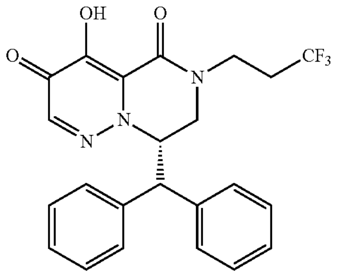 97 | 1 | M + H: 444 |
| 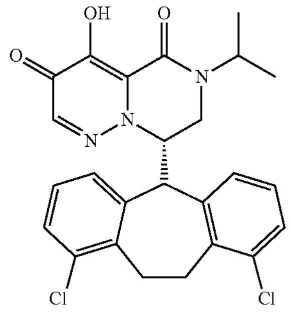 98 | 1 | M + H: 484; 486 |

-continued
| Compound | Example No. | Mass Spec. |
| --- | --- | --- |
| 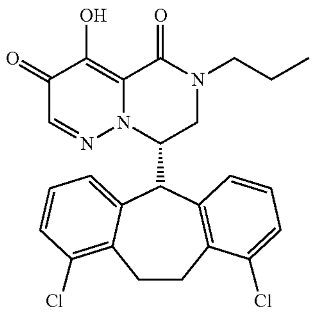 99 | 1 | M + H: 484; 486 |
| 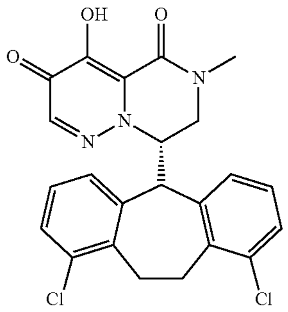 100 | 1 | M + H: 456; 458 |
| 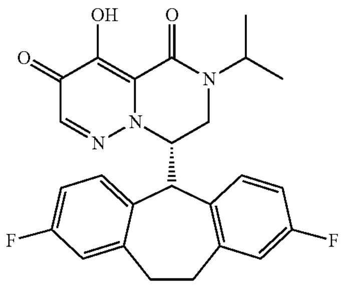 101 | 1 | M + H: 452 |
| 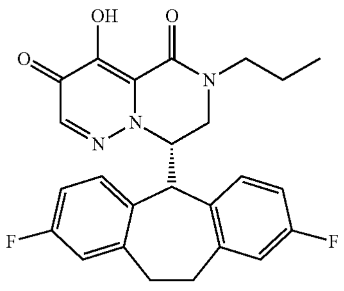 102 | 1 | M + H: 452 |

-continued
| Compound | Example No. | Mass Spec. |
|---|---|---|
| 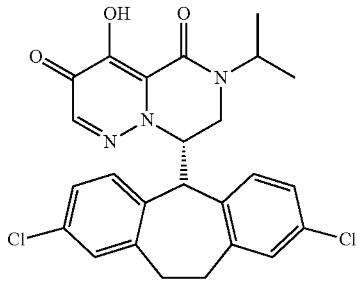 103 | 1 | M + H: 484; 486 |
| 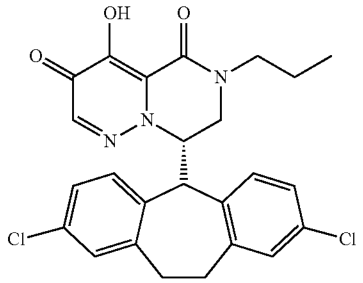 104 | 1 | M + H: 484; 486 |
| 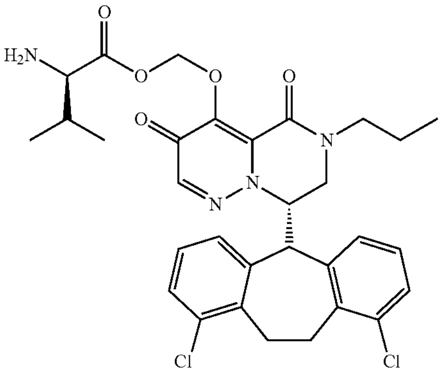 105 | 2 | M + H: 613; 615 |
| 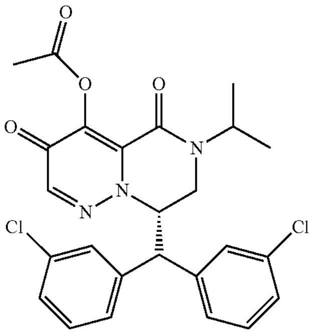 107 | 3 | M + H: 501 |

The stereochemistry of compounds 42, 43, 46, 48, 50, 51, 57, 58, 59, 62, 63, 64, 65, 80. 90, 91 and 94 are relatively assigned.

Example 14

Compounds of Formula (I)

For some compounds, the foregoing syntheses are exemplary and can be used as a starting point to prepare additional compounds of Formula (I). Examples of additional compounds of Formula (I) are shown below. These compounds can be prepared in various ways, including those synthetic schemes shown and described herein. Those skilled in the art will be able to recognize modifications of the disclosed syntheses and to devise routes based on the disclosures herein; all such modifications and alternate routes are within the scope of the claims.

44

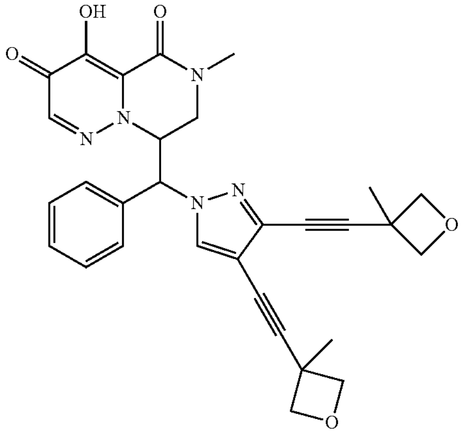

45

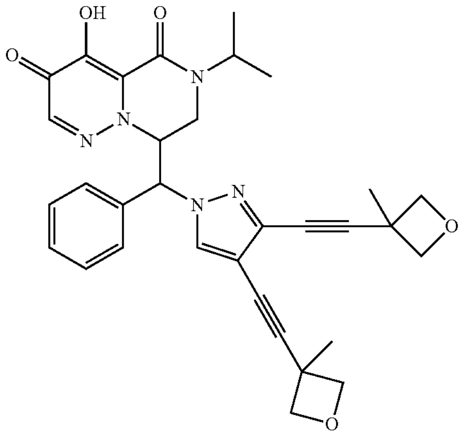

-continued

47

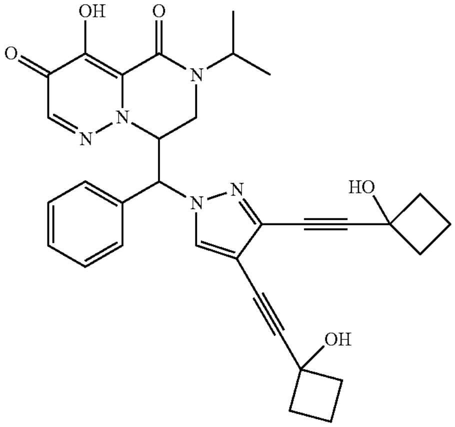

106

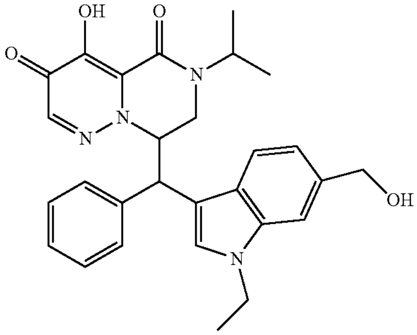

Example A

Influenza Antiviral Assay

Human lung carcinoma A549 cells (ATCC, Manassas, Va.) were plated at a density of $5\times10^4$ cells/mL ($5\times10^3$ cells/well) in assay media (Ham's F12 media supplemented with 0.3% FBS, 1% penicillin/streptomycin (all Mediatech, Manassas, Va.) and 1% DMSO (Sigma-Aldrich, St Louis, Mo.)) in black 96-well plates. Alternatively, Madin-Darby canine kidney epithelial cells (MDCK, ATCC), were plated at a density of $1\times10^5$ cells/mL ($1\times10^4$ cells/well) in assay media (DMEM supplemented with 0.3% FBS, 1% penicillin/streptomycin and 1% DMSO) in 96-well plates. After 24 hours, serially diluted test compounds were added to cells and incubated for an additional 24 hours. Cells were infected with 250 IU/well of Influenza strain A549_A/WSN/33 (H1N1) (Virapur, San Diego Calif.) and incubated for 20 hours at 37° C., 5% $CO_2$. The cell culture supernatant was aspirated off and 50 µL of 25 µM 2'-(4-Methylumbelliferyl)-a-D-N-acetylneuraminic acid (Sigma-Aldrich) dissolved in 33 mM MES, pH 6.5 (Emerald Biosystems, Bainbridge Island, Wash.) was added to the cells. After incubation for 45 min at 30° C., reactions were stopped by addition of 150 µL stop solution (100 mM glycine, pH 10.5, 25% ethanol, all Sigma-Aldrich). Fluorescence was measured with excitation and emission filters of 355 and 460 nm, respectively, on a Victor X3 multi-label plate reader (Perkin Elmer, Waltham, Mass.). Cytotoxicity of uninfected parallel cultures was determined by addition of 100 µL, of CellTiter-Glo® reagent (Promega, Madison, Wis.), and incubation for 10 min at RT. Luminescence was measured on a Victor X3 multi-label plate reader.

Compounds of Formula (I) are active in the assay as noted in Table 1, where ‘A’ indicates an $EC_{50}$<20 μM, ‘B’ indicates an $EC_{50}$ of ≥20 μM and <100 μM and ‘C’ indicates an $EC_{50}$≥100 μM.

TABLE 1

| No. | % Inhibition |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 29 | A |
| 30 | A |
| 31 | A |
| 33 | A |
| 34 | A |
| 35 | A |
| 36 | A |
| 37 | A |
| 38 | A |
| 39 | A |
| 40 | A |
| 41 | A |
| 43 | A |
| 46 | B |
| 50 | A |
| 51 | A |
| 52 | A |
| 54 | A |
| 55 | A |
| 56 | A |
| 57 | A |
| 58 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |

TABLE 1-continued

| No. | % Inhibition |
|---|---|
| 86 | A |
| 87 | A |
| 88 | A |
| 89 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 107 | A |

Example B

EN PA FRET Inhibition Assay

EN PA FRET inhibition assay was performed using a 19 nucleotide synthetic oligoribonucleotide substrate: 5'-FAM-AUUUUGUUUUUAAUAUUUC-BHQ-3' (Integrated DNA Technologies, Inc., Coralville, Iowa) (SEQ. ID. NO. 1). Upon RNA cleavage, the fluorescent FAM group is released from the BHQ quencher. The PA sequence used to produce active enzyme is derived from any one of multiple influenza A virus strains (e.g., A/goose/Nanchang/3-120/01 (H3N2), A/Victoria/3/1975 (H3N2), A/Brisbane/10/2007 (H3N2), A/WSN/33 (H1N1), A/CA/4/2009 (H1N1), A/CA/5/2009 (H1N1), A/Shanghai/1/2013 (H7N9), A/Guizhou/1/2009 (H5N1)). The full length recombinant protein was expressed from a baculovirus vector in insect cells. Full length EN PA was used in this assay at an effective concentration of 1 to 10 Nm, together with 50 Nm FRET probe with a final volume of 20 ml cleavage buffer (20 Mm Tris Ph8, 100 Mm NaCl, 5% Glycerol, 10 Mm (3-ME, 0.01% Tween-20, 2 Mm $MnCl_2$).

Compounds described herein were added to a 384-well black polypropylene plate. Fluorescence was measured in a continuous mode up to 30 minutes with a Wallac 1420 Victor$^3$V multilabel counter (PerkinElmer Life Sciences, Shelton, Conn.) (excitation 485 nm; emission 535 nm). Measured $IC_{50}$ is defined as the concentration at which fluorescence is 50% that of the uninhibited control (DMSO). $IC_{50}$ was calculated by fitting the data to the sigmoidal equation Y=% Min+(% Max−% Min)/(1+X/$IC_{50}$), where Y corresponds to the percent relative enzyme activity, Max is the maximum enzyme activity in the presence of DMSO, Min is the inhibited activity at saturating concentration of compound, and X corresponds to the compound concentration. The $IC_{50}$ values were derived from the mean of a minimum of two independent experiments.

Compounds of Formula (I) are potent in the assay as noted in Table 2, where ‘A’ indicates an $IC_{50}$<250 Nm, ‘B’ indicates an $IC_{50}$ of ≥250 Nm and <1000 Nm and ‘C’ indicates an $IC_{50}$≥1000 Nm.

TABLE 2

| No. | Potency |
|---|---|
| 1 | A |
| 2 | C |

TABLE 2-continued

| No. | Potency |
|---|---|
| 3 | A |
| 4 | A |
| 5 | A |
| 6 | B |
| 7 | A |
| 8 | A |
| 9 | A |
| 10 | A |
| 11 | A |
| 12 | B |
| 13 | A |
| 14 | A |
| 15 | A |
| 16 | A |
| 17 | A |
| 18 | A |
| 19 | A |
| 20 | B |
| 21 | A |
| 22 | C |
| 23 | A |
| 24 | A |
| 25 | A |
| 26 | A |
| 27 | A |
| 28 | A |
| 29 | A |
| 30 | A |
| 31 | A |
| 33 | B |
| 34 | A |
| 35 | C |
| 36 | A |
| 37 | A |
| 38 | A |
| 39 | A |
| 40 | A |
| 41 | A |
| 42 | C |
| 43 | B |
| 46 | B |
| 48 | C |
| 49 | C |
| 50 | B |
| 51 | B |
| 52 | A |
| 54 | A |
| 55 | A |
| 56 | A |
| 57 | A |
| 58 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | C |
| 78 | A |
| 79 | A |
| 80 | C |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 107 | A |

Example C

Influenza B Assay

Viruses:

The influenza virus strains B/Malaysia/2506/2004 and B/Victoria/504/2000 are purchased from Virapur (San Diego, Calif.). The viruses are previously titrated on MDCK cells at Virapur using the $TCID_{50}$ method.

Human Cell Lines:

Human lung carcinoma A549 cells are purchased from the ATCC (Manassas, Va., cat # CCL-185) and cultured in Ham's F12 media supplemented with 10% FBS, 1% penicillin/streptomycin, 1% HEPES, 1% non-essential amino acids and 1% Glutamine (all Mediatech, Manassas, Va.). A549 cells are maintained at 37° C. in a humidified 5% $CO_2$ atmosphere.

Fluorescence-Based Influenza Neuraminidase Assay:

Determination of the $EC_{50}$ and $CC_{50}$ in the fluorescence-based Influenza neuraminidase assay is performed by the following procedure. 24 hours prior to infection, A549 cells in assay media (Ham's F12 media supplemented with 0.3% FBS, 1% penicillin/streptomycin, 1% HEPES, 1% non-essential amino acids and 1% Glutamine) are plated at a density of $1\times10^5$ cells/mL ($1\times10^4$ cells/well) in white 96-well plates. On the day of infection, serially diluted compounds are added to cells. Cells are infected with 500 IU/well of influenza strains B/Malaysia/2506/2004 or B/Victoria/504/2000 and incubated for 20 h at 37° C., 5% $CO_2$. The cell culture supernatant is aspirated off and 50 μL of 25 μM 2'-(4-Methylumbelliferyl)-a-D-N-acetyl-neuraminic acid (Sigma-Aldrich) dissolved in 33 mM MES, pH 6.5 (Emerald Biosystems, Bainbridge Island, Wash.) is added to the cells. After incubation for 45 mins at 37° C., reactions are stopped by the addition of 150 μL, stop solution (100 mM glycine, pH 10.5, 25% EtOH, all Sigma-Aldrich). Fluorescence is measured with excitation and emission filters of 355 and 460 nm, respectively, on a Victor X3 multi-label plate reader (Perkin Elmer, Waltham, Mass.).

Cell Viability Assay:

Promega's CellTiter-Glo Luminescent Cell Viability Assay (Cat. #G7572) is used to measure cell viability. Assay plates are set up as described above and CellTiter-Glo reagent (100 μL) is added to each well and incubated at room temperature for 10 mins. Luminescence is recorded using a Perkin Elmer multilabel counter Victor3V. The $CC_{50}$, the concentration of the drug required to reduce the number of viable cells by 50% in relation to the untreated cell control value, is calculated from the plot of percentage reductions of the luminescence value against the drug concentrations using the Microsoft Excel forecast function.

Example D

Combination Studies 24 h prior to infection, dog kidney epithelial MDCK cells (ATCC, Manassas, Va.) are plated in maintenance media (DMEM media supplemented with 10% FBS, 1% penicillin/streptomycin, 1% non-essential amino acids, 1% Glutamine and 1% HEPES (all Mediatech, Manassas, Va.) at a density of $15\times10^4$ cells/mL ($15\times10^3$ cells/well) in white 96-well plates with clear bottoms. At the day of infection, maintenance media is removed from cells. Compounds are serially diluted in assay media (MEM media without phenol-red, supplemented with 0.3% FBS, 1% penicillin/streptomycin, 1% non-essential amino acids, 1% Glutamine and 1% HEPES (all Mediatech, Manassas, Va.) and 4 μg/mL TPCK-treated trypsin (Affymetrix, Santa Clara, Calif.)) and added to cells. To determine drug-drug interactions (synergy), one compound is diluted horizontally and the second compound vertically to create a checker-board matrix of compound combinations at variable concentrations. Cells are infected at a MOI of 0.001 to 0.05 with Influenza strain A/Port Chalmers/1/73 (H3N2) (Virapur, San Diego Calif.) and incubated for three days at 37° C., 5% $CO_2$. 100 μL of the cell culture supernatant is aspirated off and 100 μL CellTiter-Glo® reagent (Promega, Madison, Wis.) is added to the cells. After incubation for 10 mins at RT, luminescence is measured on a Victor X3 multi-label plate reader (Perkin Elmer, Waltham, Mass.). Cytotoxicity of uninfected parallel cultures is determined at the same time. Drug interactions are calculated using the MacSynergy™ II tool developed by M. N. Prichard and C. Shipman Jr. (Prichard, M. N. et al., *Antiviral Res.* (1990) 14(4-5):181-205).

The volumes of synergy (positive volumes) or antagonism (negative volumes) represent the relative quantity of synergism or antagonism per change in the concentrations of the two drugs. Synergy and antagonism volumes are defined based on the Bliss independence model. In this model, synergy volumes of less than −25 indicate antagonistic interactions, volumes in the −25-25 range indicate additive behavior, volumes in the 25-100 range indicate synergistic behavior and volumes >100 indicate strong synergistic behavior. Determination of in vitro additive, synergistic and strongly synergistic behavior for combinations of compounds can be of utility in predicting therapeutic benefits for administering the combinations of compounds in vivo to infected patients.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, wherein the compound of Formula (I) has the structure:

(I)

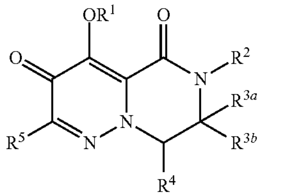

wherein:

$R^1$ is selected from the group consisting of hydrogen, an unsubstituted $C_{1-4}$ alkyl, an optionally substituted heterocyclyl, $—C(=O)Y^1$, $—C(=O)—O—Y^1$, $—(CH_2)—O—C(=O)—Y^1$, $—(CH_2)—O—C(=O)—O—Y^1$, $—(CHCH_3)—O—C(=O)—Y^1$ and $—(CHCH_3)—O—C(=O)—O—Y^1$;

$R^2$ is selected from the group consisting of hydrogen, an optionally substituted $C_{1-6}$ alkyl, an optionally substituted $C_{2-6}$ alkenyl, an optionally substituted heterocyclyl, an optionally substituted cycloalkyl($C_{1-6}$ alkyl), an optionally substituted aryl($C_{1-6}$ alkyl), an optionally substituted heteroaryl(C 1-6 alkyl) and an optionally substituted heterocyclyl($C_{1-6}$ alkyl);

$R^{3a}$ and $R^{3b}$ are independently hydrogen or an optionally substituted $C_{1-4}$ alkyl;

$R^4$ is selected from the group consisting of:

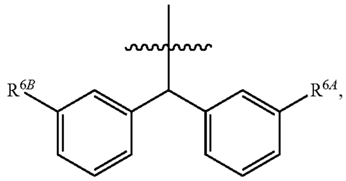,

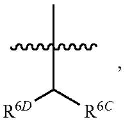,

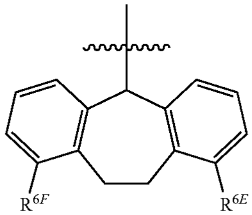 and

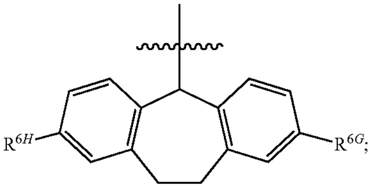;

$R^{6A}$ and $R^{6B}$ are each hydrogen, each fluoro or each chloro; or $R^{6A}$ and $R^{6B}$ are independently hydrogen, an unsubstituted $C_{1-4}$ alkyl or an unsubstituted $C_{2-4}$ alkynyl, provided that at least one of $R^{6A}$ and $R^{6B}$ is an unsubstituted $C_{1-4}$ alkyl or an unsubstituted $C_{2-4}$ alkynyl;

$R^{6C}$ is an optionally substituted aryl or an optionally substituted heteroaryl;

$R^{6D}$ is an optionally substituted heteroaryl;

$R^{6E}$ and $R^{6F}$ are each hydrogen or each fluoro;

$R^{6G}$ and $R^{6H}$ are each fluoro or each chloro;

$R^5$ is selected from the group consisting of hydrogen, halogen, —CN, an optionally substituted $C_{1-6}$ alkyl, an optionally substituted aryl, an optionally substituted heteroaryl, —$CH_2OH$, —$CH(Y^2)(OH)$ and —$C(O)Y^2$;

$Y^1$ and $Y^2$ are independently selected from the group consisting of an optionally substituted $C_{1-6}$ alkyl, an optionally substituted $C_{3-6}$ cycloalkyl, an optionally substituted aryl, an optionally substituted heteroaryl, an optionally substituted heterocyclyl, a mono-substituted amino group, a di-substituted amino and —$C(R^7)_2NHR^8$; and each $R^7$ and $R^8$ are independently hydrogen or an optionally substituted $C_{1-4}$ alkyl; and provided that:

when $R^4$ is

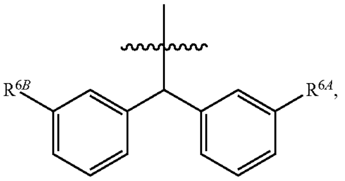, wherein $R^{6A}$ and $R^{6B}$ are each hydrogen, and $R^2$ is hydrogen, $CH_3$, —$CH_2CH_3$, —$CH_2CH_2CH_3$, —$CH_2CH_2CH_2CH_3$, —$CH(CH_3)_2$, —$CH(CH_2CH_3)_2$, —$CH_2CH(CH_3)_2$, —$CH(CH_3)CF_3$, —$CH_2$—($C_3$-cyclopropyl), tetrahydro-2H-pyran, —$CH_2CH_2OH$, —$CH_2CH_2OCH_3$ or —$C(CH_3)_2CH_2OCH_3$; then $R^1$ is not hydrogen, —$C(=O)CH_3$, —$C(=O)CH(CH_3)_2$, —$C(=O)CH_2CH(CH_3)_2$, —$C(=O)$—($C_{5-6}$-cycloalkyl), —$C(=O)$-(tetrahydro-2H-pyran), —$C(=O)$—O—$CH(CH_3)_2$, —$C(=O)$—O—$CH_2CH(CH_3)_2$, —$CH_2$—O—$C(=O)CH(CH_3)(NH_2)$, —$CH_2$—O—$C(=O)CH(CH(CH_3)_2)(NH_2)$ or —$CH_2$—O—$C(=O)C((CH_3)_2)(NH_2)$;

when $R^4$ is

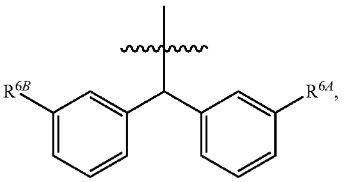, wherein $R^{6A}$ and $R^{6B}$ are each fluoro, and $R^2$ is —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$CH_2$—($C_3$-cyclopropyl), -unsubstituted benzyl, —$CH_2CH_2OH$ or —$CH_2CH_2OCH_3$; then $R^1$ is not hydrogen, —$CH_2CH_3$, —$C(=O)CH_3$, —$C(=O)CH(CH_3)_2$, —$CH_2$—O—$C(=O)$—O-(phenyl substituted with methyl and nitro), —$CH_2$—O—$C(=O)$—NH—$CH_2CH_2$-(morpholine), —$CH_2$—O—$C(=O)CH(CH(CH_3)_2)(NH_2)$ or —$CH_2$—O—$C(=O)NH(CH_3)$;

when $R^4$ is

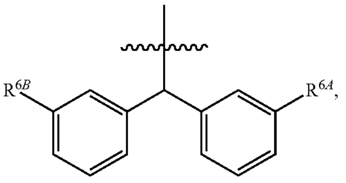, wherein $R^{6A}$ and $R^{6B}$ are each chloro, and $R^2$ is —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$CH_2$—($C_3$-cyclopropyl), —$CH_2CH_2OH$ or —$CH_2CH_2OCH_3$; then $R^1$ is not hydrogen or —$C(=O)CH(CH_3)_2$;

when $R^4$ is

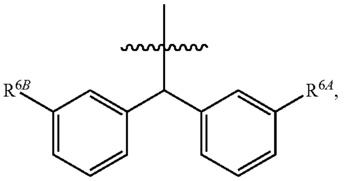, wherein one of $R^{6A}$ and $R^{6B}$ is an unsubstituted $C_{1-4}$ alkyl; then $R^1$ is not hydrogen;

when $R^4$ is

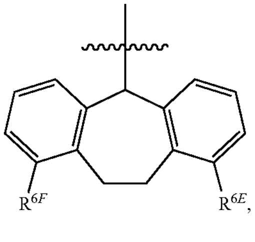, wherein $R^{6E}$ and $R^{6F}$ are each hydrogen, and $R^2$ is —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$CH_2$—($C_3$-cyclopropyl), an unsubstituted benzyl, —$CH(CH_3)CF_3$, —$CH_2CH_2OH$ or —$CH_2CH_2OCH_3$; then $R^1$ is not hydrogen or —C(═O)CH$(CH_3)_2$;

when $R^4$ is

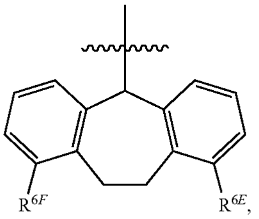

wherein $R^{6E}$ and $R^{6F}$ are each fluoro, and $R^2$ is —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$CH_2$—($C_3$-cyclopropyl), —$CH_2CH_2OH$ or —$CH_2CH_2OCH_3$; then $R^1$ is not hydrogen or —C(═O)$CH(CH_3)_2$;

when $R^4$ is

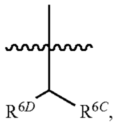

wherein $R^{6C}$ is pyrazolyl and $R^{6D}$ is unsubstituted phenyl; then $R^{6C}$ is a di-substituted pyrazolyl;

wherein when $R^4$ is

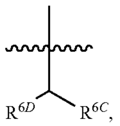

wherein $R^{6C}$ is an optionally substituted imidazolyl or an optionally substituted pyridinyl; then $R^{6D}$ is not an optionally substituted phenyl; and when $R^4$ is

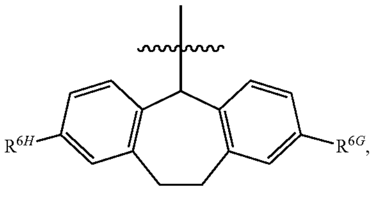

wherein $R^{6G}$ and $R^{6H}$ are each fluoro or each chloro, and $R^2$ is —$CH_3$; then $R^1$ is not hydrogen.

2. The compound of claim 1, or a pharmaceutically acceptable salt thereof, wherein $R^4$ is

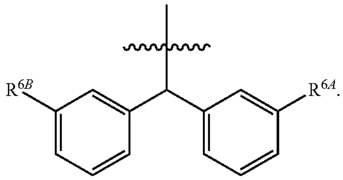

3. The compound of claim 2, or a pharmaceutically acceptable salt thereof, wherein $R^{6A}$ and $R^{6B}$ are each hydrogen.

4. The compound of claim 2, or a pharmaceutically acceptable salt thereof, wherein $R^{6A}$ and $R^{6B}$ are each fluoro or each chloro.

5. The compound of claim 2, or a pharmaceutically acceptable salt thereof, wherein one of $R^{6A}$ and $R^{6B}$ is an unsubstituted $C_{1-4}$ alkyl or an unsubstituted $C_{2-4}$ alkynyl.

6. The compound of claim 1, or a pharmaceutically acceptable salt thereof, wherein $R^4$ is

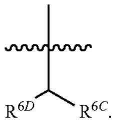

7. The compound of claim 6, or a pharmaceutically acceptable salt thereof, wherein $R^{6C}$ is an optionally substituted aryl or an optionally substituted heteroaryl.

8. The compound of claim 6, or a pharmaceutically acceptable salt thereof, wherein $R^{6D}$ is an optionally substituted heteroaryl.

9. The compound of claim 1, or a pharmaceutically acceptable salt thereof, wherein $R^4$ is

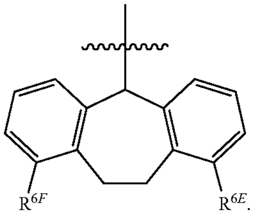

10. The compound of claim 9, or a pharmaceutically acceptable salt thereof, wherein $R^{6E}$ and $R^{6F}$ are each hydrogen.

11. The compound of claim 9, or a pharmaceutically acceptable salt thereof, wherein $R^{6E}$ and $R^{6F}$ are each fluoro.

12. The compound of claim 1, or a pharmaceutically acceptable salt thereof, wherein $R^4$ is

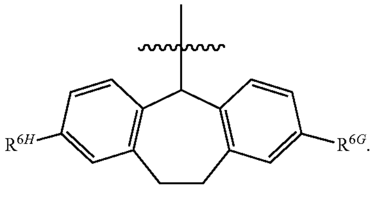

13. The compound of claim 12, or a pharmaceutically acceptable salt thereof, wherein $R^{6G}$ and $R^{6H}$ are each fluoro or each chloro.

14. The compound of claim 1, or a pharmaceutically acceptable salt thereof, wherein $R^2$ is hydrogen.

15. The compound of claim 1, or a pharmaceutically acceptable salt thereof, wherein $R^2$ is an optionally substituted $C_{1-6}$ alkyl.

16. The compound of claim 1, or a pharmaceutically acceptable salt thereof, wherein $R^2$ is an optionally substituted $C_{2-6}$ alkenyl.

17. The compound of claim 1, or a pharmaceutically acceptable salt thereof, wherein $R^1$ is hydrogen.

18. The compound of claim 1, or a pharmaceutically acceptable salt thereof, wherein $R^1$ is an unsubstituted $C_{1-4}$ alkyl or an optionally substituted heterocyclyl.

19. The compound of claim 1, or a pharmaceutically acceptable salt thereof, wherein $R^1$ is $-C(=O)Y^1$, $-C(=O)-O-Y^1$, $-(CH_2)-O-C(=O)-Y^1$, $-(CH_2)-O-C(=O)-O-Y^1$, $-(CHCH_3)-O-C(=O)-Y^1$ and $-(CHCH_3)-O-C(=O)-O-Y^1$.

20. The compound of claim 19, or a pharmaceutically acceptable salt thereof, wherein $Y^1$ is an optionally substituted $C_{1-6}$ alkyl or an optionally substituted $C_{3-6}$ cycloalkyl.

21. The compound of claim 19, or a pharmaceutically acceptable salt thereof, wherein $Y^1$ is an optionally substituted aryl, an optionally substituted heteroaryl or an optionally substituted heterocyclyl.

22. The compound of claim 19, or a pharmaceutically acceptable salt thereof, wherein $Y^1$ is a mono-substituted amino group, a di-substituted amino or $-C(R^7)_2NHR^8$.

23. The compound of claim 22, or a pharmaceutically acceptable salt thereof, wherein $-C(R^7)_2NHR^8$ is selected from

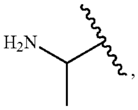,
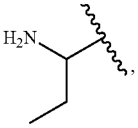,
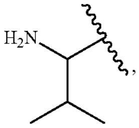,
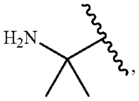,
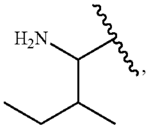,
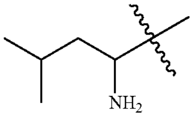
and
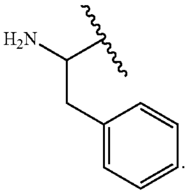.

24. The compound of claim 1, or a pharmaceutically acceptable salt thereof, wherein $R^5$ is hydrogen.

25. The compound of claim 1, or a pharmaceutically acceptable salt thereof, wherein $R^{3a}$ is hydrogen; and $R^{3b}$ is hydrogen.

26. The compound of claim 1, wherein the compound is selected from the group consisting of:

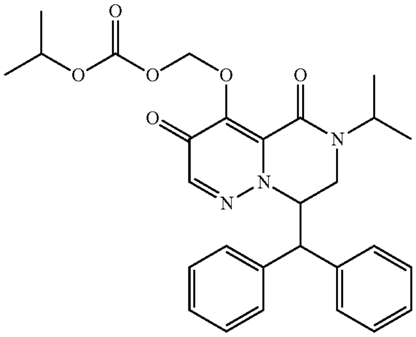,
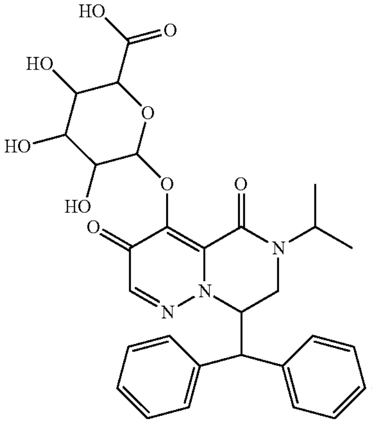,
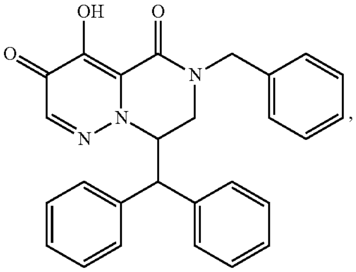,
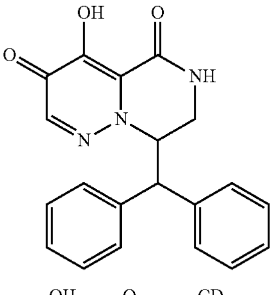,
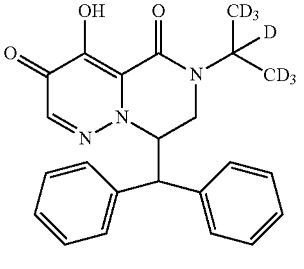
and

-continued
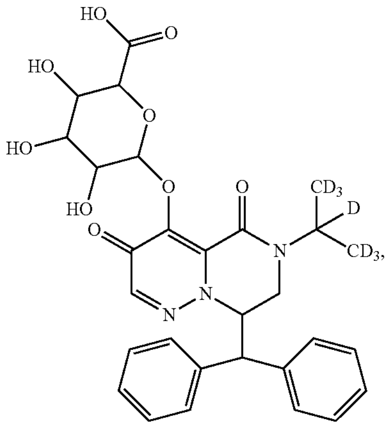
or a pharmaceutically acceptable salt of any of the foregoing.
27. The compound of claim 1, wherein the compound is selected from the group consisting of:
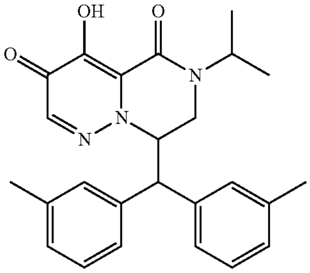
,
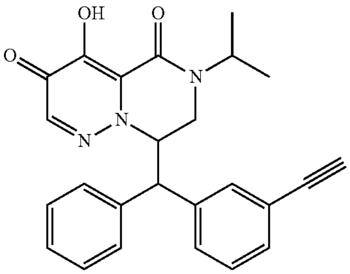
,
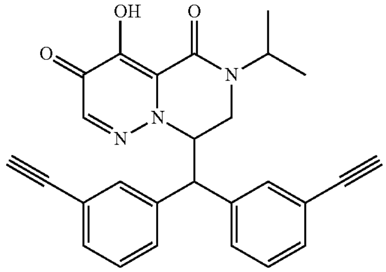
,
-continued
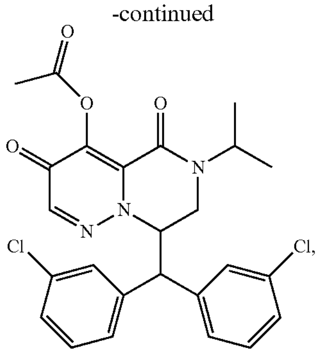
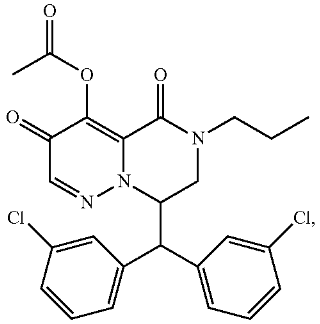
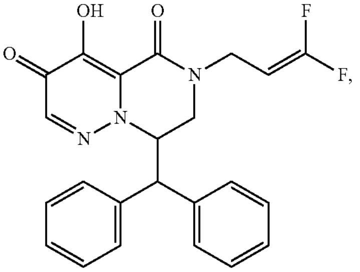
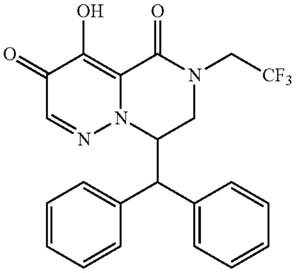
and
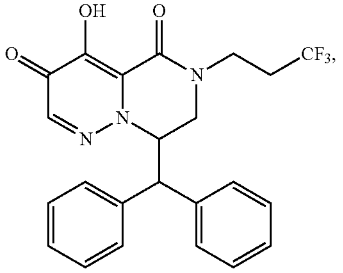
or a pharmaceutically acceptable salt of any of the foregoing.
28. The compound of claim 1, wherein the compound is selected from the group consisting of:

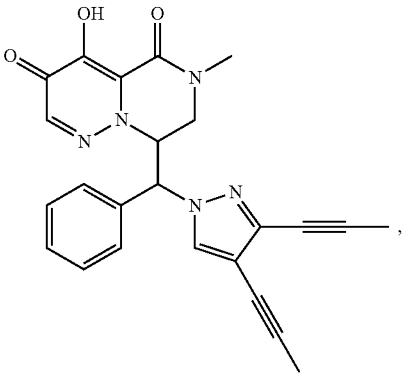
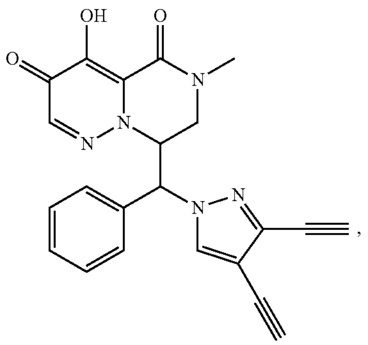
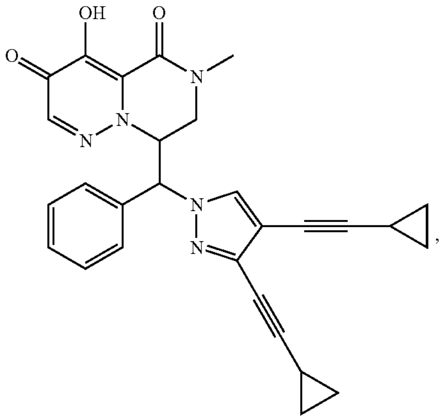
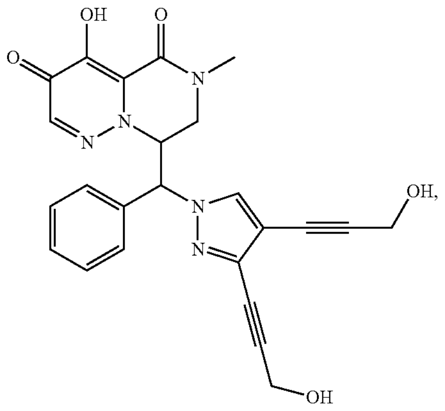
-continued
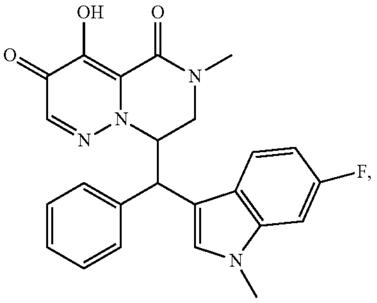
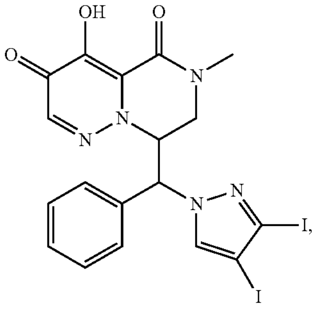
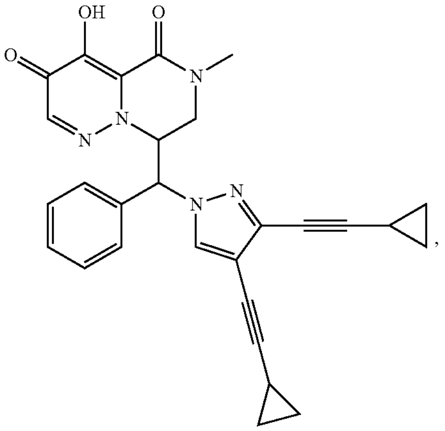
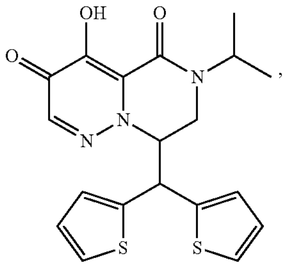
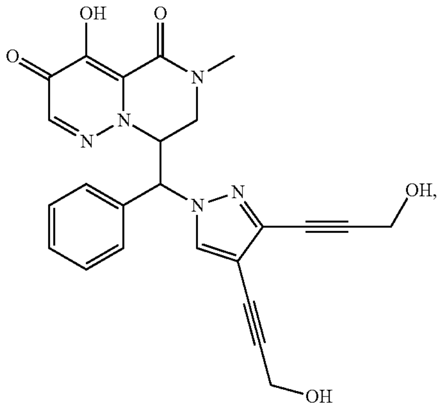

-continued
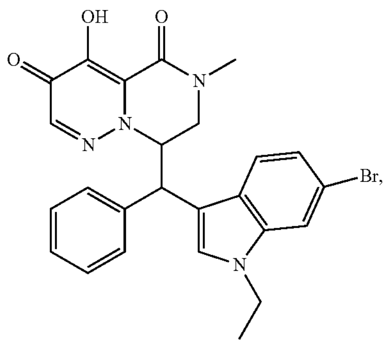
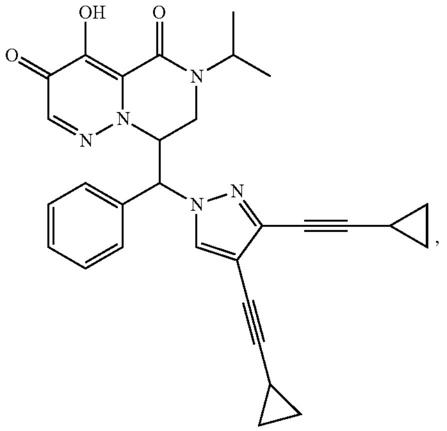
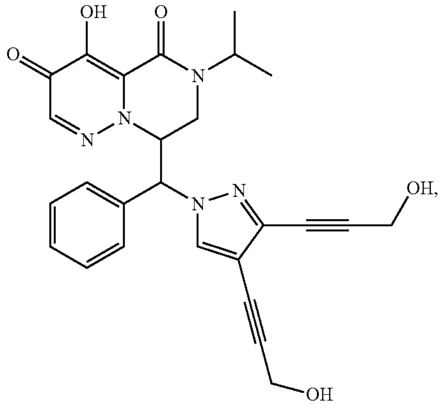
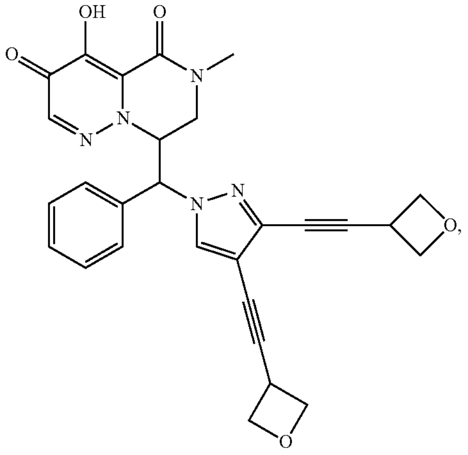
-continued
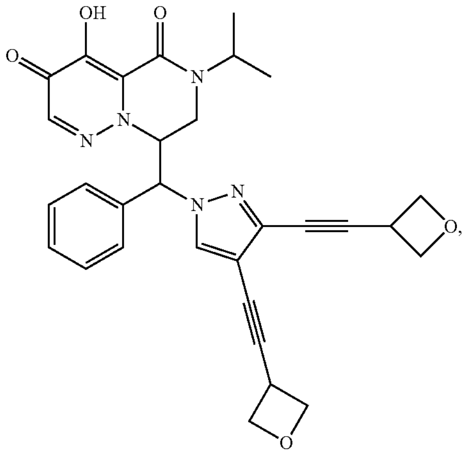
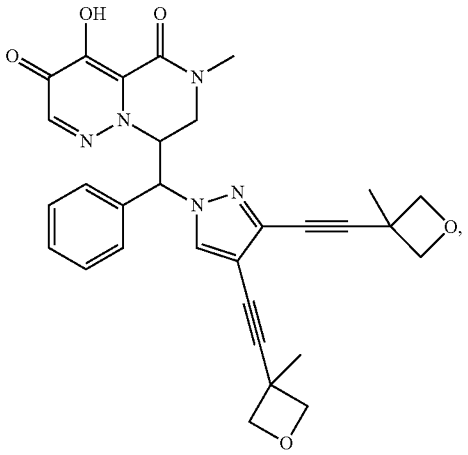
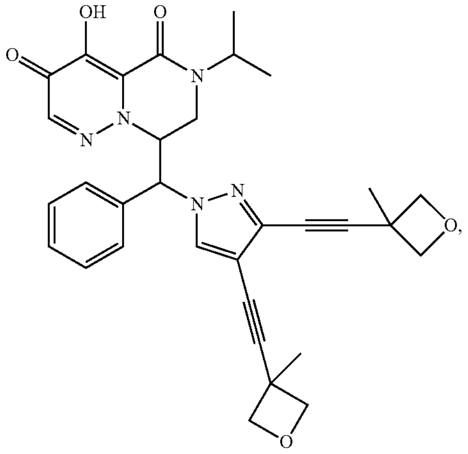

-continued
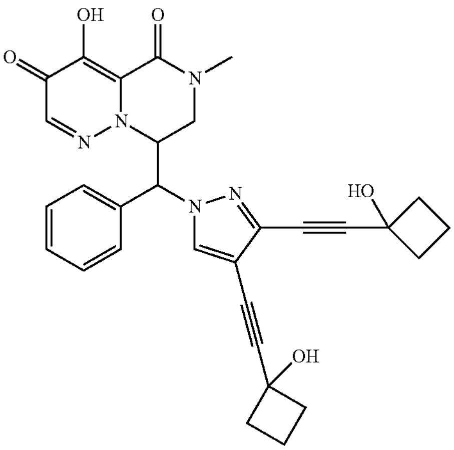
,
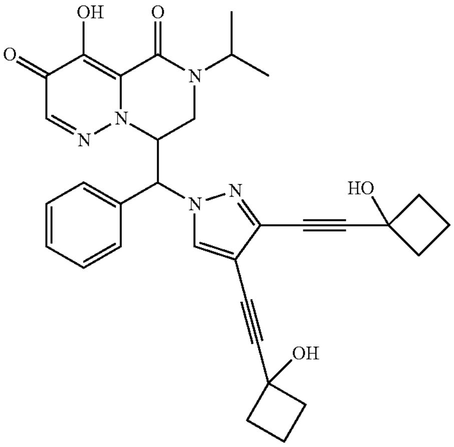
,
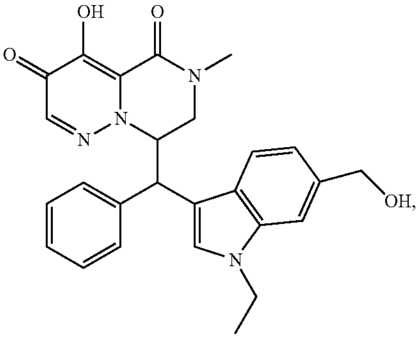
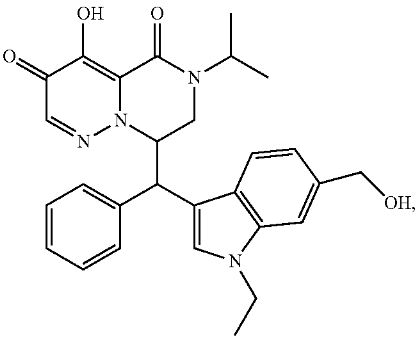
-continued
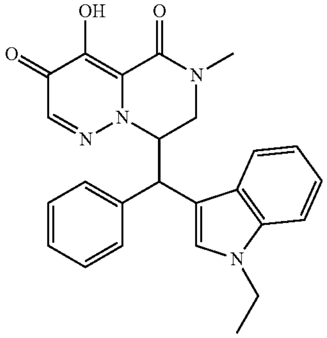
,
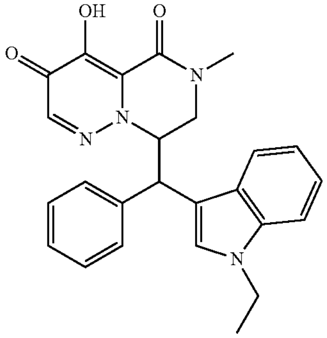
,
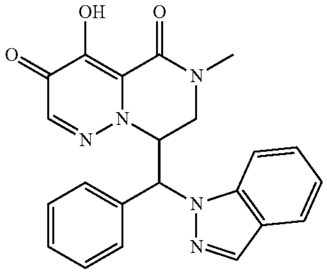
,
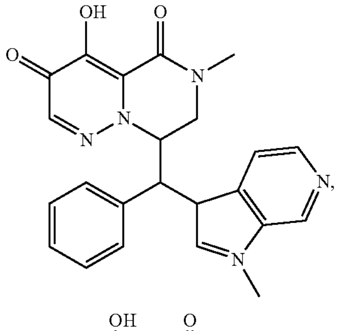
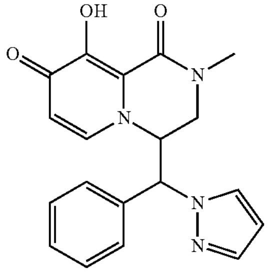
,

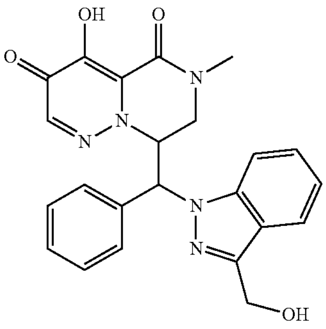
and
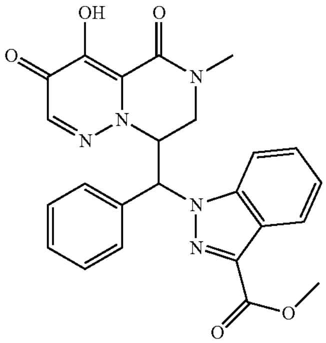
,
or a pharmaceutically acceptable salt of any of the foregoing.
29. A Compound selected from the group consisting of:
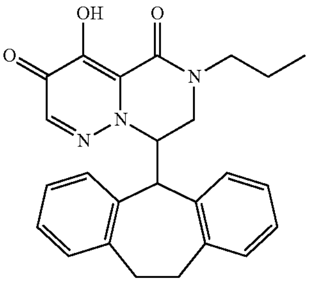
,
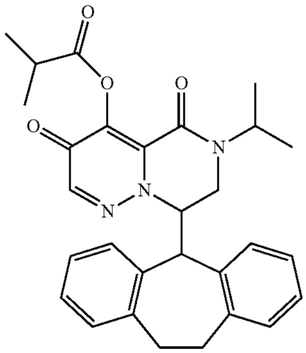
,
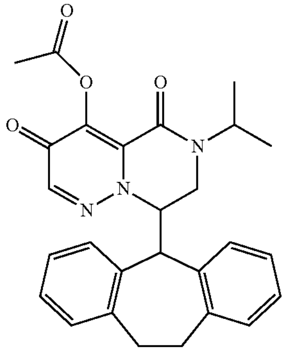
,
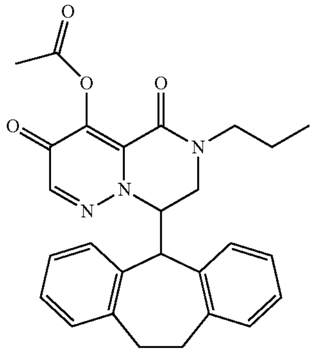
,
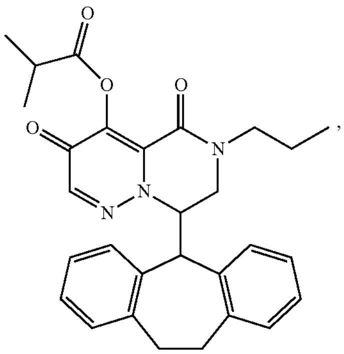
,
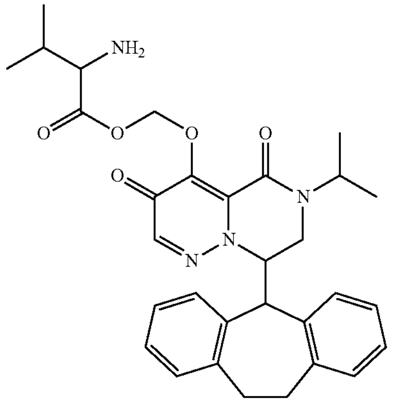
, -continued
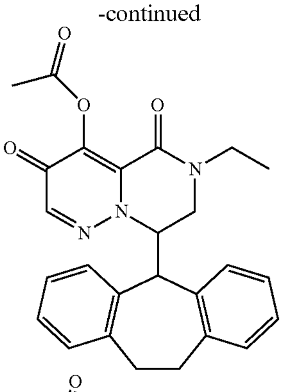
,
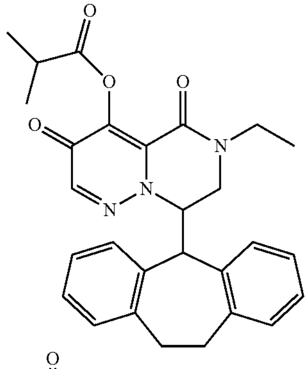
,
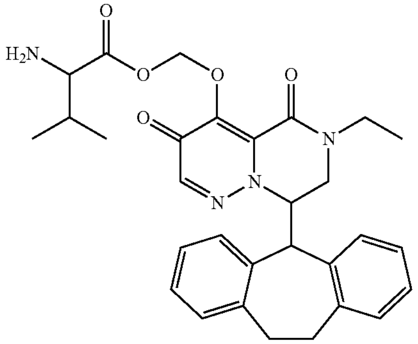
,
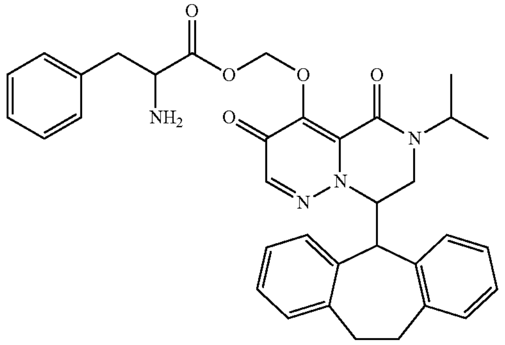
,
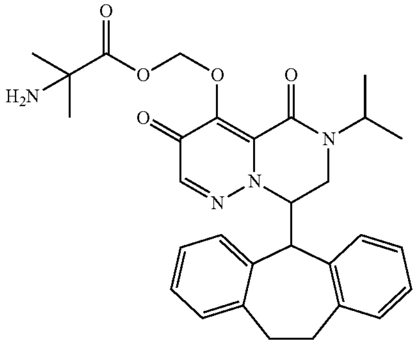
,
-continued
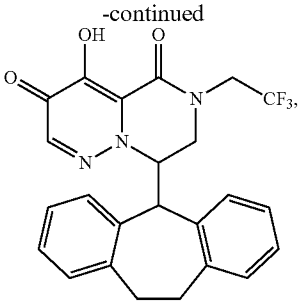
,
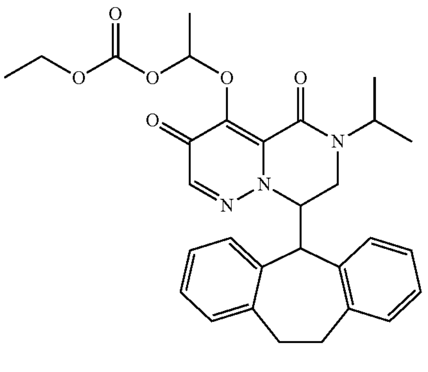
,
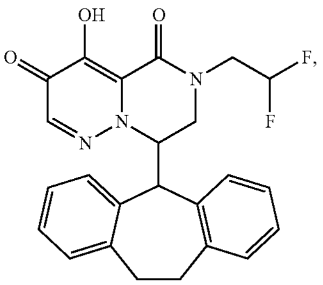
,
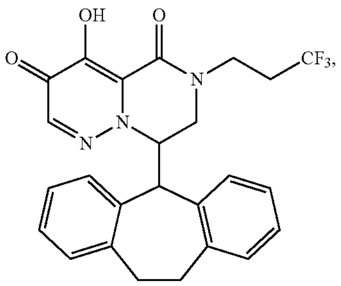
,
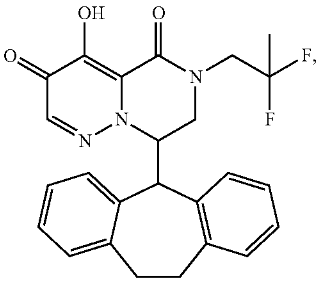
, -continued
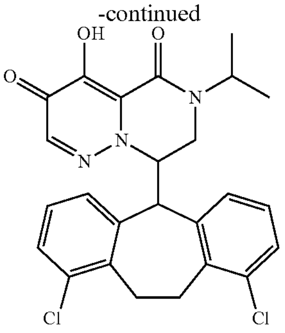
,
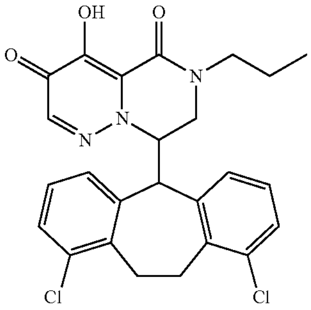
,
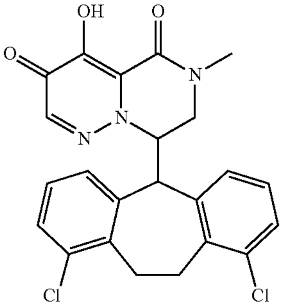
,
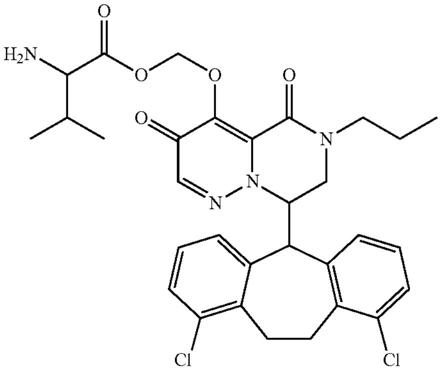
,
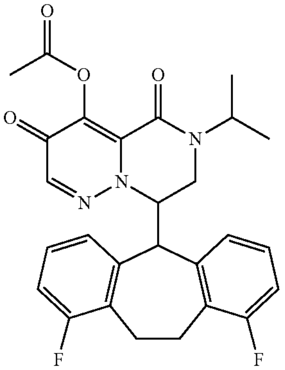
,
-continued
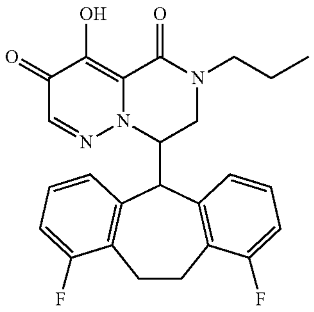
,
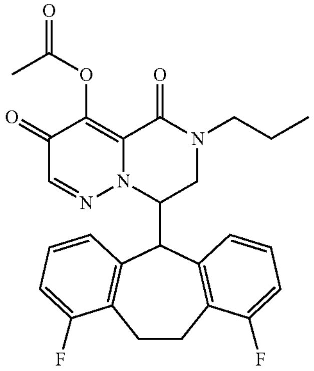
,
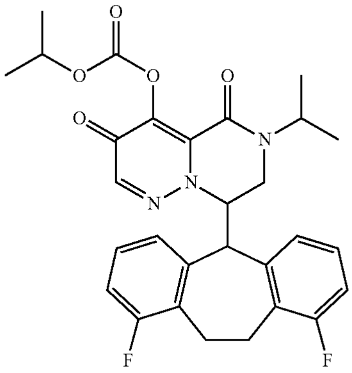
,
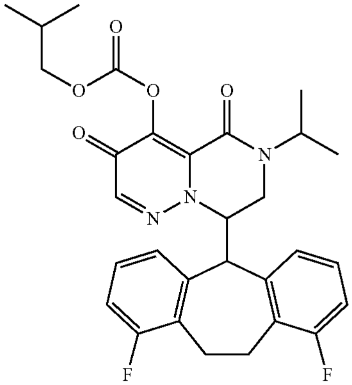
, -continued
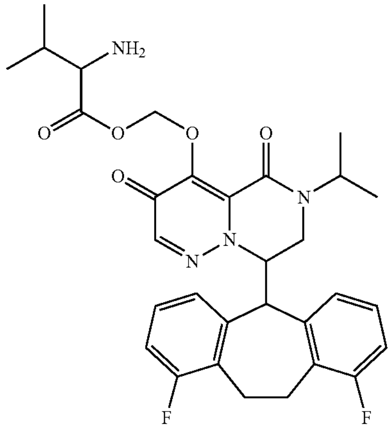,
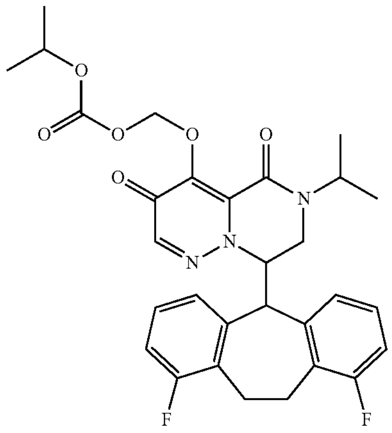,
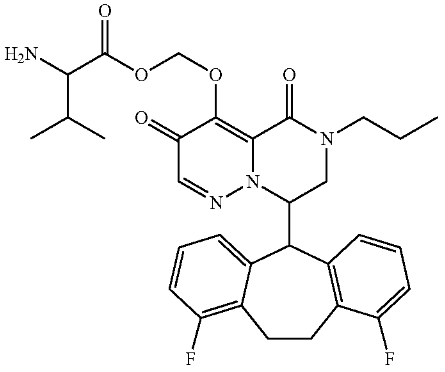,
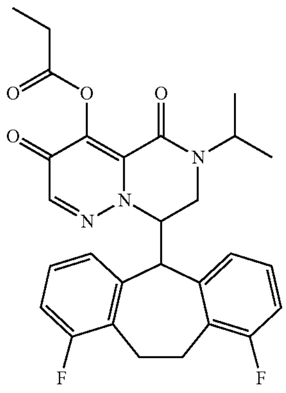,
-continued
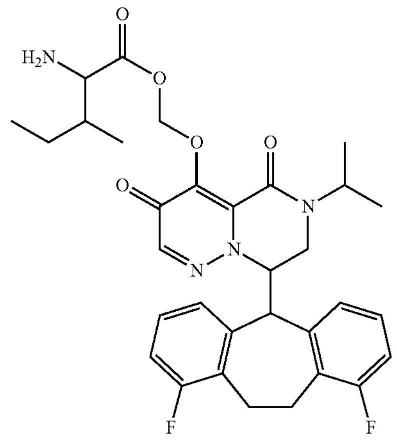,
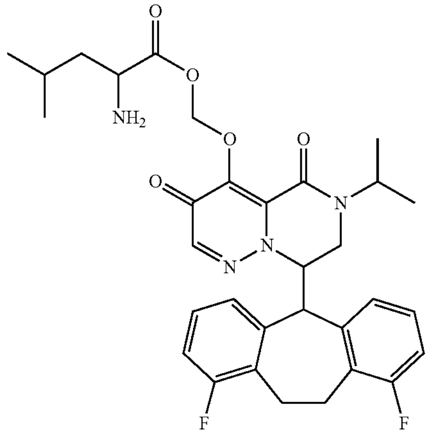,
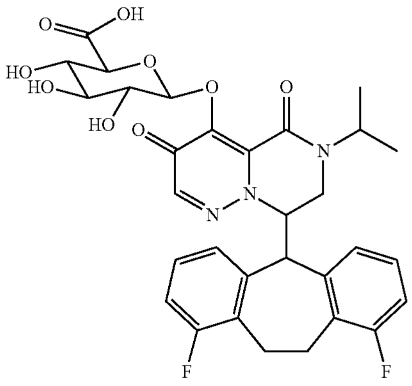,
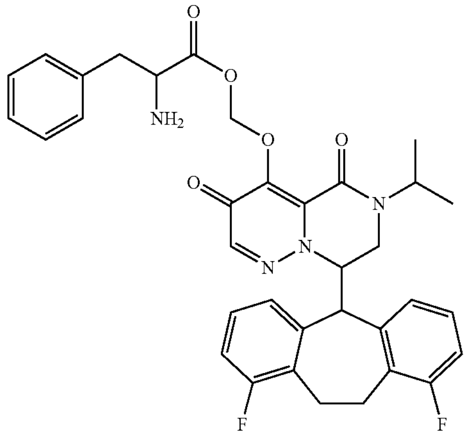, -continued
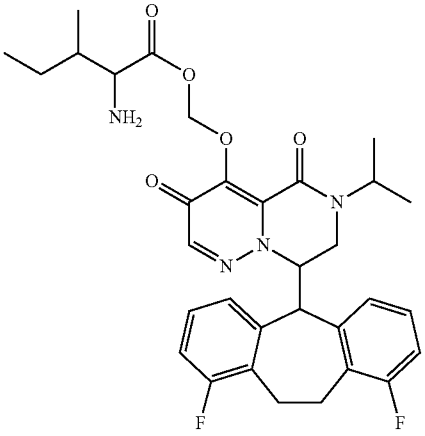
,
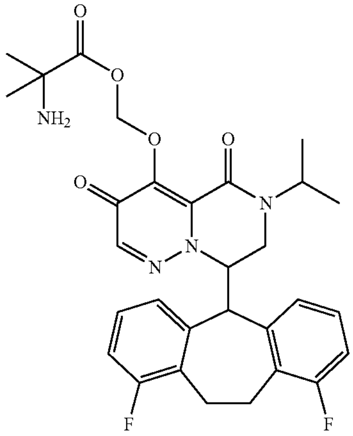
,
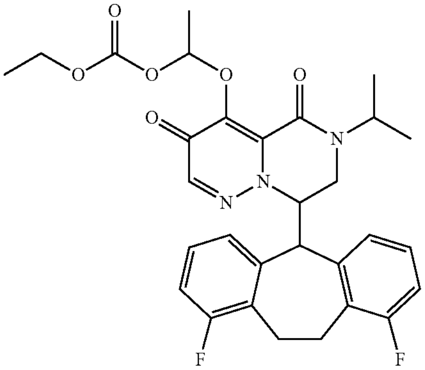
,
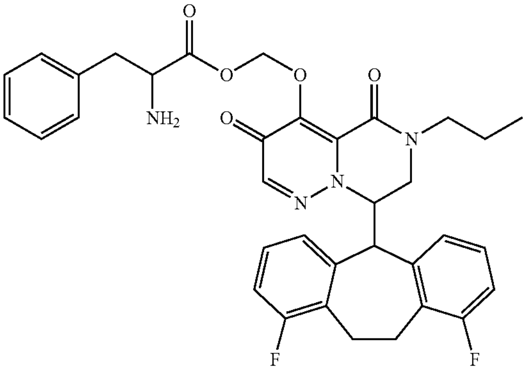
,
-continued
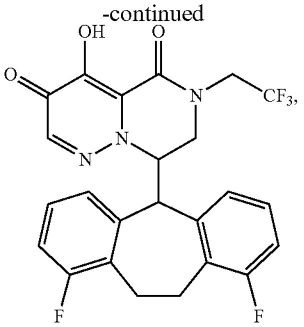
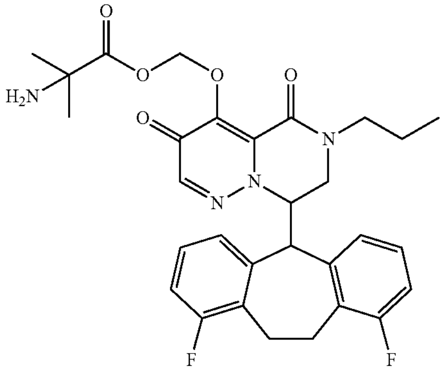
,
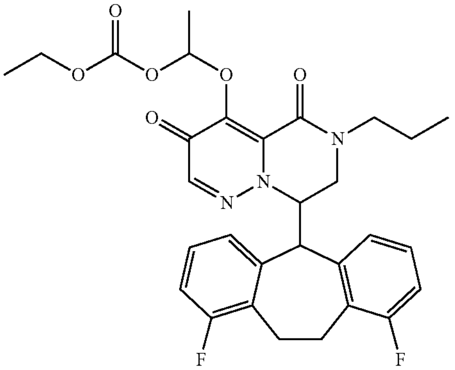
,
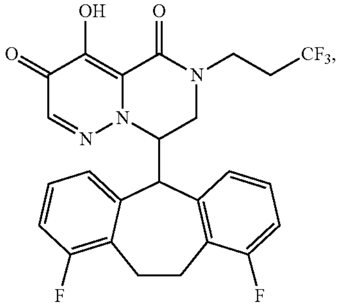
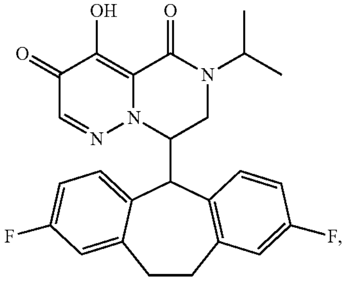

-continued
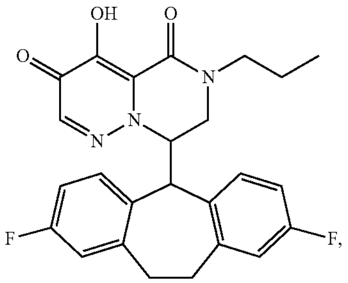
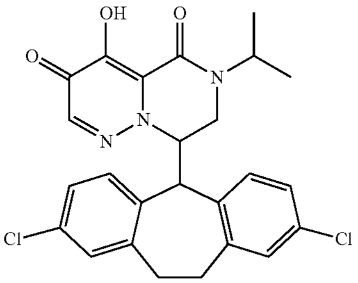
and
-continued
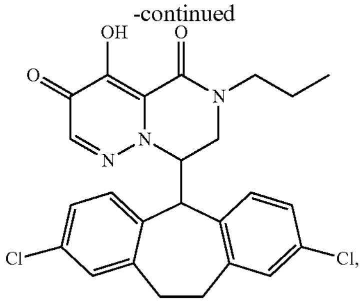
or a pharmaceutically acceptable salt of any of the foregoing.
30. The compound of claim 1, wherein the compound is a compound of the following structure:
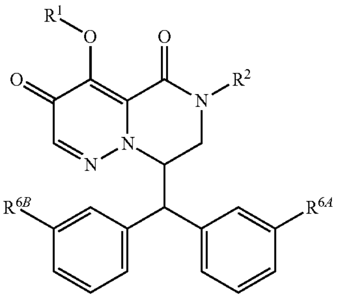
wherein the compound is selected from the group consisting of:
| $R^2$ | $R^1$ | $R^{6A}$ | $R^{6B}$ |
|---|---|---|---|
| 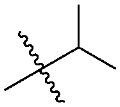 [SMILES: *C(C)C] | 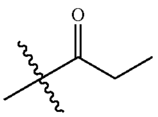 [SMILES: *C(=O)CC] | H | H |
| 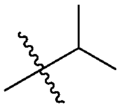 [SMILES: *C(C)C] | 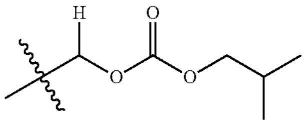 [SMILES: *COC(=O)OCC(C)C] | H | H |
| 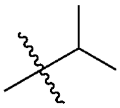 [SMILES: *C(C)C] | 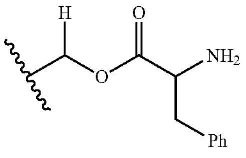 [SMILES: *COC(=O)C(N)Cc1ccccc1] | H | H |
| 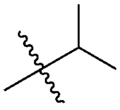 [SMILES: *C(C)C] | 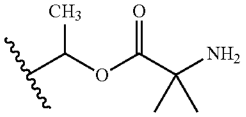 [SMILES: *C(C)OC(=O)C(C)(C)N] | H | H |
| 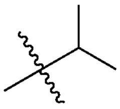 [SMILES: *C(C)C] | 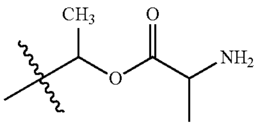 | H | H |

-continued
| $R^2$ | $R^1$ | $R^{6A}$ | $R^{6B}$ |
|---|---|---|---|
| 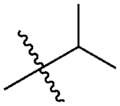 [SMILES: *C(C)C] | 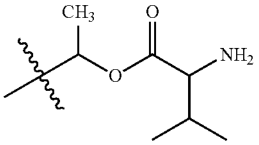 | H | H |
| 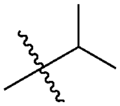 [SMILES: *C(C)C] | 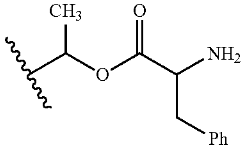 | H | H |
| 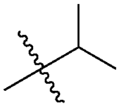 [SMILES: *C(C)C] | 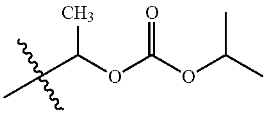 [SMILES: *C(C)OC(=O)OC(C)C] | H | H |
| 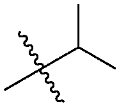 [SMILES: *C(C)C] | 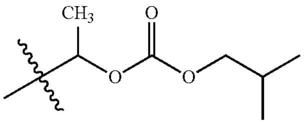 [SMILES: *C(C)OC(=O)OCC(C)C] | H | H |
| —$CH_3$ | 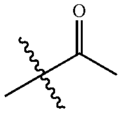 [SMILES: *C(C)=O] | H | H |
| —$CH_3$ | 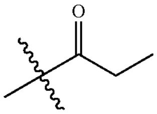 [SMILES: *C(=O)CC] | H | H |
| —$CH_3$ | 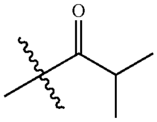 [SMILES: *C(=O)C(C)C] | H | H |
| —$CH_3$ | 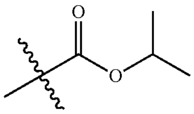 [SMILES: *C(=O)OC(C)C] | H | H |
| —$CH_3$ | 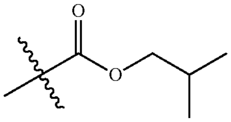 [SMILES: *C(=O)OCC(C)C] | H | H |
| —$CH_3$ | 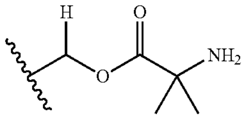 [SMILES: *COC(=O)C(C)(C)N] | H | H |
| —$CH_3$ | 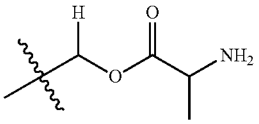 [SMILES: *COC(=O)C(C)N] | H | H |

-continued
| $R^2$ | $R^1$ | $R^{6A}$ | $R^{6B}$ |
|---|---|---|---|
| $—CH_3$ | 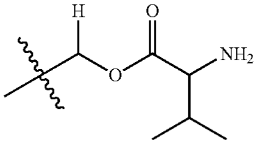 [SMILES: *COC(=O)C(N)C(C)C] | H | H |
| $—CH_3$ | 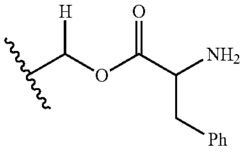 [SMILES: *COC(=O)C(N)Cc1ccccc1] | H | H |
| $—CH_3$ | 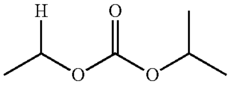 | H | H |
| $—CH_3$ | 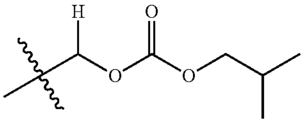 [SMILES: *COC(=O)OCC(C)C] | H | H |
| $—CH_3$ | 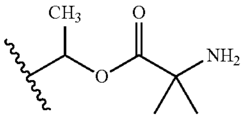 [SMILES: *C(C)OC(=O)C(C)(C)N] | H | H |
| $—CH_3$ | 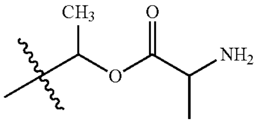 | H | H |
| $—CH_3$ | 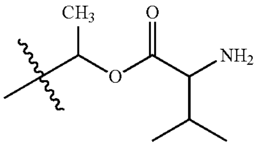 | H | H |
| $—CH_3$ | 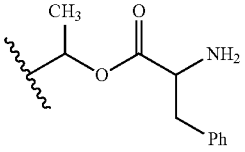 [SMILES: *C(C)OC(=O)C(N)Cc1ccccc1] | H | H |
| $—CH_3$ | 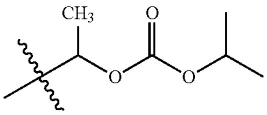 [SMILES: *C(C)OC(=O)OC(C)C] | H | H |
| $—CH_3$ | 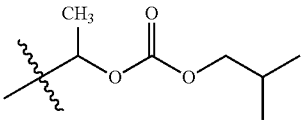 [SMILES: *C(C)OC(=O)OCC(C)C] | H | H |
| $—CH_2CH_3$ | 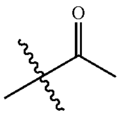 [SMILES: *C(C)=O] | H | H |

-continued
| $R^2$ | $R^1$ | $R^{6A}$ | $R^{6B}$ |
|---|---|---|---|
| $—CH_2CH_3$ | 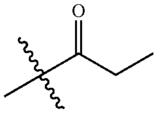 [SMILES: *C(=O)CC] | H | H |
| $—CH_2CH_3$ | 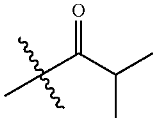 [SMILES: *C(=O)C(C)C] | H | H |
| $—CH_2CH_3$ | 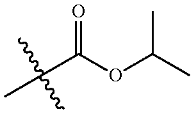 [SMILES: *C(=O)OC(C)C] | H | H |
| $—CH_2CH_3$ | 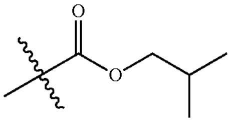 [SMILES: *C(=O)OCC(C)C] | H | H |
| $—CH_2CH_3$ | 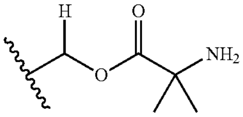 [SMILES: *COC(=O)C(C)(C)N] | H | H |
| $—CH_2CH_3$ | 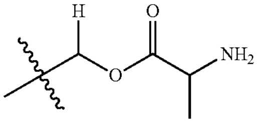 | H | H |
| $—CH_2CH_3$ | 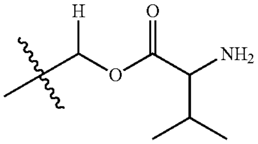 [SMILES: *COC(=O)C(N)C(C)C] | H | H |
| $—CH_2CH_3$ | 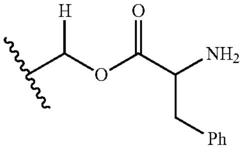 [SMILES: *COC(=O)C(N)Cc1ccccc1] | H | H |
| $—CH_2CH_3$ | 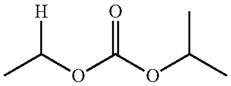 | H | H |
| $—CH_2CH_3$ | 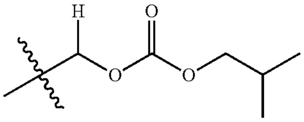 [SMILES: *COC(=O)OCC(C)C] | H | H |
| $—CH_2CH_3$ | 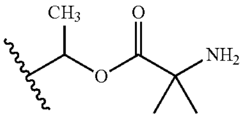 | H | H |

-continued
| $R^2$ | $R^1$ | $R^{6A}$ | $R^{6B}$ |
|---|---|---|---|
| $—CH_2CH_3$ | 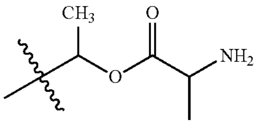 | H | H |
| $—CH_2CH_3$ | 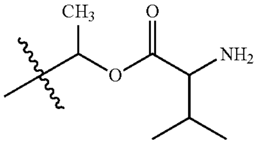 [SMILES: *C(C)OC(=O)C(N)C(C)C] | H | H |
| $—CH_2CH_3$ | 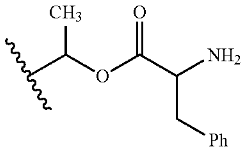 [SMILES: *C(C)OC(=O)C(N)Cc1ccccc1] | H | H |
| $—CH_2CH_3$ | 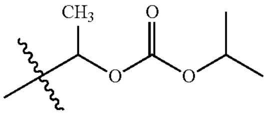 [SMILES: *C(C)OC(=O)OC(C)C] | H | H |
| $—CH_2CH_3$ | 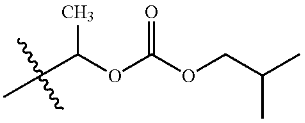 | H | H |
| $—CH_2CH(CH_3)_2$ | 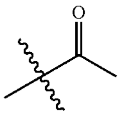 [SMILES: *C(C)=O] | H | H |
| $—CH_2CH(CH_3)_2$ | 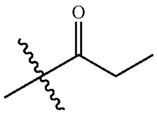 [SMILES: *C(=O)CC] | H | H |
| $—CH_2CH(CH_3)_2$ | 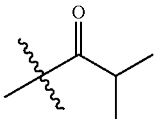 [SMILES: *C(=O)C(C)C] | H | H |
| $—CH_2CH(CH_3)_2$ | 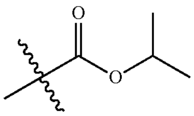 [SMILES: *C(=O)OC(C)C] | H | H |
| $—CH_2CH(CH_3)_2$ | 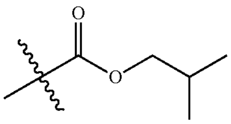 [SMILES: *C(=O)OCC(C)C] | H | H |
| $—CH_2CH(CH_3)_2$ | 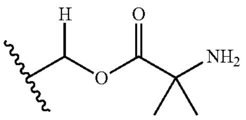 [SMILES: *COC(=O)C(C)(C)N] | H | H |

-continued
| $R^2$ | $R^1$ | $R^{6A}$ | $R^{6B}$ |
|---|---|---|---|
| $—CH_2CH(CH_3)_2$ | 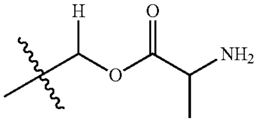 [SMILES: *COC(=O)C(C)N] | H | H |
| $—CH_2CH(CH_3)_2$ | 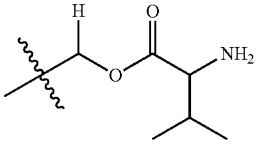 [SMILES: *COC(=O)C(N)C(C)C] | H | H |
| $—CH_2CH(CH_3)_2$ | 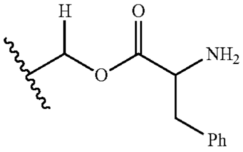 [SMILES: *COC(=O)C(N)Cc1ccccc1] | H | H |
| $—CH_2CH(CH_3)_2$ | 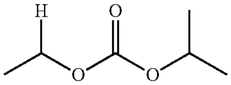 | H | H |
| $—CH_2CH(CH_3)_2$ | 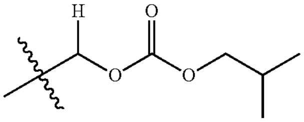 [SMILES: *COC(=O)OCC(C)C] | H | H |
| $—CH_2CH(CH_3)_2$ | 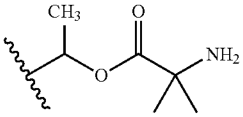 [SMILES: *C(C)OC(=O)C(C)(C)N] | H | H |
| $—CH_2CH(CH_3)_2$ | 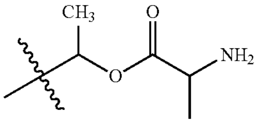 | H | H |
| $—CH_2CH(CH_3)_2$ | 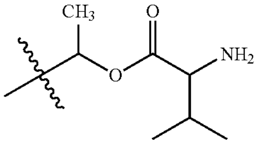 | H | H |
| $—CH_2CH(CH_3)_2$ | 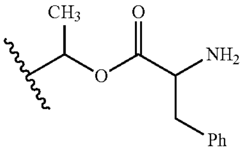 | H | H |
| $—CH_2CH(CH_3)_2$ | 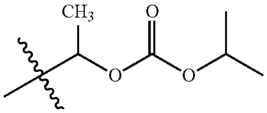 [SMILES: *C(C)OC(=O)OC(C)C] | H | H |
| $—CH_2CH(CH_3)_2$ | 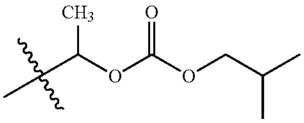 | H | H |

-continued
| $R^2$ | $R^1$ | $R^{6A}$ | $R^{6B}$ |
|---|---|---|---|
| $—CH_2CH_2CH_3$ | 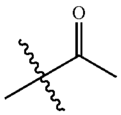 [SMILES: *C(C)=O] | H | H |
| $—CH_2CH_2CH_3$ | 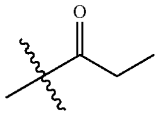 [SMILES: *C(=O)CC] | H | H |
| $—CH_2CH_2CH_3$ | 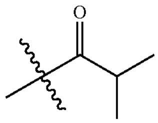 [SMILES: *C(=O)C(C)C] | H | H |
| $—CH_2CH_2CH_3$ | 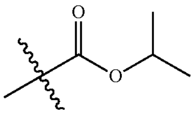 [SMILES: *C(=O)OC(C)C] | H | H |
| $—CH_2CH_2CH_3$ | 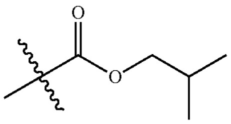 [SMILES: *C(=O)OCC(C)C] | H | H |
| $—CH_2CH_2CH_3$ | 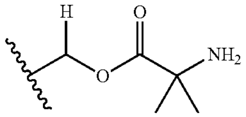 [SMILES: *COC(=O)C(C)(C)N] | H | H |
| $—CH_2CH_2CH_3$ | 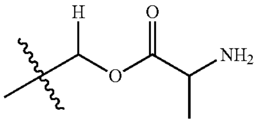 [SMILES: *COC(=O)C(C)N] | H | H |
| $—CH_2CH_2CH_3$ | 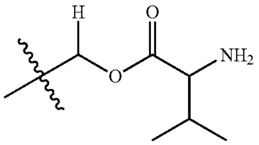 [SMILES: *COC(=O)C(N)C(C)C] | H | H |
| $—CH_2CH_2CH_3$ | 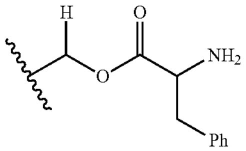 | H | H |
| $—CH_2CH_2CH_3$ | 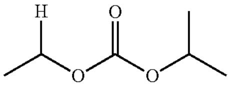 | H | H |
| $—CH_2CH_2CH_3$ | 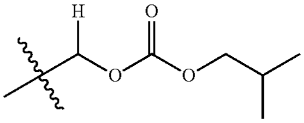 [SMILES: *COC(=O)OCC(C)C] | H | H |

-continued
| $R^2$ | $R^1$ | $R^{6A}$ | $R^{6B}$ |
|---|---|---|---|
| $—CH_2CH_2CH_3$ | 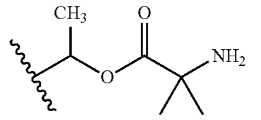 | H | H |
| $—CH_2CH_2CH_3$ | 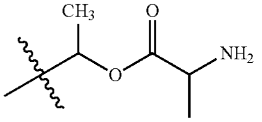 | H | H |
| $—CH_2CH_2CH_3$ | 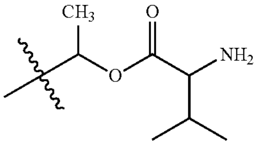 | H | H |
| $—CH_2CH_2CH_3$ | 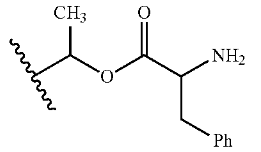 | H | H |
| $—CH_2CH_2CH_3$ | 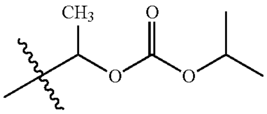 [SMILES: *C(C)OC(=O)OC(C)C] | H | H |
| $—CH_2CH_2CH_3$ | 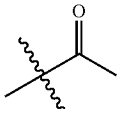 [SMILES: *C(C)=O] | H | H |
| $—CH_2CH_2CH_2CH_3$ | 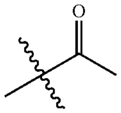 [SMILES: *C(C)=O] | H | H |
| $—CH_2CH_2CH_2CH_3$ | 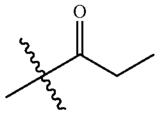 [SMILES: *C(=O)CC] | H | H |
| $—CH_2CH_2CH_2CH_3$ | 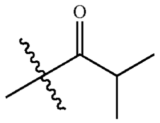 [SMILES: *C(=O)C(C)C] | H | H |
| $—CH_2CH_2CH_2CH_3$ | 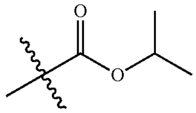 [SMILES: *C(=O)OC(C)C] | H | H |
| $—CH_2CH_2CH_2CH_3$ | 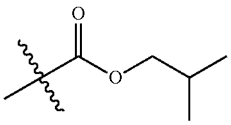 [SMILES: *C(=O)OCC(C)C] | H | H |

-continued
| $R^2$ | $R^1$ | $R^{6A}$ | $R^{6B}$ |
|---|---|---|---|
| $—CH_2CH_2CH_2CH_3$ | 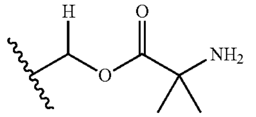 [SMILES: *COC(=O)C(C)(C)N] | H | H |
| $—CH_2CH_2CH_2CH_3$ | 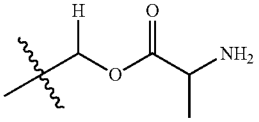 | H | H |
| $—CH_2CH_2CH_2CH_3$ | 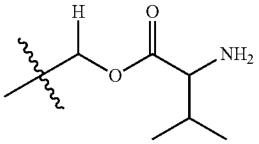 [SMILES: *COC(=O)C(N)C(C)C] | H | H |
| $—CH_2CH_2CH_2CH_3$ | 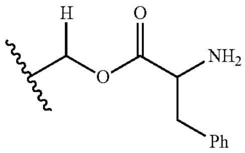 [SMILES: *COC(=O)C(N)Cc1ccccc1] | H | H |
| $—CH_2CH_2CH_2CH_3$ | 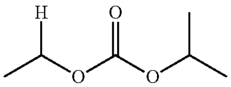 | H | H |
| $—CH_2CH_2CH_2CH_3$ | 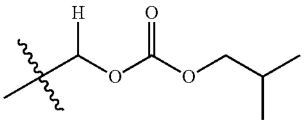 [SMILES: *COC(=O)OCC(C)C] | H | H |
| $—CH_2CH_2CH_2CH_3$ | 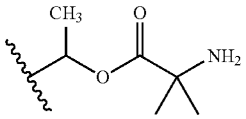 [SMILES: *C(C)OC(=O)C(C)(C)N] | H | H |
| $—CH_2CH_2CH_2CH_3$ | 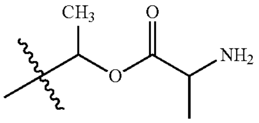 [SMILES: *C(C)OC(=O)C(C)N] | H | H |
| $—CH_2CH_2CH_2CH_3$ | 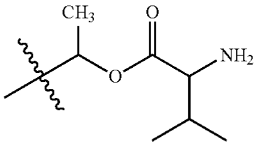 [SMILES: *C(C)OC(=O)C(N)C(C)C] | H | H |
| $—CH_2CH_2CH_2CH_3$ | 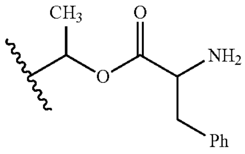 | H | H |
| $—CH_2CH_2CH_2CH_3$ | 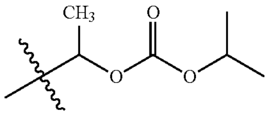 [SMILES: *C(C)OC(=O)OC(C)C] | H | H |

-continued
| $R^2$ | $R^1$ | $R^{6A}$ | $R^{6B}$ |
|---|---|---|---|
| $—CH_2CH_2CH_2CH_3$ | 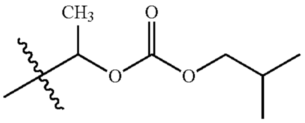 | H | H |
| 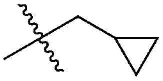 [SMILES: *CC1CC1] | 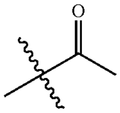 [SMILES: *C(C)=O] | H | H |
| 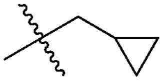 [SMILES: *CC1CC1] | 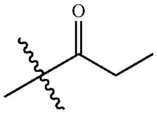 [SMILES: *C(=O)CC] | H | H |
| 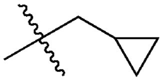 | 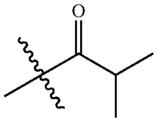 [SMILES: *C(=O)C(C)C] | H | H |
| 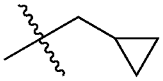 [SMILES: *CC1CC1] | 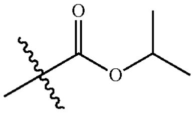 [SMILES: *C(=O)OC(C)C] | H | H |
| 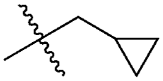 [SMILES: *CC1CC1] | 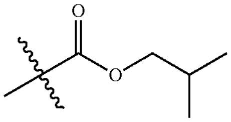 [SMILES: *C(=O)OCC(C)C] | H | H |
| 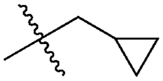 [SMILES: *CC1CC1] | 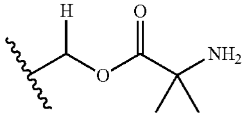 [SMILES: *COC(=O)C(C)(C)N] | H | H |
| 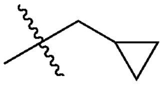 | 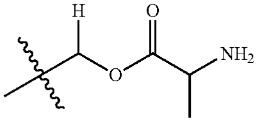 [SMILES: *COC(=O)C(C)N] | H | H |
| 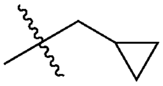 [SMILES: *CC1CC1] | 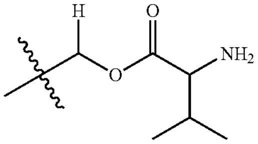 [SMILES: *COC(=O)C(N)C(C)C] | H | H |
| 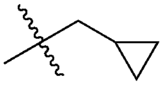 [SMILES: *CC1CC1] | 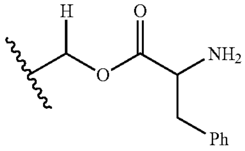 [SMILES: *COC(=O)C(N)Cc1ccccc1] | H | H |
| 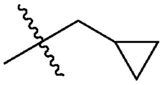 [SMILES: *CC1CC1] | 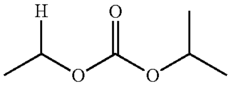 | H | H |

-continued
| $R^2$ | $R^1$ | $R^{6A}$ | $R^{6B}$ |
|---|---|---|---|
| 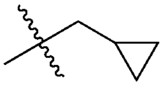 [SMILES: *CC1CC1] | 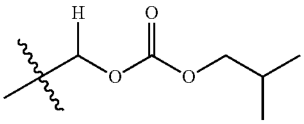 [SMILES: *COC(=O)OCC(C)C] | H | H |
| 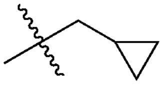 [SMILES: *CC1CC1] | 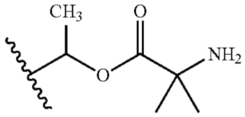 [SMILES: *C(C)OC(=O)C(C)(C)N] | H | H |
| 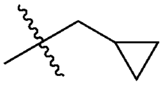 | 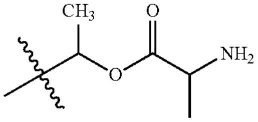 | H | H |
| 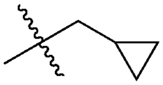 | 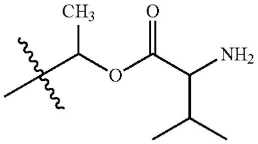 | H | H |
| 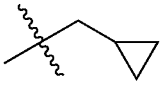 [SMILES: *CC1CC1] | 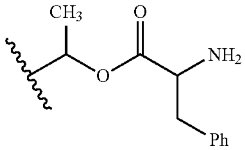 | H | H |
| 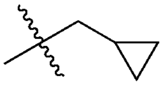 [SMILES: *CC1CC1] | 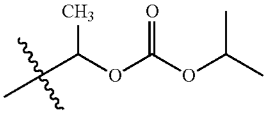 [SMILES: *C(C)OC(=O)OC(C)C] | H | H |
| 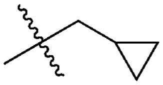 | 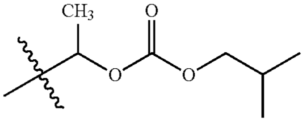 | H | H |
| 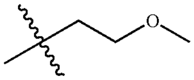 [SMILES: *CCOC] | 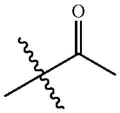 [SMILES: *C(C)=O] | H | H |
| 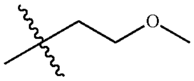 [SMILES: *CCOC] | 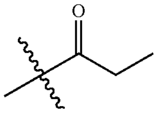 [SMILES: *C(=O)CC] | H | H |
| 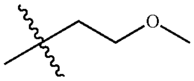 [SMILES: *CCOC] | 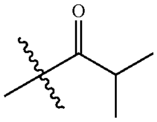 [SMILES: *C(=O)C(C)C] | H | H |
| 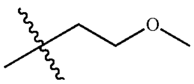 [SMILES: *CCOC] | 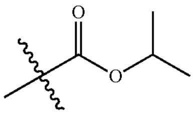 [SMILES: *C(=O)OC(C)C] | H | H |

-continued
| $R^2$ | $R^1$ | $R^{6A}$ | $R^{6B}$ |
|---|---|---|---|
| 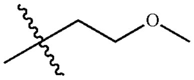 [SMILES: *CCOC] | 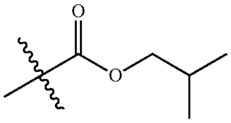 [SMILES: *C(=O)OCC(C)C] | H | H |
| 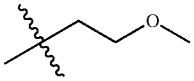 [SMILES: *CCOC] | 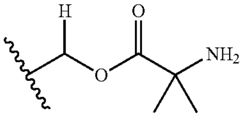 [SMILES: *COC(=O)C(C)(C)N] | H | H |
| 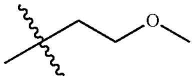 [SMILES: *CCOC] | 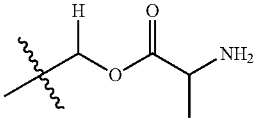 [SMILES: *COC(=O)C(C)N] | H | H |
| 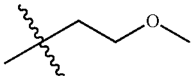 [SMILES: *CCOC] | 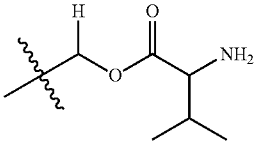 [SMILES: *COC(=O)C(N)C(C)C] | H | H |
| 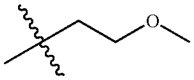 [SMILES: *CCOC] | 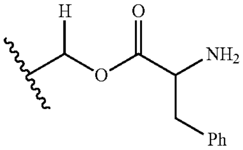 [SMILES: *COC(=O)C(N)Cc1ccccc1] | H | H |
| 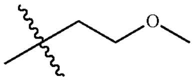 [SMILES: *CCOC] | 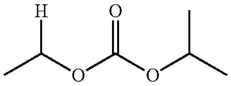 | H | H |
| 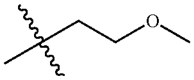 [SMILES: *CCOC] | 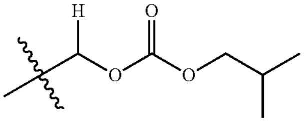 [SMILES: *COC(=O)OCC(C)C] | H | H |
| 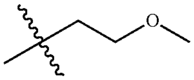 [SMILES: *CCOC] | 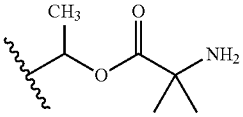 | H | H |
| 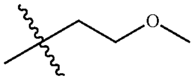 [SMILES: *CCOC] | 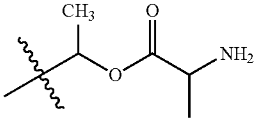 | H | H |
| 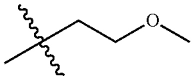 [SMILES: *CCOC] | 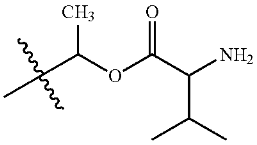 | H | H |
| 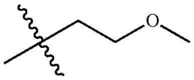 [SMILES: *CCOC] | 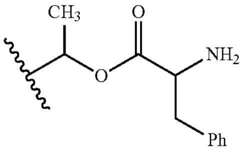 | H | H |

-continued
| $R^2$ | $R^1$ | $R^{6A}$ | $R^{6B}$ |
|---|---|---|---|
| 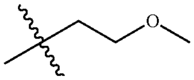 [SMILES: *CCOC] | 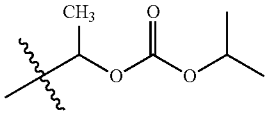 [SMILES: *C(C)OC(=O)OC(C)C] | H | H |
| 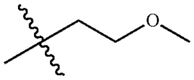 [SMILES: *CCOC] | 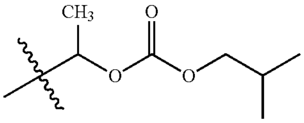 | H | H |
| 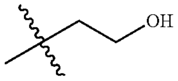 [SMILES: *CCO] | 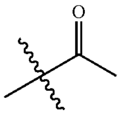 [SMILES: *C(C)=O] | H | H |
| 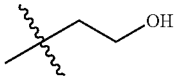 [SMILES: *CCO] | 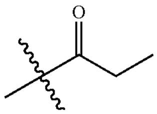 [SMILES: *C(=O)CC] | H | H |
| 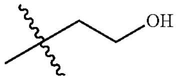 [SMILES: *CCO] | 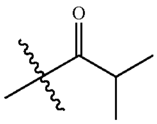 [SMILES: *C(=O)C(C)C] | H | H |
| 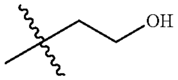 [SMILES: *CCO] | 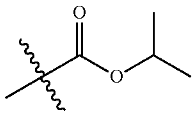 [SMILES: *C(=O)OC(C)C] | H | H |
| 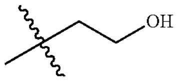 [SMILES: *CCO] | 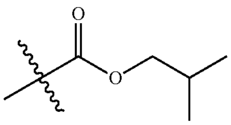 [SMILES: *C(=O)OCC(C)C] | H | H |
| 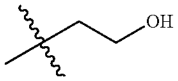 [SMILES: *CCO] | 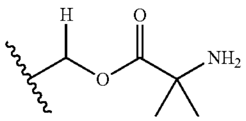 [SMILES: *COC(=O)C(C)(C)N] | H | H |
| 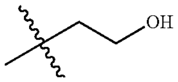 [SMILES: *CCO] | 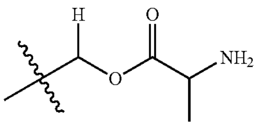 [SMILES: *COC(=O)C(C)N] | H | H |
| 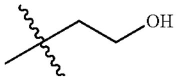 [SMILES: *CCO] | 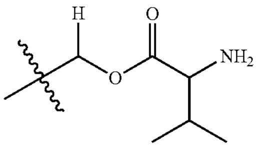 [SMILES: *COC(=O)C(N)C(C)C] | H | H |
| 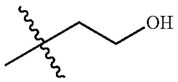 [SMILES: *CCO] | 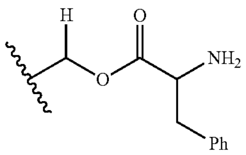 [SMILES: *COC(=O)C(N)Cc1ccccc1] | H | H |

-continued
| $R^2$ | $R^1$ | $R^{6A}$ | $R^{6B}$ |
|---|---|---|---|
| 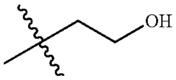 [SMILES: *CCO] | 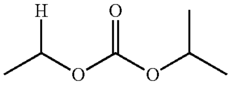 | H | H |
| 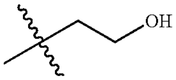 [SMILES: *CCO] | 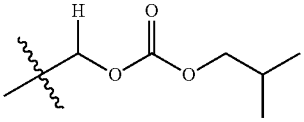 [SMILES: *COC(=O)OCC(C)C] | H | H |
| 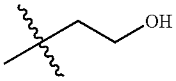 [SMILES: *CCO] | 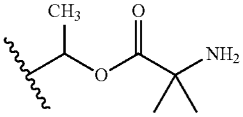 [SMILES: *C(C)OC(=O)C(C)(C)N] | H | H |
| 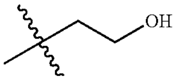 [SMILES: *CCO] | 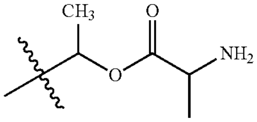 | H | H |
| 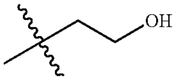 [SMILES: *CCO] | 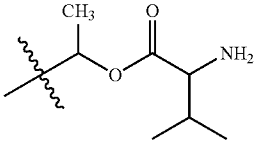 | H | H |
| 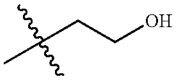 [SMILES: *CCO] | 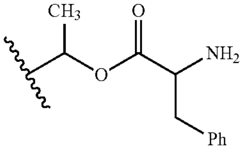 | H | H |
| 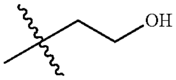 [SMILES: *CCO] | 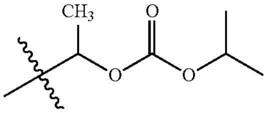 [SMILES: *C(C)OC(=O)OC(C)C] | H | H |
| 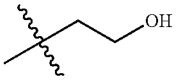 [SMILES: *CCO] | 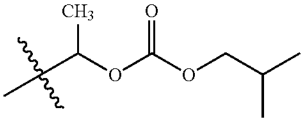 | H | H |
| $—CH_2CH=CF_2$ | 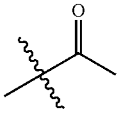 [SMILES: *C(C)=O] | H | H |
| $—CH_2CH=CF_2$ | 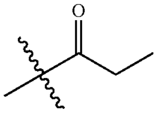 [SMILES: *C(=O)CC] | H | H |
| $—CH_2CH=CF_2$ | 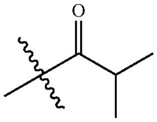 [SMILES: *C(=O)C(C)C] | H | H |

-continued
| $R^2$ | $R^1$ | $R^{6A}$ | $R^{6B}$ |
|---|---|---|---|
| $—CH_2CH=CF_2$ | 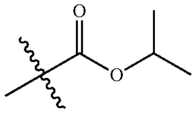 [SMILES: *C(=O)OC(C)C] | H | H |
| $—CH_2CH=CF_2$ | 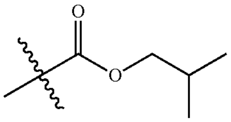 [SMILES: *C(=O)OCC(C)C] | H | H |
| $—CH_2CH=CF_2$ | 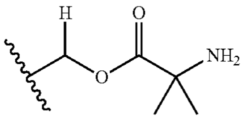 [SMILES: *COC(=O)C(C)(C)N] | H | H |
| $—CH_2CH=CF_2$ | 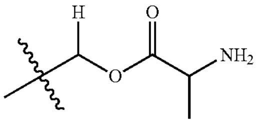 [SMILES: *COC(=O)C(C)N] | H | H |
| $—CH_2CH=CF_2$ | 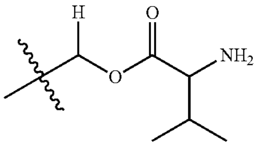 [SMILES: *COC(=O)C(N)C(C)C] | H | H |
| $—CH_2CH=CF_2$ | 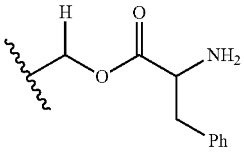 [SMILES: *COC(=O)C(N)Cc1ccccc1] | H | H |
| $—CH_2CH=CF_2$ | 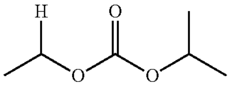 | H | H |
| $—CH_2CH=CF_2$ | 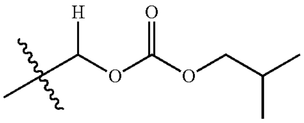 [SMILES: *COC(=O)OCC(C)C] | H | H |
| $—CH_2CH=CF_2$ | 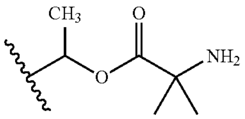 [SMILES: *C(C)OC(=O)C(C)(C)N] | H | H |
| $—CH_2CH=CF_2$ | 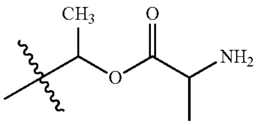 | H | H |
| $—CH_2CH=CF_2$ | 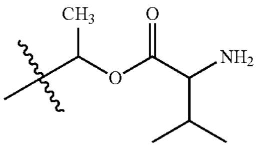 | H | H |

-continued
| $R^2$ | $R^1$ | $R^{6A}$ | $R^{6B}$ |
|---|---|---|---|
| $—CH_2CH{=}CF_2$ | 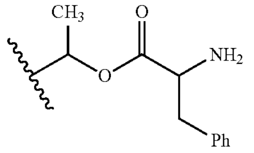 | H | H |
| $—CH_2CH{=}CF_2$ | 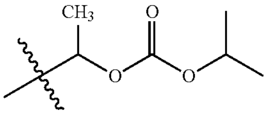 [SMILES: *C(C)OC(=O)OC(C)C] | H | H |
| $—CH_2CH{=}CF_2$ | 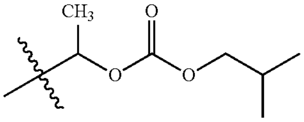 | H | H |
| $—CH_2CF_3$ | 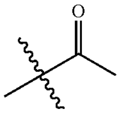 [SMILES: *C(C)=O] | H | H |
| $—CH_2CF_3$ | 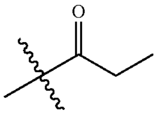 [SMILES: *C(=O)CC] | H | H |
| $—CH_2CF_3$ | 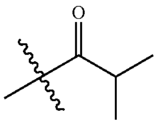 [SMILES: *C(=O)C(C)C] | H | H |
| $—CH_2CF_3$ | 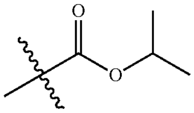 [SMILES: *C(=O)OC(C)C] | H | H |
| $—CH_2CF_3$ | 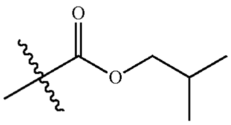 [SMILES: *C(=O)OCC(C)C] | H | H |
| $—CH_2CF_3$ | 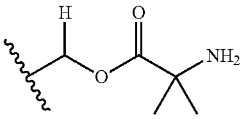 [SMILES: *COC(=O)C(C)(C)N] | H | H |
| $—CH_2CF_3$ | 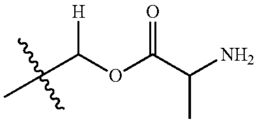 | H | H |
| $—CH_2CF_3$ | 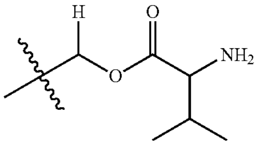 [SMILES: *COC(=O)C(N)C(C)C] | H | H |

-continued
| $R^2$ | $R^1$ | $R^{6A}$ | $R^{6B}$ |
|---|---|---|---|
| $-CH_2CF_3$ | 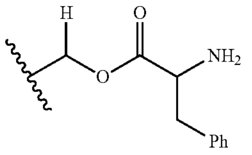 [SMILES: *COC(=O)C(N)Cc1ccccc1] | H | H |
| $-CH_2CF_3$ | 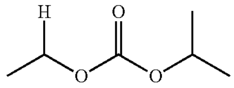 | H | H |
| $-CH_2CF_3$ | 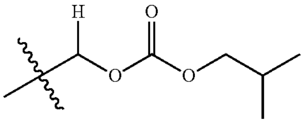 [SMILES: *COC(=O)OCC(C)C] | H | H |
| $-CH_2CF_3$ | 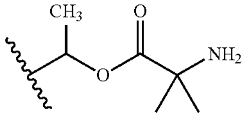 [SMILES: *C(C)OC(=O)C(C)(C)N] | H | H |
| $-CH_2CF_3$ | 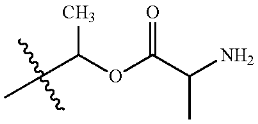 | H | H |
| $-CH_2CF_3$ | 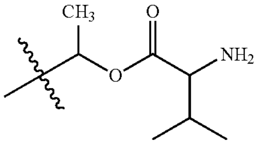 | H | H |
| $-CH_2CF_3$ | 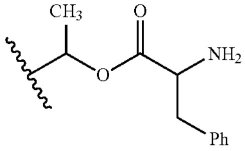 | H | H |
| $-CH_2CF_3$ | 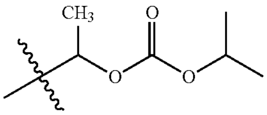 | H | H |
| $-CH_2CF_3$ | 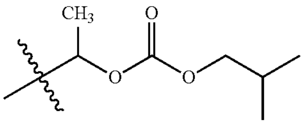 [SMILES: *C(C)OC(=O)OCC(C)C] | H | H |
| $-CH_2CH_2CF_3$ | 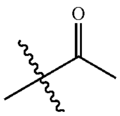 [SMILES: *C(C)=O] | H | H |
| $-CH_2CH_2CF_3$ | 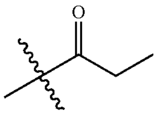 [SMILES: *C(=O)CC] | H | H |

-continued
| $R^2$ | $R^1$ | $R^{6A}$ | $R^{6B}$ |
|---|---|---|---|
| $—CH_2CH_2CF_3$ | 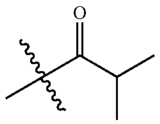 [SMILES: *C(=O)C(C)C] | H | H |
| $—CH_2CH_2CF_3$ | 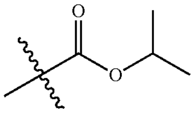 [SMILES: *C(=O)OC(C)C] | H | H |
| $—CH_2CH_2CF_3$ | 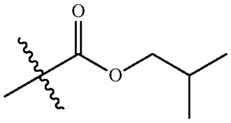 [SMILES: *C(=O)OCC(C)C] | H | H |
| $—CH_2CH_2CF_3$ | 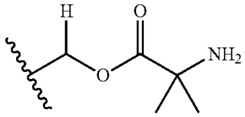 [SMILES: *COC(=O)C(C)(C)N] | H | H |
| $—CH_2CH_2CF_3$ | 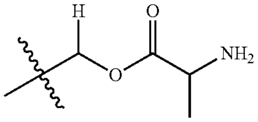 [SMILES: *COC(=O)C(C)N] | H | H |
| $—CH_2CH_2CF_3$ | 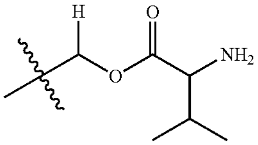 [SMILES: *COC(=O)C(N)C(C)C] | H | H |
| $—CH_2CH_2CF_3$ | 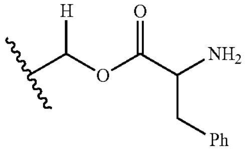 | H | H |
| $—CH_2CH_2CF_3$ | 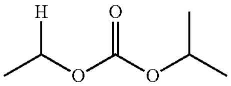 | H | H |
| $—CH_2CH_2CF_3$ | 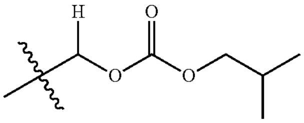 [SMILES: *COC(=O)OCC(C)C] | H | H |
| $—CH_2CH_2CF_3$ | 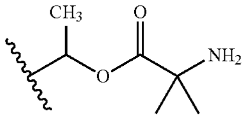 [SMILES: *C(C)OC(=O)C(C)(C)N] | H | H |
| $—CH_2CH_2CF_3$ | 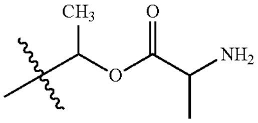 | H | H |

-continued
| $R^2$ | $R^1$ | $R^{6A}$ | $R^{6B}$ |
|---|---|---|---|
| $-CH_2CH_2CF_3$ | 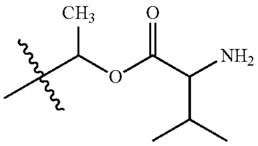 | H | H |
| $-CH_2CH_2CF_3$ | 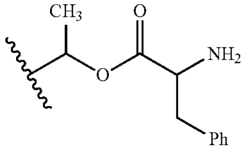 | H | H |
| $-CH_2CH_2CF_3$ | 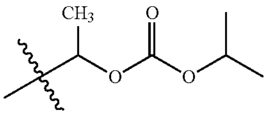 [SMILES: *C(C)OC(=O)OC(C)C] | H | H |
| $-CH_2CH_2CF_3$ | 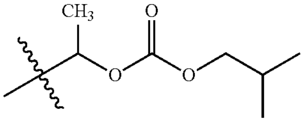 [SMILES: *C(C)OC(=O)OCC(C)C] | H | H |
| $-CH_2CHF_2$ | 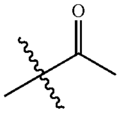 [SMILES: *C(C)=O] | H | H |
| $-CH_2CHF_2$ | 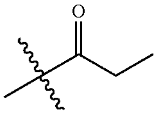 [SMILES: *C(=O)CC] | H | H |
| $-CH_2CHF_2$ | 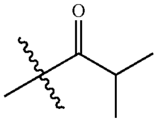 [SMILES: *C(=O)C(C)C] | H | H |
| $-CH_2CHF_2$ | 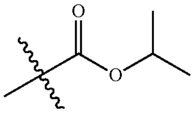 [SMILES: *C(=O)OC(C)C] | H | H |
| $-CH_2CHF_2$ | 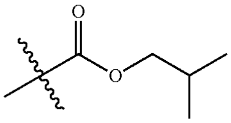 [SMILES: *C(=O)OCC(C)C] | H | H |
| $-CH_2CHF_2$ | 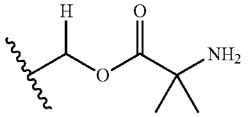 [SMILES: *COC(=O)C(C)(C)N] | H | H |
| $-CH_2CHF_2$ | 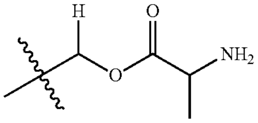 [SMILES: *COC(=O)C(C)N] | H | H |

-continued
| $R^2$ | $R^1$ | $R^{6A}$ | $R^{6B}$ |
|---|---|---|---|
| $—CH_2CHF_2$ | 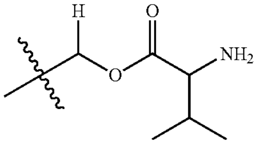 [SMILES: *COC(=O)C(N)C(C)C] | H | H |
| $—CH_2CHF_2$ | 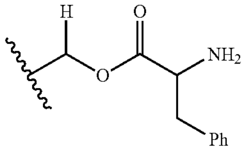 [SMILES: *COC(=O)C(N)Cc1ccccc1] | H | H |
| $—CH_2CHF_2$ | 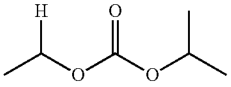 | H | H |
| $—CH_2CHF_2$ | 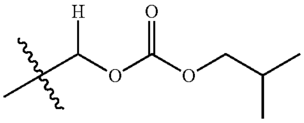 [SMILES: *COC(=O)OCC(C)C] | H | H |
| $—CH_2CHF_2$ | 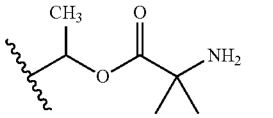 [SMILES: *C(C)OC(=O)C(C)(C)N] | H | H |
| $—CH_2CHF_2$ | 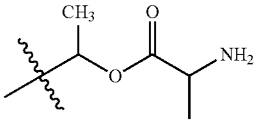 | H | H |
| $—CH_2CHF_2$ | 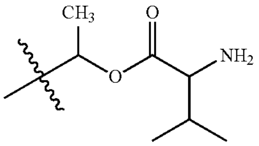 | H | H |
| $—CH_2CHF_2$ | 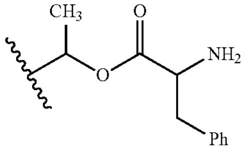 [SMILES: *C(C)OC(=O)C(N)Cc1ccccc1] | H | H |
| $—CH_2CHF_2$ | 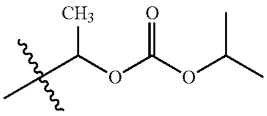 [SMILES: *C(C)OC(=O)OC(C)C] | H | H |
| $—CH_2CHF_2$ | 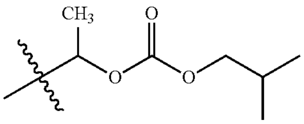 [SMILES: *C(C)OC(=O)OCC(C)C] | H | H |
| $—CH_2C(CH_3)F_2$ | 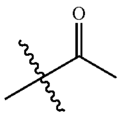 [SMILES: *C(C)=O] | H | H |

-continued
| $R^2$ | $R^1$ | $R^{6A}$ | $R^{6B}$ |
|---|---|---|---|
| $—CH_2C(CH_3)F_2$ | 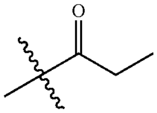 [SMILES: *C(=O)CC] | H | H |
| $—CH_2C(CH_3)F_2$ | 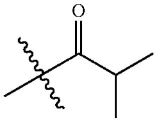 [SMILES: *C(=O)C(C)C] | H | H |
| $—CH_2C(CH_3)F_2$ | 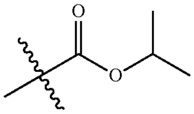 [SMILES: *C(=O)OC(C)C] | H | H |
| $—CH_2C(CH_3)F_2$ | 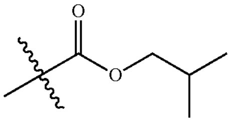 [SMILES: *C(=O)OCC(C)C] | H | H |
| $—CH_2C(CH_3)F_2$ | 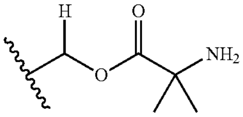 [SMILES: *COC(=O)C(C)(C)N] | H | H |
| $—CH_2C(CH_3)F_2$ | 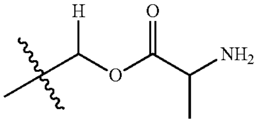 | H | H |
| $—CH_2C(CH_3)F_2$ | 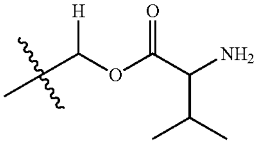 [SMILES: *COC(=O)C(N)C(C)C] | H | H |
| $—CH_2C(CH_3)F_3$ | 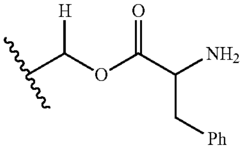 [SMILES: *COC(=O)C(N)Cc1ccccc1] | H | H |
| $—CH_2C(CH_3)F_3$ | 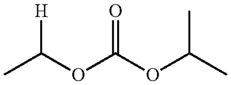 | H | H |
| $—CH_2C(CH_3)F_3$ | 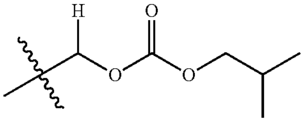 [SMILES: *COC(=O)OCC(C)C] | H | H |
| $—CH_2C(CH_3)F_3$ | 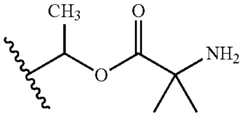 | H | H |

-continued
| $R^2$ | $R^1$ | $R^{6A}$ | $R^{6B}$ |
|---|---|---|---|
| $-CH_2C(CH_3)F_3$ | 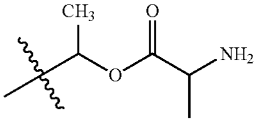 | H | H |
| $-CH_2C(CH_3)F_3$ | 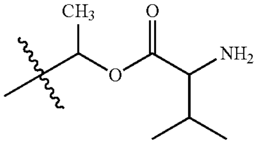 | H | H |
| $-CH_2C(CH_3)F_3$ | 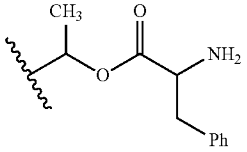 | H | H |
| $-CH_2C(CH_3)F_3$ | 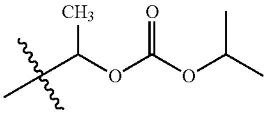 [SMILES: *C(C)OC(=O)OC(C)C] | H | H |
| $-CH_2C(CH_3)F_3$ | 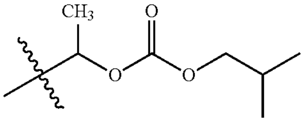 | H | H |
| 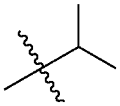 [SMILES: *C(C)C] | 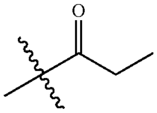 [SMILES: *C(=O)CC] | F | F |
| 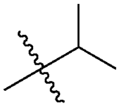 [SMILES: *C(C)C] | 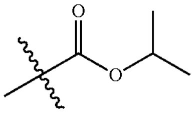 [SMILES: *C(=O)OC(C)C] | F | F |
| 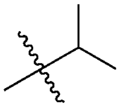 [SMILES: *C(C)C] | 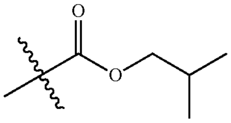 [SMILES: *C(=O)OCC(C)C] | F | F |
| 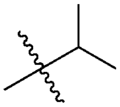 [SMILES: *C(C)C] | 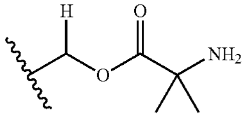 [SMILES: *COC(=O)C(C)(C)N] | F | F |
| 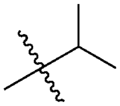 [SMILES: *C(C)C] | 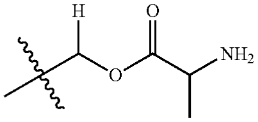 [SMILES: *COC(=O)C(C)N] | F | F |
| 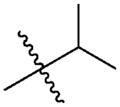 [SMILES: *C(C)C] | 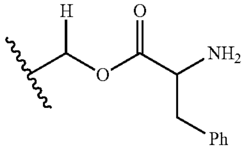 | F | F |

-continued
| $R^2$ | $R^1$ | $R^{6A}$ | $R^{6B}$ |
|---|---|---|---|
| 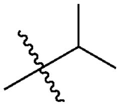 [SMILES: *C(C)C] | 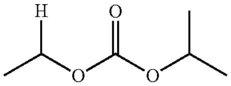 | F | F |
| 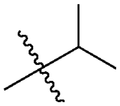 [SMILES: *C(C)C] | 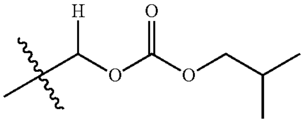 [SMILES: *COC(=O)OCC(C)C] | F | F |
| 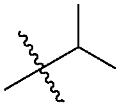 [SMILES: *C(C)C] | 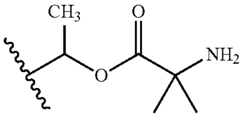 [SMILES: *C(C)OC(=O)C(C)(C)N] | F | F |
| 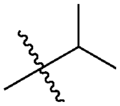 [SMILES: *C(C)C] | 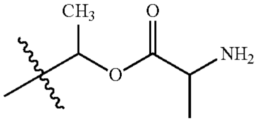 | F | F |
| 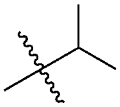 [SMILES: *C(C)C] | 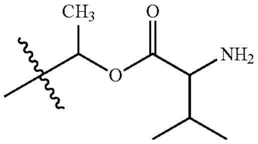 | F | F |
| 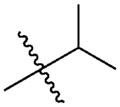 [SMILES: *C(C)C] | 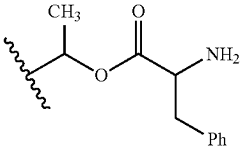 | F | F |
| 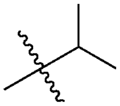 [SMILES: *C(C)C] | 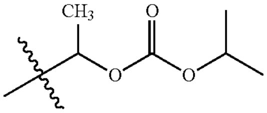 [SMILES: *C(C)OC(=O)OC(C)C] | F | F |
| 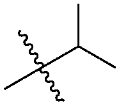 [SMILES: *C(C)C] | 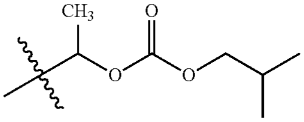 [SMILES: *C(C)OC(=O)OCC(C)C] | F | F |
| $—CH_3$ | 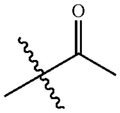 [SMILES: *C(C)=O] | F | F |
| $—CH_3$ | 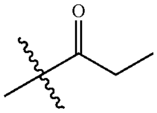 [SMILES: *C(=O)CC] | F | F |
| $—CH_3$ | 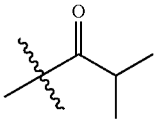 [SMILES: *C(=O)C(C)C] | F | F |

-continued
| $R^2$ | $R^1$ | $R^{6A}$ | $R^{6B}$ |
|---|---|---|---|
| —$CH_3$ | 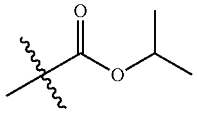 [SMILES: *C(=O)OC(C)C] | F | F |
| —$CH_3$ | 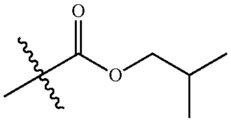 [SMILES: *C(=O)OCC(C)C] | F | F |
| —$CH_3$ | 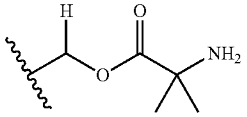 [SMILES: *COC(=O)C(C)(C)N] | F | F |
| —$CH_3$ | 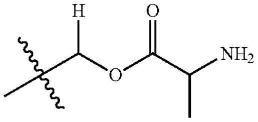 [SMILES: *COC(=O)C(C)N] | F | F |
| —$CH_3$ | 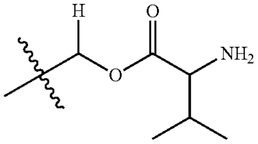 [SMILES: *COC(=O)C(N)C(C)C] | F | F |
| —$CH_3$ | 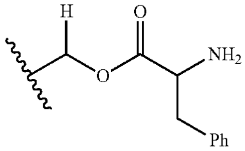 [SMILES: *COC(=O)C(N)Cc1ccccc1] | F | F |
| —$CH_3$ | 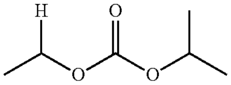 | F | F |
| —$CH_3$ | 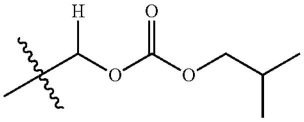 [SMILES: *COC(=O)OCC(C)C] | F | F |
| —$CH_3$ | 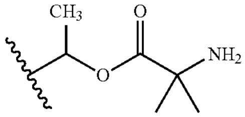 [SMILES: *C(C)OC(=O)C(C)(C)N] | F | F |
| —$CH_3$ | 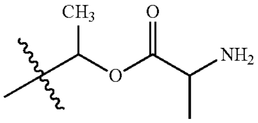 | F | F |
| —$CH_3$ | 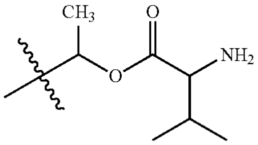 | F | F |

-continued
| $R^2$ | $R^1$ | $R^{6A}$ | $R^{6B}$ |
|---|---|---|---|
| $-CH_3$ | 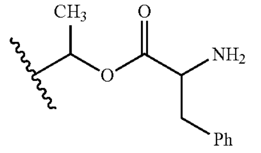 | F | F |
| $-CH_3$ | 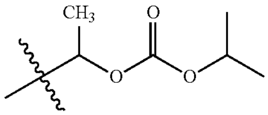 [SMILES: *C(C)OC(=O)OC(C)C] | F | F |
| $-CH_3$ | 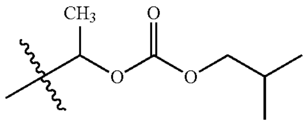 | F | F |
| $-CH_2CH_3$ | 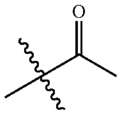 [SMILES: *C(C)=O] | F | F |
| $-CH_2CH_3$ | 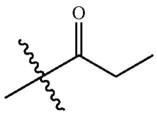 [SMILES: *C(=O)CC] | F | F |
| $-CH_2CH_3$ | 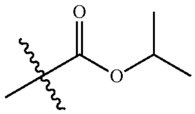 [SMILES: *C(=O)OC(C)C] | F | F |
| $-CH_2CH_3$ | 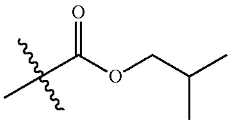 [SMILES: *C(=O)OCC(C)C] | F | F |
| $-CH_2CH_3$ | 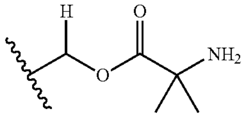 [SMILES: *COC(=O)C(C)(C)N] | F | F |
| $-CH_2CH_3$ | 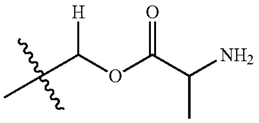 [SMILES: *COC(=O)C(C)N] | F | F |
| $-CH_2CH_3$ | 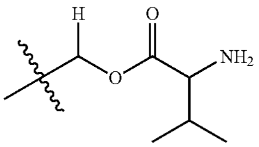 [SMILES: *COC(=O)C(N)C(C)C] | F | F |
| $-CH_2CH_3$ | 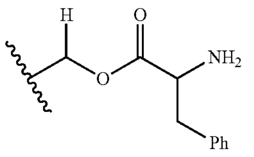 | F | F |

-continued
| $R^2$ | $R^1$ | $R^{6A}$ | $R^{6B}$ |
|---|---|---|---|
| $—CH_2CH_3$ | 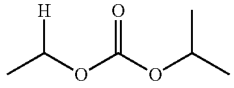 | F | F |
| $—CH_2CH_3$ | 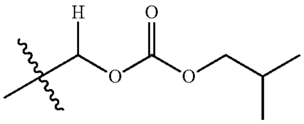 [SMILES: *COC(=O)OCC(C)C] | F | F |
| $—CH_2CH_3$ | 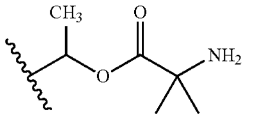 [SMILES: *C(C)OC(=O)C(C)(C)N] | F | F |
| $—CH_2CH_3$ | 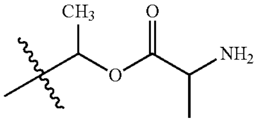 | F | F |
| $—CH_2CH_3$ | 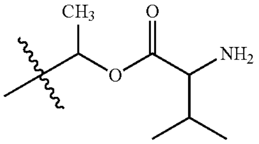 | F | F |
| $—CH_2CH_3$ | 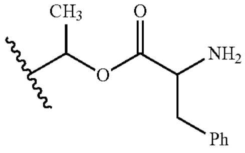 | F | F |
| $—CH_2CH_3$ | 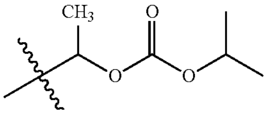 [SMILES: *C(C)OC(=O)OC(C)C] | F | F |
| $—CH_2CH_3$ | 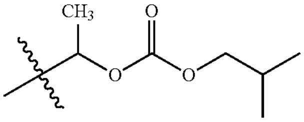 | F | F |
| $—CH_2CH(CH_3)_2$ | 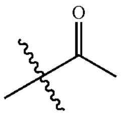 [SMILES: *C(C)=O] | F | F |
| $—CH_2CH(CH_3)_2$ | 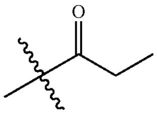 [SMILES: *C(=O)CC] | F | F |
| $—CH_2CH(CH_3)_2$ | 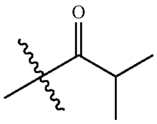 [SMILES: *C(=O)C(C)C] | F | F |

-continued
| $R^2$ | $R^1$ | $R^{6A}$ | $R^{6B}$ |
|---|---|---|---|
| $—CH_2CH(CH_3)_2$ | 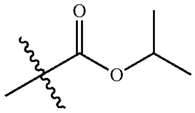 [SMILES: *C(=O)OC(C)C] | F | F |
| $—CH_2CH(CH_3)_2$ | 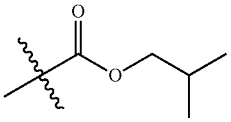 [SMILES: *C(=O)OCC(C)C] | F | F |
| $—CH_2CH(CH_3)_2$ | 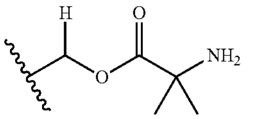 [SMILES: *COC(=O)C(C)(C)N] | F | F |
| $—CH_2CH(CH_3)_2$ | 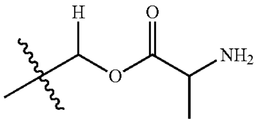 [SMILES: *COC(=O)C(C)N] | F | F |
| $—CH_2CH(CH_3)_2$ | 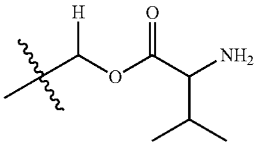 [SMILES: *COC(=O)C(N)C(C)C] | F | F |
| $—CH_2CH(CH_3)_2$ | 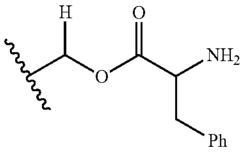 [SMILES: *COC(=O)C(N)Cc1ccccc1] | F | F |
| $—CH_2CH(CH_3)_2$ | 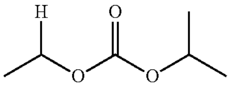 | F | F |
| $—CH_2CH(CH_3)_2$ | 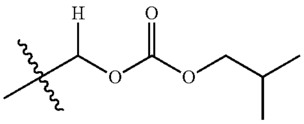 [SMILES: *COC(=O)OCC(C)C] | F | F |
| $—CH_2CH(CH_3)_2$ | 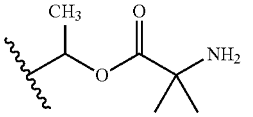 [SMILES: *C(C)OC(=O)C(C)(C)N] | F | F |
| $—CH_2CH(CH_3)_2$ | 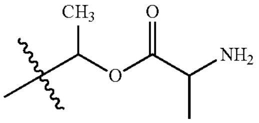 | F | F |
| $—CH_2CH(CH_3)_2$ | 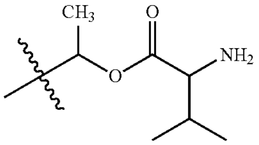 | F | F |

-continued
| $R^2$ | $R^1$ | $R^{6A}$ | $R^{6B}$ |
|---|---|---|---|
| $—CH_2CH(CH_3)_2$ | 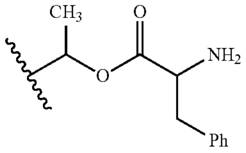 | F | F |
| $—CH_2CH(CH_3)_2$ | 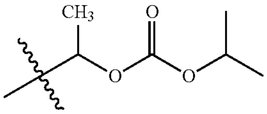 [SMILES: *C(C)OC(=O)OC(C)C] | F | F |
| $—CH_2CH(CH_3)_2$ | 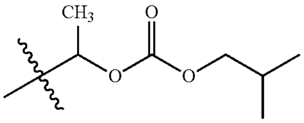 | F | F |
| $—CH_2CH_2CH_3$ | 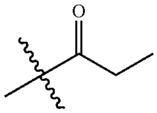 [SMILES: *C(=O)CC] | F | F |
| $—CH_2CH_2CH_3$ | 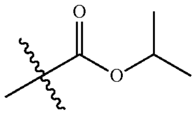 [SMILES: *C(=O)OC(C)C] | F | F |
| $—CH_2CH_2CH_3$ | 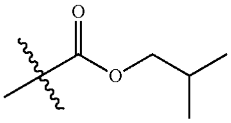 [SMILES: *C(=O)OCC(C)C] | F | F |
| $—CH_2CH_2CH_3$ | 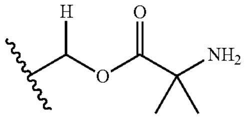 [SMILES: *COC(=O)C(C)(C)N] | F | F |
| $—CH_2CH_2CH_3$ | 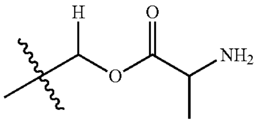 [SMILES: *COC(=O)C(C)N] | F | F |
| $—CH_2CH_2CH_3$ | 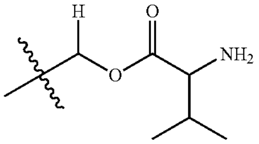 [SMILES: *COC(=O)C(N)C(C)C] | F | F |
| $—CH_2CH_2CH_3$ | 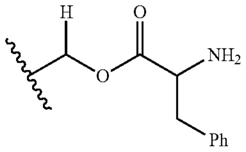 [SMILES: *COC(=O)C(N)Cc1ccccc1] | F | F |
| $—CH_2CH_2CH_3$ | 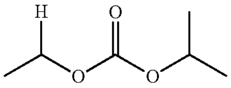 | F | F |

-continued
| $R^2$ | $R^1$ | $R^{6A}$ | $R^{6B}$ |
|---|---|---|---|
| $—CH_2CH_2CH_3$ | 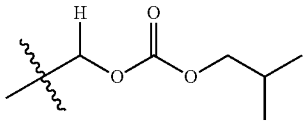 [SMILES: *COC(=O)OCC(C)C] | F | F |
| $—CH_2CH_2CH_3$ | 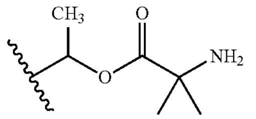 [SMILES: *C(C)OC(=O)C(C)(C)N] | F | F |
| $—CH_2CH_2CH_3$ | 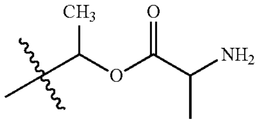 | F | F |
| $—CH_2CH_2CH_3$ | 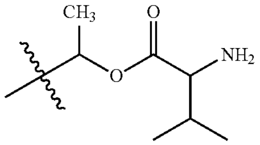 [SMILES: *C(C)OC(=O)C(N)C(C)C] | F | F |
| $—CH_2CH_2CH_3$ | 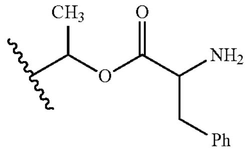 | F | F |
| $—CH_2CH_2CH_3$ | 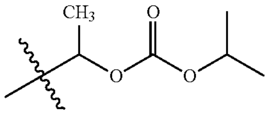 | F | F |
| $—CH_2CH_2CH_3$ | 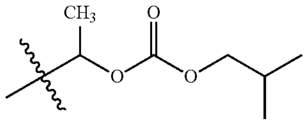 [SMILES: *C(C)OC(=O)OCC(C)C] | F | F |
| $—CH_2CH_2CH_2CH_3$ | 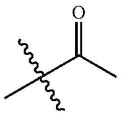 [SMILES: *C(C)=O] | F | F |
| $—CH_2CH_2CH_2CH_3$ | 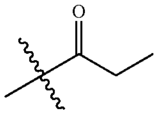 | F | F |
| $—CH_2CH_2CH_2CH_3$ | 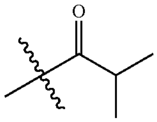 [SMILES: *C(=O)C(C)C] | F | F |
| $—CH_2CH_2CH_2CH_3$ | 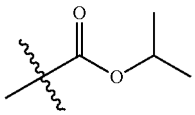 [SMILES: *C(=O)OC(C)C] | F | F |

-continued
| $R^2$ | $R^1$ | $R^{6A}$ | $R^{6B}$ |
|---|---|---|---|
| $—CH_2CH_2CH_2CH_3$ | 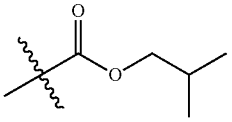 [SMILES: *C(=O)OCC(C)C] | F | F |
| $—CH_2CH_2CH_2CH_3$ | 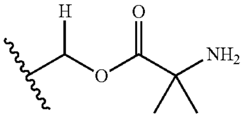 [SMILES: *COC(=O)C(C)(C)N] | F | F |
| $—CH_2CH_2CH_2CH_3$ | 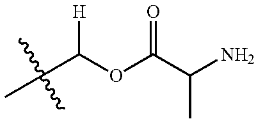 [SMILES: *COC(=O)C(C)N] | F | F |
| $—CH_2CH_2CH_2CH_3$ | 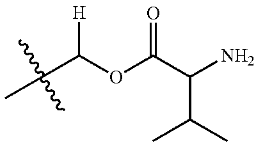 [SMILES: *COC(=O)C(N)C(C)C] | F | F |
| $—CH_2CH_2CH_2CH_3$ | 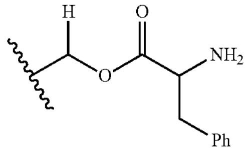 [SMILES: *COC(=O)C(N)Cc1ccccc1] | F | F |
| $—CH_2CH_2CH_2CH_3$ | 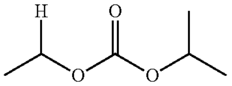 | F | F |
| $—CH_2CH_2CH_2CH_3$ | 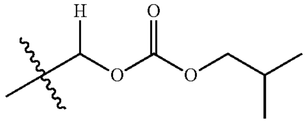 [SMILES: *COC(=O)OCC(C)C] | F | F |
| $—CH_2CH_2CH_2CH_3$ | 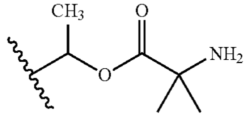 [SMILES: *C(C)OC(=O)C(C)(C)N] | F | F |
| $—CH_2CH_2CH_2CH_3$ | 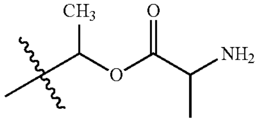 | F | F |
| $—CH_2CH_2CH_2CH_3$ | 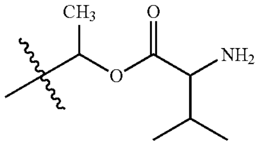 | F | F |
| $—CH_2CH_2CH_2CH_3$ | 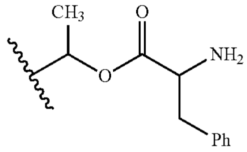 | F | F |

-continued
| $R^2$ | $R^1$ | $R^{6A}$ | $R^{6B}$ |
|---|---|---|---|
| $—CH_2CH_2CH_2CH_3$ | 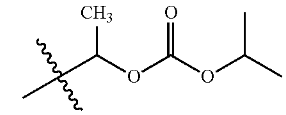 [SMILES: *C(C)OC(=O)OC(C)C] | F | F |
| $—CH_2CH_2CH_2CH_3$ | 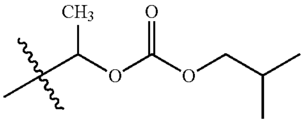 | F | F |
| 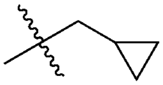 | 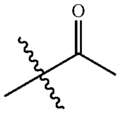 [SMILES: *C(C)=O] | F | F |
| 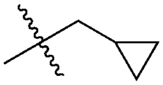 | 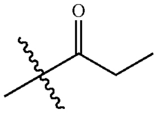 [SMILES: *C(=O)CC] | F | F |
| 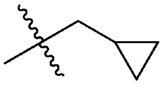 | 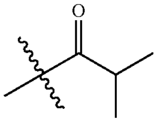 [SMILES: *C(=O)C(C)C] | F | F |
| 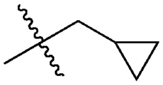 | 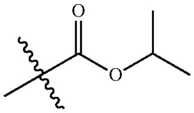 [SMILES: *C(=O)OC(C)C] | F | F |
| 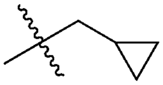 | 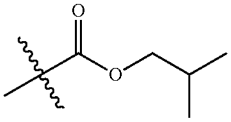 [SMILES: *C(=O)OCC(C)C] | F | F |
| 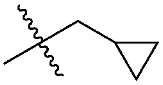 | 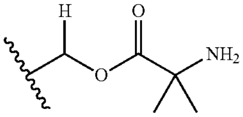 [SMILES: *COC(=O)C(C)(C)N] | F | F |
| 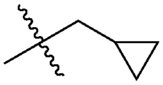 | 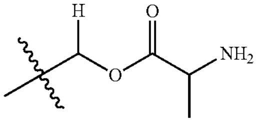 [SMILES: *COC(=O)C(C)N] | F | F |
| 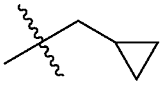 [SMILES: *CC1CC1] | 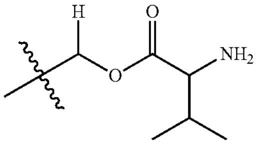 [SMILES: *COC(=O)C(N)C(C)C] | F | F |
| 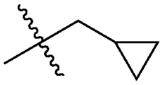 | 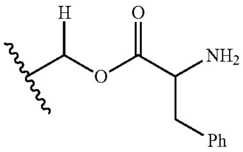 [SMILES: *COC(=O)C(N)Cc1ccccc1] | F | F |

-continued
| $R^2$ | $R^1$ | $R^{6A}$ | $R^{6B}$ |
|---|---|---|---|
| 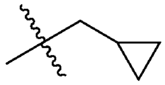 | 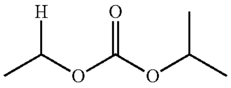 | F | F |
| 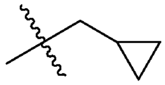 [SMILES: *CC1CC1] | 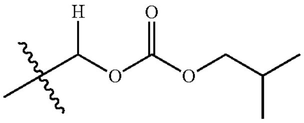 [SMILES: *COC(=O)OCC(C)C] | F | F |
| 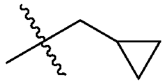 [SMILES: *CC1CC1] | 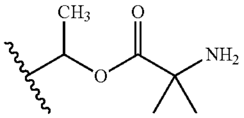 [SMILES: *C(C)OC(=O)C(C)(C)N] | F | F |
| 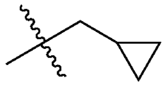 [SMILES: *CC1CC1] | 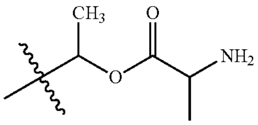 [SMILES: *C(C)OC(=O)C(C)N] | F | F |
| 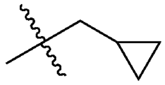 | 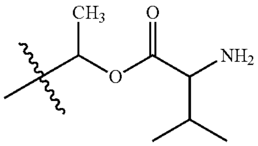 [SMILES: *C(C)OC(=O)C(N)C(C)C] | F | F |
| 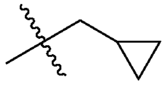 [SMILES: *CC1CC1] | 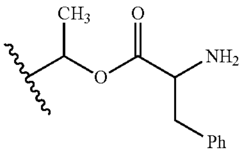 [SMILES: *C(C)OC(=O)C(N)Cc1ccccc1] | F | F |
| 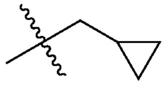 [SMILES: *CC1CC1] | 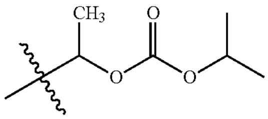 [SMILES: *C(C)OC(=O)OC(C)C] | F | F |
| 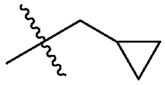 [SMILES: *CC1CC1] | 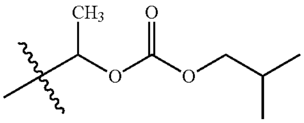 [SMILES: *C(C)OC(=O)OCC(C)C] | F | F |
| 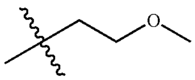 [SMILES: *CCOC] | 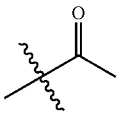 [SMILES: *C(C)=O] | F | F |
| 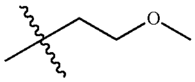 | 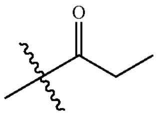 [SMILES: *C(=O)CC] | F | F |
| 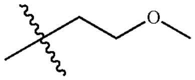 [SMILES: *CCOC] | 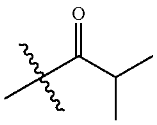 [SMILES: *C(=O)C(C)C] | F | F |

-continued
| $R^2$ | $R^1$ | $R^{6A}$ | $R^{6B}$ |
|---|---|---|---|
| 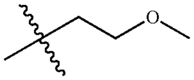 [SMILES: *CCOC] | 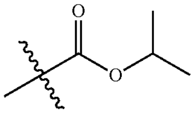 [SMILES: *C(=O)OC(C)C] | F | F |
| 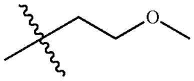 [SMILES: *CCOC] | 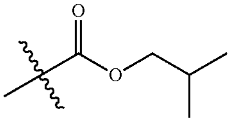 [SMILES: *C(=O)OCC(C)C] | F | F |
| 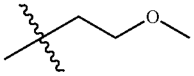 [SMILES: *CCOC] | 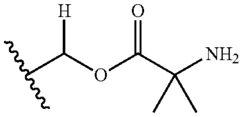 [SMILES: *COC(=O)C(C)(C)N] | F | F |
| 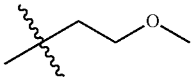 [SMILES: *CCOC] | 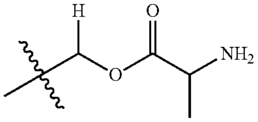 [SMILES: *COC(=O)C(C)N] | F | F |
| 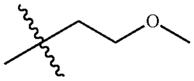 [SMILES: *CCOC] | 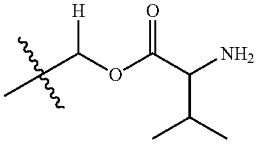 [SMILES: *COC(=O)C(N)C(C)C] | F | F |
| 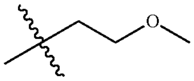 [SMILES: *CCOC] | 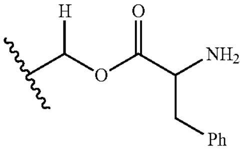 [SMILES: *COC(=O)C(N)Cc1ccccc1] | F | F |
| 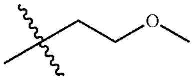 [SMILES: *CCOC] | 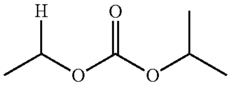 | F | F |
| 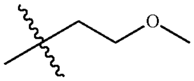 [SMILES: *CCOC] | 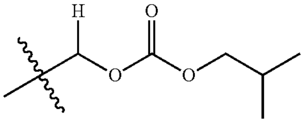 [SMILES: *COC(=O)OCC(C)C] | F | F |
| 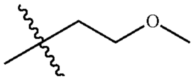 [SMILES: *CCOC] | 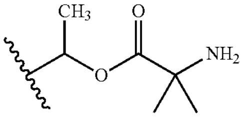 [SMILES: *C(C)OC(=O)C(C)(C)N] | F | F |
| 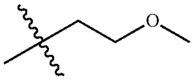 [SMILES: *CCOC] | 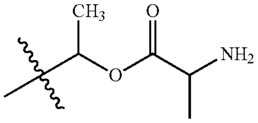 [SMILES: *C(C)OC(=O)C(C)N] | F | F |
| 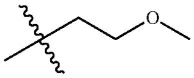 [SMILES: *CCOC] | 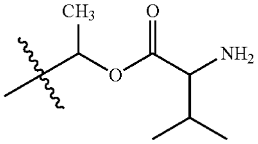 [SMILES: *C(C)OC(=O)C(N)C(C)C] | F | F |

-continued
| $R^2$ | $R^1$ | $R^{6A}$ | $R^{6B}$ |
|---|---|---|---|
| 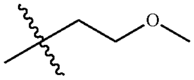 [SMILES: *CCOC] | 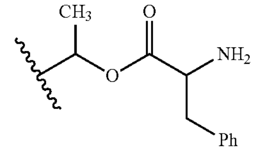 | F | F |
| 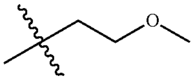 [SMILES: *CCOC] | 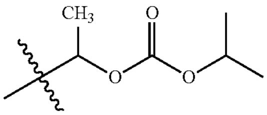 [SMILES: *C(C)OC(=O)OC(C)C] | F | F |
| 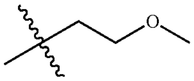 [SMILES: *CCOC] | 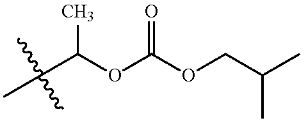 [SMILES: *C(C)OC(=O)OCC(C)C] | F | F |
| 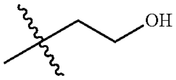 [SMILES: *CCO] | 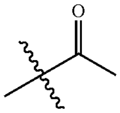 [SMILES: *C(C)=O] | F | F |
| 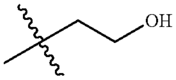 [SMILES: *CCO] | 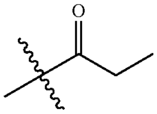 [SMILES: *C(=O)CC] | F | F |
| 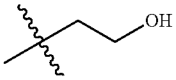 [SMILES: *CCO] | 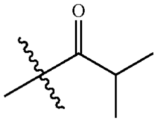 [SMILES: *C(=O)C(C)C] | F | F |
| 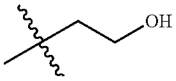 [SMILES: *CCO] | 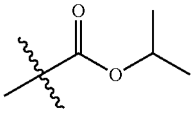 [SMILES: *C(=O)OC(C)C] | F | F |
| 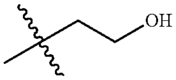 [SMILES: *CCO] | 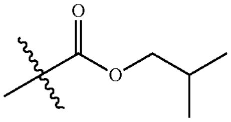 [SMILES: *C(=O)OCC(C)C] | F | F |
| 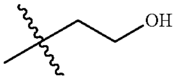 [SMILES: *CCO] | 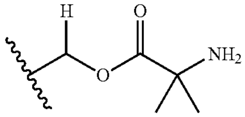 [SMILES: *COC(=O)C(C)(C)N] | F | F |
| 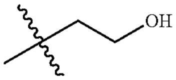 [SMILES: *CCO] | 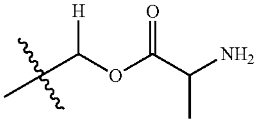 [SMILES: *COC(=O)C(C)N] | F | F |
| 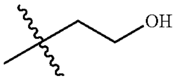 [SMILES: *CCO] | 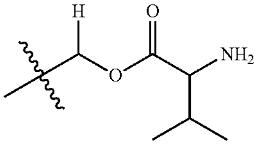 [SMILES: *COC(=O)C(N)C(C)C] | F | F |

-continued
| $R^2$ | $R^1$ | $R^{6A}$ | $R^{6B}$ |
|---|---|---|---|
| 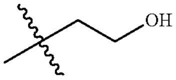 [SMILES: *CCO] | 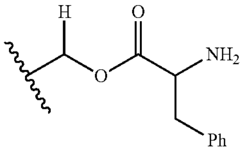 [SMILES: *COC(=O)C(N)Cc1ccccc1] | F | F |
| 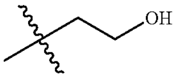 [SMILES: *CCO] | 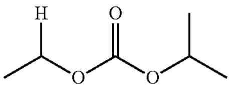 | F | F |
| 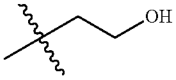 [SMILES: *CCO] | 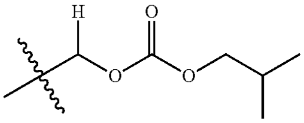 [SMILES: *COC(=O)OCC(C)C] | F | F |
| 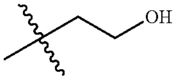 [SMILES: *CCO] | 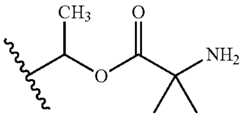 [SMILES: *C(C)OC(=O)C(C)(C)N] | F | F |
| 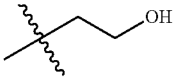 [SMILES: *CCO] | 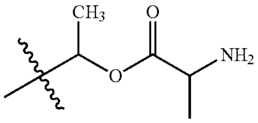 [SMILES: *C(C)OC(=O)C(C)N] | F | F |
| 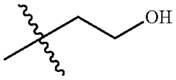 [SMILES: *CCO] | 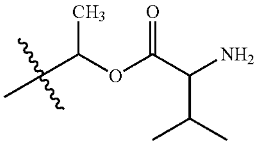 [SMILES: *C(C)OC(=O)C(N)C(C)C] | F | F |
| 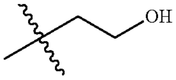 [SMILES: *CCO] | 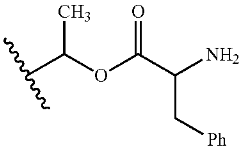 | F | F |
| 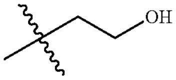 [SMILES: *CCO] | 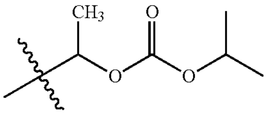 [SMILES: *C(C)OC(=O)OC(C)C] | F | F |
| 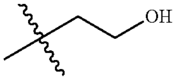 [SMILES: *CCO] | 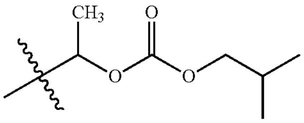 [SMILES: *C(C)OC(=O)OCC(C)C] | F | F |
| $—CH_2CH═CF_2$ | 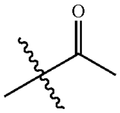 [SMILES: *C(C)=O] | F | F |
| $—CH_2CH═CF_2$ | 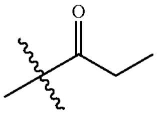 [SMILES: *C(=O)CC] | F | F |

-continued
| $R^2$ | $R^1$ | $R^{6A}$ | $R^{6B}$ |
|---|---|---|---|
| $—CH_2CH{=}CF_2$ | 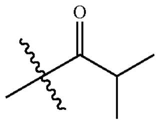 [SMILES: *C(=O)C(C)C] | F | F |
| $—CH_2CH{=}CF_2$ | 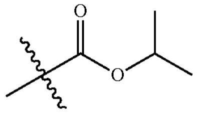 [SMILES: *C(=O)OC(C)C] | F | F |
| $—CH_2CH{=}CF_2$ | 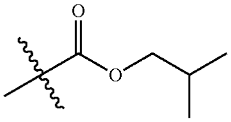 [SMILES: *C(=O)OCC(C)C] | F | F |
| $—CH_2CH{=}CF_2$ | 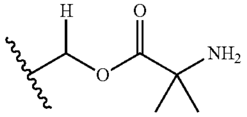 [SMILES: *COC(=O)C(C)(C)N] | F | F |
| $—CH_2CH{=}CF_2$ | 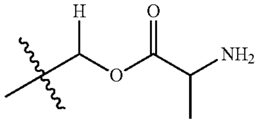 [SMILES: *COC(=O)C(C)N] | F | F |
| $—CH_2CH{=}CF_2$ | 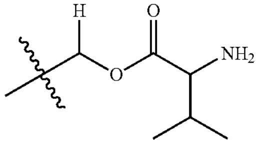 [SMILES: *COC(=O)C(N)C(C)C] | F | F |
| $—CH_2CH{=}CF_2$ | 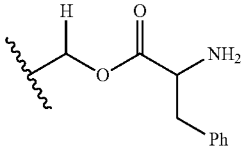 | F | F |
| $—CH_2CH{=}CF_2$ | 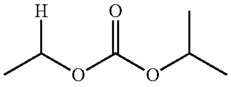 | F | F |
| $—CH_2CH{=}CF_2$ | 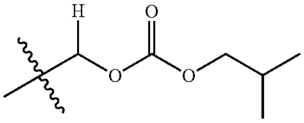 [SMILES: *COC(=O)OCC(C)C] | F | F |
| $—CH_2CH{=}CF_2$ | 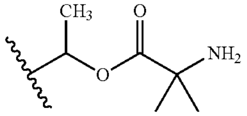 [SMILES: *C(C)OC(=O)C(C)(C)N] | F | F |
| $—CH_2CH{=}CF_2$ | 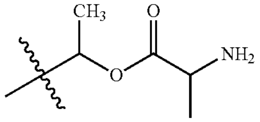 [SMILES: *C(C)OC(=O)C(C)N] | F | F |

-continued
| $R^2$ | $R^1$ | $R^{6A}$ | $R^{6B}$ |
|---|---|---|---|
| $—CH_2CH{=}CF_2$ | 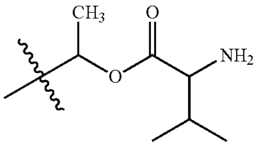 [SMILES: *C(C)OC(=O)C(N)C(C)C] | F | F |
| $—CH_2CH{=}CF_2$ | 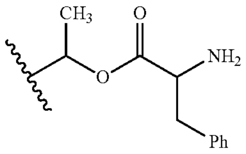 [SMILES: *C(C)OC(=O)C(N)Cc1ccccc1] | F | F |
| $—CH_2CH{=}CF_2$ | 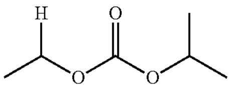 | F | F |
| $—CH_2CH{=}CF_2$ | 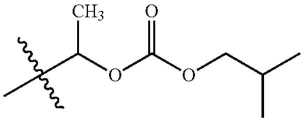 | F | F |
| $—CH_2CF_3$ | 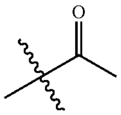 [SMILES: *C(C)=O] | F | F |
| $—CH_2CF_3$ | 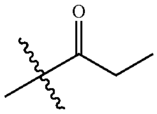 [SMILES: *C(=O)CC] | F | F |
| $—CH_2CF_3$ | 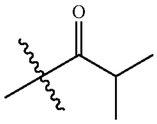 [SMILES: *C(=O)C(C)C] | F | F |
| $—CH_2CF_3$ | 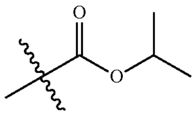 [SMILES: *C(=O)OC(C)C] | F | F |
| $—CH_2CF_3$ | 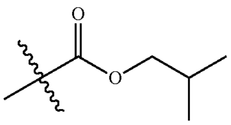 [SMILES: *C(=O)OCC(C)C] | F | F |
| $—CH_2CF_3$ | 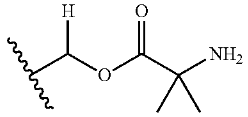 [SMILES: *COC(=O)C(C)(C)N] | F | F |
| $—CH_2CF_3$ | 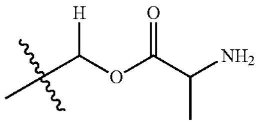 [SMILES: *COC(=O)C(C)N] | F | F |

-continued
| $R^2$ | $R^1$ | $R^{6A}$ | $R^{6B}$ |
|---|---|---|---|
| $—CH_2CF_3$ | 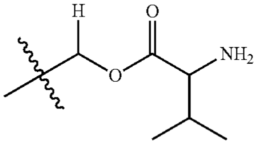 [SMILES: *COC(=O)C(N)C(C)C] | F | F |
| $—CH_2CF_3$ | 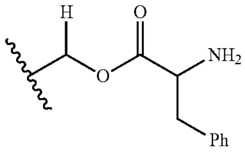 [SMILES: *COC(=O)C(N)Cc1ccccc1] | F | F |
| $—CH_2CF_3$ | 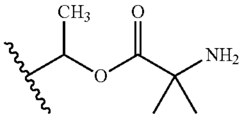 [SMILES: *C(C)OC(=O)C(C)(C)N] | F | F |
| $—CH_2CF_3$ | 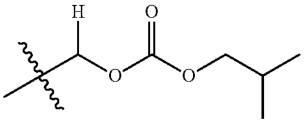 [SMILES: *COC(=O)OCC(C)C] | F | F |
| $—CH_2CF_3$ | 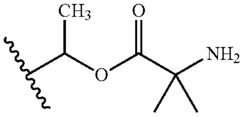 [SMILES: *C(C)OC(=O)C(C)(C)N] | F | F |
| $—CH_2CF_3$ | 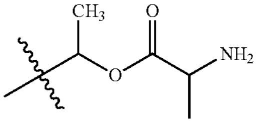 [SMILES: *C(C)OC(=O)C(C)N] | F | F |
| $—CH_2CF_3$ | 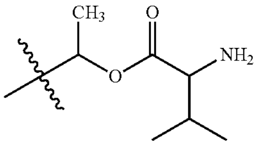 [SMILES: *C(C)OC(=O)C(N)C(C)C] | F | F |
| $—CH_2CF_3$ | 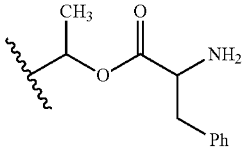 [SMILES: *C(C)OC(=O)C(N)Cc1ccccc1] | F | F |
| $—CH_2CF_3$ | 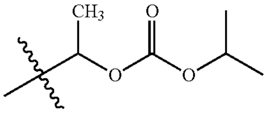 [SMILES: *C(C)OC(=O)OC(C)C] | F | F |
| $—CH_2CF_3$ | 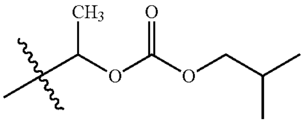 [SMILES: *C(C)OC(=O)OCC(C)C] | F | F |
| $—CH_2CH_2CF_3$ | 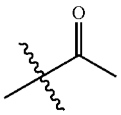 [SMILES: *C(C)=O] | F | F |

-continued
| $R^2$ | $R^1$ | $R^{6A}$ | $R^{6B}$ |
|---|---|---|---|
| $—CH_2CH_2CF_3$ | 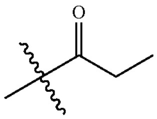 [SMILES: *C(=O)CC] | F | F |
| $—CH_2CH_2CF_3$ | 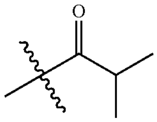 [SMILES: *C(=O)C(C)C] | F | F |
| $—CH_2CH_2CF_3$ | 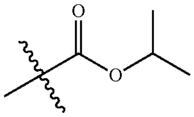 [SMILES: *C(=O)OC(C)C] | F | F |
| $—CH_2CH_2CF_3$ | 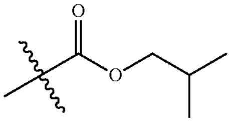 [SMILES: *C(=O)OCC(C)C] | F | F |
| $—CH_2CH_2CF_3$ | 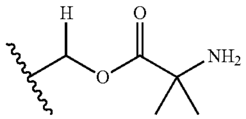 [SMILES: *COC(=O)C(C)(C)N] | F | F |
| $—CH_2CH_2CF_3$ | 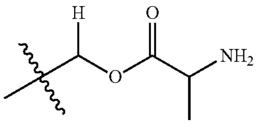 [SMILES: *COC(=O)C(C)N] | F | F |
| $—CH_2CH_2CF_3$ | 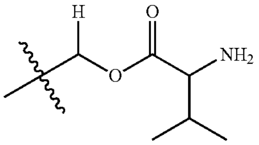 [SMILES: *COC(=O)C(N)C(C)C] | F | F |
| $—CH_2CH_2CF_3$ | 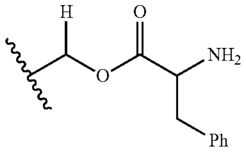 | F | F |
| $—CH_2CH_2CF_3$ | 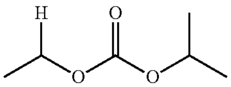 | F | F |
| $—CH_2CH_2CF_3$ | 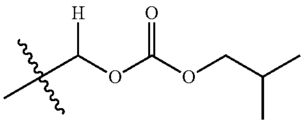 [SMILES: *COC(=O)OCC(C)C] | F | F |
| $—CH_2CH_2CF_3$ | 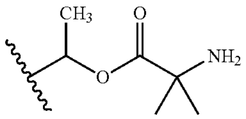 [SMILES: *C(C)OC(=O)C(C)(C)N] | F | F |

-continued
| $R^2$ | $R^1$ | $R^{6A}$ | $R^{6B}$ |
|---|---|---|---|
| $—CH_2CH_2CF_3$ | 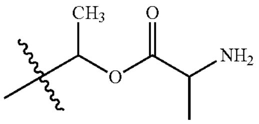 [SMILES: *C(C)OC(=O)C(C)N] | F | F |
| $—CH_2CH_2CF_3$ | 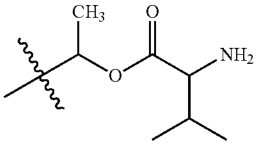 [SMILES: *C(C)OC(=O)C(N)C(C)C] | F | F |
| $—CH_2CH_2CF_3$ | 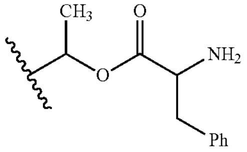 | F | F |
| $—CH_2CH_2CF_3$ | 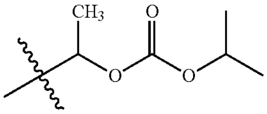 [SMILES: *C(C)OC(=O)OC(C)C] | F | F |
| $—CH_2CH_2CF_3$ | 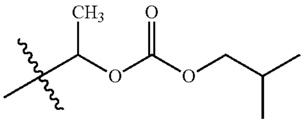 [SMILES: *C(C)OC(=O)OCC(C)C] | F | F |
| $—CH_2CHF_2$ | 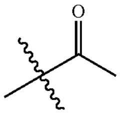 [SMILES: *C(C)=O] | F | F |
| $—CH_2CHF_2$ | 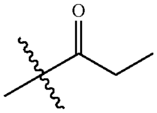 [SMILES: *C(=O)CC] | F | F |
| $—CH_2CHF_2$ | 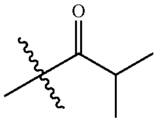 [SMILES: *C(=O)C(C)C] | F | F |
| $—CH_2CHF_2$ | 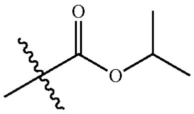 [SMILES: *C(=O)OC(C)C] | F | F |
| $—CH_2CHF_2$ | 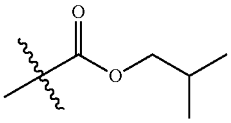 [SMILES: *C(=O)OCC(C)C] | F | F |
| $—CH_2CHF_2$ | 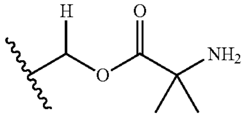 [SMILES: *COC(=O)C(C)(C)N] | F | F |

-continued
| $R^2$ | $R^1$ | $R^{6A}$ | $R^{6B}$ |
|---|---|---|---|
| $—CH_2CHF_2$ | 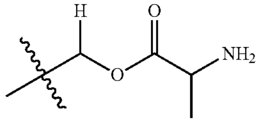 [SMILES: *COC(=O)C(C)N] | F | F |
| $—CH_2CHF_2$ | 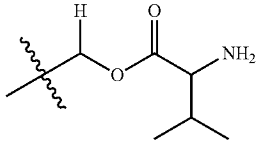 [SMILES: *COC(=O)C(N)C(C)C] | F | F |
| $—CH_2CHF_2$ | 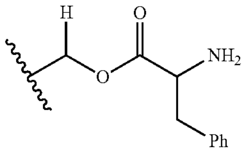 [SMILES: *COC(=O)C(N)Cc1ccccc1] | F | F |
| $—CH_2CHF_2$ | 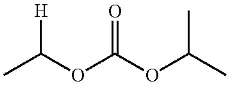 | F | F |
| $—CH_2CHF_2$ | 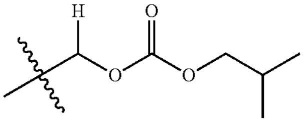 [SMILES: *COC(=O)OCC(C)C] | F | F |
| $—CH_2CHF_2$ | 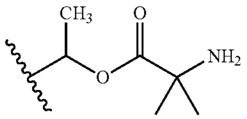 [SMILES: *C(C)OC(=O)C(C)(C)N] | F | F |
| $—CH_2CHF_2$ | 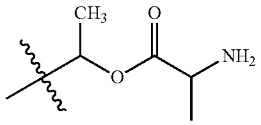 [SMILES: *C(C)OC(=O)C(C)N] | F | F |
| $—CH_2CHF_2$ | 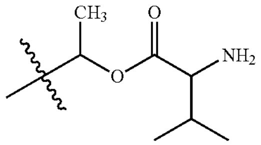 [SMILES: *C(C)OC(=O)C(N)C(C)C] | F | F |
| $—CH_2CHF_2$ | 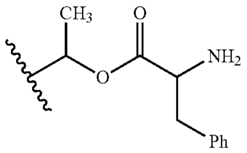 [SMILES: *C(C)OC(=O)C(N)Cc1ccccc1] | F | F |
| $—CH_2CHF_2$ | 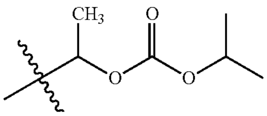 [SMILES: *C(C)OC(=O)OC(C)C] | F | F |
| $—CH_2CHF_2$ | 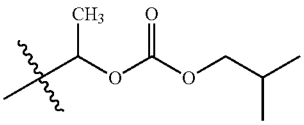 [SMILES: *C(C)OC(=O)OCC(C)C] | F | F |

-continued
| $R^2$ | $R^1$ | $R^{6A}$ | $R^{6B}$ |
|---|---|---|---|
| $—CH_2C(CH_3)F_2$ | 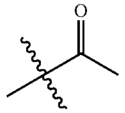 [SMILES: *C(C)=O] | F | F |
| $—CH_2C(CH_3)F_2$ | 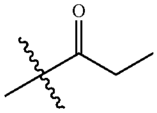 [SMILES: *C(=O)CC] | F | F |
| $—CH_2C(CH_3)F_2$ | 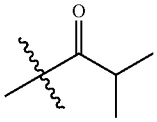 [SMILES: *C(=O)C(C)C] | F | F |
| $—CH_2C(CH_3)F_2$ | 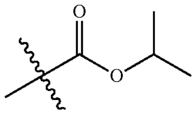 [SMILES: *C(=O)OC(C)C] | F | F |
| $—CH_2C(CH_3)F_2$ | 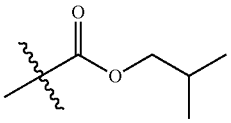 [SMILES: *C(=O)OCC(C)C] | F | F |
| $—CH_2C(CH_3)F_2$ | 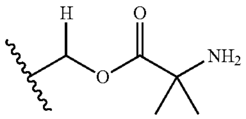 [SMILES: *COC(=O)C(C)(C)N] | F | F |
| $—CH_2C(CH_3)F_2$ | 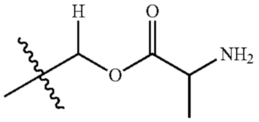 [SMILES: *COC(=O)C(C)N] | F | F |
| $—CH_2C(CH_3)F_2$ | 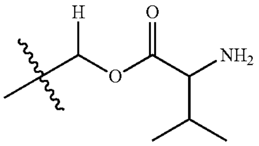 [SMILES: *COC(=O)C(N)C(C)C] | F | F |
| $—CH_2C(CH_3)F_2$ | 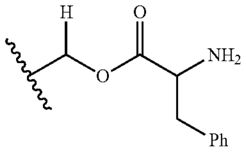 [SMILES: *COC(=O)C(N)Cc1ccccc1] | F | F |
| $—CH_2C(CH_3)F_2$ | 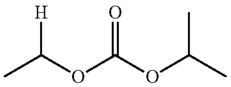 | F | F |
| $—CH_2C(CH_3)F_2$ | 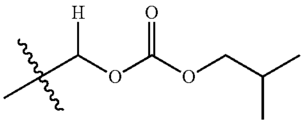 [SMILES: *COC(=O)OCC(C)C] | F | F |
| $—CH_2C(CH_3)F_2$ | 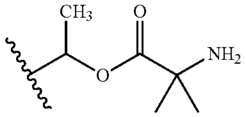 | F | F |

-continued
| $R^2$ | $R^1$ | $R^{6A}$ | $R^{6B}$ |
|---|---|---|---|
| $—CH_2C(CH_3)F_2$ | 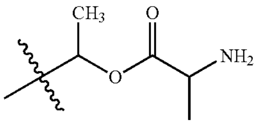 [SMILES: *C(C)OC(=O)C(C)N] | F | F |
| $—CH_2C(CH_3)F_2$ | 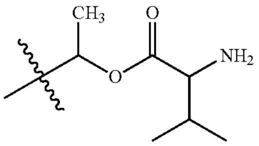 [SMILES: *C(C)OC(=O)C(N)C(C)C] | F | F |
| $—CH_2C(CH_3)F_2$ | 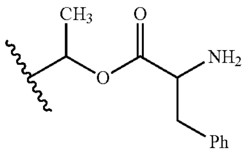 | F | F |
| $—CH_2C(CH_3)F_2$ | 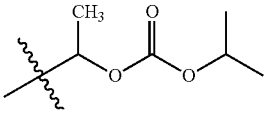 [SMILES: *C(C)OC(=O)OC(C)C] | F | F |
| $—CH_2C(CH_3)F_2$ | 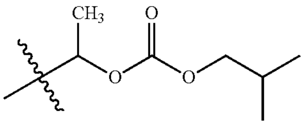 [SMILES: *C(C)OC(=O)OCC(C)C] | F | F |
| 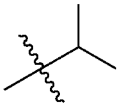 [SMILES: *C(C)C] | 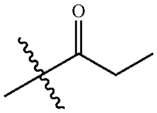 [SMILES: *C(=O)CC] | Cl | Cl |
| 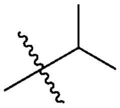 [SMILES: *C(C)C] | 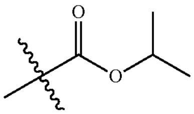 [SMILES: *C(=O)OC(C)C] | Cl | Cl |
| 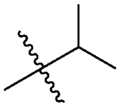 [SMILES: *C(C)C] | 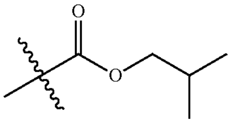 [SMILES: *C(=O)OCC(C)C] | Cl | Cl |
| 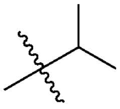 [SMILES: *C(C)C] | 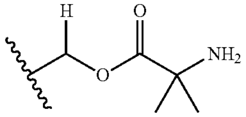 [SMILES: *COC(=O)C(C)(C)N] | Cl | Cl |
| 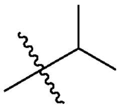 [SMILES: *C(C)C] | 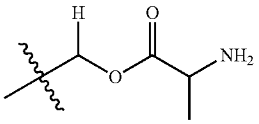 [SMILES: *COC(=O)C(C)N] | Cl | Cl |
| 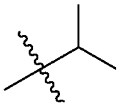 [SMILES: *C(C)C] | 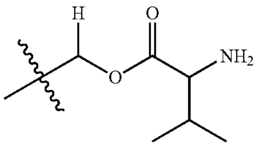 [SMILES: *COC(=O)C(N)C(C)C] | Cl | Cl |

-continued
| $R^2$ | $R^1$ | $R^{6A}$ | $R^{6B}$ |
|---|---|---|---|
| 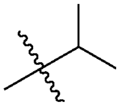 [SMILES: *C(C)C] | 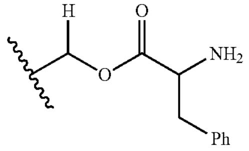 [SMILES: *COC(=O)C(N)Cc1ccccc1] | Cl | Cl |
| 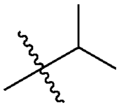 [SMILES: *C(C)C] | 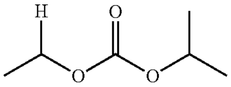 | Cl | Cl |
| 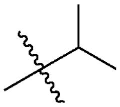 [SMILES: *C(C)C] | 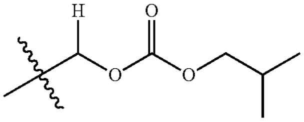 [SMILES: *COC(=O)OCC(C)C] | Cl | Cl |
| 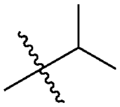 [SMILES: *C(C)C] | 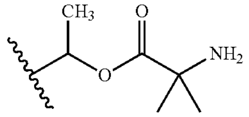 [SMILES: *C(C)OC(=O)C(C)(C)N] | Cl | Cl |
| 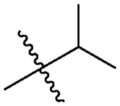 [SMILES: *C(C)C] | 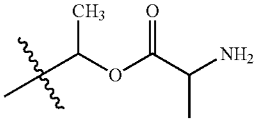 [SMILES: *C(C)OC(=O)C(C)N] | Cl | Cl |
| 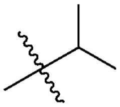 [SMILES: *C(C)C] | 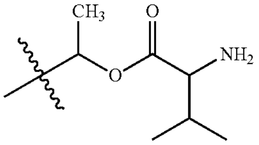 [SMILES: *C(C)OC(=O)C(N)C(C)C] | Cl | Cl |
| 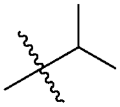 [SMILES: *C(C)C] | 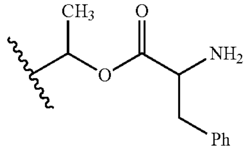 [SMILES: *C(C)OC(=O)C(N)Cc1ccccc1] | Cl | Cl |
| 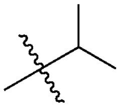 [SMILES: *C(C)C] | 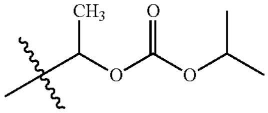 [SMILES: *C(C)OC(=O)OC(C)C] | Cl | Cl |
| 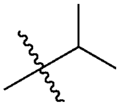 [SMILES: *C(C)C] | 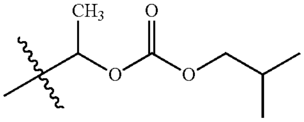 [SMILES: *C(C)OC(=O)OCC(C)C] | Cl | Cl |
| —$CH_3$ | 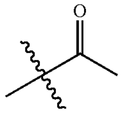 [SMILES: *C(C)=O] | Cl | Cl |
| —$CH_3$ | 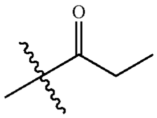 [SMILES: *C(=O)CC] | Cl | Cl |

-continued
| $R^2$ | $R^1$ | $R^{6A}$ | $R^{6B}$ |
|---|---|---|---|
| $—CH_3$ | 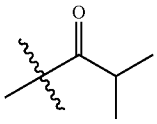 [SMILES: *C(=O)C(C)C] | Cl | Cl |
| $—CH_3$ | 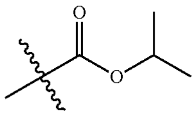 [SMILES: *C(=O)OC(C)C] | Cl | Cl |
| $—CH_3$ | 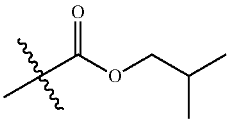 [SMILES: *C(=O)OCC(C)C] | Cl | Cl |
| $—CH_3$ | 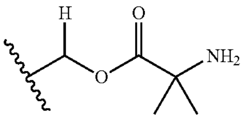 [SMILES: *COC(=O)C(C)(C)N] | Cl | Cl |
| $—CH_3$ | 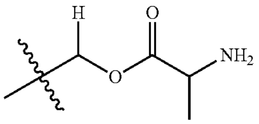 | Cl | Cl |
| $—CH_3$ | 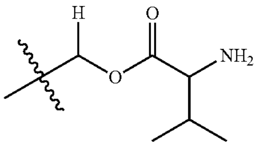 [SMILES: *COC(=O)C(N)C(C)C] | Cl | Cl |
| $—CH_3$ | 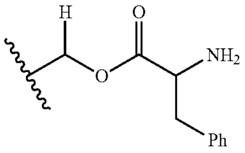 | Cl | Cl |
| $—CH_3$ | 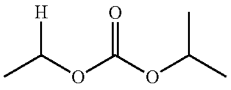 | Cl | Cl |
| $—CH_3$ | 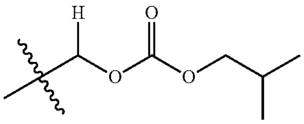 [SMILES: *COC(=O)OCC(C)C] | Cl | Cl |
| $—CH_3$ | 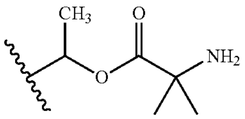 [SMILES: *C(C)OC(=O)C(C)(C)N] | Cl | Cl |
| $—CH_3$ | 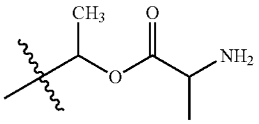 [SMILES: *C(C)OC(=O)C(C)N] | Cl | Cl |

-continued
| $R^2$ | $R^1$ | $R^{6A}$ | $R^{6B}$ |
|---|---|---|---|
| —$CH_3$ | 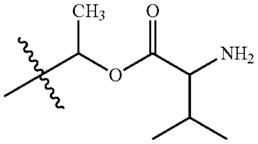 [SMILES: *C(C)OC(=O)C(N)C(C)C] | Cl | Cl |
| —$CH_3$ | 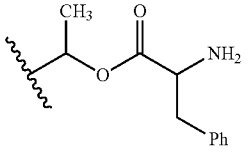 | Cl | Cl |
| —$CH_3$ | 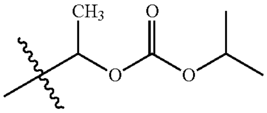 [SMILES: *C(C)OC(=O)OC(C)C] | Cl | Cl |
| —$CH_3$ | 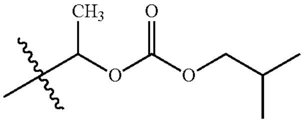 | Cl | Cl |
| | 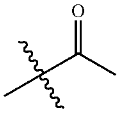 [SMILES: *C(C)=O] | | |
| —$CH_2CH_3$ | 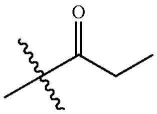 [SMILES: *C(=O)CC] | Cl | Cl |
| —$CH_2CH_3$ | 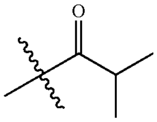 [SMILES: *C(=O)C(C)C] | Cl | Cl |
| —$CH_2CH_3$ | 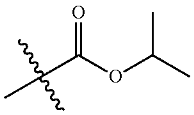 [SMILES: *C(=O)OC(C)C] | Cl | Cl |
| —$CH_2CH_3$ | 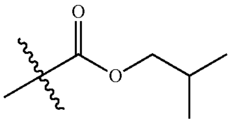 [SMILES: *C(=O)OCC(C)C] | Cl | Cl |
| —$CH_2CH_3$ | 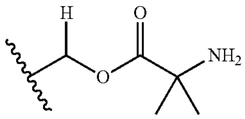 [SMILES: *COC(=O)C(C)(C)N] | Cl | Cl |
| —$CH_2CH_3$ | 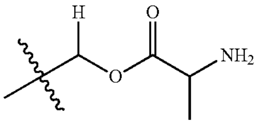 [SMILES: *COC(=O)C(C)N] | Cl | Cl |

-continued
| $R^2$ | $R^1$ | $R^{6A}$ | $R^{6B}$ |
|---|---|---|---|
| $—CH_2CH_3$ | 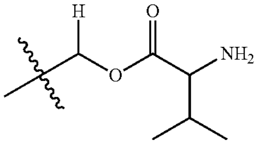 [SMILES: *COC(=O)C(N)C(C)C] | Cl | Cl |
| $—CH_2CH_3$ | 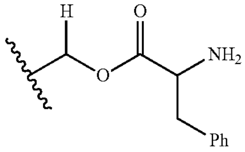 [SMILES: *COC(=O)C(N)Cc1ccccc1] | Cl | Cl |
| $—CH_2CH_3$ | 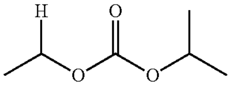 | Cl | Cl |
| $—CH_2CH_3$ | 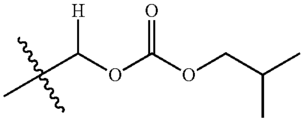 [SMILES: *COC(=O)OCC(C)C] | Cl | Cl |
| $—CH_2CH_3$ | 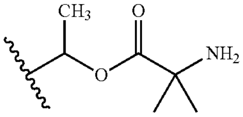 [SMILES: *C(C)OC(=O)C(C)(C)N] | Cl | Cl |
| $—CH_2CH_3$ | 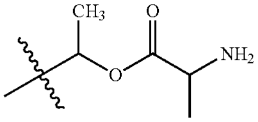 [SMILES: *C(C)OC(=O)C(C)N] | Cl | Cl |
| $—CH_2CH_3$ | 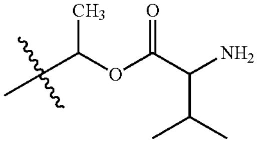 [SMILES: *C(C)OC(=O)C(N)C(C)C] | Cl | Cl |
| $—CH_2CH_3$ | 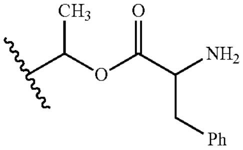 [SMILES: *C(C)OC(=O)C(N)Cc1ccccc1] | Cl | Cl |
| $—CH_2CH_3$ | 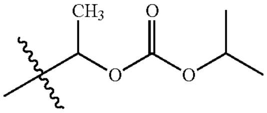 [SMILES: *C(C)OC(=O)OC(C)C] | Cl | Cl |
| $—CH_2CH_3$ | 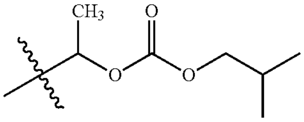 [SMILES: *C(C)OC(=O)OCC(C)C] | Cl | Cl |
| $—CH_2CH(CH_3)_2$ | H | Cl | Cl |
| $—CH_2CH(CH_3)_2$ | 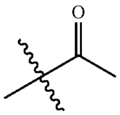 [SMILES: *C(C)=O] | Cl | Cl |

-continued
| $R^2$ | $R^1$ | $R^{6A}$ | $R^{6B}$ |
|---|---|---|---|
| $—CH_2CH(CH_3)_2$ | 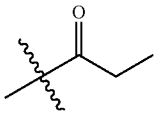 [SMILES: *C(=O)CC] | Cl | Cl |
| $—CH_2CH(CH_3)_2$ | 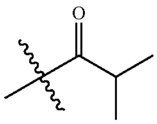 [SMILES: *C(=O)C(C)C] | Cl | Cl |
| $—CH_2CH(CH_3)_2$ | 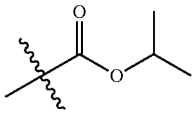 [SMILES: *C(=O)OC(C)C] | Cl | Cl |
| $—CH_2CH(CH_3)_2$ | 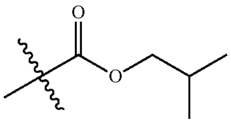 [SMILES: *C(=O)OCC(C)C] | Cl | Cl |
| $—CH_2CH(CH_3)_2$ | 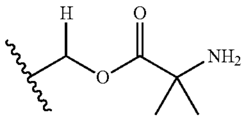 [SMILES: *COC(=O)C(C)(C)N] | Cl | Cl |
| $—CH_2CH(CH_3)_2$ | 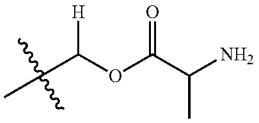 [SMILES: *COC(=O)C(C)N] | Cl | Cl |
| $—CH_2CH(CH_3)_2$ | 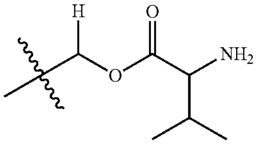 [SMILES: *COC(=O)C(N)C(C)C] | | |
| $—CH_2CH(CH_3)_2$ | 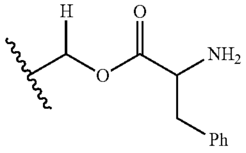 [SMILES: *COC(=O)C(N)Cc1ccccc1] | Cl | Cl |
| $—CH_2CH(CH_3)_2$ | 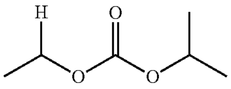 | Cl | Cl |
| $—CH_2CH(CH_3)_2$ | 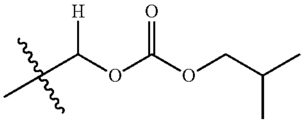 [SMILES: *COC(=O)OCC(C)C] | Cl | Cl |
| $—CH_2CH(CH_3)_2$ | 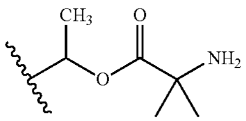 [SMILES: *C(C)OC(=O)C(C)(C)N] | Cl | Cl |

-continued
| $R^2$ | $R^1$ | $R^{6A}$ | $R^{6B}$ |
|---|---|---|---|
| $—CH_2CH(CH_3)_2$ | 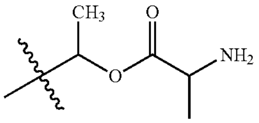 | Cl | Cl |
| $—CH_2CH(CH_3)_2$ | 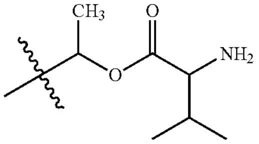 [SMILES: *C(C)OC(=O)C(N)C(C)C] | Cl | Cl |
| $—CH_2CH(CH_3)_2$ | 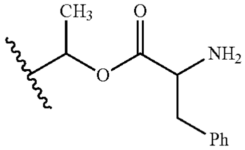 [SMILES: *C(C)OC(=O)C(N)Cc1ccccc1] | Cl | Cl |
| $—CH_2CH(CH_3)_2$ | 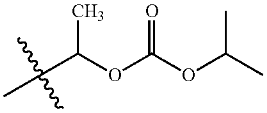 [SMILES: *C(C)OC(=O)OC(C)C] | Cl | Cl |
| $—CH_2CH(CH_3)_2$ | 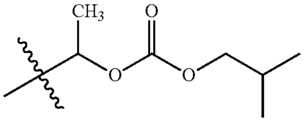 [SMILES: *C(C)OC(=O)OCC(C)C] | Cl | Cl |
| $—CH_2CH_2CH_3$ | 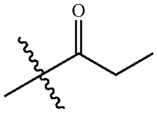 [SMILES: *C(=O)CC] | Cl | Cl |
| $—CH_2CH_2CH_3$ | 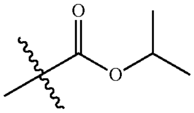 [SMILES: *C(=O)OC(C)C] | Cl | Cl |
| $—CH_2CH_2CH_3$ | 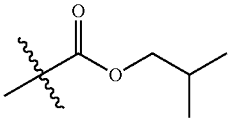 [SMILES: *C(=O)OCC(C)C] | Cl | Cl |
| $—CH_2CH_2CH_3$ | 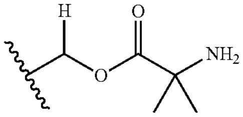 [SMILES: *COC(=O)C(C)(C)N] | Cl | Cl |
| $—CH_2CH_2CH_3$ | 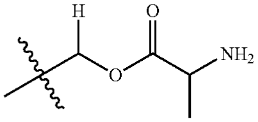 [SMILES: *COC(=O)C(C)N] | Cl | Cl |
| $—CH_2CH_2CH_3$ | 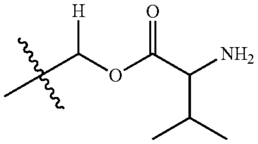 [SMILES: *COC(=O)C(N)C(C)C] | Cl | Cl |

-continued
| $R^2$ | $R^1$ | $R^{6A}$ | $R^{6B}$ |
|---|---|---|---|
| $—CH_2CH_2CH_3$ | 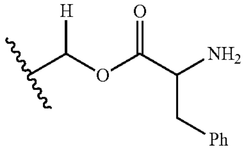 | Cl | Cl |
| $—CH_2CH_2CH_3$ | 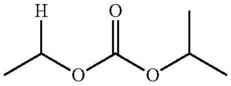 | Cl | Cl |
| $—CH_2CH_2CH_3$ | 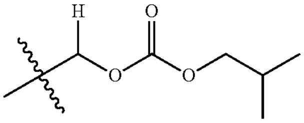 [SMILES: *COC(=O)OCC(C)C] | Cl | Cl |
| $—CH_2CH_2CH_3$ | 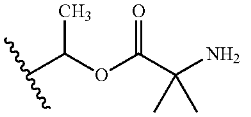 [SMILES: *C(C)OC(=O)C(C)(C)N] | Cl | Cl |
| $—CH_2CH_2CH_3$ | 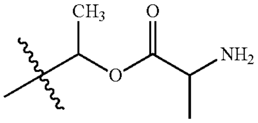 | Cl | Cl |
| $—CH_2CH_2CH_3$ | 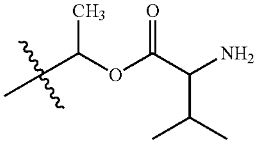 [SMILES: *C(C)OC(=O)C(N)C(C)C] | Cl | Cl |
| $—CH_2CH_2CH_3$ | 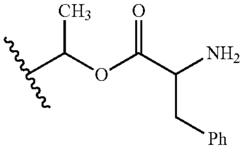 [SMILES: *C(C)OC(=O)C(N)Cc1ccccc1] | Cl | Cl |
| $—CH_2CH_2CH_3$ | 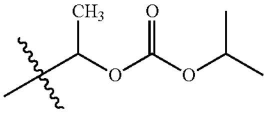 [SMILES: *C(C)OC(=O)OC(C)C] | Cl | Cl |
| $—CH_2CH_2CH_3$ | 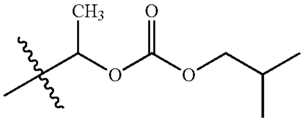 [SMILES: *C(C)OC(=O)OCC(C)C] | Cl | Cl |
| $—CH_2CH_2CH_2CH_3$ | H | Cl | Cl |
| $—CH_2CH_2CH_2CH_3$ | 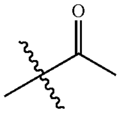 [SMILES: *C(C)=O] | Cl | Cl |
| $—CH_2CH_2CH_2CH_3$ | 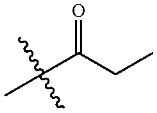 [SMILES: *C(=O)CC] | Cl | Cl |

-continued
| $R^2$ | $R^1$ | $R^{6A}$ | $R^{6B}$ |
|---|---|---|---|
| $—CH_2CH_2CH_2CH_3$ | 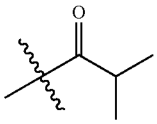 [SMILES: *C(=O)C(C)C] | Cl | Cl |
| $—CH_2CH_2CH_2CH_3$ | 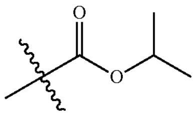 [SMILES: *C(=O)OC(C)C] | Cl | Cl |
| $—CH_2CH_2CH_2CH_3$ | 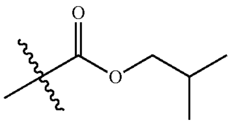 [SMILES: *C(=O)OCC(C)C] | Cl | Cl |
| $—CH_2CH_2CH_2CH_3$ | 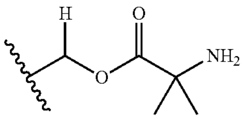 | Cl | Cl |
| $—CH_2CH_2CH_2CH_3$ | 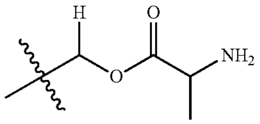 [SMILES: *COC(=O)C(C)N] | Cl | Cl |
| $—CH_2CH_2CH_2CH_3$ | 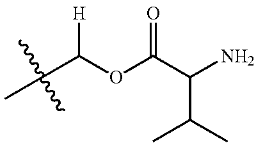 [SMILES: *COC(=O)C(N)C(C)C] | Cl | Cl |
| $—CH_2CH_2CH_2CH_3$ | 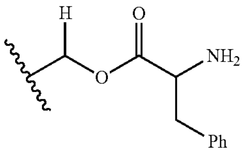 [SMILES: *COC(=O)C(N)Cc1ccccc1] | Cl | Cl |
| $—CH_2CH_2CH_2CH_3$ | 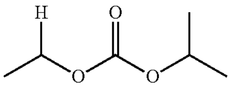 | Cl | Cl |
| $—CH_2CH_2CH_2CH_3$ | 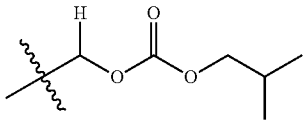 [SMILES: *COC(=O)OCC(C)C] | Cl | Cl |
| $—CH_2CH_2CH_2CH_3$ | 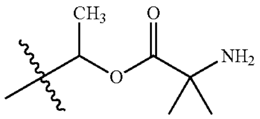 [SMILES: *C(C)OC(=O)C(C)(C)N] | Cl | Cl |
| $—CH_2CH_2CH_2CH_3$ | 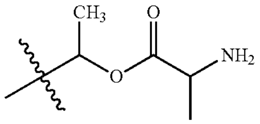 [SMILES: *C(C)OC(=O)C(C)N] | Cl | Cl |

-continued
| $R^2$ | $R^1$ | $R^{6A}$ | $R^{6B}$ |
|---|---|---|---|
| $—CH_2CH_2CH_2CH_3$ | 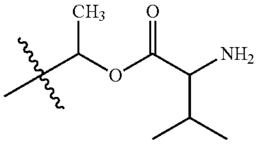 [SMILES: *C(C)OC(=O)C(N)C(C)C] | Cl | Cl |
| $—CH_2CH_2CH_2CH_3$ | 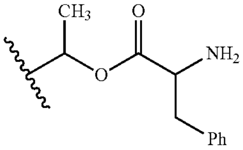 [SMILES: *C(C)OC(=O)C(N)Cc1ccccc1] | Cl | Cl |
| $—CH_2CH_2CH_2CH_3$ | 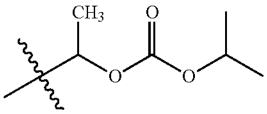 [SMILES: *C(C)OC(=O)OC(C)C] | Cl | Cl |
| $—CH_2CH_2CH_2CH_3$ | 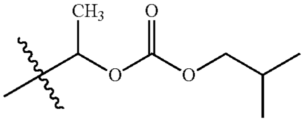 | Cl | Cl |
| 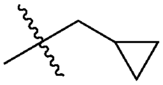 [SMILES: *CC1CC1] | 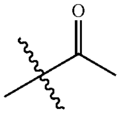 [SMILES: *C(C)=O] | Cl | Cl |
| 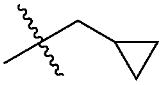 | 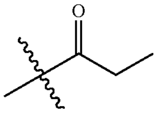 [SMILES: *C(=O)CC] | Cl | Cl |
| 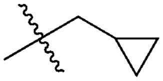 [SMILES: *CC1CC1] | 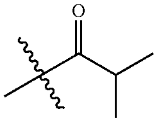 [SMILES: *C(=O)C(C)C] | Cl | Cl |
| 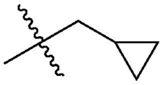 | 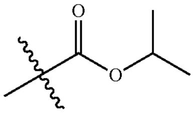 | Cl | Cl |
| 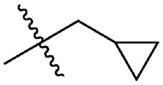 [SMILES: *CC1CC1] | 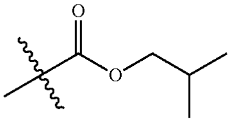 [SMILES: *C(=O)OCC(C)C] | Cl | Cl |
| 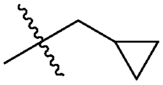 [SMILES: *CC1CC1] | 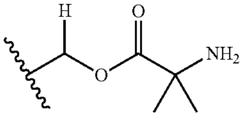 [SMILES: *COC(=O)C(C)(C)N] | Cl | Cl |
| 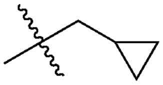 | 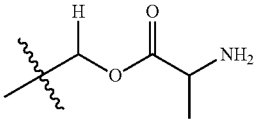 [SMILES: *COC(=O)C(C)N] | Cl | Cl |

-continued
| $R^2$ | $R^1$ | $R^{6A}$ | $R^{6B}$ |
|---|---|---|---|
| 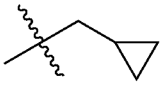 | 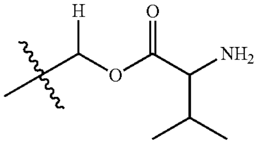 [SMILES: *COC(=O)C(N)C(C)C] | Cl | Cl |
| 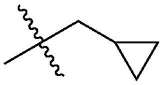 [SMILES: *CC1CC1] | 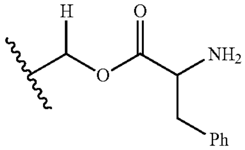 [SMILES: *COC(=O)C(N)Cc1ccccc1] | Cl | Cl |
| 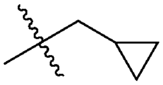 [SMILES: *CC1CC1] | 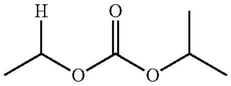 | Cl | Cl |
| 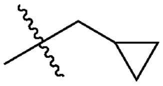 [SMILES: *CC1CC1] | 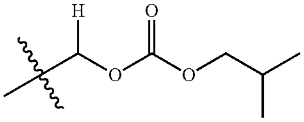 [SMILES: *COC(=O)OCC(C)C] | Cl | Cl |
| 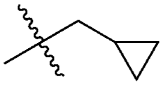 [SMILES: *CC1CC1] | 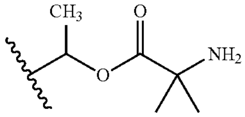 [SMILES: *C(C)OC(=O)C(C)(C)N] | Cl | Cl |
| 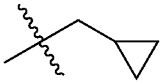 [SMILES: *CC1CC1] | 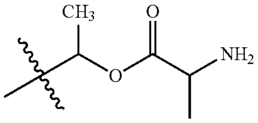 | Cl | Cl |
| 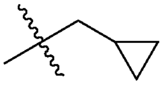 [SMILES: *CC1CC1] | 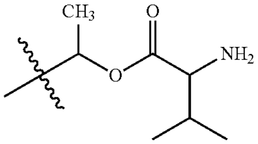 [SMILES: *C(C)OC(=O)C(N)C(C)C] | Cl | Cl |
| 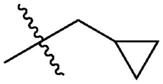 [SMILES: *CC1CC1] | 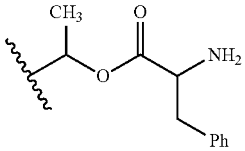 | Cl | Cl |
| 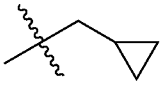 | 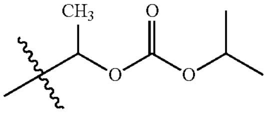 [SMILES: *C(C)OC(=O)OC(C)C] | Cl | Cl |
| 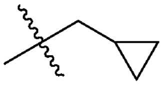 [SMILES: *CC1CC1] | 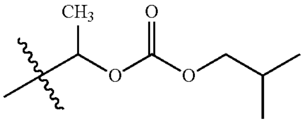 [SMILES: *C(C)OC(=O)OCC(C)C] | Cl | Cl |
| 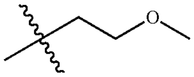 [SMILES: *CCOC] | H | Cl | Cl |

-continued
| $R^2$ | $R^1$ | $R^{6A}$ | $R^{6B}$ |
|---|---|---|---|
| 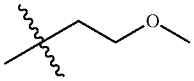 [SMILES: *CCOC] | 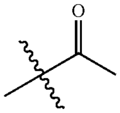 [SMILES: *C(C)=O] | Cl | Cl |
| 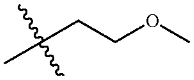 [SMILES: *CCOC] | 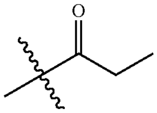 [SMILES: *C(=O)CC] | Cl | Cl |
| 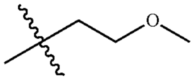 [SMILES: *CCOC] | 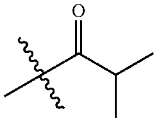 [SMILES: *C(=O)C(C)C] | Cl | Cl |
| 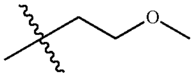 [SMILES: *CCOC] | 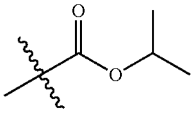 [SMILES: *C(=O)OC(C)C] | Cl | Cl |
| 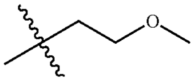 [SMILES: *CCOC] | 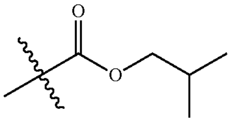 [SMILES: *C(=O)OCC(C)C] | Cl | Cl |
| 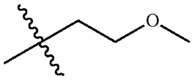 [SMILES: *CCOC] | 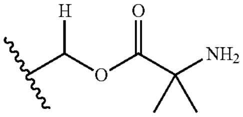 [SMILES: *COC(=O)C(C)(C)N] | Cl | Cl |
| 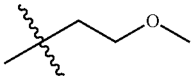 [SMILES: *CCOC] | 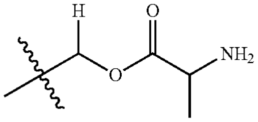 [SMILES: *COC(=O)C(C)N] | Cl | Cl |
| 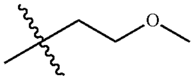 [SMILES: *CCOC] | 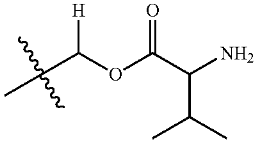 | Cl | Cl |
| 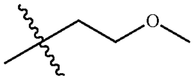 [SMILES: *CCOC] | 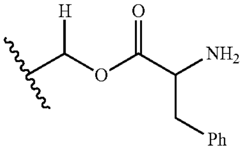 [SMILES: *COC(=O)C(N)Cc1ccccc1] | Cl | Cl |
| 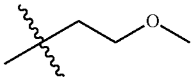 [SMILES: *CCOC] | 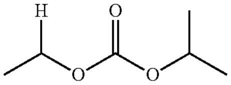 | Cl | Cl |
| 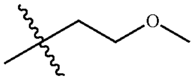 [SMILES: *CCOC] | 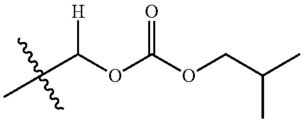 [SMILES: *COC(=O)OCC(C)C] | Cl | Cl |

-continued
| $R^2$ | $R^1$ | $R^{6A}$ | $R^{6B}$ |
| --- | --- | --- | --- |
| 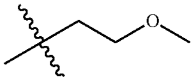 [SMILES: *CCOC] | 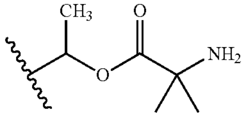 [SMILES: *C(C)OC(=O)C(C)(C)N] | Cl | Cl |
| 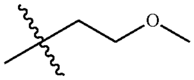 [SMILES: *CCOC] | 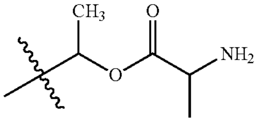 [SMILES: *C(C)OC(=O)C(C)N] | Cl | Cl |
| 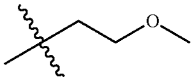 [SMILES: *CCOC] | 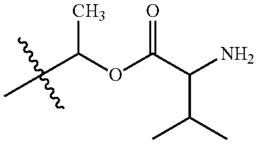 [SMILES: *C(C)OC(=O)C(N)C(C)C] | Cl | Cl |
| 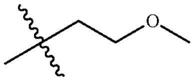 [SMILES: *CCOC] | 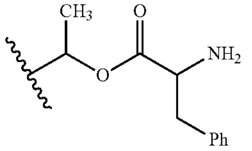 [SMILES: *C(C)OC(=O)C(N)Cc1ccccc1] | Cl | Cl |
| 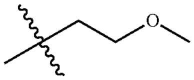 [SMILES: *CCOC] | 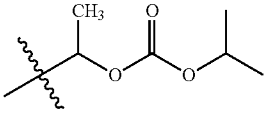 [SMILES: *C(C)OC(=O)OC(C)C] | Cl | Cl |
| 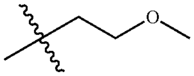 [SMILES: *CCOC] | 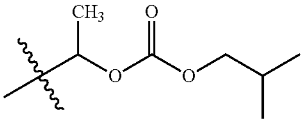 [SMILES: *C(C)OC(=O)OCC(C)C] | Cl | Cl |
| 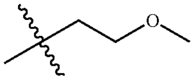 [SMILES: *CCOC] | H | Cl | Cl |
| 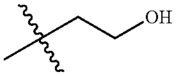 [SMILES: *CCO] | 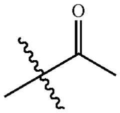 [SMILES: *C(C)=O] | Cl | Cl |
| 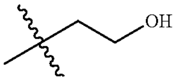 [SMILES: *CCO] | 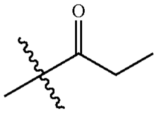 [SMILES: *C(=O)CC] | Cl | Cl |
| 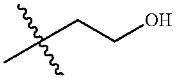 [SMILES: *CCO] | 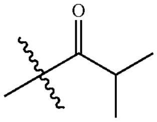 [SMILES: *C(=O)C(C)C] | Cl | Cl |
| 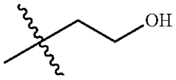 [SMILES: *CCO] | 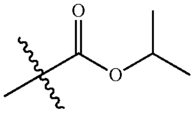 [SMILES: *C(=O)OC(C)C] | Cl | Cl |

-continued
| $R^2$ | $R^1$ | $R^{6A}$ | $R^{6B}$ |
|---|---|---|---|
| 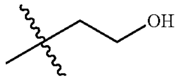 [SMILES: *CCO] | 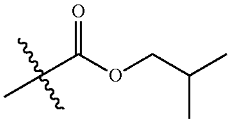 [SMILES: *C(=O)OCC(C)C] | Cl | Cl |
| 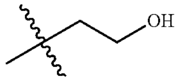 [SMILES: *CCO] | 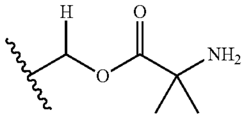 [SMILES: *COC(=O)C(C)(C)N] | Cl | Cl |
| 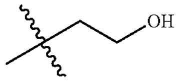 [SMILES: *CCO] | 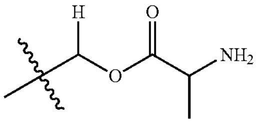 [SMILES: *COC(=O)C(C)N] | Cl | Cl |
| 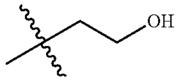 [SMILES: *CCO] | 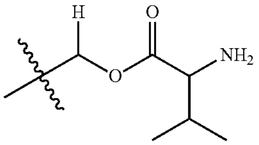 [SMILES: *COC(=O)C(N)C(C)C] | Cl | Cl |
| 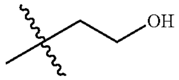 [SMILES: *CCO] | 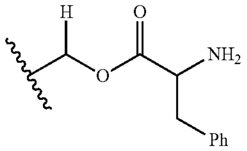 | Cl | Cl |
| 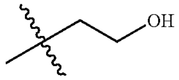 [SMILES: *CCO] | 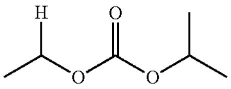 | Cl | Cl |
| 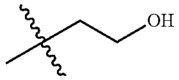 [SMILES: *CCO] | 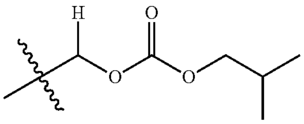 [SMILES: *COC(=O)OCC(C)C] | Cl | Cl |
| 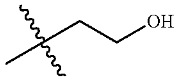 [SMILES: *CCO] | 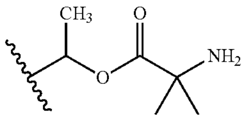 [SMILES: *C(C)OC(=O)C(C)(C)N] | Cl | Cl |
| 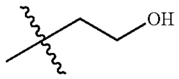 [SMILES: *CCO] | 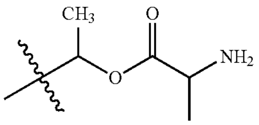 | Cl | Cl |
| 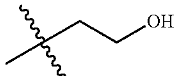 [SMILES: *CCO] | 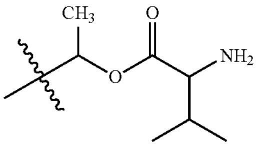 [SMILES: *C(C)OC(=O)C(N)C(C)C] | Cl | Cl |
| 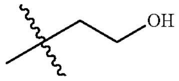 [SMILES: *CCO] | 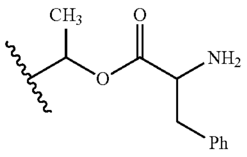 | Cl | Cl |

-continued
| $R^2$ | $R^1$ | $R^{6A}$ | $R^{6B}$ |
|---|---|---|---|
| 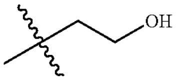 [SMILES: *CCO] | 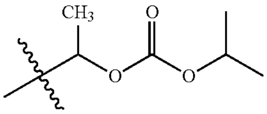 | Cl | Cl |
| 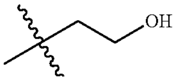 [SMILES: *CCO] | 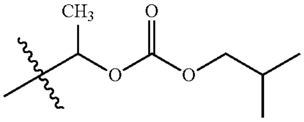 | Cl | Cl |
| $—CH_2CH{=}CF_2$ | 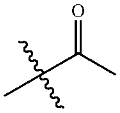 [SMILES: *C(C)=O] | Cl | Cl |
| $—CH_2CH{=}CF_2$ | 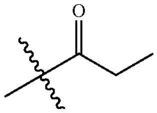 [SMILES: *C(=O)CC] | Cl | Cl |
| $—CH_2CH{=}CF_2$ | 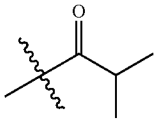 [SMILES: *C(=O)C(C)C] | Cl | Cl |
| $—CH_2CH{=}CF_2$ | 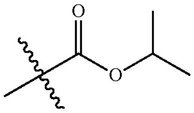 [SMILES: *C(=O)OC(C)C] | Cl | Cl |
| $—CH_2CH{=}CF_2$ | 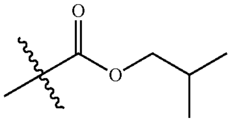 [SMILES: *C(=O)OCC(C)C] | Cl | Cl |
| $—CH_2CH{=}CF_2$ | 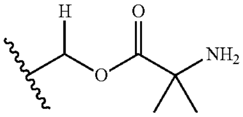 [SMILES: *COC(=O)C(C)(C)N] | Cl | Cl |
| $—CH_2CH{=}CF_2$ | 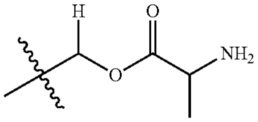 [SMILES: *COC(=O)C(C)N] | Cl | Cl |
| $—CH_2CH{=}CF_2$ | 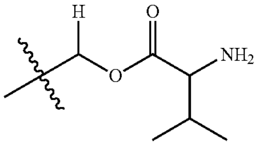 [SMILES: *COC(=O)C(N)C(C)C] | Cl | Cl |
| $—CH_2CH{=}CF_2$ | 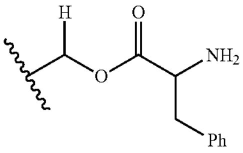 [SMILES: *COC(=O)C(N)Cc1ccccc1] | Cl | Cl |

-continued
| $R^2$ | $R^1$ | $R^{6A}$ | $R^{6B}$ |
|---|---|---|---|
| $-CH_2CH{=}CF_2$ | 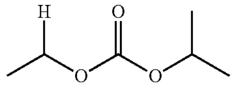 | Cl | Cl |
| $-CH_2CH{=}CF_2$ | 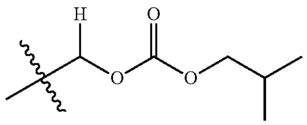 [SMILES: *COC(=O)OCC(C)C] | Cl | Cl |
| $-CH_2CH{=}CF_2$ | 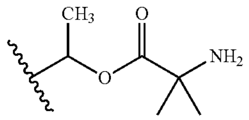 | Cl | Cl |
| $-CH_2CH{=}CF_2$ | 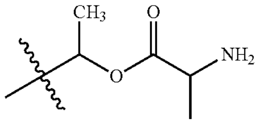 [SMILES: *C(C)OC(=O)C(C)N] | Cl | Cl |
| $-CH_2CH{=}CF_2$ | 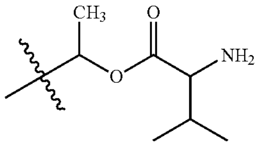 [SMILES: *C(C)OC(=O)C(N)C(C)C] | Cl | Cl |
| $-CH_2CH{=}CF_2$ | 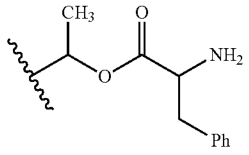 [SMILES: *C(C)OC(=O)C(N)Cc1ccccc1] | Cl | Cl |
| $-CH_2CH{=}CF_2$ | 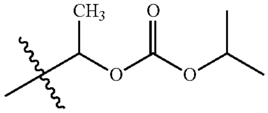 [SMILES: *C(C)OC(=O)OC(C)C] | Cl | Cl |
| $-CH_2CH{=}CF_2$ | 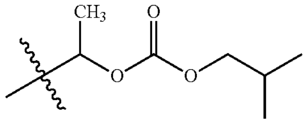 [SMILES: *C(C)OC(=O)OCC(C)C] | Cl | Cl |
| $-CH_2CF_3$ | 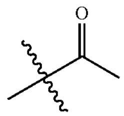 [SMILES: *C(C)=O] | Cl | Cl |
| $-CH_2CF_3$ | 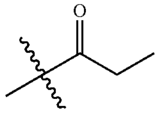 [SMILES: *C(=O)CC] | Cl | Cl |
| $-CH_2CF_3$ | 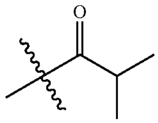 [SMILES: *C(=O)C(C)C] | Cl | Cl |

-continued
| $R^2$ | $R^1$ | $R^{6A}$ | $R^{6B}$ |
|---|---|---|---|
| $—CH_2CF_3$ | 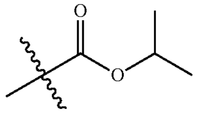 [SMILES: *C(=O)OC(C)C] | Cl | Cl |
| $—CH_2CF_3$ | 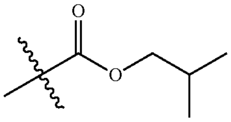 [SMILES: *C(=O)OCC(C)C] | Cl | Cl |
| $—CH_2CF_3$ | 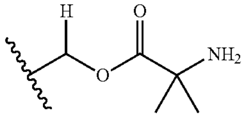 [SMILES: *COC(=O)C(C)(C)N] | Cl | Cl |
| $—CH_2CF_3$ | 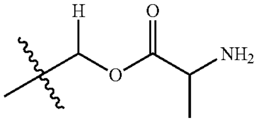 [SMILES: *COC(=O)C(C)N] | Cl | Cl |
| $—CH_2CF_3$ | 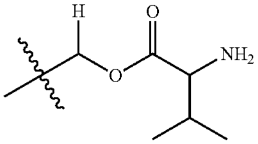 [SMILES: *COC(=O)C(N)C(C)C] | Cl | Cl |
| $—CH_2CF_3$ | 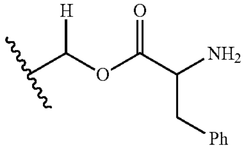 [SMILES: *COC(=O)C(N)Cc1ccccc1] | Cl | Cl |
| $—CH_2CF_3$ | 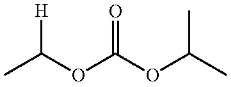 | Cl | Cl |
| $—CH_2CF_3$ | 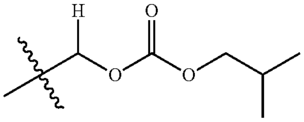 [SMILES: *COC(=O)OCC(C)C] | Cl | Cl |
| $—CH_2CF_3$ | 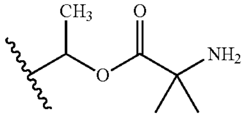 [SMILES: *C(C)OC(=O)C(C)(C)N] | Cl | Cl |
| $—CH_2CF_3$ | 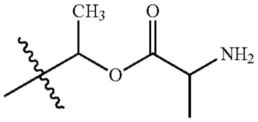 [SMILES: *C(C)OC(=O)C(C)N] | Cl | Cl |
| $—CH_2CF_3$ | 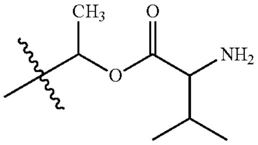 [SMILES: *C(C)OC(=O)C(N)C(C)C] | Cl | Cl |

-continued
| $R^2$ | $R^1$ | $R^{6A}$ | $R^{6B}$ |
|---|---|---|---|
| $—CH_2CF_3$ | 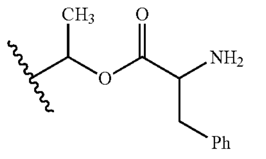 [SMILES: *C(C)OC(=O)C(N)Cc1ccccc1] | Cl | Cl |
| $—CH_2CF_3$ | 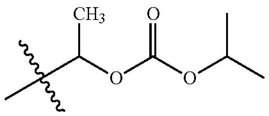 [SMILES: *C(C)OC(=O)OC(C)C] | Cl | Cl |
| $—CH_2CF_3$ | 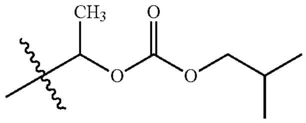 [SMILES: *C(C)OC(=O)OCC(C)C] | Cl | Cl |
| $—CH_2CH_2CF_3$ | 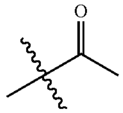 [SMILES: *C(C)=O] | Cl | Cl |
| $—CH_2CH_2CF_3$ | 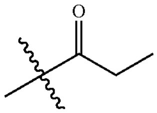 [SMILES: *C(=O)CC] | Cl | Cl |
| $—CH_2CH_2CF_3$ | 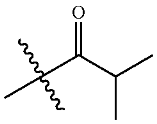 [SMILES: *C(=O)C(C)C] | Cl | Cl |
| $—CH_2CH_2CF_3$ | 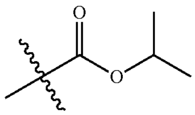 [SMILES: *C(=O)OC(C)C] | Cl | Cl |
| $—CH_2CH_2CF_3$ | 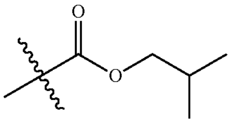 [SMILES: *C(=O)OCC(C)C] | Cl | Cl |
| $—CH_2CH_2CF_3$ | 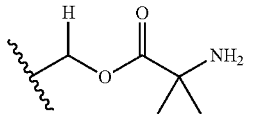 [SMILES: *COC(=O)C(C)(C)N] | Cl | Cl |
| $—CH_2CH_2CF_3$ | 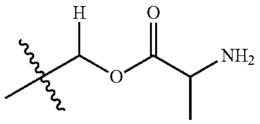 [SMILES: *COC(=O)C(C)N] | Cl | Cl |
| $—CH_2CH_2CF_3$ | 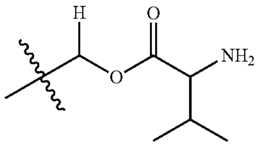 [SMILES: *COC(=O)C(N)C(C)C] | Cl | Cl |

-continued
| $R^2$ | $R^1$ | $R^{6A}$ | $R^{6B}$ |
|---|---|---|---|
| $—CH_2CH_2CF_3$ | 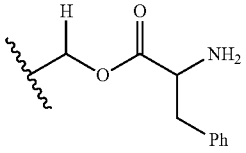 [SMILES: *COC(=O)C(N)Cc1ccccc1] | Cl | Cl |
| $—CH_2CH_2CF_3$ | 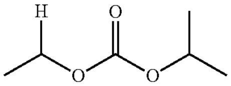 | Cl | Cl |
| $—CH_2CH_2CF_3$ | 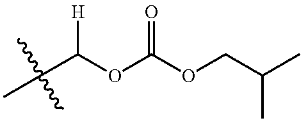 [SMILES: *COC(=O)OCC(C)C] | Cl | Cl |
| $—CH_2CH_2CF_3$ | 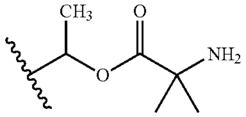 [SMILES: *C(C)OC(=O)C(C)(C)N] | Cl | Cl |
| $—CH_2CH_2CF_3$ | 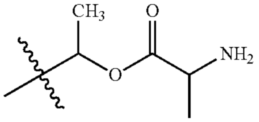 [SMILES: *C(C)OC(=O)C(C)N] | Cl | Cl |
| $—CH_2CH_2CF_3$ | 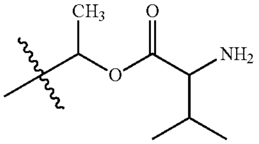 [SMILES: *C(C)OC(=O)C(N)C(C)C] | Cl | Cl |
| $—CH_2CH_2CF_3$ | 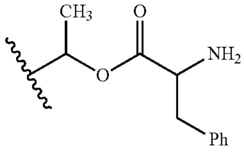 [SMILES: *C(C)OC(=O)C(N)Cc1ccccc1] | Cl | Cl |
| $—CH_2CH_2CF_3$ | 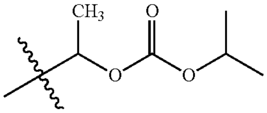 [SMILES: *C(C)OC(=O)OC(C)C] | Cl | Cl |
| $—CH_2CH_2CF_3$ | 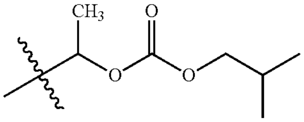 [SMILES: *C(C)OC(=O)OCC(C)C] | Cl | Cl |
| $—CH_2CHF_2$ | 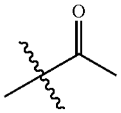 [SMILES: *C(C)=O] | Cl | Cl |
| $—CH_2CHF_2$ | 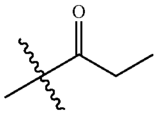 [SMILES: *C(=O)CC] | Cl | Cl |

-continued
| $R^2$ | $R^1$ | $R^{6A}$ | $R^{6B}$ |
|---|---|---|---|
| $—CH_2CHF_2$ | 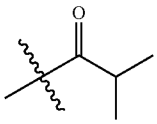 [SMILES: *C(=O)C(C)C] | Cl | Cl |
| $—CH_2CHF_2$ | 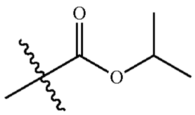 [SMILES: *C(=O)OC(C)C] | Cl | Cl |
| $—CH_2CHF_2$ | 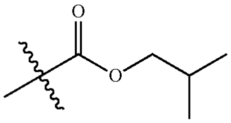 [SMILES: *C(=O)OCC(C)C] | Cl | Cl |
| $—CH_2CHF_2$ | 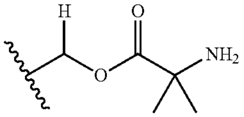 [SMILES: *COC(=O)C(C)(C)N] | Cl | Cl |
| $—CH_2CHF_2$ | 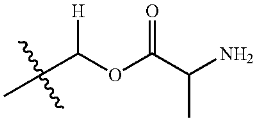 [SMILES: *COC(=O)C(C)N] | Cl | Cl |
| $—CH_2CHF_2$ | 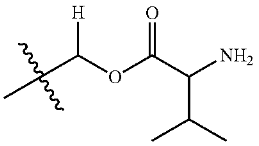 [SMILES: *COC(=O)C(N)C(C)C] | Cl | Cl |
| $—CH_2CHF_2$ | 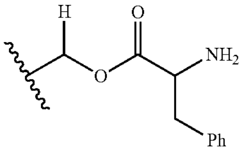 [SMILES: *COC(=O)C(N)Cc1ccccc1] | Cl | Cl |
| $—CH_2CHF_2$ | 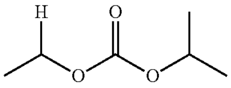 | Cl | Cl |
| $—CH_2CHF_2$ | 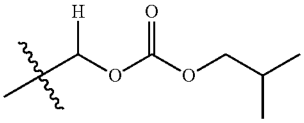 [SMILES: *COC(=O)OCC(C)C] | Cl | Cl |
| $—CH_2CHF_2$ | 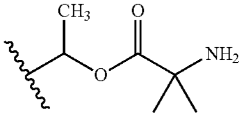 [SMILES: *C(C)OC(=O)C(C)(C)N] | Cl | Cl |
| $—CH_2CHF_2$ | 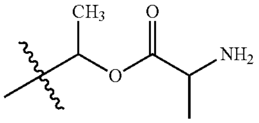 [SMILES: *C(C)OC(=O)C(C)N] | Cl | Cl |

-continued
| $R^2$ | $R^1$ | $R^{6A}$ | $R^{6B}$ |
|---|---|---|---|
| $—CH_2CHF_2$ | 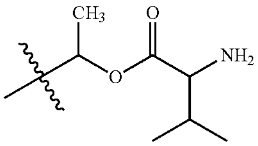 [SMILES: *C(C)OC(=O)C(N)C(C)C] | Cl | Cl |
| $—CH_2CHF_2$ | 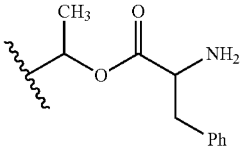 [SMILES: *C(C)OC(=O)C(N)Cc1ccccc1] | Cl | Cl |
| $—CH_2CHF_2$ | 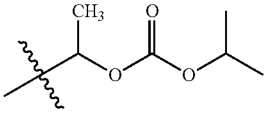 [SMILES: *C(C)OC(=O)OC(C)C] | Cl | Cl |
| $—CH_2CHF_2$ | 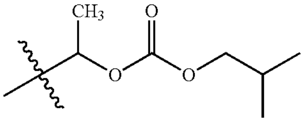 [SMILES: *C(C)OC(=O)OCC(C)C] | Cl | Cl |
| $—CH_2C(CH_3)F_2$ | 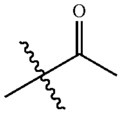 [SMILES: *C(C)=O] | Cl | Cl |
| $—CH_2C(CH_3)F_2$ | 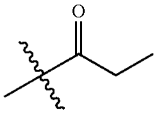 [SMILES: *C(=O)CC] | Cl | Cl |
| $—CH_2C(CH_3)F_2$ | 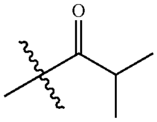 [SMILES: *C(=O)C(C)C] | Cl | Cl |
| $—CH_2C(CH_3)F_2$ | 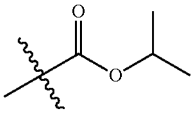 [SMILES: *C(=O)OC(C)C] | Cl | Cl |
| $—CH_2C(CH_3)F_2$ | 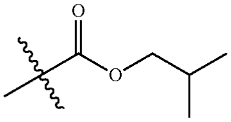 [SMILES: *C(=O)OCC(C)C] | Cl | Cl |
| $—CH_2C(CH_3)F_2$ | 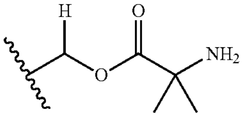 [SMILES: *COC(=O)C(C)(C)N] | Cl | Cl |
| $—CH_2C(CH_3)F_2$ | 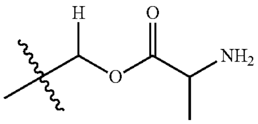 [SMILES: *COC(=O)C(C)N] | Cl | Cl |

-continued
| R² | R¹ | R6A | R6B |
|---|---|---|---|
| —$CH_2C(CH_3)F_2$ | 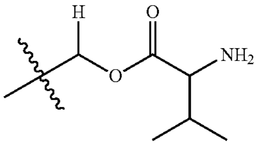 [SMILES: *COC(=O)C(N)C(C)C] | Cl | Cl |
| —$CH_2C(CH_3)F_2$ | 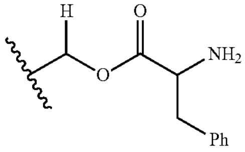 | Cl | Cl |
| —$CH_2C(CH_3)F_2$ | 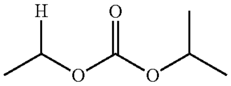 | Cl | Cl |
| —$CH_2C(CH_3)F_2$ | 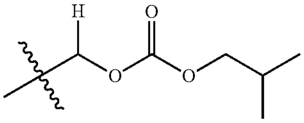 [SMILES: *COC(=O)OCC(C)C] | Cl | Cl |
| —$CH_2C(CH_3)F_2$ | 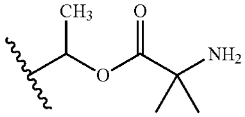 [SMILES: *C(C)OC(=O)C(C)(C)N] | Cl | Cl |
| —$CH_2C(CH_3)F_2$ | 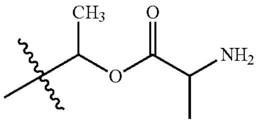 [SMILES: *C(C)OC(=O)C(C)N] | Cl | Cl |
| —$CH_2C(CH_3)F_2$ | 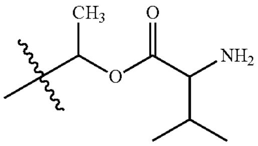 [SMILES: *C(C)OC(=O)C(N)C(C)C] | Cl | Cl |
| —$CH_2C(CH_3)F_2$ | 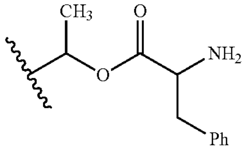 [SMILES: *C(C)OC(=O)C(N)Cc1ccccc1] | Cl | Cl |
| —$CH_2C(CH_3)F_2$ | 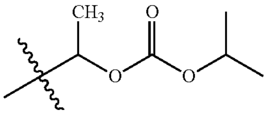 [SMILES: *C(C)OC(=O)OC(C)C] and | Cl | Cl |
| —$CH_2C(CH_3)F_2$ | 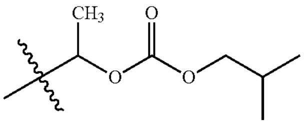 [SMILES: *C(C)OC(=O)OCC(C)C] | Cl | Cl, | or a pharmaceutically acceptable salt of any of the foregoing; or
a compound of the following structure:
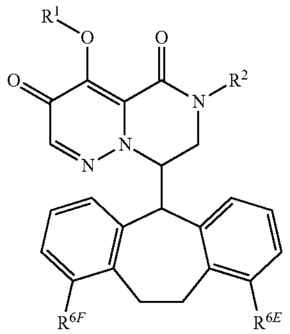
wherein the compound is selected from the group consisting of:
| $R^2$ | $R^1$ | $R^{6E}$ | $R^{6F}$ |
|---|---|---|---|
| 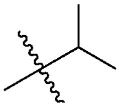 [SMILES: *C(C)C] | 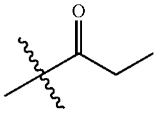 [SMILES: *C(=O)CC] | H | H |
| 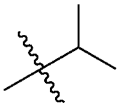 [SMILES: *C(C)C] | 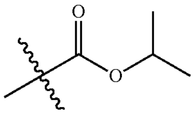 [SMILES: *C(=O)OC(C)C] | H | H |
| 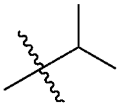 [SMILES: *C(C)C] | 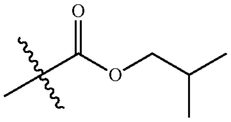 [SMILES: *C(=O)OCC(C)C] | H | H |
| 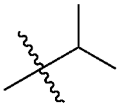 [SMILES: *C(C)C] | 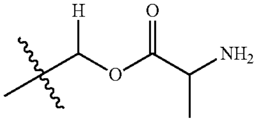 [SMILES: *COC(=O)C(C)N] | H | H |
| 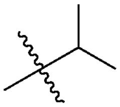 [SMILES: *C(C)C] | 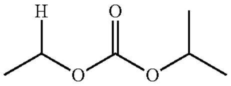 | H | H |
| 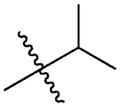 [SMILES: *C(C)C] | 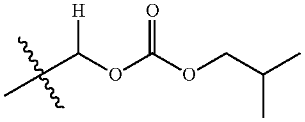 [SMILES: *COC(=O)OCC(C)C] | H | H |
| 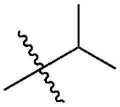 [SMILES: *C(C)C] | 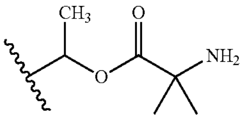 [SMILES: *C(C)OC(=O)C(C)(C)N] | H | H |
| 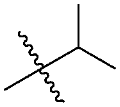 [SMILES: *C(C)C] | 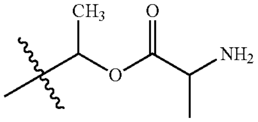 [SMILES: *C(C)OC(=O)C(C)N] | H | H |

-continued
| $R^2$ | $R^1$ | $R^{6E}$ | $R^{6F}$ |
|---|---|---|---|
| 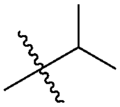 [SMILES: *C(C)C] | 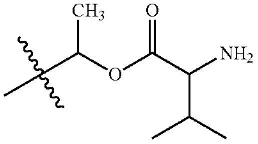 [SMILES: *C(C)OC(=O)C(N)C(C)C] | H | H |
| 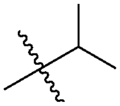 [SMILES: *C(C)C] | 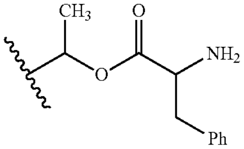 | H | H |
| 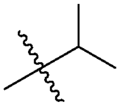 [SMILES: *C(C)C] | 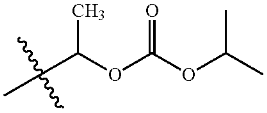 [SMILES: *C(C)OC(=O)OC(C)C] | H | H |
| 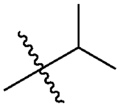 [SMILES: *C(C)C] | 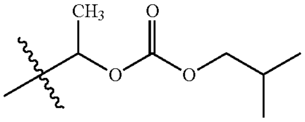 | H | H |
| $-CH_3$ | 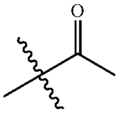 [SMILES: *C(C)=O] | H | H |
| $-CH_3$ | 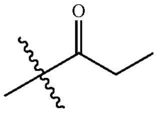 [SMILES: *C(=O)CC] | H | H |
| $-CH_3$ | 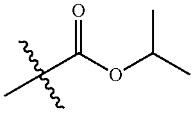 [SMILES: *C(=O)OC(C)C] | H | H |
| $-CH_3$ | 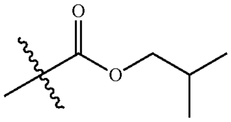 [SMILES: *C(=O)OCC(C)C] | H | H |
| $-CH_3$ | 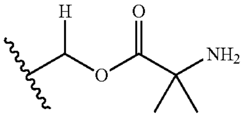 [SMILES: *COC(=O)C(C)(C)N] | H | H |
| $-CH_3$ | 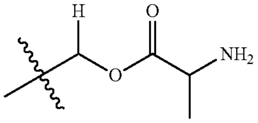 [SMILES: *COC(=O)C(C)N] | H | H |
| $-CH_3$ | 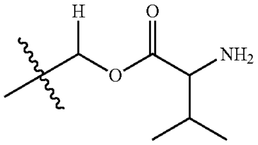 [SMILES: *COC(=O)C(N)C(C)C] | H | H |

-continued
| $R^2$ | $R^1$ | $R^{6E}$ | $R^{6F}$ |
|---|---|---|---|
| —$CH_3$ | 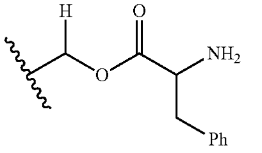 [SMILES: *COC(=O)C(N)Cc1ccccc1] | H | H |
| —$CH_3$ | 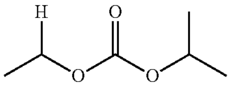 | H | H |
| —$CH_3$ | 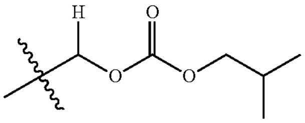 [SMILES: *COC(=O)OCC(C)C] | H | H |
| —$CH_3$ | 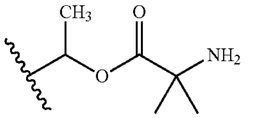 [SMILES: *C(C)OC(=O)C(C)(C)N] | H | H |
| —$CH_3$ | 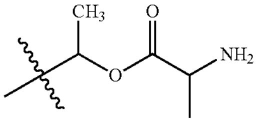 [SMILES: *C(C)OC(=O)C(C)N] | H | H |
| —$CH_3$ | 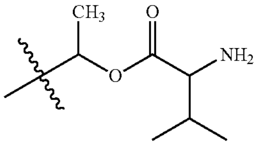 [SMILES: *C(C)OC(=O)C(N)C(C)C] | H | H |
| —$CH_3$ | 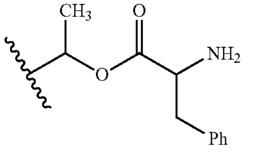 [SMILES: *C(C)OC(=O)C(N)Cc1ccccc1] | H | H |
| —$CH_3$ | 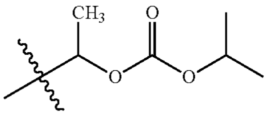 [SMILES: *C(C)OC(=O)OC(C)C] | H | H |
| —$CH_3$ | 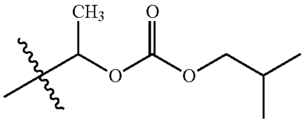 | H | H |
| —$CH_2CH_3$ | 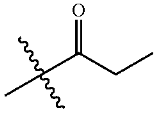 [SMILES: *C(=O)CC] | H | H |
| —$CH_2CH_3$ | 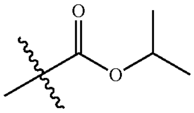 [SMILES: *C(=O)OC(C)C] | H | H |

-continued
| $R^2$ | $R^1$ | $R^{6E}$ | $R^{6F}$ |
|---|---|---|---|
| $—CH_2CH_3$ | 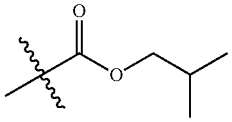 [SMILES: *C(=O)OCC(C)C] | H | H |
| $—CH_2CH_3$ | 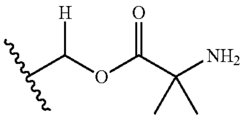 [SMILES: *COC(=O)C(C)(C)N] | H | H |
| $—CH_2CH_3$ | 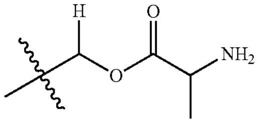 [SMILES: *COC(=O)C(C)N] | H | H |
| $—CH_2CH_3$ | 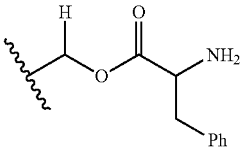 | H | H |
| $—CH_2CH_3$ | 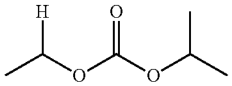 | H | H |
| $—CH_2CH_3$ | 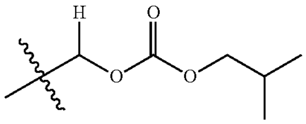 [SMILES: *COC(=O)OCC(C)C] | H | H |
| $—CH_2CH_3$ | 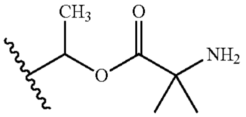 [SMILES: *C(C)OC(=O)C(C)(C)N] | H | H |
| $—CH_2CH_3$ | 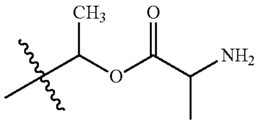 [SMILES: *C(C)OC(=O)C(C)N] | H | H |
| $—CH_2CH_3$ | 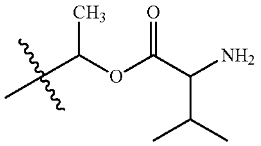 [SMILES: *C(C)OC(=O)C(N)C(C)C] | H | H |
| $—CH_2CH_3$ | 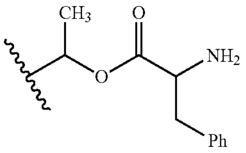 | H | H |
| $—CH_2CH_3$ | 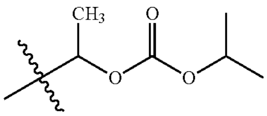 [SMILES: *C(C)OC(=O)OC(C)C] | H | H |

-continued
| $R^2$ | $R^1$ | $R^{6E}$ | $R^{6F}$ |
|---|---|---|---|
| $—CH_2CH_3$ | 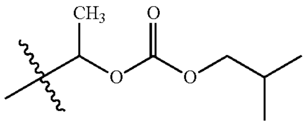 [SMILES: *C(C)OC(=O)OCC(C)C] | H | H |
| $—CH_2CH(CH_3)_2$ | H | H | H |
| $—CH_2CH(CH_3)_2$ | 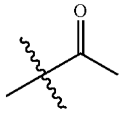 [SMILES: *C(C)=O] | H | H |
| $—CH_2CH(CH_3)_2$ | 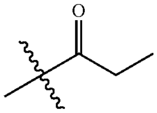 [SMILES: *C(=O)CC] | H | H |
| $—CH_2CH(CH_3)_2$ | 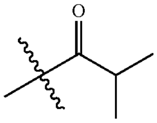 [SMILES: *C(=O)C(C)C] | H | H |
| $—CH_2CH(CH_3)_2$ | 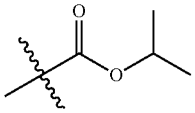 [SMILES: *C(=O)OC(C)C] | H | H |
| $—CH_2CH(CH_3)_2$ | 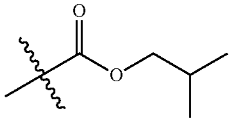 [SMILES: *C(=O)OCC(C)C] | H | H |
| $—CH_2CH(CH_3)_2$ | 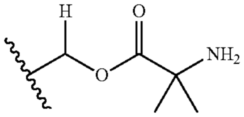 [SMILES: *COC(=O)C(C)(C)N] | H | H |
| $—CH_2CH(CH_3)_2$ | 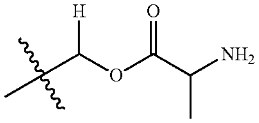 [SMILES: *COC(=O)C(C)N] | H | H |
| $—CH_2CH(CH_3)_2$ | 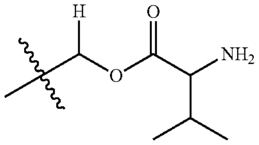 [SMILES: *COC(=O)C(N)C(C)C] | H | H |
| $—CH_2CH(CH_3)_2$ | 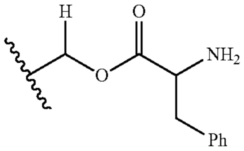 [SMILES: *COC(=O)C(N)Cc1ccccc1] | H | H |
| $—CH_2CH(CH_3)_2$ | 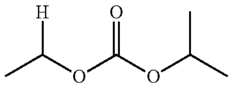 | H | H |

-continued
| $R^2$ | $R^1$ | $R^{6E}$ | $R^{6F}$ |
|---|---|---|---|
| $—CH_2CH(CH_3)_2$ | 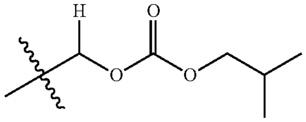 [SMILES: *COC(=O)OCC(C)C] | H | H |
| $—CH_2CH(CH_3)_2$ | 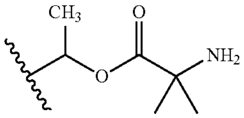 | H | H |
| $—CH_2CH(CH_3)_2$ | 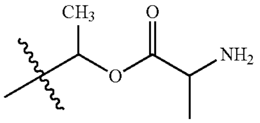 [SMILES: *C(C)OC(=O)C(C)N] | H | H |
| $—CH_2CH(CH_3)_2$ | 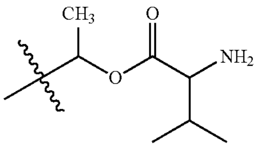 | H | H |
| $—CH_2CH(CH_3)_2$ | 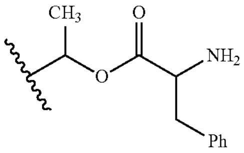 | H | H |
| $—CH_2CH(CH_3)_2$ | 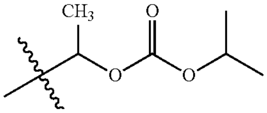 [SMILES: *C(C)OC(=O)OC(C)C] | H | H |
| $—CH_2CH(CH_3)_2$ | 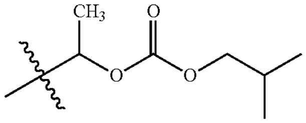 [SMILES: *C(C)OC(=O)OCC(C)C] | H | H |
| $—CH_2CH_2CH_3$ | 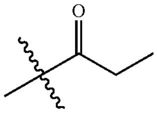 [SMILES: *C(=O)CC] | H | H |
| $—CH_2CH_2CH_3$ | 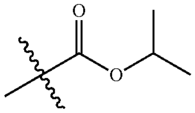 [SMILES: *C(=O)OC(C)C] | H | H |
| $—CH_2CH_2CH_3$ | 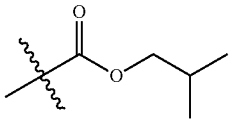 [SMILES: *C(=O)OCC(C)C] | H | H |
| $—CH_2CH_2CH_3$ | 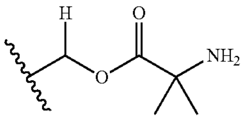 [SMILES: *COC(=O)C(C)(C)N] | H | H |

-continued
| $R^2$ | $R^1$ | $R^{6E}$ | $R^{6F}$ |
|---|---|---|---|
| $—CH_2CH_2CH_3$ | 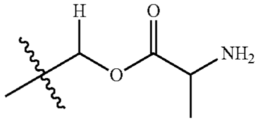 | H | H |
| $—CH_2CH_2CH_3$ | 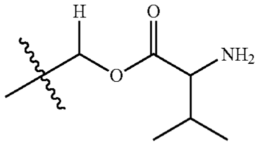 [SMILES: *COC(=O)C(N)C(C)C] | H | H |
| $—CH_2CH_2CH_3$ | 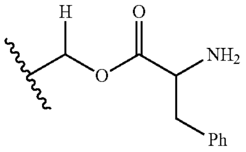 [SMILES: *COC(=O)C(N)Cc1ccccc1] | H | H |
| $—CH_2CH_2CH_3$ | 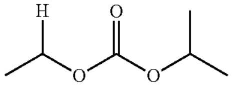 | H | H |
| $—CH_2CH_2CH_3$ | 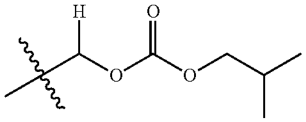 [SMILES: *COC(=O)OCC(C)C] | H | H |
| $—CH_2CH_2CH_3$ | 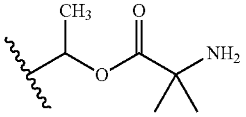 [SMILES: *C(C)OC(=O)C(C)(C)N] | H | H |
| $—CH_2CH_2CH_3$ | 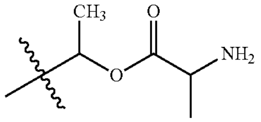 [SMILES: *C(C)OC(=O)C(C)N] | H | H |
| $—CH_2CH_2CH_3$ | 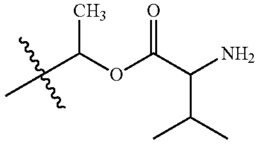 [SMILES: *C(C)OC(=O)C(N)C(C)C] | H | H |
| $—CH_2CH_2CH_3$ | 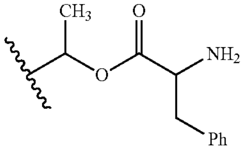 [SMILES: *C(C)OC(=O)C(N)Cc1ccccc1] | H | H |
| $—CH_2CH_2CH_3$ | 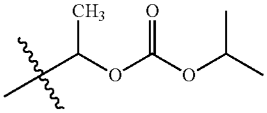 [SMILES: *C(C)OC(=O)OC(C)C] | H | H |
| $—CH_2CH_2CH_3$ | 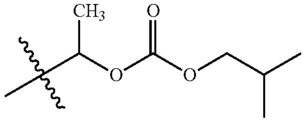 [SMILES: *C(C)OC(=O)OCC(C)C] | H | H |
| $—CH_2CH_2CH_2CH_3$ | H | H | H |

-continued
| $R^2$ | $R^1$ | $R^{6E}$ | $R^{6F}$ |
|---|---|---|---|
| $—CH_2CH_2CH_2CH_3$ | 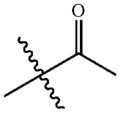 [SMILES: *C(C)=O] | H | H |
| $—CH_2CH_2CH_2CH_3$ | 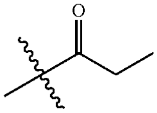 [SMILES: *C(=O)CC] | H | H |
| $—CH_2CH_2CH_2CH_3$ | 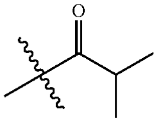 [SMILES: *C(=O)C(C)C] | H | H |
| $—CH_2CH_2CH_2CH_3$ | 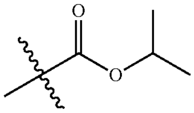 [SMILES: *C(=O)OC(C)C] | H | H |
| $—CH_2CH_2CH_2CH_3$ | 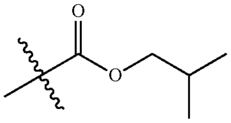 [SMILES: *C(=O)OCC(C)C] | H | H |
| $—CH_2CH_2CH_2CH_3$ | 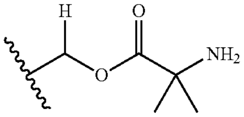 [SMILES: *COC(=O)C(C)(C)N] | H | H |
| $—CH_2CH_2CH_2CH_3$ | 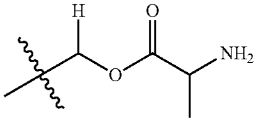 | H | H |
| $—CH_2CH_2CH_2CH_3$ | 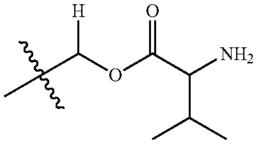 [SMILES: *COC(=O)C(N)C(C)C] | H | H |
| $—CH_2CH_2CH_2CH_3$ | 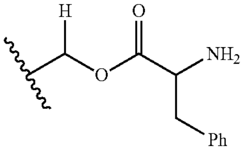 [SMILES: *COC(=O)C(N)Cc1ccccc1] | H | H |
| $—CH_2CH_2CH_2CH_3$ | 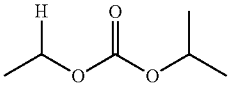 | H | H |
| $—CH_2CH_2CH_2CH_3$ | 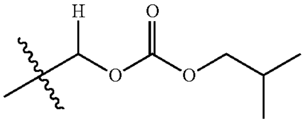 | H | H |

-continued
| $R^2$ | $R^1$ | $R^{6E}$ | $R^{6F}$ |
|---|---|---|---|
| $—CH_2CH_2CH_2CH_3$ | 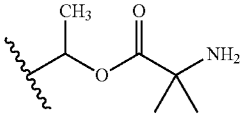 [SMILES: *C(C)OC(=O)C(C)(C)N] | H | H |
| $—CH_2CH_2CH_2CH_3$ | 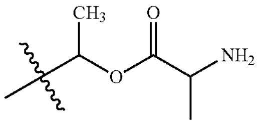 [SMILES: *C(C)OC(=O)C(C)N] | H | H |
| $—CH_2CH_2CH_2CH_3$ | 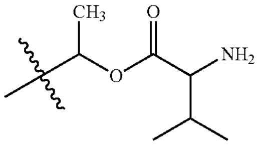 [SMILES: *C(C)OC(=O)C(N)C(C)C] | H | H |
| $—CH_2CH_2CH_2CH_3$ | 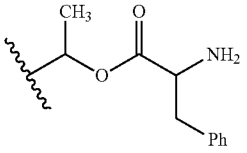 [SMILES: *C(C)OC(=O)C(N)Cc1ccccc1] | H | H |
| $—CH_2CH_2CH_2CH_3$ | 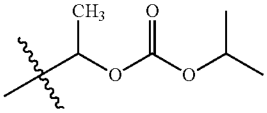 [SMILES: *C(C)OC(=O)OC(C)C] | H | H |
| $—CH_2CH_2CH_2CH_3$ | 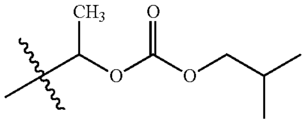 [SMILES: *C(C)OC(=O)OCC(C)C] | H | H |
| 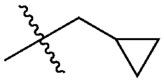 | H | H | H |
| 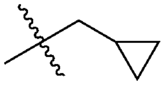 [SMILES: *CC1CC1] | 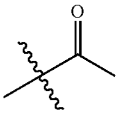 [SMILES: *C(C)=O] | H | H |
| 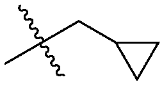 [SMILES: *CC1CC1] | 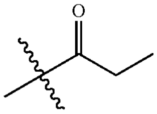 [SMILES: *C(=O)CC] | H | H |
| 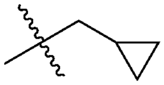 | 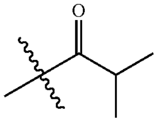 [SMILES: *C(=O)C(C)C] | H | H |
| 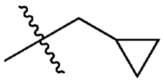 | 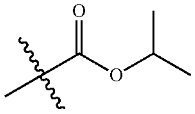 [SMILES: *C(=O)OC(C)C] | H | H |

-continued
| $R^2$ | $R^1$ | $R^{6E}$ | $R^{6F}$ |
|---|---|---|---|
| 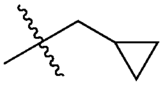 [SMILES: *CC1CC1] | 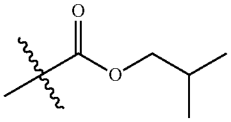 [SMILES: *C(=O)OCC(C)C] | H | H |
| 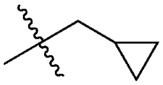 [SMILES: *CC1CC1] | 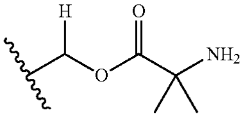 [SMILES: *COC(=O)C(C)(C)N] | H | H |
| 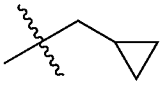 [SMILES: *CC1CC1] | 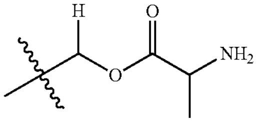 | H | H |
| 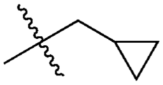 [SMILES: *CC1CC1] | 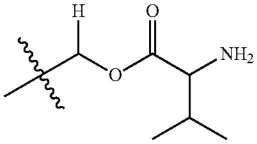 [SMILES: *COC(=O)C(N)C(C)C] | H | H |
| 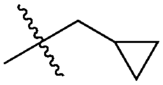 | 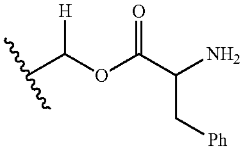 [SMILES: *COC(=O)C(N)Cc1ccccc1] | H | H |
| 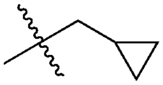 [SMILES: *CC1CC1] | 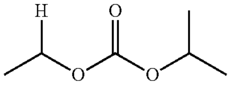 | H | H |
| 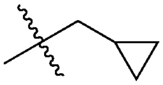 | 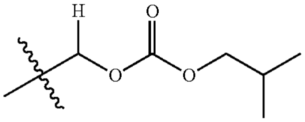 [SMILES: *COC(=O)OCC(C)C] | H | H |
| 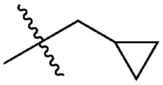 | 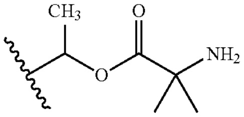 [SMILES: *C(C)OC(=O)C(C)(C)N] | H | H |
| 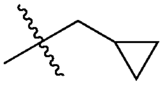 | 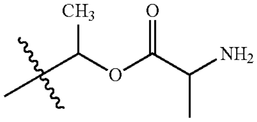 | H | H |
| 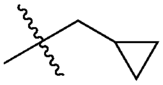 [SMILES: *CC1CC1] | 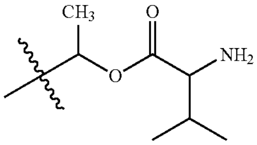 | H | H |
| 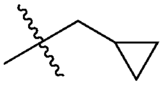 | 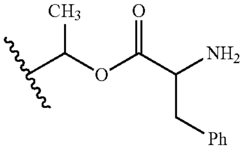 | H | H |

-continued
| $R^2$ | $R^1$ | $R^{6E}$ | $R^{6F}$ |
|---|---|---|---|
| 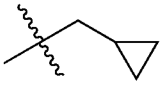 [SMILES: *CC1CC1] | 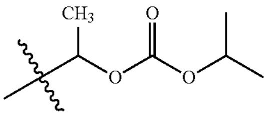 [SMILES: *C(C)OC(=O)OC(C)C] | H | H |
| 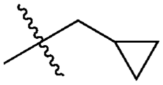 [SMILES: *CC1CC1] | 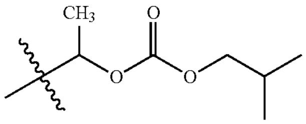 | H | H |
| 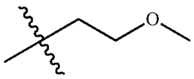 [SMILES: *CCOC] | H | H | H |
| 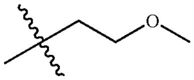 [SMILES: *CCOC] | 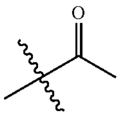 [SMILES: *C(C)=O] | H | H |
| 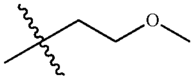 [SMILES: *CCOC] | 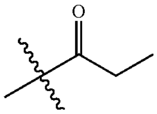 [SMILES: *C(=O)CC] | H | H |
| 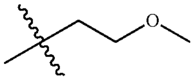 [SMILES: *CCOC] | 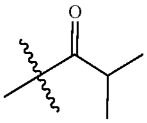 [SMILES: *C(=O)C(C)C] | H | H |
| 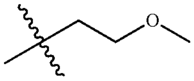 [SMILES: *CCOC] | 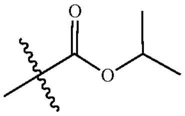 [SMILES: *C(=O)OC(C)C] | H | H |
| 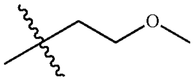 [SMILES: *CCOC] | 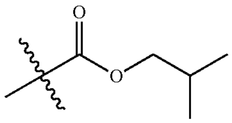 [SMILES: *C(=O)OCC(C)C] | H | H |
| 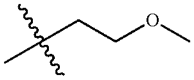 [SMILES: *CCOC] | 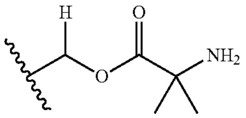 [SMILES: *COC(=O)C(C)(C)N] | H | H |
| 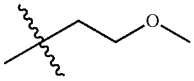 [SMILES: *CCOC] | 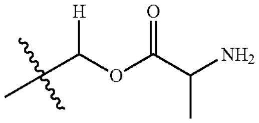 [SMILES: *COC(=O)C(C)N] | H | H |
| 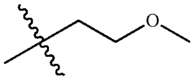 [SMILES: *CCOC] | 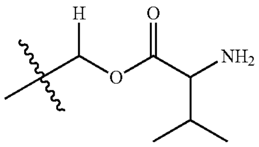 [SMILES: *COC(=O)C(N)C(C)C] | H | H |

-continued
| $R^2$ | $R^1$ | $R^{6E}$ | $R^{6F}$ |
|---|---|---|---|
| 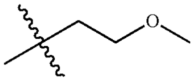 [SMILES: *CCOC] | 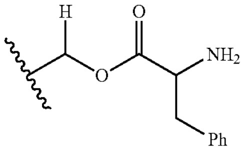 | H | H |
| 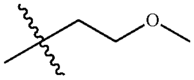 [SMILES: *CCOC] | 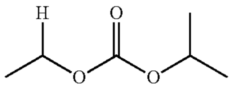 | H | H |
| 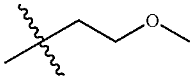 [SMILES: *CCOC] | 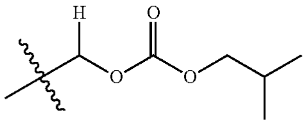 [SMILES: *COC(=O)OCC(C)C] | H | H |
| 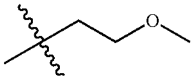 [SMILES: *CCOC] | 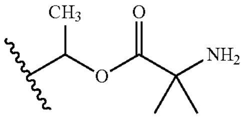 | H | H |
| 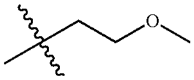 [SMILES: *CCOC] | 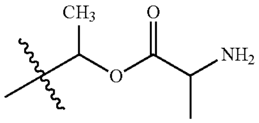 | H | H |
| 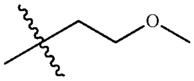 [SMILES: *CCOC] | 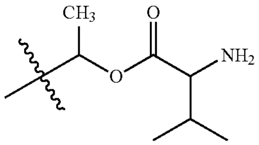 | H | H |
| 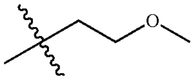 [SMILES: *CCOC] | 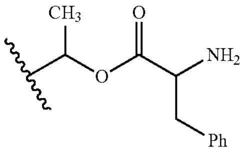 | H | H |
| 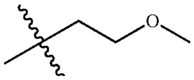 | 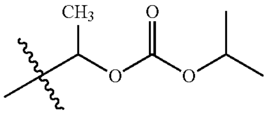 [SMILES: *C(C)OC(=O)OC(C)C] | H | H |
| 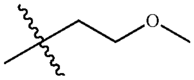 | 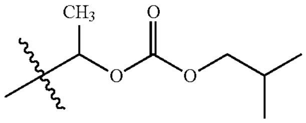 | H | H |
| 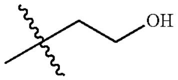 [SMILES: *CCO] | H | H | H |
| 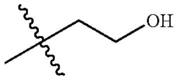 [SMILES: *CCO] | 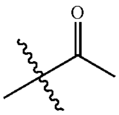 [SMILES: *C(C)=O] | H | H |
| 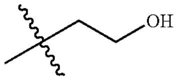 | 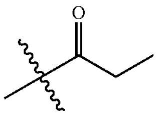 [SMILES: *C(=O)CC] | H | H |

-continued
| $R^2$ | $R^1$ | $R^{6E}$ | $R^{6F}$ |
|---|---|---|---|
| 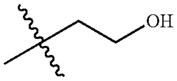 | 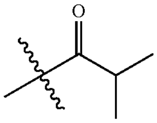 [SMILES: *C(=O)C(C)C] | H | H |
| 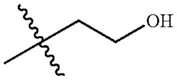 | 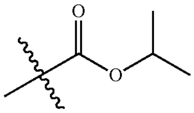 [SMILES: *C(=O)OC(C)C] | H | H |
| 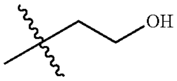 [SMILES: *CCO] | 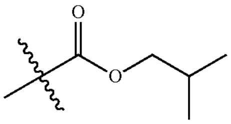 [SMILES: *C(=O)OCC(C)C] | H | H |
| 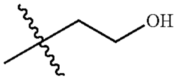 | 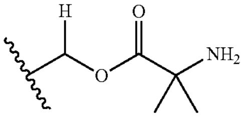 [SMILES: *COC(=O)C(C)(C)N] | H | H |
| 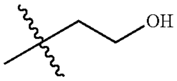 | 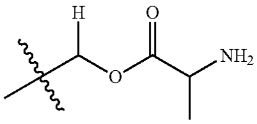 | H | H |
| 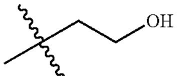 | 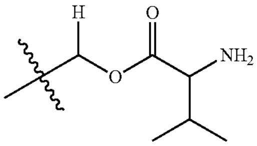 [SMILES: *COC(=O)C(N)C(C)C] | H | H |
| 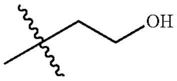 [SMILES: *CCO] | 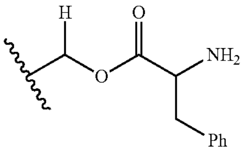 [SMILES: *COC(=O)C(N)Cc1ccccc1] | H | H |
| 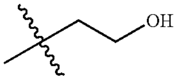 | 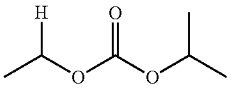 | H | H |
| 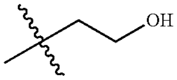 [SMILES: *CCO] | 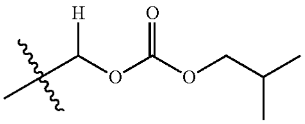 [SMILES: *COC(=O)OCC(C)C] | H | H |
| 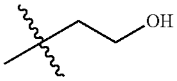 | 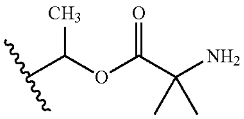 [SMILES: *C(C)OC(=O)C(C)(C)N] | H | H |
| 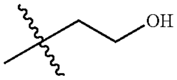 [SMILES: *CCO] | 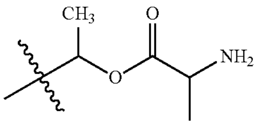 | H | H |

-continued
| $R^2$ | $R^1$ | $R^{6E}$ | $R^{6F}$ |
|---|---|---|---|
| 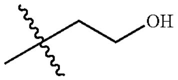 [SMILES: *CCO] | 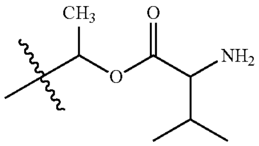 | H | H |
| 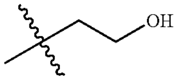 [SMILES: *CCO] | 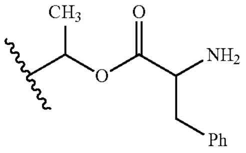 | H | H |
| 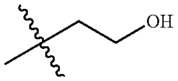 | 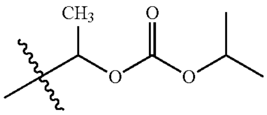 [SMILES: *C(C)OC(=O)OC(C)C] | H | H |
| 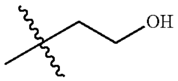 [SMILES: *CCO] | 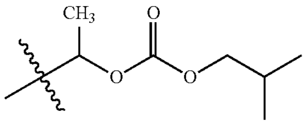 [SMILES: *C(C)OC(=O)OCC(C)C] | H | H |
| $—CH_2CH═CF_2$ | 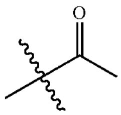 [SMILES: *C(C)=O] | H | H |
| $—CH_2CH═CF_2$ | 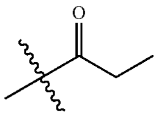 [SMILES: *C(=O)CC] | H | H |
| $—CH_2CH═CF_2$ | 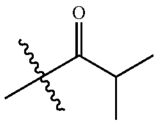 [SMILES: *C(=O)C(C)C] | H | H |
| $—CH_2CH═CF_2$ | 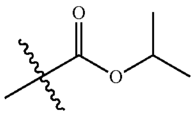 [SMILES: *C(=O)OC(C)C] | H | H |
| $—CH_2CH═CF_2$ | 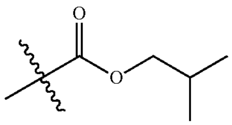 [SMILES: *C(=O)OCC(C)C] | H | H |
| $—CH_2CH═CF_2$ | 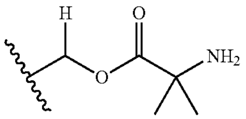 [SMILES: *COC(=O)C(C)(C)N] | H | H |
| $—CH_2CH═CF_2$ | 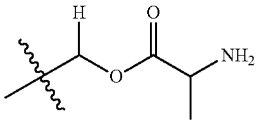 | H | H |

-continued
| $R^2$ | $R^1$ | $R^{6E}$ | $R^{6F}$ |
|---|---|---|---|
| $—CH_2CH═CF_2$ | 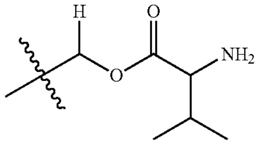 [SMILES: *COC(=O)C(N)C(C)C] | H | H |
| $—CH_2CH═CF_2$ | 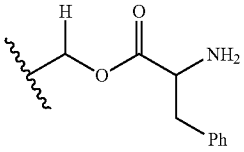 [SMILES: *COC(=O)C(N)Cc1ccccc1] | H | H |
| $—CH_2CH═CF_2$ | 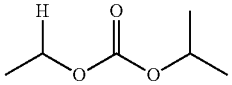 | H | H |
| $—CH_2CH═CF_2$ | 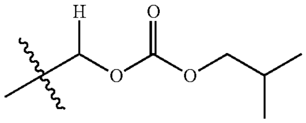 [SMILES: *COC(=O)OCC(C)C] | H | H |
| $—CH_2CH═CF_2$ | 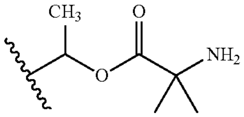 [SMILES: *C(C)OC(=O)C(C)(C)N] | H | H |
| $—CH_2CH═CF_2$ | 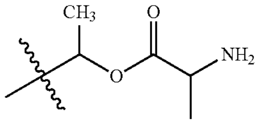 | H | H |
| $—CH_2CH═CF_2$ | 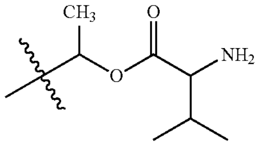 | H | H |
| $—CH_2CH═CF_2$ | 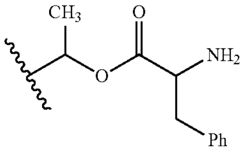 | H | H |
| $—CH_2CH═CF_2$ | 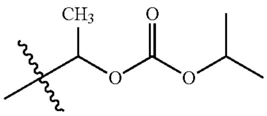 [SMILES: *C(C)OC(=O)OC(C)C] | H | H |
| $—CH_2CH═CF_2$ | 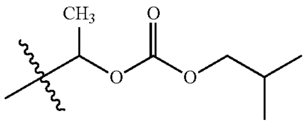 [SMILES: *C(C)OC(=O)OCC(C)C] | H | H |
| $—CH_2CF_3$ | 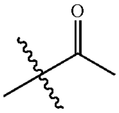 [SMILES: *C(C)=O] | H | H |

-continued
| $R^2$ | $R^1$ | $R^{6E}$ | $R^{6F}$ |
|---|---|---|---|
| $—CH_2CF_3$ | 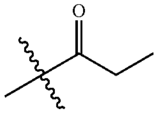 [SMILES: *C(=O)CC] | H | H |
| $—CH_2CF_3$ | 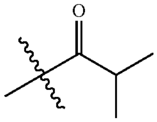 [SMILES: *C(=O)C(C)C] | H | H |
| $—CH_2CF_3$ | 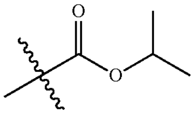 [SMILES: *C(=O)OC(C)C] | H | H |
| $—CH_2CF_3$ | 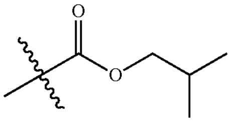 [SMILES: *C(=O)OCC(C)C] | H | H |
| $—CH_2CF_3$ | 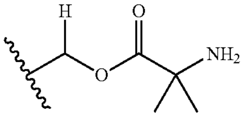 [SMILES: *COC(=O)C(C)(C)N] | H | H |
| $—CH_2CF_3$ | 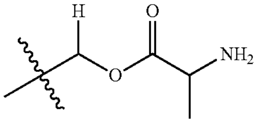 | H | H |
| $—CH_2CF_3$ | 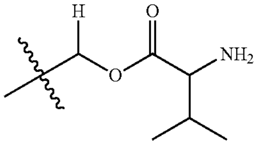 [SMILES: *COC(=O)C(N)C(C)C] | H | H |
| $—CH_2CF_3$ | 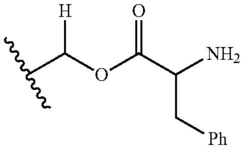 [SMILES: *COC(=O)C(N)Cc1ccccc1] | H | H |
| $—CH_2CF_3$ | 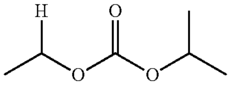 | H | H |
| $—CH_2CF_3$ | 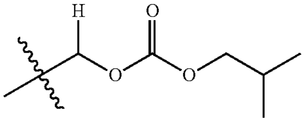 [SMILES: *COC(=O)OCC(C)C] | H | H |
| $—CH_2CF_3$ | 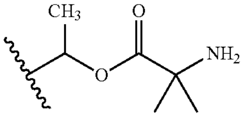 | H | H |

-continued
| $R^2$ | $R^1$ | $R^{6E}$ | $R^{6F}$ |
|---|---|---|---|
| $—CH_2CF_3$ | 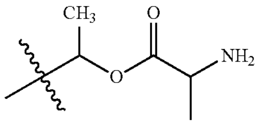 | H | H |
| $—CH_2CF_3$ | 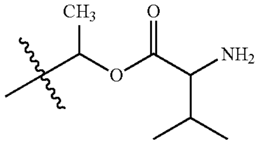 | H | H |
| $—CH_2CF_3$ | 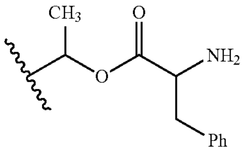 | H | H |
| $—CH_2CF_3$ | 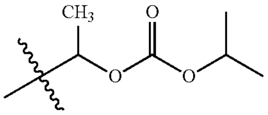 [SMILES: *C(C)OC(=O)OC(C)C] | H | H |
| $—CH_2CF_3$ | 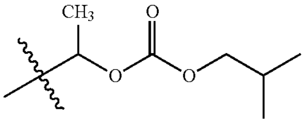 | H | H |
| $—CH_2CH_2CF_3$ | 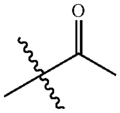 [SMILES: *C(C)=O] | H | H |
| $—CH_2CH_2CF_3$ | 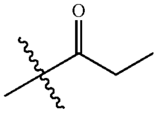 [SMILES: *C(=O)CC] | H | H |
| $—CH_2CH_2CF_3$ | 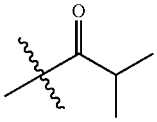 [SMILES: *C(=O)C(C)C] | H | H |
| $—CH_2CH_2CF_3$ | 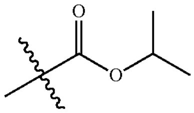 [SMILES: *C(=O)OC(C)C] | H | H |
| $—CH_2CH_2CF_3$ | 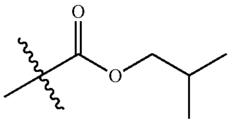 [SMILES: *C(=O)OCC(C)C] | H | H |
| $—CH_2CH_2CF_3$ | 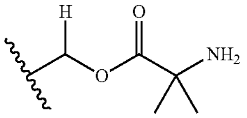 [SMILES: *COC(=O)C(C)(C)N] | H | H |

-continued
| $R^2$ | $R^1$ | $R^{6E}$ | $R^{6F}$ |
|---|---|---|---|
| $—CH_2CH_2CF_3$ | 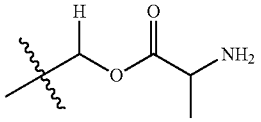 [SMILES: *COC(=O)C(C)N] | H | H |
| $—CH_2CH_2CF_3$ | 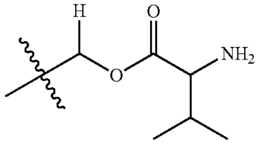 [SMILES: *COC(=O)C(N)C(C)C] | H | H |
| $—CH_2CH_2CF_3$ | 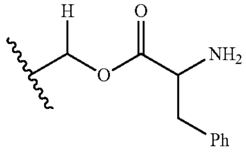 [SMILES: *COC(=O)C(N)Cc1ccccc1] | H | H |
| $—CH_2CH_2CF_3$ | 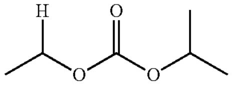 | H | H |
| $—CH_2CH_2CF_3$ | 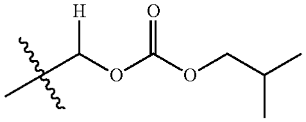 [SMILES: *COC(=O)OCC(C)C] | H | H |
| $—CH_2CH_2CF_3$ | 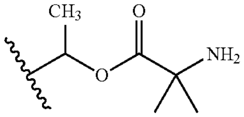 | H | H |
| $—CH_2CH_2CF_3$ | 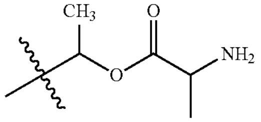 | H | H |
| $—CH_2CH_2CF_3$ | 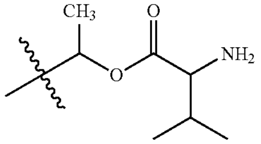 | H | H |
| $—CH_2CH_2CF_3$ | 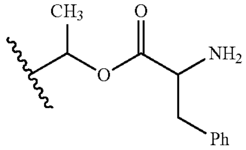 | H | H |
| $—CH_2CH_2CF_3$ | 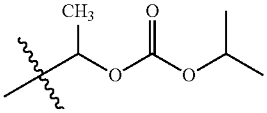 [SMILES: *C(C)OC(=O)OC(C)C] | H | H |
| $—CH_2CH_2CF_3$ | 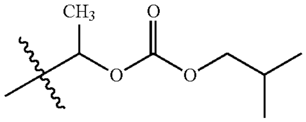 | H | H |

-continued
| $R^2$ | $R^1$ | $R^{6E}$ | $R^{6F}$ |
|---|---|---|---|
| $—CH_2CHF_2$ | 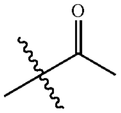 [SMILES: *C(C)=O] | H | H |
| $—CH_2CHF_2$ | 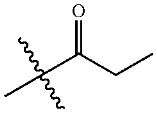 [SMILES: *C(=O)CC] | H | H |
| $—CH_2CHF_2$ | 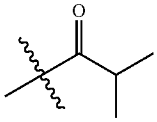 [SMILES: *C(=O)C(C)C] | H | H |
| $—CH_2CHF_2$ | 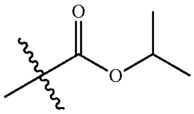 [SMILES: *C(=O)OC(C)C] | H | H |
| $—CH_2CHF_2$ | 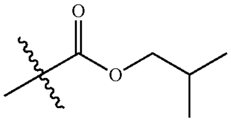 [SMILES: *C(=O)OCC(C)C] | H | H |
| $—CH_2CHF_2$ | 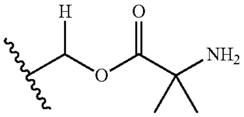 [SMILES: *COC(=O)C(C)(C)N] | H | H |
| $—CH_2CHF_2$ | 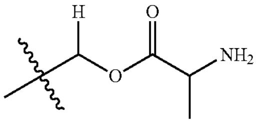 | H | H |
| $—CH_2CHF_2$ | 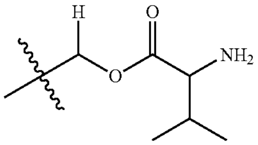 [SMILES: *COC(=O)C(N)C(C)C] | H | H |
| $—CH_2CHF_2$ | 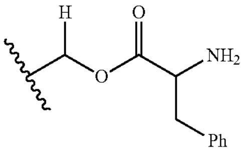 | H | H |
| $—CH_2CHF_2$ | 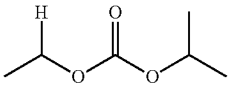 | H | H |
| $—CH_2CHF_2$ | 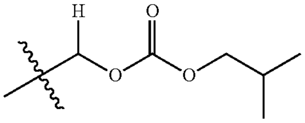 [SMILES: *COC(=O)OCC(C)C] | H | H |

-continued
| $R^2$ | $R^1$ | $R^{6E}$ | $R^{6F}$ |
|---|---|---|---|
| —$CH_2CHF_2$ | 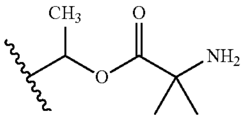 [SMILES: *C(C)OC(=O)C(C)(C)N] | H | H |
| —$CH_2CHF_2$ | 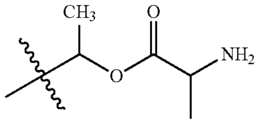 | H | H |
| —$CH_2CHF_2$ | 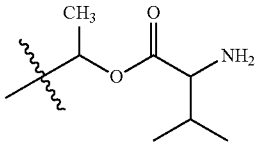 | H | H |
| —$CH_2CHF_2$ | 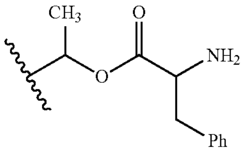 | H | H |
| —$CH_2CHF_2$ | 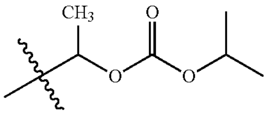 [SMILES: *C(C)OC(=O)OC(C)C] | H | H |
| —$CH_2CHF_2$ | 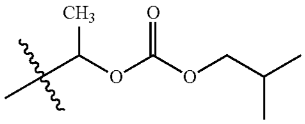 | H | H |
| —$CH_2C(CH_3)F_2$ | 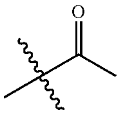 [SMILES: *C(C)=O] | H | H |
| —$CH_2C(CH_3)F_2$ | 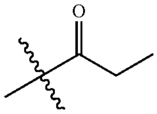 [SMILES: *C(=O)CC] | H | H |
| —$CH_2C(CH_3)F_2$ | 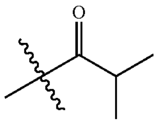 [SMILES: *C(=O)C(C)C] | H | H |
| —$CH_2C(CH_3)F_2$ | 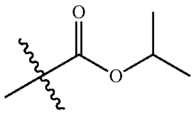 [SMILES: *C(=O)OC(C)C] | H | H |
| —$CH_2C(CH_3)F_2$ | 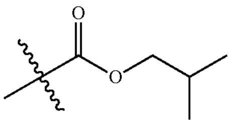 [SMILES: *C(=O)OCC(C)C] | H | H |

-continued
| $R^2$ | $R^1$ | $R^{6E}$ | $R^{6F}$ |
|---|---|---|---|
| $—CH_2C(CH_3)F_2$ | 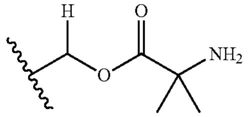 [SMILES: *COC(=O)C(C)(C)N] | H | H |
| $—CH_2C(CH_3)F_2$ | 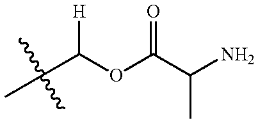 | H | H |
| $—CH_2C(CH_3)F_2$ | 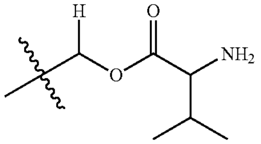 [SMILES: *COC(=O)C(N)C(C)C] | H | H |
| $—CH_2C(CH_3)F_2$ | 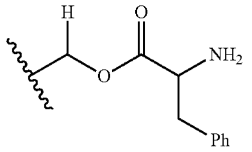 | H | H |
| $—CH_2C(CH_3)F_2$ | 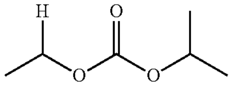 | H | H |
| $—CH_2C(CH_3)F_2$ | 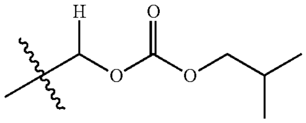 [SMILES: *COC(=O)OCC(C)C] | H | H |
| $—CH_2C(CH_3)F_2$ | 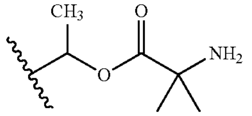 [SMILES: *C(C)OC(=O)C(C)(C)N] | H | H |
| $—CH_2C(CH_3)F_2$ | 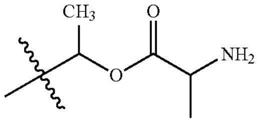 | H | H |
| $—CH_2C(CH_3)F_2$ | 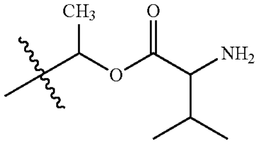 | H | H |
| $—CH_2C(CH_3)F_2$ | 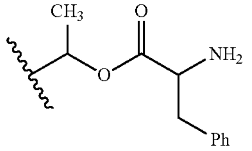 | H | H |
| $—CH_2C(CH_3)F_2$ | 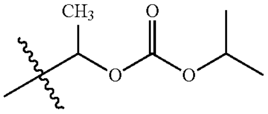 [SMILES: *C(C)OC(=O)OC(C)C] | H | H |

-continued
| $R^2$ | $R^1$ | $R^{6E}$ | $R^{6F}$ |
|---|---|---|---|
| $—CH_2C(CH_3)F_2$ | 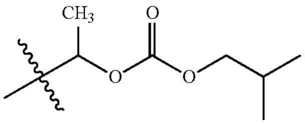 [SMILES: *C(C)OC(=O)OCC(C)C] | H | H |
| 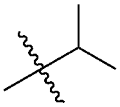 [SMILES: *C(C)C] | 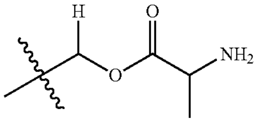 [SMILES: *COC(=O)C(C)N] | F | F |
| 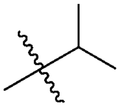 [SMILES: *C(C)C] | 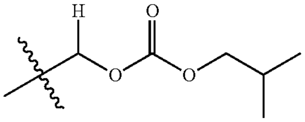 [SMILES: *COC(=O)OCC(C)C] | F | F |
| 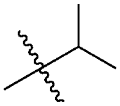 [SMILES: *C(C)C] | 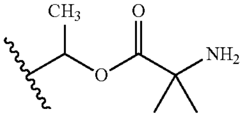 [SMILES: *C(C)OC(=O)C(C)(C)N] | F | F |
| 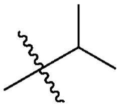 [SMILES: *C(C)C] | 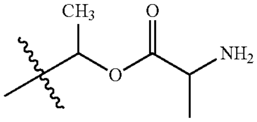 | F | F |
| 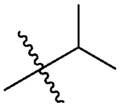 [SMILES: *C(C)C] | 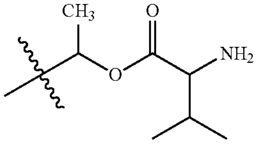 | F | F |
| 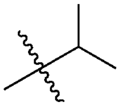 [SMILES: *C(C)C] | 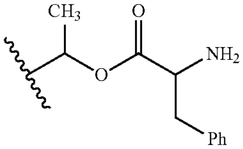 | F | F |
| 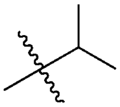 [SMILES: *C(C)C] | 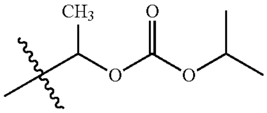 [SMILES: *C(C)OC(=O)OC(C)C] | F | F |
| 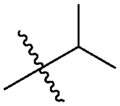 [SMILES: *C(C)C] | 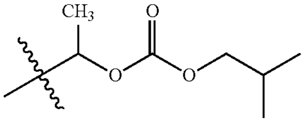 [SMILES: *C(C)OC(=O)OCC(C)C] | F | F |
| $—CH_3$ | 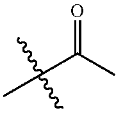 [SMILES: *C(C)=O] | F | F |
| $—CH_3$ | 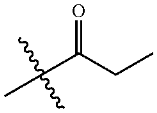 [SMILES: *C(=O)CC] | F | F |

-continued
| $R^2$ | $R^1$ | $R^{6E}$ | $R^{6F}$ |
|---|---|---|---|
| $—CH_3$ | 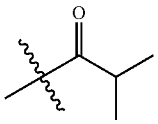 [SMILES: *C(=O)C(C)C] | F | F |
| $—CH_3$ | 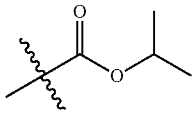 [SMILES: *C(=O)OC(C)C] | F | F |
| $—CH_3$ | 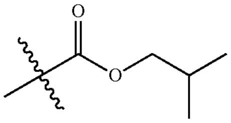 [SMILES: *C(=O)OCC(C)C] | F | F |
| $—CH_3$ | 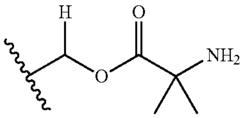 [SMILES: *COC(=O)C(C)(C)N] | F | F |
| $—CH_3$ | 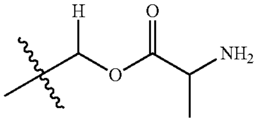 [SMILES: *COC(=O)C(C)N] | F | F |
| $—CH_3$ | 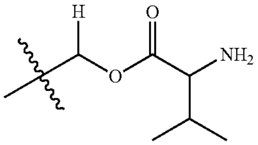 [SMILES: *COC(=O)C(N)C(C)C] | F | F |
| $—CH_3$ | 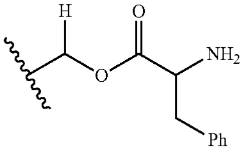 [SMILES: *COC(=O)C(N)Cc1ccccc1] | F | F |
| $—CH_3$ | 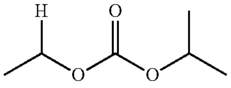 | F | F |
| $—CH_3$ | 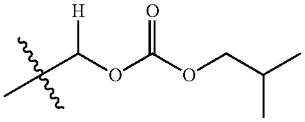 [SMILES: *COC(=O)OCC(C)C] | F | F |
| $—CH_3$ | 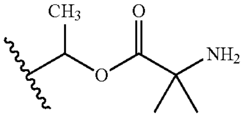 | F | F |
| $—CH_3$ | 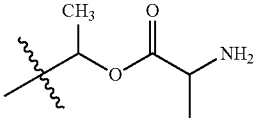 | F | F |

-continued
| $R^2$ | $R^1$ | $R^{6E}$ | $R^{6F}$ |
|---|---|---|---|
| $—CH_3$ | 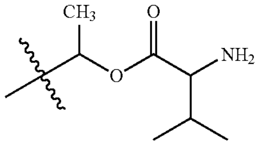 | F | F |
| $—CH_3$ | 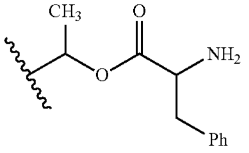 | F | F |
| $—CH_3$ | 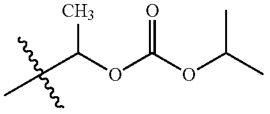 [SMILES: *C(C)OC(=O)OC(C)C] | F | F |
| $—CH_3$ | 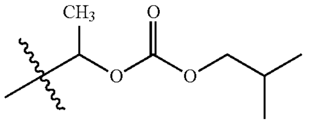 | F | F |
| $—CH_2CH_3$ | H | F | F |
| $—CH_2CH_3$ | 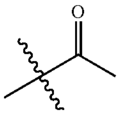 [SMILES: *C(C)=O] | F | F |
| $—CH_2CH_3$ | 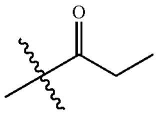 [SMILES: *C(=O)CC] | F | F |
| $—CH_2CH_3$ | 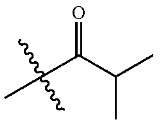 [SMILES: *C(=O)C(C)C] | F | F |
| $—CH_2CH_3$ | 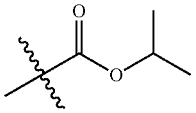 [SMILES: *C(=O)OC(C)C] | F | F |
| $—CH_2CH_3$ | 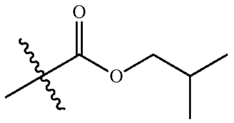 [SMILES: *C(=O)OCC(C)C] | F | F |
| $—CH_2CH_3$ | 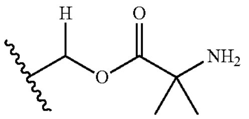 [SMILES: *COC(=O)C(C)(C)N] | F | F |
| $—CH_2CH_3$ | 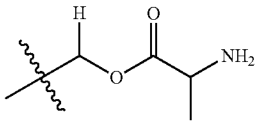 | F | F |

-continued
| $R^2$ | $R^1$ | $R^{6E}$ | $R^{6F}$ |
|---|---|---|---|
| $—CH_2CH_3$ | 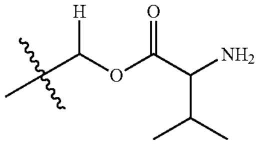 [SMILES: *COC(=O)C(N)C(C)C] | F | F |
| $—CH_2CH_3$ | 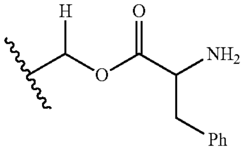 | F | F |
| $—CH_2CH_3$ | 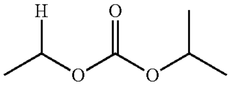 | F | F |
| $—CH_2CH_3$ | 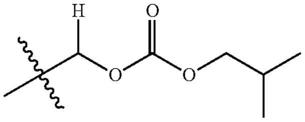 [SMILES: *COC(=O)OCC(C)C] | F | F |
| $—CH_2CH_3$ | 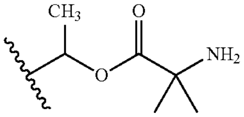 | F | F |
| $—CH_2CH_3$ | 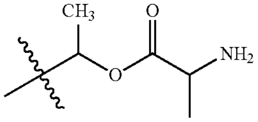 | F | F |
| $—CH_2CH_3$ | 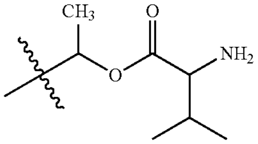 | F | F |
| $—CH_2CH_3$ | 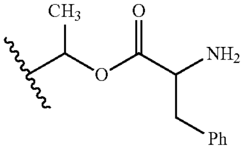 | F | F |
| $—CH_2CH_3$ | 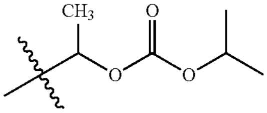 [SMILES: *C(C)OC(=O)OC(C)C] | F | F |
| $—CH_2CH_3$ | 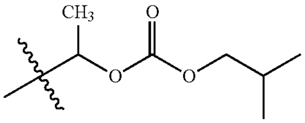 | F | F |
| $—CH_2CH(CH_3)_2$ | H | F | F |
| $—CH_2CH(CH_3)_2$ | 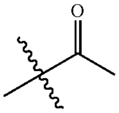 [SMILES: *C(C)=O] | F | F |

-continued
| $R^2$ | $R^1$ | $R^{6E}$ | $R^{6F}$ |
|---|---|---|---|
| $—CH_2CH(CH_3)_2$ | 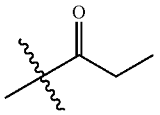 [SMILES: *C(=O)CC] | F | F |
| $—CH_2CH(CH_3)_2$ | 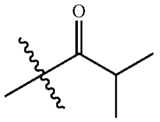 [SMILES: *C(=O)C(C)C] | F | F |
| $—CH_2CH(CH_3)_2$ | 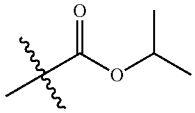 [SMILES: *C(=O)OC(C)C] | F | F |
| $—CH_2CH(CH_3)_2$ | 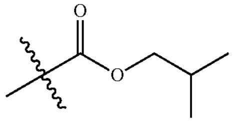 [SMILES: *C(=O)OCC(C)C] | F | F |
| $—CH_2CH(CH_3)_2$ | 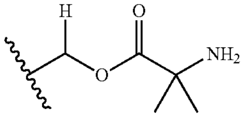 [SMILES: *COC(=O)C(C)(C)N] | F | F |
| $—CH_2CH(CH_3)_2$ | 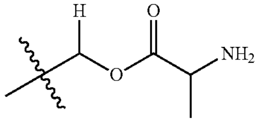 [SMILES: *COC(=O)C(C)N] | F | F |
| $—CH_2CH(CH_3)_2$ | 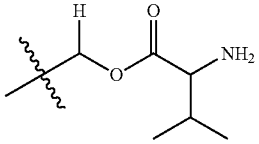 [SMILES: *COC(=O)C(N)C(C)C] | F | F |
| $—CH_2CH(CH_3)_2$ | 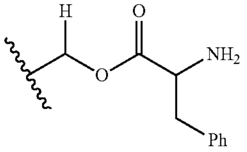 [SMILES: *COC(=O)C(N)Cc1ccccc1] | F | F |
| $—CH_2CH(CH_3)_2$ | 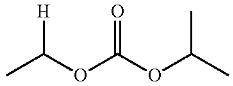 | F | F |
| $—CH_2CH(CH_3)_2$ | 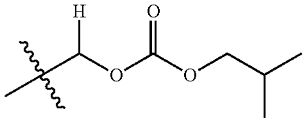 [SMILES: *COC(=O)OCC(C)C] | F | F |
| $—CH_2CH(CH_3)_2$ | 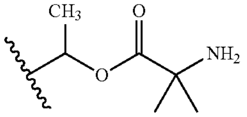 | F | F |

-continued
| $R^2$ | $R^1$ | $R^{6E}$ | $R^{6F}$ |
|---|---|---|---|
| $-CH_2CH(CH_3)_2$ | 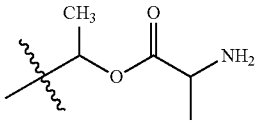 | F | F |
| $-CH_2CH(CH_3)_2$ | 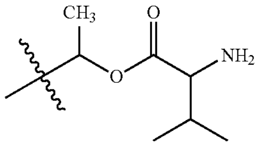 | F | F |
| $-CH_2CH(CH_3)_2$ | 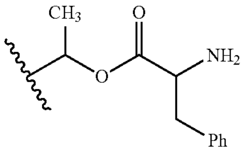 | F | F |
| $-CH_2CH(CH_3)_2$ | 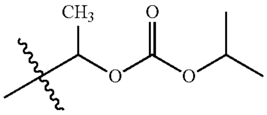 [SMILES: *C(C)OC(=O)OC(C)C] | F | F |
| $-CH_2CH(CH_3)_2$ | 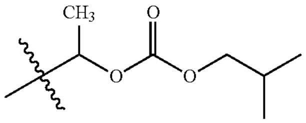 | F | F |
| $-CH_2CH_2CH_3$ | 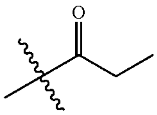 [SMILES: *C(=O)CC] | F | F |
| $-CH_2CH_2CH_3$ | 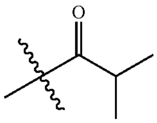 [SMILES: *C(=O)C(C)C] | F | F |
| $-CH_2CH_2CH_3$ | 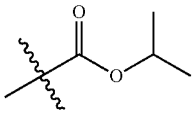 [SMILES: *C(=O)OC(C)C] | F | F |
| $-CH_2CH_2CH_3$ | 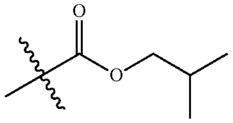 [SMILES: *C(=O)OCC(C)C] | F | F |
| $-CH_2CH_2CH_3$ | 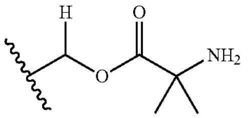 [SMILES: *COC(=O)C(C)(C)N] | F | F |
| $-CH_2CH_2CH_3$ | 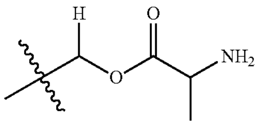 [SMILES: *COC(=O)C(C)N] | F | F |

-continued
| $R^2$ | $R^1$ | $R^{6E}$ | $R^{6F}$ |
|---|---|---|---|
| $-CH_2CH_2CH_3$ | 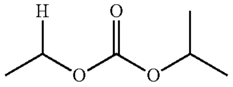 | F | F |
| $-CH_2CH_2CH_3$ | 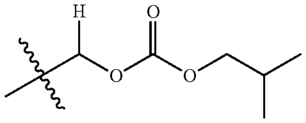 [SMILES: *COC(=O)OCC(C)C] | F | F |
| $-CH_2CH_2CH_3$ | 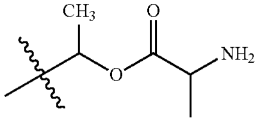 | F | F |
| $-CH_2CH_2CH_3$ | 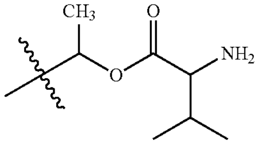 | F | F |
| $-CH_2CH_2CH_3$ | 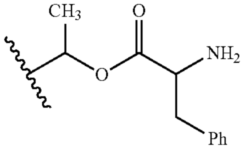 | F | F |
| $-CH_2CH_2CH_3$ | 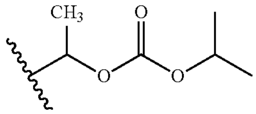 [SMILES: *C(C)OC(=O)OC(C)C] | F | F |
| $-CH_2CH_2CH_3$ | 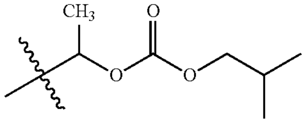 [SMILES: *C(C)OC(=O)OCC(C)C] | F | F |
| $-CH_2CH_2CH_2CH_3$ | H | F | F |
| $-CH_2CH_2CH_2CH_3$ | 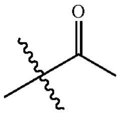 [SMILES: *C(C)=O] | F | F |
| $-CH_2CH_2CH_2CH_3$ | 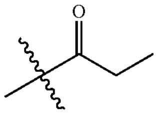 [SMILES: *C(=O)CC] | F | F |
| $-CH_2CH_2CH_2CH_3$ | 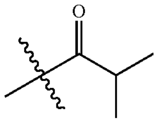 [SMILES: *C(=O)C(C)C] | F | F |
| $-CH_2CH_2CH_2CH_3$ | 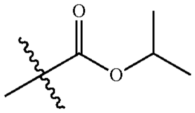 [SMILES: *C(=O)OC(C)C] | F | F |

-continued
| $R^2$ | $R^1$ | $R^{6E}$ | $R^{6F}$ |
|---|---|---|---|
| $—CH_2CH_2CH_2CH_3$ | 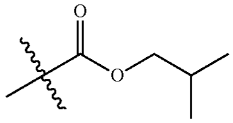 [SMILES: *C(=O)OCC(C)C] | F | F |
| $—CH_2CH_2CH_2CH_3$ | 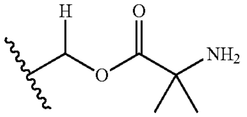 [SMILES: *COC(=O)C(C)(C)N] | F | F |
| $—CH_2CH_2CH_2CH_3$ | 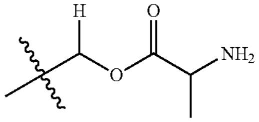 | F | F |
| $—CH_2CH_2CH_2CH_3$ | 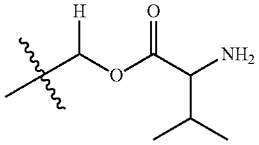 [SMILES: *COC(=O)C(N)C(C)C] | F | F |
| $—CH_2CH_2CH_2CH_3$ | 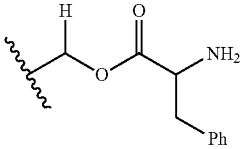 [SMILES: *COC(=O)C(N)Cc1ccccc1] | F | F |
| $—CH_2CH_2CH_2CH_3$ | 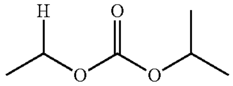 | F | F |
| $—CH_2CH_2CH_2CH_3$ | 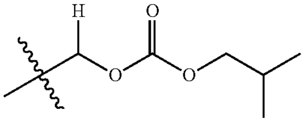 [SMILES: *COC(=O)OCC(C)C] | F | F |
| $—CH_2CH_2CH_2CH_3$ | 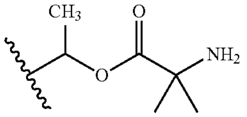 [SMILES: *C(C)OC(=O)C(C)(C)N] | F | F |
| $—CH_2CH_2CH_2CH_3$ | 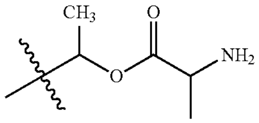 | F | F |
| $—CH_2CH_2CH_2CH_3$ | 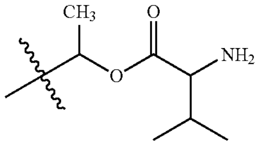 | F | F |
| $—CH_2CH_2CH_2CH_3$ | 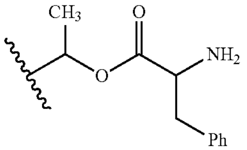 | F | F |

-continued
| $R^2$ | $R^1$ | $R^{6E}$ | $R^{6F}$ |
|---|---|---|---|
| $—CH_2CH_2CH_2CH_3$ | 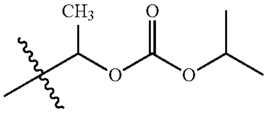 [SMILES: *C(C)OC(=O)OC(C)C] | F | F |
| $—CH_2CH_2CH_2CH_3$ | 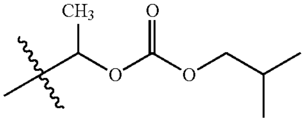 | F | F |
| 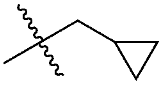 | H | F | F |
| 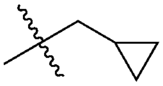 [SMILES: *CC1CC1] | 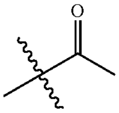 [SMILES: *C(C)=O] | F | F |
| 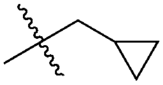 [SMILES: *CC1CC1] | 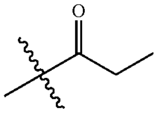 [SMILES: *C(=O)CC] | F | F |
| 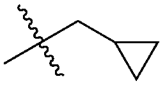 | 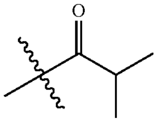 [SMILES: *C(=O)C(C)C] | F | F |
| 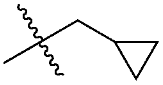 [SMILES: *CC1CC1] | 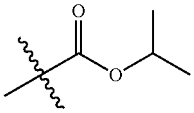 [SMILES: *C(=O)OC(C)C] | F | F |
| 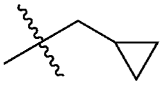 | 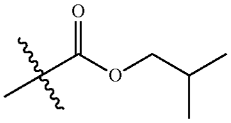 [SMILES: *C(=O)OCC(C)C] | F | F |
| 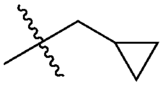 [SMILES: *CC1CC1] | 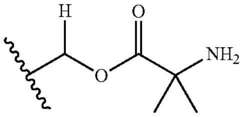 [SMILES: *COC(=O)C(C)(C)N] | F | F |
| 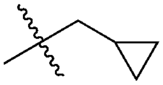 [SMILES: *CC1CC1] | 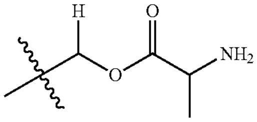 [SMILES: *COC(=O)C(C)N] | F | F |
| 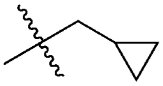 [SMILES: *CC1CC1] | 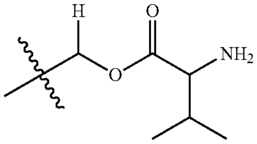 [SMILES: *COC(=O)C(N)C(C)C] | F | F |

-continued
| $R^2$ | $R^1$ | $R^{6E}$ | $R^{6F}$ |
|---|---|---|---|
| 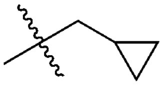 [SMILES: *CC1CC1] | 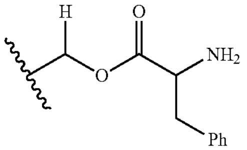 | F | F |
| 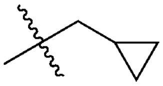 [SMILES: *CC1CC1] | 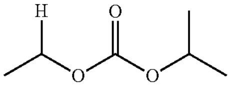 | F | F |
| 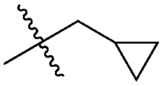 [SMILES: *CC1CC1] | 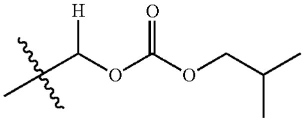 [SMILES: *COC(=O)OCC(C)C] | F | F |
| 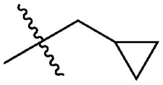 | 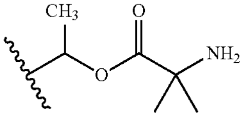 [SMILES: *C(C)OC(=O)C(C)(C)N] | F | F |
| 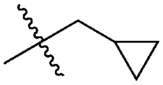 [SMILES: *CC1CC1] | 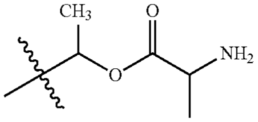 | F | F |
| 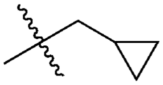 | 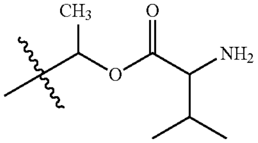 [SMILES: *C(C)OC(=O)C(N)C(C)C] | F | F |
| 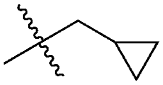 [SMILES: *CC1CC1] | 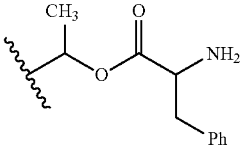 [SMILES: *C(C)OC(=O)C(N)Cc1ccccc1] | F | F |
| 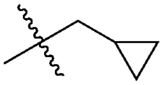 | 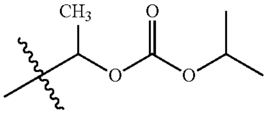 | F | F |
| 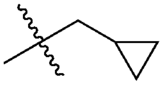 | 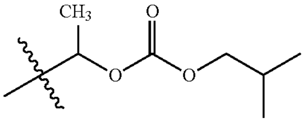 | F | F |
| 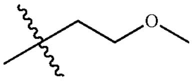 [SMILES: *CCOC] | H | F | F |
| 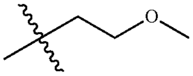 [SMILES: *CCOC] | 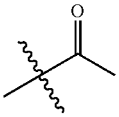 [SMILES: *C(C)=O] | F | F |

-continued
| $R^2$ | $R^1$ | $R^{6E}$ | $R^{6F}$ |
| --- | --- | --- | --- |
| 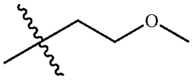 [SMILES: *CCOC] | 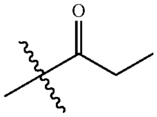 [SMILES: *C(=O)CC] | F | F |
| 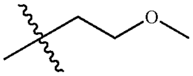 [SMILES: *CCOC] | 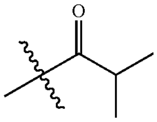 [SMILES: *C(=O)C(C)C] | F | F |
| 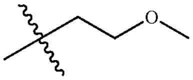 [SMILES: *CCOC] | 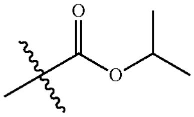 [SMILES: *C(=O)OC(C)C] | F | F |
| 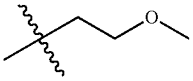 [SMILES: *CCOC] | 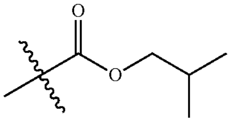 [SMILES: *C(=O)OCC(C)C] | F | F |
| 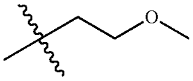 [SMILES: *CCOC] | 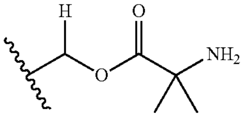 [SMILES: *COC(=O)C(C)(C)N] | F | F |
| 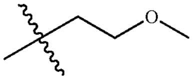 [SMILES: *CCOC] | 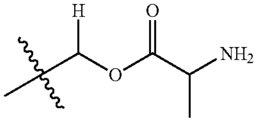 [SMILES: *COC(=O)C(C)N] | F | F |
| 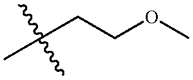 [SMILES: *CCOC] | 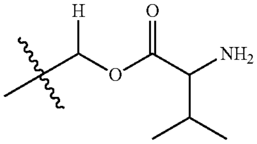 | F | F |
| 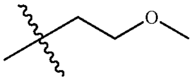 [SMILES: *CCOC] | 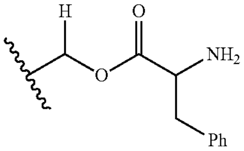 [SMILES: *COC(=O)C(N)Cc1ccccc1] | F | F |
| 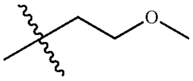 [SMILES: *CCOC] | 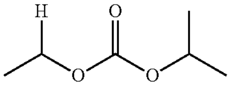 | F | F |
| 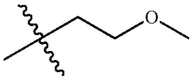 [SMILES: *CCOC] | 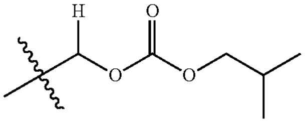 [SMILES: *COC(=O)OCC(C)C] | F | F |
| 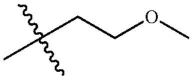 [SMILES: *CCOC] | 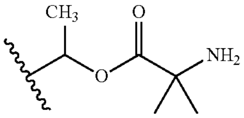 | F | F |

-continued
| $R^2$ | $R^1$ | $R^{6E}$ | $R^{6F}$ |
|---|---|---|---|
| 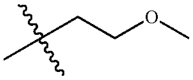 [SMILES: *CCOC] | 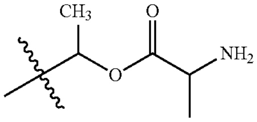 | F | F |
| 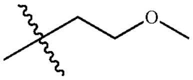 [SMILES: *CCOC] | 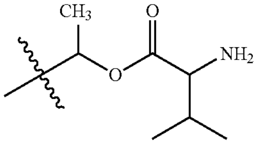 [SMILES: *C(C)OC(=O)C(N)C(C)C] | F | F |
| 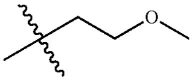 [SMILES: *CCOC] | 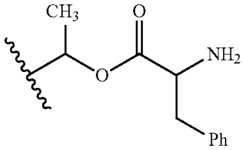 [SMILES: *C(C)OC(=O)C(N)Cc1ccccc1] | F | F |
| 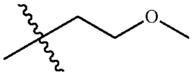 [SMILES: *CCOC] | 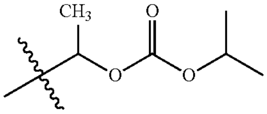 [SMILES: *C(C)OC(=O)OC(C)C] | F | F |
| 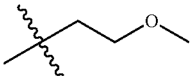 [SMILES: *CCOC] | 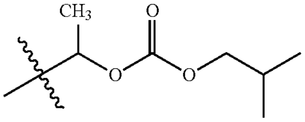 | F | F |
| 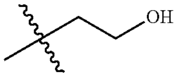 [SMILES: *CCO] | H | F | F |
| 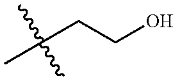 [SMILES: *CCO] | 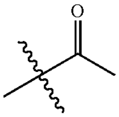 [SMILES: *C(C)=O] | F | F |
| 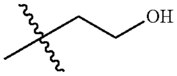 [SMILES: *CCO] | 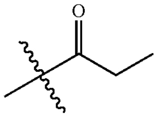 [SMILES: *C(=O)CC] | F | F |
| 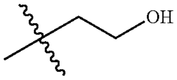 | 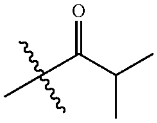 [SMILES: *C(=O)C(C)C] | F | F |
| 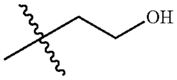 | 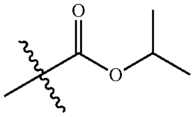 [SMILES: *C(=O)OC(C)C] | F | F |
| 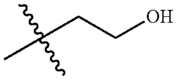 [SMILES: *CCO] | 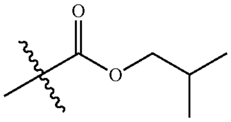 [SMILES: *C(=O)OCC(C)C] | F | F |

-continued
| $R^2$ | $R^1$ | $R^{6E}$ | $R^{6F}$ |
| --- | --- | --- | --- |
| 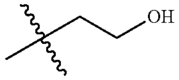 [SMILES: *CCO] | 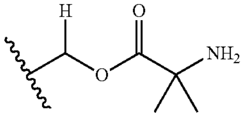 | F | F |
| 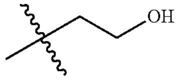 [SMILES: *CCO] | 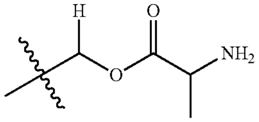 | F | F |
| 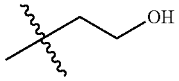 | 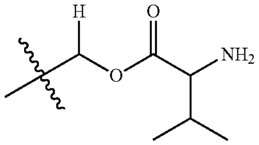 [SMILES: *COC(=O)C(N)C(C)C] | F | F |
| 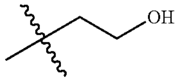 | 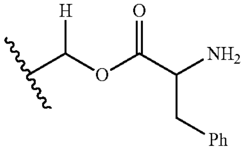 | F | F |
| 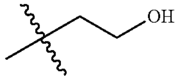 | 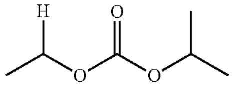 | F | F |
| 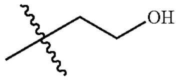 | 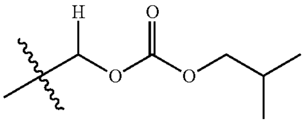 [SMILES: *COC(=O)OCC(C)C] | F | F |
| 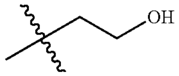 [SMILES: *CCO] | 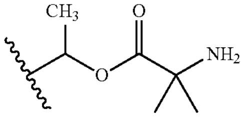 [SMILES: *C(C)OC(=O)C(C)(C)N] | F | F |
| 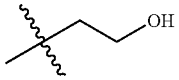 [SMILES: *CCO] | 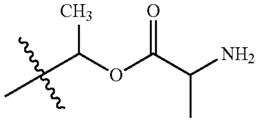 [SMILES: *C(C)OC(=O)C(C)N] | F | F |
| 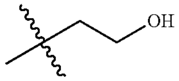 | 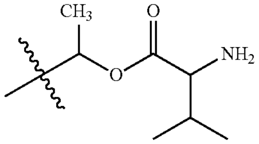 [SMILES: *C(C)OC(=O)C(N)C(C)C] | F | F |
| 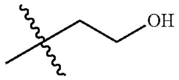 [SMILES: *CCO] | 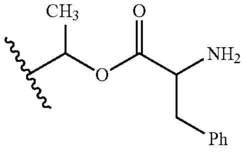 [SMILES: *C(C)OC(=O)C(N)Cc1ccccc1] | F | F |
| 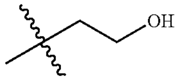 [SMILES: *CCO] | 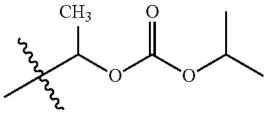 | F | F |

-continued
| $R^2$ | $R^1$ | $R^{6E}$ | $R^{6F}$ |
|---|---|---|---|
| 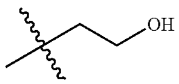 [SMILES: *CCO] | 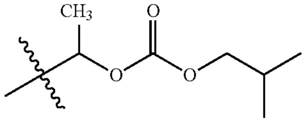 [SMILES: *C(C)OC(=O)OCC(C)C] | F | F |
| $-CH_2CH{=}CF_2$ | 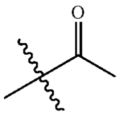 [SMILES: *C(C)=O] | F | F |
| $-CH_2CH{=}CF_2$ | 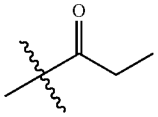 [SMILES: *C(=O)CC] | F | F |
| $-CH_2CH{=}CF_2$ | 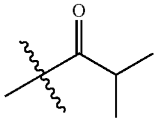 [SMILES: *C(=O)C(C)C] | F | F |
| $-CH_2CH{=}CF_2$ | 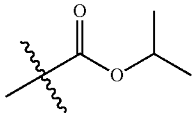 [SMILES: *C(=O)OC(C)C] | F | F |
| $-CH_2CH{=}CF_2$ | 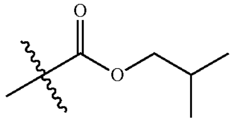 [SMILES: *C(=O)OCC(C)C] | F | F |
| $-CH_2CH{=}CF_2$ | 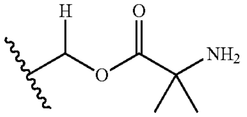 [SMILES: *COC(=O)C(C)(C)N] | F | F |
| $-CH_2CH{=}CF_2$ | 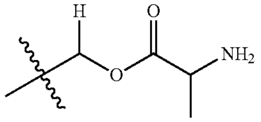 [SMILES: *COC(=O)C(C)N] | F | F |
| $-CH_2CH{=}CF_2$ | 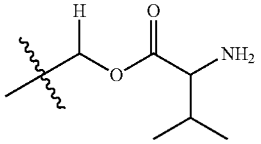 [SMILES: *COC(=O)C(N)C(C)C] | F | F |
| $-CH_2CH{=}CF_2$ | 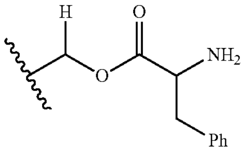 [SMILES: *COC(=O)C(N)Cc1ccccc1] | F | F |
| $-CH_2CH{=}CF_2$ | 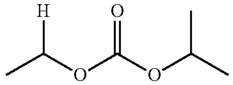 | F | F |

-continued
| $R^2$ | $R^1$ | $R^{6E}$ | $R^{6F}$ |
|---|---|---|---|
| $—CH_2CH═CF_2$ | 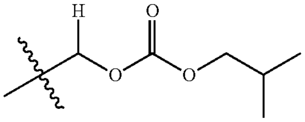 [SMILES: *COC(=O)OCC(C)C] | F | F |
| $—CH_2CH═CF_2$ | 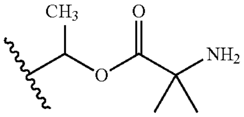 | F | F |
| $—CH_2CH═CF_2$ | 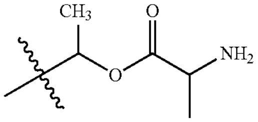 [SMILES: *C(C)OC(=O)C(C)N] | F | F |
| $—CH_2CH═CF_2$ | 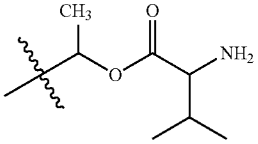 [SMILES: *C(C)OC(=O)C(N)C(C)C] | F | F |
| $—CH_2CH═CF_2$ | 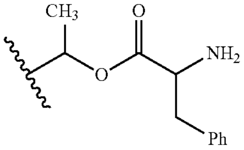 [SMILES: *C(C)OC(=O)C(N)Cc1ccccc1] | F | F |
| $—CH_2CH═CF_2$ | 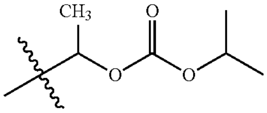 [SMILES: *C(C)OC(=O)OC(C)C] | F | F |
| $—CH_2CH═CF_2$ | 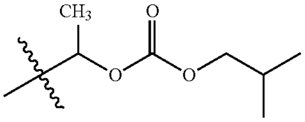 [SMILES: *C(C)OC(=O)OCC(C)C] | F | F |
| $—CH_2CF_3$ | 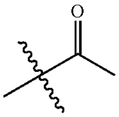 [SMILES: *C(C)=O] | F | F |
| $—CH_2CF_3$ | 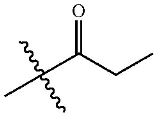 [SMILES: *C(=O)CC] | F | F |
| $—CH_2CF_3$ | 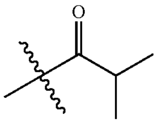 [SMILES: *C(=O)C(C)C] | F | F |
| $—CH_2CF_3$ | 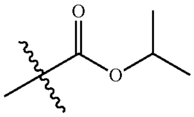 [SMILES: *C(=O)OC(C)C] | F | F |

-continued
| $R^2$ | $R^1$ | $R^{6E}$ | $R^{6F}$ |
|---|---|---|---|
| $—CH_2CF_3$ | 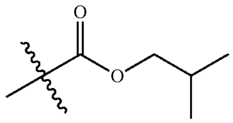 [SMILES: *C(=O)OCC(C)C] | F | F |
| $—CH_2CF_3$ | 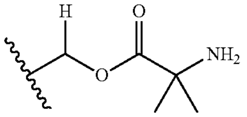 [SMILES: *COC(=O)C(C)(C)N] | F | F |
| $—CH_2CF_3$ | 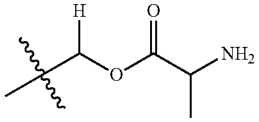 | F | F |
| $—CH_2CF_3$ | 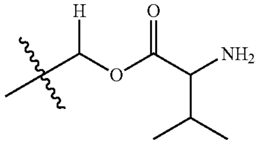 [SMILES: *COC(=O)C(N)C(C)C] | F | F |
| $—CH_2CF_3$ | 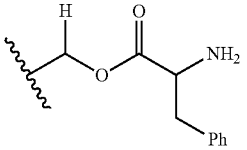 [SMILES: *COC(=O)C(N)Cc1ccccc1] | F | F |
| $—CH_2CF_3$ | 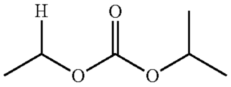 | F | F |
| $—CH_2CF_3$ | 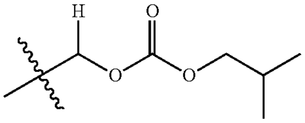 | F | F |
| $—CH_2CF_3$ | 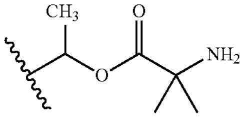 | F | F |
| $—CH_2CF_3$ | 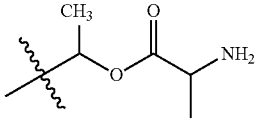 | F | F |
| $—CH_2CF_3$ | 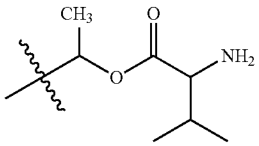 [SMILES: *C(C)OC(=O)C(N)C(C)C] | F | F |
| $—CH_2CF_3$ | 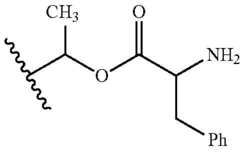 [SMILES: *C(C)OC(=O)C(N)Cc1ccccc1] | F | F |

-continued
| $R^2$ | $R^1$ | $R^{6E}$ | $R^{6F}$ |
|---|---|---|---|
| —$CH_2CF_3$ | 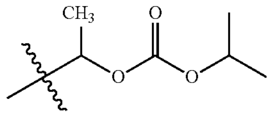 [SMILES: *C(C)OC(=O)OC(C)C] | F | F |
| —$CH_2CF_3$ | 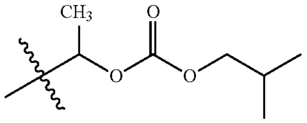 | F | F |
| —$CH_2CH_2CF_3$ | 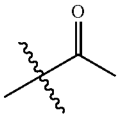 [SMILES: *C(C)=O] | F | F |
| —$CH_2CH_2CF_3$ | 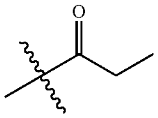 [SMILES: *C(=O)CC] | F | F |
| —$CH_2CH_2CF_3$ | 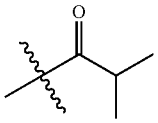 [SMILES: *C(=O)C(C)C] | F | F |
| —$CH_2CH_2CF_3$ | 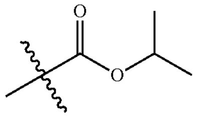 [SMILES: *C(=O)OC(C)C] | F | F |
| —$CH_2CH_2CF_3$ | 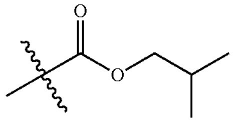 [SMILES: *C(=O)OCC(C)C] | F | F |
| —$CH_2CH_2CF_3$ | 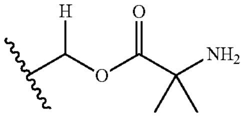 [SMILES: *COC(=O)C(C)(C)N] | F | F |
| —$CH_2CH_2CF_3$ | 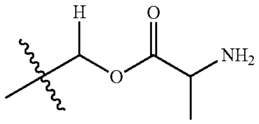 [SMILES: *COC(=O)C(C)N] | F | F |
| —$CH_2CH_2CF_3$ | 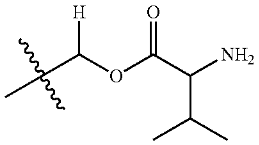 [SMILES: *COC(=O)C(N)C(C)C] | F | F |
| —$CH_2CH_2CF_3$ | 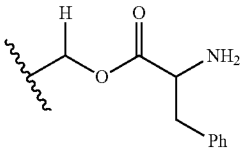 [SMILES: *COC(=O)C(N)Cc1ccccc1] | F | F |

-continued
| $R^2$ | $R^1$ | $R^{6E}$ | $R^{6F}$ |
|---|---|---|---|
| $-CH_2CH_2CF_3$ | 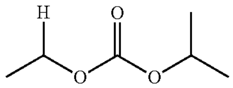 | F | F |
| $-CH_2CH_2CF_3$ | 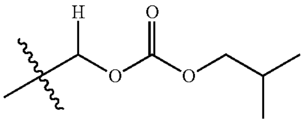 [SMILES: *COC(=O)OCC(C)C] | F | F |
| $-CH_2CH_2CF_3$ | 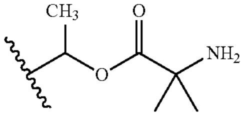 [SMILES: *C(C)OC(=O)C(C)(C)N] | F | F |
| $-CH_2CH_2CF_3$ | 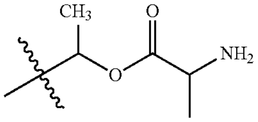 | F | F |
| $-CH_2CH_2CF_3$ | 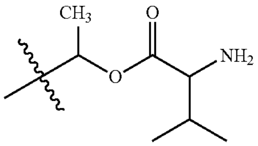 [SMILES: *C(C)OC(=O)C(N)C(C)C] | F | F |
| $-CH_2CH_2CF_3$ | 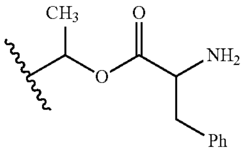 [SMILES: *C(C)OC(=O)C(N)Cc1ccccc1] | F | F |
| $-CH_2CH_2CF_3$ | 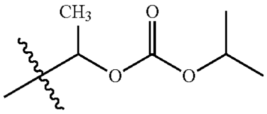 [SMILES: *C(C)OC(=O)OC(C)C] | F | F |
| $-CH_2CH_2CF_3$ | 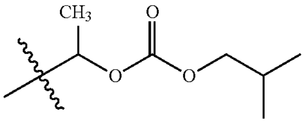 [SMILES: *C(C)OC(=O)OCC(C)C] | F | F |
| $-CH_2CHF_2$ | 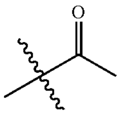 [SMILES: *C(C)=O] | F | F |
| $-CH_2CHF_2$ | 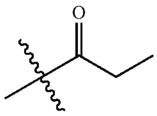 [SMILES: *C(=O)CC] | F | F |
| $-CH_2CHF_2$ | 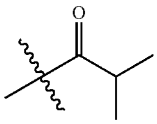 [SMILES: *C(=O)C(C)C] | F | F |

-continued
| $R^2$ | $R^1$ | $R^{6E}$ | $R^{6F}$ |
|---|---|---|---|
| $—CH_2CHF_2$ | 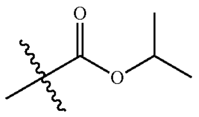 [SMILES: *C(=O)OC(C)C] | F | F |
| $—CH_2CHF_2$ | 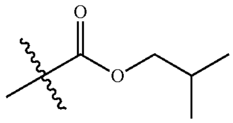 [SMILES: *C(=O)OCC(C)C] | F | F |
| $—CH_2CHF_2$ | 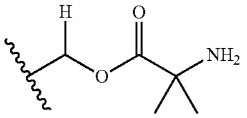 [SMILES: *COC(=O)C(C)(C)N] | F | F |
| $—CH_2CHF_2$ | 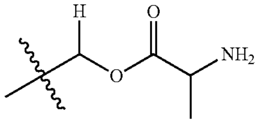 | F | F |
| $—CH_2CHF_2$ | 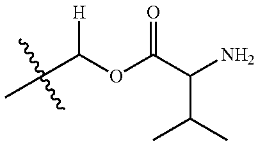 [SMILES: *COC(=O)C(N)C(C)C] | F | F |
| $—CH_2CHF_2$ | 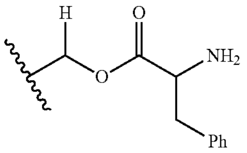 [SMILES: *COC(=O)C(N)Cc1ccccc1] | F | F |
| $—CH_2CHF_2$ | 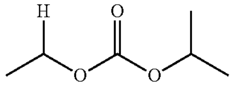 | F | F |
| $—CH_2CHF_2$ | 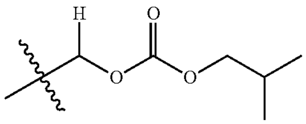 [SMILES: *COC(=O)OCC(C)C] | F | F |
| $—CH_2CHF_2$ | 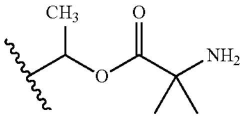 [SMILES: *C(C)OC(=O)C(C)(C)N] | F | F |
| $—CH_2CHF_2$ | 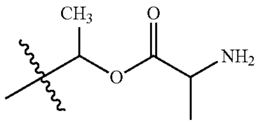 [SMILES: *C(C)OC(=O)C(C)N] | F | F |
| $—CH_2CHF_2$ | 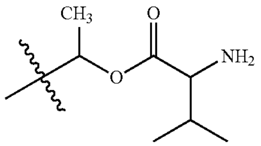 [SMILES: *C(C)OC(=O)C(N)C(C)C] | F | F |

-continued
| $R^2$ | $R^1$ | $R^{6E}$ | $R^{6F}$ |
|---|---|---|---|
| $-CH_2CHF_2$ | 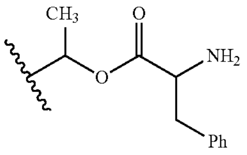 [SMILES: *C(C)OC(=O)C(N)Cc1ccccc1] | F | F |
| $-CH_2CHF_2$ | 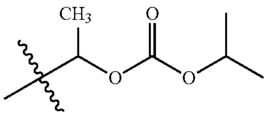 | F | F |
| $-CH_2CHF_2$ | 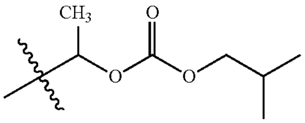 | F | F |
| $-CH_2C(CH_3)F_2$ | 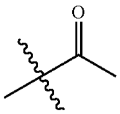 [SMILES: *C(C)=O] | F | F |
| $-CH_2C(CH_3)F_2$ | 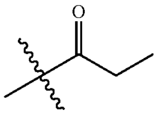 [SMILES: *C(=O)CC] | F | F |
| $-CH_2C(CH_3)F_2$ | 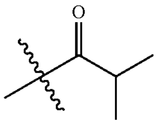 [SMILES: *C(=O)C(C)C] | F | F |
| $-CH_2C(CH_3)F_2$ | 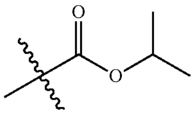 [SMILES: *C(=O)OC(C)C] | F | F |
| $-CH_2C(CH_3)F_2$ | 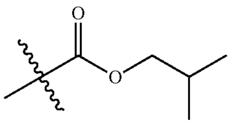 [SMILES: *C(=O)OCC(C)C] | F | F |
| $-CH_2C(CH_3)F_2$ | 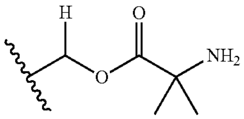 [SMILES: *COC(=O)C(C)(C)N] | F | F |
| $-CH_2C(CH_3)F_2$ | 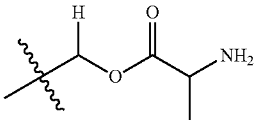 [SMILES: *COC(=O)C(C)N] | F | F |
| $-CH_2C(CH_3)F_2$ | 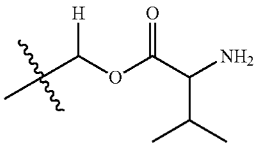 [SMILES: *COC(=O)C(N)C(C)C] | F | F |

-continued
| $R^2$ | $R^1$ | $R^{6E}$ | $R^{6F}$ |
|---|---|---|---|
| $—CH_2C(CH_3)F_2$ | 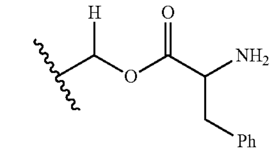 [SMILES: *COC(=O)C(N)Cc1ccccc1] | F | F |
| $—CH_2C(CH_3)F_2$ | 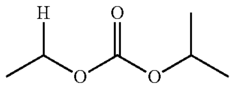 | F | F |
| $—CH_2C(CH_3)F_2$ | 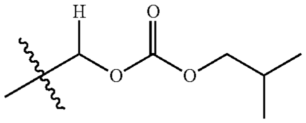 [SMILES: *COC(=O)OCC(C)C] | F | F |
| $—CH_2C(CH_3)F_2$ | 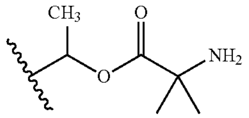 [SMILES: *C(C)OC(=O)C(C)(C)N] | F | F |
| $—CH_2C(CH_3)F_2$ | 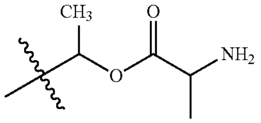 | F | F |
| $—CH_2C(CH_3)F_2$ | 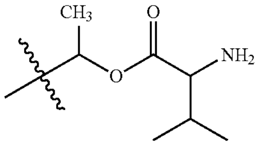 | F | F |
| $—CH_2C(CH_3)F_2$ | 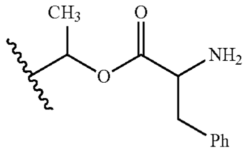 [SMILES: *C(C)OC(=O)C(N)Cc1ccccc1] | F | F |
| $—CH_2C(CH_3)F_2$ | 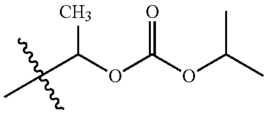 [SMILES: *C(C)OC(=O)OC(C)C] | F | F |
| and | | | |
| $—CH_2C(CH_3)F_2$ | 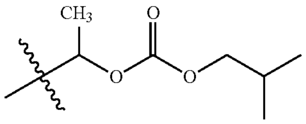 | F | F, | or a pharmaceutically acceptable salt of any of the foregoing; or
a compound of the following structure:
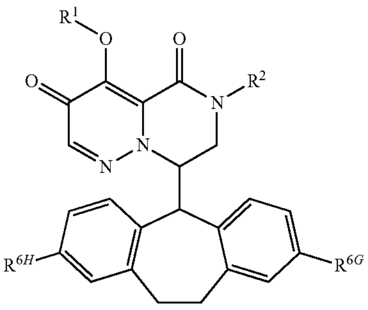
wherein the compound is selected from the group consisting of:
| $R^2$ | $R^1$ | $R^{6G}$ | $R^{6H}$ |
|---|---|---|---|
| 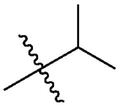 [SMILES: *C(C)C] | 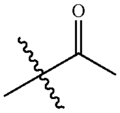 [SMILES: *C(C)=O] | Cl | Cl |
| 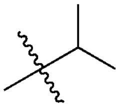 [SMILES: *C(C)C] | 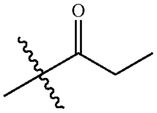 [SMILES: *C(=O)CC] | Cl | Cl |
| 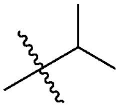 [SMILES: *C(C)C] | 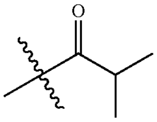 [SMILES: *C(=O)C(C)C] | Cl | Cl |
| 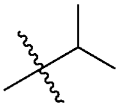 [SMILES: *C(C)C] | 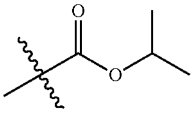 [SMILES: *C(=O)OC(C)C] | Cl | Cl |
| 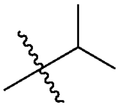 [SMILES: *C(C)C] | 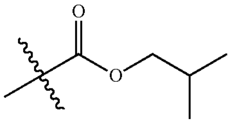 [SMILES: *C(=O)OCC(C)C] | Cl | Cl |
| 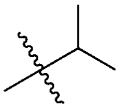 [SMILES: *C(C)C] | 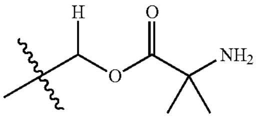 [SMILES: *COC(=O)C(C)(C)N] | Cl | Cl |
| 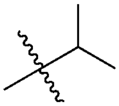 [SMILES: *C(C)C] | 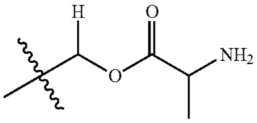 [SMILES: *COC(=O)C(C)N] | Cl | Cl |
| 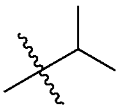 [SMILES: *C(C)C] | 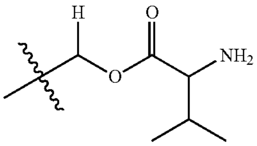 [SMILES: *COC(=O)C(N)C(C)C] | Cl | Cl |
-continued
| $R^2$ | $R^1$ | $R^{6G}$ | $R^{6H}$ |
|---|---|---|---|
| 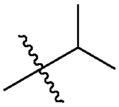 [SMILES: *C(C)C] | 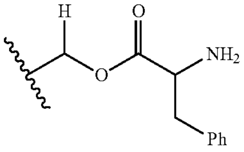 [SMILES: *COC(=O)C(N)Cc1ccccc1] | Cl | Cl |
| 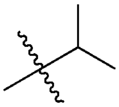 [SMILES: *C(C)C] | 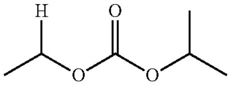 | Cl | Cl |
| 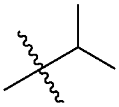 [SMILES: *C(C)C] | 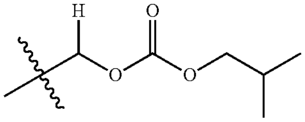 | Cl | Cl |
| 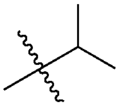 [SMILES: *C(C)C] | 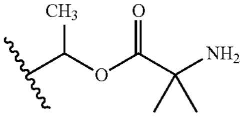 | Cl | Cl |
| 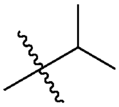 [SMILES: *C(C)C] | 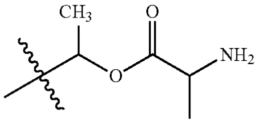 | Cl | Cl |
| 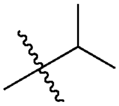 [SMILES: *C(C)C] | 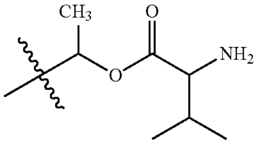 [SMILES: *C(C)OC(=O)C(N)C(C)C] | Cl | Cl |
| 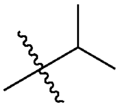 [SMILES: *C(C)C] | 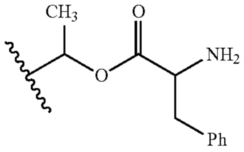 [SMILES: *C(C)OC(=O)C(N)Cc1ccccc1] | Cl | Cl |
| 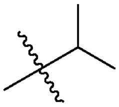 [SMILES: *C(C)C] | 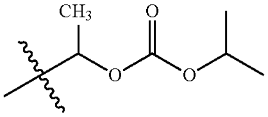 [SMILES: *C(C)OC(=O)OC(C)C] | Cl | Cl |
| 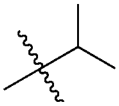 [SMILES: *C(C)C] | 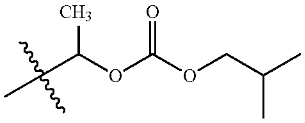 | Cl | Cl |
| $—CH_3$ | 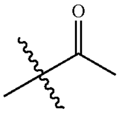 [SMILES: *C(C)=O] | Cl | Cl |
| $—CH_3$ | 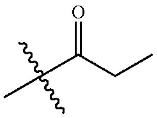 [SMILES: *C(=O)CC] | Cl | Cl |

-continued
| $R^2$ | $R^1$ | $R^{6G}$ | $R^{6H}$ |
|---|---|---|---|
| $—CH_3$ | 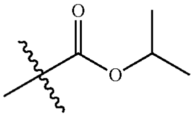 [SMILES: *C(=O)OC(C)C] | Cl | Cl |
| $—CH_3$ | 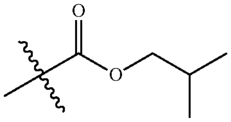 [SMILES: *C(=O)OCC(C)C] | Cl | Cl |
| $—CH_3$ | 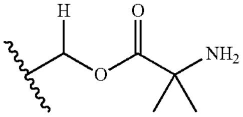 [SMILES: *COC(=O)C(C)(C)N] | Cl | Cl |
| $—CH_3$ | 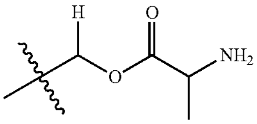 [SMILES: *COC(=O)C(C)N] | Cl | Cl |
| $—CH_3$ | 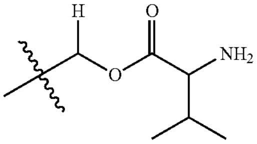 [SMILES: *COC(=O)C(N)C(C)C] | Cl | Cl |
| $—CH_3$ | 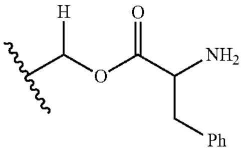 [SMILES: *COC(=O)C(N)Cc1ccccc1] | Cl | Cl |
| $—CH_3$ | 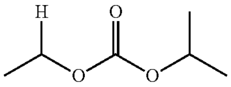 | Cl | Cl |
| $—CH_3$ | 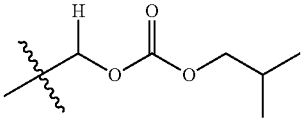 [SMILES: *COC(=O)OCC(C)C] | Cl | Cl |
| $—CH_3$ | 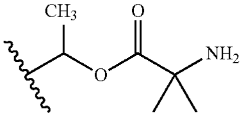 | Cl | Cl |
| $—CH_3$ | 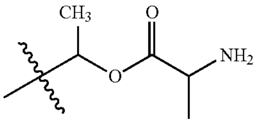 | Cl | Cl |
| $—CH_3$ | 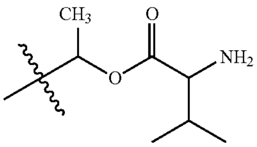 [SMILES: *C(C)OC(=O)C(N)C(C)C] | Cl | Cl |
-continued
| $R^2$ | $R^1$ | $R^{6G}$ | $R^{6H}$ |
|---|---|---|---|
| $—CH_3$ | 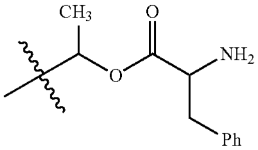 [SMILES: *C(C)OC(=O)C(N)Cc1ccccc1] | Cl | Cl |
| $—CH_3$ | 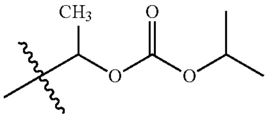 [SMILES: *C(C)OC(=O)OC(C)C] | Cl | Cl |
| $—CH_3$ | 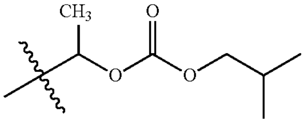 | Cl | Cl |
| $—CH_2CH_3$ | 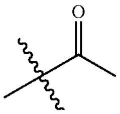 [SMILES: *C(C)=O] | Cl | Cl |
| $—CH_2CH_3$ | 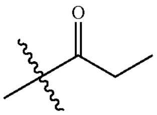 [SMILES: *C(=O)CC] | Cl | Cl |
| $—CH_2CH_3$ | 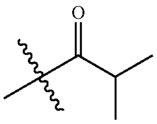 [SMILES: *C(=O)C(C)C] | Cl | Cl |
| $—CH_2CH_3$ | 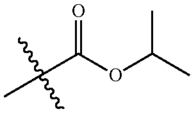 [SMILES: *C(=O)OC(C)C] | Cl | Cl |
| $—CH_2CH_3$ | 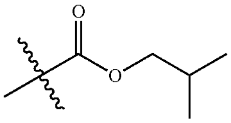 [SMILES: *C(=O)OCC(C)C] | Cl | Cl |
| $—CH_2CH_3$ | 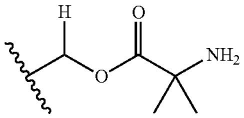 [SMILES: *COC(=O)C(C)(C)N] | Cl | Cl |
| $—CH_2CH_3$ | 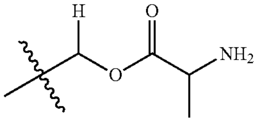 [SMILES: *COC(=O)C(C)N] | Cl | Cl |
| $—CH_2CH_3$ | 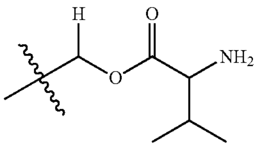 [SMILES: *COC(=O)C(N)C(C)C] | Cl | Cl |

-continued

| $R^2$ | $R^1$ | $R^{6G}$ | $R^{6H}$ |
|---|---|---|---|
| $—CH_2CH_3$ | 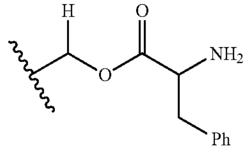 [SMILES: *COC(=O)C(N)Cc1ccccc1] | Cl | Cl |
| $—CH_2CH_3$ | 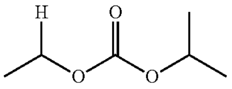 | Cl | Cl |
| $—CH_2CH_3$ | 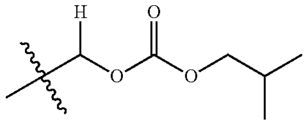 [SMILES: *COC(=O)OCC(C)C] | Cl | Cl |
| $—CH_2CH_3$ | 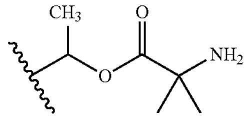 [SMILES: *C(C)OC(=O)C(C)(C)N] | Cl | Cl |
| $—CH_2CH_3$ | 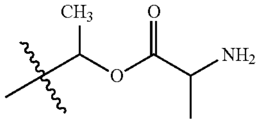 | Cl | Cl |
| $—CH_2CH_3$ | 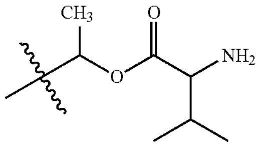 | Cl | Cl |
| $—CH_2CH_3$ | 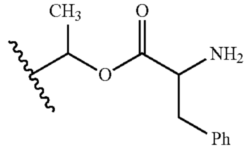 [SMILES: *C(C)OC(=O)C(N)Cc1ccccc1] | Cl | Cl |
| $—CH_2CH_3$ | 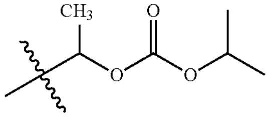 [SMILES: *C(C)OC(=O)OC(C)C] | Cl | Cl |
| $—CH_2CH_3$ | 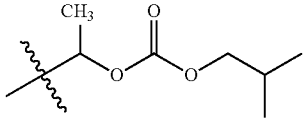 | Cl | Cl |
| $—CH_2CH(CH_3)_2$ | H | Cl | Cl |
| $—CH_2CH(CH_3)_2$ | 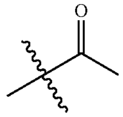 [SMILES: *C(C)=O] | Cl | Cl |
| $—CH_2CH(CH_3)_2$ | 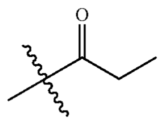 [SMILES: *C(=O)CC] | Cl | Cl |

-continued

| $R^2$ | $R^1$ | $R^{6G}$ | $R^{6H}$ |
|---|---|---|---|
| $—CH_2CH(CH_3)_2$ | 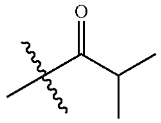 [SMILES: *C(=O)C(C)C] | Cl | Cl |
| $—CH_2CH(CH_3)_2$ | 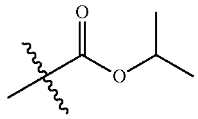 [SMILES: *C(=O)OC(C)C] | Cl | Cl |
| $—CH_2CH(CH_3)_2$ | 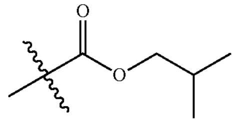 [SMILES: *C(=O)OCC(C)C] | Cl | Cl |
| $—CH_2CH(CH_3)_2$ | 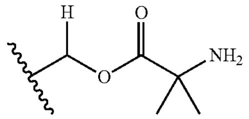 [SMILES: *COC(=O)C(C)(C)N] | Cl | Cl |
| $—CH_2CH(CH_3)_2$ | 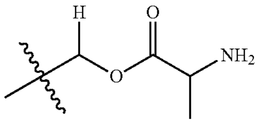 [SMILES: *COC(=O)C(C)N] | Cl | Cl |
| $—CH_2CH(CH_3)_2$ | 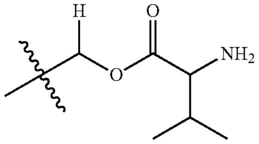 [SMILES: *COC(=O)C(N)C(C)C] | Cl | Cl |
| $—CH_2CH(CH_3)_2$ | 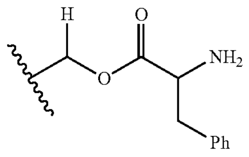 [SMILES: *COC(=O)C(N)Cc1ccccc1] | Cl | Cl |
| $—CH_2CH(CH_3)_2$ | 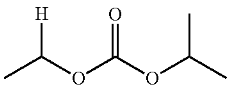 | Cl | Cl |
| $—CH_2CH(CH_3)_2$ | 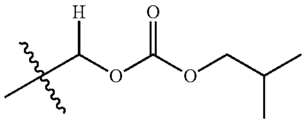 [SMILES: *COC(=O)OCC(C)C] | Cl | Cl |
| $—CH_2CH(CH_3)_2$ | 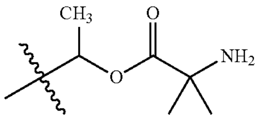 [SMILES: *C(C)OC(=O)C(C)(C)N] | Cl | Cl |
| $—CH_2CH(CH_3)_2$ | 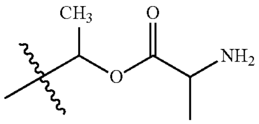 [SMILES: *C(C)OC(=O)C(C)N] | Cl | Cl |

-continued

| $R^2$ | $R^1$ | $R^{6G}$ | $R^{6H}$ |
|---|---|---|---|
| $—CH_2CH(CH_3)_2$ | 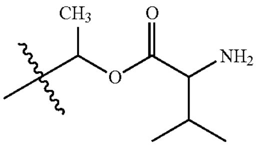 [SMILES: *C(C)OC(=O)C(N)C(C)C] | Cl | Cl |
| $—CH_2CH(CH_3)_2$ | 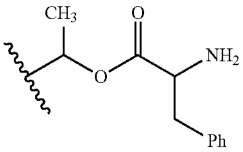 [SMILES: *C(C)OC(=O)C(N)Cc1ccccc1] | Cl | Cl |
| $—CH_2CH(CH_3)_2$ | 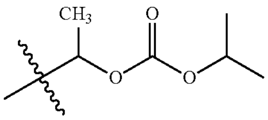 [SMILES: *C(C)OC(=O)OC(C)C] | Cl | Cl |
| $—CH_2CH(CH_3)_2$ | 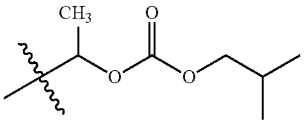 [SMILES: *C(C)OC(=O)OCC(C)C] | Cl | Cl |
| $—CH_2CH_2CH_3$ | 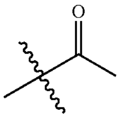 [SMILES: *C(C)=O] | Cl | Cl |
| $—CH_2CH_2CH_3$ | 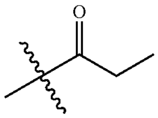 [SMILES: *C(=O)CC] | Cl | Cl |
| $—CH_2CH_2CH_3$ | 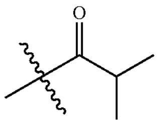 [SMILES: *C(=O)C(C)C] | Cl | Cl |
| $—CH_2CH_2CH_3$ | 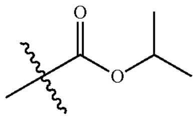 [SMILES: *C(=O)OC(C)C] | Cl | Cl |
| $—CH_2CH_2CH_3$ | 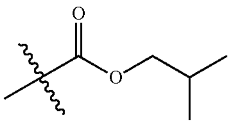 [SMILES: *C(=O)OCC(C)C] | Cl | Cl |
| $—CH_2CH_2CH_3$ | 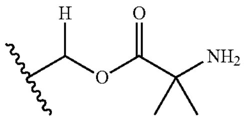 [SMILES: *COC(=O)C(C)(C)N] | Cl | Cl |
| $—CH_2CH_2CH_3$ | 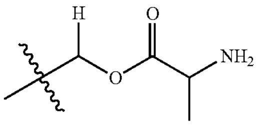 [SMILES: *COC(=O)C(C)N] | Cl | Cl |

-continued

| $R^2$ | $R^1$ | $R^{6G}$ | $R^{6H}$ |
|---|---|---|---|
| $—CH_2CH_2CH_3$ | 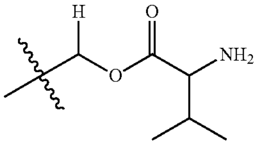 [SMILES: *COC(=O)C(N)C(C)C] | Cl | Cl |
| $—CH_2CH_2CH_3$ | 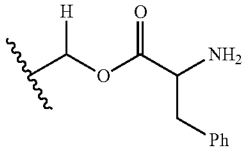 [SMILES: *COC(=O)C(N)Cc1ccccc1] | Cl | Cl |
| $—CH_2CH_2CH_3$ | 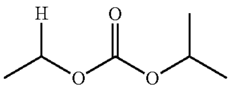 | Cl | Cl |
| $—CH_2CH_2CH_3$ | 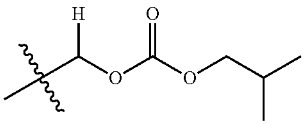 [SMILES: *COC(=O)OCC(C)C] | Cl | Cl |
| $—CH_2CH_2CH_3$ | 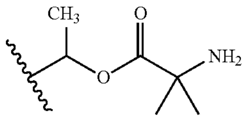 [SMILES: *C(C)OC(=O)C(C)(C)N] | Cl | Cl |
| $—CH_2CH_2CH_3$ | 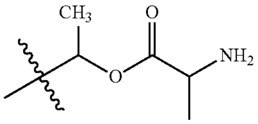 [SMILES: *C(C)OC(=O)C(C)N] | Cl | Cl |
| $—CH_2CH_2CH_3$ | 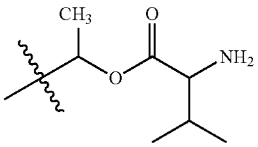 | Cl | Cl |
| $—CH_2CH_2CH_3$ | 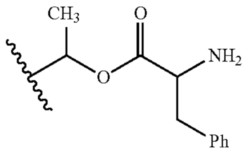 [SMILES: *C(C)OC(=O)C(N)Cc1ccccc1] | Cl | Cl |
| $—CH_2CH_2CH_3$ | 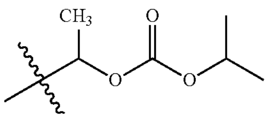 [SMILES: *C(C)OC(=O)OC(C)C] | Cl | Cl |
| $—CH_2CH_2CH_3$ | 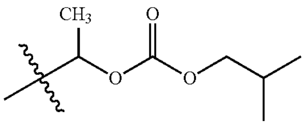 | Cl | Cl |
| $—CH_2CH_2CH_2CH_3$ | H | Cl | Cl |
| $—CH_2CH_2CH_2CH_3$ | 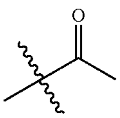 [SMILES: *C(C)=O] | Cl | Cl |

-continued

| $R^2$ | $R^1$ | $R^{6G}$ | $R^{6H}$ |
|---|---|---|---|
| $—CH_2CH_2CH_2CH_3$ | 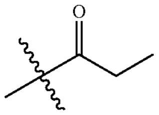 [SMILES: *C(=O)CC] | Cl | Cl |
| $—CH_2CH_2CH_2CH_3$ | 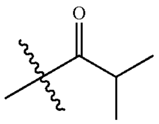 [SMILES: *C(=O)C(C)C] | Cl | Cl |
| $—CH_2CH_2CH_2CH_3$ | 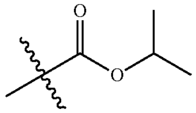 [SMILES: *C(=O)OC(C)C] | Cl | Cl |
| $—CH_2CH_2CH_2CH_3$ | 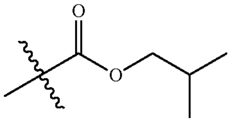 [SMILES: *C(=O)OCC(C)C] | Cl | Cl |
| $—CH_2CH_2CH_2CH_3$ | 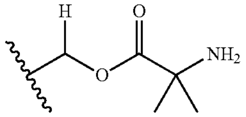 [SMILES: *COC(=O)C(C)(C)N] | Cl | Cl |
| $—CH_2CH_2CH_2CH_3$ | 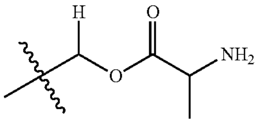 [SMILES: *COC(=O)C(C)N] | Cl | Cl |
| $—CH_2CH_2CH_2CH_3$ | 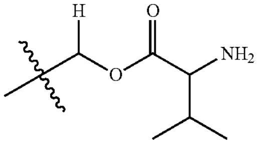 [SMILES: *COC(=O)C(N)C(C)C] | Cl | Cl |
| $—CH_2CH_2CH_2CH_3$ | 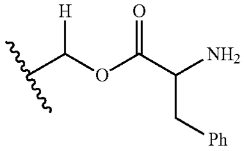 [SMILES: *COC(=O)C(N)Cc1ccccc1] | Cl | Cl |
| $—CH_2CH_2CH_2CH_3$ | 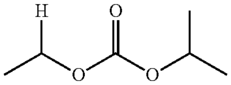 | Cl | Cl |
| $—CH_2CH_2CH_2CH_3$ | 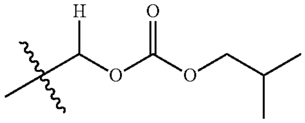 [SMILES: *COC(=O)OCC(C)C] | Cl | Cl |
| $—CH_2CH_2CH_2CH_3$ | 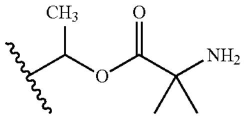 [SMILES: *C(C)OC(=O)C(C)(C)N] | Cl | Cl |

-continued

| $R^2$ | $R^1$ | $R^{6G}$ | $R^{6H}$ |
|---|---|---|---|
| $—CH_2CH_2CH_2CH_3$ | 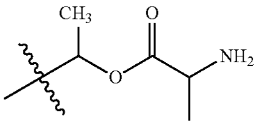 | Cl | Cl |
| $—CH_2CH_2CH_2CH_3$ | 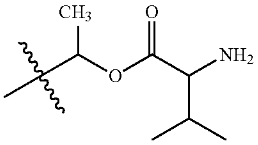 | Cl | Cl |
| $—CH_2CH_2CH_2CH_3$ | 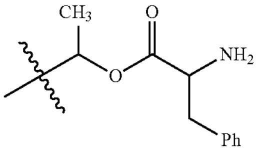 [SMILES: *C(C)OC(=O)C(N)Cc1ccccc1] | Cl | Cl |
| $—CH_2CH_2CH_2CH_3$ | 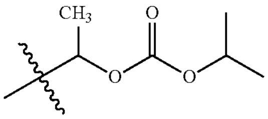 [SMILES: *C(C)OC(=O)OC(C)C] | Cl | Cl |
| $—CH_2CH_2CH_2CH_3$ | 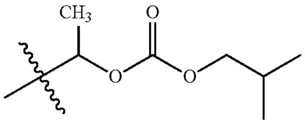 | Cl | Cl |
| 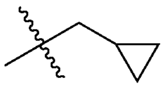 [SMILES: *CC1CC1] | H | Cl | Cl |
| 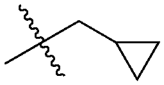 [SMILES: *CC1CC1] | 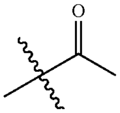 [SMILES: *C(C)=O] | Cl | Cl |
| 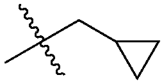 [SMILES: *CC1CC1] | 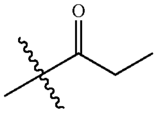 [SMILES: *C(=O)CC] | Cl | Cl |
| 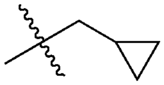 [SMILES: *CC1CC1] | 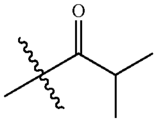 [SMILES: *C(=O)C(C)C] | Cl | Cl |
| 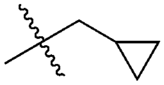 [SMILES: *CC1CC1] | 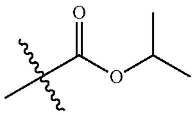 | Cl | Cl |
| 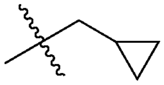 [SMILES: *CC1CC1] | 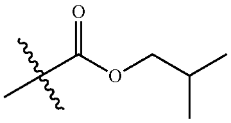 [SMILES: *C(=O)OCC(C)C] | Cl | Cl |

-continued
| $R^2$ | $R^1$ | $R^{6G}$ | $R^{6H}$ |
|---|---|---|---|
| 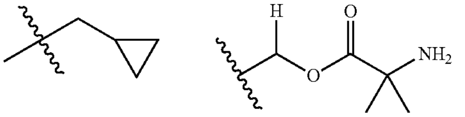 | | Cl | Cl |
| 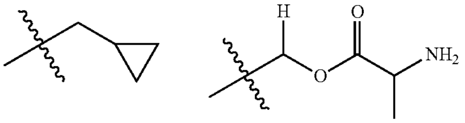 | | Cl | Cl |
| 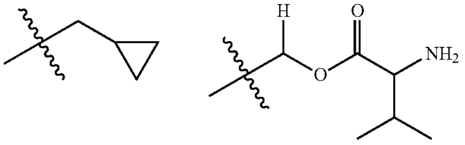 | | Cl | Cl |
| 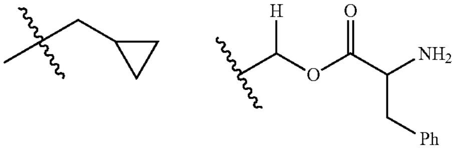 | | Cl | Cl |
| 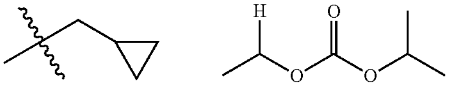 | | Cl | Cl |
| 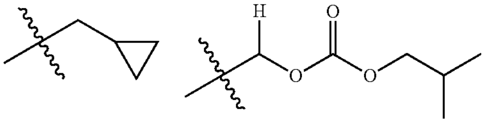 | | Cl | Cl |
| 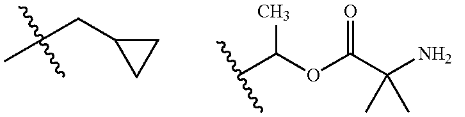 | | Cl | Cl |
| 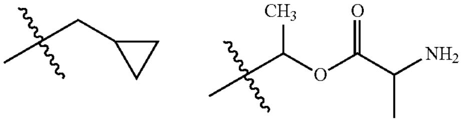 | | Cl | Cl |
| 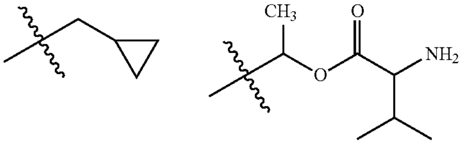 | | Cl | Cl |
| 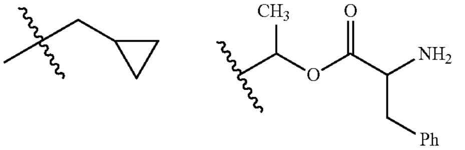 | | Cl | Cl |
| 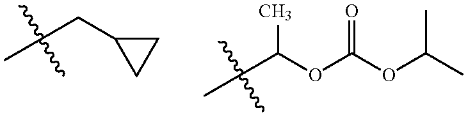 | | Cl | Cl |
-continued
| $R^2$ | $R^1$ | $R^{6G}$ | $R^{6H}$ |
|---|---|---|---|
| 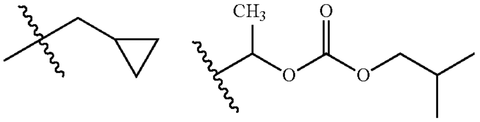 | | Cl | Cl |
| 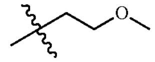 [SMILES: *CCOC] | H | Cl | Cl |
| 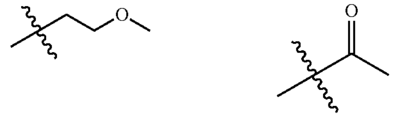 | | Cl | Cl |
| 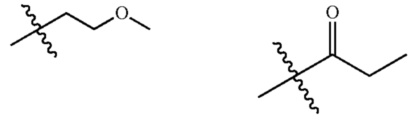 | | Cl | Cl |
| 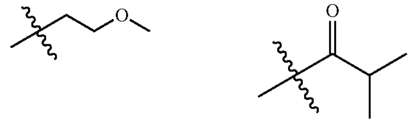 | | Cl | Cl |
| 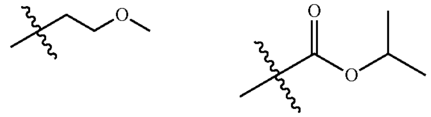 | | Cl | Cl |
| 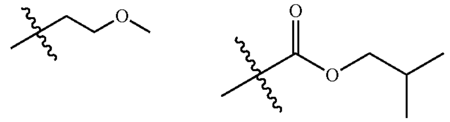 | | Cl | Cl |
| 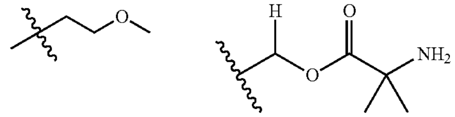 | | Cl | Cl |
| 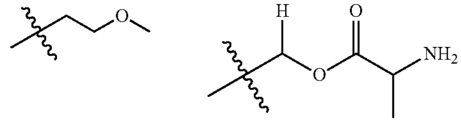 | | Cl | Cl |
| 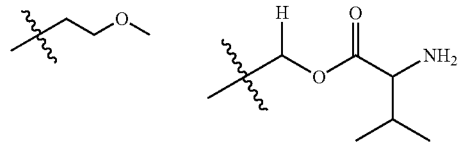 | | Cl | Cl |
| 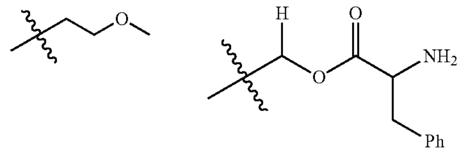 | | Cl | Cl |
| 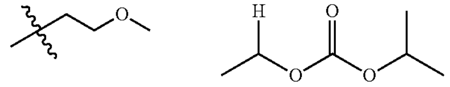 | | Cl | Cl |

-continued
| $R^2$ | $R^1$ | $R^{6G}$ | $R^{6H}$ |
|---|---|---|---|
| 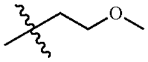 [SMILES: *CCOC] | 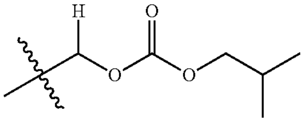 [SMILES: *COC(=O)OCC(C)C] | Cl | Cl |
| 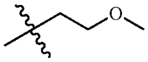 [SMILES: *CCOC] | 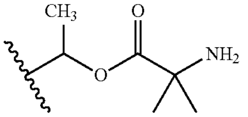 [SMILES: *C(C)OC(=O)C(C)(C)N] | Cl | Cl |
| 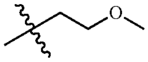 [SMILES: *CCOC] | 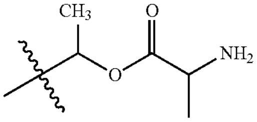 [SMILES: *C(C)OC(=O)C(C)N] | Cl | Cl |
| 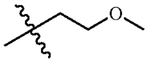 | 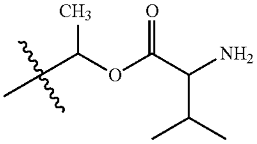 [SMILES: *C(C)OC(=O)C(N)C(C)C] | Cl | Cl |
| 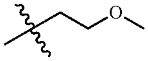 [SMILES: *CCOC] | 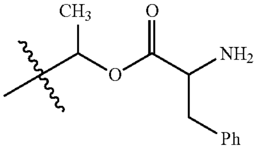 | Cl | Cl |
| 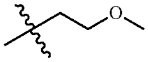 [SMILES: *CCOC] | 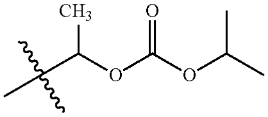 [SMILES: *C(C)OC(=O)OC(C)C] | Cl | Cl |
| 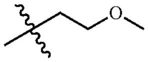 | 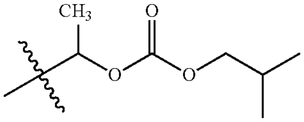 | Cl | Cl |
| 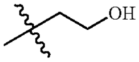 [SMILES: *CCO] | H | Cl | Cl |
| 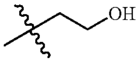 [SMILES: *CCO] | 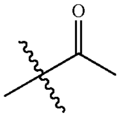 [SMILES: *C(C)=O] | Cl | Cl |
| 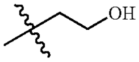 | 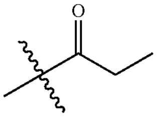 [SMILES: *C(=O)CC] | Cl | Cl |
| 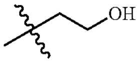 [SMILES: *CCO] | 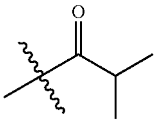 [SMILES: *C(=O)C(C)C] | Cl | Cl |
| 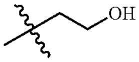 | 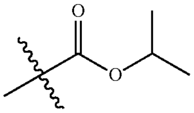 [SMILES: *C(=O)OC(C)C] | Cl | Cl |
-continued
| $R^2$ | $R^1$ | $R^{6G}$ | $R^{6H}$ |
|---|---|---|---|
| 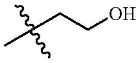 | 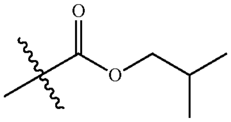 [SMILES: *C(=O)OCC(C)C] | Cl | Cl |
| 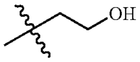 [SMILES: *CCO] | 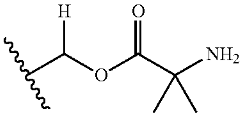 [SMILES: *COC(=O)C(C)(C)N] | Cl | Cl |
| 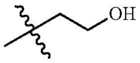 | 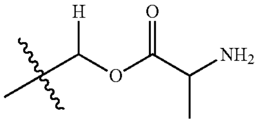 [SMILES: *COC(=O)C(C)N] | Cl | Cl |
| 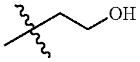 | 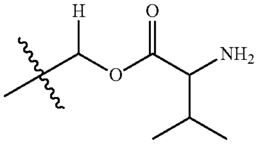 [SMILES: *COC(=O)C(N)C(C)C] | Cl | Cl |
| 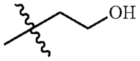 [SMILES: *CCO] | 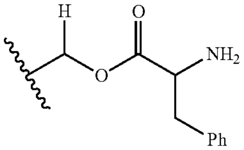 [SMILES: *COC(=O)C(N)Cc1ccccc1] | Cl | Cl |
| 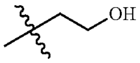 [SMILES: *CCO] | 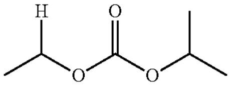 | Cl | Cl |
|  | 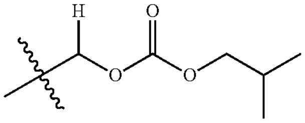 [SMILES: *COC(=O)OCC(C)C] | Cl | Cl |
|  | 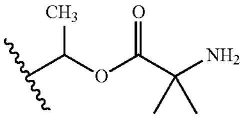 [SMILES: *C(C)OC(=O)C(C)(C)N] | Cl | Cl |
|  | 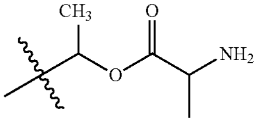 | Cl | Cl |
|  | 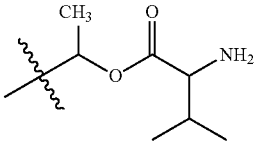 [SMILES: *C(C)OC(=O)C(N)C(C)C] | Cl | Cl |
|  | 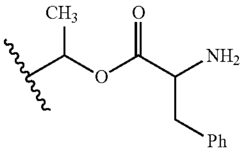 [SMILES: *C(C)OC(=O)C(N)Cc1ccccc1] | Cl | Cl |

-continued

| $R^2$ | $R^1$ | $R^{6G}$ | $R^{6H}$ |
|---|---|---|---|
| 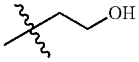 [SMILES: *CCO] | 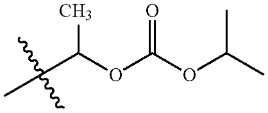 [SMILES: *C(C)OC(=O)OC(C)C] | Cl | Cl |
| 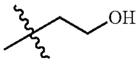 [SMILES: *CCO] | 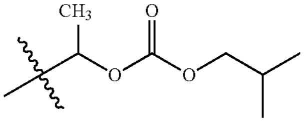 | Cl | Cl |
| $-CH_2CH{=}CF_2$ | 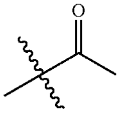 [SMILES: *C(C)=O] | Cl | Cl |
| $-CH_2CH{=}CF_2$ | 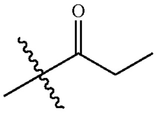 [SMILES: *C(=O)CC] | Cl | Cl |
| $-CH_2CH{=}CF_2$ | 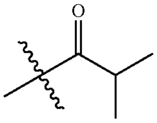 [SMILES: *C(=O)C(C)C] | Cl | Cl |
| $-CH_2CH{=}CF_2$ | 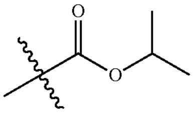 [SMILES: *C(=O)OC(C)C] | Cl | Cl |
| $-CH_2CH{=}CF_2$ | 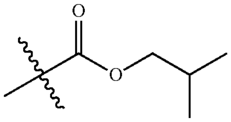 [SMILES: *C(=O)OCC(C)C] | Cl | Cl |
| $-CH_2CH{=}CF_2$ | 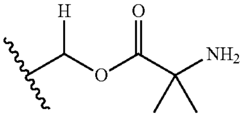 [SMILES: *COC(=O)C(C)(C)N] | Cl | Cl |
| $-CH_2CH{=}CF_2$ | 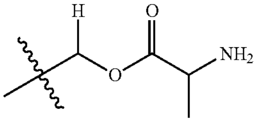 [SMILES: *COC(=O)C(C)N] | Cl | Cl |
| $-CH_2CH{=}CF_2$ | 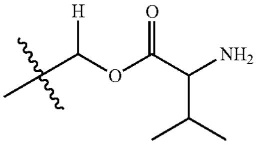 [SMILES: *COC(=O)C(N)C(C)C] | Cl | Cl |
| $-CH_2CH{=}CF_2$ | 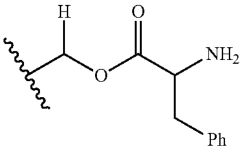 [SMILES: *COC(=O)C(N)Cc1ccccc1] | Cl | Cl |

-continued

| $R^2$ | $R^1$ | $R^{6G}$ | $R^{6H}$ |
|---|---|---|---|
| $-CH_2CH{=}CF_2$ | 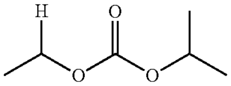 | Cl | Cl |
| $-CH_2CH{=}CF_2$ | 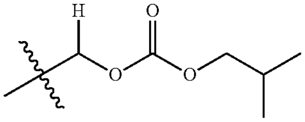 [SMILES: *COC(=O)OCC(C)C] | Cl | Cl |
| $-CH_2CH{=}CF_2$ | 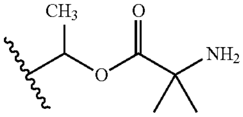 [SMILES: *C(C)OC(=O)C(C)(C)N] | Cl | Cl |
| $-CH_2CH{=}CF_2$ | 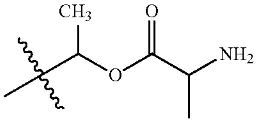 | Cl | Cl |
| $-CH_2CH{=}CF_2$ | 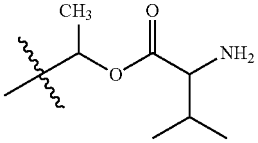 | Cl | Cl |
| $-CH_2CH{=}CF_2$ | 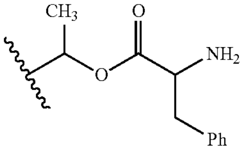 [SMILES: *C(C)OC(=O)C(N)Cc1ccccc1] | Cl | Cl |
| $-CH_2CH{=}CF_2$ | 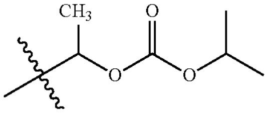 [SMILES: *C(C)OC(=O)OC(C)C] | Cl | Cl |
| $-CH_2CH{=}CF_2$ | 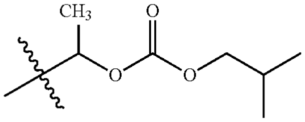 [SMILES: *C(C)OC(=O)OCC(C)C] | Cl | Cl |
| $-CH_2CF_3$ | 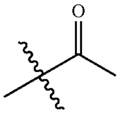 [SMILES: *C(C)=O] | Cl | Cl |
| $-CH_2CF_3$ | 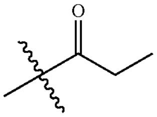 [SMILES: *C(=O)CC] | Cl | Cl |
| $-CH_2CF_3$ | 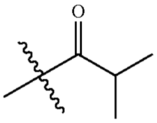 [SMILES: *C(=O)C(C)C] | Cl | Cl |

-continued
| $R^2$ | $R^1$ | $R^{6G}$ | $R^{6H}$ |
|---|---|---|---|
| $—CH_2CF_3$ | 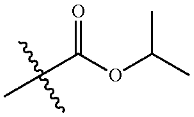 [SMILES: *C(=O)OC(C)C] | Cl | Cl |
| $—CH_2CF_3$ | 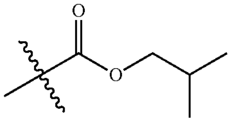 [SMILES: *C(=O)OCC(C)C] | Cl | Cl |
| $—CH_2CF_3$ | 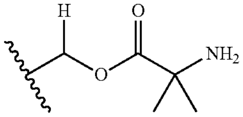 | Cl | Cl |
| $—CH_2CF_3$ | 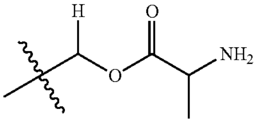 [SMILES: *COC(=O)C(C)N] | Cl | Cl |
| $—CH_2CF_3$ | 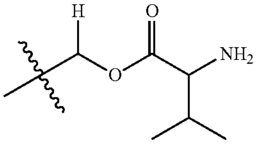 [SMILES: *COC(=O)C(N)C(C)C] | Cl | Cl |
| $—CH_2CF_3$ | 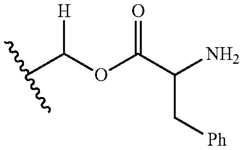 [SMILES: *COC(=O)C(N)Cc1ccccc1] | Cl | Cl |
| $—CH_2CF_3$ | 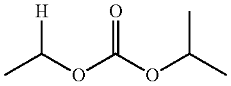 | Cl | Cl |
| $—CH_2CF_3$ | 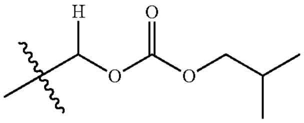 [SMILES: *COC(=O)OCC(C)C] | Cl | Cl |
| $—CH_2CF_3$ | 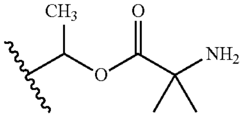 [SMILES: *C(C)OC(=O)C(C)(C)N] | Cl | Cl |
| $—CH_2CF_3$ | 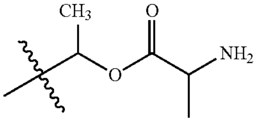 | Cl | Cl |
| $—CH_2CF_3$ | 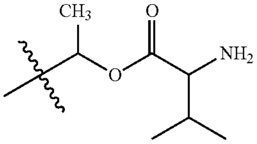 | Cl | Cl |
-continued
| $R^2$ | $R^1$ | $R^{6G}$ | $R^{6H}$ |
|---|---|---|---|
| $—CH_2CF_3$ | 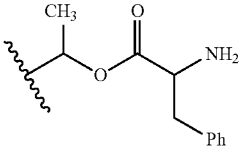 [SMILES: *C(C)OC(=O)C(N)Cc1ccccc1] | Cl | Cl |
| $—CH_2CF_3$ | 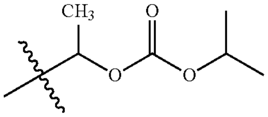 [SMILES: *C(C)OC(=O)OC(C)C] | Cl | Cl |
| $—CH_2CF_3$ | 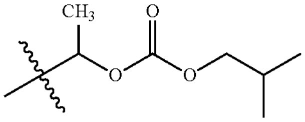 [SMILES: *C(C)OC(=O)OCC(C)C] | Cl | Cl |
| $—CH_2CH_2CF_3$ | 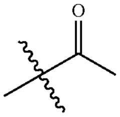 [SMILES: *C(C)=O] | Cl | Cl |
| $—CH_2CH_2CF_3$ | 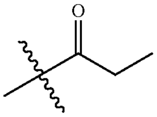 [SMILES: *C(=O)CC] | Cl | Cl |
| $—CH_2CH_2CF_3$ | 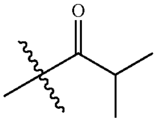 [SMILES: *C(=O)C(C)C] | Cl | Cl |
| $—CH_2CH_2CF_3$ | 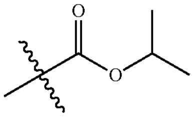 [SMILES: *C(=O)OC(C)C] | Cl | Cl |
| $—CH_2CH_2CF_3$ | 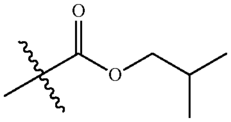 [SMILES: *C(=O)OCC(C)C] | Cl | Cl |
| $—CH_2CH_2CF_3$ | 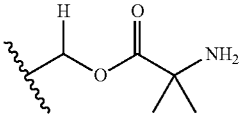 [SMILES: *COC(=O)C(C)(C)N] | Cl | Cl |
| $—CH_2CH_2CF_3$ | 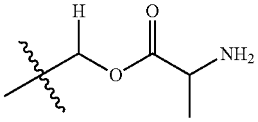 [SMILES: *COC(=O)C(C)N] | Cl | Cl |
| $—CH_2CH_2CF_3$ | 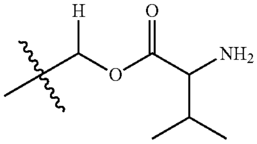 [SMILES: *COC(=O)C(N)C(C)C] | Cl | Cl |

-continued

| $R^2$ | $R^1$ | $R^{6G}$ | $R^{6H}$ |
|---|---|---|---|
| $—CH_2CH_2CF_3$ | 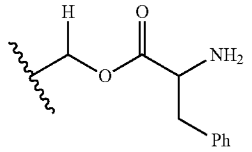 [SMILES: *COC(=O)C(N)Cc1ccccc1] | Cl | Cl |
| $—CH_2CH_2CF_3$ | 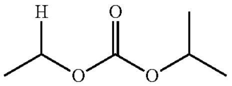 | Cl | Cl |
| $—CH_2CH_2CF_3$ | 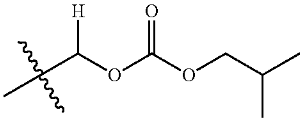 [SMILES: *COC(=O)OCC(C)C] | Cl | Cl |
| $—CH_2CH_2CF_3$ | 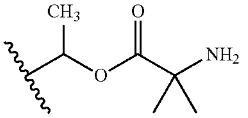 [SMILES: *C(C)OC(=O)C(C)(C)N] | Cl | Cl |
| $—CH_2CH_2CF_3$ | 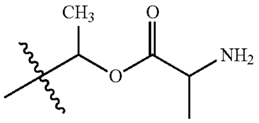 [SMILES: *C(C)OC(=O)C(C)N] | Cl | Cl |
| $—CH_2CH_2CF_3$ | 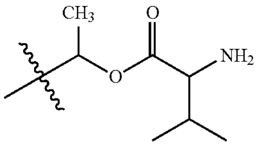 [SMILES: *C(C)OC(=O)C(N)C(C)C] | Cl | Cl |
| $—CH_2CH_2CF_3$ | 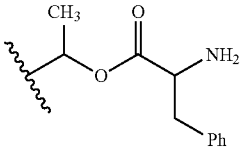 [SMILES: *C(C)OC(=O)C(N)Cc1ccccc1] | Cl | Cl |
| $—CH_2CH_2CF_3$ | 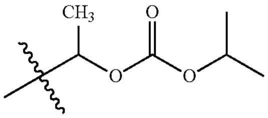 [SMILES: *C(C)OC(=O)OC(C)C] | Cl | Cl |
| $—CH_2CH_2CF_3$ | 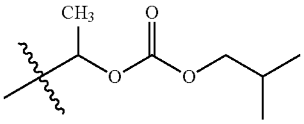 [SMILES: *C(C)OC(=O)OCC(C)C] | Cl | Cl |
| $—CH_2CHF_2$ | 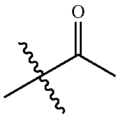 [SMILES: *C(C)=O] | Cl | Cl |
| $—CH_2CHF_2$ | 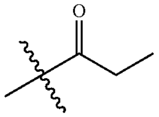 [SMILES: *C(=O)CC] | Cl | Cl |

-continued

| $R^2$ | $R^1$ | $R^{6G}$ | $R^{6H}$ |
|---|---|---|---|
| $—CH_2CHF_2$ | 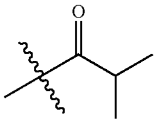 [SMILES: *C(=O)C(C)C] | Cl | Cl |
| $—CH_2CHF_2$ | 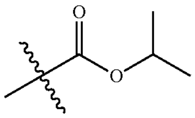 [SMILES: *C(=O)OC(C)C] | Cl | Cl |
| $—CH_2CHF_2$ | 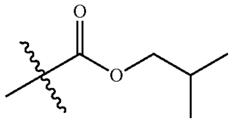 [SMILES: *C(=O)OCC(C)C] | Cl | Cl |
| $—CH_2CHF_2$ | 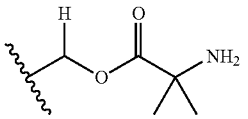 [SMILES: *COC(=O)C(C)(C)N] | Cl | Cl |
| $—CH_2CHF_2$ | 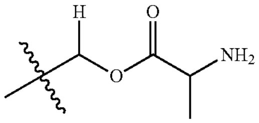 [SMILES: *COC(=O)C(C)N] | Cl | Cl |
| $—CH_2CHF_2$ | 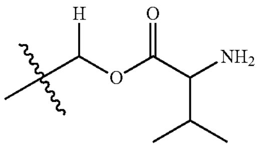 [SMILES: *COC(=O)C(N)C(C)C] | Cl | Cl |
| $—CH_2CHF_2$ | 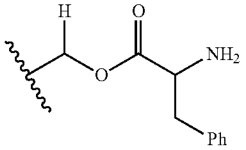 [SMILES: *COC(=O)C(N)Cc1ccccc1] | Cl | Cl |
| $—CH_2CHF_2$ | 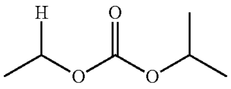 | Cl | Cl |
| $—CH_2CHF_2$ | 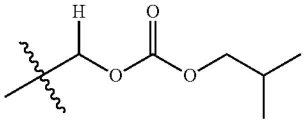 [SMILES: *COC(=O)OCC(C)C] | Cl | Cl |
| $—CH_2CHF_2$ | 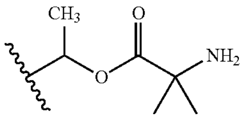 [SMILES: *C(C)OC(=O)C(C)(C)N] | Cl | Cl |
| $—CH_2CHF_2$ | 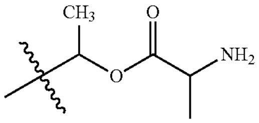 | Cl | Cl |

-continued

| $R^2$ | $R^1$ | $R^{6G}$ | $R^{6H}$ |
|---|---|---|---|
| $-CH_2CHF_2$ | 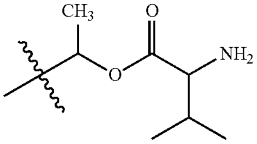 [SMILES: *C(C)OC(=O)C(N)C(C)C] | Cl | Cl |
| $-CH_2CHF_2$ | 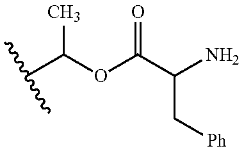 [SMILES: *C(C)OC(=O)C(N)Cc1ccccc1] | Cl | Cl |
| $-CH_2CHF_2$ | 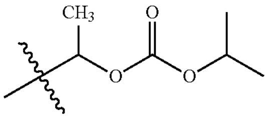 [SMILES: *C(C)OC(=O)OC(C)C] | Cl | Cl |
| $-CH_2CHF_2$ | 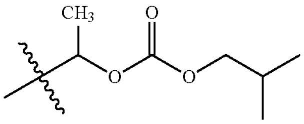 [SMILES: *C(C)OC(=O)OCC(C)C] | Cl | Cl |
| $-CH_2C(CH_3)F_2$ | 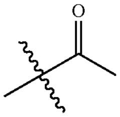 [SMILES: *C(C)=O] | Cl | Cl |
| $-CH_2C(CH_3)F_2$ | 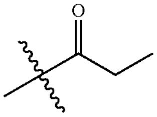 [SMILES: *C(=O)CC] | Cl | Cl |
| $-CH_2C(CH_3)F_2$ | 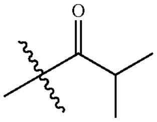 [SMILES: *C(=O)C(C)C] | Cl | Cl |
| $-CH_2C(CH_3)F_2$ | 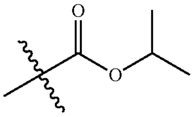 [SMILES: *C(=O)OC(C)C] | Cl | Cl |
| $-CH_2C(CH_3)F_2$ | 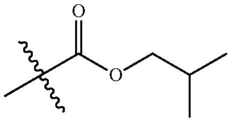 [SMILES: *C(=O)OCC(C)C] | Cl | Cl |
| $-CH_2C(CH_3)F_2$ | 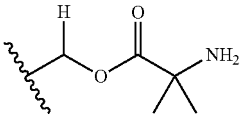 [SMILES: *COC(=O)C(C)(C)N] | Cl | Cl |
| $-CH_2C(CH_3)F_2$ | 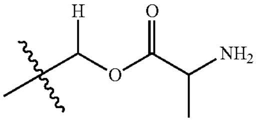 [SMILES: *COC(=O)C(C)N] | Cl | Cl |

-continued

| $R^2$ | $R^1$ | $R^{6G}$ | $R^{6H}$ |
|---|---|---|---|
| $-CH_2C(CH_3)F_2$ | 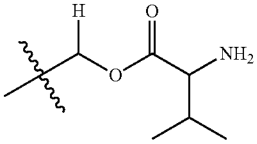 [SMILES: *COC(=O)C(N)C(C)C] | Cl | Cl |
| $-CH_2C(CH_3)F_2$ | 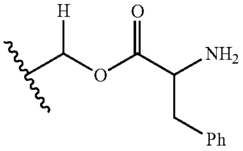 [SMILES: *COC(=O)C(N)Cc1ccccc1] | Cl | Cl |
| $-CH_2C(CH_3)F_2$ | 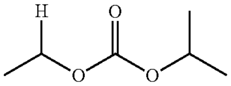 | Cl | Cl |
| $-CH_2C(CH_3)F_2$ | 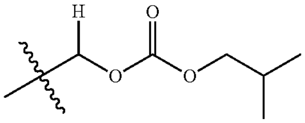 | Cl | Cl |
| $-CH_2C(CH_3)F_2$ | 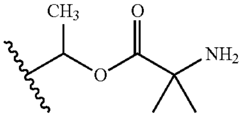 [SMILES: *C(C)OC(=O)C(C)(C)N] | Cl | Cl |
| $-CH_2C(CH_3)F_2$ | 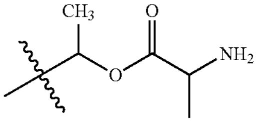 [SMILES: *C(C)OC(=O)C(C)N] | Cl | Cl |
| $-CH_2C(CH_3)F_2$ | 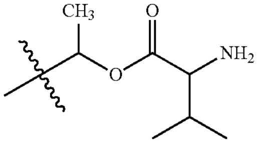 [SMILES: *C(C)OC(=O)C(N)C(C)C] | Cl | Cl |
| $-CH_2C(CH_3)F_2$ | 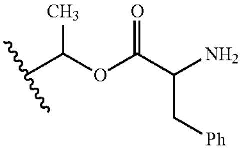 [SMILES: *C(C)OC(=O)C(N)Cc1ccccc1] | Cl | Cl |
| $-CH_2C(CH_3)F_2$ | 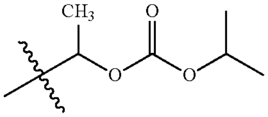 [SMILES: *C(C)OC(=O)OC(C)C] | Cl | Cl |
| $-CH_2C(CH_3)F_2$ | 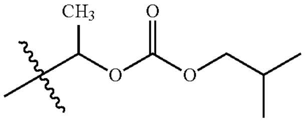 | Cl | Cl |
| 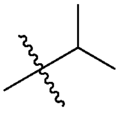 [SMILES: *C(C)C] | 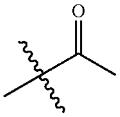 [SMILES: *C(C)=O] | F | F |

-continued
| $R^2$ | $R^1$ | $R^{6G}$ | $R^{6H}$ |
|---|---|---|---|
| 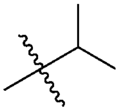 [SMILES: *C(C)C] | 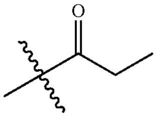 [SMILES: *C(=O)CC] | F | F |
| 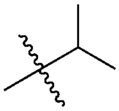 [SMILES: *C(C)C] | 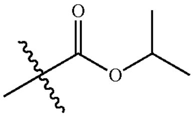 [SMILES: *C(=O)OC(C)C] | F | F |
| 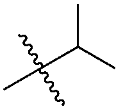 [SMILES: *C(C)C] | 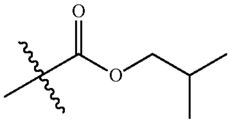 [SMILES: *C(=O)OCC(C)C] | F | F |
| 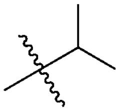 [SMILES: *C(C)C] | 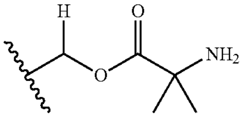 [SMILES: *COC(=O)C(C)(C)N] | F | F |
| 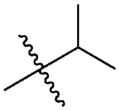 [SMILES: *C(C)C] | 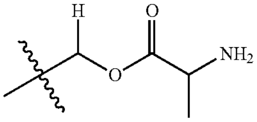 [SMILES: *COC(=O)C(C)N] | F | F |
| 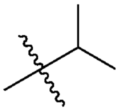 [SMILES: *C(C)C] | 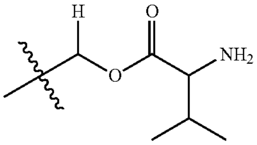 [SMILES: *COC(=O)C(N)C(C)C] | F | F |
| 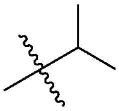 [SMILES: *C(C)C] | 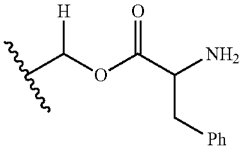 [SMILES: *COC(=O)C(N)Cc1ccccc1] | F | F |
| 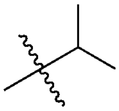 [SMILES: *C(C)C] | 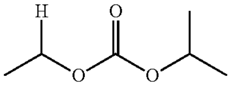 | F | F |
| 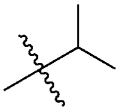 [SMILES: *C(C)C] | 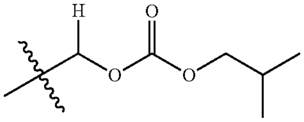 [SMILES: *COC(=O)OCC(C)C] | F | F |
| 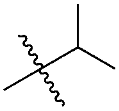 [SMILES: *C(C)C] | 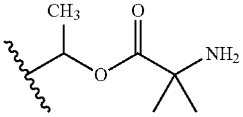 [SMILES: *C(C)OC(=O)C(C)(C)N] | F | F |
| 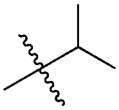 [SMILES: *C(C)C] | 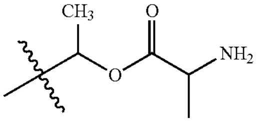 [SMILES: *C(C)OC(=O)C(C)N] | F | F |
| 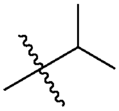 [SMILES: *C(C)C] | 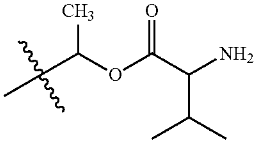 [SMILES: *C(C)OC(=O)C(N)C(C)C] | F | F |
| 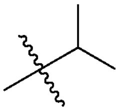 [SMILES: *C(C)C] | 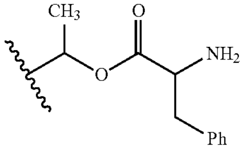 [SMILES: *C(C)OC(=O)C(N)Cc1ccccc1] | F | F |
| 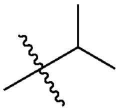 [SMILES: *C(C)C] | 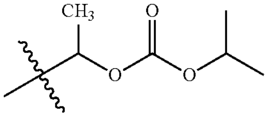 [SMILES: *C(C)OC(=O)OC(C)C] | F | F |
| 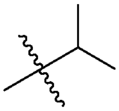 [SMILES: *C(C)C] | 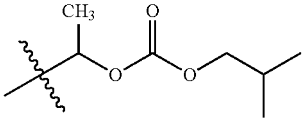 | F | F |
| —$CH_3$ | 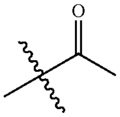 [SMILES: *C(C)=O] | F | F |
| —$CH_3$ | 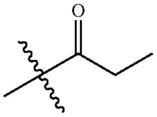 [SMILES: *C(=O)CC] | F | F |
| —$CH_3$ | 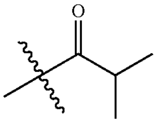 [SMILES: *C(=O)C(C)C] | F | F |
| —$CH_3$ | 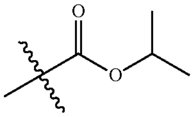 [SMILES: *C(=O)OC(C)C] | F | F |
| —$CH_3$ | 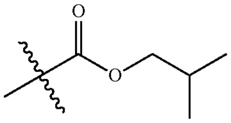 [SMILES: *C(=O)OCC(C)C] | F | F |
| —$CH_3$ | 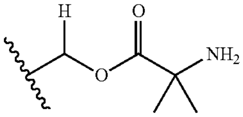 [SMILES: *COC(=O)C(C)(C)N] | F | F |
| —$CH_3$ | 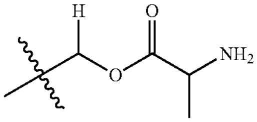 [SMILES: *COC(=O)C(C)N] | F | F |

-continued
| $R^2$ | $R^1$ | $R^{6G}$ | $R^{6H}$ |
|---|---|---|---|
| $—CH_3$ | 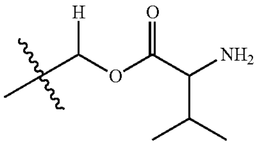 [SMILES: *COC(=O)C(N)C(C)C] | F | F |
| $—CH_3$ | 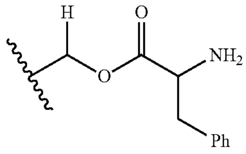 [SMILES: *COC(=O)C(N)Cc1ccccc1] | F | F |
| $—CH_3$ | 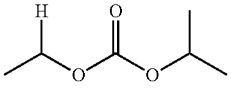 | F | F |
| $—CH_3$ | 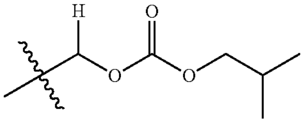 [SMILES: *COC(=O)OCC(C)C] | F | F |
| $—CH_3$ | 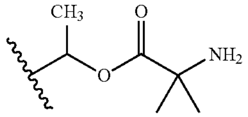 [SMILES: *C(C)OC(=O)C(C)(C)N] | F | F |
| $—CH_3$ | 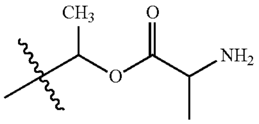 [SMILES: *C(C)OC(=O)C(C)N] | F | F |
| $—CH_3$ | 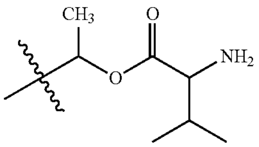 | F | F |
| $—CH_3$ | 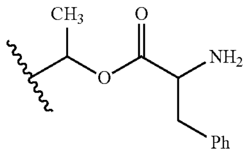 [SMILES: *C(C)OC(=O)C(N)Cc1ccccc1] | F | F |
| $—CH_3$ | 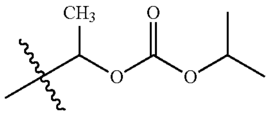 [SMILES: *C(C)OC(=O)OC(C)C] | F | F |
| $—CH_3$ | 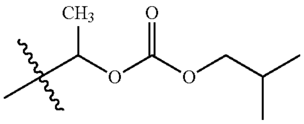 | F | F |
| $—CH_2CH_3$ | H | F | F |
| $—CH_2CH_3$ | 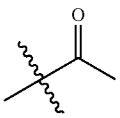 [SMILES: *C(C)=O] | F | F |
-continued
| $R^2$ | $R^1$ | $R^{6G}$ | $R^{6H}$ |
|---|---|---|---|
| $—CH_2CH_3$ | 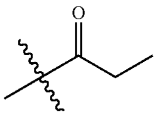 [SMILES: *C(=O)CC] | F | F |
| $—CH_2CH_3$ | 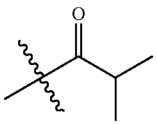 [SMILES: *C(=O)C(C)C] | F | F |
| $—CH_2CH_3$ | 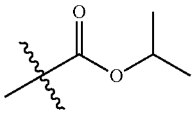 [SMILES: *C(=O)OC(C)C] | F | F |
| $—CH_2CH_3$ | 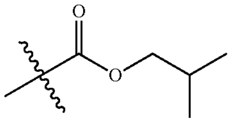 [SMILES: *C(=O)OCC(C)C] | F | F |
| $—CH_2CH_3$ | 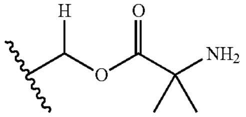 [SMILES: *COC(=O)C(C)(C)N] | F | F |
| $—CH_2CH_3$ | 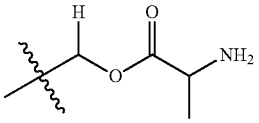 [SMILES: *COC(=O)C(C)N] | F | F |
| $—CH_2CH_3$ | 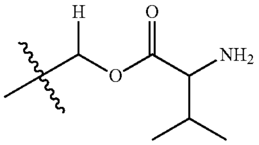 [SMILES: *COC(=O)C(N)C(C)C] | F | F |
| $—CH_2CH_3$ | 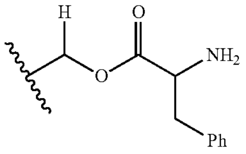 [SMILES: *COC(=O)C(N)Cc1ccccc1] | F | F |
| $—CH_2CH_3$ | 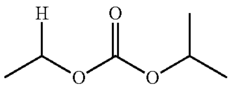 | F | F |
| $—CH_2CH_3$ | 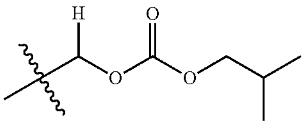 [SMILES: *COC(=O)OCC(C)C] | F | F |
| $—CH_2CH_3$ | 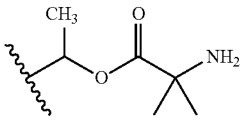 [SMILES: *C(C)OC(=O)C(C)(C)N] | F | F |

-continued
| $R^2$ | $R^1$ | $R^{6G}$ | $R^{6H}$ |
|---|---|---|---|
| $—CH_2CH_3$ | 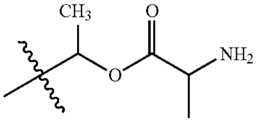 [SMILES: *C(C)OC(=O)C(C)N] | F | F |
| $—CH_2CH_3$ | 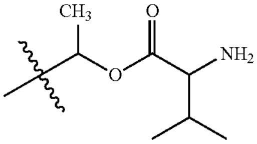 [SMILES: *C(C)OC(=O)C(N)C(C)C] | F | F |
| $—CH_2CH_3$ | 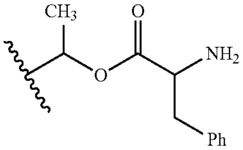 | F | F |
| $—CH_2CH_3$ | 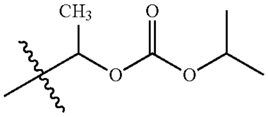 [SMILES: *C(C)OC(=O)OC(C)C] | F | F |
| $—CH_2CH_3$ | 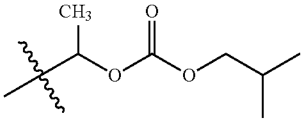 [SMILES: *C(C)OC(=O)OCC(C)C] | F | F |
| $—CH_2CH(CH_3)_2$ | H | F | F |
| $—CH_2CH(CH_3)_2$ | 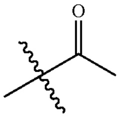 [SMILES: *C(C)=O] | F | F |
| $—CH_2CH(CH_3)_2$ | 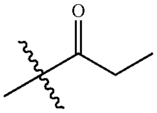 [SMILES: *C(=O)CC] | F | F |
| $—CH_2CH(CH_3)_2$ | 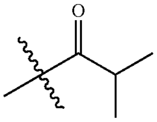 [SMILES: *C(=O)C(C)C] | F | F |
| $—CH_2CH(CH_3)_2$ | 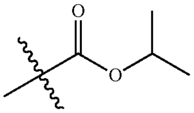 [SMILES: *C(=O)OC(C)C] | F | F |
| $—CH_2CH(CH_3)_2$ | 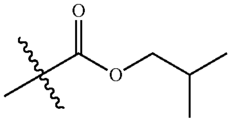 [SMILES: *C(=O)OCC(C)C] | F | F |
| $—CH_2CH(CH_3)_2$ | 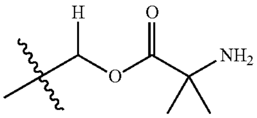 [SMILES: *COC(=O)C(C)(C)N] | F | F |
-continued
| $R^2$ | $R^1$ | $R^{6G}$ | $R^{6H}$ |
|---|---|---|---|
| $—CH_2CH(CH_3)_2$ | 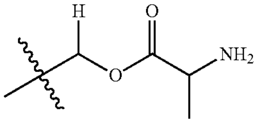 [SMILES: *COC(=O)C(C)N] | F | F |
| $—CH_2CH(CH_3)_2$ | 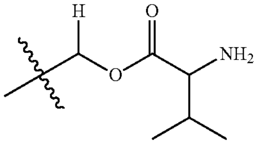 [SMILES: *COC(=O)C(N)C(C)C] | F | F |
| $—CH_2CH(CH_3)_2$ | 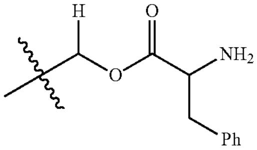 [SMILES: *COC(=O)C(N)Cc1ccccc1] | F | F |
| $—CH_2CH(CH_3)_2$ | 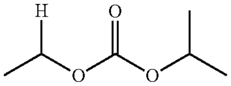 | F | F |
| $—CH_2CH(CH_3)_2$ | 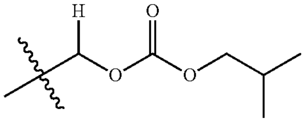 [SMILES: *COC(=O)OCC(C)C] | F | F |
| $—CH_2CH(CH_3)_2$ | 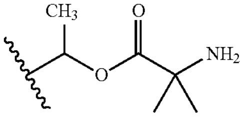 [SMILES: *C(C)OC(=O)C(C)(C)N] | F | F |
| $—CH_2CH(CH_3)_2$ | 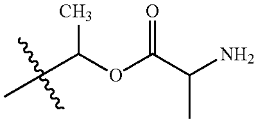 | F | F |
| $—CH_2CH(CH_3)_2$ | 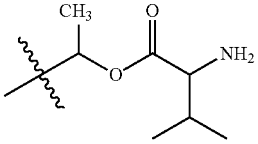 [SMILES: *C(C)OC(=O)C(N)C(C)C] | F | F |
| $—CH_2CH(CH_3)_2$ | 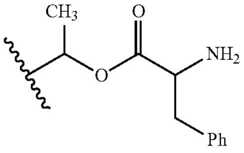 | F | F |
| $—CH_2CH(CH_3)_2$ | 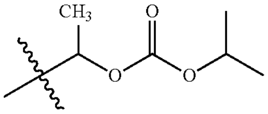 [SMILES: *C(C)OC(=O)OC(C)C] | F | F |
| $—CH_2CH(CH_3)_2$ | 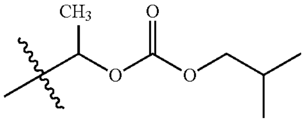 [SMILES: *C(C)OC(=O)OCC(C)C] | F | F |

-continued
| $R^2$ | $R^1$ | $R^{6G}$ | $R^{6H}$ |
|---|---|---|---|
| $—CH_2CH_2CH_3$ | 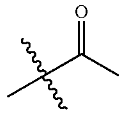 [SMILES: *C(C)=O] | F | F |
| $—CH_2CH_2CH_3$ | 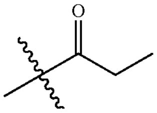 [SMILES: *C(=O)CC] | F | F |
| $—CH_2CH_2CH_3$ | 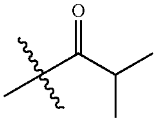 [SMILES: *C(=O)C(C)C] | F | F |
| $—CH_2CH_2CH_3$ | 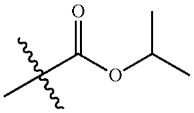 [SMILES: *C(=O)OC(C)C] | F | F |
| $—CH_2CH_2CH_3$ | 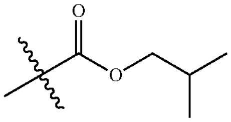 [SMILES: *C(=O)OCC(C)C] | F | F |
| $—CH_2CH_2CH_3$ | 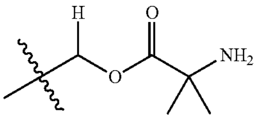 [SMILES: *COC(=O)C(C)(C)N] | F | F |
| $—CH_2CH_2CH_3$ | 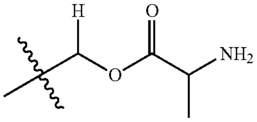 [SMILES: *COC(=O)C(C)N] | F | F |
| $—CH_2CH_2CH_3$ | 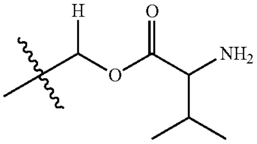 [SMILES: *COC(=O)C(N)C(C)C] | F | F |
| $—CH_2CH_2CH_3$ | 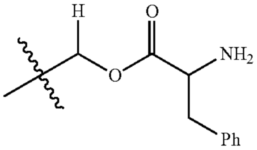 [SMILES: *COC(=O)C(N)Cc1ccccc1] | F | F |
| $—CH_2CH_2CH_3$ | 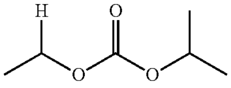 | F | F |
| $—CH_2CH_2CH_3$ | 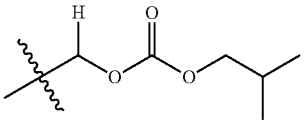 [SMILES: *COC(=O)OCC(C)C] | F | F |
-continued
| $R^2$ | $R^1$ | $R^{6G}$ | $R^{6H}$ |
|---|---|---|---|
| $—CH_2CH_2CH_3$ | 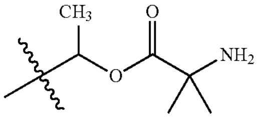 | F | F |
| $—CH_2CH_2CH_3$ | 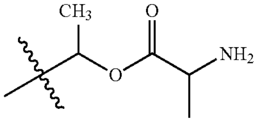 [SMILES: *C(C)OC(=O)C(C)N] | F | F |
| $—CH_2CH_2CH_3$ | 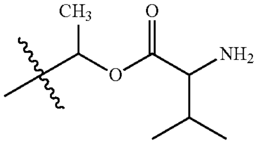 | F | F |
| $—CH_2CH_2CH_3$ | 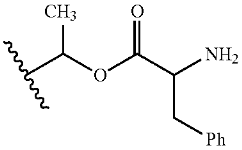 | F | F |
| $—CH_2CH_2CH_3$ | 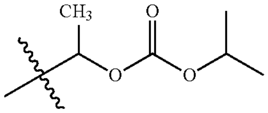 | F | F |
| $—CH_2CH_2CH_3$ | 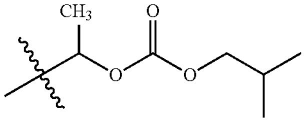 | F | F |
| $—CH_2CH_2CH_2CH_3$ | H | F | F |
| $—CH_2CH_2CH_2CH_3$ | 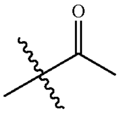 [SMILES: *C(C)=O] | F | F |
| $—CH_2CH_2CH_2CH_3$ | 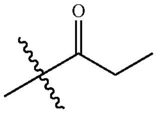 [SMILES: *C(=O)CC] | F | F |
| $—CH_2CH_2CH_2CH_3$ | 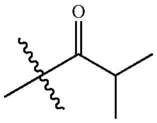 [SMILES: *C(=O)C(C)C] | F | F |
| $—CH_2CH_2CH_2CH_3$ | 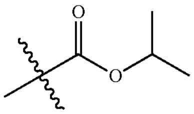 [SMILES: *C(=O)OC(C)C] | F | F |
| $—CH_2CH_2CH_2CH_3$ | 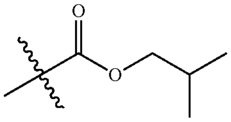 [SMILES: *C(=O)OCC(C)C] | F | F |

-continued
| $R^2$ | $R^1$ | $R^{6G}$ | $R^{6H}$ |
|---|---|---|---|
| $—CH_2CH_2CH_2CH_3$ | 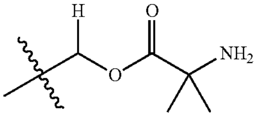 [SMILES: *COC(=O)C(C)(C)N] | F | F |
| $—CH_2CH_2CH_2CH_3$ | 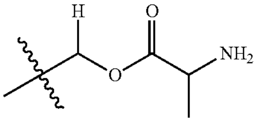 | F | F |
| $—CH_2CH_2CH_2CH_3$ | 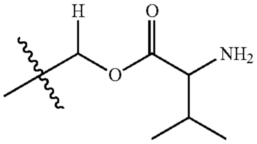 [SMILES: *COC(=O)C(N)C(C)C] | F | F |
| $—CH_2CH_2CH_2CH_3$ | 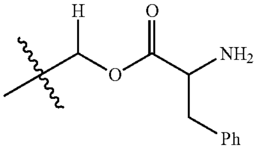 [SMILES: *COC(=O)C(N)Cc1ccccc1] | F | F |
| $—CH_2CH_2CH_2CH_3$ | 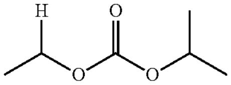 | F | F |
| $—CH_2CH_2CH_2CH_3$ | 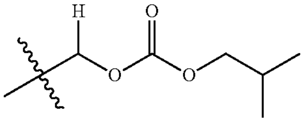 [SMILES: *COC(=O)OCC(C)C] | F | F |
| $—CH_2CH_2CH_2CH_3$ | 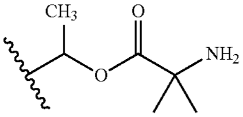 | F | F |
| $—CH_2CH_2CH_2CH_3$ | 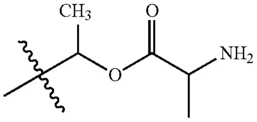 [SMILES: *C(C)OC(=O)C(C)N] | F | F |
| $—CH_2CH_2CH_2CH_3$ | 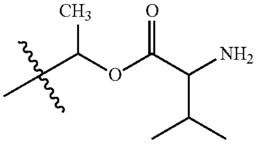 | F | F |
| $—CH_2CH_2CH_2CH_3$ | 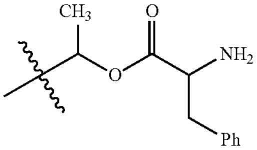 | F | F |
| $—CH_2CH_2CH_2CH_3$ | 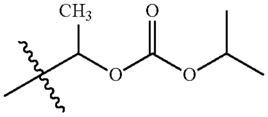 [SMILES: *C(C)OC(=O)OC(C)C] | F | F |
-continued
| $R^2$ | $R^1$ | $R^{6G}$ | $R^{6H}$ |
|---|---|---|---|
| $—CH_2CH_2CH_2CH_3$ | 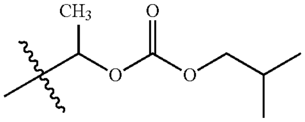 | F | F |
| 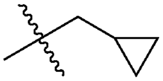 [SMILES: *CC1CC1] | H | F | F |
| 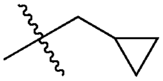 [SMILES: *CC1CC1] | 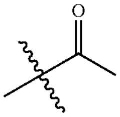 [SMILES: *C(C)=O] | F | F |
| 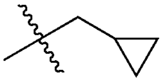 [SMILES: *CC1CC1] | 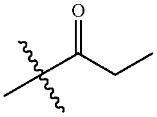 [SMILES: *C(=O)CC] | F | F |
| 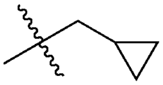 | 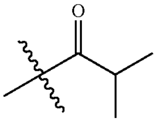 [SMILES: *C(=O)C(C)C] | F | F |
| 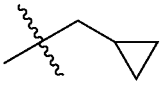 [SMILES: *CC1CC1] | 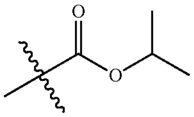 [SMILES: *C(=O)OC(C)C] | F | F |
| 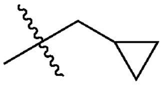 [SMILES: *CC1CC1] | 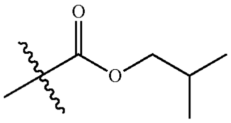 [SMILES: *C(=O)OCC(C)C] | F | F |
| 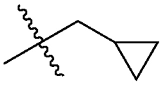 [SMILES: *CC1CC1] | 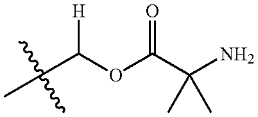 [SMILES: *COC(=O)C(C)(C)N] | F | F |
| 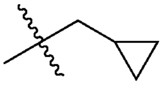 | 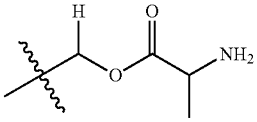 [SMILES: *COC(=O)C(C)N] | F | F |
| 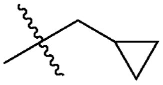 [SMILES: *CC1CC1] | 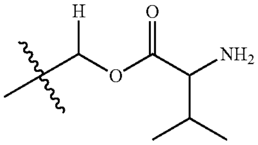 [SMILES: *COC(=O)C(N)C(C)C] | F | F |
| 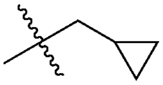 [SMILES: *CC1CC1] | 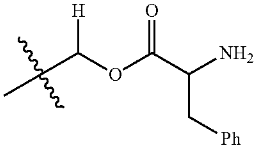 [SMILES: *COC(=O)C(N)Cc1ccccc1] | F | F |
| 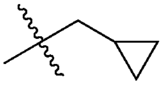 | 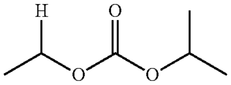 | F | F |

-continued
| $R^2$ | $R^1$ | $R^{6G}$ | $R^{6H}$ |
|---|---|---|---|
| 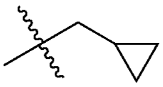 [SMILES: *CC1CC1] | 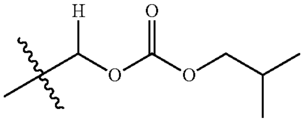 [SMILES: *COC(=O)OCC(C)C] | F | F |
| 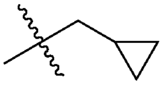 | 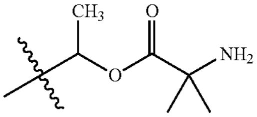 [SMILES: *C(C)OC(=O)C(C)(C)N] | F | F |
| 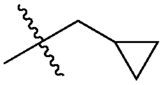 [SMILES: *CC1CC1] | 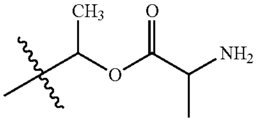 [SMILES: *C(C)OC(=O)C(C)N] | F | F |
| 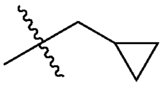 [SMILES: *CC1CC1] | 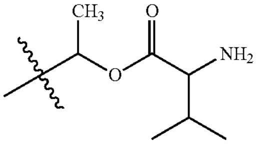 [SMILES: *C(C)OC(=O)C(N)C(C)C] | F | F |
| 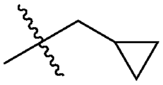 [SMILES: *CC1CC1] | 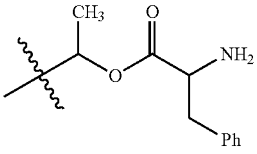 [SMILES: *C(C)OC(=O)C(N)Cc1ccccc1] | F | F |
| 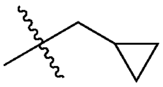 [SMILES: *CC1CC1] | 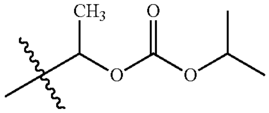 [SMILES: *C(C)OC(=O)OC(C)C] | F | F |
| 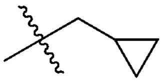 [SMILES: *CC1CC1] | 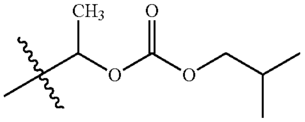 | F | F |
| 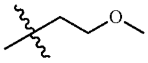 [SMILES: *CCOC] | H | F | F |
| 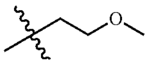 [SMILES: *CCOC] | 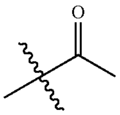 [SMILES: *C(C)=O] | F | F |
| 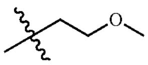 [SMILES: *CCOC] | 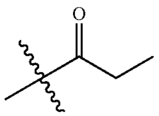 [SMILES: *C(=O)CC] | F | F |
| 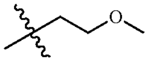 [SMILES: *CCOC] | 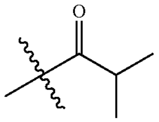 [SMILES: *C(=O)C(C)C] | F | F |
-continued
| $R^2$ | $R^1$ | $R^{6G}$ | $R^{6H}$ |
|---|---|---|---|
| 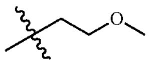 [SMILES: *CCOC] | 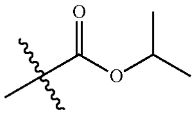 [SMILES: *C(=O)OC(C)C] | F | F |
| 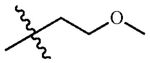 [SMILES: *CCOC] | 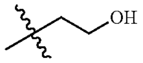 [SMILES: *CCO] | F | F |
| 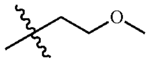 [SMILES: *CCOC] | 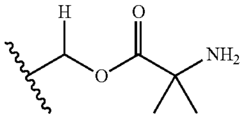 [SMILES: *COC(=O)C(C)(C)N] | F | F |
| 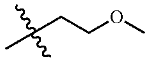 [SMILES: *CCOC] | 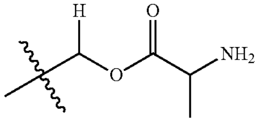 [SMILES: *COC(=O)C(C)N] | F | F |
| 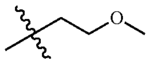 [SMILES: *CCOC] | 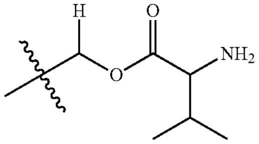 [SMILES: *COC(=O)C(N)C(C)C] | F | F |
| 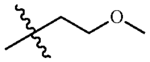 [SMILES: *CCOC] | 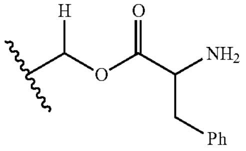 [SMILES: *COC(=O)C(N)Cc1ccccc1] | F | F |
| 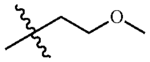 | 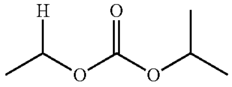 | F | F |
| 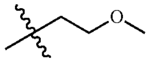 [SMILES: *CCOC] | 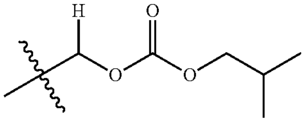 [SMILES: *COC(=O)OCC(C)C] | F | F |
| 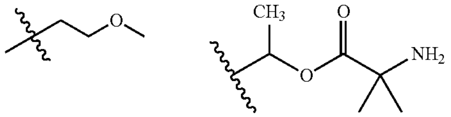 | | F | F |
| 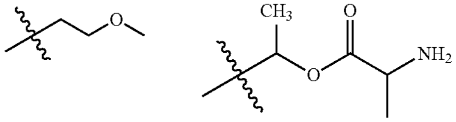 | | F | F |
| 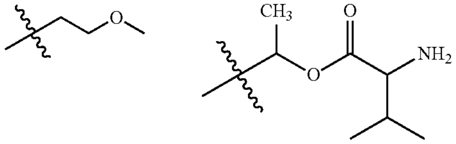 | | F | F |

-continued
| $R^2$ | $R^1$ | $R^{6G}$ | $R^{6H}$ |
|---|---|---|---|
| 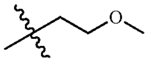 [SMILES: *CCOC] | 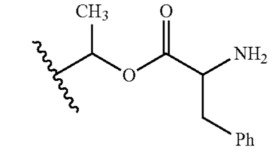 [SMILES: *C(C)OC(=O)C(N)Cc1ccccc1] | F | F |
| 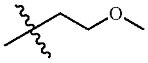 [SMILES: *CCOC] | 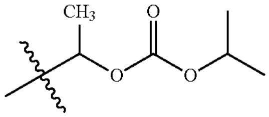 [SMILES: *C(C)OC(=O)OC(C)C] | F | F |
| 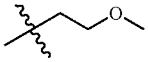 | 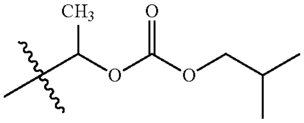 | F | F |
| 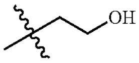 [SMILES: *CCO] | H | F | F |
| 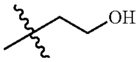 | 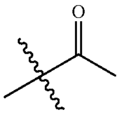 | F | F |
| 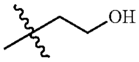 [SMILES: *CCO] | 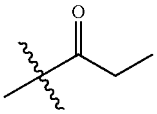 [SMILES: *C(=O)CC] | F | F |
| 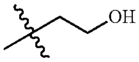 [SMILES: *CCO] | 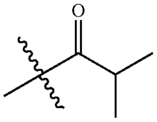 [SMILES: *C(=O)C(C)C] | F | F |
| 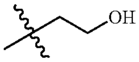 [SMILES: *CCO] | 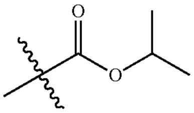 [SMILES: *C(=O)OC(C)C] | F | F |
| 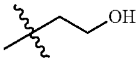 [SMILES: *CCO] | 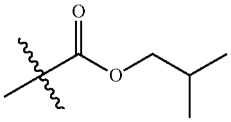 [SMILES: *C(=O)OCC(C)C] | F | F |
| 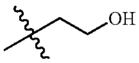 | 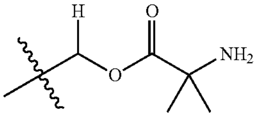 | F | F |
| 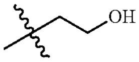 [SMILES: *CCO] | 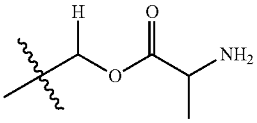 [SMILES: *COC(=O)C(C)N] | F | F |
| 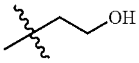 [SMILES: *CCO] | 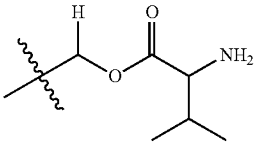 [SMILES: *COC(=O)C(N)C(C)C] | F | F |
-continued
| $R^2$ | $R^1$ | $R^{6G}$ | $R^{6H}$ |
|---|---|---|---|
| 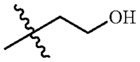 [SMILES: *CCO] | 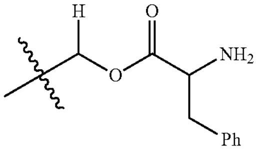 [SMILES: *COC(=O)C(N)Cc1ccccc1] | F | F |
| 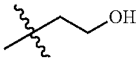 | 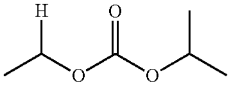 | F | F |
| 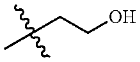 [SMILES: *CCO] | 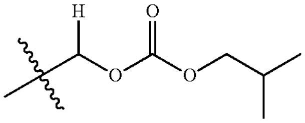 | F | F |
| 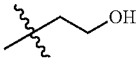 [SMILES: *CCO] | 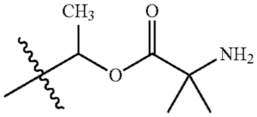 [SMILES: *C(C)OC(=O)C(C)(C)N] | F | F |
| 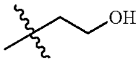 [SMILES: *CCO] | 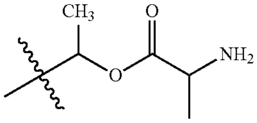 [SMILES: *C(C)OC(=O)C(C)N] | F | F |
| 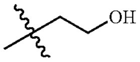 [SMILES: *CCO] | 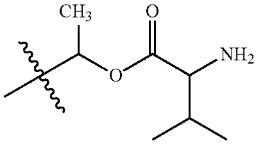 [SMILES: *C(C)OC(=O)C(N)C(C)C] | F | F |
| 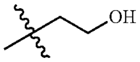 | 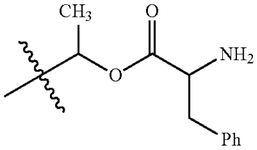 [SMILES: *C(C)OC(=O)C(N)Cc1ccccc1] | F | F |
| 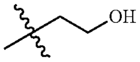 [SMILES: *CCO] | 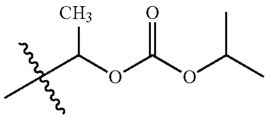 [SMILES: *C(C)OC(=O)OC(C)C] | F | F |
| 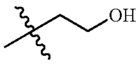 |  | F | F |
| $-CH_2CH{=}CF_2$ |  | F | F |
| $-CH_2CH{=}CF_2$ |  | F | F |

-continued
| $R^2$ | $R^1$ | $R^{6G}$ | $R^{6H}$ |
|---|---|---|---|
| $—CH_2CH═CF_2$ | 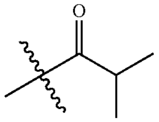 [SMILES: *C(=O)C(C)C] | F | F |
| $—CH_2CH═CF_2$ | 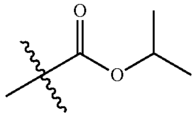 [SMILES: *C(=O)OC(C)C] | F | F |
| $—CH_2CH═CF_2$ | 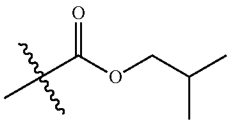 [SMILES: *C(=O)OCC(C)C] | F | F |
| $—CH_2CH═CF_2$ | 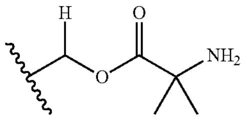 [SMILES: *COC(=O)C(C)(C)N] | F | F |
| $—CH_2CH═CF_2$ | 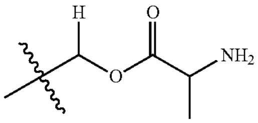 [SMILES: *COC(=O)C(C)N] | F | F |
| $—CH_2CH═CF_2$ | 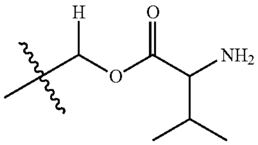 [SMILES: *COC(=O)C(N)C(C)C] | F | F |
| $—CH_2CH═CF_2$ | 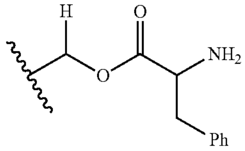 [SMILES: *COC(=O)C(N)Cc1ccccc1] | F | F |
| $—CH_2CH═CF_2$ | 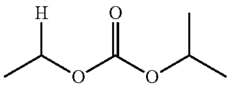 | F | F |
| $—CH_2CH═CF_2$ | 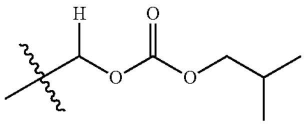 [SMILES: *COC(=O)OCC(C)C] | F | F |
| $—CH_2CH═CF_2$ | 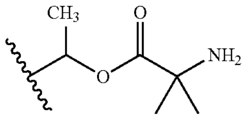 [SMILES: *C(C)OC(=O)C(C)(C)N] | F | F |
| $—CH_2CH═CF_2$ | 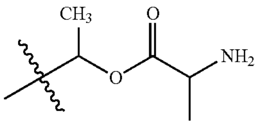 | F | F |
-continued
| $R^2$ | $R^1$ | $R^{6G}$ | $R^{6H}$ |
|---|---|---|---|
| $—CH_2CH═CF_2$ | 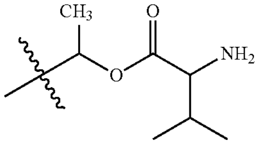 | F | F |
| $—CH_2CH═CF_2$ | 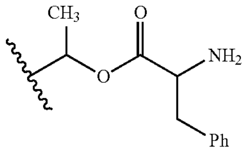 | F | F |
| $—CH_2CH═CF_2$ | 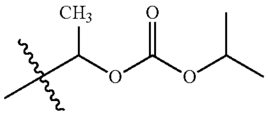 [SMILES: *C(C)OC(=O)OC(C)C] | F | F |
| $—CH_2CH═CF_2$ | 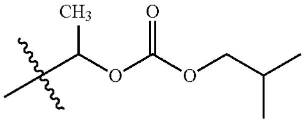 | F | F |
| $—CH_2CF_3$ | 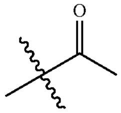 [SMILES: *C(C)=O] | F | F |
| $—CH_2CF_3$ | 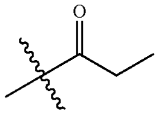 [SMILES: *C(=O)CC] | F | F |
| $—CH_2CF_3$ | 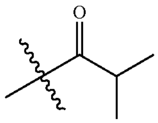 [SMILES: *C(=O)C(C)C] | F | F |
| $—CH_2CF_3$ | 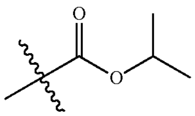 [SMILES: *C(=O)OC(C)C] | F | F |
| $—CH_2CF_3$ | 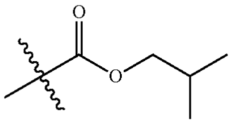 [SMILES: *C(=O)OCC(C)C] | F | F |
| $—CH_2CF_3$ | 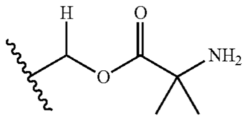 [SMILES: *COC(=O)C(C)(C)N] | F | F |
| $—CH_2CF_3$ | 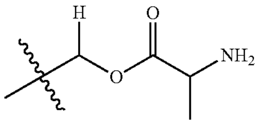 [SMILES: *COC(=O)C(C)N] | F | F |

-continued
| $R^2$ | $R^1$ | $R^{6G}$ | $R^{6H}$ |
|---|---|---|---|
| $—CH_2CF_3$ | 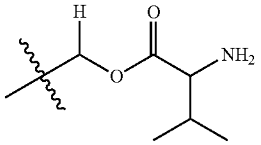 [SMILES: *COC(=O)C(N)C(C)C] | F | F |
| $—CH_2CF_3$ | 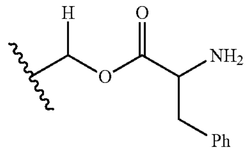 [SMILES: *COC(=O)C(N)Cc1ccccc1] | F | F |
| $—CH_2CF_3$ | 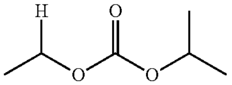 | F | F |
| $—CH_2CF_3$ | 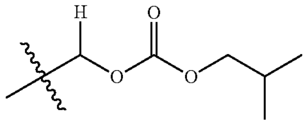 [SMILES: *COC(=O)OCC(C)C] | F | F |
| $—CH_2CF_3$ | 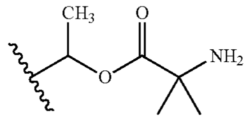 [SMILES: *C(C)OC(=O)C(C)(C)N] | F | F |
| $—CH_2CF_3$ | 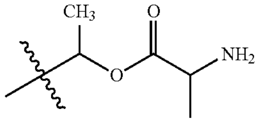 [SMILES: *C(C)OC(=O)C(C)N] | F | F |
| $—CH_2CF_3$ | 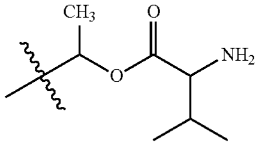 [SMILES: *C(C)OC(=O)C(N)C(C)C] | F | F |
| $—CH_2CF_3$ | 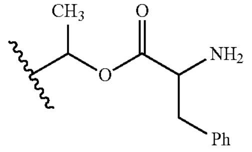 [SMILES: *C(C)OC(=O)C(N)Cc1ccccc1] | F | F |
| $—CH_2CF_3$ | 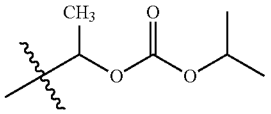 | F | F |
| $—CH_2CF_3$ | 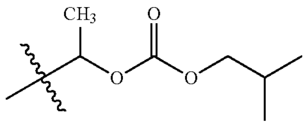 | F | F |
| $—CH_2CH_2CF_3$ | 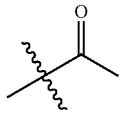 [SMILES: *C(C)=O] | F | F |
-continued
| $R^2$ | $R^1$ | $R^{6G}$ | $R^{6H}$ |
|---|---|---|---|
| $—CH_2CH_2CF_3$ | 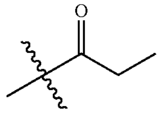 [SMILES: *C(=O)CC] | F | F |
| $—CH_2CH_2CF_3$ | 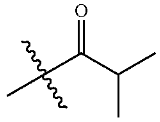 [SMILES: *C(=O)C(C)C] | F | F |
| $—CH_2CH_2CF_3$ | 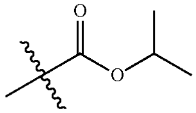 [SMILES: *C(=O)OC(C)C] | F | F |
| $—CH_2CH_2CF_3$ | 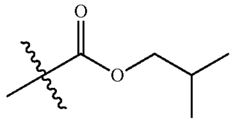 [SMILES: *C(=O)OCC(C)C] | F | F |
| $—CH_2CH_2CF_3$ | 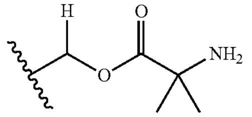 [SMILES: *COC(=O)C(C)(C)N] | F | F |
| $—CH_2CH_2CF_3$ | 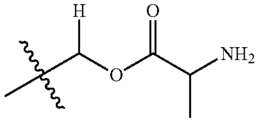 [SMILES: *COC(=O)C(C)N] | F | F |
| $—CH_2CH_2CF_3$ | 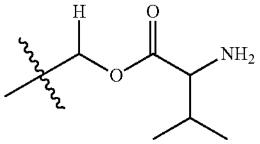 [SMILES: *COC(=O)C(N)C(C)C] | F | F |
| $—CH_2CH_2CF_3$ | 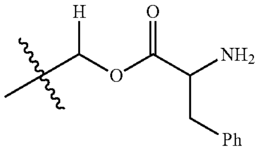 [SMILES: *COC(=O)C(N)Cc1ccccc1] | F | F |
| $—CH_2CH_2CF_3$ | 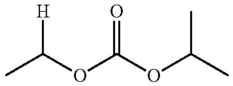 | F | F |
| $—CH_2CH_2CF_3$ | 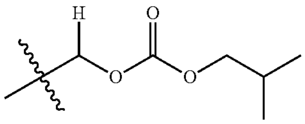 [SMILES: *COC(=O)OCC(C)C] | F | F |
| $—CH_2CH_2CF_3$ | 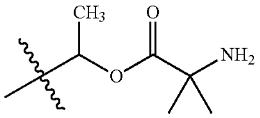 [SMILES: *C(C)OC(=O)C(C)(C)N] | F | F |

-continued
| $R^2$ | $R^1$ | $R^{6G}$ | $R^{6H}$ |
|---|---|---|---|
| $—CH_2CH_2CF_3$ | 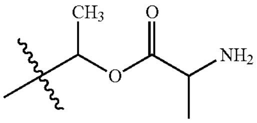 [SMILES: *C(C)OC(=O)C(C)N] | F | F |
| $—CH_2CH_2CF_3$ | 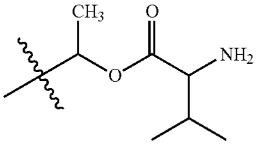 [SMILES: *C(C)OC(=O)C(N)C(C)C] | F | F |
| $—CH_2CH_2CF_3$ | 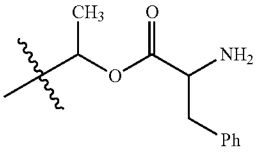 [SMILES: *C(C)OC(=O)C(N)Cc1ccccc1] | F | F |
| $—CH_2CH_2CF_3$ | 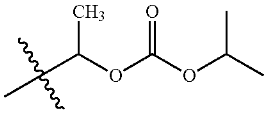 [SMILES: *C(C)OC(=O)OC(C)C] | F | F |
| $—CH_2CH_2CF_3$ | 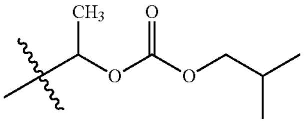 [SMILES: *C(C)OC(=O)OCC(C)C] | F | F |
| $—CH_2CHF_2$ | 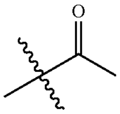 [SMILES: *C(C)=O] | F | F |
| $—CH_2CHF_2$ | 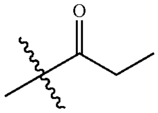 [SMILES: *C(=O)CC] | F | F |
| $—CH_2CHF_2$ | 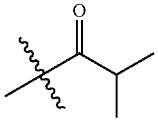 [SMILES: *C(=O)C(C)C] | F | F |
| $—CH_2CHF_2$ | 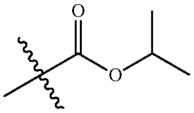 [SMILES: *C(=O)OC(C)C] | F | F |
| $—CH_2CHF_2$ | 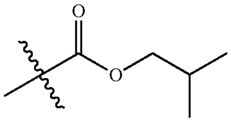 [SMILES: *C(=O)OCC(C)C] | F | F |
| $—CH_2CHF_2$ | 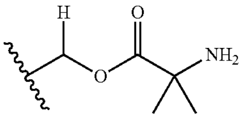 | F | F |
-continued
| $R^2$ | $R^1$ | $R^{6G}$ | $R^{6H}$ |
|---|---|---|---|
| $—CH_2CHF_2$ | 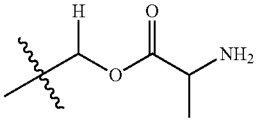 [SMILES: *COC(=O)C(C)N] | F | F |
| $—CH_2CHF_2$ | 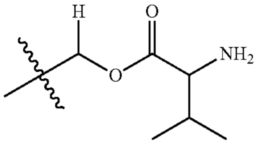 [SMILES: *COC(=O)C(N)C(C)C] | F | F |
| $—CH_2CHF_2$ | 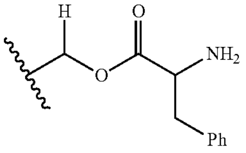 [SMILES: *COC(=O)C(N)Cc1ccccc1] | F | F |
| $—CH_2CHF_2$ | 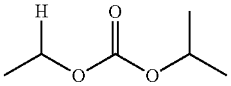 | F | F |
| $—CH_2CHF_2$ | 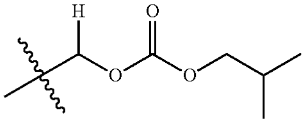 | F | F |
| $—CH_2CHF_2$ | 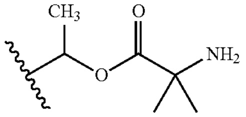 [SMILES: *C(C)OC(=O)C(C)(C)N] | F | F |
| $—CH_2CHF_2$ | 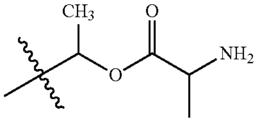 | F | F |
| $—CH_2CHF_2$ | 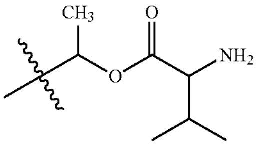 | F | F |
| $—CH_2CHF_2$ | 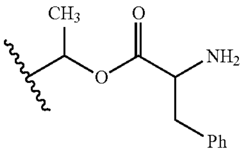 [SMILES: *C(C)OC(=O)C(N)Cc1ccccc1] | F | F |
| $—CH_2CHF_2$ | 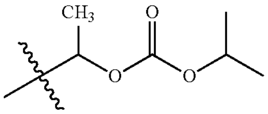 [SMILES: *C(C)OC(=O)OC(C)C] | F | F |
| $—CH_2CHF_2$ | 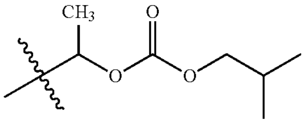 [SMILES: *C(C)OC(=O)OCC(C)C] | F | F |

-continued

| $R^2$ | $R^1$ | $R^{6G}$ | $R^{6H}$ |
|---|---|---|---|
| —$CH_2C(CH_3)F_2$ | 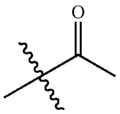 [SMILES: *C(C)=O] | F | F |
| —$CH_2C(CH_3)F_2$ | 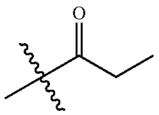 [SMILES: *C(=O)CC] | F | F |
| —$CH_2C(CH_3)F_2$ | 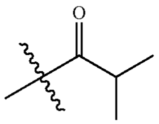 [SMILES: *C(=O)C(C)C] | F | F |
| —$CH_2C(CH_3)F_2$ | 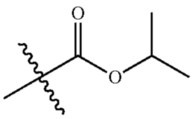 [SMILES: *C(=O)OC(C)C] | F | F |
| —$CH_2C(CH_3)F_2$ | 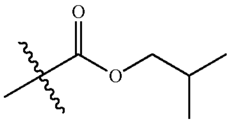 [SMILES: *C(=O)OCC(C)C] | F | F |
| —$CH_2C(CH_3)F_2$ | 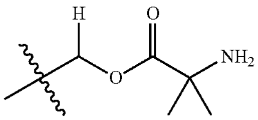 [SMILES: *COC(=O)C(C)(C)N] | F | F |
| —$CH_2C(CH_3)F_2$ | 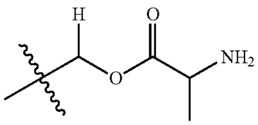 [SMILES: *COC(=O)C(C)N] | F | F |
| —$CH_2C(CH_3)F_2$ | 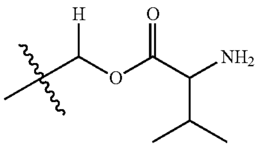 [SMILES: *COC(=O)C(N)C(C)C] | F | F |
| —$CH_2C(CH_3)F_2$ | 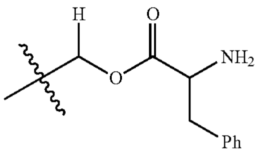 [SMILES: *COC(=O)C(N)Cc1ccccc1] | F | F |
| —$CH_2C(CH_3)F_2$ | 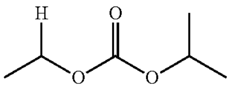 | F | F |
| —$CH_2C(CH_3)F_2$ | 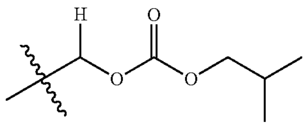 [SMILES: *COC(=O)OCC(C)C] | F | F |

-continued

| $R^2$ | $R^1$ | $R^{6G}$ | $R^{6H}$ |
|---|---|---|---|
| —$CH_2C(CH_3)F_2$ | 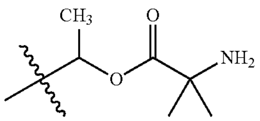 | F | F |
| —$CH_2C(CH_3)F_2$ | 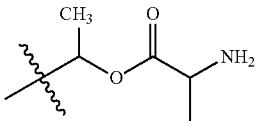 [SMILES: *C(C)OC(=O)C(C)N] | F | F |
| —$CH_2C(CH_3)F_2$ | 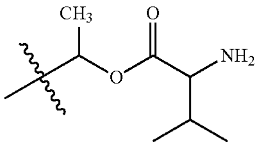 | F | F |
| —$CH_2C(CH_3)F_2$ | 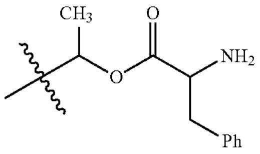 [SMILES: *C(C)OC(=O)C(N)Cc1ccccc1] | F | F |
| —$CH_2C(CH_3)F_2$ | 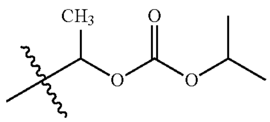 [SMILES: *C(C)OC(=O)OC(C)C] | F | F |
| and —$CH_2C(CH_3)F_2$ | 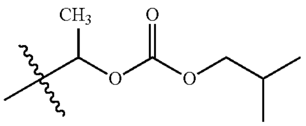 | F | F, |

or a pharmaceutically acceptable salt of any of the foregoing.

31. A compound selected from the group consisting of:

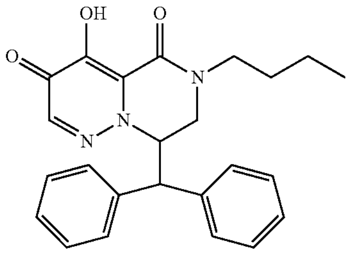

,

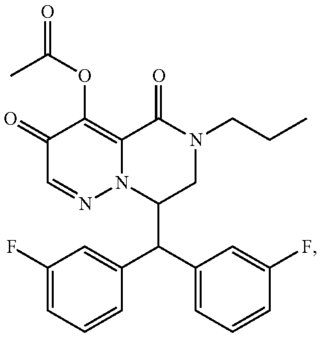

,

-continued

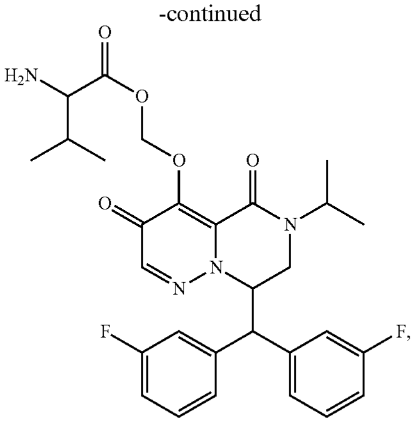

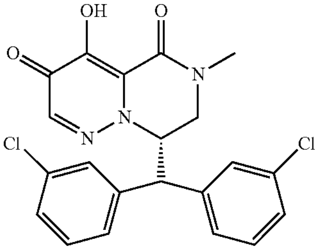

and

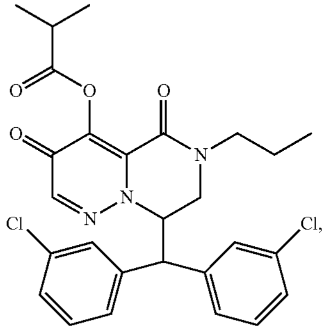

or a pharmaceutically acceptable salt of any of the foregoing.

32. A pharmaceutical composition comprising an effective amount of a compound of claim 1, or a pharmaceutically acceptable salt thereof, and a pharmaceutically acceptable carrier, diluent, excipient, or combination thereof.

33. A method for ameliorating or treating an orthomyxovirus infection comprising administering to a subject suffering from the orthomyxovirus infection an effective amount of a compound of claim 1, or a pharmaceutically acceptable salt thereof, wherein the orthomyxovirus infection is selected from the group consisting of an influenza A infection and an influenza B infection.

34. A method for inhibiting replication of an orthomyxovirus comprising contacting a cell infected with the orthomyxovirus with an effective amount of a compound of claim 1, or a pharmaceutically acceptable salt thereof, wherein the orthomyxovirus is selected from the group consisting of an influenza A virus and an influenza B virus.

35. The method of claim 34, wherein the orthomyxovirus is an influenza A virus.

36. The method of claim 34, further comprising one or more additional agents.

37. The method of claim 36, wherein the orthomyxovirus is an influenza virus; and wherein the one or more additional agents is selected from the group consisting of a neuraminidase inhibitor, a M2 protein inhibitor, a polymerase inhibitor, a PB2 inhibitor, amantadine, rimantadine, zanamivir, oseltamivir, peramivir, laninamivir, laninamivir octanoate, favipiravir, fludase, a triple combination of amantadine HCl, oseltamivir and ribavirin, an immuno-modulator, beraprost, ribavirin, (R)-3-((5-fluoro-2-(5-fluoro-1H-pyrrolo[2,3-b]pyridin-3-yl)pyrimidin-4-yl)amino)-4,4-dimethylpentanoic acid, (2S,3S)-3-((5-fluoro-2-(5-fluoro-1H-pyrrolo[2,3-b]pyridin-3-yl)pyrimidin-4-yl)amino)bicyclo[2.2.2]octane-2-carboxylic acid, (S)-8-benzhydryl-4-hydroxy-6-isopropyl-7,8-dihydro-3H-pyrazino[1,2-b]pyridazine-3,5(6H)-dione, and (S)-8-benzhydryl-6-isopropyl-3,5-dioxo-5,6,7,8-tetrahydro-3H-pyrazino[1,2-b]pyridazin-4-yl isobutyrate.

38. A method for inhibiting endonuclease activity of an influenza endonuclease comprising contacting the active site of the endonuclease with an effective amount of a compound of claim 1, or a pharmaceutically acceptable salt thereof.

39. The method of claim 34, wherein the orthomyxovirus is an influenza B virus.

* * * * *

UNITED STATES PATENT AND TRADEMARK OFFICE
CERTIFICATE OF CORRECTION

PATENT NO. : 10,208,045 B2
APPLICATION NO. : 15/065627
DATED : February 19, 2019
INVENTOR(S) : Robert Than Hendricks et al.

It is certified that error appears in the above-identified patent and that said Letters Patent is hereby corrected as shown below:

In the Claims

At Column 332, Claim number 1, Line number 63, please replace “heteroaryl(C 1-6 alkyl)” with -- heteroaryl($C_{1-6}$ alkyl) --;

At Column 333, Claim number 1, Line number 65, please replace “$CH_3$,” with -- -$CH_3$, --;

At Column 346, Claim number 28, Line numbers 16-30, please delete

“ 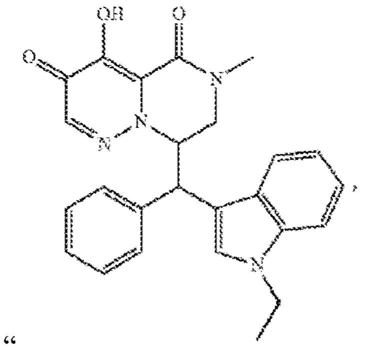 ,”;

At Column 347, Claim number 29, Line number 36, please replace “Compound” with -- compound --;

At Columns 371-372, Claim number 30, sixth structure from the top, please replace “ 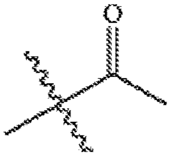 ”

with -- 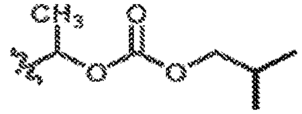 --;

Signed and Sealed this
Third Day of December, 2019

Andrei Iancu
*Director of the United States Patent and Trademark Office*

At Column 431-432, Claim number 30, third structure from the top, please replace
" 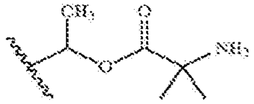 " with -- 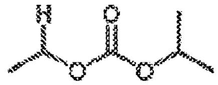 --;
At Column 451-452, Claim number 30, seventh structure from the top, please insert
-- Cl Cl -- after " 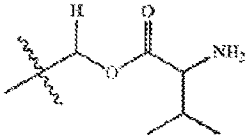 "; and
At Column 602, Claim number 30, second structure from the top under the column for "$R^1$", please replace " 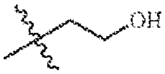 " with -- 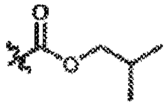 --.

```
                         SEQUENCE LISTING


<160> NUMBER OF SEQ ID NOS: 1

<210> SEQ ID NO 1
<211> LENGTH: 19
<212> TYPE: RNA
<213> ORGANISM: Artificial Sequence
<220> FEATURE:
<223> OTHER INFORMATION: synthetic oligoribonucleotide

<400> SEQUENCE: 1

auuuuguuuu uaauauuuc                                          19
```